US009326973B2

(12) United States Patent
Hewawasam et al.

(10) Patent No.: US 9,326,973 B2
(45) Date of Patent: May 3, 2016

(54) HEPATITIS C VIRUS INHIBITORS

(71) Applicant: Bristol-Myers Squibb Company, Princeton, NJ (US)

(72) Inventors: Piyasena Hewawasam, Middletown, CT (US); John F. Kadow, Wallingford, CT (US); Omar D. Lopez, Wallingford, CT (US); Nicholas A. Meanwell, East Hampton, CT (US); Yong Tu, Cheshire, CT (US); Alan Xiangdong Wang, Wallingford, CT (US); Ningning Xu, Wallingford, CT (US); Samayamunthula Venkata Satya Arun Kumar Gupta, Bangalore (IN); Pothukanuri Srinivasu, Bangalore (IN); Indasi Gopi Kumar, Bangalore (IN); Ponugupati Suresh Kumar, Bangalore (IN); Makonen Belema, North Haven, CT (US); Robert A. Fridell, Guilford, CT (US); Min Gao, Madison, CT (US); Julie A. Lemm, Durham, CT (US); Donald R. O'Boyle, II, Killingworth, CT (US); Jin-Hua Sun, North Haven, CT (US); Chunfu Wang, Cheshire, CT (US); Ying-Kai Wang, Rocky Hill, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 289 days.

(21) Appl. No.: 13/735,224

(22) Filed: Jan. 7, 2013

(65) Prior Publication Data

US 2013/0183269 A1 Jul. 18, 2013

Related U.S. Application Data

(60) Provisional application No. 61/663,902, filed on Jun. 25, 2012, provisional application No. 61/586,558, filed on Jan. 13, 2012.

(51) Int. Cl.
| | |
|---|---|
| *A61K 31/415* | (2006.01) |
| *A61K 31/675* | (2006.01) |
| *A61K 38/00* | (2006.01) |
| *A61K 31/4178* | (2006.01) |
| *A61K 31/407* | (2006.01) |
| *A61K 31/4184* | (2006.01) |
| *A61K 31/422* | (2006.01) |
| *A61K 31/423* | (2006.01) |
| *A61K 31/428* | (2006.01) |
| *A61K 31/437* | (2006.01) |
| *A61K 31/444* | (2006.01) |
| *A61K 31/4545* | (2006.01) |
| *A61K 31/4709* | (2006.01) |
| *A61K 31/496* | (2006.01) |
| *A61K 31/497* | (2006.01) |
| *A61K 31/498* | (2006.01) |
| *A61K 31/501* | (2006.01) |
| *A61K 31/506* | (2006.01) |
| *A61K 31/519* | (2006.01) |

(Continued)

(52) U.S. Cl.
CPC .......... *A61K 31/4178* (2013.01); *A61K 31/407* (2013.01); *A61K 31/4184* (2013.01); *A61K 31/422* (2013.01); *A61K 31/423* (2013.01); *A61K 31/428* (2013.01); *A61K 31/437* (2013.01); *A61K 31/444* (2013.01); *A61K 31/4545* (2013.01); *A61K 31/4709* (2013.01); *A61K 31/496* (2013.01); *A61K 31/497* (2013.01); *A61K 31/498* (2013.01); *A61K 31/501* (2013.01); *A61K 31/506* (2013.01); *A61K 31/519* (2013.01); *A61K 31/5377* (2013.01); *A61K 31/55* (2013.01); *A61K 31/7056* (2013.01); *A61K 38/05* (2013.01); *A61K 38/21* (2013.01); *A61K 38/212* (2013.01); *A61K 38/217* (2013.01); *A61K 45/06* (2013.01); *C07D 403/14* (2013.01); *C07D 491/113* (2013.01)

(58) Field of Classification Search
CPC .............. A61K 31/4178; A61K 38/00; A61K 2300/00; C07F 9/6512
USPC ............................................ 514/397, 4.3, 86
See application file for complete search history.

(56) References Cited

U.S. PATENT DOCUMENTS

| 5,654,451 A | 8/1997 | Kari |
| 7,745,636 B2 | 6/2010 | Bachand et al. |

(Continued)

FOREIGN PATENT DOCUMENTS

| WO | WO 94/15909 | 7/1994 |
| WO | WO 2004/005264 | 1/2004 |

(Continued)

OTHER PUBLICATIONS

Cordek, D.G, et al, "Targeting the NS5A Protein of HCV: An Emerging Option," Drugs of the Future, vol. 36, No. 9, pp. 691-711, 2011.

(Continued)

*Primary Examiner* — Shengjun Wang
(74) *Attorney, Agent, or Firm* — Pamela A. Mingo

(57) ABSTRACT

The present disclosure is generally directed to antiviral compounds, and more specifically directed to combinations of compounds which can inhibit the function of the NS5A protein encoded by Hepatitis C virus (HCV), compositions comprising such combinations, and methods for inhibiting the function of the NS5A protein.

13 Claims, No Drawings

(51) Int. Cl.

| | |
|---|---|
| A61K 31/5377 | (2006.01) |
| A61K 31/55 | (2006.01) |
| A61K 31/7056 | (2006.01) |
| A61K 38/05 | (2006.01) |
| A61K 38/21 | (2006.01) |
| A61K 45/06 | (2006.01) |
| C07D 403/14 | (2006.01) |
| C07D 491/113 | (2006.01) |

(56) References Cited

U.S. PATENT DOCUMENTS

| | | | |
|---|---|---|---|
| 7,894,996 | B2 | 2/2011 | Rice et al. |
| 8,178,531 | B2 | 5/2012 | Or et al. |
| 8,288,562 | B2 | 10/2012 | Bachand et al. |
| 8,303,944 | B2 | 11/2012 | Bachand et al. |
| 8,492,553 | B2 | 7/2013 | Bachand et al. |
| 8,492,554 | B2 | 7/2013 | Chen et al. |
| 2010/0158862 | A1 | 6/2010 | Kim et al. |
| 2011/0020272 | A1* | 1/2011 | Schubert ............... 424/85.2 |
| 2011/0092415 | A1 | 4/2011 | DeGoey et al. |
| 2011/0206637 | A1 | 8/2011 | Or et al. |
| 2011/0237636 | A1 | 9/2011 | Belema et al. |
| 2011/0268697 | A1 | 11/2011 | Kim et al. |
| 2013/0004457 | A1 | 1/2013 | Bachand et al. |
| 2013/0012540 | A1 | 1/2013 | Lavoie et al. |
| 2013/0071352 | A1 | 3/2013 | Dousson et al. |
| 2013/0072523 | A1 | 3/2013 | Liu et al. |
| 2013/0085147 | A1 | 4/2013 | Lopez et al. |
| 2013/0115193 | A1 | 5/2013 | Lavoie et al. |
| 2013/0157894 | A1* | 6/2013 | Sun et al. ............... 506/9 |

FOREIGN PATENT DOCUMENTS

| | | |
|---|---|---|
| WO | WO 2006/022442 | 3/2006 |
| WO | WO 2006/093867 | 9/2006 |
| WO | WO 2006/133326 | 12/2006 |
| WO | WO 2007/031791 | 3/2007 |
| WO | WO 2007/058384 | 5/2007 |
| WO | WO 2007/076034 | 7/2007 |
| WO | WO 2007/077186 | 7/2007 |
| WO | WO 2007/081517 | 7/2007 |
| WO | WO 2007/138242 | 12/2007 |
| WO | WO 2008/021927 | 2/2008 |
| WO | WO 2008/021928 | 2/2008 |
| WO | WO 2008/021936 | 2/2008 |
| WO | WO 2008/070447 | 6/2008 |
| WO | WO 2008/133753 | 11/2008 |
| WO | WO 2008/144380 | 11/2008 |
| WO | WO 2009/020825 | 2/2009 |
| WO | WO 2009/020828 | 2/2009 |
| WO | WO 2009/102318 * | 8/2009 |
| WO | WO 2009/102568 | 8/2009 |
| WO | WO 2009/102633 | 8/2009 |
| WO | WO 2009/102694 | 8/2009 |
| WO | WO 2010/017401 | 2/2010 |
| WO | WO 2010/039793 | 4/2010 |
| WO | WO 2010/062821 | 6/2010 |
| WO | WO 2010/065668 | 6/2010 |
| WO | WO 2010/065674 | 6/2010 |
| WO | WO 2010/065681 | 6/2010 |
| WO | WO 2010/075376 | 7/2010 |
| WO | WO 2010/091413 | 8/2010 |
| WO | WO 2010/094977 | 8/2010 |
| WO | WO 2010/096302 | 8/2010 |
| WO | WO 2010/096462 | 8/2010 |
| WO | WO 2010/096777 | 8/2010 |
| WO | WO 2010/099527 | 9/2010 |
| WO | WO 2010/111483 | 9/2010 |
| WO | WO 2010/111534 | 9/2010 |
| WO | WO 2010/111673 | 9/2010 |
| WO | WO 2010/117635 | 10/2010 |
| WO | WO 2010/117704 | 10/2010 |
| WO | WO 2010/117977 | 10/2010 |
| WO | WO 2010/120621 | 10/2010 |
| WO | WO 2010/120935 | 10/2010 |
| WO | WO 2010/122162 | 10/2010 |
| WO | WO 2010/132538 | 11/2010 |
| WO | WO 2010/132601 | 11/2010 |
| WO | WO 2010/138368 | 12/2010 |
| WO | WO 2010/138488 | 12/2010 |
| WO | WO 2010/138790 | 12/2010 |
| WO | WO 2010/138791 | 12/2010 |
| WO | WO 2010/144646 | 12/2010 |
| WO | WO 2010/148006 | 12/2010 |
| WO | WO 2011/004276 | 1/2011 |
| WO | WO 2011/009084 | 1/2011 |
| WO | WO 2011/015657 | 2/2011 |
| WO | WO 2011/015658 | 2/2011 |
| WO | WO 2011/026920 | 3/2011 |
| WO | WO 2011/028596 | 3/2011 |
| WO | WO 2011/031904 | 3/2011 |
| WO | WO 2011/031934 | 3/2011 |
| WO | WO 2011/046811 | 4/2011 |
| WO | WO 2011/050146 | 4/2011 |
| WO | WO 2011/054834 | 5/2011 |
| WO | WO 2011/059850 | 5/2011 |
| WO | WO 2011/059887 | 5/2011 |
| WO | WO 2011/060000 | 5/2011 |
| WO | WO 2011/066241 | 6/2011 |
| WO | WO 2011/068941 | 6/2011 |
| WO | WO 2011/075439 | 6/2011 |
| WO | WO 2011/075607 | 6/2011 |
| WO | WO 2011/075615 | 6/2011 |
| WO | WO 2011/079327 | 6/2011 |
| WO | WO 2011/081918 | 7/2011 |
| WO | WO 2011/082077 | 7/2011 |
| WO | WO 2011/087740 | 7/2011 |
| WO | WO 2011/091417 | 7/2011 |
| WO | WO 2011/091446 | 7/2011 |
| WO | WO 2011/091532 | 8/2011 |
| WO | WO 2011/109037 | 9/2011 |
| WO | WO 2011/112429 | 9/2011 |
| WO | WO 2011/119853 | 9/2011 |
| WO | WO 2011/119860 | 9/2011 |
| WO | WO 2011/119870 | 9/2011 |
| WO | WO 2011/127350 | 10/2011 |
| WO | WO 2011/146401 | 11/2011 |
| WO | WO 2011/149856 | 12/2011 |
| WO | WO 2011/150243 | 12/2011 |
| WO | WO 2011/153396 | 12/2011 |
| WO | WO 2011/154871 | 12/2011 |
| WO | WO 2011/156543 | 12/2011 |
| WO | WO 2011/156578 | 12/2011 |
| WO | WO 2012/003642 | 1/2012 |
| WO | WO 2012/009394 | 1/2012 |
| WO | WO 2012/013643 | 2/2012 |
| WO | WO 2012/018325 | 2/2012 |
| WO | WO 2012/018534 | 2/2012 |
| WO | WO 2012/018829 | 2/2012 |
| WO | WO 2012/020036 | 2/2012 |
| WO | WO 2012/021591 | 2/2012 |
| WO | WO 2012/021704 | 2/2012 |
| WO | WO 2012/027712 | 3/2012 |
| WO | WO 2012/040389 | 3/2012 |
| WO | WO 2012/040923 | 4/2012 |
| WO | WO 2012/040924 | 4/2012 |
| WO | WO 2012/041014 | 4/2012 |
| WO | WO 2012/041227 | 4/2012 |
| WO | WO 2012/048421 | 4/2012 |
| WO | WO 2012/050848 | 4/2012 |
| WO | WO 2012/050850 | 4/2012 |
| WO | WO 2012/050918 | 4/2012 |
| WO | WO 2012/051361 | 4/2012 |
| WO | WO 2012/061552 | 5/2012 |
| WO | WO 2012/068234 | 5/2012 |
| WO | WO 2012/074437 | 6/2012 |
| WO | WO 2012/083043 | 6/2012 |
| WO | WO 2012/083048 | 6/2012 |
| WO | WO 2012/083053 | 6/2012 |
| WO | WO 2012/083058 | 6/2012 |
| WO | WO 2012/083059 | 6/2012 |
| WO | WO 2012/083061 | 6/2012 |

(56) References Cited

FOREIGN PATENT DOCUMENTS

| | | |
|---|---|---|
| WO | WO 2012/083164 | 6/2012 |
| WO | WO 2012/083170 | 6/2012 |
| WO | WO 2012/087596 | 6/2012 |
| WO | WO 2012/087976 | 6/2012 |
| WO | WO 2012/109080 | 8/2012 |
| WO | WO 2012/116257 | 8/2012 |
| WO | WO 2012/122716 | 9/2012 |
| WO | WO 2012/123298 | 9/2012 |
| WO | WO 2012/125926 | 9/2012 |
| WO | WO 2012/135581 | 10/2012 |
| WO | WO 2012/154777 | 11/2012 |
| WO | WO 2012/162578 | 11/2012 |
| WO | WO 2012/162580 | 11/2012 |
| WO | WO 2012/166716 | 12/2012 |
| WO | WO 2012/175581 | 12/2012 |
| WO | WO 2013/007106 | 1/2013 |
| WO | WO 2013/021337 | 2/2013 |
| WO | WO 2013/021344 | 2/2013 |
| WO | WO 2013/022810 | 2/2013 |
| WO | WO 2013/028953 | 2/2013 |
| WO | WO 2013/030750 | 3/2013 |
| WO | WO 2013/039876 | 3/2013 |
| WO | WO 2013/039878 | 3/2013 |
| WO | WO 2013/052362 | 4/2013 |
| WO | WO 2013/052369 | 4/2013 |
| WO | WO 2013/053657 | 4/2013 |
| WO | WO 2013/059278 | 4/2013 |
| WO | WO 2013/059630 | 4/2013 |
| WO | WO 2013/059638 | 4/2013 |
| WO | WO 2013/066753 | 5/2013 |
| WO | WO 2013/075029 | 5/2013 |
| WO | WO 2013/087743 | 6/2013 |
| WO | WO 2013/095275 | 6/2013 |
| WO | WO 2013/098313 | 7/2013 |
| WO | WO 2013/098320 | 7/2013 |
| WO | WO 2013/101550 | 7/2013 |
| WO | WO 2013/101552 | 7/2013 |

OTHER PUBLICATIONS

Graham, Emily J.S., et al, "Colony-Forming Assays Reveal enhanced Suppression of Hepatitis C Virus Replication Using Combinations of Direct-Acting Antivirals," Journal of Virological Methods, vol. 174, No. 1, pp. 153-157, 2011.
Journal of Hepatology, vol. 54, No. Supp. 1, p. S316, 2011.
Fridell, R.A. et al., "Distinct Functions of NS5A in Hepatitis C Virus RNA Replication Uncovered by Studies with the NS5A Inhibitor BMS-790052", Journal of Virology, vol. 85, No. 14, pp. 7312-7320 (2011).
Fridell, R.A. et al., "Genotypic and Phenotypic Analysis of Variants Resistant to Hepatitis C Virus Nonstructural Protein 5A Replication Complex Inhibitor BMS-790052 in Humans: In Vitro and In Vivo Correlations", Hepatology, vol. 54, No. 6, pp. 1924-1935 (2011).
Fridell, R.A. et al., "Resistance Analysis of the Hepatitis C Virus NS5A Inhibitor BMS-790052 in an In Vitro Replicon System", Antimicrobial Agents and Chemotherapy, vol. 54, No. 9, pp. 3641-3650 (2010).
Gao, M. et al., "Chemical genetics strategy identifies an HCV NS5A inhibitor with a potent clinical effect", Nature, vol. 465, pp. 96-100 (2010).
Lemm, J.A. et al., "Discovery of Potent Hepatitis C Virus NS5A Inhibitors with Dimeric Structures", Antimicrobial Agents and Chemotherapy, vol. 55, No. 8, pp. 3795-3802 (2011).
Lemm, J.A. et al., "Identification of Hepatitis C Virus NS5A Inhibitors", Journal of Virology, vol. 84, No. 1, pp. 482-491 (2010).
Nettles, R.E. et al., "Multiple Ascending Dose Study of BMS-790052, a Nonstructural Protein 5A Replication Complex Inhibitor, in Patients Infected with Hepatitis C Virus Genotype 1", Hepatology, vol. 54, No. 6, pp. 1956-1965 (2011).
O'Boyle II, D.R. et al., "Development of a Cell-Based High-Throughput Specificity Screen Using a Hepatitis C Virus-Bovine Viral Diarrhea Virus Dual Replicon Assay", Antimicrobial Agents and Chemotherapy, vol. 49, No. 4, pp. 1346-1353 (2005).
Pelosi, L.A. et al., "Effect on Hepatitis C Virus Replication of Combinations of Direct-Acting Antivirals, Including NS5A Inhibitor Daclatasvir", Antimicrobial Agents and Chemotherapy, vol. 56, No. 10, pp. 5230-5239 (2012).
Qiu, D. et al., "The effects of NS5A inhibitors on NS5A phosphorylation, polyprotein processing and localization", Journal of General Virology, vol. 92, pp. 2502-2511 (2011).
Romine, J.L. et al., "Inhibitors of HCV NS5A: From Iminothiazolidinones to Symmetrical Stilbenes", ACS Medicinal Chemistry Letters, vol. 2, pp. 224-229 (2011).
Sun, J.-H. et al., "Impact of a Baseline Polymorphism on the Emergence of Resistance to the Hepatitis C Virus Nonstructural Protein 5A Replication Complex Inhibitor, BMS-790052", Hepatology, vol. 55, No. 6, pp. 1692-1699 (2012).
Wang, C. et al., "Hepatitis C Virus RNA Elimination and Development of Resistance in Replicon Cells Treated with BMS-790052", Antimicrobial Agents and Chemotherapy, vol. 56, No. 3, pp. 1350-1358 (2012).
Wang, C. et al., In Vitro Activity of BMS-790052 on Hepatitis C Virus Genotype 4 NS5A, Antimicrobial Agents and Chemotherapy, vol. 56, No. 3, pp. 1588-1590 (2012).
Wang, C. et al., In Vitro Activity of Daclatasvir on Hepatitis C Virus Genotype 3 NS5A, Antimicrobial Agents and Chemotherapy, vol. 57, No. 1, pp. 611-613 (2013).
Lemm et al., U.S. Appl. No. 13/792,898, filed Mar. 11, 2013.
Bachand et al., U.S. Appl. No. 13/919,027, filed Jun. 17, 2013.
Hewawasam et al., U.S. Appl. No. 13/933,495, filed Jul. 2, 2013.
Pack et al., U.S. Appl. No. 13/956,928, filed Aug. 1, 2013.

* cited by examiner

HEPATITIS C VIRUS INHIBITORS

CROSS-REFERENCE TO RELATED APPLICATIONS

This application claims the benefit of U.S. Provisional Application Ser. No. 61/663,902 filed Jun. 25, 2012 and U.S. Provisional Application Ser. No. 61/586,558 filed Jan. 13, 2012.

The present disclosure is generally directed to antiviral compounds, and more specifically directed to combinations of compounds which can inhibit the function of the NS5A protein encoded by Hepatitis C virus (HCV), compositions comprising such combinations, and methods for inhibiting the function of the NS5A protein.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Over the past decade the standard of care for the treatment of chronic HCV employed a combination of pegylated-interferon and ribavirin. The treatment has a non-optimal success rate in achieving sustained viral response (SVR) against the six major HCV genotypes, with a particularly low success rate against genotype 1, and causes numerous side effects. Recently approved drugs targeting the HCV NS3/4A protease (PIs) (Victrelis® and Incivek®) are administered with pegylated-interferon and ribavirin and provide a major improvement in the percentage of patients who experience SVR and the treatment duration required to achieve SVR. However, there is a clear and urgent need to develop additional therapies to combat protease inhibitor resistance, to improve efficacy across all HCV genotypes, and to advance antiviral therapy towards the ultimate goal of an interferon-free cure.

HCV is a positive-stranded RNA virus of approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein is a cofactor for the NS3 protease. The formation of a NS3-NS4A complex is necessary for proper protease activity. The NS3 protein also exhibits nucleoside triphosphatase and RNA helicase activities. NS5A is a multi-functional protein required for viral RNA replication and virion assembly. NS5B (also referred to herein as HCV polymerase) is a RNA-dependent RNA polymerase that is responsible for viral RNA synthesis.

Considerable heterogeneity is found within the nucleotide and encoded amino acid sequence throughout the HCV genome due to the high error rate of the encoded RNA-dependent RNA polymerase which lacks a proof-reading capability. The clinical significance of the genetic heterogeneity of HCV is the propensity for mutations to arise during monotherapy treatment, thus combination therapies with HCV inhibitors that have pan-genotype coverage and act via independent mechanisms are desired.

Compounds which selectively inhibit HCV viral replication and are useful for treating HCV-infected patients are desired. In particular, compounds which effectively inhibit the function of the NS5A protein are desired. The function and the essential role of NS5A protein for HCV replication are described, for example, in the following references: S. L. Tan, et al., *Virology*, 284:1-12 (2001); K.-J. Park, et al., *J. Biol. Chem.*, 30711-30718 (2003); T. L. Tellinghuisen, et al., *Nature*, 435, 374 (2005); R. A. Love, et al., *J. Virol*, 83, 4395 (2009); N. Appel, et al., *J. Biol. Chem.*, 281, 9833 (2006); L. Huang, *J. Biol. Chem.*, 280, 36417 (2005); M. Gao, et al, *Nature* (2010); C. Rice, et al., WO2006093867.

A method has been described to identify compounds that demonstrate synergistic inhibition of HCV replicon activity when combined with the HCV NS5A inhibitor such as BMS-790052 (PCT/US2011/043785, filed Jul. 13, 2011). In brief, each compound, when tested individually versus some NS5A resistant variants, is essentially inactive or much less active and only has synergistic inhibitory activity when tested in combination with an NS5A-targeting compound. The synergistic compounds were identified using titrations of test compounds in the presence of fixed concentrations of HCV NS5A inhibitors such as BMS-790052.

In a first aspect the present disclosure provides a combination comprising an NS5A-targeting compound and an NS5A synergist, which, when administered, provides synergistic anti-HCV activity against variants that contain mutation(s) conferring resistance to the NS5A-targeting compound alone. In a first embodiment of the first aspect the combination comprises two or more pharmaceutically acceptable carriers. In a second embodiment the NS5A-targeting compound and the NS5A synergist are combined in the same pharmaceutically acceptable carrier.

In a third embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound of formula (I):

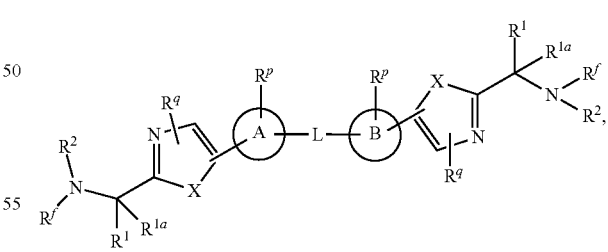

or a pharmaceutically acceptable salt thereof, wherein

L is absent or selected from $C_2$alkyl, $C_2$alkenyl, $C_2$alkynyl, $C_4$alkynyl, and $C_3$cycloalkyl A is absent or selected from isoquinolinyl, naphthyl, phenyl, pyrazinyl, pyridinyl, pyrimidinyl, and quinolinyl;

B is selected from anthracenyl, benzofuranyl, bicycloalkyl, indanyl, indolyl, naphthyl, phenyl, pyridinyl, pyrimidinyl, pyrazinyl, tetrahydronaphthyl, thienyl, and

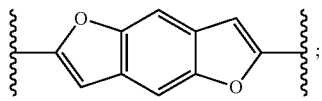 [SMILES: *c1cc2cc3oc(*)cc3cc2o1]

each X is independently selected from O and NR$^{q'}$, wherein R$^{q'}$ is selected from hydrogen, alkyl, hydroxy, and —NH$_2$;

each R$^1$ is independently selected from alkoxyalkyl, alkyl, aryl, arylalkyl, cycloalkyl, haloalkyl, heterocyclyl, and hydroxyalkyl;

each R$^{1a}$ is independently selected from hydrogen and alkyl; or

R$^1$ and R$^{1a}$, together with the carbon atom to which they are attached, form a saturated or unsaturated 3- to 6-membered spirocyclic ring, wherein the spirocyclic ring, when between 4- and 6-members, can be optionally fused to a phenyl ring, and wherein each ring system is optionally substituted with one or two groups independently selected from alkyl and halo;

each R$^f$ is independently selected from hydrogen, methyl, hydroxy, and —NH$_2$(R$^z$), wherein R$^z$ is alkyl;

each R$^p$ is independently selected from hydrogen, alkyl, cyano, halo, haloalkoxy, and haloalkyl;

each R$^q$ is independently selected from hydrogen, alkyl, halo, and —P(O)—(OR)$_2$, wherein each R is the same or a different alkyl group; and each R$^2$ is independently selected from hydrogen, alkenylcarbonyl, alkoxyalkylcarbonyl, alkoxyalkylcarbonylcarbonyl, alkoxycarbonyl, alkoxycarbonylalkylcarbonyl, alkoxycarbonylcarbonyl, alkyl, alkylcarbonyl, alkylcarbonylalkylcarbonyl, alkylcarbonylcarbonyl, alkylsulfinyl, alkylsulfonyl, alkynyl, alkynyloxycarbonyl, alkynylcarbonyl, arylcarbonyl, arylcarbonylcarbonyl, arylalkenylcarbonyl, arylalkoxycarbonyl, arylalkylcarbonyl, aryloxyalkylcarbonyl, arylsulfanylalkylcarbonyl, arylsulfinyl, arylsulfonyl, bicycloalkylcarbonyl, carboxyalkylcarbonyl, carboxycarbonyl, cyanoalkylcarbonyl, (cycloalkenyl)alkylcarbonyl, (cycloalkyl)alkyl, (cycloalkyl)alkylcarbonyl, cycloalkylcarbonyl, cycloalkylcarbonylcarbonyl, cycloalkyloxycarbonyl, haloalkenylcarbonyl, haloalkoxyalkylcarbonyl, haloalkylcarbonyl, haloalkylcarbonylcarbonyl, heterocyclyl, (heterocyclyl)alkylcarbonyl, heterocyclylcarbonyl, heterocyclylcarbonylalkylcarbonyl, heterocyclylcarbonylcarbonyl, hydroxyalkenylcarbonyl, hydroxyalkylcarbonyl, (NR$^c$R$^d$)alkylcarbonyl, (NR$^c$R$^d$)carbonyl, (NR$^c$R$^d$)carbonylalkylcarbonyl, (NR$^c$R$^d$)carbonylcarbonyl, and

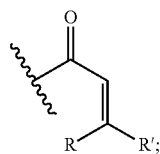

wherein R and R' are each alkyl, or, together with the carbon atom to which they are attached, form a five- or six-membered ring optionally containing one oxygen or nitrogen atom; or R$^2$ and R$^f$, together with the nitrogen atom to which they are attached, forms a five- or six-membered ring optionally substituted with one or two groups independently selected from alkoxycarbonylamino and oxo; or R$^2$ and R$^f$, together with the nitrogen atom to which they are attached, form

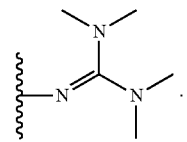

In a fourth embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound of formula (II)

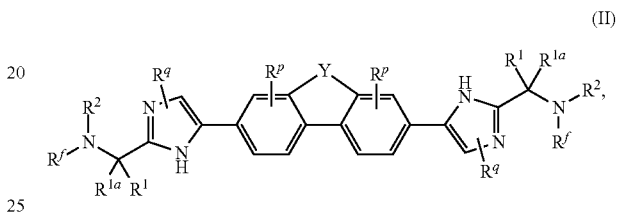

(II)

or a pharmaceutically acceptable salt thereof, wherein:

Y is selected from O, O(CR$^z$)$_2$, and (C(R$^z$)$_2$)$_n$, wherein n is 1 or 2, and each R$^z$ is independently selected from hydrogen, alkyl, and halo;

each R$^1$ is independently selected from alkoxyalkyl, alkyl, aryl, arylalkyl, cycloalkyl, haloalkyl, heterocyclyl, and hydroxyalkyl;

each R$^{1a}$ is independently selected from hydrogen and alkyl; or

R$^1$ and R$^{1a}$, together with the carbon atom to which they are attached, form a saturated or unsaturated 3- to 6-membered spirocyclic ring, wherein the spirocyclic ring, when between 4- and 6-members, can be optionally fused to a phenyl ring, and wherein each ring system is optionally substituted with one or two groups independently selected from alkyl and halo;

each R$^f$ is independently selected from hydrogen, methyl, hydroxy, and —NH$_2$(R$^z$), wherein R$^z$ is alkyl;

each R$^p$ is independently selected from hydrogen, alkyl, cyano, halo, haloalkoxy, and haloalkyl;

each R$^q$ is independently selected from hydrogen, alkyl, halo, and —P(O)—(OR)$_2$, wherein each R is the same or a different alkyl group; and each R$^2$ is independently selected from alkenylcarbonyl, alkoxyalkylcarbonyl, alkoxyalkylcarbonylcarbonyl, alkoxycarbonyl, alkoxycarbonylalkylcarbonyl, alkoxycarbonylcarbonyl, alkyl, alkylcarbonyl, alkylcarbonylalkylcarbonyl, alkylcarbonylcarbonyl, alkylsulfinyl, alkylsulfonyl, alkynyl, alkynyloxycarbonyl, alkynylcarbonyl, arylcarbonyl, arylcarbonylcarbonyl, arylalkenylcarbonyl, arylalkoxycarbonyl, arylalkylcarbonyl, aryloxyalkylcarbonyl, arylsulfanylalkylcarbonyl, arylsulfinyl, arylsulfonyl, bicycloalkylcarbonyl, carboxyalkylcarbonyl, carboxycarbonyl, cyanoalkylcarbonyl, (cycloalkenyl)alkylcarbonyl, (cycloalkyl)alkyl, (cycloalkyl)alkylcarbonyl, cycloalkylcarbonyl, cycloalkylcarbonylcarbonyl, cycloalkyloxycarbonyl, haloalkenylcarbonyl, haloalkoxyalkylcarbonyl, haloalkylcarbonyl, haloalkylcarbonylcarbonyl, heterocyclyl, (heterocyclyl)alkylcarbonyl, heterocyclylcarbonyl, heterocyclylcarbonylalkylcarbonyl, heterocyclylcarbonylcarbonyl, hydroxyalkenylcarbonyl, hydroxyalkylcarbonyl, (NR$^c$R$^d$)

alkylcarbonyl, (NR$^c$R$^d$)carbonyl, (NR$^c$R$^d$)carbonylalkylcarbonyl, (NR$^c$R$^d$)carbonylcarbonyl, and

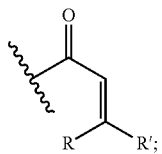

wherein R and R' are each alkyl, or, together with the carbon atom to which they are attached, form a five- or six-membered ring optionally containing one oxygen or nitrogen atom; or R$^2$ and R$^f$, together with the nitrogen atom to which they are attached, form

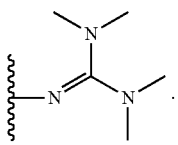

In a fifth embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound of formula (III)

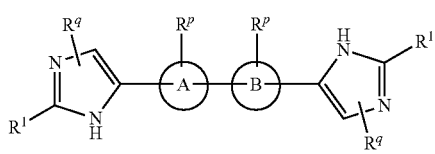

(III)

or a pharmaceutically acceptable salt thereof, wherein:

A and B are independently selected from isoquinolinyl, naphthyl, phenyl, pyrazinyl, pyridinyl, pyrimidinyl, and quinolinyl;

each R$^p$ is independently selected from hydrogen, alkyl, cyano, halo, haloalkoxy, and haloalkyl;

each R$^q$ is independently selected from hydrogen, alkyl, halo, and —P(O)—(OR)$_2$, wherein each R is the same or a different alkyl group;

each R$^1$ is independently selected from:

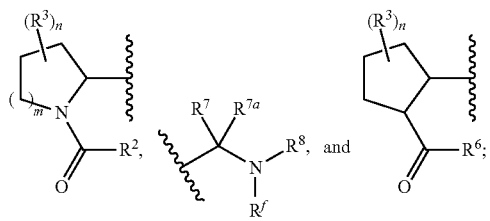

wherein m is 0, 1, 2, or 3; and
n is 0, 1, 2, or 3;

provided that at least one R$^1$ is other than

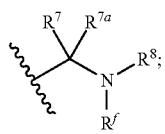

each R$^2$ is independently selected from alkenyl, alkoxy, alkoxyalkyl, alkoxyalkylcarbonyl, alkoxycarbonyl, alkoxycarbonylalkyl, alkyl, alkylcarbonyl, alkylcarbonylalkyl, alkynyl, alkynyloxy, aryl, arylalkenyl, arylalkoxy, arylalkyl, arylcarbonyl, aryloxy, aryloxyalkyl, arylsulfanylalkyl, carboxy, carboxyalkyl, cyanoalkyl, (cycloalkenyl)alkyl, cycloalkyl, (cycloalkyl)alkyl, cycloalkylcarbonyl, cycloalkyloxy, haloalkenyl, haloalkoxyalkyl, haloalkyl, heterocyclyl, (heterocyclyl)alkyl, heterocyclylcarbonylalkyl, heterocyclylcarbonyl, hydroxyalkenyl, hydroxyalkyl, —NR$^c$R$^d$, (NR$^c$R$^d$)alkyl, (NR$^c$R$^d$)carbonylalkyl; and

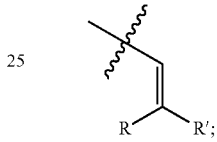

wherein R and R' are each alkyl, or, together with the carbon atom to which they are attached, form a five- or six-membered ring optionally containing one oxygen or nitrogen atom;

each R$^3$ is independently selected from alkyl, halo, and hydroxy; wherein the alkyl can optionally form a fused three- to six-membered ring with an adjacent carbon, a bridged four- or five-membered ring with another carbon atom on the ring, or a spirocyclic three- to six-membered ring with the carbon atom to which it is attached; wherein each ring is optionally substituted with one or two groups independently selected from alkoxy, alkyl, halo, and haloalkyl;

each R$^6$ is —N(R')—N(R'')(R'''); wherein each R' and R'' is independently selected from hydrogen, alkyl, cycloalkyl, and haloalkyl; each R''' is independently selected from alkoxycarbonyl, alkyl, and aryl; or, R'' and R''', together with the nitrogen atom to which they are attached, form a ring selected from carbazole, morpholine, N-methylpiperazine, piperidine, and pyrrolidine;

each R$^7$ is independently selected from alkoxyalkyl, alkyl, aryl, arylalkyl, cycloalkyl, haloalkyl, heterocyclyl, and hydroxyalkyl;

each R$^{7a}$ is independently selected from hydrogen and alkyl; or

R$^7$ and R$^{7a}$, together with the carbon atom to which they are attached, form a saturated or unsaturated 3- to 6-membered spirocyclic ring, wherein the spirocyclic ring, when between 4- and 6-members, can be optionally fused to a phenyl ring, and wherein each ring system is optionally substituted with one or two groups independently selected from alkyl and halo;

each R$^f$ is independently selected from hydrogen, methyl, hydroxy, and —NH$_2$(R$^z$), wherein R$^z$ is alkyl; and each R$^8$ is independently selected from alkenylcarbonyl, alkoxyalkylcarbonyl, alkoxyalkylcarbonylcarbonyl, alkoxycarbonyl, alkoxycarbonylalkylcarbonyl, alkoxycarbonylcarbonyl, alkyl, alkylcarbonyl, alkylcarbonylalkylcarbonyl, alkylcarbonylcarbonyl, alkylsulfinyl, alkylsulfonyl, alkynyl, alkynyloxycarbonyl, alkynylcarbonyl, arylcarbonyl, arylcarbonylcarbonyl, arylalkenylcarbonyl, arylalkoxycarbonyl, arylalkylcarbonyl, aryloxyalkylcarbonyl, arylsulfanylalkylcarbonyl, arylsulfinyl, arylsulfonyl, bicycloalkylcarbonyl, carboxyalkylcarbonyl, carboxycarbonyl, cyanoalkylcarbonyl, (cycloalkenyl)alkylcarbonyl, (cycloalkyl)alkyl, (cycloalkyl)alkylcarbonyl, cycloalkylcarbonyl, cycloalkylcarbonylcarbonyl, cycloalkyloxycarbonyl, haloalkenylcarbonyl, haloalkoxyalkylcarbonyl, haloalkylcarbonyl, haloalkylcarbonylcarbonyl, heterocyclyl, (heterocyclyl)alkylcarbonyl, heterocyclylcarbonyl, heterocyclylcarbonylalkylcarbonyl, heterocyclylcarbonylcarbonyl, hydroxyalkenylcarbonyl, hydroxyalkylcarbonyl, (NR$^c$R$^d$)alkylcarbonyl, (NR$^c$R$^d$)carbonyl, (NR$^c$R$^d$)carbonylalkylcarbonyl, (NR$^c$R$^d$)carbonylcarbonyl, and

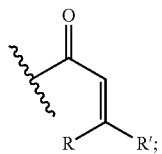

wherein R and R' are each alkyl, or, together with the carbon atom to which they are attached, form a five- or six-membered ring optionally containing one oxygen or nitrogen atom; or R$^8$ and R$^f$, together with the nitrogen atom to which they are attached, forms a five- or six-membered ring optionally substituted with one or two groups independently selected from alkoxycarbonylamino and oxo; or R$^2$ and R$^f$, together with the nitrogen atom to which they are attached, form

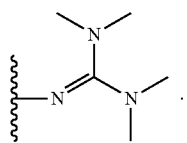

In a sixth embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound of formula (IV)

each R$^{1a}$ is independently selected from hydrogen and alkyl; or

R$^1$ and R$^{1a}$, together with the carbon atom to which they are attached, form a saturated or unsaturated 3- to 6-membered spirocyclic ring, wherein the spirocyclic ring, when between 4- and 6-members, can be optionally fused to a phenyl ring, and wherein each ring system is optionally substituted with one or two groups independently selected from alkyl and halo;

each R$^f$ is independently selected from hydrogen, methyl, hydroxy, and —NH$_2$(R$^z$), wherein R$^z$ is alkyl;

each R$^p$ is independently selected from hydrogen, alkyl, cyano, halo, haloalkoxy, and haloalkyl;

each R$^q$ is independently selected from hydrogen, alkyl, halo, and —P(O)—(OR)$_2$, wherein each R is the same or a different alkyl group;

each R$^2$ is independently selected from alkenylcarbonyl, alkoxyalkylcarbonyl, alkoxyalkylcarbonylcarbonyl, alkoxycarbonyl, alkoxycarbonylalkylcarbonyl, alkoxycarbonylcarbonyl, alkyl, alkylcarbonyl, alkylcarbonylalkylcarbonyl, alkylcarbonylcarbonyl, alkylsulfinyl, alkylsulfonyl, alkynyl, alkynyloxycarbonyl, alkynylcarbonyl, arylcarbonyl, arylcarbonylcarbonyl, arylalkenylcarbonyl, arylalkoxycarbonyl, arylalkylcarbonyl, aryloxyalkylcarbonyl, arylsulfanylalkylcarbonyl, arylsulfinyl, arylsulfonyl, bicycloalkylcarbonyl, carboxyalkylcarbonyl, carboxycarbonyl, cyanoalkylcarbonyl, (cycloalkenyl)alkylcarbonyl, (cycloalkyl)alkyl, (cycloalkyl)alkylcarbonyl, cycloalkylcarbonyl, cycloalkylcarbonylcarbonyl, cycloalkyloxycarbonyl, haloalkenylcarbonyl, haloalkoxyalkylcarbonyl, haloalkylcarbonyl, haloalkylcarbonylcarbonyl, heterocyclyl, (heterocyclyl)alkylcarbonyl, heterocyclylcarbonyl, heterocyclylcarbonylalkylcarbonyl, heterocyclylcarbonylcarbonyl, hydroxyalkenylcarbonyl, hydroxyalkylcarbonyl, (NR$^c$R$^d$)alkylcarbonyl, (NR$^c$R$^d$)carbonyl, (NR$^c$R$^d$)carbonylalkylcarbonyl, (NR$^c$R$^d$)carbonylcarbonyl, and

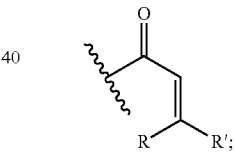

wherein R and R' are each alkyl, or, together with the carbon atom to which they are attached, form a five- or six-membered ring optionally containing one oxygen or nitrogen atom; or

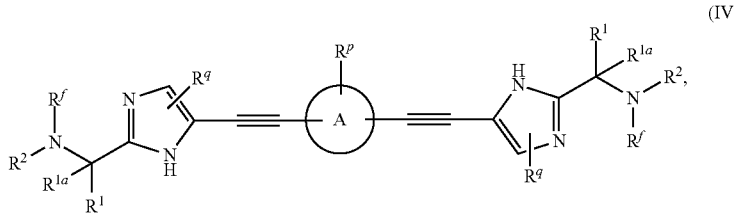

(IV)

or a pharmaceutically acceptable salt thereof, wherein:

A is absent or selected from isoquinolinyl, naphthyl, phenyl, pyrazinyl, pyridinyl, pyrimidinyl, and quinolinyl;

each R$^1$ is independently selected from alkoxyalkyl, alkyl, aryl, arylalkyl, cycloalkyl, haloalkyl, heterocyclyl, and hydroxyalkyl;

R$^2$ and R$^f$, together with the nitrogen atom to which they are attached, forms a five- or six-membered ring optionally substituted with one or two groups independently selected from alkoxycarbonylamino and oxo; or R$^2$ and R$^f$, together with the nitrogen atom to which they are attached, form

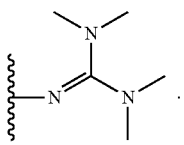 [SMILES: *N=C(N(C)C)N(C)C ; "."]

In a seventh embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound of formula (V)

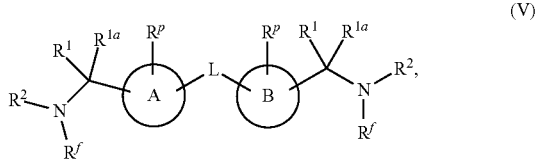

or a pharmaceutically acceptable salt thereof, wherein:

L is absent or selected from $C_2$alkenyl, $C_2$alkynyl, $C_4$alkynyl, and phenyl;

A and B are independently selected from azabenzimidazole; azamaphthoimidazole;

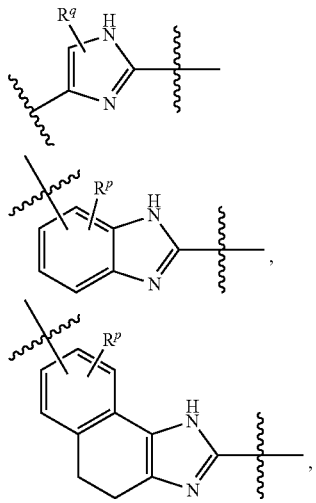

and;

each $R^1$ is independently selected from alkoxyalkyl, alkyl, aryl, arylalkyl, cycloalkyl, haloalkyl, heterocyclyl, and hydroxyalkyl;

each $R^{1a}$ is independently selected from hydrogen and alkyl; or $R^1$ and $R^{1a}$, together with the carbon atom to which they are attached, form a saturated or unsaturated 3- to 6-membered spirocyclic ring, wherein the spirocyclic ring, when between 4- and 6-members, can be optionally fused to a phenyl ring, and wherein each ring system is optionally substituted with one or two groups independently selected from alkyl and halo;

each $R^f$ is independently selected from hydrogen, methyl, hydroxy, and —$NH_2(R^z)$, wherein $R^z$ is alkyl;

each $R^p$ is independently selected from hydrogen, alkyl, cyano, halo, haloalkoxy, and haloalkyl;

each $R^q$ is independently selected from hydrogen, alkyl, halo, and —P(O)—$(OR)_2$, wherein each R is the same or a different alkyl group; and each $R^2$ is independently selected from alkenylcarbonyl, alkoxyalkylcarbonyl, alkoxyalkylcarbonylcarbonyl, alkoxycarbonyl, alkoxycarbonylalkylcarbonyl, alkoxycarbonylcarbonyl, alkyl, alkylcarbonyl, alkylcarbonylalkylcarbonyl, alkylcarbonylcarbonyl, alkylsulfinyl, alkylsulfonyl, alkynyl, alkynyloxycarbonyl, alkynylcarbonyl, arylcarbonyl, arylcarbonylcarbonyl, arylalkenylcarbonyl, arylalkoxycarbonyl, arylalkylcarbonyl, aryloxyalkylcarbonyl, arylsulfanylalkylcarbonyl, arylsulfinyl, arylsulfonyl, bicycloalkylcarbonyl, carboxyalkylcarbonyl, carboxycarbonyl, cyanoalkylcarbonyl, (cycloalkenyl)alkylcarbonyl, (cycloalkyl)alkyl, (cycloalkyl)alkylcarbonyl, cycloalkylcarbonyl, cycloalkylcarbonylcarbonyl, cycloalkyloxycarbonyl, haloalkenylcarbonyl, haloalkoxyalkylcarbonyl, haloalkylcarbonyl, haloalkylcarbonylcarbonyl, heterocyclyl, (heterocyclyl)alkylcarbonyl, heterocyclylcarbonyl, heterocyclylcarbonylalkylcarbonyl, heterocyclylcarbonylcarbonyl, hydroxyalkenylcarbonyl, hydroxyalkylcarbonyl, $(NR^cR^d)$alkylcarbonyl, $(NR^cR^d)$carbonyl, $(NR^cR^d)$carbonylalkylcarbonyl, $(NR^cR^d)$carbonylcarbonyl, and

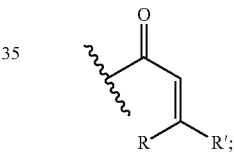

wherein R and R' are each alkyl, or, together with the carbon atom to which they are attached, form a five- or six-membered ring optionally containing one oxygen or nitrogen atom; or $R^2$ and $R^f$, together with the nitrogen atom to which they are attached, forms a five- or six-membered ring optionally substituted with one or two groups independently selected from alkoxycarbonylamino and oxo; or $R^2$ and $R^f$, together with the nitrogen atom to which they are attached, form

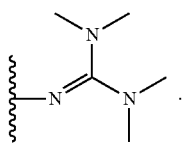 [SMILES: *N=C(N(C)C)N(C)C ; "."]

In an eighth embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound of formula (VI)

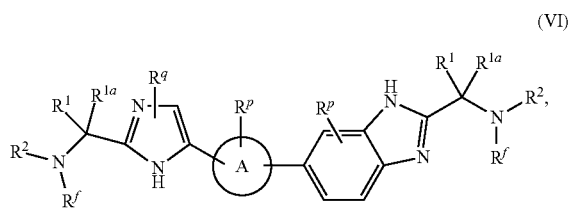

or a pharmaceutically acceptable salt thereof, wherein:

A is selected from isoquinolinyl, naphthyl, phenyl, pyrazinyl, pyridinyl, pyrimidinyl, quinolinyl,

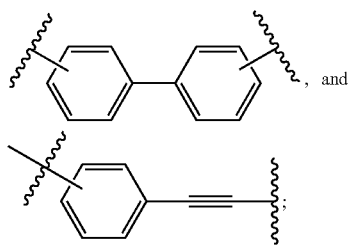

each $R^1$ is independently selected from alkoxyalkyl, alkyl, aryl, arylalkyl, cycloalkyl, haloalkyl, heterocyclyl, and hydroxyalkyl;

each $R^{1a}$ is independently selected from hydrogen and alkyl; or $R^1$ and $R^{1a}$, together with the carbon atom to which they are attached, form a saturated or unsaturated 3- to 6-membered spirocyclic ring, wherein the spirocyclic ring, when between 4- and 6-members, can be optionally fused to a phenyl ring, and wherein each ring system is optionally substituted with one or two groups independently selected from alkyl and halo;

each $R^f$ is independently selected from hydrogen, methyl, hydroxy, and $-NH_2(R^z)$, wherein $R^z$ is alkyl;

each $R^q$ is independently selected from hydrogen, alkyl, halo, and $-P(O)-(OR)_2$, wherein each R is the same or a different alkyl group;

each $R^p$ is independently selected from hydrogen, alkyl, cyano, halo, haloalkoxy, and haloalkyl; and each $R^2$ is independently selected from alkenylcarbonyl, alkoxyalkylcarbonyl, alkoxyalkylcarbonylcarbonyl, alkoxycarbonyl, alkoxycarbonylalkylcarbonyl, alkoxycarbonylcarbonyl, alkyl, alkylcarbonyl, alkylcarbonylalkylcarbonyl, alkylcarbonylcarbonyl, alkylsulfinyl, alkylsulfonyl, alkynyl, alkynyloxycarbonyl, alkynylcarbonyl, arylcarbonyl, arylcarbonylcarbonyl, arylalkenylcarbonyl, arylalkoxycarbonyl, arylalkylcarbonyl, aryloxyalkylcarbonyl, arylsulfanylalkylcarbonyl, arylsulfinyl, arylsulfonyl, bicycloalkylcarbonyl, carboxyalkylcarbonyl, carboxycarbonyl, cyanoalkylcarbonyl, (cycloalkenyl)alkylcarbonyl, (cycloalkyl)alkyl, (cycloalkyl)alkylcarbonyl, cycloalkylcarbonyl, cycloalkylcarbonylcarbonyl, cycloalkyloxycarbonyl, haloalkenylcarbonyl, haloalkoxyalkylcarbonyl, haloalkylcarbonyl, haloalkylcarbonylcarbonyl, heterocyclyl, (heterocyclyl)alkylcarbonyl, heterocyclylcarbonyl, heterocyclylcarbonylalkylcarbonyl, heterocyclylcarbonylcarbonyl, hydroxyalkenylcarbonyl, hydroxyalkylcarbonyl, $(NR^cR^d)$alkylcarbonyl, $(NR^cR^d)$carbonyl, $(NR^cR^d)$carbonylalkylcarbonyl, $(NR^cR^d)$carbonylcarbonyl, and

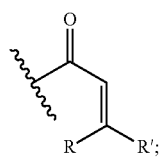

wherein R and R' are each alkyl, or, together with the carbon atom to which they are attached, form a five- or six-membered ring optionally containing one oxygen or nitrogen atom; or $R^2$ and $R^f$, together with the nitrogen atom to which they are attached, forms a five- or six-membered ring optionally substituted with one or two groups independently selected from alkoxycarbonylamino and oxo; or $R^2$ and $R^f$, together with the nitrogen atom to which they are attached, form

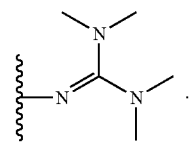 [SMILES: *N=C(N(C)C)N(C)C ; "."]

In a ninth embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A-targeting compound is a compound of formula (VII):

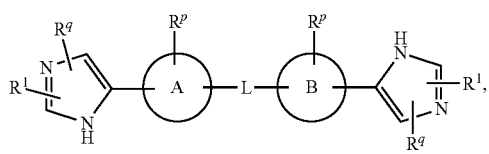

or a pharmaceutically acceptable salt thereof, wherein:

L is absent or selected from $-O-$, $-CH_2-O-CH_2-$, $-OCH_2-$, $C_2$alkyl, $C_2$alkynyl, cyclopropyl, ethynylbenzyl, phenyl, pyrazinyl, and pyridinyl;

A is selected from aryl, cycloalkenyl, and heteroaryl;

B is selected from aryl, bicycloalkyl, cycloalkenyl, and heteroaryl;

each $R^1$ is independently selected from

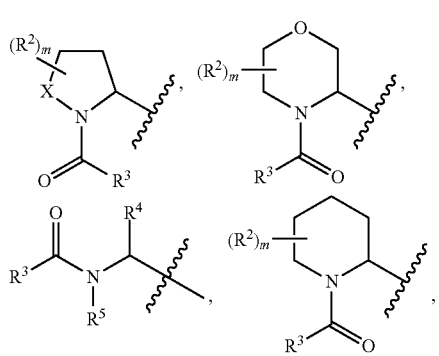

-continued

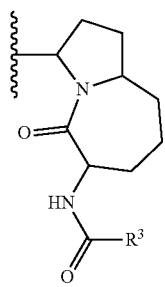

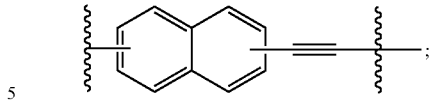

X and Y are each independently selected from

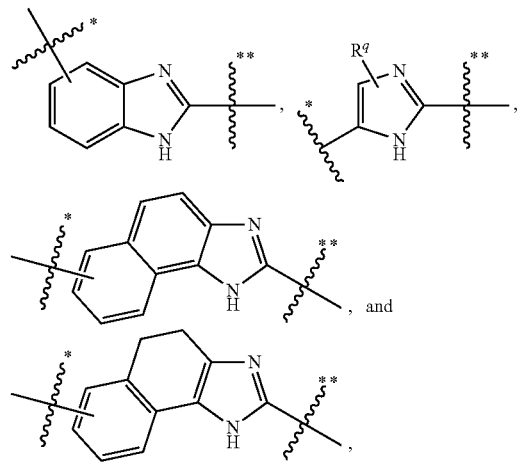

wherein

denotes the point of attachment to L and

denotes the point of attachment to the pyrrolidine ring;

each $R^q$ is independently selected from hydrogen, alkyl, halo, and —P(O)—(OR)$_2$, wherein each R is the same or a different alkyl group;

$R^1$ and $R^2$ are each independently selected from alkoxy, alkyl, halo, haloalkyl, and hydroxy; wherein the alkyl can optionally form a fused three- to six-membered ring with an adjacent carbon, a bridged four- or five-membered ring with another carbon atom on the ring, or a spirocyclic three- to six-membered ring with the carbon atom to which it is attached; wherein each ring is optionally substituted with one or two groups independently selected from alkyl, halo, and haloalkyl; or $R^2$, together with the carbon atom to which it is attached, forms a C$_2$ olefin; and $R^3$ and $R^4$ are each independently selected from alkoxy, alkyl, arylalkoxy, arylalkyl, cycloalkyl, (cycloalkyl)alkyl, cycloalkyloxy, heterocyclyl, heterocyclylalkyl, (NR$^c$R$^d$)alkenyl, and (NR$^c$R$^d$)alkyl.

each m is independently 0, 1, or 2;

each X is independently selected from CH$_2$, NH, and NR$^a$; wherein R$^a$ is alkyl;

each R$^2$ is independently selected from alkyl, halo, and hydroxy; wherein the alkyl can optionally form a fused three- to six-membered ring with an adjacent carbon, a bridged four- or five-membered ring with another carbon atom on the ring, or a spirocyclic three- to six-membered ring with the carbon atom to which it is attached; wherein each ring is optionally substituted with one or two groups independently selected from alkyl, halo, and haloalkyl; or R$^2$, together with the carbon atom to which it is attached, forms a C$_2$ olefin each R$^3$ is independently selected from alkoxy, alkyl, arylalkoxy, arylalkyl, cycloalkyl, (cycloalkyl)alkyl, cycloalkyloxy, heterocyclyl, heterocyclylalkyl, (NR$^c$R$^d$)alkenyl, and (NR$^c$R$^d$)alkyl;

each R$^4$ is independently selected from hydrogen, alkyl, cycloalkyl, and haloalkyl;

each R$^5$ is independently selected from hydrogen and alkyl;

each R$^p$ is independently selected from hydrogen, alkyl, cyano, halo, haloalkoxy, and haloalkyl; and each R$^q$ is independently selected from hydrogen, alkyl, halo, and —P(O)—(OR)$_2$, wherein each R is the same or a different alkyl group.

In a tenth embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A-targeting compound is a compound of formula (VIII):

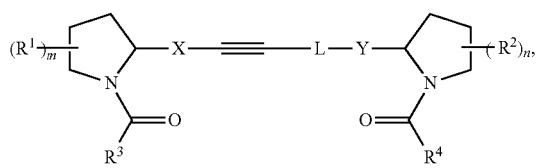

(VIII)

or a pharmaceutically acceptable salt thereof, wherein:

m and n are independently 0, 1, or 2;

L is absent or selected from C$_2$ alkynyl, naphthyl, phenyl, pyridinyl, pyrazinyl, pyrimidinyl, and In an eleventh embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A-targeting compound is a compound of formula (IX):

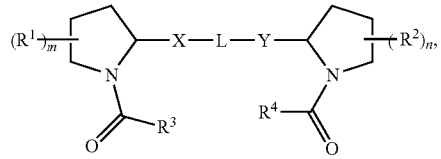

or a pharmaceutically acceptable salt thereof, wherein:
L is absent or selected from $C_2$alkyl, —C(O)—, isoquinolinyl, naphthyl, phenyl, pyrimidinyl, pyrazinyl, pyridinyl, quinolinyl,

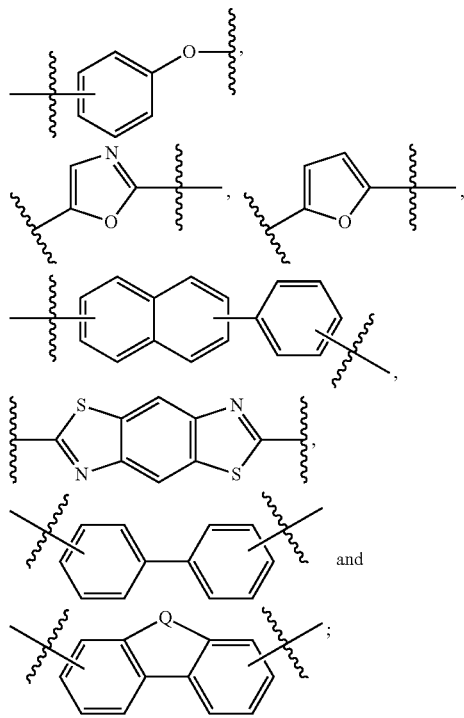

wherein Q is selected from O, $O(CR^z)_2$, and $(C(R^z)_2)_n$, wherein n is 1 or 2, and each $R^z$ is independently selected from hydrogen, alkyl, and halo;
X and Y are each independently selected from

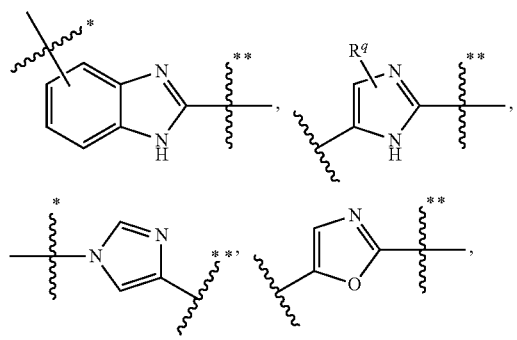

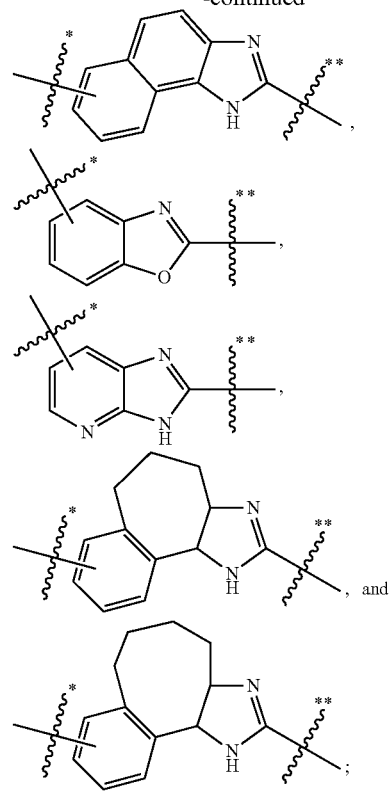

wherein

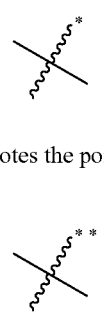

denotes the point of attachment to L and

denotes the point of attachment to the pyrrolidine ring;
each $R^q$ is independently selected from hydrogen, alkyl, halo, and —P(O)—$(OR)_2$, wherein each R is the same or a different alkyl group;
provided that when L is

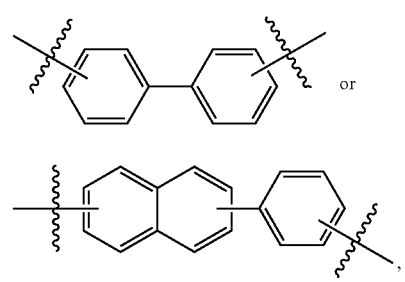

one of X and Y is other than

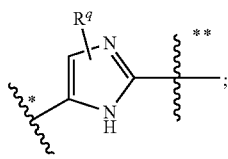

m and n are each 0, 1, or 2;

$R^1$ and $R^2$ are each independently selected from alkyl, halo, and hydroxy; wherein the alkyl can optionally form a fused three- to six-membered ring with an adjacent carbon, a bridged four- or five-membered ring with another carbon atom on the ring, or a spirocyclic three- to six-membered ring with the carbon atom to which it is attached; wherein each ring is optionally substituted with one or two groups independently selected from alkyl, halo, and haloalkyl; or $R^2$, together with the carbon atom to which it is attached, forms a $C_2$ olefin; and $R^3$ and $R^4$ are each independently selected from alkoxy, alkyl, arylalkoxy, arylalkyl, cycloalkyl, (cycloalkyl)alkyl, cycloalkyloxy, heterocyclyl, heterocyclylalkyl, $(NR^cR^d)$alkenyl, and $(NR^cR^d)$alkyl.

In a twelfth embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A-targeting compound is a compound of formula (X):

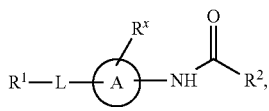 (X)

or a pharmaceutically acceptable salt thereof, wherein:
A is selected from indanyl, phenyl and pyridinyl;
L is absent or selected from $C_2$alkenyl, $C_2$alkynyl,

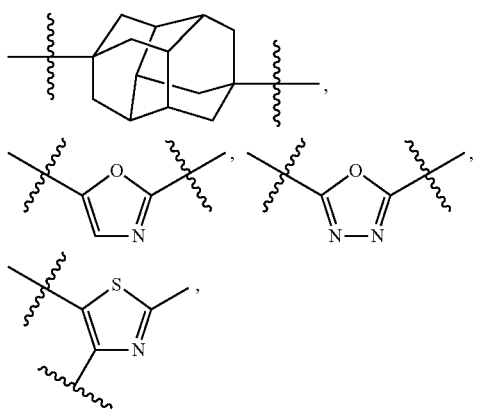

$R^1$ is selected from

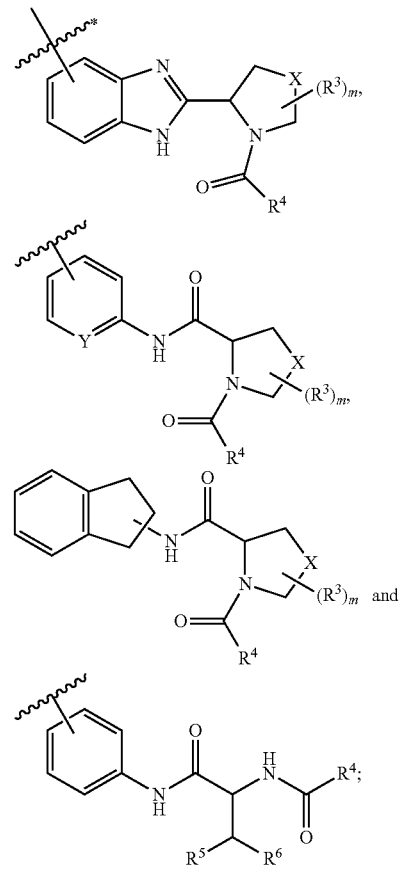

wherein

denotes the point of attachment to L;
$R^2$ is selected from

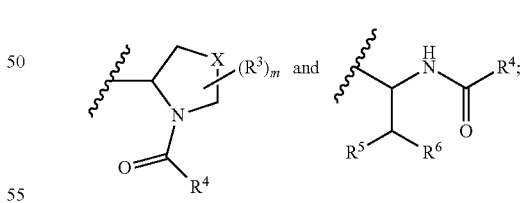

each m is independently 0, 1, or 2;
each $R^3$ is independently selected from alkyl, halo, and hydroxy; or
$R^3$, together with the carbon atom to which it is attached, forms a $C_2$ olefin; and
each $R^4$ is independently selected from alkoxy, alkyl, arylalkoxy, arylalkyl, cycloalkyl, (cycloalkyl)alkyl, cycloalkyloxy, heterocyclyl, heterocyclylalkyl, $(NR^cR^d)$alkenyl, and $(NR^cR^d)$alkyl;
each $R^5$ and $R^6$ are independently selected from hydrogen and methyl;

R$^x$ is selected from hydrogen and alkyl; and

X is selected from CH$_2$, CH$_2$CH$_2$, CHR$^3$, C(R$^3$)$_2$, and O.

In a thirteenth embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A-targeting compound is a compound of formula (XI):

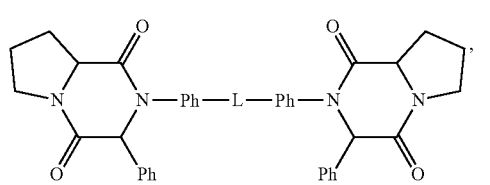

(XI)

or a pharmaceutically acceptable salt thereof, wherein:

L is selected from C$_2$alkenyl and

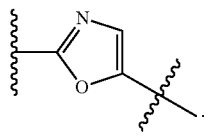 [SMILES: *c1cnc(*)o1]

In a fourteenth embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A-targeting compound is a compound of formula (XII):

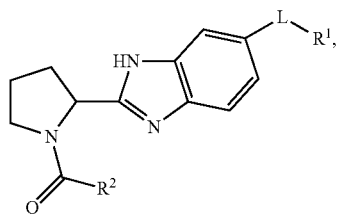

(XII)

or a pharmaceutically acceptable salt thereof, wherein:

L is

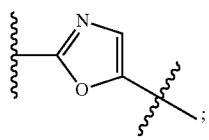 [SMILES: *c1cnc(*)o1]

R$^1$ is selected from

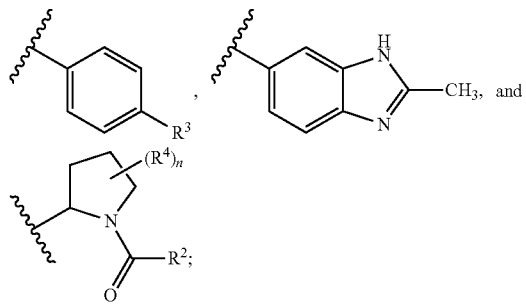

each R$^2$ is independently selected from alkoxy, alkyl, arylalkoxy, arylalkyl, cycloalkyl, (cycloalkyl)alkyl, cycloalkyloxy, heterocyclyl, heterocyclylalkyl, (NR$^c$R$^d$)alkenyl, and (NR$^c$R$^d$)alkyl;

n is 0, 1, or 2;

each R$^3$ is selected from hydrogen, hydroxy, —NR$^a$R$^b$, and

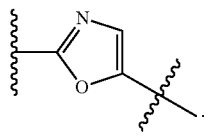 [SMILES: *c1cnc(*)o1]

and each R$^4$ is independently selected from alkyl, halo, and hydroxy; wherein the alkyl can optionally form a fused three- to six-membered ring with an adjacent carbon, a bridged four- or five-membered ring with another carbon atom on the ring, or a spirocyclic three- to six-membered ring with the carbon atom to which it is attached; wherein each ring is optionally substituted with one or two groups independently selected from alkyl, halo, and haloalkyl; or two R$^4$ groups together, form an ethylene group.

In a fifteenth embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A-targeting compound is a compound of formula (XIII):

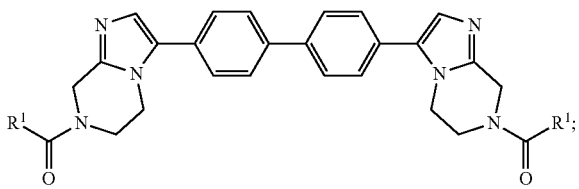

XIII or a pharmaceutically acceptable salt thereof, wherein:

each R$^1$ is independently selected from alkoxy, alkyl, arylalkoxy, arylalkyl, cycloalkyl, (cycloalkyl)alkyl, cycloalkyloxy, heterocyclyl, heterocyclylalkyl, (NR$^c$R$^d$)alkenyl, and (NR$^c$R$^d$)alkyl.

In a sixteenth embodiment the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A-targeting compound is a compound of formula (XIV):

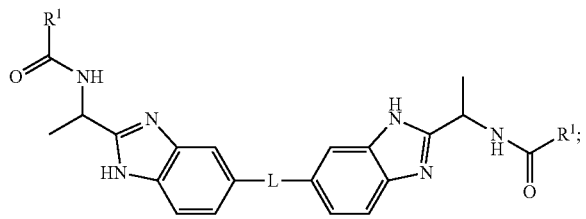

or a pharmaceutically acceptable salt thereof, wherein:
L is $C_2$alkyl; and
each $R^1$ is independently selected from alkoxy, alkyl, arylalkoxy, arylalkyl, cycloalkyl, (cycloalkyl)alkyl, cycloalkyloxy, heterocyclyl, heterocyclylalkyl, $(NR^cR^d)$alkenyl, and $(NR^cR^d)$alkyl.

In a sixteenth embodiment the NS5A-targeting compound is selected from

In a second aspect the present disclosure provides a combination comprising an NS5A-targeting compound and an NS5A synergist, or pharmaceutically acceptable salts thereof, and a pharmaceutically acceptable carrier. In a first embodiment of the second aspect, the composition further comprises one or two additional compounds having anti-HCV activity. In a second embodiment of the second aspect, at least one of the additional compounds is an interferon or a ribavirin. In a third embodiment of the second aspect, the interferon is selected from interferon alpha 2B, pegylated interferon alpha, consensus interferon, interferon alpha 2A, pegylated interferon lambda, and lymphoblastoid interferon tau.

In a fourth embodiment of the second aspect, the present disclosure provides a combination comprising an NS5A-targeting compound and an NS5A synergist, or pharmaceutically acceptable salts thereof, a pharmaceutically acceptable carrier, and at least one additional compound having anti-HCV activity, wherein at least one of the additional compounds is selected from interleukin 2, interleukin 6, interleu-

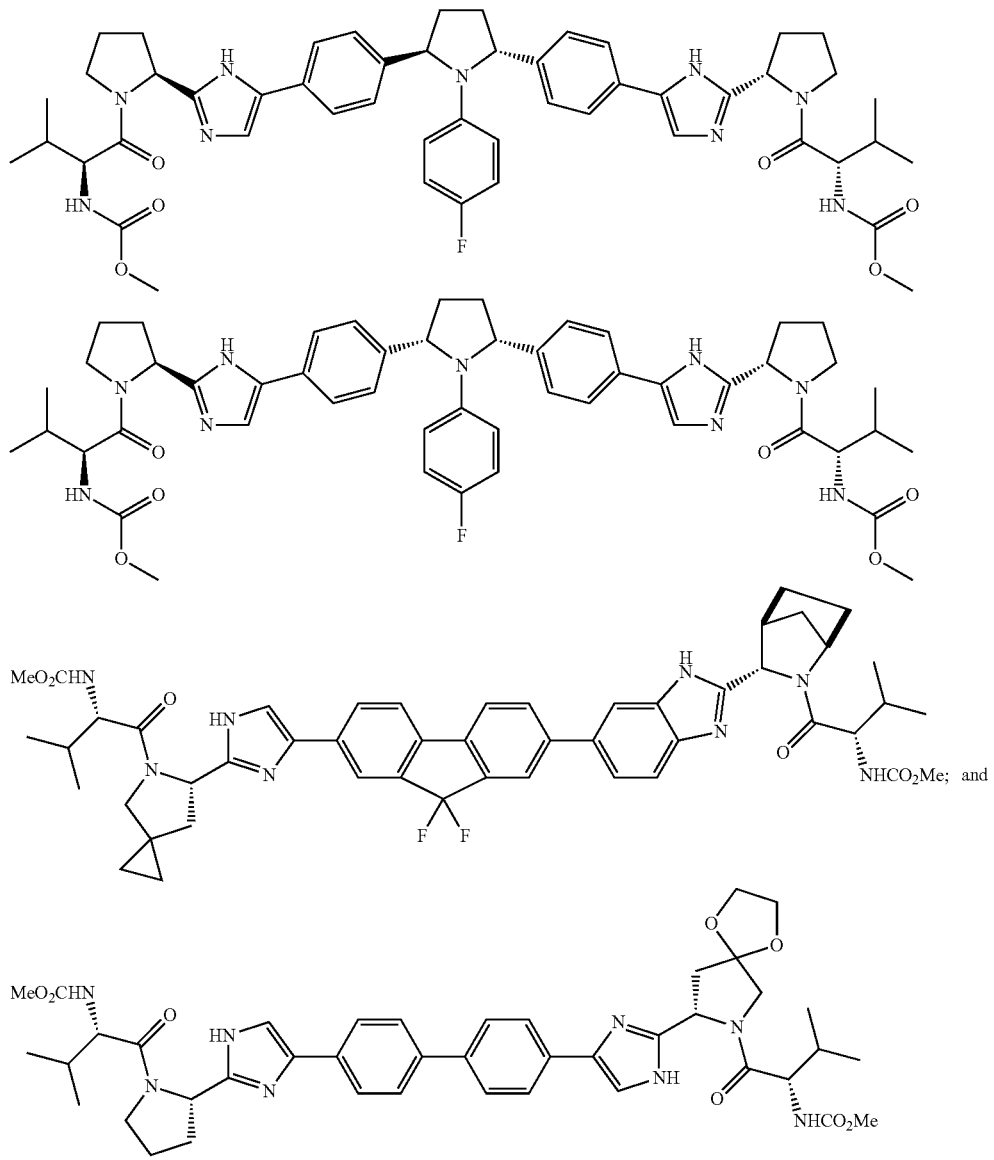

kin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a fifth embodiment the present disclosure provides a combination comprising an NS5A-targeting compound and an NS5A synergist, or pharmaceutically acceptable salts thereof, a pharmaceutically acceptable carrier, and at least one additional compound having anti-HCV activity, wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a combination comprising an NS5A-targeting compound and an NS5A synergist, or pharmaceutically acceptable salts thereof. In a first embodiment of the third aspect the method further comprises administering one or two additional compounds having anti-HCV activity prior to, after or simultaneously with the combination. In a second embodiment of the third aspect, at least one of the additional compounds is an interferon or a ribavirin. In a third embodiment of the third aspect, the interferon is selected from interferon alpha 2B, pegylated interferon alpha, consensus interferon, interferon alpha 2A, pegylated interferon lambda, and lymphoblastoid interferon tau.

In a fourth embodiment of the third aspect the present disclosure provides a method of treating an HCV infection in a patient, comprising administering to the patient a therapeutically effective amount of a combination comprising an NS5A-targeting compound and an NS5A synergist, which, when administered, provides synergistic anti-HCV activity against variants that contain mutation(s) conferring resistance to the NS5A-targeting compound alone or pharmaceutically acceptable salts thereof and administering at least one additional compound having anti-HCV activity prior to, after or simultaneously with the combination, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a fifth embodiment of the third aspect the present disclosure provides a method of treating an HCV infection in a patient, comprising administering to the patient a therapeutically effective amount of a combination comprising an NS5A-targeting compound and an NS5A synergist, which, when administered, provides synergistic anti-HCV activity against variants that contain mutation(s) conferring resistance to the NS5A-targeting compound alone or pharmaceutically acceptable salts thereof and administering one or two additional compounds having anti-HCV activity prior to, after or simultaneously with the combination, or pharmaceutically acceptable salts thereof, wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

In some instances, the number of carbon atoms in any particular group is denoted before the recitation of the group. For example, the term "$C_{2-6}$ alkenyl" denotes an alkenyl group containing two to six carbon atoms. Where these designations exist they supercede all other definitions contained herein.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, the two $R^2$ groups may be the same or different.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term "aryl".

As used herein, the term "NS5A synergist" refers to a molecule that alone shows a weaker activity against HCV wild type than the NS5A-targeting compound, but when combined with an NS5A-targeting compound shows a greater than three-fold increase in $EC_{50}$ potency than the potency of the NS5A-targeting compound alone.

As used herein, the term "synergistic anti-HCV activity" refers to a greater than three-fold increase in $EC_{50}$ potency than the potency of the NS5A-targeting compound alone.

As used herein, the term "NS5A-targeting compound", refers to a molecule that inhibits HCV replication for which at least one resistance substitution maps to the NS5A protein and most commonly within, but not limited to, the first 100 residues of NS5A.

The term "alkenyl," as used herein, refers to a straight or branched chain group of two to six carbon atoms containing at least one carbon-carbon double bond.

The term "alkenylcarbonyl," as used herein, refers to an alkenyl group attached to the parent molecular moiety through a carbonyl group.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkoxy," as used herein, refers to an alkoxyalkyl group attached to the parent molecular moiety through an oxygen atom.

The term "alkoxyalkoxycarbonyl," as used herein, refers to an alkoxyalkoxy group attached to the parent molecular moiety through a carbonyl group.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkoxycarbonylalkyl," as used herein, refers to an alkyl group substituted with one or two alkoxycarbonyl groups.

The term "alkoxycarbonylalkylcarbonyl," as used herein, refers to an alkoxycarbonylalkyl group attached to the parent molecular moiety through a carbonyl group.

The term "alkoxycarbonylcarbonyl," as used herein, refers to an alkoxycarbonyl group attached to the parent molecular moiety through a second carbonyl group.

The term "alkoxycarbonylamino," as used herein, refers to R"O—C(O)—N(H)—, wherein R" is an alkyl group.

The term "alkyl," as used herein, refers to a group derived from a straight or branched chain saturated hydrocarbon containing from one to seven carbon atoms.

The term "alkylcarbonyl," as used herein, refers to an alkyl group attached to the parent molecular moiety through a carbonyl group.

The term "alkylcarbonylalkyl," as used herein, refers to an alkyl group substituted with one, two, or three alkylcarbonyl groups.

The term "alkylcarbonylalkylcarbonyl," as used herein, refers to an alkylcarbonylalkyl group attached to the parent molecular moiety through a carbonyl group.

The term "alkylcarbonylcarbonyl," as used herein, refers to an alkylcarbonyl group attached to the parent molecular moiety through a second carbonyl group.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfinyl," as used herein, refers to an alkyl group attached to the parent molecular moiety through a sulfinyl group.

The term "alkylsulfonyl," as used herein, refers to an alkyl group attached to the parent molecular moiety through a sulfonyl group.

The term "alkynyl," as used herein, refers to a straight or branched chain hydrocarbon of two to six carbon atoms containing at least one carbon-carbon triple bond.

The term "alkynyloxy," as used herein, refers to an alkynyl group attached to the parent molecular moiety through an oxygen atom.

The term "alkynyloxycarbonyl," as used herein, refers to an alkynyloxy group attached to the parent molecular moiety through a carbonyl group.

The term "aryl," as used herein, refers to a phenyl group, or a bicyclic or tricyclic fused ring system wherein at least one ring is a phenyl group. Bicyclic fused ring systems consist of a phenyl group fused to a four- to six-membered aromatic or non-aromatic carbocyclic ring. Tricyclic fused ring systems consist of a bicyclic fused ring system fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkenyl, alkoxy, alkoxyalkyl, alkoxycarbonyl, alkyl, alkylcarbonyl, a second aryl group, aryloxy, alkoxy, arylalkyl, arylcarbonyl, aryloxy, cyano, cycloalkyl, halo, haloalkoxy, haloalkyl, heterocyclyl, heterocyclylalkyl, heterocyclylcarbonyl, hydroxy, hydroxyalkyl, nitro, —NR$^x$R$^y$, (NR$^x$R$^y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the aryl part of the aryloxy, the cycloalkyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkenyl," as used herein, refers to an alkenyl group substituted with one, two, or three aryl groups.

The term "arylalkenylcarbonyl," as used herein, refers to an arylalkenyl group attached to the parent molecular moiety through a carbonyl group.

The term "arylalkoxy," as used herein, refers to an aryl group attached to the parent molecular moiety through an alkoxy group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one, two, or three additional groups independently selected from alkoxy, alkylcarbonyloxy, halo, haloalkoxy, haloalkyl, heterocyclyl, hydroxy, and —NR$^c$R$^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, —NR$^x$R$^y$, and oxo.

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "arylcarbonylcarbonyl," as used herein, refers to an arylcarbonyl group attached to the parent molecular moiety through a carbonyl group.

The term "aryloxy," as used herein, refers to an aryl group attached to the parent molecular moiety through an oxygen atom.

The term "aryloxyalkyl," as used herein, refers to an alkyl group substituted with one, two, or three aryloxy groups.

The term "aryloxyalkylcarbonyl," as used herein, refers to an aryloxyalkyl group attached to the parental molecular moiety through a carbonyl group.

The term "aryloxycarbonyl," as used herein, refers to an aryloxy group attached to the parent molecular moiety through a carbonyl group.

The term "arylsulfanyl," as used herein, refers to an aryl group attached to the parent molecular moiety through a sulfur atom.

The term "arylsulfanylalkyl," as used herein, refers to an alkyl group substituted with one, two, or three arylsulfanyl groups. The alkyl part of the arylsulfanylalkyl group can be further optionally substituted with one or two halo groups.

The term "arylsulfanylalkylcarbonyl," as used herein, refers to an arylsulfanylalkyl group attached to the parent molecular moiety through a carbonyl group.

The term "arylsulfonyl," as used herein, refers to an aryl group attached to the parent molecular moiety through a sulfonyl group.

The term "bicycloalkyl," as used herein, refers to a saturated, fused, bridged, or spirocyclic bicyclic hydrocarbon ring system having six to twelve carbon atoms and zero heteroatoms. The bicycloalkyl groups of the present disclosure are optionally substituted with one, two, or three groups independently selected from alkyl, halo, and haloalkyl.

The term "bicycloalkylcarbonyl," as used herein, refers to a bicycloalkyl group attached to the parent molecular moiety through a carbonyl group.

The term "carbonyl," as used herein, refers to —C(O)—.

The term "carboxy," as used herein, refers to —CO$_2$H.

The term "carboxyalkyl," as used herein, refers to an alkyl group substituted with one, two, or three carboxy groups.

The term "carboxyalkylcarbonyl," as used herein, refers to a carboxyalkyl group attached to the parent molecular moiety through a carbonyl group.

The term "carboxycarbonyl," as used herein, refers to a carboxy group attached to the parent molecular moiety through a carbonyl group.

The term "cyano," as used herein, refers to —CN.

The term "cyanoalkyl," as used herein, refers to an alkyl group substituted with one, two, or three cyano groups.

The term "cyanoalkylcarbonyl," as used herein, refers to a cyanoalkyl group attached to the parent molecular moiety through a carbonyl group.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl. The cycloalkenyl groups of the present disclosure are optionally substituted with one, two, or three alkyl groups.

The term "(cycloalkenyl)alkyl," as used herein, refers to an alkyl group substituted with one, two, or three cycloalkenyl groups. The alkyl part of the (cycloalkenyl)alkyl may be further optionally substituted with an alkoxycarbonyl group.

The term "cycloalkyl," as used herein, refers to a saturated monocyclic, bicyclic, or tricyclic hydrocarbon ring system having three to fourteen carbon atoms and zero heteroatoms. The bicyclic and tricyclic systems can be fused, bridged, or spirocyclic, or any combination thereof. Representative examples of cycloalkyl groups include, but are not limited to, cyclopropyl, cyclopentyl, bicyclo[3.1.1]heptyl, and adamantyl. The cycloalkyl groups of the present disclosure are optionally substituted with one, two, three, four, or five substituents independently selected from alkenyl, alkoxy, alkoxyalkyl, alkoxycarbonyl, alkyl, alkylcarbonyl, alkylcarbonyloxy, aryl, arylalkyl, cyano, cycloalkenyl, a second cycloalkyl group, an exocyclic double bond optionally substituted with one or two halo groups, halo, haloalkoxy, haloalkyl, heterocyclyl, heterocyclylcarbonyl, heterocyclylcarbonyloxy, hydroxy, hydroxyalkyl, nitro, —NR$^x$R$^y$, (NR$^x$R$^y$)alkyl, (NR$^x$R$^y$)carbonyloxy, and oxo; wherein the aryl, the aryl part of the arylalkyl, the cycloalkenyl, the second cycloalkyl group, and the heterocyclyl are further optionally substituted with one, two, or three substituents independently selected from alkoxy, alkyl, cyano, halo, haloalkoxy, haloalkyl, and hydroxy.

The term "(cycloalkyl)alkyl," as used herein, refers to an alkyl group substituted with one, two, or three cycloalkyl groups. The alkyl part of the (cycloalkyl)alkyl may be further optionally substituted with one or two groups independently selected from alkoxy, alkoxycarbonyl, halo, and hydroxy.

The term "(cycloalkyl)alkylcarbonyl," as used herein, refers to a (cycloalkyl)alkyl group attached to the parent molecular moiety through a carbonyl group.

The term "cycloalkylcarbonyl," as used herein, refers to a cycloalkyl group attached to the parent molecular moiety through a carbonyl group.

The term "cycloalkylcarbonylcarbonyl," as used herein, refers to a cycloalkylcarbonyl group attached to the parent molecular moiety through a carbonyl group.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "cycloalkylsulfonyl," as used herein, refers to a cycloalkyl group attached to the parent molecular moiety through a sulfonyl group.

The term "formyl," as used herein, refers to —CHO.

The term "halo," as used herein, refers to Cl, Br, F, or I.

The term "haloalkenyl," as used herein, refers to an alkenyl group substituted with one, two, three, or four halogen atoms.

The term "haloalkoxy," as used herein, refers to a haloalkyl group attached to the parent molecular moiety through an oxygen atom.

The term "haloalkoxyalkyl," as used herein, refers to an alkyl group substituted with one, two, or three haloalkoxy groups.

The term "haloalkoxyalkylcarbonyl," as used herein, refers to a haloalkoxyalkyl group attached to the parent molecular moiety through a carbonyl group.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "haloalkylcarbonyl," as used herein, refers to a haloalkyl group attached to the parent molecular moiety through a carbonyl group.

The term "haloalkylcarbonylcarbonyl," as used herein, refers to a haloalkylcarbonyl group attached to the parent molecular moiety through a carbonyl group.

The term "heteroaryl," as used herein, refers to an aromatic five- or six-membered ring where at least one atom is selected from N, O, and S, and the remaining atoms are carbon. The term "heteroaryl" also includes bicyclic systems where a heteroaryl ring is fused to a four- to six-membered aromatic or non-aromatic ring containing zero, one, or two additional heteroatoms selected from N, O, and S. The heteroaryl groups are attached to the parent molecular moiety through any substitutable carbon or nitrogen atom in the group. Representative examples of heteroaryl groups include, but are not limited to, benzoxadiazolyl, benzoxazolyl, benzofuranyl, benzothienyl, furanyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, and triazinyl.

The term "heterocyclyl," as used herein, refers to a monocyclic four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic and tricyclic systems wherein at least one of the rings is a heterocycle. The bicyclic and tricyclic systems may be fused, spirocyclic, bridged, or a combination thereof. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isoquinolinyl, isothiazolyl, isoxazolyl, morpholinyl, oxazolyl, oxetanyl, piperazinyl, piperidinyl, pyrazolyl, pyridinyl, pyrrolidinyl, pyrrolopyridinyl, pyrrolyl, quinolinyl, tetrahydrofuranyl, tetrahydropyranyl, thiazolyl, thienyl, and thiomorpholinyl. The heterocyclyl groups of the present disclosure are optionally substituted with one, two, three, four, or five substituents independently selected from alkenyl, alkoxy, alkoxyalkoxycarbonyl, alkoxyalkyl, alkoxyalkylcarbonyl, alkoxycarbonyl, alkyl, alkylcarbonyl, alkylsulfonyl, aryl, arylalkoxycarbonyl, arylalkyl, arylcarbonyl, cyano, cycloalkylcarbonyl, cycloalkyloxycarbonyl, an exocyclic double bond optionally substituted with one or two halo groups, halo, haloalkoxy, haloalkoxycarbonyl, haloalkyl, a second heterocyclyl group, heterocyclylalkyl, heterocyclylcarbonyl, hydroxy, hydroxyalkyl, nitro, —NR$^x$R$^y$, (NR$^x$R$^y$)alkyl, and oxo, wherein the alkyl part of the arylalkyl and the heterocyclylalkyl are unsubstituted and wherein the aryl, the aryl part of the arylalkyl, the aryl part of the arylcarbonyl, the cycloalkyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, hydroxy, and nitro.

The term "heterocyclylalkoxy," as used herein, refers to a heterocyclyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one, two, or three additional groups independently selected from alkoxy, alkylcarbonyloxy, aryl, halo, haloalkoxy, haloalkyl, hydroxy, and —NR$^c$R$^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^x$R$^y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclylcarbonylalkyl," as used herein, refers to an alkyl group substituted with one, two, or three heterocyclylcarbonyl groups.

The term "heterocyclylcarbonylalkylcarbonyl," as used herein, refers to a heterocyclylcarbonylalkyl group attached to the parent molecular moiety through a carbonyl group.

The term "heterocyclylcarbonylcarbonyl," as used herein, refers to a heterocyclylcarbonyl group attached to the parent molecular moiety through a carbonyl group.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkenyl," as used herein, refers to an alkenyl group substituted with one, two, or three hydroxy groups.

The term "hydroxyalkyl," as used herein, refers to an alkyl group substituted with one, two, or three hydroxy groups. The alkyl part of the hydroxyalkyl is further optionally substituted with one, two, or three halo groups.

The term "hydroxyalkylcarbonyl," as used herein, refers to a hydroxyalkyl group attached to the parent molecular moiety through a carbonyl group.

The term "nitro," as used herein, refers to —NO$_2$.

The term "—NR$^c$R$^d$," as used herein, refers to two groups, R$^c$ and R$^d$, which are attached to the parent molecular moiety through a nitrogen atom. R$^c$ and R$^d$ are independently selected from hydrogen, alkenyloxycarbonyl, alkoxyalkyl, alkoxyalkylcarbonyl, alkoxycarbonyl, alkyl, alkylcarbonyl, alkylsulfonyl, alkynyl, alkynyloxycarbonyl, aryl, arylalkoxycarbonyl, arylalkyl, arylalkylcarbonyl, arylcarbonyl, aryloxycarbonyl, arylsulfonyl, cyanoalkyl, cycloalkyl, cycloalkyloxy, cycloalkyloxycarbonyl, cycloalkylsulfonyl, formyl, haloalkoxycarbonyl, haloalkyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^x$R$^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "(NR$^c$R$^d$)alkenyl," as used herein, refers to

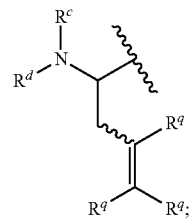

wherein R$^c$ and R$^d$ are as defined herein and each R$^q$ is independently hydrogen or C$_{1-3}$ alkyl.

The term "(NR$^c$R$^d$)alkyl," as used herein, refers to an alkyl group substituted with one, two, or three —NR$^c$R$^d$ groups. The alkyl part of the (NR$^c$R$^d$)alkyl is further optionally substituted with one or two additional groups selected from alkoxy, alkoxyalkylcarbonyl, alkoxycarbonyl, alkylsulfanyl, arylalkoxycarbonyl, carboxy, cycloalkyl, heterocyclyl, heterocyclylcarbonyl, hydroxy, and (NR$^e$R$^f$)carbonyl; wherein the heterocyclyl is further optionally substituted with one, two, three, four, or five substituents independently selected from alkoxy, alkyl, cyano, halo, haloalkoxy, haloalkyl, and nitro.

The term "(NR$^c$R$^d$)alkylcarbonyl," as used herein, refers to an (NR$^c$R$^d$)alkyl group attached to the parent molecular moiety through a carbonyl group. The alkyl part of the (NR$^c$R$^d$) alkylcarbonyl can be optionally substituted with one or two groups independently selected from aryl, and cycloalkyl.

The term "(NR$^c$R$^d$)carbonyl," as used herein, refers to an —NR$^c$R$^d$ group attached to the parent molecular moiety through a carbonyl group.

The term "(NR$^c$R$^d$)carbonylalkyl," as used herein, refers to an alkyl group substituted with one, two, or three (NR$^c$R$^d$) carbonyl groups.

The term "(NR$^c$R$^d$)carbonylalkylcarbonyl," as used herein, refers to an (NR$^c$R$^d$)carbonylalkyl group attached to the parent molecular moiety through a carbonyl group.

The term "(NR$^c$R$^d$)carbonylcarbonyl," as used herein, refers to an (NR$^c$R$^d$)carbonyl group attached to the parent molecular moiety through a carbonyl group.

The term "—NR$^e$R$^f$," as used herein, refers to two groups, R$^e$ and R$^f$, which are attached to the parent molecular moiety through a nitrogen atom. R$^e$ and R$^f$ are independently selected from hydrogen, alkyl, unsubstituted aryl, unsubstituted arylalkyl, unsubstituted cycloalkyl, unsubstituted (cycloalkyl) alkyl, unsubstituted heterocyclyl, unsubstituted heterocyclylalkyl, (NR$^x$R$^y$)alkyl, and (NR$^x$R$^y$)carbonyl.

The term "(NR$^e$R$^f$)alkyl," as used herein, refers to an alkyl group substituted with one, two, or three —NR$^e$R$^f$ groups.

The term "(NR$^e$R$^f$)alkylcarbonyl," as used herein, refers to an (NR$^e$R$^f$)alkyl group attached to the parent molecular moiety through a carbonyl group.

The term "(NR$^e$R$^f$)carbonyl," as used herein, refers to an —NR$^e$R$^f$ group attached to the parent molecular moiety through a carbonyl group.

The term "(NR$^e$R$^f$)sulfonyl," as used herein, refers to an —NR$^e$R$^f$ group attached to the parent molecular moiety through a sulfonyl group.

The term "—NR$^x$R$^y$," as used herein, refers to two groups, R$^x$ and R$^y$, which are attached to the parent molecular moiety through a nitrogen atom. R$^x$ and R$^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, haloalkoxycarbonyl, haloalkyl, unsubstituted heterocyclyl, unsubstituted heterocyclylcarbonyloxy, and (NR$^{x'}$R$^{y'}$)carbonyl, wherein R$^{x'}$ and R$^{y'}$ are independently selected from hydrogen and alkyl.

The term "(NR$^{x'}$R$^{y'}$)" as used herein, refers to two groups, R$^{x'}$ and R$^{y'}$, which are attached to the parent molecular moiety through a nitrogen atom. R$^{x'}$ and R$^{y'}$ are independently selected from hydrogen and alkyl.

The term "(NR$^x$R$^y$)alkyl," as used herein, refers to an alkyl group substituted with one, two, or three —NR$^x$R$^y$ groups.

The term "(NR$^x$R$^y$)carbonyl," as used herein, refers to an —NR$^x$R$^y$ group attached to the parent molecular moiety through a carbonyl group.

The term "(NR$^{x'}$R$^{y'}$)carbonyl," as used herein, refers to an —NR$^{x'}$R$^{y'}$ group attached to the parent molecular moiety through a carbonyl group.

The term "oxo," as used herein, refers to =O.

The term "sulfinyl," as used herein, refers to —S(O)—.

The term "sulfonyl," as used herein, refers to —SO$_2$—.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The compounds of the present disclosure also exist as tautomers; therefore the present disclosure also encompasses all tautomeric forms.

The term "compounds of the present disclosure", and equivalent expressions, are meant to embrace the compounds making up the combination of the present disclosure and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of each compound of the combination, as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of the compounds comprising the combination or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of the combination and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing the compounds of the combination, or pharmaceutically acceptable salts thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of the combination and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology* 2003, 38, 1282; *Biochem. Biophys. Res. Commun.* 2004, 313, 42; *J. Gastroenterol.* 2003, 38, 567).

Table A below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE A

| Brand Name | Physiological Class | Type of Inhibitor or Target | Source Company |
| --- | --- | --- | --- |
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |

TABLE A-continued

| Brand Name | Physiological Class | Type of Inhibitor or Target | Source Company |
|---|---|---|---|
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |

TABLE A-continued

| Brand Name | Physiological Class | Type of Inhibitor or Target | Source Company |
| --- | --- | --- | --- |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |
| daclatasvir | Antiviral | NS5A inhibitor | Bristol-Myers Squibb |
| BMS-791325 | Antiviral | NS5B Polymerase Inhibitor | Bristol-Myers Squibb |

TABLE A-continued

| Brand Name | Physiological Class | Type of Inhibitor or Target | Source Company |
|---|---|---|---|
| ACH-3102 | Antiviral | NS5A inhibitor | Bristol-Myers Squibb |
| asunaprevir | Antiviral | serine protease inhibitor | Bristol-Myers Squibb |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: min or mins for minutes; TFA for trifluoroacetic acid; ACN or MeCN for acetonitrile; MeOH for methanol; OAc for acetate; Bn for benzyl; DCM for dichloromethane; DIEA or DiPEA or DIPEA for diisopropylethylamine; HATU for O-(7-azabenzotriazol-1-yl)-N,N,N',N'-tetramethyluronium hexafluorophosphate; EtOAc for ethyl acetate; RT or rt for room temperature or retention time (context will dictate); h or hr or hrs for hours; DMSO for dimethylsulfoxide; DME for dimethoxyethane; DMF for N,N-dimethylformamide; Boc or BOC for tert-butyoxycarbonyl; Hex for hexanes; Et for ethyl; AcOH for acetic acid; THF for tetrahydrofuran; n-BuLi for n-butyllithium; NBS for N-bromosuccinimide; Ph for phenyl; TBTU for O-(benzotriazol-1-yl)-N,N,N',N'-tetramethyluronium tetrafluoroborate; TEA or Et$_3$N for triethylamine; DMAP for 4-N,N-dimethylaminopyridine; Cbz for carbobenzyloxy; HBTU for O-benzotriazole-N,N,N',N'-tetramethyluronium hexafluorophosphate; EtOH for ethanol; Ph for phenyl; Me for methyl; TMSCN for trimethylsilylcyanide; PCC for pyridinium chlorochromate; DCC for dicyclohexylcarbodiimide; DMA for N,N-dimethylacetamide; DEA for diethylamine; Et$_2$O for diethyl ether; BuOH for butanol; EtO for ethoxide; Bu$_2$O for dibutyl ether; AcCl for acetyl chloride; TPP for meso-tetraphenylporphyrin; TBAF for tetrabutylammonium fluoride; dppf for diphenylphosphinoferrocene; DDQ for 2,3-dichloro-5,6-dicyano-1,4-benzoquinone; LDA for lithium diisopropylamide; PCC for pyridinium chlorochromate; OMe for methoxide; CDI for 1,1-carbonyldiimidazole; DCE for 1,2-dichloroethane; and HMPA for hexamethylphosphorictriamide.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Starting materials can be obtained from commercial sources or prepared by well-established literature methods known to those of ordinary skill in the art.

LC-MS Methods
Condition N-1:
Column=Phenomenex, 2.0×50 mm, 3 μm
Start % B=0; Final % B=100
Gradient time=4 min; Stop time=5 min
Flow Rate=0.8 mL/min; Wavelength=220 nm
Solvent A=0.1% TFA in 10% methanol/90% water
Solvent B=0.1% TFA in 90% methanol/10% water
Oven temp.=40° C.
Condition N-2:
Column=Sunfire, C18, 3.0×150 mm, 3.5 μm
Start % B=0; Final % B=100
Gradient time=15 min; Stop time=18 min
Flow Rate=1 mL/min
Wavelength 1=220 nm; Wavelength 2=254 nm
Solvent A=0.1% TFA in 5% MeCN/95% water
Solvent B=0.1% TFA in 95% MeCN/5% water
LC-MS Method YT-1
Start % B=0; Final % B=100
Gradient Time=3 min; Stop Time=4 min
Flow Rate=0.8 mL/min; Wavelength=220 nm
Solvent Pair=MeOH:H$_2$O:TFA
Solvent A=10% MeOH-90% H$_2$O-0.1% TFA
Solvent B=90% MeOH-10% H$_2$O-0.1% TFA
Column: Phenomenex 2.0×30 mm 3 um
LC-MS Method YT-2
Start % B=0; Final % B=100
Gradient Time=4 min; Stop time=5 min
Flow Rate=1 mL/min; Wavelength=220 nm
Solvent Pair=MeOH:H$_2$O:TFA
Solvent A=10% MeOH-90% H$_2$O-0.1% TFA
Solvent B=90% MeOH-10% H$_2$O-0.1% TFA
Column: Phenomenex 2.0×30 mm 3 μm
LC-MS Method YT-3
Start % B=0; Final % B=100
Gradient Time=2 min; Stop time=3 min
Flow Rate=0.8 mL/min; Wavelength=220 nm
Solvent Pair=MeOH:H$_2$O:TFA
Solvent A=10% MeOH-90% H$_2$O-0.1% TFA
Solvent B=90% MeOH-10% H$_2$O-0.1% TFA
Column: Phenomenex 2.0×30 mm 3 μm
LC-MS Method P-1
Start % B=0; Final % B=100
Gradient Time=3 min; Stop Time=4 min
Flow Rate=0.8 mL/min; Wavelength=220 nm
Solvent A=10% MeOH-90% H$_2$O-0.1% TFA
Solvent B=90% MeOH-10% H$_2$O-0.1% TFA Column: Phenomenex 2.0×50 mm 3 um
LC-MS Method P-2
Start % B=0; Final % B=100
Gradient Time=2 min; Stop time=3 min
Flow Rate=1 mL/min; Wavelength=220 nm
Solvent A=10% MeOH-90% $H_2O$-0.1% TFA
Solvent B=90% MeOH-10% $H_2O$-0.1% TFA
Column: Phenomenex 2.0×30 mm 3 um
LC-MS Method P-3
Start % B=0; Final % B=100
Gradient Time=4 min; Stop time=5 min
Flow Rate=0.8 mL/min; Wavelength=220 nm
Solvent A=10% MeOH-90% $H_2O$-0.1% TFA
Solvent B=90% MeOH-10% $H_2O$-0.1% TFA
Column: Phenomenex 2.0×50 mm
LC-MS Method PS-1
Wavelength=220 nm
Mobile Phase: A=5:95 ACN:Water; B=95:5 ACN:Water;
Modifier=10 mM $NH_4OAc$
Gradient: 0%-100% B over 8 minutes, then 1 minute hold at 100% B,
Flow Rate=2.0 mL/min
Column: Supelco Ascentis Express 4.5×50 mm 3 um C18
LC-MS Method PS-2
Mobile Phase A: 5:95 acetonitrile:water with 10 mM ammonium acetate;
Mobile Phase B: 95:5 acetonitrile:water with 10 mM ammonium acetate;
Gradient: 0.5 min hold at 0% B, 0-100% B over 4 minutes, then 0.5 minute hold at 100% B; Flow Rate=1 mL/min. Column. Waters BEH C18, 2.0×50 mm, 1.7-1 μm particles
LC-MS Method PS-3
Mobile Phase A: 5:95 methanol:water with 10 mM ammonium acetate;
Mobile Phase B: 95:5 methanol:water with 10 mM ammonium acetate;
Gradient: 0.5 min hold at 0% B, 0-100% B over 4 minutes, then a 0.5 minute hold at 100% B; Flow Rate=0.5 mL/min; Column; Waters BEH C18
Condition L-1:
Column=Phenomenex, 2.0×50 mm, 3 um
Start % B=0; Final % B=100
Gradient time=4 min; Stop time=5 min
Flow Rate=0.8 mL/min; Wavelength=220 nm
Solvent A=0.1% TFA in 10% MeCN/90% water
Solvent B=0.1% TFA in 90% MeCN/10% water
Oven temp.=40° C.
Condition L-2:
Column=Phenomenex, 3.0×2 mm, 3 um
Start % B=0; Final % B=100
Gradient time=2 min; Stop time=3 min
Flow Rate=1 mL/min; Wavelength=220 nm
Solvent A=0.1% TFA in 10% MeCN/90% water
Solvent B=0.1% TFA in 90% MeCN/10% water
Oven temp.=40° C.
Condition W-1:
Column=Phenomenex, 2.0×30 mm, 3 um
Start % B=0; Final % B=100
Gradient time=2 min; Stop time=3 min
Flow Rate=1 mL/min; Wavelength=220 nm
Solvent A=0.1% TFA in 10% MeOH/90% water
Solvent B=0.1% TFA in 90% MeOH/10% water
Oven temp.=40° C.
Condition W-2:
Column=Phenomenex Luna C18, 2.0×30 mm, 3 um
Start % B=0; Final % B=100
Gradient time=2 min; Stop time=3 min
Flow Rate=1 mL/min; Wavelength=220 nm
Solvent A=0.1% TFA in 10% $CH_3CN$/90% water
Solvent B=0.1% TFA in 90% $CH_3CN$/10% water
Oven temp.=40° C.
Condition W-3:
Column=Phenomenex Luna C18, 2.0×30 mm, 3 um
Start % B=30; Final % B=100
Gradient time=4 min; Stop time=5 min
Flow Rate=1 mL/min; Wavelength=220 nm
Solvent A=10 mM $NH_4OAc$ in 5% $CH_3OH$/95% water
Solvent B=10 mM $NH_4OAc$ in 95% $CH_3OH$/5% water
Oven temp.=40° C.
Condition B-1:
Column=Xbridge phenyl, 4.6×150 mm, 3.5 um
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min; Stop time=23 min
Isocratic time=3 min
Flow Rate=1 mL/min; Wavelength=220 & 254 nm
Condition B-2:
Column=Sunfire C18, 4.6×150 mm, 3.5 um
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min; Stop time=23 min
Isocratic time=3 min
Flow Rate=1 mL/min; Wavelength=220 & 254 nm
Condition B-3:
Column=YMC triart, 4.6×150 mm, 5 um
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min; Stop time=23 min
Isocratic time=3 min
Flow Rate=1 mL/min; Wavelength=220 & 254 nm
Condition B-4:
Column=Sunfire C18, 4.6×150 mm, 3.5 um
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=0; Final % B=50
Gradient time-1=15 min
Final % B=100
Gradient time-2=3 min
Isocratic time=5 min
Stop time=28 min
Flow Rate=1 mL/min; Wavelength=220 & 254 nm
Condition B-5:
Column=Sunfire C18, 4.6×150 mm, 3.5 um
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=25 min; Stop time=36 min
Isocratic time=5 min
Flow Rate=1 mL/min; Wavelength=220 & 254 nm
Condition B-6:
Column=Xbridge phenyl, 4.6×150 mm, 3.5 um Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=25 min; Stop time=36 min
Isocratic time=5 min
Flow Rate=1 mL/min; Wavelength=220 & 254 nm
Condition B-7:
Column=Eclipse XDB C18, 4.6×150 mm, 3.5 um
Solvent A=20 mM NH$_4$OAc in H$_2$O
Solvent B=CH$_3$CN
Start % B=10; Final % B=100
Gradient time=25 min; Stop time=36 min
Isocratic time=5 min
Flow Rate=1 mL/min; Wavelength=220 & 254 nm
Condition B-8:
Column=Eclipse XDB C18, 4.6×150 mm, 3.5 um
Solvent A=20 mM NH$_4$OAc in H$_2$O
Solvent B=CH$_3$CN
Start % B=10; Final % B=100
Gradient time=12 min; Stop time=26 min
Isocratic time=8 min
Flow Rate=1 mL/min; Wavelength=220 & 254 nm
Condition B-9:
Column=Zorbax SB C18, 4.6×50 mm, 5 um
Solvent A=MeOH (10%)+0.1% TFA in H$_2$O (90%)
Solvent B=MeOH (90%)+0.1% TFA in H$_2$O (10%)
Start % B=0; Final % B=100
Gradient time=2 min; Stop time=3 min
Flow Rate=5 mL/min; Wavelength=220 nm
Condition B-10:
Column=Purospher@star RP-18, 4.0×55 mm, 3 um
Solvent A=ACN (10%)+20 mM NH$_4$OAc in H$_2$O (90%)
Solvent B=ACN (90%)+20 mM NH$_4$OAc in H$_2$O (10%)
Start % B=0; Final % B=100
Gradient time=2 min; Stop time=3 min
Isocratic time=0.5 min
Flow Rate=2.5 mL/min; Wavelength=220 nm
Condition B-11:
Column=Purospher@star RP-18, 4.0×55 mm, 3 um
Solvent A=ACN (10%)+20 mM NH$_4$OAc in H$_2$O (90%)
Solvent B=ACN (90%)+20 mM NH$_4$OAc in H$_2$O (10%)
Start % B=0; Final % B=100
Gradient time=1.8 min; Stop time=4 min
Isocratic time=1.5 min
Flow Rate=2.5 mL/min; Wavelength=220 nm
Condition B-12:
Column=Ascentis Express C18, 2.1×50 mm, 2.7 um
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.4 min; Stop time=4 min
Stop time=4 min
Flow Rate=1 mL/min; Wavelength=220 nm
Condition B-13:
Column=Ascentis Express C8, 2.1×50 mm, 2.7 um
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.5 min; Stop time=4 min
Isocratic time=1.7 min
Flow Rate=1 mL/min; Wavelength=220 nm
Condition B-14:
Column=Ascentis Express C8, 2.1×50 mm, 2.7 um
Solvent A=CH$_3$CN (10%)+10 mM NH$_4$COOH in H$_2$O (90%)
Solvent B=CH$_3$CN (90%)+10 mM NH$_4$COOH in H$_2$O (10%)
Start % B=0; Final % B=100
Gradient time=1.6 min; Stop time=4 min
Isocratic time=1.6 min
Flow Rate=1 mL/min; Wavelength=220 nm
Condition B-15:
Column=Ascentis Express C18 2.1×50 mm, 2.7 um
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.5 min; Stop time=4 min
Isocratic time=1.7 min
Flow Rate=1 mL/min; Wavelength=220 nm
Condition B-16:
Column=Acquity BEH C18, 2.1×50 mm, 3 um
Solvent A=ACN (5%)+5 mM NH$_4$OAc in H$_2$O (95%)
Solvent B=ACN (95%)+5 mM NH$_4$OAc in H$_2$O (5%)
Start % B=5; Final % B=95
Gradient time=1.1 min; Stop time=2.4 min
Isocratic time=0.6 min
Flow Rate=0.8 mL/min; Wavelength=220 nm
Condition B-17:
Column=ACE Excel 2 C18, 3.0×50 mm, 2.0 um
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=5; Final % B=100
Gradient time=1.8 min; Stop time=4 min
Isocratic time=0.8 min
Flow Rate=1.2 mL/min; Wavelength=220 nm
Condition B-18:
Column=BEH C18, 3.0×50 mm, 5.0 um
Solvent A=CH$_3$CN (5%)+10 mM NH$_4$OAc in H$_2$O (95%)
Solvent B=CH$_3$CN (95%)+10 mM NH$_4$OAc in H$_2$O (5%)
Start % B=5; Final % B=100
Gradient time=1.8 min; Stop time=4 min
Isocratic time=1.4 min
Flow Rate=1.2 mL/min; Wavelength=220 nm
Condition B-19:
Column=Xbridge C18, 2.1×50 mm, 2.5 um
Solvent A=CH$_3$CN (5%)+10 mM NH$_4$HCO$_3$ in H$_2$O (95%)
Solvent B=CH$_3$CN (95%)+10 mM NH$_4$HCO$_3$ in H$_2$O (5%)
Start % B=0; Final % B=100
Gradient time=1.7 min; Stop time=4 min
Isocratic time=1.5 min
Flow Rate=1.0 mL/min; Wavelength=220 nm
Condition B-20:
Column=Zorbax SB-Aq, 4.6×50 mm, 3.5 um
Solvent A=CH$_3$CN (5%)+10 mM NH$_4$COOH in H$_2$O (95%)
Solvent B=CH$_3$CN (95%)+10 mM NH$_4$COOH in H$_2$O (5%)
Start % B=5; Final % B=95
Gradient time=1.7 min; Stop time=4 min
Isocratic time=1.5 min
Flow Rate=1.0 mL/min; Wavelength=220 nm
Condition B-21:
Column=Ascentis Express C18, 2.1×50 mm, 2.7 um
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.6 min; Stop time=4 min
Isocratic time=1.6 min
Flow Rate=1 mL/min; Wavelength=220 nm
Condition B-22:
Column=Ascentis Express C8, 2.1×50 mm, 2.7 um
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.5 min; Stop time=4 min
Isocratic time=1.7 min Flow Rate=1 mL/min; Wavelength=220 nm
Condition B-23:
Column=Zorbax SB C18, 4.6×50 mm, 3.5 um
Solvent A=ACN (10%)+20 mM NH$_4$OAc in H$_2$O (90%)
Solvent B=ACN (90%)+20 mM NH$_4$OAc in H$_2$O (10%)
Start % B=0; Final % B=100
Gradient time=2.5 min; Stop time=3 min
Flow Rate=2.5 mL/min; Wavelength=220 nm
Condition B-24:
Column=Zorbax SB C18, 2.1×30 mm, 3.5 um
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=6; Final % B=100
Gradient time=1.5 min; Stop time=3 min
Isocratic time=1.7 min
Flow Rate=2.5 mL/min; Wavelength=220 nm
Condition B-25:
Column=Zorbax SB-Aq, 4.6×50 mm, 3.5 um
Solvent A=ACN (10%)+0.1% HCOOH in H$_2$O (90%)
Solvent B=ACN (90%)+0.1% HCOOH in H$_2$O (10%)
Start % B=0; Final % B=20
Gradient time-1=1.5 min;
Final % B=95
Gradient time-2=2.5 min; Stop time=4 min
Flow Rate=1 mL/min; Wavelength=220 nm
Condition B-26:
Column=Xbridge BEH C18, 2.1×50 mm, 2.5 um
Solvent A=0.1% HCOOH in H$_2$O
Solvent B=0.07% HCOOH in ACN
Start % B=10; Final % B=100
Gradient time=2.0 min; Stop time=4.0 min
Isocratic time=1. min
Flow Rate=1.2 mL/min; Wavelength=220 nm
Condition B-27:
Column=Zorbax SB C18, 2.1×30 mm, 3.5 um
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=6; Final % B=100
Gradient time=1.5 min; Stop time=3 min
Isocratic time=0.7 min
Flow Rate=1.5 mL/min; Wavelength=220 nm
Condition B-28:
Column=Ascentis Express C18, 4.6×50 mm, 2.7 um
Solvent A=CH$_3$CN (5%)+10 mM NH$_4$COOH in H$_2$O (95%)
Solvent B=CH$_3$CN (95%)+10 mM NH$_4$COOH in H$_2$O (5%)
Start % B=0; Final % B=100
Gradient time=4 min; Stop time=5 min
Flow Rate=4.0 mL/min; Wavelength=220 nm
Condition B-29:
Column=Xbridge C18, 2.1×50 mm, 2.5 um
Solvent A=10 mM NH$_4$HCO$_3$
Solvent B=CH$_3$CN
Start % A=100; Final % B=100
Gradient time=1.7 min; Stop time=4 min
Isocratic time=1.5 min
Flow Rate=1.0 mL/min; Wavelength=220 nm
Condition B-30:
Column=Sunfire C18, 4.6×150 mm, 3.5 um
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=12 min; Stop time=18 min
Isocratic time=3 min
Flow Rate=1 mL/min; Wavelength=220 & 254 nm
Condition B-31:
Column=XBridge, 4.6×150 mm, 3.5 um
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=12 min; Stop time=18 min
Isocratic time=3 min
Flow Rate=1 mL/min; Wavelength=220 & 254 nm
Condition B-32:
Column=Sunfire C18, 4.6×150 mm, 3.5 um
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=12 min; Stop time=20 min
Isocratic time=3 min
Flow Rate=1 mL/min; Wavelength=220 & 254 nm
Condition B-33:
Column=Zorbax-SB-CN, 4.6×150 mm, 5.0 um
Solvent A=CH$_3$CN (10%)+10 mM NH$_4$COOH in H$_2$O (90%)
Solvent B=CH$_3$CN (90%)+10 mM NH$_4$COOH in H$_2$O (10%)
Start % B=10; Final % B=100
Gradient time=20 min; Stop time=27 min
Isocratic time=5 min
Flow Rate=1 mL/min; Wavelength=220 & 254 nm
Condition B-34:
Column=Kinetex C-18, 2.1×50 mm, 2.6 um
Solvent A=ACN (2%)+0.1% NH$_4$COOH in H$_2$O (98%)
Solvent B=ACN (98%)+0.1% NH$_4$COOH in H$_2$O (2%)
Start % B=0; Final % B=100
Gradient time=1.7 min; Stop time=4 min
Isocratic time=1.5 min
Flow Rate=1 mL/min; Wavelength=220 nm
Condition B-35:
Column=Xbridge phenyl, 4.6×150 mm, 3.5 um
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=12 min; Stop time=18 min
Isocratic time=3 min
Flow Rate=1 mL/min; Wavelength=220 & 254 nm
Condition B-36:
Column=Eclipse XDB C18, 4.6×150 mm, 3.5 um
Solvent A=10 mM NH$_4$OAc in H$_2$O
Solvent B=CH$_3$CN
Start % B=10; Final % B=100
Gradient time=12 min; Stop time=17 min
Isocratic time=3 min
Flow Rate=1 mL/min; Wavelength=220 & 254 nm
Condition B-37:
Column=Zorbax SB C18, 4.6×50 mm, 3.5 um
Solvent A=ACN (10%)+20 mM NH$_4$OAc in H$_2$O (90%)
Solvent B=ACN (90%)+20 mM NH$_4$OAc in H$_2$O (10%)
Start % B=10; Final % B=100
Gradient time=2.0 min; Stop time=3 min
Flow Rate=2.5 mL/min; Wavelength=220 nm

Example N-1

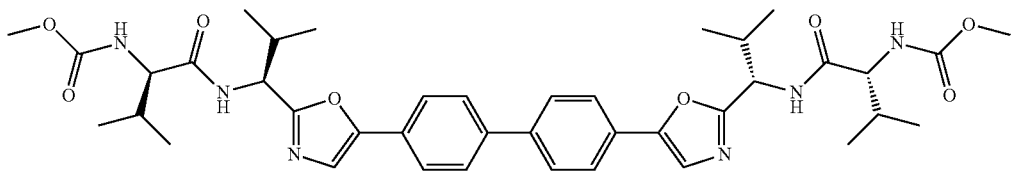

Example N-1

Step a

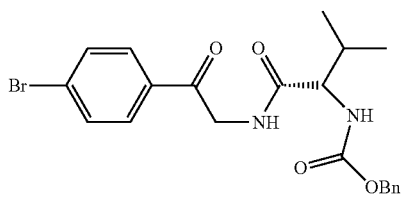

To a suspension of 2-amino-1-(4-bromophenyl)ethanone, HCl (1 g, 3.99 mmol) in DCM was added (S)-2-(benzyloxycarbonylamino)-3-methylbutanoic acid (1.003 g, 3.99 mmol), DIPEA (1.534 mL, 8.78 mmol) and HATU (1.518 g, 3.99 mmol). The reaction mixture was stirred at rt for 16 hrs. The reaction mixture was diluted with EtOAc, washed with sat. NaHCO$_3$, water and sat. NaCl, dried over anhydrous Na$_2$SO$_4$, filtered and concentrated to yield the product (S)-benzyl 1-(2-(4-bromophenyl)-2-oxoethylamino)-3-methyl-1-oxobutan-2-ylcarbamate as a pale yellow solid. The product was used without further purification. LC/MS (Cond. N-1): [M+H]$^+$ 447.12, R$_t$=3.766 min.

Example N-1

Step b

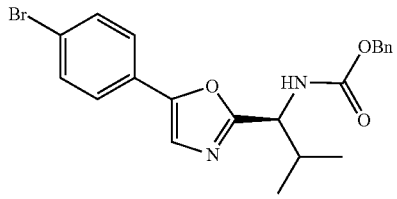 [SMILES: CC(C)[C@H](NC(=O)OCc1ccccc1)c1ncc(-c2ccc(Br)cc2)o1]

To a solution of (S)-benzyl 1-(2-(4-bromophenyl)-2-oxoethylamino)-3-methyl-1-oxobutan-2-ylcarbamate (1.9 g, 4.25 mmol) in pyridine (6 mL) was added POCl$_3$ (3 mL, 32.2 mmol) at rt. The reaction mixture was heated at 75° C. for 3 hr. The reaction mixture was diluted with EtOAc, slowly poured into a cold sat. NaHCO$_3$ solution at 0° C. The organic phase was washed with water, sat. NaCl, dried over anhydrous Na$_2$SO$_4$, filtered and concentrated to yield an oil. The residue was charged to an 80 g silica gel cartridge which was eluted with a 20 min gradient of 0-100% EtOAc in hexane. The product (S)-benzyl 1-(5-(4-bromophenyl)oxazol-2-yl)-2-methylpropylcarbamate (0.71 g) was collected as a yellow oil. LC/MS (Cond. N-1): [M+H]$^+$ 429.17, R$_t$=4.193 min. $^1$H NMR (400 MHz, DMSO-d$_6$) ppm 8.06 (1H, d, J=8.78 Hz), 7.59-7.75 (5H, m), 7.16-7.41 (5H, m), 5.07 (2H, s), 4.58 (1H, t, J=8.16 Hz), 2.20 (1H, dq, J=13.90, 6.91 Hz), 0.97 (3H, d, J=6.78 Hz), 0.86 (3H, d, J=6.78 Hz).

Example N-1

Step c

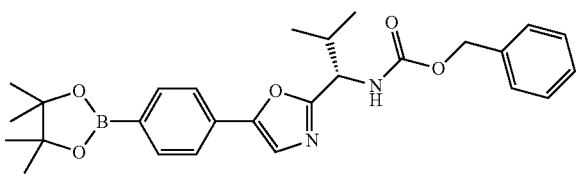 [SMILES: CC(C)[C@H](NC(=O)OCc1ccccc1)c1ncc(-c2ccc(B3OC(C)(C)C(C)(C)O3)cc2)o1]

To a solution of 4,4,4',4',5,5,5',5'-octamethyl-2,2'-bi(1,3,2-dioxaborolane) (0.461 g, 1.817 mmol) and (S)-benzyl 1-(5-(4-bromophenyl)oxazol-2-yl)-2-methylpropylcarbamate (0.39 g, 0.908 mmol) in dioxane (3 mL) was added potassium acetate (0.223 g, 2.271 mmol). The reaction mixture was degassed for 5 mins followed by the addition of tetrakis(triphenylphosphine)palladium(0) (0.052 g, 0.045 mmol). The reaction mixture was heated at 85° C. for 6 hours. The reaction mixture was diluted with EtOAc, washed with sat. NaHCO$_3$, water, sat. NaCl, dried over anhydrous Na$_2$SO$_4$, filtered and concentrated to yield an oil. The crude product was charged to a 40 g silica gel cartridge which was eluted with a 20 min gradient of 0-100% EtOAc in hexane. The product (S)-benzyl 2-methyl-1-(5-(4-(4,4,5,5-tetramethyl-1,3,2-dioxaborolan-2-yl)phenyl)oxazol-2-yl)propylcarbamate (0.35 g) was collected as a yellow oil. LC/MS (Cond. N-1): [M+H]$^+$ 477.31, R$_t$=4.353 min.

Example N-1

Step d

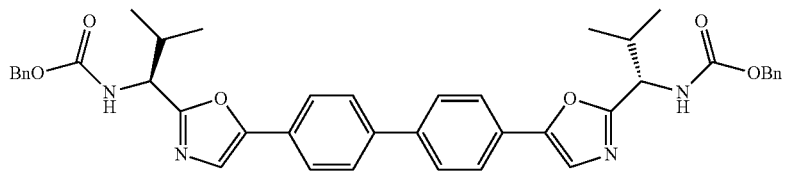 [SMILES: CC(C)[C@H](NC(=O)OCc1ccccc1)c1ncc(-c2ccc(-c3ccc(-c4cnc([C@@H](NC(=O)OCc5ccccc5)C(C)C)o4)cc3)cc2)o1]

To a solution of (S)-benzyl 2-methyl-1-(5-(4-(4,4,5,5-tetramethyl-1,3,2-dioxaborolan-2-yl)phenyl)oxazol-2-yl)propylcarbamate (0.35 g, 0.735 mmol) and (S)-benzyl 1-(5-(4-bromophenyl)oxazol-2-yl)-2-methylpropylcarbamate (0.35 g, 0.815 mmol) in DME (1 mL) and water (0.25 mL) was added sodium bicarbonate (0.309 g, 3.67 mmol). The reaction mixture was degassed for 5 mins followed by the addition of tetrakis(triphenylphosphine)palladium(0) (0.042 g, 0.037 mmol). The reaction mixture was heated at 80° C. for 6 hours. The reaction mixture was diluted with EtOAc, washed with sat. NaHCO$_3$, water, sat. NaCl, dried over anhydrous Na$_2$SO$_4$, filtered and concentrated to yield a solid. The crude product was charged to a 80 g silica gel cartridge which was eluted with a 20 min gradient of 0-100% EtOAc in hexane. The product benzyl (1S,1'S)-1,1'-(5,5'-(biphenyl-4,4'-diyl) bis(oxazole-5,2-diyl))bis(2-methylpropane-1,1-diyl)dicarbamate (0.32 g) was collected as a yellow solid. LC/MS (Cond. N-1): [M+H]$^+$ 699.37, R$_t$=4.53 min.

Example N-1

Step e

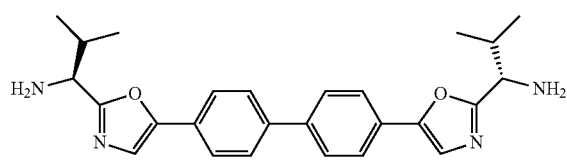 [SMILES: CC(C)[C@H](N)c1ncc(-c2ccc(-c3ccc(-c4cnc([C@@H](N)C(C)C)o4)cc3)cc2)o1]

To a mixture of benzyl (1S,1'S)-1,1'-(5,5'-(biphenyl-4,4'-diyl)bis(oxazole-5,2-diyl))bis(2-methylpropane-1,1-diyl)dicarbamate (0.1 g, 0.143 mmol) in ethanol (2 mL) was added Pd/C (0.015 g, 0.014 mmol) followed by the addition of 6 N HCl/dioxane (0.1 mL) under N$_2$. The reaction mixture was stirred at rt under H$_2$ for 4 days. The reaction mixture was filtered and the solid was washed with EtOAc. The filtrate was concentrated to yield (1S,1'S)-1,1'-(5,5'-(biphenyl-4,4'-diyl) bis(oxazole-5,2-diyl))bis(2-methylpropan-1-amine) (0.06 g) as a pale yellow solid. LC/MS (Cond. N-1): [M+Na]$^+$ 453.25, R$_t$=3.05 min.

Example N-1

To a mixture of (1S,1'S)-1,1'-(5,5'-(biphenyl-4,4'-diyl)bis(oxazole-5,2-diyl))bis(2-methylpropan-1-amine) (0.03 g), (R)-2-(methoxycarbonylamino)-3-methylbutanoic acid (0.024 g, 0.139 mmol) and HATU (0.058 g, 0.153 mmol) in DMF (1 mL) was added DIEA (0.049 mL, 0.279 mmol). The reaction mixture was stirred at rt for 1 hr. The reaction mixture was purified by reverse phase HPLC to yield Example N-1 (0.015 g) as a white solid. LC/MS (Cond. N-1): [M+H]$^+$ 745.49, R$_t$=4.183 min. $^1$H NMR (400 MHz, MeOD) ppm 7.74-7.87 (8H, m), 7.50 (2H, s), 4.92-5.01 (4H, m), 3.63 (6H, s), 2.30-2.44 (2H, m), 2.10 (2H, d, J=6.78 Hz), 1.04-1.12 (6H, m), 0.99 (16H, dd, J=9.41, 6.90 Hz), 0.96 (2H, s).

Example N-2

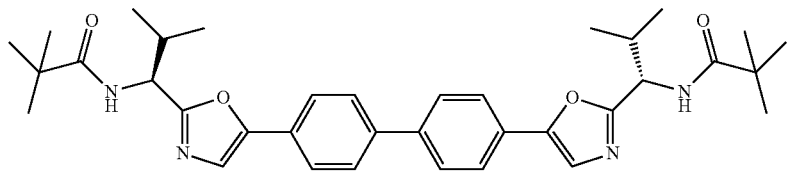 [SMILES: CC(C)[C@H](NC(=O)C(C)(C)C)c1ncc(-c2ccc(-c3ccc(-c4cnc([C@@H](NC(=O)C(C)(C)C)C(C)C)o4)cc3)cc2)o1]

To a mixture of (1S,1'S)-1,1'-(5,5'-(biphenyl-4,4'-diyl)bis(oxazole-5,2-diyl))bis(2-methylpropan-1-amine) (0.03 g), pivalic acid (0.014 g, 0.139 mmol) and HATU (0.058 g, 0.153 mmol) in DMF (1 mL) was added DIEA (0.049 mL, 0.279 mmol). The reaction mixture was stirred at rt for 1 hr. The reaction mixture was purified by reverse phase HPLC to yield Example N-2 (0.010 g) as a white solid. LC/MS (Cond. N-1): [M+H]$^+$ 599.45, R$_t$=4.408 min. $^1$H NMR (400 MHz, MeOD) ppm 7.74-7.82 (8H, m), 7.50 (2H, s), 4.97-4.99 (1H, m), 4.96 (1H, s), 2.29-2.47 (2H, m), 1.21-1.30 (18H, m), 1.04-1.10 (6H, m), 0.95 (6H, d, J=6.53 Hz).

Example N-3

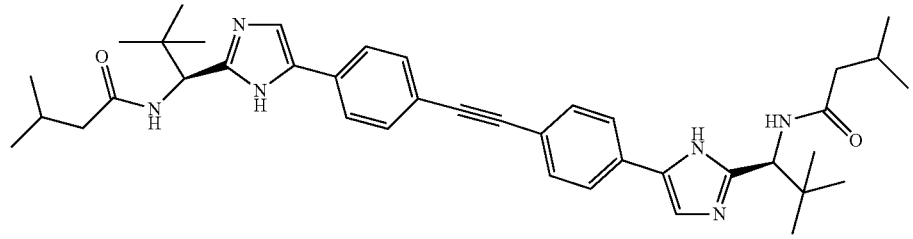 [SMILES: CC(C)CC(=O)N[C@H](c1ncc(-c2ccc(C#Cc3ccc(-c4cnc([C@@H](NC(=O)CC(C)C)C(C)(C)C)[nH]4)cc3)cc2)[nH]1)C(C)(C)C]

Example N-3

Step a

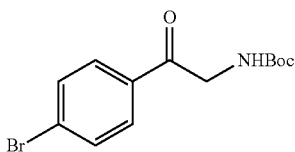

To a suspension of 2-amino-1-(4-bromophenyl)ethanone, HCl (4.0 g, 15.97 mmol) in DCM (50.0 mL) was added sodium bicarbonate (4.02 g, 47.9 mmol). Then Boc-anhydride (3.89 mL, 16.77 mmol) and DIEA (3 mL, 17.18 mmol) was added to the solution and the reaction mixture was stirred at rt for 2 hrs. The reaction mixture was diluted with EtOAc and water, the organic phase was washed with 5% citric acid, water and sat. NaCl, dried over anhydrous $Na_2SO_4$, filtered and concentrated to yield tert-butyl 2-(4-bromophenyl)-2-oxoethylcarbamate (5.0 g) as a yellow solid, which was used in the next step without further purification. $^1$H NMR (400 MHz, MeOD) ppm 7.89 (2H, m), 7.68 (2H, m, J=8.53 Hz), 4.52 (2H, s), 1.38-1.51 (9H, m). LC/MS (Cond. N-1): $R_t$=3.56 min. LC/MS: Anal. Calcd. For [M+Na]$^+$ $C_{13}H_{16}BrNaNO_3$: 336.03; found: 335.97.

Example N-3

Step b

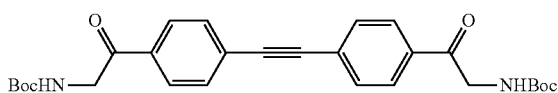

To a solution of tert-butyl 2-(4-bromophenyl)-2-oxoethylcarbamate (2.0 g, 6.37 mmol) in DMF (5 mL) was added 1,2-bis(trimethylstannyl)ethyne (1.119 g, 3.18 mmol). The reaction mixture was degassed, tetrakis(triphenylphosphine)palladium(0) (0.184 g, 0.159 mmol) was added, and the mixture was heated at 90° C. for 4 hrs. The crude reaction mixture was charged to a 90 g silica gel cartridge which was eluted with a 20 min gradient of 0-60% EtOAc in hexane. Tert-butyl 2,2'-(4,4'-(ethyne-1,2-diyl)bis(4,1-phenylene))bis(2-oxoethane-2,1-diyl)dicarbamate (0.83 g) was collected as a yellow solid. LC/MS (Cond. N-1): $R_t$=4.1 min. LC/MS: Anal. Calcd. For [M+Na]$^+$ $C_{28}H_{32}NaN_2O_6$: 515.23; found: 515.10.

Example N-3

Step c

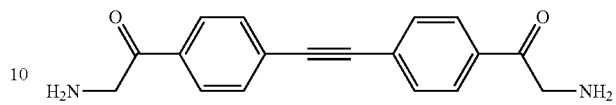

To a solution of tert-butyl 2,2'-(4,4'-(ethyne-1,2-diyl)bis(4,1-phenylene))bis(2-oxoethane-2,1-diyl)dicarbamate (1.13 g, 2.294 mmol) in 1,4-dioxane (5 mL) was added 4 M HCl in dioxane (4 mL, 16.00 mmol). The reaction mixture was stirred at rt for 2 hrs. The reaction mixture was concentrated to dryness to yield a yellow solid. The solid was washed with hexane and EtOAc, then dried to yield 1,1'-(4,4'-(ethyne-1,2-diyl)bis(4,1-phenylene))bis(2-aminoethanone), 2 HCl (0.508 g). $^1$H NMR (400 MHz, MeOD) ppm 8.10 (4H, d, J=8.53 Hz), 7.78 (4H, d, J=8.53 Hz), 4.64 (4H, s). LC/MS (Cond. N-1): $R_t$=1.94 min. LC/MS: Anal. Calcd. For [M+H]$^+$ $C_{18}H_{17}N_2O_2$: 293.12; found: 293.07.

Example N-3

Step d

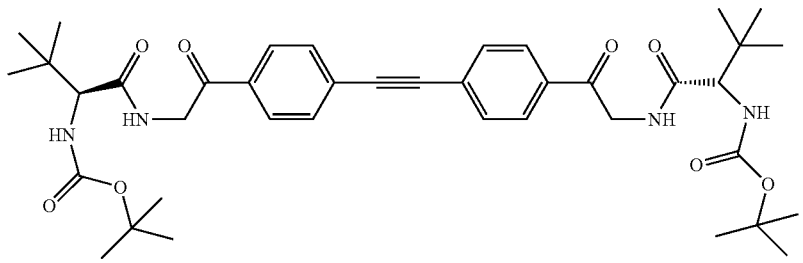

To a mixture of (S)-2-(tert-butoxycarbonylamino)-3,3-dimethylbutanoic acid (0.190 g, 0.821 mmol), 1,1'-(4,4'-(ethyne-1,2-diyl)bis(4,1-phenylene))bis(2-aminoethanone), 2 HCl (0.15 g, 0.411 mmol), HATU (0.312 g, 0.821 mmol) in DCM (2 mL) was added DIEA (0.359 mL, 2.053 mmol). The reaction mixture was stirred at rt for 3 hrs. The reaction mixture was charged to a 40 g silica gel cartridge which was eluted with a 20 min gradient of 0-100% EtOAc in hexane. Tert-butyl (2S,2'S)-1,1'-(2,2'-(4,4'-(ethyne-1,2-diyl)bis(4,1-phenylene))bis(2-oxoethane-2,1-diyl))bis(azanediyl)bis(3,3-dimethyl-1-oxobutane-2,1-diyl)dicarbamate (0.3 g) was collected as a yellow solid. LC/MS (Cond. N-1): [M+Na]$^+$ 741.70, $R_t$=4.39 min.

Example N-3

Step e

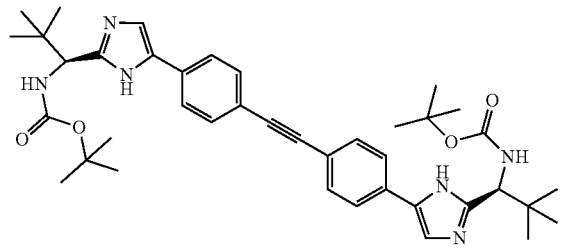 [SMILES: CC(C)(C)OC(=O)N[C@H](c1ncc(-c2ccc(C#Cc3ccc(-c4cnc([C@@H](NC(=O)OC(C)(C)C)C(C)(C)C)[nH]4)cc3)cc2)[nH]1)C(C)(C)C]

In a sealed tube, a mixture of tert-butyl (2S,2'S)-1,1'-(2,2'-(4,4'-(ethyne-1,2-diyl)bis(4,1-phenylene))bis(2-oxoethane-2,1-diyl))bis(azanediyl)bis(3,3-dimethyl-1-oxobutane-2,1-diyl)dicarbamate (0.3 g, 0.417 mmol) and ammonium acetate (0.322 g, 4.17 mmol) in xylene (5 mL) was heated at 130° C. for 3 hrs. The reaction mixture was diluted by EtOAc and water, the organic layer was washed with sat. NaHCO₃ and sat. NaCl, dried over anhydrous Na₂SO₄, filtered and concentrated. The residue was charged to a 40 g silica gel cartridge which was eluted with a 15 min gradient of 0-100% EtOAc/Hex. The product tert-butyl (1S,1'S)-1,1'-(5,5'-(4,4'-(ethyne-1,2-diyl)bis(4,1-phenylene))bis(1H-imidazole-5,2-diyl))bis(2,2-dimethylpropane-1,1-diyl)dicarbamate (0.12 g) was collected as a yellow solid. LC/MS (Cond. N-1): [M+H]⁺ 681.52, $R_f$=3.418 min.

Example N-3

Step f

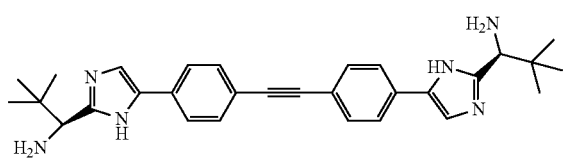 [SMILES: CC(C)(C)[C@H](N)c1ncc(-c2ccc(C#Cc3ccc(-c4cnc([C@@H](N)C(C)(C)C)[nH]4)cc3)cc2)[nH]1]

To a reaction mixture of tert-butyl (1S,1'S)-1,1'-(5,5'-(4,4'-(ethyne-1,2-diyl)bis(4,1-phenylene))bis(1H-imidazole-5,2-diyl))bis(2,2-dimethylpropane-1,1-diyl)dicarbamate (0.12 g, 0.176 mmol) in DCM (3 mL) was added 4 M hydrogen chloride in dioxane (2 ml, 8.00 mmol) and some MeOH. The reaction was stirred at rt for 4 hrs, then concentrated to dryness to yield (1S,1'S)-1,1'-(5,5'-(4,4'-(ethyne-1,2-diyl)bis(4,1-phenylene))bis(1H-imidazole-5,2-diyl))bis(2,2-dimethylpropan-1-amine), 4 HCl (0.1 g) as a yellow solid. LC/MS (Cond. N-1): [M+H]⁺ 481.32, $R_f$=3.228 min.

Example N-3

To a mixture of 3-methylbutanoic acid (0.018 g, 0.176 mmol), (1S,1'S)-1,1'-(5,5'-(4,4'-(ethyne-1,2-diyl)bis(4,1-phenylene))bis(1H-imidazole-5,2-diyl))bis(2,2-dimethylpropan-1-amine), 4 HCl (0.05 g, 0.080 mmol) and HATU (0.067 g, 0.176 mmol) in DMF (1 mL) was added DIEA (0.084 mL, 0.479 mmol). The reaction mixture was stirred at rt for 1 hr. The reaction mixture was purified by reverse phase HPLC to yield TFA salt of Example N-3 (0.008 g) as a white solid. LC/MS (Cond. N-1): [M+H]⁺ 649.54, $R_f$=3.456 min. ¹H NMR (400 MHz, MeOD) ppm 7.92 (2H, s), 7.77-7.82 (4H, m), 7.68-7.73 (4H, m), 4.95 (2H, s), 2.17-2.35 (4H, m), 1.98-2.14 (2H, m), 1.09-1.17 (18H, m), 0.91-1.00 (12H, m).

Examples N-4 to N-6

Example N-4 to N-6 (bis-TFA salt) were prepared starting from aminoketone N-3c and appropriate starting materials, obtained from commercial sources, by employing the procedures described for the synthesis of Example N-3.

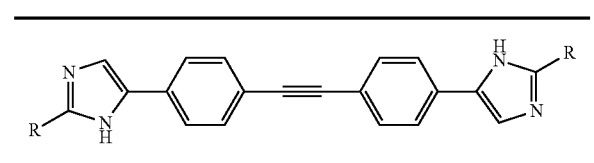

| Example | R | Analytical conditions |
|---|---|---|
| N-4 | 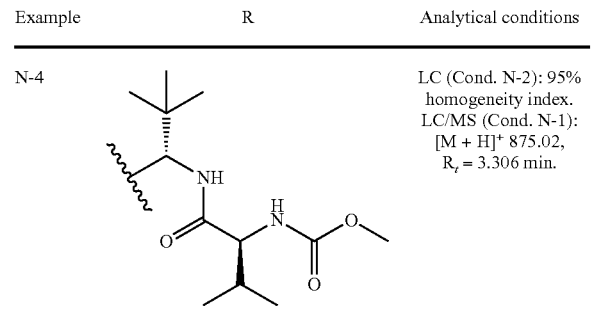 | LC (Cond. N-2): 95% homogeneity index. LC/MS (Cond. N-1): [M + H]⁺ 875.02, $R_t$ = 3.306 min. |
| N-5 | 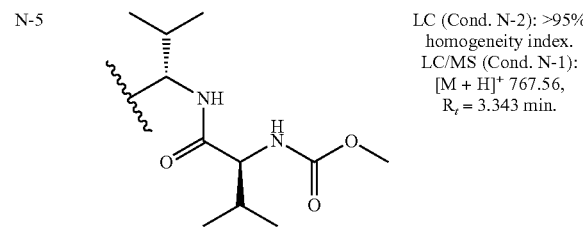 | LC (Cond. N-2): >95% homogeneity index. LC/MS (Cond. N-1): [M + H]⁺ 767.56, $R_t$ = 3.343 min. |
| N-6 | 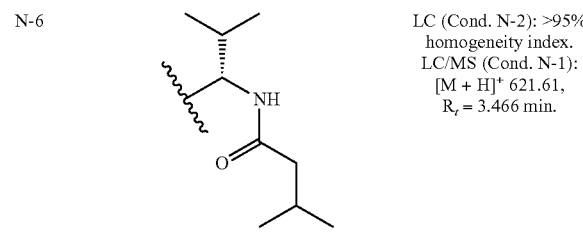 | LC (Cond. N-2): >95% homogeneity index. LC/MS (Cond. N-1): [M + H]⁺ 621.61, $R_t$ = 3.466 min. |

Examples N-7 to N-9 and P-1 to P-2

Examples N-7 to N-9 and P-1 to P-2 (bis-TFA salt) were prepared starting from 2-bromo-1-(4-(6-(2-bromoacetyl)naphthalen-2-yl)phenyl)ethanone and appropriate starting materials, obtained from commercial sources, by employing the procedures described for the synthesis of Example N-3.

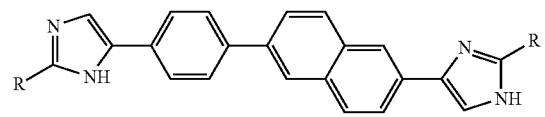

| Example | R | Analytical conditions |
|---|---|---|
| N-7 | 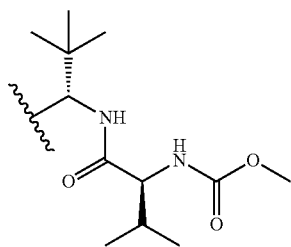 [SMILES: *[C@@H](NC(=O)[C@@H](NC(=O)OC)C(C)C)C(C)(C)C] | LC (Cond. N-2): 95% homogeneity index. LC/MS (Cond. N-1): [M + H]⁺ 821.56, $R_t$ = 3.316 min. |
| N-8 | 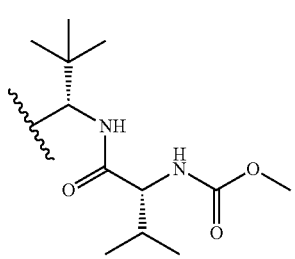 | LC (Cond. N-2): >95% homogeneity index. LC/MS (Cond. N-1): [M + H]⁺ 821.55, $R_t$ = 3.348 min. |

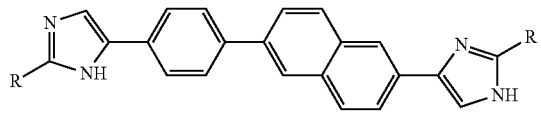

| Example | R | Analytical conditions |
|---|---|---|
| N-9 |  | LC (Cond. N-2): >95% homogeneity index. LC/MS (Cond. N-1): [M + H]⁺ 675.51, $R_t$ = 3.488 min. |
| P-1 | 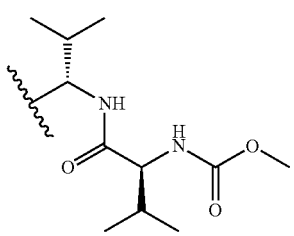 [SMILES: *[C@@H](NC(=O)[C@@H](NC(=O)OC)C(C)C)C(C)C] | LC (Cond. 2): >95% homogeneity index. LC/MS (Cond. 3): [M + H]⁺ 793.60, $R_t$ = 2.25 min. |
| P-2 | 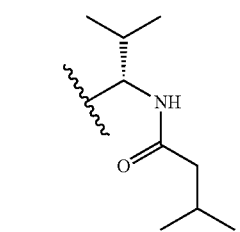 [SMILES: *[C@@H](NC(=O)CC(C)C)C(C)C] | LC (Cond. 2): >95% homogeneity index. LC/MS (Cond. 3): [M + H]⁺ 647.60, $R_t$ = 2.38 min. |

Example N-10

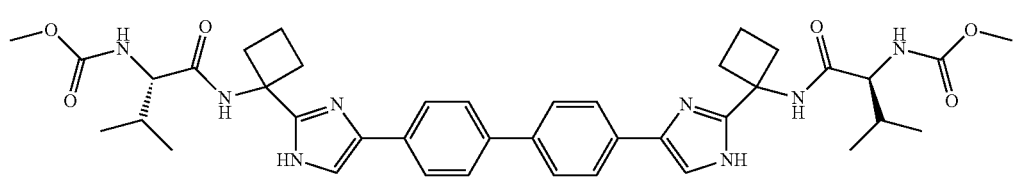

Example N-10

Step a

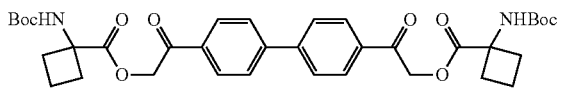

To a solution of 1,1'-(biphenyl-4,4'-diyl)bis(2-bromoethanone) (0.25 g, 0.631 mmol) and Boc-1-amino-1-cyclobutanecarboxylic acid (0.285 g, 1.326 mmol) in DCM was added DIEA (0.243 mL, 1.389 mmol). The reaction mixture was stirred at rt for 3 hrs. The reaction mixture was charged to a 40 g silica gel cartridge which was eluted with a 15 min gradient of 0-100% EtOAc in hexane. The product 2,2'-(biphenyl-4, 4'-diyl)bis(2-oxoethane-2,1-diyl)bis(1-(tert-butoxycarbonylamino)cyclobutanecarboxylate) (0.25 g) was collected as a white solid. LC/MS (Cond. N-1): [M+Na]$^+$ 687.47, R$_t$=4.37 min.

Example N-10

Step b

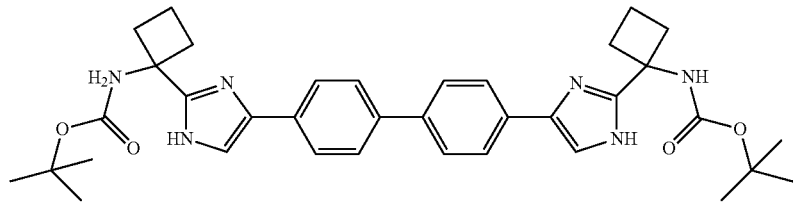 [SMILES: CC(C)(C)OC(=O)NC1(c2nc(-c3ccc(-c4ccc(-c5c[nH]c(C6(NC(=O)OC(C)(C)C)CCC6)n5)cc4)cc3)c[nH]2)CCC1]

In a sealed tube, a mixture of 2,2'-(biphenyl-4,4'-diyl)bis (2-oxoethane-2,1-diyl)bis(1-(tert-butoxycarbonylamino)cyclobutanecarboxylate) (0.25 g, 0.376 mmol) and ammonium acetate (0.290 g, 3.76 mmol) in xylene was heated at 130° C. for 4 hrs. The reaction mixture was diluted with EtOAc and water, the organic layer was washed with sat. NaHCO$_3$ and sat. NaCl, dried over anhydrous Na$_2$SO$_4$, filtered and concentrated. The residue was charged to a 40 g silica gel cartridge which was eluted with a 15 min gradient of 0-100% EtOAc/ Hex. The product tert-butyl 1,1'-(4,4'-(biphenyl-4,4'-diyl)bis (1H-imidazole-4,2-diyl))bis(cyclobutane-1,1-diyl)dicarbamate (0.1 g) was collected as a yellow solid. LC/MS (Cond. N-1): [M+H]$^+$ 625.23, R$_t$=3.201 min.

Example N-10

Step c

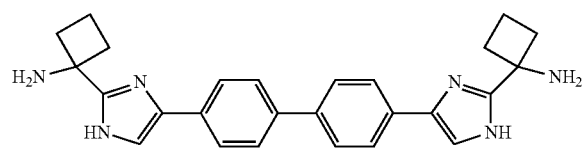 [SMILES: NC1(c2nc(-c3ccc(-c4ccc(-c5c[nH]c(C6(N)CCC6)n5)cc4)cc3)c[nH]2)CCC1]

To a reaction mixture of tert-butyl 1,1'-(4,4'-(biphenyl-4, 4'-diyl)bis(1H-imidazole-4,2-diyl))bis(cyclobutane-1,1-diyl)dicarbamate (0.1 g, 0.160 mmol) in DCM was added 4 M hydrogen chloride in dioxane (2 ml, 8.00 mmol) and MeOH (0.1 mL). The reaction was stirred at rt for 4 hrs. The reaction mixture was concentrated to dryness to yield 1,1'-(4,4'-(biphenyl-4,4'-diyl)bis(1H-imidazole-4,2-diyl))dicyclobutanamine, 4 HCl (0.08 g) as a yellow solid. LC/MS (Cond. N-1): [M+H]$^+$ 425.22, R$_t$=2.502 min.

Example N-10

To a mixture of 1,1'-(4,4'-(biphenyl-4,4'-diyl)bis(1H-imidazole-4,2-diyl))dicyclobutanamine, 4 HCl (0.034 g, 0.08 mmol), (S)-2-(methoxycarbonylamino)-3-methylbutanoic acid (0.014 g, 0.080 mmol) and HATU (0.067 g, 0.176 mmol) in DMF (1 mL) was added DIEA (0.056 mL, 0.320 mmol). The reaction mixture was stirred at rt for 1 hr. The reaction mixture was purified by reverse phase HPLC to yield TFA salt of Example N-10 (0.035 g) as a white solid. LC/MS (Cond. N-1): [M+H]$^+$ 739.51, R$_t$=3.033 min. $^1$H NMR (400 MHz, MeOD) ppm 7.80-7.96 (10H, m), 3.89 (2H, d, J=7.28 Hz), 3.64 (6H, s), 2.90-3.00 (2H, m), 2.77-2.89 (2H, m), 2.64 (4H, ddd, J=13.74, 8.60, 5.52 Hz), 2.20-2.36 (2H, m), 2.00-2.19 (4H, m), 1.02 (12H, t, J=7.03 Hz).

Examples N-11 to N-27

Example N-11 to N-27 (bis-TFA) were prepared from 1,1'-(biphenyl-4,4'-diyl)bis(2-bromoethanone) and appropriate starting materials, obtained from commercial sources, by employing the procedures described for the synthesis of Example N-10.

| Example | R | Analytical conditions |
|---|---|---|
| N-11 | ![structure] | LC (Cond. N-2): >95% homogeneity index. LC/MS (Cond. N-1): [M + H]$^+$ 593.48, R$_t$ = 3.143 min. |
| N-12 | ![structure] | LC (Cond. N-2): >95% homogeneity index. LC/MS (Cond. N-1): [M + H]$^+$ 621.54, R$_t$ = 3.191 min. |

63

-continued

| Example | R | Analytical conditions |
|---|---|---|
| N-13 | (cyclopentyl)-NH-C(=O)-CH(iPr)-NH-C(=O)-OMe | LC (Cond. N-2): >95% homogeneity index. LC/MS (Cond. N-1): [M + H]⁺ 767.56, $R_t$ = 3.095 min. |
| N-14 | (cyclopent-2-enyl)-NH-C(=O)-CH(iPr)-NH-C(=O)-OMe | LC (Cond. N-2): >95% homogeneity index. LC/MS (Cond. N-1): [M + H]⁺ 763.46, $R_t$ = 2.951 min. |
| N-15 | (cyclopent-3-enyl)-NH-C(=O)-CH(iPr)-NH-C(=O)-OMe | LC (Cond. N-2): >95% homogeneity index. LC/MS (Cond. N-1): [M + H]⁺ 763.46, $R_t$ = 2.948 min. |
| N-16 | (cyclopent-2-enyl)-NH-C(=O)-CH₂-CH(CH₃)₂ | LC (Cond. N-2): >95% homogeneity index. LC/MS (Cond. N-1): [M + H]⁺ 617.48, $R_t$ = 3.085 min. |

64

-continued

| Example | R | Analytical conditions |
|---|---|---|
| N-17 | (2,3-dihydro-1H-inden-2-yl)-NH-C(=O)-CH(iPr)-NH-C(=O)-OMe | LC (Cond. N-2): >95% homogeneity index. LC/MS (Cond. N-1): [M + H]⁺ 863.49, $R_t$ = 3.291 min. |
| N-18 | (2,3-dihydro-1H-inden-2-yl)-NH-C(=O)-CH(iPr)-NH-C(=O)-OMe | LC (Cond. N-2): >95% homogeneity index. LC/MS (Cond. N-1): [M + H]⁺ 863.43, $R_t$ = 3.415 min. |
| N-19 | (2,3-dihydro-1H-inden-2-yl)-NH-C(=O)-CH₂-CH(CH₃)₂ | LC (Cond. N-2): >95% homogeneity index. LC/MS (Cond. N-1): [M + H]⁺ 717.52, $R_t$ = 3.523 min. |
| N-20 | (cyclopropyl)-NH-C(=O)-CH(iPr)-NH-C(=O)-OMe | LC (Cond. N-2): >95% homogeneity index. LC/MS (Cond. N-1): [M + H]⁺ 711.51, $R_t$ = 2.79 min. |

-continued

| Example | R | Analytical conditions |
|---|---|---|
| N-21 | (1-isobutyramido-cyclopropyl) | LC (Cond. N-2): >95% homogeneity index. LC/MS (Cond. N-1): [M + H]+ 565.46, R$_t$ = 2.848 min. |
| N-22 | (1-(methoxycarbonyl-Val-amido)-cyclohexyl) | LC (Cond. N-2): >95% homogeneity index. LC/MS (Cond. N-1): [M + H]+ 795.58, R$_t$ = 3.07 min. |
| N-23 | (1-(methoxycarbonyl-Val-amido)-cyclohexyl) | LC (Cond. N-2): >95% homogeneity index. LC/MS (Cond. N-1): [M + H]+ 795.58, R$_t$ = 3.07 min. |
| N-24 | (1-isovaleramido-cyclohexyl) | LC (Cond. N-2): >95% homogeneity index. LC/MS (Cond. N-1): [M + H]+ 649.54, R$_t$ = 3.211 min. |

-continued

| Example | R | Analytical conditions |
|---|---|---|
| N-25 | (2-(methoxycarbonyl-Val-amido)-2-methylpropyl) | LC (Cond. N-2): >95% homogeneity index. LC/MS (Cond. N-1): [M + H]+ 715.51, R$_t$ = 2.798 min. |
| N-26 | (2-isovaleramido-2-methylpropyl) | LC (Cond. N-2): >95% homogeneity index. LC/MS (Cond. N-1): [M + H]+ 569.47, R$_t$ = 2.891 min. |
| N-27 | (1-(methoxycarbonyl-Val-amido)-cyclopentyl) | LC (Cond. N-2): >95% homogeneity index. LC/MS (Cond. 3): [M + H]+ 767.40, R$_t$ = 2.17 min. |

Example N-28

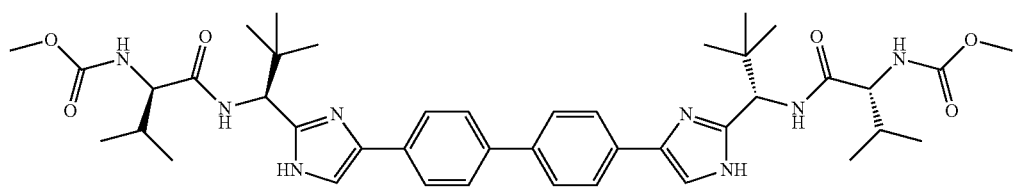

Example N-28

Step a

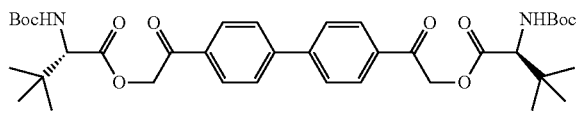 [SMILES: CC(C)(C)OC(=O)N[C@H](C(=O)OCC(=O)c1ccc(-c2ccc(C(=O)COC(=O)[C@@H](NC(=O)OC(C)(C)C)C(C)(C)C)cc2)cc1)C(C)(C)C]

To a solution of 1,1'-(biphenyl-4,4'-diyl)bis(2-bromoethanone) (0.85 g, 2.146 mmol) and (S)-2-(tert-butoxycarbonylamino)-3,3-dimethylbutanoic acid (1.042 g, 4.51 mmol) in DCM (3 mL) was added DIEA (0.825 mL, 4.72 mmol). The reaction mixture was stirred at rt for 16 hrs. The reaction was diluted with EtOAc, washed with sat. NaHCO$_3$, water and sat. NaCl, dried over anhydrous Na$_2$SO$_4$, filtered and concentrated to yield the product (2S,2'S)-2,2'-(biphenyl-4,4'-diyl)bis(2-oxoethane-2,1-diyl)bis(2-(tert-butoxycarbonylamino)-3,3-dimethylbutanoate) (1.5 g) as a pale yellow solid. LC/MS (Cond. N-1): [M+H]$^+$ 697.41, R$_t$=4.488 min.

Example N-28

Step b

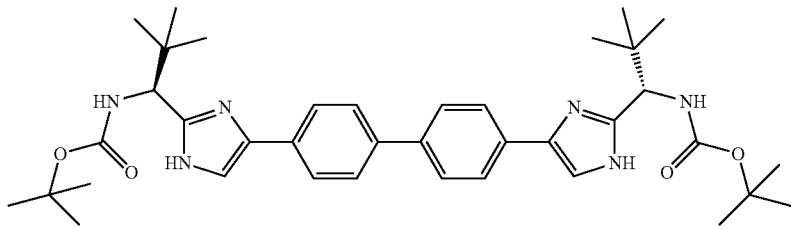 [SMILES: CC(C)(C)OC(=O)N[C@H](c1nc(-c2ccc(-c3ccc(-c4c[nH]c([C@@H](NC(=O)OC(C)(C)C)C(C)(C)C)n4)cc3)cc2)c[nH]1)C(C)(C)C]

In a sealed tube, a mixture of (2S,2'S)-2,2'-(biphenyl-4,4'-diyl)bis(2-oxoethane-2,1-diyl)bis(2-(tert-butoxycarbonylamino)-3,3-dimethylbutanoate) (1.5 g, 2.153 mmol) and ammonium acetate (1.659 g, 21.53 mmol) in xylene was heated at 130° C. for 3 hrs. The reaction mixture was diluted with EtOAc and water, the organic layer was washed with sat. NaHCO$_3$ and sat. NaCl, dried over anhydrous Na$_2$SO$_4$, filtered and concentrated. The residue was charged to 80 g silica gel cartridge which was eluted with a 15 min gradient of 0-100% EtOAc/Hex. The product tert-butyl (1S,1'S)-1,1'-(4,4'-(biphenyl-4,4'-diyl)bis(1H-imidazole-4,2-diyl))bis(2,2-dimethylpropane-1,1-diyl)dicarbamate (0.86 g) was collected as a yellow solid. LC/MS (Cond. N-1): [M+H]$^+$ 657.55, R$_t$=3.295 min.

Example N-28

Step c

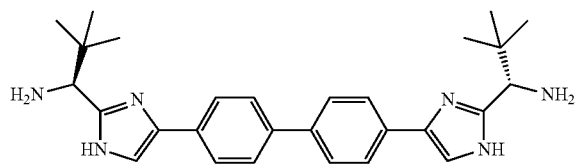 [SMILES: CC(C)(C)[C@H](N)c1nc(-c2ccc(-c3ccc(-c4c[nH]c([C@@H](N)C(C)(C)C)n4)cc3)cc2)c[nH]1]

To a reaction mixture of tert-butyl (1S,1'S)-1,1'-(4,4'-(biphenyl-4,4'-diyl)bis(1H-imidazole-4,2-diyl))bis(2,2-dimethylpropane-1,1-diyl)dicarbamate (0.86 g, 1.309 mmol) in DCM (3 mL) was added 4 M hydrogen chloride in dioxane (2 ml, 8.00 mmol) and some MeOH. The reaction was stirred at rt for 4 hrs. The reaction mixture was concentrated to dryness to yield (1S,1'S)-1,1'-(4,4'-(biphenyl-4,4'-diyl)bis(1H-imidazole-4,2-diyl))bis(2,2-dimethylpropan-1-amine), 4 HCl (0.8 g) as a yellow solid. LC/MS (Cond. N-1): [M+H]$^+$ 457.35, R$_t$=2.988 min.

Example N-28

To a mixture of (1S,1'S)-1,1'-(4,4'-(biphenyl-4,4'-diyl)bis(1H-imidazole-4,2-diyl))bis(2,2-dimethylpropan-1-amine), 4 HCl (0.07 g, 0.116 mmol), (R)-2-(methoxycarbonylamino)-3-methylbutanoic acid (0.041 g, 0.232 mmol) and HATU (0.097 g, 0.256 mmol) in DMF (1 mL) was added DIEA (0.081 mL, 0.465 mmol). The reaction mixture was stirred at rt for 1 hr. The reaction mixture was purified by reverse phase HPLC to yield TFA salt of Example N-28 (0.06 g) as a white solid. LC/MS (Cond. N-1): [M+H]$^+$ 771.71, R$_t$=3.29 min. $^1$H NMR (400 MHz, MeOD) ppm 7.79-8.02 (10H, m), 4.95 (2H, s), 4.06 (2H, d, J=7.53 Hz), 3.58-3.72 (6H, m), 2.03 (2H, dq, J=13.87, 6.84 Hz), 1.10-1.25 (18H, m), 0.89-1.08 (12H, m).

Examples N-29 to N-44 and P-3 to P-10

Examples N-29 to N-44 and P-3 to P-10 (bis-TFA salt) were prepared starting from 1,1'-(biphenyl-4,4'-diyl)bis(2-bromoethanone) and appropriate starting materials, obtained from commercial sources, by employing the procedures described for the synthesis of Example N-28.

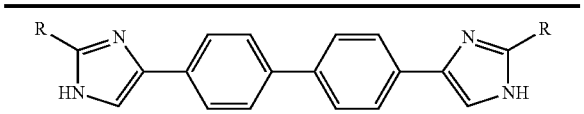

| Example | R | Analytical conditions |
|---|---|---|
| N-29 | 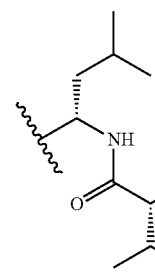 | LC (Cond. N-2): >95% homogeneity index. LC/MS (Cond. N-1): [M + H]$^+$ 771.71, R$_t$ = 3.35 min. |

-continued

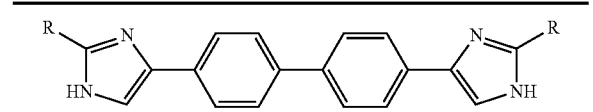

| Example | R | Analytical conditions |
|---|---|---|
| N-30 | | LC (Cond. N-2): >95% homogeneity index. LC/MS (Cond. N-1): [M + H]⁺ 771.71, $R_t$ = 3.35 min. |
| N-31 | | LC (Cond. N-2): >95% homogeneity index. LC/MS (Cond. N-1): [M + H]⁺ 625.69, $R_t$ = 3.498 min. |
| N-32 | | LC (Cond. N-2): >95% homogeneity index. LC/MS (Cond. N-1): [M + H]⁺ 771.71, $R_t$ = 3.348 min. |
| N-33 | | LC (Cond. N-2): >95% homogeneity index. LC/MS (Cond. N-1): [M + H]⁺ 771.71, $R_t$ = 3.35 min. |
| N-34 | | LC (Cond. N-2): >95% homogeneity index. LC/MS (Cond. N-1): [M + H]⁺ 625.45, $R_t$ = 3.411 min. |

-continued

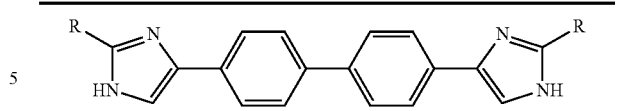

| Example | R | Analytical conditions |
|---|---|---|
| N-35 | | LC (Cond. N-2): >95% homogeneity index. LC/MS (Cond. N-1): [M + H]⁺ 771.71, $R_t$ = 3.43 min. |
| N-36 | | LC (Cond. N-2): >95% homogeneity index. LC/MS (Cond. N-1): [M + H]⁺ 625.69, $R_t$ = 3.366 min. |
| N-37 | | LC (Cond. N-2): >95% homogeneity index. LC/MS (Cond. N-1): [M + H]⁺ 687.45, $R_t$ = 2.873 min. |
| N-38 | | LC (Cond. N-2): >95% homogeneity index. LC/MS (Cond. N-1): [M + H]⁺ 687.45, $R_t$ = 2.896 min. |
| N-39 | | LC (Cond. N-2): >95% homogeneity index. LC/MS (Cond. N-1): [M + H]⁺ 541.42, $R_t$ = 3.071 min. |
| N-40 | | LC (Cond. N-2): >95% homogeneity index. LC/MS (Cond. N-1): [M + H]⁺ 715.51, $R_t$ = 2.945 min. |

-continued

| Example | R | Analytical conditions |
|---|---|---|
| N-41 | (S)-CH(Et)-NH-C(O)-CH(iPr)-NH-C(O)-OMe | LC (Cond. N-2): >95% homogeneity index. LC/MS (Cond. N-1): [M + H]⁺ 715.44, R_t = 3.023 min. |
| N-42 | (S)-CH(Et)-NH-C(O)-CH₂-CH(Me)₂ | LC (Cond. N-2): >95% homogeneity index. LC/MS (Cond. N-1): [M + H]⁺ 569.47, R_t = 3.133 min. |
| N-43 | (S)-CH(cyclopentyl)-NH-C(O)-CH(iPr)-NH-C(O)-OMe | LC (Cond. N-2): >95% homogeneity index. LC/MS (Cond. N-1): [M + H]⁺ 795.58, R_t = 3.236 min. |
| N-44 | (S)-CH(cyclopentyl)-NH-C(O)-C(Me)₃ | LC (Cond. N-2): >95% homogeneity index. LC/MS (Cond. N-1): [M + H]⁺ 649.54, R_t = 3.42 min. |
| P-3 | (S)-CH(cyclopropyl)-NH-C(O)-CH(iPr)-NH-C(O)-OMe | LC (Cond. N-2): >95% homogeneity index. LC/MS (Cond. P-1): [M + H]⁺ 739.6, R_t = 2.103 min. |

-continued

| Example | R | Analytical conditions |
|---|---|---|
| P-4 | (S)-CH(CH₂-C(Me)₃)-NH-C(O)-CH₂-CH(Me)₂ | LC (Cond. N-2): >95% homogeneity index. LC/MS (Cond. P-3): [M + H]⁺ 653.54, R_t = 3.485 min. |
| P-5 | (S)-CH(Ph)-NH-C(O)-CH₂-CH(Me)₂ | LC (Cond. N-2): >95% homogeneity index. LC/MS (Cond. P-3): [M + H]⁺ 665.49, R_t = 3.220 min. |
| P-6 | (S)-CH(CH₂Ph)-NH-C(O)-CH₂-CH(Me)₂ | LC (Cond. N-2): >95% homogeneity index. LC/MS (Cond. P-3): [M + H]⁺ 693.42, R_t = 3.431 min. |
| P-7 | (S)-CH(CH₂-naphthyl)-NH-C(O)-CH₂-CH(Me)₂ | LC (Cond. N-2): >95% homogeneity index. LC/MS (Cond. P-3): [M + H]⁺ 793.8, R_t = 3.483 min. |

73
-continued

| Example | R | Analytical conditions |
|---|---|---|
| P-8 | (naphthylmethyl-CH(NH-)-C(O)-CH2-CH(CH3)2 group) | LC (Cond. N-2): >95% homogeneity index. LC/MS (Cond. P-3): [M + H]+ 793.7, $R_t$ = 3.446 min. |
| P-9 | (C(OMe)(CH3)2-CH(NH-)-C(O)-C(CH3)3 group) | LC (Cond. N-2): >95% homogeneity index. LC/MS (Cond. P-3): [M + H]+ 657.40, $R_t$ = 3.158 min. |
| P-10 | (C(OMe)(CH3)2-CH(NH-)-C(O)-C(CH3)2-CH2F group) | LC (Cond. N-2): >95% homogeneity index. LC/MS (Cond. P-3): [M + H]+ 693.38, $R_t$ = 3.071 min. |

Examples N-45a; N-45b; N-45c

74

(1S,1'S)-1,1'-(4,4'-(biphenyl-4,4'-diyl)bis(1H-imidazole-4,2-diyl))bis(2,2-dimethylpropan-1-amine), 4 HCl was coupled with 2,2-difluorocyclopropanecarboxylic acid by employing the procedure described for the synthesis of Example N-28. The resultant three diastereomers (TFA salts) were separated by employing the following condition: Column=Phenomenex AXIA 5 u 30×100 mm column, Start % B=0; Final % B=65; Gradient time=20 min; Stop time=22 min; Flow Rate=40 mL/min; Wavelength=220 nm; Solvent A=0.1% TFA in 10% MeOH/90% water; Solvent B=0.1% TFA in 90% MeOH/10% water. Example N-45a: LC/MS (Cond. N-1): [M+H]+ 665.43, $R_t$=3.051 min. $^1$H NMR (400 MHz, MeOD) ppm 7.82-7.93 (10H, m), 4.92-4.96 (2H, m), 2.89 (2H, ddd, J=13.05, 10.79, 7.78 Hz), 1.93-2.08 (2H, m), 1.75-1.91 (2H, m), 1.03-1.23 (18H, m). Example N-45b: LC/MS (Cond. N-1): [M+H]+ 665.43, $R_t$=3.111 min. $^1$H NMR (400 MHz, MeOD) ppm 7.92 (2H, d, J=6.78 Hz), 7.83-7.90 (8H, m), 4.94-4.96 (1H, s), 4.93 (1H, s), 2.78-2.98 (2H, m), 1.89-2.08 (2H, m), 1.73-1.89 (2H, m), 1.10-1.20 (18H, m). Example N-45c: LC/MS (Cond. N-1): [M+H]+ 665.43, $R_t$=3.15 min. $^1$H NMR (400 MHz, MeOD) ppm 7.92 (2H, s), 7.84-7.92 (8H, m), 4.94 (2H, s), 2.83 (2H, ddd, J=13.05, 10.79, 7.78 Hz), 1.90-2.03 (2H, m), 1.73-1.86 (2H, m), 1.09-1.21 (18H, m).

Examples N-46 to N-66, N-111 to N-117, P-11 to P-47, Y-1 to Y-10

Examples N-46 to N-66, N-111 to N-117, P-11 to P-47, Y-1 to Y-10 (bis-TFA salt) were prepared starting from (1S,1'S)-1,1'-(4,4'-(biphenyl-4,4'-diyl)bis(1H-imidazole-4,2-diyl))bis(2,2-dimethylpropan-1-amine), 4 HCl and appropriate starting acid obtained from commercial sources or prepared in house, by employing the procedures described for the synthesis of Example N-28.

TABLE 1

N,N'-(1S,1'S)-1,1'-(4,4'-(biphenyl-4,4'-diyl)bis(1H-imidazole-4,2-diyl))bis(2,2-dimethylpropane-1,1-diyl)diamides

| Example | R | LC-MS Method | Retention Time (min) | Obs. Mass ion (M + H)+ |
|---|---|---|---|---|
| N-46 | (C(O)-C(CH3)3 group) | N-1 | 3.393 | 625.48 |

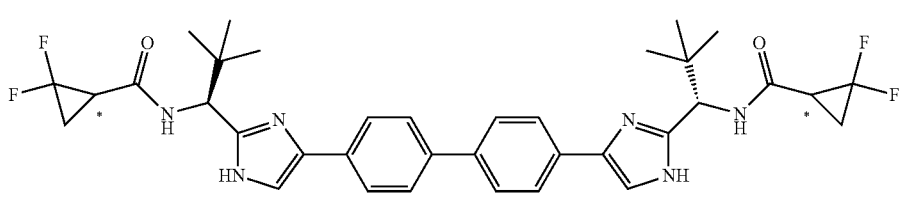 [SMILES: CC(C)(C)[C@H](NC(=O)C1CC1(F)F)c1nc(-c2ccc(-c3ccc(-c4c[nH]c([C@@H](NC(=O)C5CC5(F)F)C(C)(C)C)n4)cc3)cc2)c[nH]1]

TABLE 1-continued

N,N'-(1S,1'S)-1,1'-(4,4'-(biphenyl-4,4'-diyl)bis(1H-imidazole-4,2-diyl))bis(2,2-dimethylpropane-1,1-diyl)diamides

| Example | R | LC-MS Method | Retention Time (min) | Obs. Mass ion (M + H)+ |
|---|---|---|---|---|
| N-47 | 4,4-difluorocyclohexyl ketone | N-1 | 3.513 | 749.5 |
| N-48 | (2-fluorophenyl)acetyl | N-1 | 3.386 | 729.44 |
| N-49 | (4-fluorophenyl)acetyl | N-1 | 3.495 | 729.44 |
| N-50 | cyclohexylacetyl | N-1 | 3.701 | 705.63 |
| N-51 | 3,4-difluorobenzoyl | N-1 | 3.575 | 737.41 |
| N-52 | 1-(trifluoromethyl)cyclopentanecarbonyl | N-1 | 3.685 | 785.56 |
| N-53 | 5-chloropyridine-2-carbonyl | N-1 | 3.431 | 735.41 |
| N-54 | 4-methoxybenzoyl | N-1 | 3.345 | 725.46 |
| N-55 | 2,2,3-trimethylcyclopropanecarbonyl | N-1 | 3.77 | 705.56 |
| N-56 | 1-(4-chlorophenyl)cyclopropanecarbonyl | N-1 | 3.788 | 813.38 |
| N-57 | 1-(4-chlorophenyl)cyclobutanecarbonyl | N-1 | 4.02 | 841.39 |
| N-58 | 4,4-dimethylpentanoyl | N-1 | 3.683 | 681.59 |
| N-59 | 1-(methoxymethyl)cyclobutanecarbonyl | N-1 | 3.295 | 709.57 |
| N-60 | (S)-2-phenylpropanoyl | N-1 | 3.581 | 721.46 |
| N-61 | (R)-2-phenylpropanoyl | N-1 | 3.625 | 721.46 |
| N-62 | adamantane-1-carbonyl | N-1 | 4.025 | 781.65 |

TABLE 1-continued

N,N'-(1S,1'S)-1,1'-(4,4'-(biphenyl-4,4'-diyl)bis(1H-imidazole-4,2-diyl))bis(2,2-dimethylpropane-1,1-diyl)diamides

| Example | R | LC-MS Method | Retention Time (min) | Obs. Mass ion (M + H)+ |
|---|---|---|---|---|
| N-63 | (adamantyl-CH2-C(=O)-) | N-1 | 4.091 | 809.67 |
| N-64 | (5-methylthiophene-2-carbonyl) | N-1 | 3.533 | 705.36 |
| N-65 | (5-chlorothiophene-2-carbonyl) | N-1 | 3.69 | 745.02 |
| N-66 | (2,6-difluoro... 2-F,6-Cl-benzoyl) | N-1 | 3.286 | 769.12 |
| N-111A | (4,4-difluorocyclopentyl-C(=O)-) symmetrical diastereomer-1 | N-1 | 3.346 | 721.64 |
| N-111B | (4,4-difluorocyclopentyl-C(=O)-) symmetrical diastereomer-2 | N-1 | 3.40 | 721.63 |
| N-112 | (4,4-difluorocyclohexyl-CH2-C(=O)-) | N-1 | 3.591 | 777.71 |
| N-113 | (3-methyloxetan-3-yl-C(=O)-) | N-1 | 3.053 | 653.29 |
| N-114 | (5-CF3-thiophene-2-carbonyl) | N-1 | 3.631 | 813.12 |
| N-115 | (2-fluoro-2-methylpropanoyl) | N-1 | 3.12 | 633.51 |
| N-116 | (2-(2,2-difluoroethoxy)-2-methylpropanoyl) | N-1 | 3.323 | 757.55 |
| N-117 | (3-methylbutanoyl) | N-1 | 3.366 | 625.44 |
| P-11 | (2,2-dimethylbutanoyl) | P-3 | 3.443 | 653.47 |
| P-12 | (2-methoxymethyl-2-methylpropanoyl) | P-3 | 3.246 | 685.43 |
| P-13 | (2-methoxy-2-methylpropanoyl) | P-3 | 3.023 | 657.45 |
| P-14 | (1-(fluoromethyl)cyclopropanecarbonyl) | P-3 | 3.073 | 657.41 |
| P-15 | ((R)-2-methoxy-2-phenylacetyl) | P-3 | 3.358 | 753.37 |

TABLE 1-continued

N,N'-(1S,1'S)-1,1'-(4,4'-(biphenyl-4,4'-diyl)bis(1H-imidazole-4,2-diyl))bis(2,2-dimethylpropane-1,1-diyl)diamides

| Example | R | LC-MS Method | Retention Time (min) | Obs. Mass ion (M + H)+ |
|---|---|---|---|---|
| P-16 | benzo[d]isoxazol-3-ylmethyl ketone | P-3 | 3.283 | 775.34 |
| P-17 | 3,3-difluorocyclobutyl ketone | P-3 | 3.238 | 693.28 |
| P-18 | (S)-methoxy(phenyl) ketone | P-3 | 3.518 | 753.39 |
| P-19 | 3-fluoro-2,2-dimethylpropyl ketone | P-3 | 2.995 | 661.23 |
| P-20 | 4,4-difluoro-1-methylcyclohexyl ketone | P-3 | 3.273 | 777.20 |
| P-21 | 1-methoxycyclobutyl ketone | P-3 | 3.305 | 681.86 |
| P-22 | 3-fluoropyridin-2-yl ketone | P-3 | 3.091 | 703.13 |
| P-23 | 2-fluorophenyl ketone | P-3 | 3.328 | 701.14 |
| P-24 | 3-fluoropyridin-4-yl ketone | P-3 | 3.156 | 703.37 |
| P-25 | 2-(difluoromethoxy)phenyl ketone | P-3 | 3.361 | 797.49 |
| P-26 | 2-ethoxy-2-methylpropyl ketone | P-3 | 3.348 | 685.45 |
| P-27 | 1-methoxycyclopropyl ketone | P-3 | 3.171 | 653.31 |
| P-28 | 2-methoxyphenyl ketone | P-3 | 3.298 | 725.38 |
| P-29 | 2-ethoxyphenyl ketone | P-3 | 3.393 | 753.43 |
| P-30 | 1-(trifluoromethyl)cyclopropyl ketone | P-3 | 3.395 | 729.34 |
| P-31 | 3,3,3-trifluoro-2,2-dimethylpropyl ketone | P-3 | 3.498 | 733.36 |
| P-32 | 3,3-difluoro-2,2-dimethylpropyl ketone | P-3 | 3.371 | 697.40 |

TABLE 1-continued

N,N'-(1S,1'S)-1,1'-(4,4'-(biphenyl-4,4'-diyl)bis(1H-imidazole-4,2-diyl))bis(2,2-dimethylpropane-1,1-diyl)diamides

| Example | R | LC-MS Method | Retention Time (min) | Obs. Mass ion (M + H)+ |
|---|---|---|---|---|
| P-33 | 1-hydroxy-4,4-difluorocyclohexyl carbonyl | P-3 | 3.331 | 781.42 |
| P-34 | 1-methoxy-4,4-difluorocyclohexyl carbonyl | P-3 | 3.531 | 809.46 |
| P-35 | 4,4-difluoro-1-methylpyrrolidin-2-yl carbonyl | P-3 | 3.141 | 751.44 |
| P-36 | 1-methylpyrrolidin-2-yl carbonyl | P-3 | 2.860 | 679.50 |
| P-37 | 1-(hydroxymethyl)-4,4-difluorocyclohexyl carbonyl | P-3 | 3.375 | 809.50 |
| P-38 | 1-(fluoromethyl)-4,4-difluorocyclohexyl carbonyl | P-3 | 3.556 | 813.48 |
| P-39 | 1-fluoro-4,4-difluorocyclohexyl carbonyl | P-3 | 3.486 | 785.44 |
| P-40 | 4-fluorobicyclo[2.2.2]octan-1-yl carbonyl | P-3 | 3.64 | 765.51 |
| P-41 | 1-(methoxymethyl)-4,4-difluorocyclohexyl carbonyl | P-3 | 3.565 | 837.71 |
| P-42 | difluoro-octahydropentalenyl carbonyl | P-3 | 3.620 | 801.60 |
| P-43 | difluoro-octahydropentalenyl carbonyl (isomer) | P-3 | 3.676 | 801.68 |
| P-44 | difluorobicyclic carbonyl | P-3 | 3.741 | 801.68 |
| P-45 | difluorobicyclic carbonyl (isomer) | P-3 | 3.701 | 801.68 |
| P-46 | difluorospiro[3.3]heptanyl carbonyl | P-3 | 3.565 | 773.60 |
| P-47 | 1-methylcyclohexyl carbonyl | P-3 | 3.793 | 705.71 |
| Y-1 | isopropoxy pivaloyl | YT-2 | 3.37 | 713.5 |
| Y-2 | 2,2,2-trifluoroethoxy pivaloyl | YT-2 | 3.3 | 793.42 |
| Y-3 | 2-fluoroethoxy pivaloyl | YT-2 | 3.015 | 721.49 |

TABLE 1-continued
N,N'-(1S,1'S)-1,1'-(4,4'-(biphenyl-4,4'-diyl)bis(1H-imidazole-4,2-diyl))bis(2,2-dimethylpropane-1,1-diyl)diamides
| Example | R | LC-MS Method | Retention Time (min) | Obs. Mass ion (M + H)+ |
|---|---|---|---|---|
| Y-4 | | YT 1 | 2.81 | 817.52 |
| Y-5 | symmetrical diastereomer-1 | YT-1 | 2.40 | 681.49 |
| Y-6 | symmetrical diastereomer-2 | YT-1 | 2.39 | 681.49 |
| Y-7 | | YT-1 | 2.23 | 745.5 |
| Y-8 | | YT-1 | 2.41 | 761.55 |
| Y-9 | | YT-1 | 2.71 | 745.59, |
| Y-10 | | YT-1 | 4.21 | 745.6 |
Example N-67
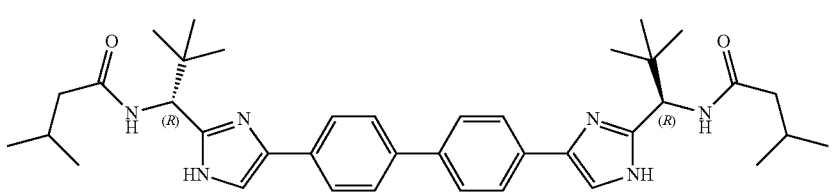

Example N-67 (bis-TFA salt) was prepared starting from 1,1'-(biphenyl-4,4'-diyl)bis(2-bromoethanone) and appropriate starting materials, obtained from commercial sources, by employing the procedures described for the synthesis of Example N-28. LC/MS (Cond. N-1): [M+H]⁺ 625.44, $R_t$=3.37 min. ¹H NMR (400 MHz, MeOD) ppm 7.92 (2H, s), 7.83-7.90 (8H, m), 4.98 (2H, s), 2.17-2.37 (4H, m), 1.99-2.15 (2H, m), 1.09-1.20 (18H, m), 0.91-1.00 (12H, m).

Example N-68

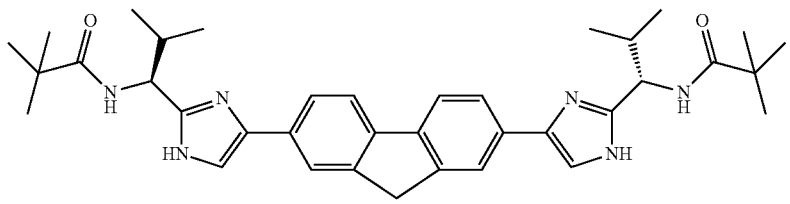 [SMILES: CC(C)[C@H](NC(=O)C(C)(C)C)c1nc(-c2ccc3c(c2)Cc2cc(-c4c[nH]c([C@@H](NC(=O)C(C)(C)C)C(C)C)n4)ccc2-3)c[nH]1]

Example N-68

Step a

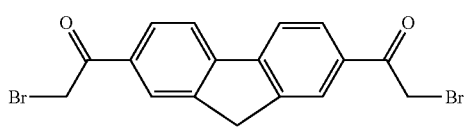

To a solution of 1,1'-(9H-fluorene-2,7-diyl)diethanone (0.5 g, 1.998 mmol) in AcOH was added a solution of Br₂ (0.226 mL, 4.39 mmol) in AcOH (1 mL) dropwise. The reaction mixture was stirred at rt for 16 hrs. The reaction mixture was diluted with EtOAc, washed with sat. Na₂SO₃, water and sat. NaCl. The solid was filtered, washed with DCM and dried to yield 1,1'-(9H-fluorene-2,7-diyl)bis(2-bromoethanone) (0.57 g).

Example N-68

Step b

To a solution of 1,1'-(9H-fluorene-2,7-diyl)bis(2-bromoethanone) (0.57 g) and (S)-2-(tert-butoxycarbonylamino)-3-methylbutanoic acid (0.637 g, 2.93 mmol) in DCM and DMF was added DIEA (0.537 mL, 3.07 mmol). The reaction mixture was stirred at rt for 6 hrs. The reaction was diluted with EtOAc, washed with sat. NaHCO₃, water and sat. NaCl, dried over anhydrous Na₂SO₄, filtered and concentrated to yield a pale yellow solid. The crude product was dissolved in a small amount of methylene chloride and charged to a 40 g silica gel cartridge which was eluted with a 20 min gradient of 0-80% EtOAc in hexane. (2S,2'S)-2,2'-(9H-fluorene-2,7-diyl)bis(2-oxoethane-2,1-diyl)bis(2-(tert-butoxycarbonylamino)-3-methylbutanoate) (0.75 g) was collected as a pale yellow solid. LC/MS (Cond. N-1): [M+Na]⁺703.40, $R_t$=4.393 min.

Example N-68

Step c

In a sealed tube, a mixture of (2S,2'S)-2,2'-(9H-fluorene-2,7-diyl)bis(2-oxoethane-2,1-diyl)bis(2-(tert-butoxycarbonylamino)-3-methylbutanoate) (0.75 g, 1.102 mmol) and ammonium acetate (0.849 g, 11.02 mmol) in xylene was heated at 130° C. for 3 hrs. The reaction mixture was diluted by EtOAc and water, the organic layer was washed with sat. NaHCO$_3$ and sat. NaCl, dried over anhydrous Na$_2$SO$_4$, filtered and concentrated. The residue was dissolved in methylene chloride and charged to a 40 g silica gel cartridge which was eluted with a 15 min gradient of 0-100% EtOAc/Hex and 100% EtOAc for 10 min. Tert-butyl (1S,1'S)-1,1'-(4,4'-(9H-fluorene-2,7-diyl)bis(1H-imidazole-4,2-diyl))bis(2-methylpropane-1,1-diyl)dicarbamate (0.28 g) was collected as a yellow solid. LC/MS (Cond. N-1): [M+H]$^+$ 641.2, R$_t$=3.38 min.

Example N-68

Step d

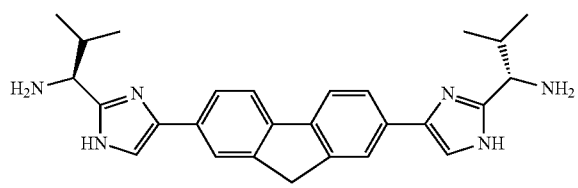 [SMILES: CC(C)[C@H](N)c1nc(-c2ccc3c(c2)Cc2cc(-c4c[nH]c([C@@H](N)C(C)C)n4)ccc2-3)c[nH]1]

To a reaction mixture of tert-butyl (1S,1'S)-1,1'-(4,4'-(9H-fluorene-2,7-diyl)bis(1H-imidazole-4,2-diyl))bis(2-methylpropane-1,1-diyl)dicarbamate (0.28 g, 0.437 mmol) in DCM was added 4 M hydrogen chloride in dioxane (2 ml) and MeOH (0.1 mL). The reaction was stirred at rt for 3 hrs. The reaction mixture was concentrated to dryness. (1S,1'S)-1,1'-(4,4'-(9H-fluorene-2,7-diyl)bis(1H-imidazole-4,2-diyl))bis(2-methylpropan-1-amine), 4 HCl (0.26 g) was collected as a yellow solid. LC/MS (Cond. N-1): [M+H]$^+$ 441.13, R$_t$=2.756 min.

Example N-68

To a mixture of (1S,1'S)-1,1'-(4,4'-(9H-fluorene-2,7-diyl)bis(1H-imidazole-4,2-diyl))bis(2-methylpropan-1-amine), 4 HCl (0.042 g), pivalic acid (0.015 g, 0.143 mmol) and HATU (0.060 g, 0.158 mmol) in DMF (Volume: 1 mL) was added DIEA (0.075 mL, 0.430 mmol). The reaction mixture was stirred at rt for 1 hr. The reaction mixture was purified by reverse phase HPLC to yield TFA salt of Example N-68 (0.033 g). LC/MS (Cond. N-1): [M+H]$^+$ 609.15, R$_t$=3.305 min. $^1$H NMR (400 MHz, MeOD) ppm 8.01 (1H, s), 7.98 (3H, d, J=5.0 Hz), 7.88 (2H, s), 7.78 (2H, dd, J=8.0, 1.5 Hz), 4.89 (2H, dt, J=9.8, 3.5 Hz), 4.06 (2H, s), 2.36-2.50 (2H, m, J=9.7, 6.6, 6.6, 6.6, 6.6 Hz), 1.21-1.27 (18H, m), 1.16 (6H, d, J=6.5 Hz), 0.92 (6H, d, J=6.8 Hz).

Example N-69 to N-73

Example N-69 to N-73 (TFA salt) were prepared starting from diamine 68d and appropriate acids by employing the procedures described for the synthesis of Example 68.

| Example | R | Analytical conditions |
|---|---|---|
| N-69 | ![1-methylcyclohexyl carbonyl] | LC (Cond. N-2): 95% homogeneity index. LC/MS (Cond. N-1): [M + H]$^+$ 689.14, R$_t$ = 3.726 min. |
| N-70 | ![4,4-difluorocyclohexyl carbonyl] | LC (Cond. N-2): >95% homogeneity index. LC/MS (Cond. N-1): [M + H]$^+$ 733.2, R$_t$ = 3.398 min. |
| N-71 | ![3,3-difluorocyclobutyl carbonyl] | LC (Cond. N-2): >95% homogeneity index. LC/MS (Cond. N-1): [M + H]$^+$ 677.19, R$_t$ = 3.235 min. |
| N-72 | ![1-methylcyclopentyl carbonyl] | LC (Cond. N-2): >95% homogeneity index. LC/MS (Cond. N-1): [M + H]$^+$ 661.23, R$_t$ = 3.55 min. |
| N-73 | ![2-fluoro-5-chlorobenzoyl] | LC (Cond. N-2): >95% homogeneity index. LC/MS (Cond. N-1): [M + H]$^+$ 753.04, R$_t$ = 3.551 min. |

Example N-74

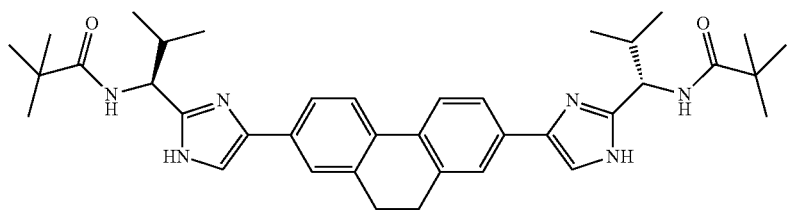 [SMILES: CC(C)[C@H](NC(=O)C(C)(C)C)c1nc(-c2ccc3c(c2)CCc2cc(-c4c[nH]c([C@@H](NC(=O)C(C)(C)C)C(C)C)n4)ccc2-3)c[nH]1]

Example N-74

Step a

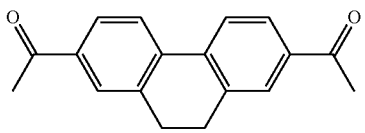

To a suspension of aluminum chloride (0.925 g, 6.94 mmol) and acetyl chloride (4.93 mL, 69.4 mmol) cooled to 0° C. was dropwise added 9,10-dihydrophenanthrene (0.5 g, 2.77 mmol) in DCM (5 mL). The reaction mixture was stirred at 0° C. for 30 min. The resulting mixture was warmed to rt and stirred at rt for 2 hrs. The reaction mixture was quenched by pouring onto ice. The aqueous phase was extracted with EtOAc. The organic phase was washed with 1 N NaOH, sat. NaCl, dried over anhydrous Na$_2$SO$_4$, filtered and concentrated to yield a oil. The crude product was dissolved in methylene chloride and charged to a 40 g silica gel cartridge which was eluted with a 20 min gradient of 0-100% EtOAc in hexane. 1,1'-(9,10-dihydrophenanthrene-2,7-diyl)diethanone (0.64 g) was collected as a yellow solid. LC/MS (Cond. N-1): [M+H]$^+$ 265.08, R$_t$=3.641 min. $^1$H NMR (400 MHz, CHLOROFORM-d) δ ppm 7.73-7.90 (6H, m), 2.90 (4H, d, J=2.26 Hz), 2.55-2.64 (6H, m).

Example N-74

Step b

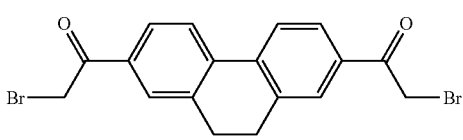

To a solution of 1,1'-(9,10-dihydrophenanthrene-2,7-diyl) diethanone (0.64 g) in AcOH (4 mL) was added a solution of Br$_2$ (0.274 mL) in AcOH (1 mL) dropwise. The reaction mixture was stirred at rt for 16 hrs. The reaction mixture was diluted with EtOAc, washed with sat. Na$_2$SO$_3$, water and sat. NaCl. The solid which precipitated in the organic phase was filtered, washed with DCM and dried to yield 1,1'-(9,10-dihydrophenanthrene-2,7-diyl)bis(2-bromoethanone) (0.5 g).

Example N-74

Step c

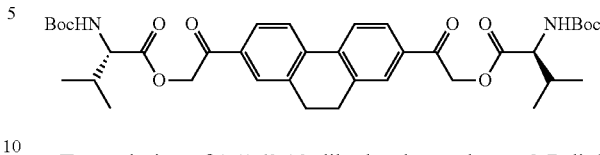

To a solution of 1,1'-(9,10-dihydrophenanthrene-2,7-diyl) bis(2-bromoethanone) (0.5 g) and (S)-2-((tert-butoxycarbonyl)amino)-3-methylbutanoic acid (0.540 g, 2.487 mmol) in DCM was added DIEA (0.455 mL). The reaction mixture was stirred at rt for 6 hrs. The reaction was diluted with EtOAc, washed with sat. NaHCO$_3$, water and sat. NaCl, dried over anhydrous Na$_2$SO$_4$, filtered and concentrated to yield a pale yellow solid. The crude product was dissolved in methylene chloride and charged to a 40 g silica gel cartridge which was eluted with a 20 min gradient from 0-80% EtOAc in hexane. (2S,2'S)-2,2'-(9,10-dihydrophenanthrene-2,7-diyl)bis(2-oxoethane-2,1-diyl)bis(2-(tert-butoxycarbonylamino)-3-methylbutanoate) (0.68 g) was collected as a pale yellow solid: LC/MS (Cond. N-1): [M+H]$^+$ 717.46, R$_t$=4.436 min.

Example N-74

Step d

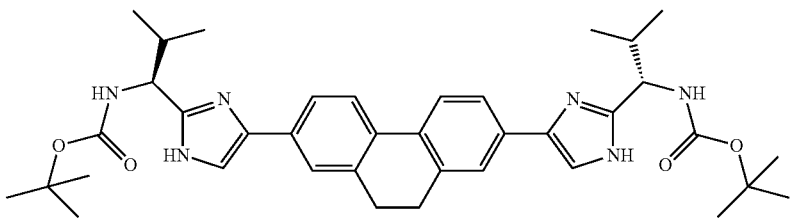 [SMILES: CC(C)[C@H](NC(=O)OC(C)(C)C)c1nc(-c2ccc3c(c2)CCc2cc(-c4c[nH]c([C@@H](NC(=O)OC(C)(C)C)C(C)C)n4)ccc2-3)c[nH]1]

In a sealed tube, a mixture of (2S,2'S)-2,2'-(9,10-dihydrophenanthrene-2,7-diyl)bis(2-oxoethane-2,1-diyl)bis(2-(tert-butoxycarbonylamino)-3-methylbutanoate) (0.68 g) and ammonium acetate (0.754 g) in xylene was heated at 130° C. for 6 hrs. The reaction mixture was diluted with EtOAc and water, the organic layer was washed with sat. NaHCO$_3$ and sat. NaCl, dried over anhydrous Na$_2$SO$_4$, filtered and concentrated. The residue was dissolved in methylene chloride and charged to a 40 g silica gel cartridge and eluted with 0-100% EtOAc in hexane under 18 min gradient. Tert-butyl (1S,1'S)-1,1'-(4,4'-(9,10-dihydrophenanthrene-2,7-diyl)bis(1H-imidazole-4,2-diyl))bis(2-methylpropane-1,1-diyl)dicarbamate (0.25 g) was collected as a yellow solid. LC/MS (Cond. N-1): [M+H]$^+$ 655.55, R$_t$=3.381 min.

Example N-74

Step e

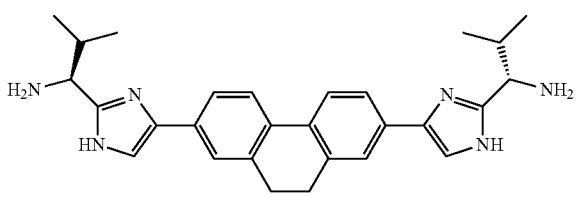 [SMILES: CC(C)[C@H](N)c1nc(-c2ccc3c(c2)CCc2cc(-c4c[nH]c([C@@H](N)C(C)C)n4)ccc2-3)c[nH]1]

To a reaction mixture of tert-butyl (1S,1'S)-1,1'-(4,4'-(9,10-dihydrophenanthrene-2,7-diyl)bis(1H-imidazole-4,2-diyl))bis(2-methylpropane-1,1-diyl)dicarbamate (0.25 g) in DCM (2 mL) was added 4 M hydrogen chloride in dioxane (2 ml) and MeOH (0.1 mL). The reaction was stirred at rt for 3 hrs. The reaction mixture was concentrated to dryness to yield (1S,1'S)-1,1'-(4,4'-(9,10-dihydrophenanthrene-2,7-diyl)bis

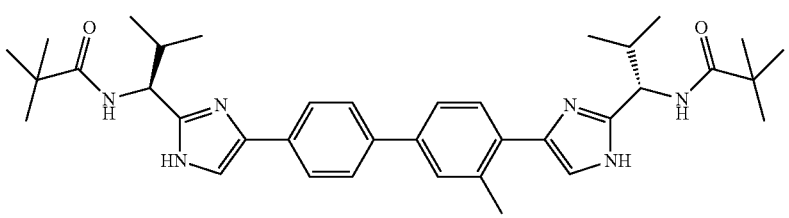 [SMILES: Cc1cc(-c2ccc(-c3c[nH]c([C@@H](NC(=O)C(C)(C)C)C(C)C)n3)cc2)ccc1-c1c[nH]c([C@@H](NC(=O)C(C)(C)C)C(C)C)n1]

(1H-imidazole-4,2-diyl))bis(2-methylpropan-1-amine), 4 HCl (0.24 g) was collected as a yellow solid. LC/MS (Cond. N-1): [M+H]$^+$ 443.23, $R_t$=2.706 min.

Example N-74

To a mixture of (1S,1'S)-1,1'-(4,4'-(9,10-dihydrophenanthrene-2,7-diyl)bis(1H-imidazole-4,2-diyl))bis(2-methylpropan-1-amine), 4 HCl (0.038 g), pivalic acid (0.013 g) and HATU (0.053 g) in DMF (1 mL) was added DIEA (0.066 mL). The reaction mixture was stirred at rt for 1 hr. The reaction mixture was purified by reverse phase HPLC to yield TFA salt of Example N-74 (0.032 g). LC/MS (Cond. N-1): [M+H]$^+$ 623.55, $R_t$=3.355 min. $^1$H NMR (400 MHz, methanol-d$_4$) ppm 8.01 (2H, d, J=8.03 Hz), 7.91 (2H, s), 7.73-7.71 (4H, m), 4.84-4.88 (2H, m), 3.01 (4H, s), 2.41 (2H, dt, J=9.54, 6.65 Hz), 1.22-1.28 (18H, m), 1.16 (6H, d, J=6.53 Hz), 0.92 (6H, d, J=6.78 Hz).

Example N-75 to N-76

Example N-75 to N-76 (TFA salt) were prepared starting from diamine N74e and appropriate acids by employing the procedures described for the synthesis of Example N-74.

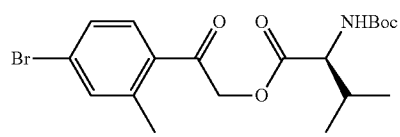 [SMILES: Cc1cc(Br)ccc1C(=O)COC(=O)[C@@H](NC(=O)OC(C)(C)C)C(C)C]

| Example | R | Analytical conditions |
|---|---|---|
| N-75 | | LC (Cond. N-2): >95% homogeneity index. LC/MS (Cond. N-1): [M + H]$^+$ 631.5, $R_t$ = 3.14 min. |
| N-76 | | LC (Cond. N-2): >95% homogeneity index. LC/MS (Cond. N-1): [M + H]$^+$ 767.36, $R_t$ = 3.518 min. |

Example N-77

Example N-77

Step a

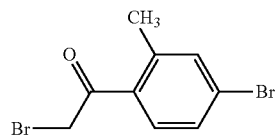

To a solution of 1-(4-bromo-2-methylphenyl)ethanone (0.525 g, 2.464 mmol) in THF was added phenyltrimethylammonium tribromide (0.926 g, 2.464 mmol). The reaction mixture was stirred at rt for 16 hrs. The reaction mixture was filtered through a plug of diatomaceous earth (Celite®), and the filtrate was concentrated to yield 2-bromo-1-(4-bromo-2-methylphenyl)-ethanone (0.61 g) as a white solid. LC/MS (Cond. N-1): [M+H]$^+$ 290.84, $R_t$=3.88 min.

Example N-77

Step b

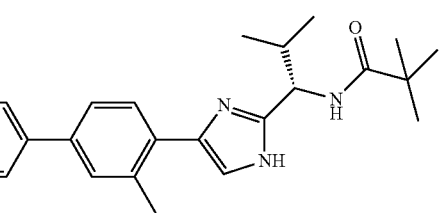

To a solution of 2-bromo-1-(4-bromo-2-methylphenyl)ethanone (0.61 g, 2.089 mmol) and (S)-2-(tert-butoxycarbonylamino)-3-methylbutanoic acid (0.454 g, 2.089 mmol) in DCM was added DIEA (0.474 mL). The reaction mixture was stirred at rt for 16 hrs. The crude product was dissolved in a small amount of methylene chloride and charged to a 80 g silica gel cartridge which was eluted with a 20 min gradient of 0-45% EtOAc in hexane. (S)-2-(4-bromo-2-methylphenyl)-2-oxoethyl 2-(tert-butoxycarbonylamino)-3-methylbutanoate (0.9 g) was collected as a pale yellow oil. LC/MS (Cond. N-1): [M+H]$^+$ 451.92, $R_t$=4.145 min.

Example N-77

Step c

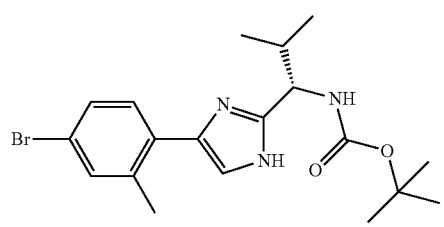 [SMILES: Cc1cc(Br)ccc1-c1c[nH]c([C@@H](NC(=O)OC(C)(C)C)C(C)C)n1]

In a sealed tube, a mixture of (S)-2-(4-bromo-2-methylphenyl)-2-oxoethyl 2-(tert-butoxycarbonylamino)-3-methylbutanoate (1.0 g, 2.335 mmol) and ammonium acetate (1.8 g, 23.35 mmol) in xylene was heated at 130° C. for 3 hrs. The reaction was diluted with EtOAc, washed with sat. NaHCO₃, water and sat. NaCl, dried over anhydrous Na₂SO₄, filtered and concentrated to yield a yellow oil. The residue was dissolved in methylene chloride and charged to a 80 g silica gel cartridge which was eluted with a 20 min gradient of 0-80% EtOAc/Hex. (S)-tert-butyl 1-(4-(4-bromo-2-methylphenyl)-1H-imidazol-2-yl)-2-methylpropylcarbamate (0.52 g) was collected as a yellow solid. LC/MS (Cond. N-1): [M+H]⁺ 408.98, R$_t$=3.296 min.

Example N-77

Step d

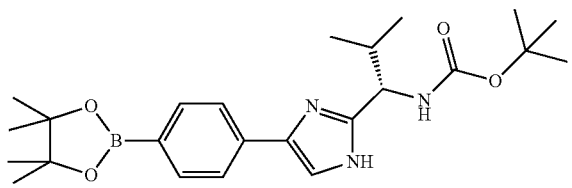 [SMILES: CC(C)[C@H](NC(=O)OC(C)(C)C)c1nc(-c2ccc(B3OC(C)(C)C(C)(C)O3)cc2)c[nH]1]

To a solution of 4,4,4',4',5,5,5',5'-octamethyl-2,2'-bi(1,3,2-dioxaborolane) (0.747 g) and (S)-tert-butyl 1-(4-(4-bromo-2-methylphenyl)-1H-imidazol-2-yl)-2-methylpropylcarbamate (0.58 g, prepared from 2-bromo-1-(4-bromophenyl)ethanon by employing the procedures described in step b-c) in dioxane was added potassium acetate (0.361 g), it was degassed for 5 mins and tetrakis(triphenylphosphine)palladium(0) (0.085 g) was added. The reaction mixture was heated at 85° C. for 14 hours. The reaction mixture was diluted with EtOAc, washed with sat. NaHCO₃, water, sat. NaCl, dried over anhydrous Na₂SO₄, filtered and concentrated to yield an oil. The crude product was dissolved in methylene chloride and charged to a 40 g silica gel cartridge which was eluted with a 20 min gradient of 0-100% EtOAc in hexane. (S)-tert-butyl 2-methyl-1-(4-(4-(4,4,5,5-tetramethyl-1,3,2-dioxaborolan-2-yl)phenyl)-1H-imidazol-2-yl)propylcarbamate (0.62 g) was collected as a yellow solid. LC/MS (Cond. N-1): [M+H]⁺ 442.19, R$_t$=3.53 min.

Example N-77

Step e

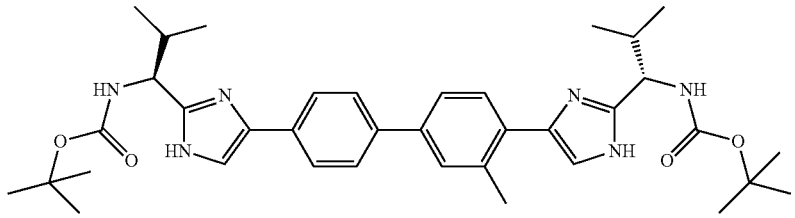 [SMILES: Cc1cc(-c2ccc(-c3c[nH]c([C@@H](NC(=O)OC(C)(C)C)C(C)C)n3)cc2)ccc1-c1c[nH]c([C@@H](NC(=O)OC(C)(C)C)C(C)C)n1]

To a solution of (S)-tert-butyl 2-methyl-1-(4-(4-(4,4,5,5-tetramethyl-1,3,2-dioxaborolan-2-yl)phenyl)-1H-imidazol-2-yl)propylcarbamate (0.562 g) and (S)-tert-butyl 1-(4-(4-bromo-2-methylphenyl)-1H-imidazol-2-yl)-2-methylpropylcarbamate (0.52 g) in DME and water was added NaHCO₃ (0.535 g), it was degassed for 5 mins and tetrakis(triphenylphosphine)palladium(0) (0.074 g) was added. The reaction mixture was heated at 80° C. for 16 hours. The reaction mixture was diluted with EtOAc, washed with sat. NaHCO₃, water, sat. NaCl, dried over anhydrous Na₂SO₄, filtered and concentrated to yield a solid. The crude product was dissolved in methylene chloride and charged to 80 g silica gel cartridge which was eluted with a 20 min gradient from 0-100% EtOAc in hexane. Tert-butyl (1S,1'S)-1,1'-(4,4'-(3-methylbiphenyl-4,4'-diyl)bis(1H-imidazole-4,2-diyl))bis(2-methylpropane-1,1-diyl)dicarbamate (0.2 g) was collected as a yellow solid. LC/MS (Cond. N-1): [M+H]⁺ 643.31, R$_t$=3.036 min.

Example N-77

Step f

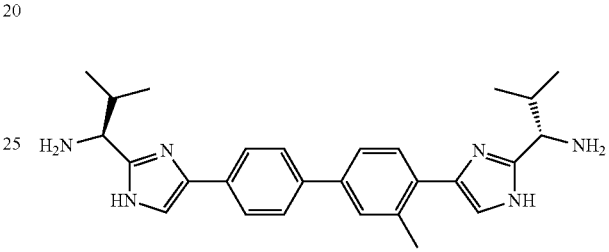

To a solution of tert-butyl (1S,1'S)-1,1'-(4,4'-(3-methylbiphenyl-4,4'-diyl)bis(1H-imidazole-4,2-diyl))bis(2-methylpropane-1,1-diyl)dicarbamate (0.2 g, 0.311 mmol) in DCM (2 mL) was added 4 M hydrogen chloride in dioxane (2 ml) and MeOH (0.1 mL). The reaction was stirred at rt for 3 h and concentrated to dryness. (1S,1'S)-1,1'-(4,4'-(3-methylbiphenyl-4,4'-diyl)bis(1H-imidazole-4,2-diyl))bis(2-methylpropan-1-amine), 4 HCl (0.2 g) was collected as a yellow solid. LC/MS (Cond. N-1): [M+H]⁺ 443.23, R$_t$=2.706 min.

Example N-77

To a mixture of (1S,1'S)-1,1'-(4,4'-(3-methylbiphenyl-4,4'-diyl)bis(1H-imidazole-4,2-diyl))bis(2-methylpropan-1-amine), 4 HCl (0.05 g), pivalic acid (0.017 g) and HATU (0.071 g) in DMF was added DIEA (0.089 mL). The reaction mixture was stirred at rt for 1 hr. The compound was purified by reverse phase HPLC to yield TFA salt of Example N-77 (0.028 g). LC/MS (Cond. N-1): [M+H]⁺ 611.29, R$_t$=2.98 min. ¹H NMR (400 MHz, MeOD) ppm 8.04 (1H, dd, J=18.9, 6.7 Hz), 7.91 (1H, s), 7.85-7.89 (3H, m), 7.75 (1H, s), 7.68-7.72 (1H, m), 7.66 (1H, s), 7.57-7.62 (1H, m), 4.83-4.90 (2H, m), 2.50 (3H, s), 2.35-2.48 (2H, m), 1.21-1.26 (18H, m), 1.13-1.19 (6H, m), 0.93 (6H, t, J=6.9 Hz).

Examples N-78 to N-84

Example N-78 to N-84 (TFA salt) were prepared starting from diamine N-77f and appropriate acids by employing the procedures described for the synthesis of Example N-77.

| Example | R | Analytical conditions |
|---|---|---|
| N-78 | 1-(3,3-difluorocyclobutyl)carbonyl | LC (Cond. N-2): >95% homogeneity index. LC/MS (Cond. N-1): [M + H]$^+$ 679.12, R$_t$ = 3.158 min. |
| N-79 | 1-methylcyclohexanecarbonyl | LC (Cond. N-2): >95% homogeneity index. LC/MS (Cond. N-1): [M + H]$^+$ 691.21, R$_t$ = 3.661 min. |
| N-80 | 1-methylcyclopentanecarbonyl | LC (Cond. N-2): >95% homogeneity index. LC/MS (Cond. N-1): [M + H]$^+$ 663.23, R$_t$ = 3.5 min. |
| N-81 | 2-chloro-6-fluorobenzoyl | LC (Cond. N-2): >95% homogeneity index. LC/MS (Cond. N-1): [M + H]$^+$ 755.03, R$_t$ = 2.87 min. |
| N-82 | 4,4-difluorocyclohexanecarbonyl | LC (Cond. N-2): >95% homogeneity index. LC/MS (Cond. N-1): [M + H]$^+$ 735.14, R$_t$ = 3.055 min. |
| N-83 | 5-chlorothiophene-2-carbonyl | LC (Cond. N-2): >95% homogeneity index. LC/MS (Cond. N-1): [M + H]$^+$ 730.09, R$_t$ = 3.21 min. |
| N-84 | 1-methyl-4,4-difluorocyclohexanecarbonyl | LC (Cond. N-2): >95% homogeneity index. LC/MS (Cond. N-1): [M + H]$^+$ 763.11, R$_t$ = 3.563 min. |

Example N-85 to N-100

Example N-85 to N-100 (TFA salt) were prepared starting from appropriate starting materials by employing the procedures described for the synthesis of Example N-77.

| Example | R | Analytical conditions |
|---|---|---|
| N-85 | 2-methoxy-2-methylpropanoyl | LC (Cond. N-2): >95% homogeneity index. LC/MS (Cond. N-1): [M + H]$^+$ 671.51, R$_t$ = 3.28 min. |
| N-86 | 2,2-dimethylpropanoyl | LC (Cond. N-2): >95% homogeneity index. LC/MS (Cond. N-1): [M + H]$^+$ 639.52, R$_t$ = 3.353 min. |
| N-87 | 2-methoxy-2-methylpropanoyl | LC (Cond. N-2): >95% homogeneity index. LC/MS (Cond. N-1): [M + H]$^+$ 647.53, R$_t$ = 3.2 min. |
| N-88 | 5-chloro-2-fluorobenzoyl | LC (Cond. N-2): >95% homogeneity index. LC/MS (Cond. N-1): [M + H]$^+$ 759.34, R$_t$ = 3.28 min. |
| N-89 | 2,2-dimethylpropanoyl | LC (Cond. N-2): >95% homogeneity index. LC/MS (Cond. N-1): [M + H]$^+$ 615.54, R$_t$ = 3.283 min. |
| N-90 | 2-fluoro-2-methylpropanoyl | LC (Cond. N-2): >95% homogeneity index. LC/MS (Cond. N-1): [M + H]$^+$ 623.49, R$_t$ = 3.096 min. |
| N-91 | 2-(2-fluoroethoxy)-2-methylpropanoyl (difluoro) | LC (Cond. N-2): >95% homogeneity index. LC/MS (Cond. N-1): [M + H]$^+$ 747.46, R$_t$ = 3.25 min. |

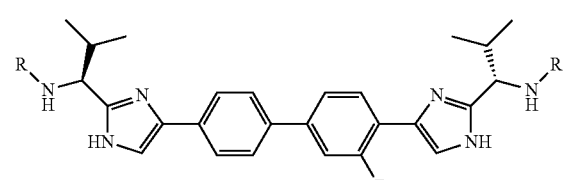

| Example | R | Analytical conditions |
|---|---|---|
| N-92 | 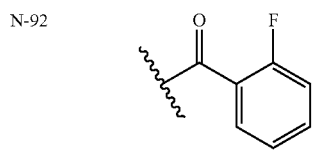 | LC (Cond. N-2): >95% homogeneity index. LC/MS (Cond. N-1): [M + H]⁺ 691.42, $R_t$ = 3.268 min. |

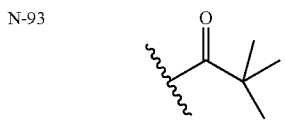

| Example | R | Analytical conditions |
|---|---|---|
| N-93 | 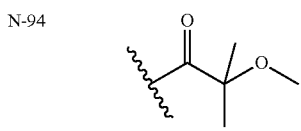 | LC (Cond. N-2): >95% homogeneity index. LC/MS (Cond. N-1): [M + H]⁺ 643.53, $R_t$ = 3.4 min. |
| N-94 | 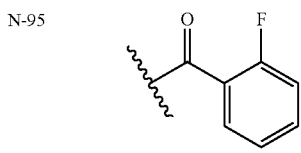 | LC (Cond. N-2): >95% homogeneity index. LC/MS (Cond. N-1): [M + H]⁺ 675.52, $R_t$ = 3.26 min. |
| N-95 | | LC (Cond. N-2): >95% homogeneity index. LC/MS (Cond. N-1): [M + H]⁺ 719.47, $R_t$ = 3.358 min. |

| Example | R | Analytical conditions |
|---|---|---|
| N-96 | | LC (Cond. N-2): >95% homogeneity index. LC/MS (Cond. N-1): [M + H]⁺ 647.53, $R_t$ = 3.05 min. |
| N-97 | | LC (Cond. N-2): >95% homogeneity index. LC/MS (Cond. N-1): [M + H]⁺ 623.42, $R_t$ = 3.03 min. |
| N-98 | | LC (Cond. N-2): >95% homogeneity index. LC/MS (Cond. N-1): [M + H]⁺ 747.46, $R_t$ = 3.235 min. |
| N-99 | | LC (Cond. N-2): >95% homogeneity index. LC/MS (Cond. N-1): [M + H]⁺ 759.34, $R_t$ = 3.49 min. |
| N-100 | | LC (Cond. N-2): >95% homogeneity index. LC/MS (Cond. N-1): [M + H]⁺ 615.54, $R_t$ = 3.28 min. |

Example N-101

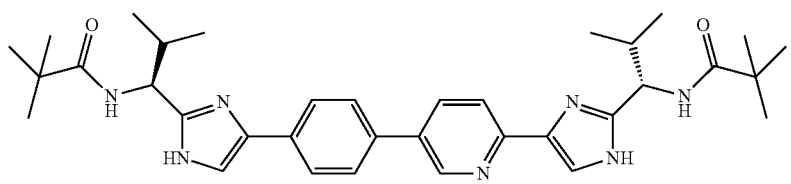 [SMILES: CC(C)[C@H](NC(=O)C(C)(C)C)c1nc(-c2ccc(-c3ccc(-c4c[nH]c([C@@H](NC(=O)C(C)(C)C)C(C)C)n4)nc3)cc2)c[nH]1]

N—((S)-2-methyl-1-(4-(4-(6-(2-((S)-2-methyl-1-pivalamidopropyl)-1H-imidazol-4-yl)pyridin-3-yl)phenyl)-1H-imidazol-2-yl)propyl)pivalamide Example N-101

Step a

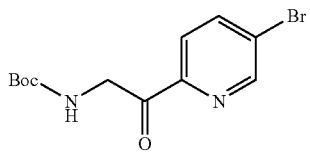 [SMILES: CC(C)(C)OC(=O)NCC(=O)c1ccc(Br)cn1]

To a mixture of 2,5-dibromopyridine (6 g, 25.3 mmol) in toluene was added n-BuLi (11.95 mL, 29.9 mmol) dropwise at −78° C. The reaction mixture was stirred at −78° C. for 2 hr. Then tert-butyl (2-(methoxy(methyl)amino)-2-oxoethyl)carbamate (2.77 g, 12.69 mmol) was added. The reaction mixture was stirred at −78° C. for 2 hr, then quenched by sat. NH$_4$Cl, diluted with EtOAc. The organic phase was washed with sat. NaCl, dried over anhydrous Na$_2$SO$_4$, filtered and concentrated to yield an oil. The crude product was dissolved in methylene chloride and charged to a 40 g silica gel cartridge which was eluted with a 20 min gradient of 0-30% EtOAc in hexane. Tert-butyl 2-(5-bromopyridin-2-yl)-2-oxoethylcarbamate (0.7 g) was collected as a yellow solid. LC/MS (Cond. N-1): [M+Na]$^+$ 337.14, RT=3.64 min. $^1$H NMR (400 MHz, METHANOL-d$_4$) ppm 8.80 (1H, dd, J=2.26, 0.75 Hz), 8.19 (1H, dd, J=8.28, 2.26 Hz), 7.96 (1H, d, J=8.28 Hz), 4.71 (2H, s), 1.49 (9H, s).

Example N-101

Step b

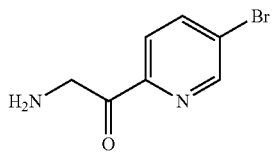

To a reaction mixture of tert-butyl 2-(5-bromopyridin-2-yl)-2-oxoethylcarbamate (0.36 g, 1.142 mmol) in DCM was added 4 M hydrogen chloride in dioxane (2 ml, 8.00 mmol) and some MeOH. The reaction was stirred at rt for 3 hrs. The reaction mixture was concentrated to dryness to yield 2-amino-1-HCl salf of (5-bromopyridin-2-yl)ethanone (0.32 g) as a yellow solid. LC/MS (Cond. N-1): [M+H]$^+$ 215.13, RT=0.945 min.

Example N-101

Step c

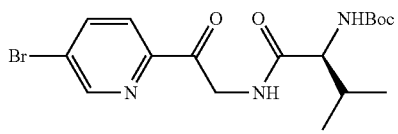

To a mixture (5-bromopyridin-2-yl)ethanone (0.16 g), (S)-2-((tert-butoxycarbonyl)amino)-3-methylbutanoic acid (0.133 g) and HATU (0.232 g) in DCM was added DIEA (0.340 mL). The reaction mixture was stirred at rt for 1 hr. The reaction mixture was purified by silica chromatography. (S)-tert-butyl 1-(2-(5-bromopyridin-2-yl)-2-oxoethylamino)-3-methyl-1-oxobutan-2-ylcarbamate (0.1 g) was collected as a yellow solid. LC/MS (Cond. N-1): [M+Na]$^+$ 436.07, RT=3.365 min.

Example N-101

Step d

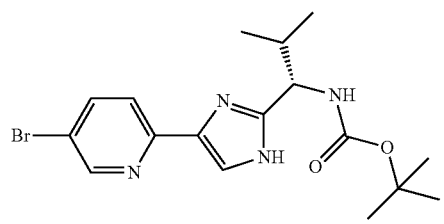 [SMILES: CC(C)[C@H](NC(=O)OC(C)(C)C)c1nc(-c2ccc(Br)cn2)c[nH]1]

In a sealed tube, a mixture of (S)-tert-butyl 1-(2-(5-bromopyridin-2-yl)-2-oxoethylamino)-3-methyl-1-oxobutan-2-ylcarbamate (0.1 g) and ammonium acetate (0.186 g) in xylene was heated at 130° C. for 3 hrs. The reaction was diluted with EtOAc, washed with sat. NaHCO$_3$, water and sat. NaCl, dried over anhydrous Na$_2$SO$_4$, filtered and concentrated to yield a yellow oil. The residue was purified by silica chromatography (0-100% EtOAc in hexane) to yield (S)-tert-butyl 1-(4-(5-bromopyridin-2-yl)-1H-imidazol-2-yl)-2-methylpropylcarbamate (0.06 g) as a pale yellow solid. LC/MS (Cond. N-1): [M+H]$^+$ 395.17, RT=3.06 min.

Example N-101

Example N-101 (TFA salt) was prepared starting from N-101d, N-77d and appropriate starting materials by employing the procedures described for the synthesis of Example N-77. LC/MS (Cond. N-1): [M+H]$^+$ 598.42, RT=3.218 min. $^1$H NMR (400 MHz, METHANOL-d$_4$) d ppm 9.03 (1H, dd, J=2.26, 0.75 Hz), 8.29 (1H, dd, J=8.41, 2.38 Hz), 8.16 (1H, s), 8.00-8.07 (1H, m), 7.90-7.97 (5H, m), 4.84-4.92 (2H, m), 2.31-2.52 (2H, m), 1.24 (18H, d, J=0.75 Hz), 1.16 (6H, dd, J=6.65, 3.14 Hz), 0.92 (6H, dd, J=6.78, 2.01 Hz).

Example N-102 to N-103

Example N-102 to N-103 (TFA salt) were prepared starting from appropriate starting materials by employing the procedures described for the synthesis of Example N-101.

| Example | R | Analytical conditions |
|---|---|---|
| N-102 | 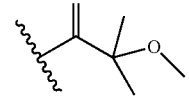 | LC (Cond. N-2): >95% homogeneity index. LC/MS (Cond. N-1): [M + H]$^+$ 630.4, R$_t$ = 3.0 min. |

-continued

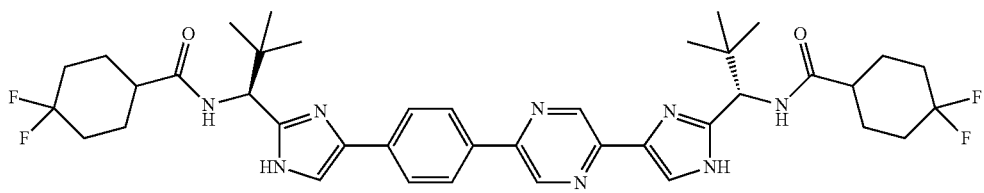 [SMILES: CC(C)(C)[C@H](NC(=O)C1CCC(F)(F)CC1)c1nc(-c2ccc(-c3cnc(-c4c[nH]c([C@@H](NC(=O)C5CCC(F)(F)CC5)C(C)(C)C)n4)cn3)cc2)c[nH]1]

| Example | R | Analytical conditions |
|---|---|---|
| N-103 | [structure: pivaloyl-type group with ketone and tert-butyl] | LC (Cond. N-2): >95% homogeneity index. LC/MS (Cond. N-1): [M + H]⁺ 598.4, R$_f$ = 3.12 min. |

Example N-104

[structure of Example N-104]

Example N-104

Step a

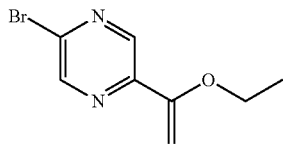

To a solution of 2,5-dibromopyrazine (1 g, 4.20 mmol) in DMF was added 1-ethoxyvinyltri-n-butyltin (1.420 mL, 4.20 mmol) and bis(triphenylphosphine)palladium(II) chloride (0.148 g, 0.210 mmol). The reaction mixture was heated at 100° C. for 4 hrs. The reaction mixture was diluted with EtOAc and aq. KF. The two phase mixture was stirred for 20 min at rt before being filtered through diatomaceous earth (Celite®). The filtrate was washed with sat. NaHCO₃, sat. NaCl, dried over anhydrous Na₂SO₄, concentrated. The crude product was purified by silica gel chromatography (0-100% EtOAc in hexane) to yield 2-bromo-5-(1-ethoxyvinyl)pyrazine (0.65 g). LC/MS (Cond. N-1): [M+H]⁺ 229.05, RT=3.799 min.

Example N-104

Step b

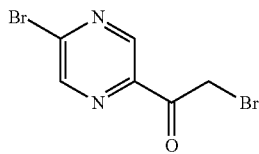

To a solution of 2-bromo-5-(1-ethoxyvinyl)pyrazine (0.65 g, 2.84 mmol) in THF and water was added NBS (0.505 g, 2.84 mmol) at 0° C. The reaction mixture was stirred at 0° C. for 1 hr, then diluted with EtOAc and aq. KF. The two phase mixture was stirred for 20 min at rt before being filtered through diatomaceous earth (Celite®). The filtrate was washed with sat. NaHCO₃, sat. NaCl, dried over anhydrous Na₂SO₄, concentrated. The crude product was purified by silica gel chromatography (0-100% EtOAc in hexane) to yield 2-bromo-1-(5-bromopyrazin-2-yl)ethanone (0.38 g) as a yellow oil. LC/MS (Cond. N-1): [M+H]⁺ 280.91, RT=2.945 min.

Example N-104

Example N-104 (TFA salt) was prepared starting from dibromo N-104b and appropriate starting materials by employing the procedures described for the synthesis of Example N-77. LC/MS (Cond. N-1): [M+H]⁺ 751.63, RT=3.461 min. ¹H NMR (400 MHz, METHANOL-d₄) ppm 9.30 (1H, d, J=1.51 Hz), 9.22 (1H, d, J=1.51 Hz), 8.33-8.39 (2H, m), 8.30 (1H, s), 7.99 (1H, s), 7.91-7.97 (2H, m), 4.99 (2H, d, J=14.81 Hz), 2.54-2.69 (2H, m), 2.04-2.21 (4H, m), 1.67-1.97 (12H, m), 1.14 (18H, d, J=2.76 Hz).

Example N-105 (TFA salt) was prepared starting from appropriate starting materials by employing the procedures described for the synthesis of Example N-104.

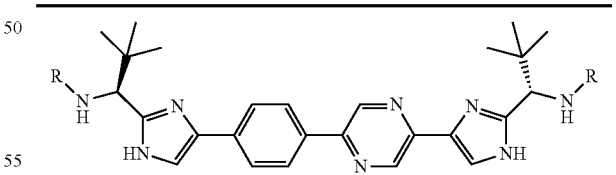

| Example | R | Analytical conditions |
|---|---|---|
| N-105 | [structure] | LC (Cond. N-2): >95% homogeneity index. LC/MS (Cond. N-1): [M + H]⁺ 627.58, R$_f$ = 3.4 min. |

Examples Y-11 to Y-12

Scheme 1

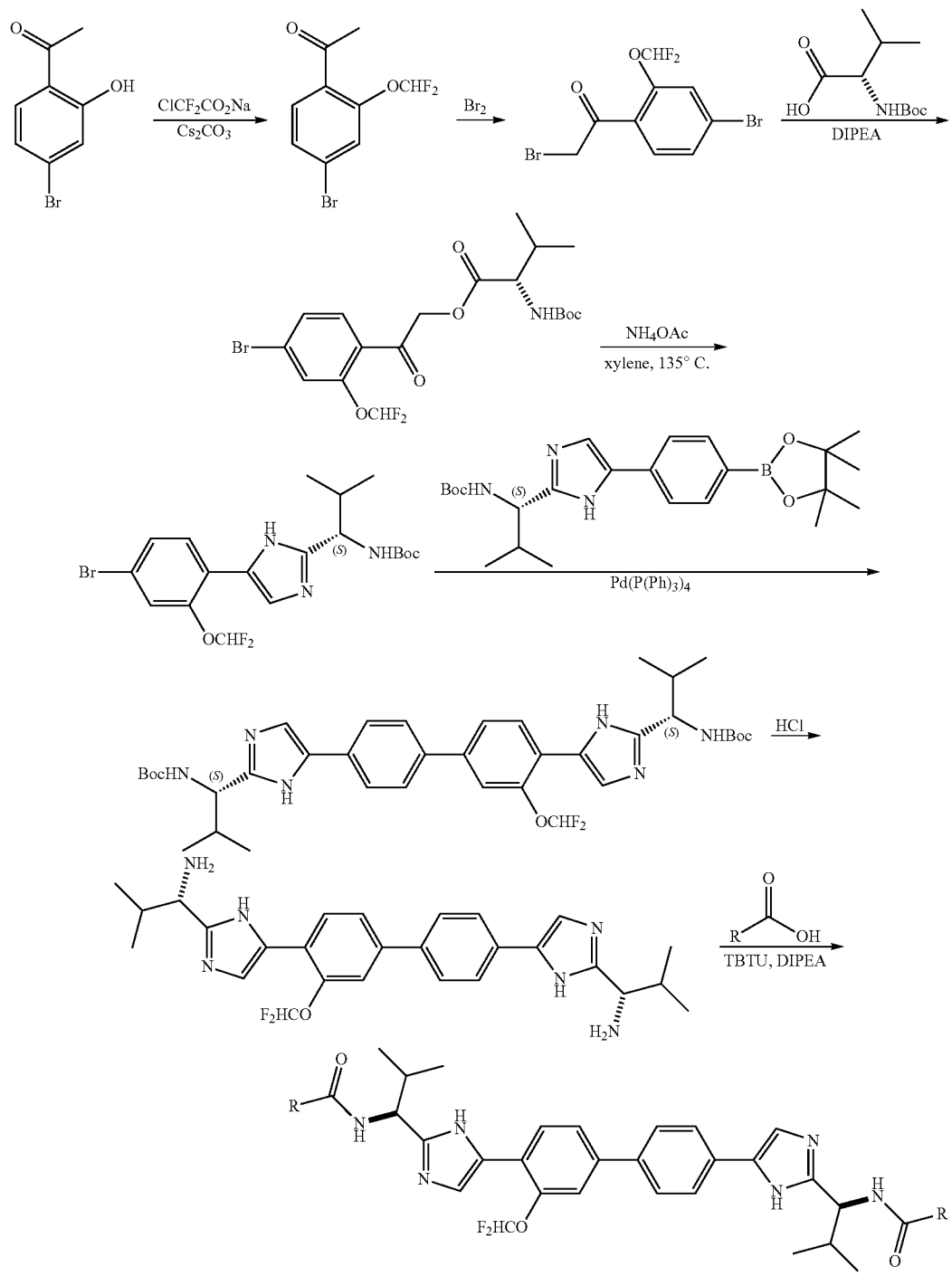

A reaction mixture of 1-(4-bromo-2-hydroxyphenyl)etha-none (1.1 g, 5.12 mmol), sodium chlorodifluoroacetate (1.96 g, 12.89 mmol), and $Cs_2CO_3$ (3.33 g, 10.23 mmol) in DMF (8 mL) was heated for 1.5 h at 100-110° C. The reaction mixture was cooled down, diluted with EtOAc. The organic phase was washed with water, brine, dried ($MgSO_4$), the solvent was removed and the residue was purified on a 25 g silica gel column (EtOAc/hexane: 0 to 50%) to afford the designated compound as a beige solid (1.2 g). $^1$H NMR (400 MHz, CHLOROFORM-d) δ 7.69 (d, J=8.3 Hz, 1H), 7.47 (dd, J=8.3, 1.8 Hz, 1H), 7.40-7.36 (m, 1H), 6.63 (t, 72.78 Hz, 1H), 2.63 (s, 3H).

To a solution of 1-(4-bromo-2-(difluoromethoxy)phenyl) ethanone (1.2 g, 4.53 mmol) in AcOH (5 mL) was added a solution of Br$_2$ (0.257 mL, 4.98 mmol) in AcOH (1 mL) dropwise. The reaction mixture was stirred at rt for 24 hrs and diluted with EtOAc. The organic phase was washed with satd. Na$_2$SO$_3$, water, brine, dried (MgSO$_4$) and the solvent was removed to afford the designated compound as a brown viscous oil which was used in the next step.

To a reaction mixture of 2-bromo-1-(4-bromo-2-(difluoromethoxy)phenyl)ethanone (0.53 g, 1.541 mmol) and (S)-2-(tert-butoxycarbonylamino)-3-methylbutanoic acid (0.402 g, 1.849 mmol) in acetonitrile (5 mL) was added DIPEA (0.3 ml, 1.718 mmol). The reaction mixture was stirred at rt for 24 hrs and another portion of (S)-2-(tert-butoxycarbonylamino)-3-methylbutanoic acid (0.2 g) and DIPEA (0.3 ml, 1.718 mmol) in acetonitrile (5 mL) was added. The reaction mixture was stirred for 24 hrs and was concentrated. The residue was purified on a 40 g silica gel column (EtOAc/hexane: 0 to 50%) to afford the designated compound as a brown mass.

A reaction mixture of ammonium acetate (3 g, 38.9 mmol) and (S)-2-(4-bromo-2-(difluoromethoxy)phenyl)-2-oxoethyl 2-((tert-butoxycarbonyl)amino)-3-methylbutanoate (0.6 g, 1.249 mmol) in xylene (3 mL) in a sealed tube was heated at 138° C. for 3 h. The reaction mixture was cooled, diluted with EtOAc, washed with satd. NaHCO$_3$, brine, dried (MgSO$_4$). The solvent was removed and the residue was purified on a 40 g silica gel column (EtOAc/hex: 0 to 100%) to afford the designated compound as a brown solid (0.21 g). $^1$H NMR (400 MHz, CHLOROFORM-d) δ 8.09 (br. s., 1H), 7.42 (s, 1H), 7.38 (d, J=7.8 Hz, 1H), 7.28 (br. s., 1H), 6.51 (t, J=74.0 Hz, 1H), 5.46 (br. s., 1H), 4.49-4.33 (m, 1H), 2.39 (d, J=16.1 Hz, 1H), 1.45 (s, 9H), 1.04 (d, J=6.3 Hz, 3H), 0.91 (d, J=6.5 Hz, 3H). LC/MS (method YT-3): [M+H]$^+$ 461.9, R$_t$=2.233 min.

Nitrogen was bubbled for 5 min through a mixture of (S)-tert-butyl (2-methyl-1-(5-(4-(4,4,5,5-tetramethyl-1,3,2-dioxaborolan-2-yl)phenyl)-1H-imidazol-2-yl)propyl)carbamate (0.242 g, 0.547 mmol), (S)-tert-butyl (1-(5-(4-bromo-2-(difluoromethoxy)phenyl)-1H-imidazol-2-yl)-2-methylpropyl)carbamate (0.21 g, 0.456 mmol) and sodium bicarbonate (0.192 g, 2.281 mmol) in DME (4 mL) and water (2 mL), Pd(PPh$_3$)$_4$ (0.026 g, 0.023 mmol) was added and nitrogen bubbling was continued for additional 3 min. The reaction mixture was stirred at 78° C. for 18 h. It was then cooled and diluted with EtOAc, washed with water, brine, dried (MgSO$_4$) and the residue was purified on a silica gel 25 g column (EtOAc/Hex: 0 to 100%) to afford the product (0.27 g). $^1$H NMR (400 MHz, MeOD) δ 8.04 (br. s., 1H), 7.81 (d, J=8.3 Hz, 2H), 7.72 (d, J=8.5 Hz, 2H), 7.62 (dd, J=8.0, 1.8 Hz, 1H), 7.49 (s, 2H), 7.39 (s, 1H), 7.20-6.77 (m, 1H), 4.56 (t, J=7.9 Hz, 2H), 2.25-2.09 (m, 2H), 1.47 (s, 9H), 1.22 (s, 9H), 1.02 (d, J=6.8 Hz, 6H), 0.92-0.88 (m, 6H). LC/MS (method YT-1): [M+H]$^+$ 695.49, R$_t$=2.66 min.

To a solution of di-tert-butyl((1S,1'S)-(5,5'-(3-(difluoromethoxy)-[1,1'-biphenyl]-4,4'-diyl)bis(1H-imidazole-5,2-diyl))bis(2-methylpropane-1,1-diyl))dicarbamate (0.27 g, 0.387 mmol) in DCM (1 mL) was added 4N HCl/Dioxane (2.5 mL, 10.00 mmol) and the reaction mixture was stirred at rt for 3 h. It was diluted with 5 ml of toluene and the volatile component was removed in vacuo to afford the product as a brown solid (0.248 g). LC/MS (method YT-1): [M+H]$^+$ 495.4, R$_t$=2.28 min.

Examples Y-11 and Y-12 were prepared as bis-TFA salts by following the general amide coupling procedure using TBTU.

Example Y-11

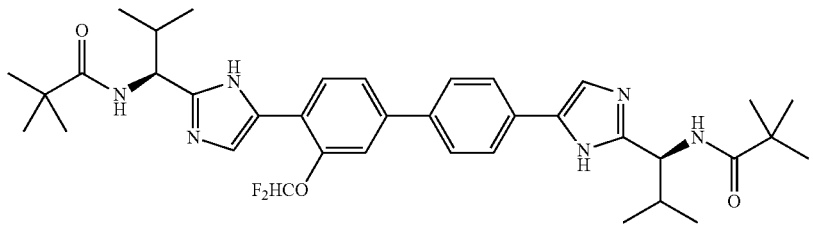 [SMILES: CC(C)[C@H](NC(=O)C(C)(C)C)c1ncc(-c2ccc(-c3ccc(-c4cnc([C@@H](NC(=O)C(C)(C)C)C(C)C)[nH]4)c(OC(F)F)c3)cc2)[nH]1]

$^1$H NMR (400 MHz, MeOD) δ ppm 7.93 (s, 1H), 7.91-7.86 (m, 5H), 7.81 (s, 1H), 7.76 (d, J=8.0 Hz, 1H), 7.68 (s, 1H), 7.14 (t, J=73.0 Hz, 1H), 2.41 (br. S., 2H), 1.24 (s, 18H), 1.15 (d, J=6.3 Hz, 6H), 0.93 (d, J=6.8 Hz, 6H). LC/MS (method YT-1): [M+H]$^+$ 663.57, R$_t$=2.65 min.

Example Y-12

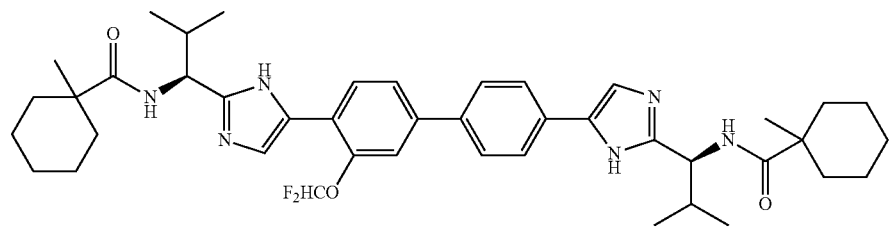 [SMILES: CC(C)[C@H](NC(=O)C1(C)CCCCC1)c1ncc(-c2ccc(-c3ccc(-c4cnc([C@@H](NC(=O)C5(C)CCCCC5)C(C)C)[nH]4)c(OC(F)F)c3)cc2)[nH]1]

LC/MS (method YT-1): [M+H]$^+$ 743.59, R$_t$=2.87 min.

Example N-106

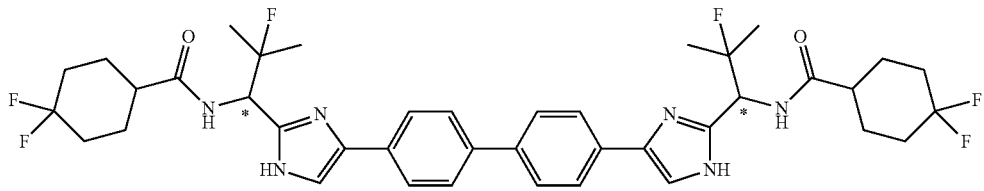 [SMILES: CC(C)(F)C(NC(=O)C1CCC(F)(F)CC1)c1nc(-c2ccc(-c3ccc(-c4c[nH]c(C(NC(=O)C5CCC(F)(F)CC5)C(C)(C)F)n4)cc3)cc2)c[nH]1]

N-106A to N-106C

Three Diastereomers

Example N-106

Step a

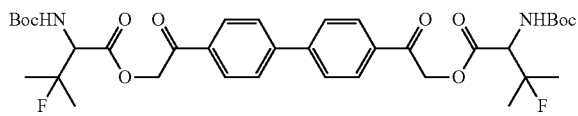

To a solution of 1,1'-([1,1'-biphenyl]-4,4'-diyl)bis(2-bromoethanone) (0.073 g, 0.185 mmol) and 2-((tert-butoxycarbonyl)amino)-3-fluoro-3-methylbutanoic acid (0.087 g, 0.370 mmol) in DCM (2 mL) was added DIEA (0.071 mL, 0.407 mmol). The reaction mixture was stirred at rt for 16 h and evaporated to dryness and the residue was purified by silica gel chromatography (0-100% EtOAc in hexane) to yield 2,2'-(biphenyl-4,4'-diyl)bis(2-oxoethane-2,1-diyl)bis(2-(tert-butoxycarbonylamino)-3-fluoro-3-methylbutanoate) (0.1 g). LC/MS (Cond. N-1): [M+H]$^+$ 727.52, RT=4.26 min.

Example N-106

Step b

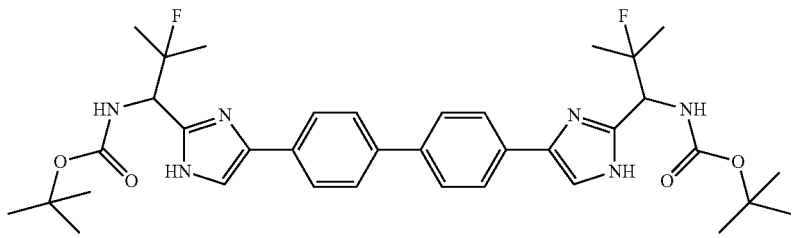 [SMILES: CC(C)(C)OC(=O)NC(c1nc(-c2ccc(-c3ccc(-c4c[nH]c(C(NC(=O)OC(C)(C)C)C(C)(C)F)n4)cc3)cc2)c[nH]1)C(C)(C)F]

In a sealed tube, a mixture of 2,2'-(biphenyl-4,4'-diyl)bis(2-oxoethane-2,1-diyl)bis(2-(tert-butoxycarbonylamino)-3-fluoro-3-methylbutanoate) (0.1 g) and ammonium acetate (0.109 g, 1.419 mmol) in xylene (2 ml) was heated at 130° C. for 3 hrs. The reaction was diluted with EtOAc, washed with sat. NaHCO$_3$, water and sat. NaCl, dried over anhydrous Na$_2$SO$_4$, filtered and concentrated to yield a yellow oil. The residue was purified by silica gel chromatography (0-100% EtOAc in hexane) to yield tert-butyl 1,1'-(4,4'-(biphenyl-4,4'-diyl)bis(1H-imidazole-4,2-diyl))bis(2-fluoro-2-methylpropane-1,1-diyl)dicarbamate as a pale yellow solid. LC/MS (Cond. N-1): [M+H]$^+$ 665.53, RT=3.325 min. $^1$H NMR (400 MHz, METHANOL-d$_4$) ppm 7.78 (4H, d, J=8.28 Hz), 7.69 (4H, d, J=8.53 Hz), 7.43 (2H, s), 4.98 (2H, m), 1.44-1.55 (21H, m), 1.41 (3H, br. s.), 1.35 (3H, s), 1.30 (3H, s). The three diastereomers were separated by chiral SFC (ChiralPak IC-H, 30×250 mm, 5 µm, Mobile Phase: 20% MeOH w/0.1% DEA/80% CO$_2$, Pressure: 120 bar, Temperature: 35° C., flow rate: 70 mL/min). Diastereomer 1: RT=8.58 min; Diastereomer 2: RT=9.78 min; Diastereomer 3: RT=11.34 min.

Example N-106A to N-106C

Example N-106A to N-106C (TFA salt) were prepared starting from the respective carbamate by using appropriate starting materials and procedures described for the synthesis of Example N-28.

Example N-106A (stereoisomer-1): LC/MS (Cond. N-1): [M+H]$^+$ 757.45, RT=3.368 min. $^1$H NMR (400 MHz, METHANOL-d$_4$) ppm 7.96 (2H, s), 7.85-7.91 (8H, m), 5.40 (1H, s), 5.34 (1H, s), 2.52-2.63 (2H, m), 2.05-2.19 (4H, m), 1.92-2.00 (2H, m), 1.70-1.91 (10H, m), 1.62 (3H, s), 1.57 (3H, s), 1.46 (3H, s), 1.41 (3H, s).

Example N-106B (stereoisomer-2): LC/MS (Cond. N-1): [M+H]$^+$ 757.63, RT=3.37 min. $^1$H NMR (400 MHz, METHANOL-d$_4$) ppm 7.98 (2H, s), 7.85-7.93 (8H, m), 5.38 (1H, s), 5.33 (1H, s), 2.51-2.63 (2H, m), 2.04-2.20 (4H, m), 1.97 (2H, d, J=9.79 Hz), 1.68-1.91 (10H, m), 1.63 (3H, s), 1.58 (3H, s), 1.46 (3H, s), 1.41 (3H, s).

Example N-106C (stereoisomer-3): LC/MS (Cond. N-1): [M+H]$^+$ 757.5, RT=3.38 min. $^1$H NMR (400 MHz, METHANOL-d$_4$) ppm 7.96 (2H, s), 7.85-7.92 (8H, m), 5.41 (1H, s), 5.35 (1H, s), 2.51-2.64 (2H, m), 2.04-2.20 (4H, m), 1.92-2.02 (2H, m), 1.66-1.92 (10H, m), 1.62 (3H, s), 1.57 (3H, s), 1.46 (3H, s), 1.41 (3H, s).

Example N-107

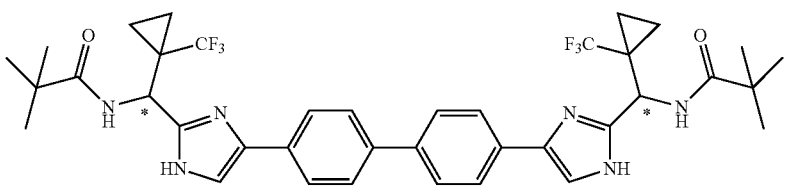 [SMILES: CC(C)(C)C(=O)NC(c1nc(-c2ccc(-c3ccc(-c4c[nH]c(C(NC(=O)C(C)(C)C)C5(C(F)(F)F)CC5)n4)cc3)cc2)c[nH]1)C1(C(F)(F)F)CC1]

N-107A to N-107B

Two Symmetrical Diastereomers

Example N-107

Step a

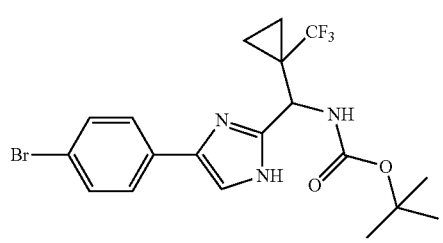 [SMILES: CC(C)(C)OC(=O)NC(c1nc(-c2ccc(Br)cc2)c[nH]1)C1(C(F)(F)F)CC1]

Tert-butyl (4-(4-bromophenyl)-1H-imidazol-2-yl)(1-(trifluoromethyl)cyclopropyl)methylcarbamate was prepared starting from appropriate starting materials by employing the procedures described for the synthesis of Example N-77. LC/MS (Cond. N-1): [M+H]$^+$ 460.12, RT=3.286 min. The two enantiomers were separated by chiral SFC (Chiralpak AD-H, 30×250 mm, 5 µm, Mobile Phase: 15% MeOH (0.1% DEA) in CO$_2$ @ 150 bar, Temperature: 35° C., flow rate: 70 mL/min) Enantiomer 1: RT=4.52 min; Enantiomer 2: RT=8.31 min.

Example N-107A to N-107B

Example N-107A to N-107B (TFA salt) were prepared starting from the individual enantiomers of the bromide N-107a and appropriate materials by employing the procedures described for the synthesis of Example N-77.

Example N-107A: LC/MS (Cond. N-1): [M+H]$^+$ 729.39, RT=3.458 min. $^1$H NMR (400 MHz, METHANOL-d$_4$) ppm 7.89-7.92 (2H, m), 7.86 (8H, s), 5.71-5.82 (2H, m), 1.17-1.32 (24H, m), 0.97 (2H, d, J=7.03 Hz).

Example N-107B: LC/MS (Cond. N-1): [M+H]$^+$ 729.39, RT=3.386 min. $^1$H NMR (400 MHz, METHANOL-d$_4$) ppm 7.89-7.92 (2H, m), 7.83-7.89 (8H, m), 5.75-5.79 (2H, m), 1.15-1.34 (24H, m), 0.90-1.03 (2H, m).

Example N-108 to N-109 (TFA salt) were prepared starting from appropriate starting materials by employing the procedures described for the synthesis of Example N-107.

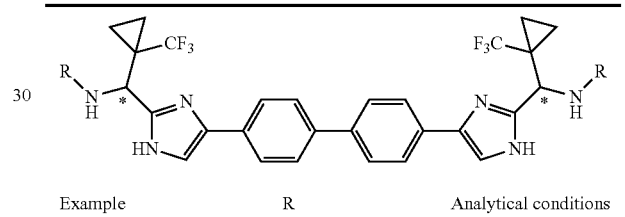

| Example | R | Analytical conditions |
|---|---|---|
| N-108A to N-108B | 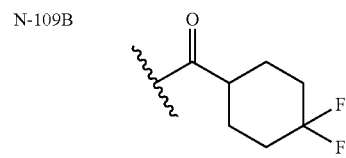 | Example 108-A: LC (Cond. N-2): >95% homogeneity index. LC/MS (Cond. N-1): [M + H]$^+$ 761.39, R$_t$ = 3.365 min. Example 108-B: LC (Cond. N-2): >95% homogeneity index. LC/MS (Cond. N-1): [M + H]$^+$ 761.39, R$_t$ = 3.371 min. |
| N-109B | | Example 109-B: LC (Cond. N-2): >95% homogeneity index. LC/MS (Cond. N-1): [M + H]$^+$ 853.4, R$_t$ = 3.47 min. |

Example N-110

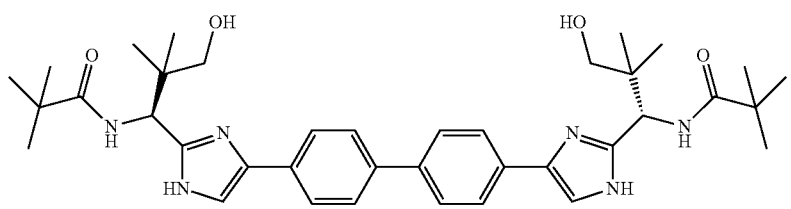 [SMILES: CC(C)(C)C(=O)N[C@H](c1nc(-c2ccc(-c3ccc(-c4c[nH]c([C@@H](NC(=O)C(C)(C)C)C(C)(C)CO)n4)cc3)cc2)c[nH]1)C(C)(C)CO]

Example N-110

Step a

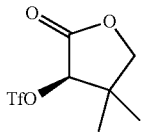 [SMILES: CC1(C)COC(=O)[C@@H]1OS(=O)(=O)C(F)(F)F]

To a solution of (R)-3-hydroxy-4,4-dimethyldihydrofuran-2(3H)-one (5 g) in DCM (5 mL) was added pyridine (3.73 mL). The reaction mixture was cooled to −78° C., and triflic anhydride (7.07 mL, 41.9 mmol) was added dropwise. The reaction mixture was stirred at −78° C. for 30 min and warmed to rt and stirred for 1 hr. The reaction was diluted with EtOAc, washed with water, sat. NaHCO$_3$, water, citric acid, water, and sat. NaCl, dried over anhydrous Na$_2$SO$_4$, filtered and concentrated to yield (R)-4,4-dimethyl-2-oxotetrahydrofuran-3-yltrifluoromethanesulfonate (10 g) as a clear oil. LC/MS (Cond. N-1): [M+H]$^+$ 263.17, RT=3.235 min. $^1$H NMR (400 MHz, CHLOROFORM-d) ppm 5.09 (1H, s), 4.04-4.20 (2H, m), 1.32 (3H, s), 1.23 (3H, s).

Example N-110

Step b

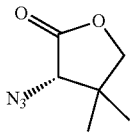

To a solution of (R)-4,4-dimethyl-2-oxotetrahydrofuran-3-yl trifluoromethanesulfonate (10 g) in DCM (10 mL) was added tetra-n-butylammonium azide (11.1 g). The reaction mixture was stirred at rt for 16 hr. The reaction was diluted with EtOAc, washed with water, sat. NaHCO$_3$, citric acid, water, and sat. NaCl, dried over anhydrous Na$_2$SO$_4$, filtered and concentrated to yield an oil. The crude product was purified by silica gel chromatography (0-100% EtOAc in hexane) to yield (S)-3-azido-4,4-dimethyldihydrofuran-2(3H)-one as a white solid. $^1$H NMR (400 MHz, CHLOROFORM-d) ppm 3.87-4.02 (3H, m), 1.17 (3H, s), 1.02 (3H, s).

Example N-110

Step c

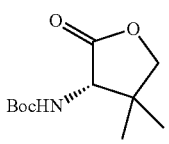 [SMILES: CC(C)(C)OC(=O)N[C@@H]1C(=O)OCC1(C)C]

To a solution of (S)-3-azido-4,4-dimethyldihydrofuran-2(3H)-one (5.52 g) in MeOH 910 mL) was added 10% Pd/C (0.379 g, 0.356 mmol) under N$_2$. The reaction mixture was stirred under H$_2$ at rt for 16 hrs. The reaction was filtered through diatomaceous earth (Celite®), washed with EtOAc and the filtrate was concentrated to yield a clear oil. To the above oil in DCM (10 mL) was added BOC$_2$O (9.09 mL) and TEA (13.88 mL). The reaction mixture was stirred at rt for 16 hrs. The reaction mixture was diluted with EtOAc, washed with sat. NaHCO$_3$, citric acid, water, sat. NaCl, dried over anhydrous Na$_2$SO$_4$, filtered and concentrated to yield an oil. The crude product was purified by silica gel chromatography (0-100% EtOAc in hexane) to yield (S)-tert-butyl 4,4-dimethyl-2-oxotetrahydrofuran-3-ylcarbamate (3.8 g) as a white solid. LC/MS (Cond. N-1): [M+Na]$^+$ 252.06, RT=2.75 min. $^1$H NMR (400 MHz, CHLOROFORM-d) ppm 4.81-4.95 (1H, m), 4.38 (1H, d, J=7.78 Hz), 3.97-4.07 (2H, m), 1.47 (9H, s), 1.25 (3H, s), 1.01 (3H, s).

Example N-110

Step d

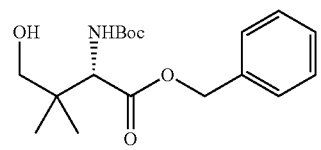 [SMILES: CC(C)(C)OC(=O)N[C@H](C(=O)OCc1ccccc1)C(C)(C)CO]

To a solution of (S)-tert-butyl 4,4-dimethyl-2-oxotetrahydrofuran-3-ylcarbamate (0.3 g) in THF (3 mL) was added a solution of KOH (0.088 g) in water (1 mL) at rt. The reaction mixture was stirred at rt for 16 hrs. The reaction mixture was concentrated to dryness to yield a white solid which was dissolved in DMF (3 mL) and treated with benzyl bromide (0.156 mL). The reaction mixture was stirred at rt for 16 hrs, then diluted with EtOAc, washed with sat. NaHCO$_3$, water, sat. NaCl, dried over anhydrous Na$_2$SO$_4$, filtered and concentrated to yield an oil. The crude product was purified by silica gel chromatography (0-100% EtOAc in hexane) to yield. (S)-benzyl 2-(tert-butoxycarbonylamino)-4-hydroxy-3,3-dimethylbutanoate (0.13 g). LC/MS (Cond. N-1): [M+Na]$^+$ 360.21, RT=3.59 min.

Example N-110

Step c

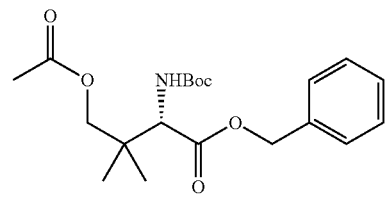 [SMILES: CC(=O)OCC(C)(C)[C@H](NC(=O)OC(C)(C)C)C(=O)OCc1ccccc1]

To a solution of (S)-benzyl 2-(tert-butoxycarbonylamino)-4-hydroxy-3,3-dimethylbutanoate (0.3 g) in DCM (3 mL) was added DMAP (0.109 g, 0.889 mmol) and acetic anhydride (0.084 mL, 0.889 mmol). The reaction mixture was stirred at rt for 16 hrs, then diluted with EtOAc, washed with sat. NaHCO$_3$, water, sat. NaCl, dried over anhydrous Na$_2$SO$_4$, filtered and concentrated to yield an oil. The crude product was purified by silica gel chromatography (0-100% EtOAc in hexane) to yield (S)-benzyl 4-acetoxy-2-(tert-butoxycarbonylamino)-3,3-dimethylbutanoate (0.31 g). LC/MS (Cond. N-1): [M+Na]$^+$ 402.22, RT=3.821 min.

Example N-110

Step d

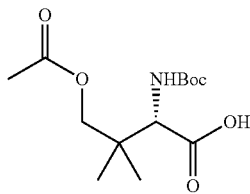 [SMILES: CC(=O)OCC(C)(C)[C@H](NC(=O)OC(C)(C)C)C(=O)O]

To a solution of (S)-benzyl 4-acetoxy-2-(tert-butoxycarbonylamino)-3,3-dimethylbutanoate (0.26 g) in MeOH (10 mL) was added 10% Pd/C (0.020 g) under $N_2$. The reaction mixture was stirred under $H_2$ at rt for 16 h. The reaction was filtered through diatomaceous earth (Celite®), washed with EtOAc and concentrated to yield (S)-4-acetoxy-2-(tert-butoxycarbonylamino)-3,3-dimethylbutanoic acid (0.18 g). LC/MS (Cond. N-1): [M+Na]$^+$ 312.21, RT=3.12 min.

To a solution of 1,1'-([1,1'-biphenyl]-4,4'-diyl)bis(2-bromoethanone) (0.123 g) and (S)-4-acetoxy-2-(tert-butoxycarbonylamino)-3,3-dimethylbutanoic acid (0.18 g) in DCM (3 mL) was added DIEA (0.120 mL). The reaction mixture was stirred at rt for 6 h then diluted with EtOAc, washed with sat. NaHCO$_3$, water and sat. NaCl, dried over anhydrous Na$_2$SO$_4$, filtered and concentrated to yield a pale yellow oil. The crude product was purified by silica gel chromatography (0-100% EtOAc in hexane) to yield (2S,2'S)-2,2'-(biphenyl-4,4'-diyl) bis(2-oxoethane-2,1-diyl)bis(4-acetoxy-2-(tert-butoxycarbonylamino)-3,3-dimethylbutanoate) (0.18 g) as a pale yellow solid. LC/MS (Cond. N-1): [M+Na]$^+$ 835.43, RT=4.173 min.

Example N-110

Step f

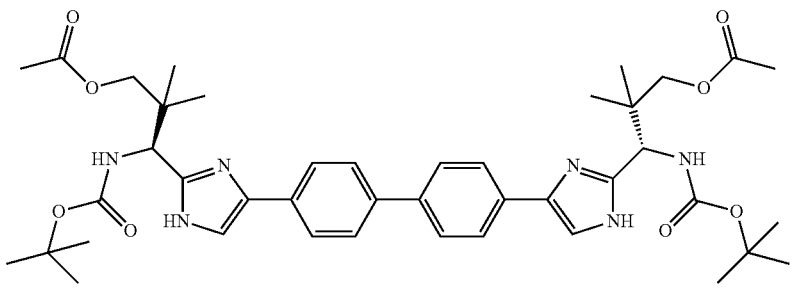

Example N-110

Step e

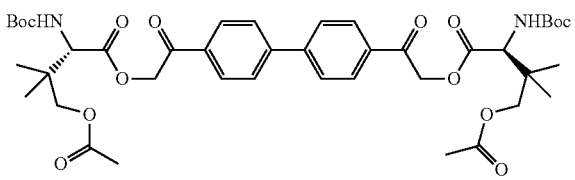 [SMILES: CC(=O)OCC(C)(C)[C@H](NC(=O)OC(C)(C)C)C(=O)OCC(=O)c1ccc(-c2ccc(C(=O)COC(=O)[C@@H](NC(=O)OC(C)(C)C)C(C)(C)COC(C)=O)cc2)cc1]

In a sealed tube, a mixture of (2S,2'S)-2,2'-(biphenyl-4,4'-diyl)bis(2-oxoethane-2,1-diyl)bis(4-acetoxy-2-(tert-butoxycarbonylamino)-3,3-dimethylbutanoate) (0.18 g) and ammonium acetate (0.171 g) in xylene was heated at 130° C. for 3 hrs. The reaction was diluted with EtOAc, washed with sat. NaHCO$_3$, water and sat. NaCl, dried over anhydrous Na$_2$SO$_4$, filtered and concentrated to yield a yellow oil. The crude product was purified by silica gel chromatography (0-100% EtOAc in hexane) to yield (3S,3'S)-3,3'-(4,4'-(biphenyl-4,4'-diyl)bis(1H-imidazole-4,2-diyl))bis(3-(tert-butoxycarbonylamino)-2,2-dimethylpropane-3,1-diyl)diacetate (0.1 g) as a pale yellow solid. LC/MS (Cond. N-1): [M+H]$^+$ 773.56, RT=3.246 min.

Example N-110

Step g

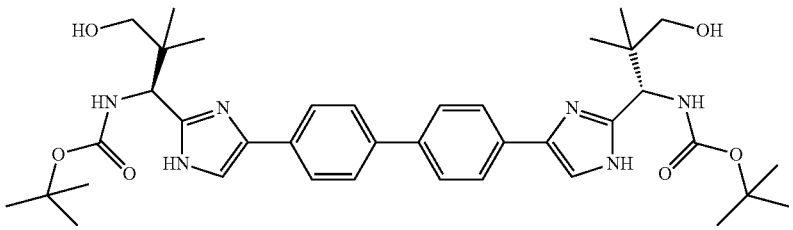 [SMILES: CC(C)(C)OC(=O)N[C@H](c1nc(-c2ccc(-c3ccc(-c4c[nH]c([C@@H](NC(=O)OC(C)(C)C)C(C)(C)CO)n4)cc3)cc2)c[nH]1)C(C)(C)CO]

A reaction mixture of (3S,3'S)-3,3'-(4,4'-(biphenyl-4,4'-diyl)bis(1H-imidazole-4,2-diyl))bis(3-(tert-butoxycarbonylamino)-2,2-dimethylpropane-3,1-diyl)diacetate (0.1 g), THF (2 mL), and 1 N NaOH (0.388 mL, 0.388 mmol) was stirred at rt for 3 hrs. The reaction was diluted with EtOAc, washed with sat. NaHCO₃, water and sat. NaCl, dried over anhydrous Na₂SO₄, filtered and concentrated to yield a yellow oil. The crude product was purified by silica gel chromatography (0-100% EtOAc in hexane) to yield tert-butyl (1S,1'S)-1,1'-(4,4'-(biphenyl-4,4'-diyl)bis(1H-imidazole-4,2-diyl))bis(3-hydroxy-2,2-dimethylpropane-1,1-diyl) dicarbamate (0.066 g) as a pale yellow solid. LC/MS (Cond. N-1): [M+H]⁺ 689.50, RT=3.211 min.

Example N-110

Example N-110 (TFA salt) was prepared starting from carbamate N-110 g and using appropriate materials by employing the procedures described for the synthesis of Example N-28. LC/MS (Cond. N-1): [M+H]⁺ 657.43, RT=2.98 min. ¹H NMR (400 MHz, METHANOL-d₄) ppm 7.92 (2H, s), 7.82-7.91 (8H, m), 5.07-5.12 (2H, m), 3.45-3.60 (4H, m), 1.24 (18H, s), 1.19 (6H, s), 0.99 (6H, s).

Example Y-13

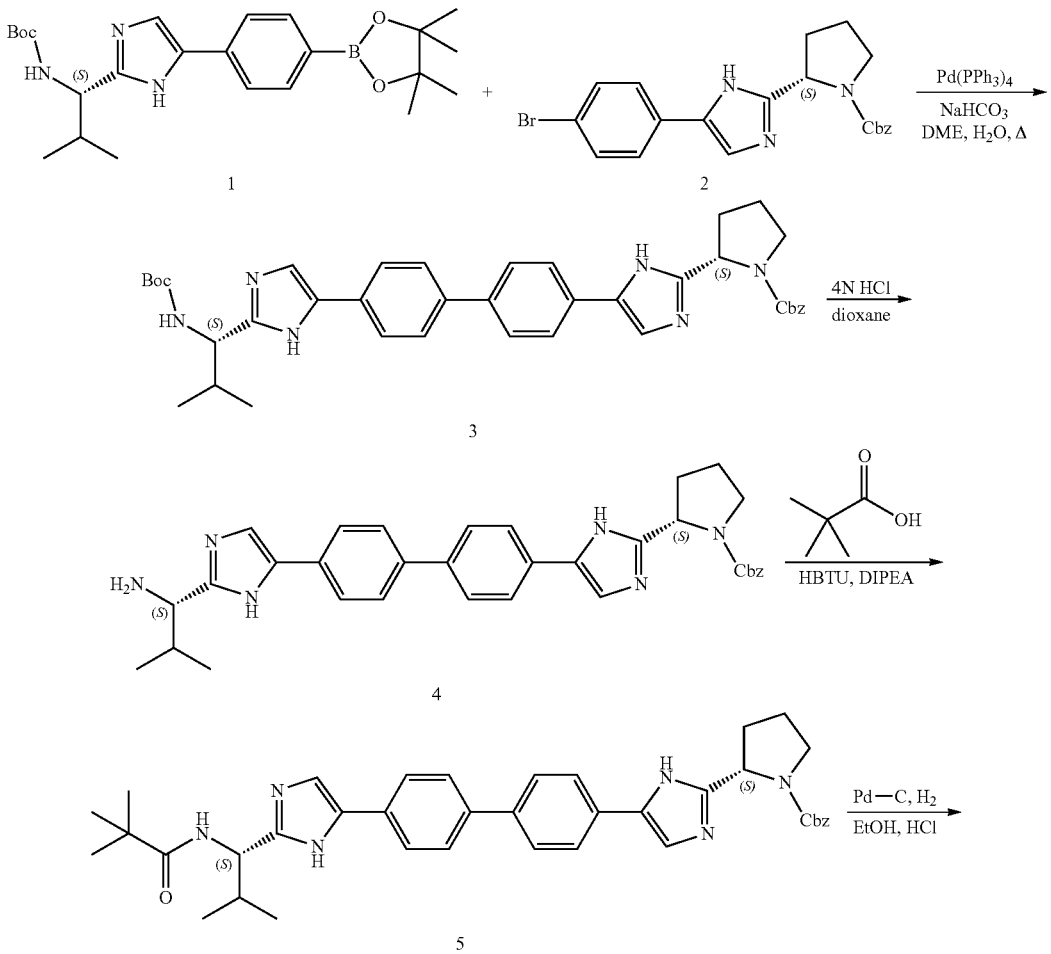

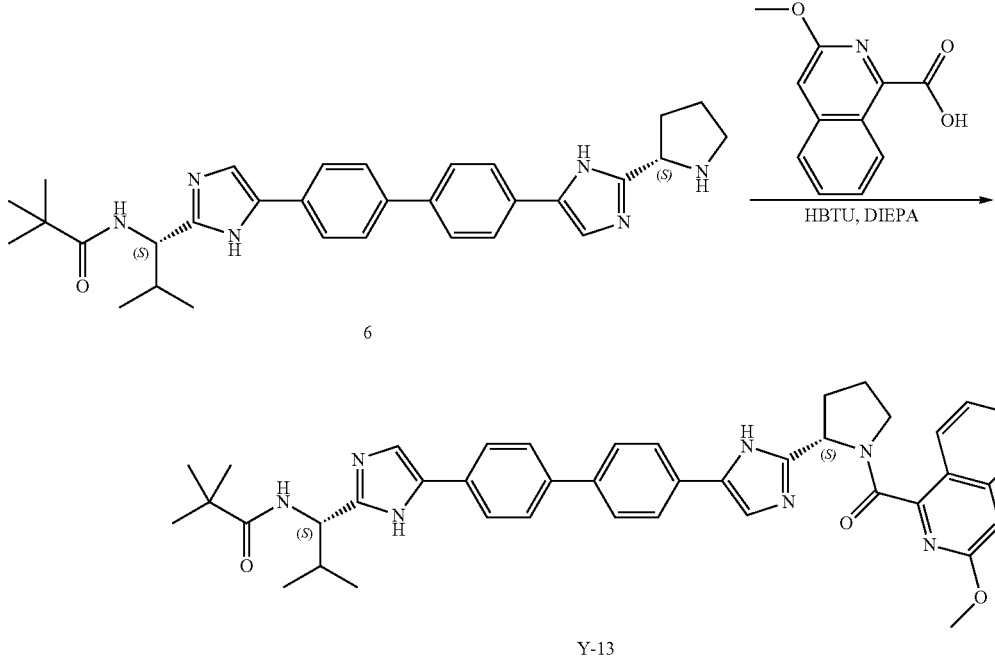

A reaction mixture of (S)-tert-butyl 2-methyl-1-(5-(4-(4,4,5,5-tetramethyl-1,3,2-dioxaborolan-2-yl)phenyl)-1H-imidazol-2-yl)propylcarbamate (prepared by employing the procedure described in U.S. Pat. Appl. Publ., 2008299075, 4 Dec. 2008) (1.47 g, 3.33 mmol), (S)-benzyl 2-(5-(4-bromophenyl)-1H-imidazol-2-yl)pyrrolidine-1-carboxylate (1.704 g, 4.00 mmol) and sodium bicarbonate (1.399 g, 16.65 mmol) in DME (15 mL) and water (8 mL) was purged with $N_2$ for 5 min and $Pd(PPh_3)_4$ (0.192 g, 0.167 mmol) was added and purged with $N_2$ for another 3 min. The reaction mixture was stirred at 78° C. for 18 h, cooled, diluted with EtOAc, washed with water, brine, dried ($MgSO_4$) and purified on a 80 g silica gel column (EtOAc/hex: 0 to 100%) to afford the compound 3 (0.58 g). LC-MS (retention time: 2.610 min, method P-1), m/z 661 $(M+H)^+$.

To a solution of (S)-benzyl 2-(5-(4'-(2-((S)-1-(tert-butoxycarbonylamino)-2-methylpropyl)-1H-imidazol-5-yl)biphenyl-4-yl)-1H-imidazol-2-yl)pyrrolidine-1-carboxylate (0.33 g, 0.499 mmol) in DCM (2 mL) was added 4 N HCl in dioxane (4 ml, 16.00 mmol) at rt. After stirring for 2 h at rt, the reaction mixture was evaporated to dryness to afford compound 4 (tris-HCl salt) as a yellow solid (335 mg). LC-MS (retention time: 2.478 min, method P-1), m/z 561 $(M+H)^+$. $^1$H NMR (400 MHz, METHANOL-$d_4$) δ ppm 7.73-8.12 (11H, m), 7.31-7.45 (2H, m), 7.04-7.20 (2H, m), 5.11-5.30 (2H, m), 4.53 (1H, d, J=8.53 Hz), 3.60-3.88 (4H, m), 2.46-2.69 (2H, m), 1.99-2.27 (3H, m), 1.25 (3H, d, J=6.53 Hz), 1.01 (3H, d, J=6.78 Hz).

To a solution of (S)-benzyl 2-(5-(4'-(2-((S)-1-amino-2-methylpropyl)-1H-imidazol-5-yl)biphenyl-4-yl)-1H-imidazol-2-yl)pyrrolidine-1-carboxylate, 3 HCl (0.2 g, 0.298 mmol) and pivalic acid (0.034 g, 0.328 mmol) in DCM (2 mL) was added N-ethyl-N-isopropylpropan-2-amine (0.309 g, 2.388 mmol) and HBTU (0.136 g, 0.358 mmol). The reaction mixture was stirred at rt for 1 h. The crude reaction mixture was purified on a 12 g silica gel column (EtOAc/hex: 0 to 100%) to afford compound 5 (145 mg). LC-MS (retention time: 2.641 min, method P-1), m/z 645 $(M+H)^+$.

Under nitrogen 10% Pd—C (11.97 mg, 0.011 mmol) was added to a solution of (S)-benzyl 2-(5-(4'-(2-((S)-2-methyl-1-pivalamidopropyl)-1H-imidazol-5-yl)biphenyl-4-yl)-1H-imidazol-2-yl)pyrrolidine-1-carboxylate (145 mg, 0.225 mmol) in EtOH containing HCl in dioxane (0.5 ml, 2.000 mmol). The suspension was stirred under balloon pressure of hydrogen at rt for two days. The suspension was filtered and the filtrate was evaporated to dryness to afford compound 6 (tris-HCl salt) as a yellow solid (124 mg). LC-MS (retention time: 2.420 min, method P-1), m/z 511 $(M+H)^+$.

To a solution of N—((S)-2-methyl-1-(5-(4'-(2-((S)-pyrrolidin-2-yl)-1H-imidazol-5-yl)biphenyl-4-yl)-1H-imidazol-2-yl)propyl)pivalamide, 3 HCl (40 mg, 0.065 mmol) and 3-methoxyisoquinoline-1-carboxylic acid (15.73 mg, 0.077 mmol) in DCM (2 mL) was added N-ethyl-N-isopropylpropan-2-amine (41.7 mg, 0.323 mmol) and HBTU (29.4 mg, 0.077 mmol). After stirring at rt for 1.5 h, the reaction mixture was diluted with MeOH (1 mL) and concentrated. The residue was purified by prep. HPLC to afford compound Y-13 as bis-TFA salt (9 mg). LC-MS (retention time: 2.658, method P-1), m/z 696.51 $(M+H)^+$. A mixture of rotamers (1:2 ratio) was observed by $^1$H NMR. $^1$H NMR (400 MHz, MeOD) data for the major rotamer: δ ppm 0.92 (d, J=6.78 Hz, 3H), 1.16 (d, J=6.53 Hz, 3H), 1.24 (s, 9H), 2.09-2.49 (m, 4H), 2.66-2.79 (m, 1H), 3.50-3.60 (m, 1H), 3.81-3.90 (m, 1H), 4.10 (s, 3H), 4.85-4.88 (m, 1H), 5.66 (dd, J=8.16, 6.65 Hz, 1H), 7.34-7.42 (m, 1H), 7.48-7.60 (m, 2H), 7.66-7.75 (m, 1H), 7.84-7.98 (m, 9H) 8.00 (s, 1H), 8.03-8.10 (m, 1H).

Examples Y-14 to Y-16

Table 2

Examples Y-14 to Y-16 (bis-TFA salt) were prepared by employing the method described in scheme 2 for the synthesis of Example Y-13.

| Example | Structure | Method | LCMS Retention time (min) | Obs. MS Ion (M + H)+ |
|---|---|---|---|---|
| Y-14 | 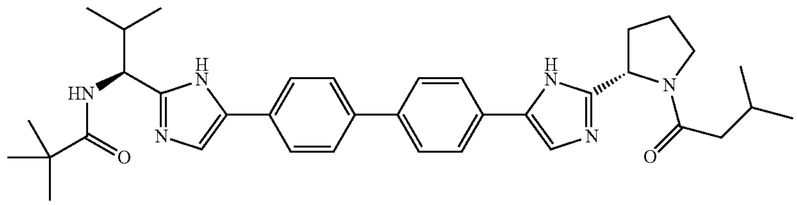 [SMILES: CC(C)CC(=O)N1CCC[C@H]1c1ncc(-c2ccc(-c3ccc(-c4cnc([C@@H](NC(=O)C(C)(C)C)C(C)C)[nH]4)cc3)cc2)[nH]1] | P-1 | 2.517 | 595.51 |
| Y-15 | 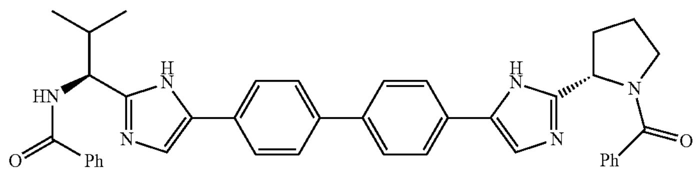 [SMILES: CC(C)[C@H](NC(=O)c1ccccc1)c1ncc(-c2ccc(-c3ccc(-c4cnc([C@@H]5CCCN5C(=O)c5ccccc5)[nH]4)cc3)cc2)[nH]1] | P-1 | 2.530 | 635.44 |
| Y-16 | 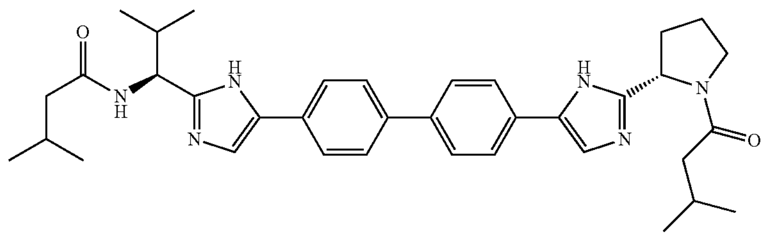 [SMILES: CC(C)CC(=O)N[C@H](c1ncc(-c2ccc(-c3ccc(-c4cnc([C@@H]5CCCN5C(=O)CC(C)C)[nH]4)cc3)cc2)[nH]1)C(C)C] | P-1 | 2.518 | 595.51 |
Example Y-17 to Y-18
Compounds Y-17 and Y-18 were prepared as shown in scheme 3.
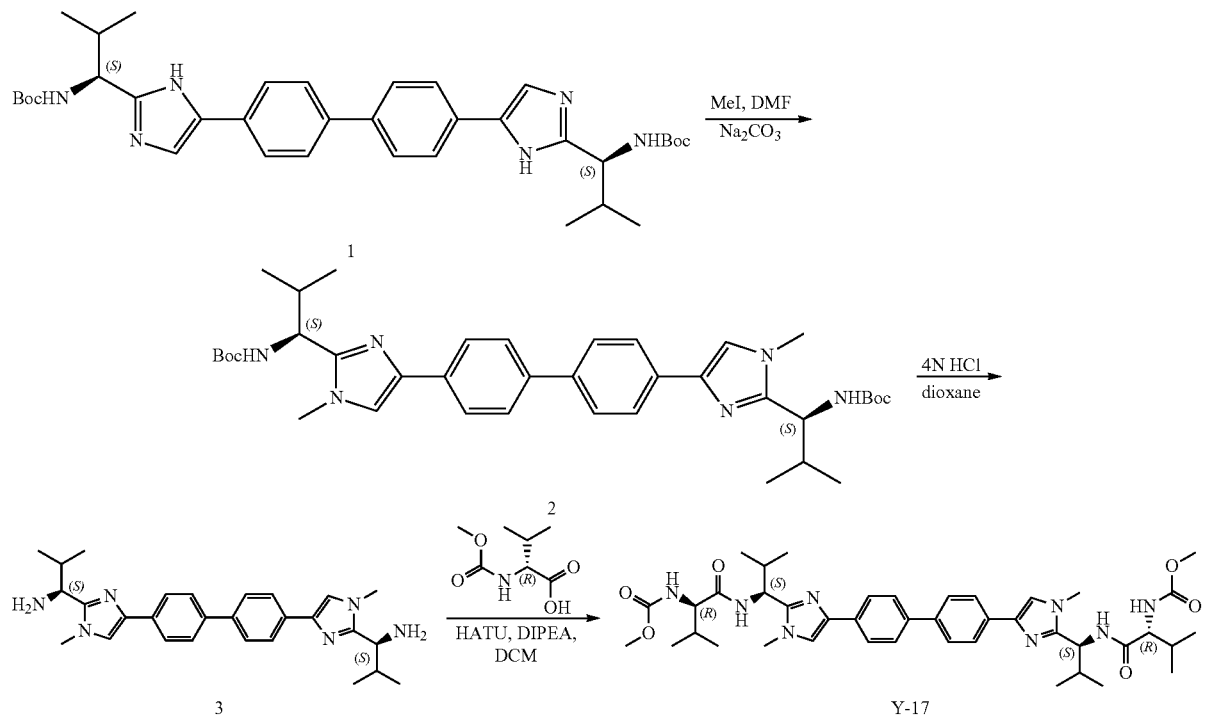
Scheme 3

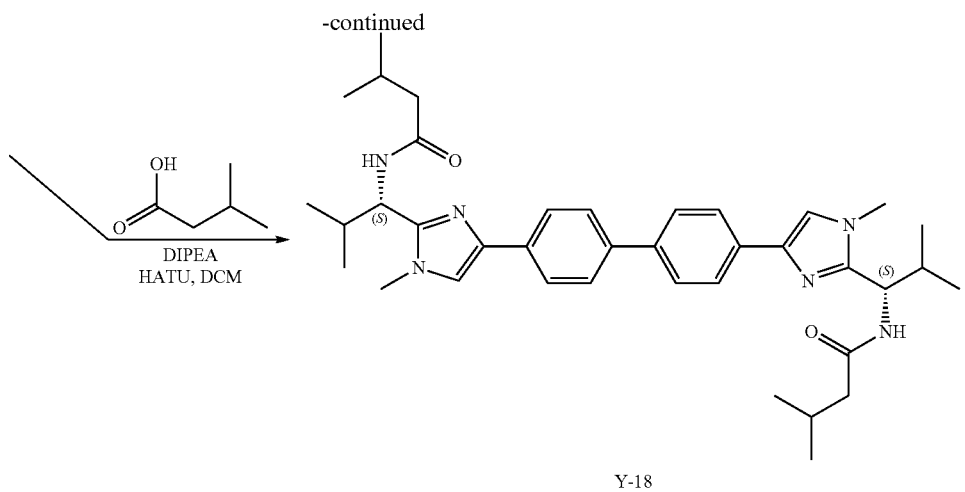

Y-18

To a solution of tert-butyl (1S,1'S)-1,1'-(5,5'-(biphenyl-4,4'-diyl)bis(1H-imidazole-5,2-diyl))bis(2-methylpropane-1,1-diyl)dicarbamate (0.45 g, 0.716 mmol) in DMF (5 mL) was added $K_2CO_3$ (0.218 g, 1.574 mmol) and cooled to −10° C. The reaction mixture was stirred for 5 min and then iodomethane (0.098 mL, 1.574 mmol) was added. The reaction mixture was stirred at rt for 18 h, diluted with EtOAc, washed with water, brine, dried ($MgSO_4$), filtered and evaporated to dryness. The residue was purified on a 25 g silica gel column (MeOH/DCM: 0% to 10%) to afford compound 2 as a yellow solid (0.17 g). LC-MS (retention time: 2.705 min, method P-1), m/z 657.48 (M+H)$^+$. $^1$H NMR (400 MHz, CHLOROFORM-d) δ ppm 7.80 (4H, d, J=8.3 Hz), 7.63 (4H, d, J=8.5 Hz), 7.10 (2H, s), 5.39 (2H, d, J=9.3 Hz), 4.59 (2H, t, J=8.7 Hz), 3.71 (6H, s), 2.19-2.33 (2H, m), 1.45 (18H, s), 1.06 (6H, d, J=6.8 Hz), 0.92 (6H, d, J=6.5 Hz).

Removal of Boc group using 4N HCl in dioxane as described in scheme 2 afforded compound 3 (4 HCl salt) as a beige solid. LC-MS (retention time: 2.503 min, method P-1), MS m/z 457.35 (M+1)$^+$.

Examples Y-17 and Y-18 were prepared by using the standard amide coupling method as shown in scheme 3 and purified by reverse phase HPLC and isolated as bis-TFA salts.

Example Y-17: LC-MS (retention time: 2.616 min, method P-1), MS m/z 771.57 (M+H)$^+$. $^1$H NMR (400 MHz, METHANOL-$d_4$) δ ppm 0.94 (d, J=6.78 Hz, 6H), 0.98-1.03 (m, 12H), 1.23 (d, J=6.53 Hz, 6H), 1.93-2.08 (m, J=14.24, 7.03, 6.81, 6.81 Hz, 2H), 2.38-2.53 (m, 2H), 3.53 (s, 6H), 3.87 (d, J=8.03 Hz, 2H), 4.05 (s, 6H), 4.85 (d, J=10.29 Hz, 2H), 7.87 (s, 8H), 7.88 (s, 2H).

Example Y-18: LC-MS (retention time: 1.812 min, method P-2), MS m/z 625.56 (M+H)$^+$.

Example P-48

Scheme 4

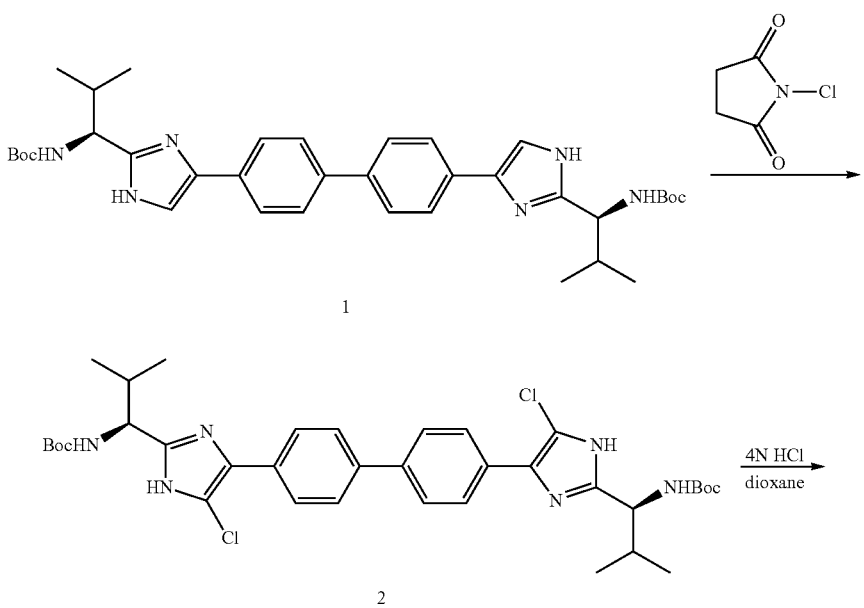

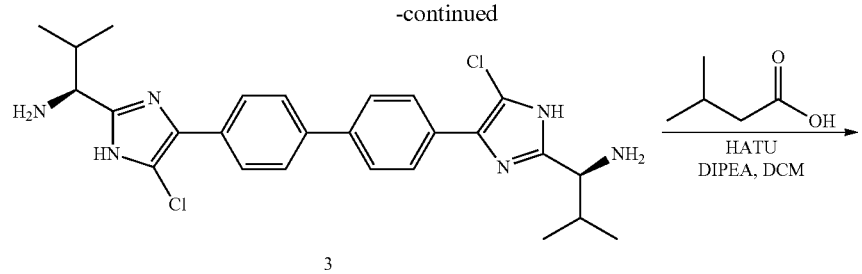

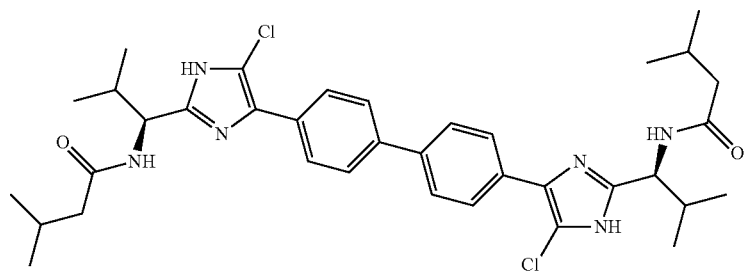

Example P-48

Neat 1-chloropyrrolidine-2,5-dione (60.5 mg, 0.444 mmol) was added to a solution of tert-butyl (1S,1'S)-1,1'-(4,4'-(biphenyl-4,4'-diyl)bis(1H-imidazole-4,2-diyl))bis(2-methylpropane-1,1-diyl)dicarbamate (133 mg, 0.212 mmol) in DMF (2 mL) and the mixture was stirred at rt overnight. The crude product was purified by silica gel FCC (3% MeOH in DCM) to afford compound 2 as a beige solid (131 mg).

A solution of 4 N HCl (1.878 mL, 7.51 mmol) in dioxane was added to a solution of compound 2 (131 mg, 0.188 mmol) in DCM (2 mL). The mixture was stirred at rt overnight and the resulting suspension was added toluene (5 mL) and evaporated to dryness to afford the compound 3 (4 HCl salt) as a yellow solid.

HATU (78 mg, 0.205 mmol) was added to a stirred solution of (1S,1'S)-1,1'-(4,4'-(biphenyl-4,4'-diyl))bis(5-chloro-1H-imidazole-4,2-diyl))bis(2-methylpropan-1-amine), 4 HCl (60 mg, 0.093 mmol), 3-methylbutanoic acid (20.96 mg, 0.205 mmol) and DIPEA (0.104 mL, 0.597 mmol) in DCM (2 mL) and the mixture was stirred at rt for 2 h. The reaction mixture was evaporated to dryness and then purified by reverse phase prep. HPLC to afford bis-TFA salt of Example P-48 as a beige solid: LC-MS (retention time: 4.48 min, method P-3), MS m/z 665.49 (M+H)$^+$.

Example P-49

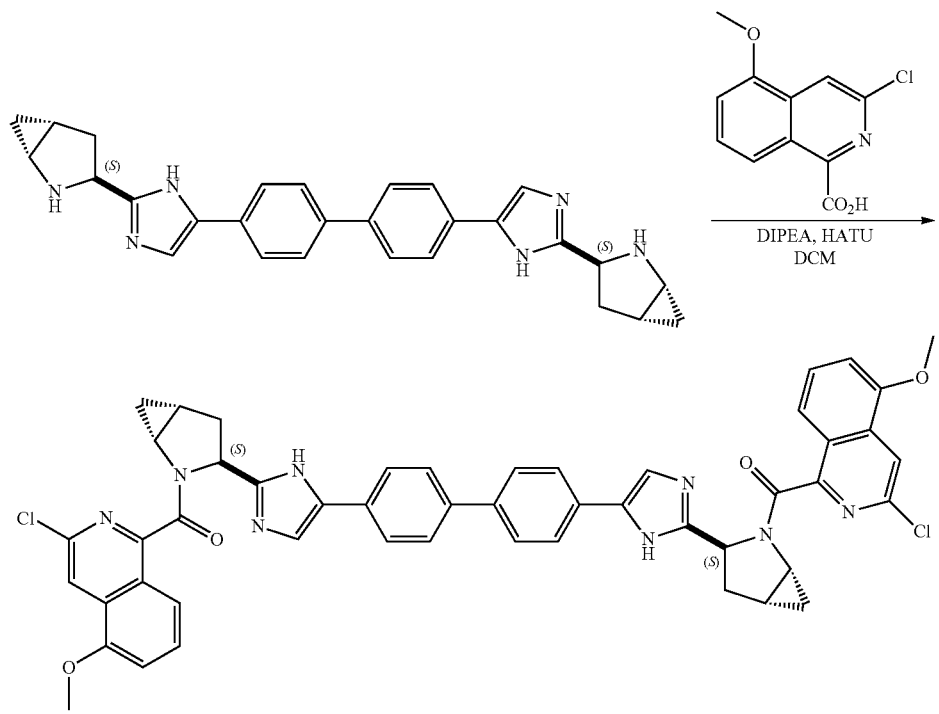

Example P-49

HATU (56.3 mg, 0.148 mmol) was added to a stirred solution of 4,4'-bis(2-((1R,3S,5R)-2-azabicyclo[3.1.0]hexan-3-yl)-1H-imidazol-5-yl)biphenyl, 4 HCl (40 mg, 0.067 mmol), 3-chloro-5-methoxyisoquinoline-1-carboxylic acid (32.0 mg, 0.135 mmol) and N-ethyl-N-isopropylpropan-2-amine (0.070 mL, 0.404 mmol) in DMF (1.0 mL) and DCM (1.0 mL) and the reaction mixture was stirred at rt for 2 h. The reaction mixture was evaporated to dryness under high vacuum and then purified by Prep HPLC to afford the TFA salt of Example P-49 (25 mg) as a beige solid: LC-MS (retention time: 1.948 min, method P-2), m/z 887.46 (M+H)$^+$.

Example P-50

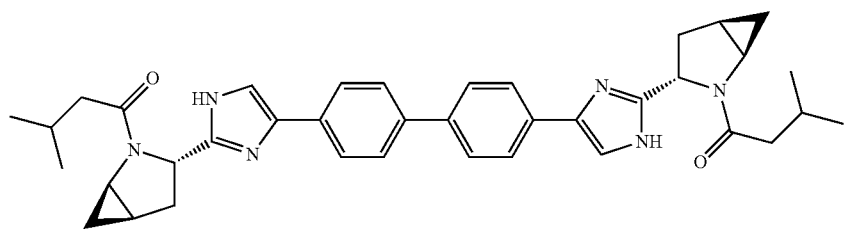 [SMILES: CC(C)CC(=O)N1[C@@H]2C[C@@H]2C[C@H]1c1nc(-c2ccc(-c3ccc(-c4c[nH]c([C@@H]5C[C@H]6C[C@H]6N5C(=O)CC(C)C)n4)cc3)cc2)c[nH]1]

Example P-50 was prepared by standard amide coupling procedure described for the preparation of Example P-49 and purified by prep. HPLC and isolated as bis-TFA salt: LC-MS (retention time: 1.682 min, method P-2), m/z 887.46 (M+H)$^+$.

Example P-51

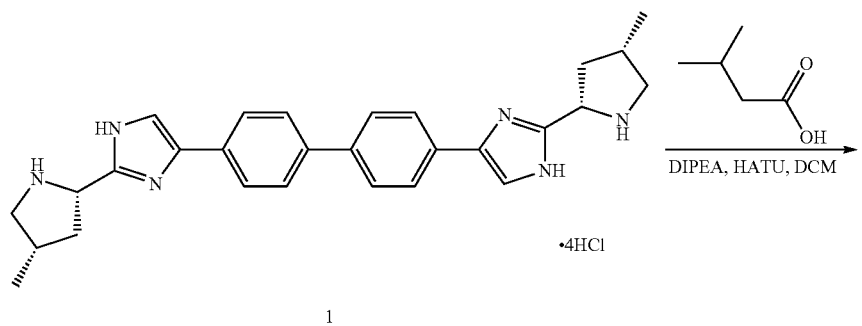

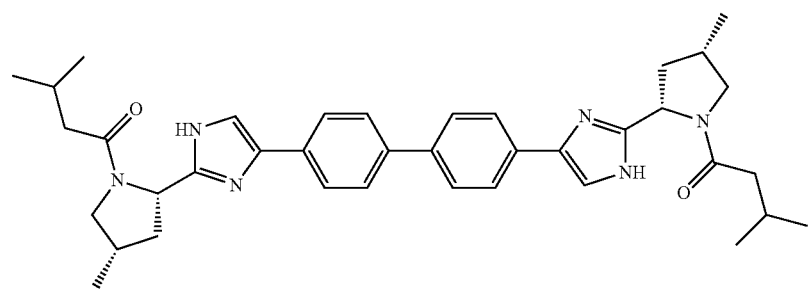

Example P-51

HATU (76 mg, 0.200 mmol) was added to a stirred solution of compound 1 (65.3 mg, 0.1 mmol), 3-methylbutanoic acid (22.47 mg, 0.220 mmol) and DIPEA (0.105 mL, 0.600 mmol) in DCM (2 mL). The mixture was stirred at rt for 2 h, evaporated to dryness and purified by prepHPLC to afford the Example P-51 (38 mg, 43%) as a white solid. LC-MS (retention time: 1.780 min, method P-2), m/z 621.61 (M+H)$^+$.

Example P-52

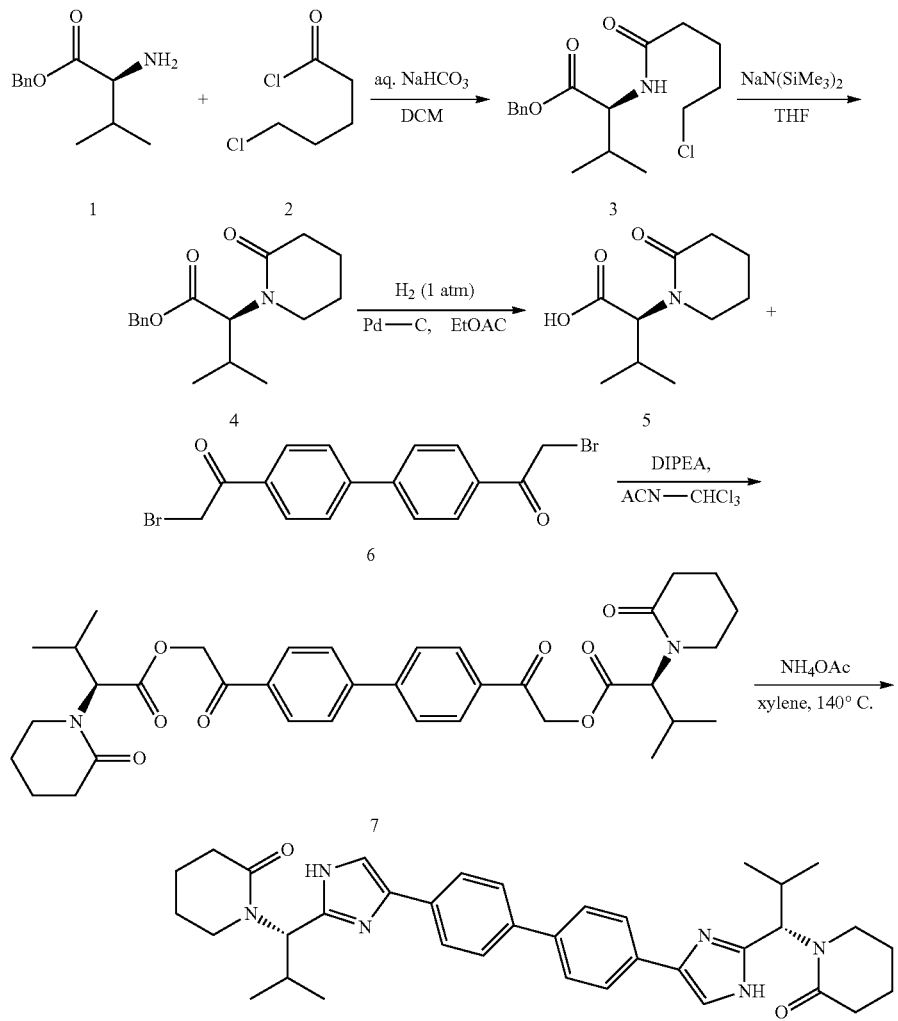

A solution of sodium bis(trimethylsilyl)amide (1.459 mL, 1.459 mmol) in THF (5 mL) was added dropwise to a stirred cold (−78° C.) solution of (S)-benzyl 2-(5-chloropentanamido)-3-methylbutanoate (490 mg, 1.459 mmol) in THF (10 mL) and the mixture was allowed to warm to rt and stirred for 2-3 h. The reaction was quenched with satd. NH$_4$Cl and diluted with ether. The organic layer was washed with water, brine and dried (Na$_2$SO$_4$). Evaporation of the solvent gave a light brown oil which was purified by silica gel FCC (3% MeOH in DCM) to afford 4 (333 mg). Intermediate 4 was To a solution of 5-chloropentanoyl chloride (533 mg, 3.30 mmol) in DCM (5 mL) was added to a stirred cold (0-5° C.) bi-phasic solution of (S)-benzyl 2-amino-3-methylbutanoate, HCl (731 mg, 3 mmol) in DCM (10 mL) and sodium bicarbonate (554 mg, 6.60 mmol) in water (5.00 mL). The mixture was stirred at rt for 2-3 h and then the organic layer was separated, washed with water, brine and dried (MgSO$_4$). Evaporation of solvent afforded compound 3 (996 mg, 95%) as a colorless oil which was used in the next step without further purification.

hydrogenated in EtOAC with 10% Pd—C under balloon pressure for 16 h to afford the debenzylated product 5 (157 mg, 54%).

DIPEA (0.220 mL, 1.259 mmol) was added to a stirred mixture of 1,1'-(biphenyl-4,4'-diyl)bis(2-bromoethanone) (227 mg, 0.572 mmol) and (S)-3-methyl-2-(2-oxopiperidin-1-yl)butanoic acid (228 mg, 1.144 mmol) in acetonitrile (3 mL) and chloroform (3 mL). The reaction mixture was stirred at rt overnight, then evaporated to dryness and purified by silica gel FCC (0-3% MeOH in DCM) to afford 7 (322 mg, 95%) as a white solid. LC-MS (retention time: 2.238 min, method P-2), m/z 633.5 (M+H)+.

A stirred suspension of (2S,2'S)-2,2'-(biphenyl-4,4'-diyl)bis(2-oxoethane-2,1-diyl)bis(3-methyl-2-(2-oxopiperidin-1-yl)butanoate) (322 mg, 0.509 mmol) and ammonium acetate (785 mg, 10.18 mmol) in xylene (6 mL) was heated at 140° C. for 2.5 h. The reaction mixture was cooled to rt and diluted with EtOAc (20 mL). The organic phase was washed with satd. NaHCO₃, water, brine and dried (Na₂SO₄) to afford a brown solid which was purified by silica gel FCC (5-10% MeOH in DCM) to afford Example P-52. LC-MS (retention time: 2.192 min, method P-2), m/z 593.5 (M+H)+.

Example P-53

Scheme 6

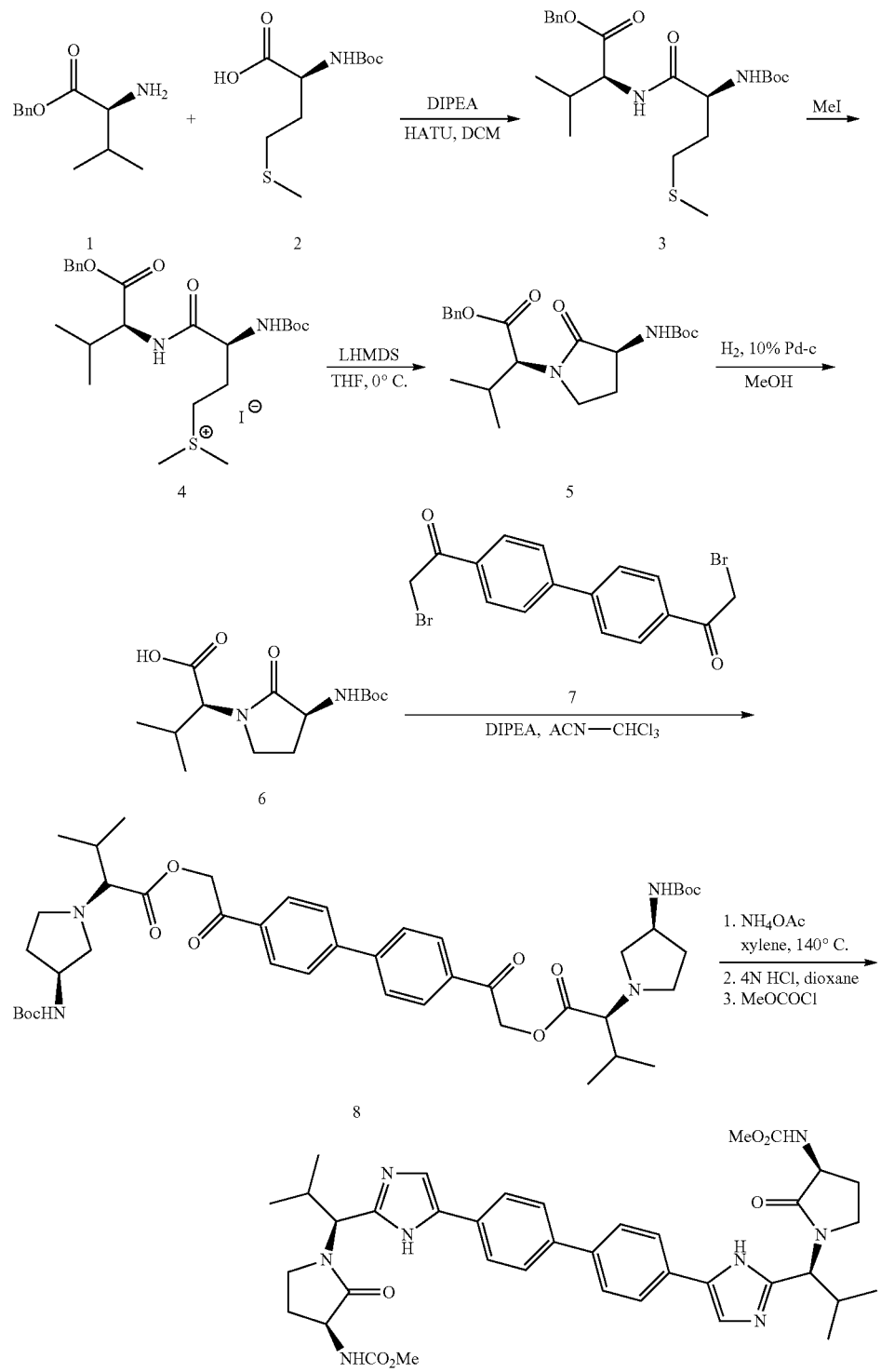

HATU (760 mg, 2.000 mmol) was added to a stirred solution of (S)-benzyl 2-amino-3-methylbutanoate, HCl (487 mg, 2 mmol), (S)-2-(tert-butoxycarbonylamino)-4-(methylthio) butanoic acid (499 mg, 2.000 mmol) and DIPEA (0.768 mL, 4.40 mmol) in DCM (5 mL) and the mixture was stirred at rt for 2 h. The crude product was purified by silica gel FCC (3% MeOH in DCM) to afford the compound 3 (854 mg, 97%) as a viscous oil. A mixture of compound 3 (0.850 g, 1.938 mmol) and iodomethane (4 mL, 64.1 mmol) was stirred at rt for 2 days. Excess MeI was removed by evaporation to dryness to afford compound 4 as a beige foam. LC-MS (retention time: 1.895 min, method P-2), m/z 453.34 (M+H)$^+$.

A solution of LiHMDS (1.000 mL, 1.000 mmol) in THF was added to a cold (0° C.) stirred solution of compound 4 (581 mg, 1 mmol) in THF (20 mL) and the mixture was stirred at 0° C. for 2 h. The reaction mixture was quenched with satd. NH$_4$Cl and diluted with ether. The organic layer was washed with water, brine and dried (Na$_2$SO$_4$). The crude product was purified by silica gel FCC (3% MeOH in DCM) to afford compound 5 (282 mg, 72%) as an oil. A stirred suspension of compound 5 (142 mg, 0.364 mmol) and 10% Pd—C (38.7 mg, 0.036 mmol) in MeOH (10 mL) was hydrogenated in a Parr shaker bottle at 50 psi for 2 h. The suspension was filtered and the filtrate was evaporated to dryness to afford compound 6 (105 mg, 96%). LC-MS (retention time: 2.252 min, method P-2), m/z 299.3 (M−H)$^−$.

A mixture of 1,1'-(biphenyl-4,4'-diyl)bis(2-bromoethanone) (69.2 mg, 0.175 mmol), compound 6 (105 mg, 0.350 mmol) and DIPEA (0.067 mL, 0.385 mmol) in acetonitrile (2 mL) and CHCl$_3$ (1 mL) was stirred at rt overnight. The reaction mixture was evaporated to dryness and then purified by silica gel FCC (3-4% MeOH in DCM) to afford compound 8 (126 mg, 87%) as a beige foam. A stirred suspension of compound 8 (126 mg, 0.151 mmol) and ammonium acetate (233 mg, 3.02 mmol) in xylene (4 mL) in a capped vial was heated at 140° C. for 2.5 h. The reaction mixture was cooled to rt and diluted with DCM (20 ml). The organic phase was washed with satd. NaHCO$_3$, water, brine and dried (Na$_2$SO$_4$) to afford a brown solid which was purified by silica gel FCC (5-10% MeOH in DCM) to afford tert-butyl (3S,3'S)-1,1'-((1S,1'S)-1,1'-(5,5'-(biphenyl-4,4'-diyl)bis(1H-imidazole-5,2-diyl))bis(2-methylpropane-1,1-diyl))bis(2-oxopyrrolidine-3,1-diyl)dicarbamate (64 mg, 54%). 4 N HCl (0.201 mL, 0.805 mmol) in dioxane was added to the above product (32 mg, 0.040 mmol) in DCM (0.5 mL). The mixture was stirred for 2 h and then evaporated to dryness to afford the deprotected intermediate as 4 HCl salt which was suspended in DCM (0.5 mL) and mixed with a solution of sodium bicarbonate (67.6 mg, 0.805 mmol) in water (1 mL) and then treated with a solution of methyl chloroformate (0.031 mL, 0.403 mmol) in DCM (0.5 mL). The mixture was stirred at rt for 1-2 h, the organic layer was separated and washed with 1 N NaOH (2 mL), water, brine and dried (MgSO$_4$). The crude product was purified by prepHPLC to afford Example P-53 (17 mg, 44%) as a white foam and isolated as bis-TFA salt. LC-MS (retention time: 1.623 min, method P-2), m/z 711.59 (M+H)$^+$.

Example P-54

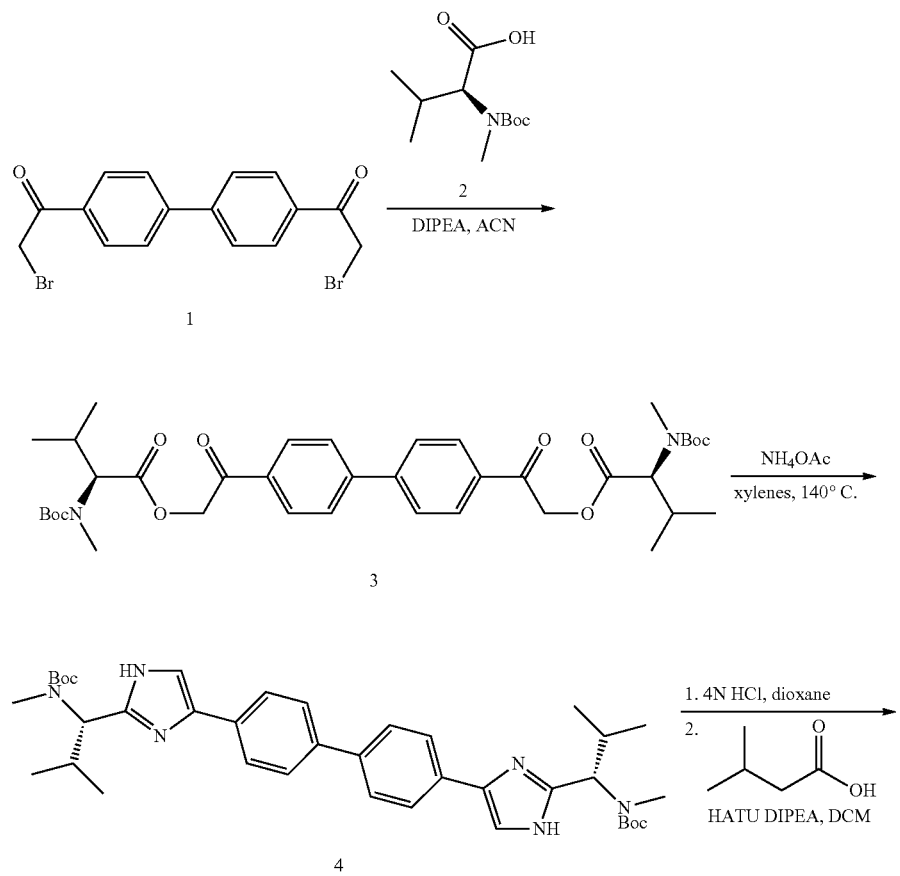

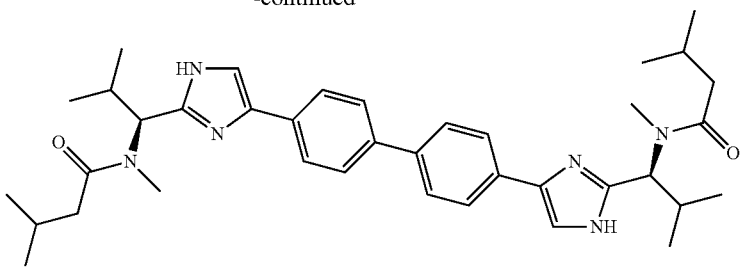

P-54

DIPEA (0.123 mL, 0.705 mmol) was added to a stirred suspension of 1,1'-(biphenyl-4,4'-diyl)bis(2-bromoethanone) (127 mg, 0.321 mmol) and (S)-2-(tert-butoxycarbonyl(methyl)amino)-3-methylbutanoic acid (74.2 mg, 0.321 mmol) in acetonitrile (2 mL) and chloroform (2 mL). The mixture was stirred at rt overnight, then evaporated to dryness and the residue was purified by silica gel FCC (0-5% MeOH in DCM) to afford compound 3 as a off-white solid (218 mg).

A stirred suspension of 3 (218 mg, 0.313 mmol) and ammonium acetate (482 mg, 6.26 mmol) in xylene (5 mL) was heated at 140° C. for 2 h. The reaction mixture was cooled to rt and diluted with EtOAc (20 ml). The organic phase was washed with satd. NaHCO$_3$, water, brine and dried (Na$_2$SO$_4$) to afford a brown solid which was purified by silica gel FCC (5-10% MeOH in DCM) to afford compound 4.

A solution of 4 N HCl in dioxane (1 mL, 4 mmol) was added to a solution of 4 (70 mg, 0.106 mmol) in DCM (1 mL). The mixture was stirred for 3 h and then evaporated to dryness to afford (1S,1'S)-1,1'-(4,4'-(biphenyl-4,4'-diyl)bis(1H-imidazole-4,2-diyl))bis(N,2-dimethylpropan-1-amine), 4 HCl (61 mg) as a yellow solid which was suspended in DCM (3 ml) and added 3-methylbutanoic acid (23 mg, 0.225 mmol), DIPEA (0.106 mL, 0.607 mmol) and HATU (85 mg, 0.223 mmol). The reaction mixture was stirred at rt for 2 h, then evaporated to dryness and the residue was purified by prep HPLC to afford the bis-TFA salt of Example P-54 as a white solid. LC-MS (retention time: 1.885 min, method P-2), m/z 625.62 (M+H)$^+$.

Example P-54.1

Example P-54.1 was prepared by using the standard amide coupling method. intermediate 1-3 (see below) and isobutyric acid and isolated as bis-TFA salt:

Example P-54.1

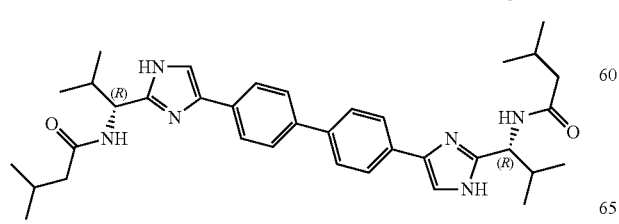

LC-MS (retention time: 2.288 min, method P-2), m/z 597.5 (M+H)+.

Example V-1

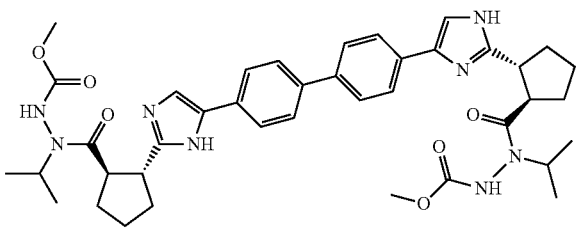 [SMILES: COC(=O)NN(C(=O)[C@@H]1CCC[C@H]1c1nc(-c2ccc(-c3ccc(-c4cnc([C@@H]5CCC[C@H]5C(=O)N(NC(=O)OC)C(C)C)[nH]4)cc3)cc2)c[nH]1)C(C)C]

Example V-1

Step a

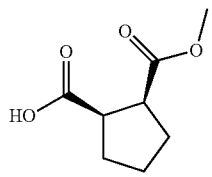

Prepared according to the following reference: *J. Org. Chem.* 2000, 65, p. 6984.

Example V-1

Step b

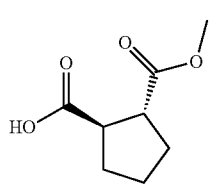

Prepared from ester V-1a according to the procedure described in Tetrahedron: Asymmetry 2006, 17, p. 620.

Example V-1

Step c

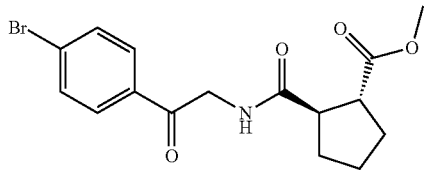 [SMILES: COC(=O)[C@@H]1CCC[C@H]1C(=O)NCC(=O)c1ccc(Br)cc1]

To a solution of 2-amino-4'-bromoacetophenone HCl (6.676 g, 0.031 mol), ester V-1b (5.37 g, 0.031 mol), and N,N-diisopropylethylamine (11 mL, 0.063 mol) in DMF (100 mL) was added HATU (13 g, 0.034 mol). The reaction mixture was stirred at rt under $N_2$ for 2 h. The volatile component was removed in vacuo, and the residue was taken up in ethyl acetate (100 mL) and washed with water. The aqueous layer was back-extracted with ethyl acetate (2×100 ml). The combined organic layer was dried over $MgSO_4$, filtered, and concentrated in vacuo. The residue was taken up in $CH_2Cl_2$ (10 mL) and loaded on a Biotage silica gel column and eluted with 75% ethyl acetate/hexanes to afford amide V-1c as a light yellow solid (10.5 g). $^1$H NMR (500 MHz, DMSO-$d_6$) δ ppm 8.27 (t, J=5.49, 1H), 7.91 (d, J=8.55, 2H), 7.76 (d, J=8.55, 2H), 4.65-4.46 (m, 2H), 3.60 (s, 3H), 3.11-2.91 (m, 2H), 2.03-1.88 (m, 2H), 1.77-1.68 (m, 1H), 1.68-1.60 (m, 3H). LC/MS: Anal. Calcd. for $[M+H]^+$ $C_{16}H_{19}^{79}BrNO_4$: 368.05; found 368.11.

Example V-1

Step d

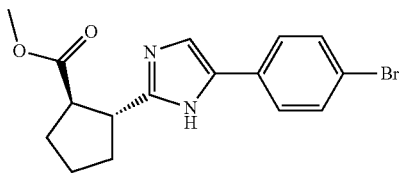 [SMILES: COC(=O)[C@@H]1CCC[C@H]1c1ncc(-c2ccc(Br)cc2)[nH]1]

A mixture of amide V-1c (7.3 g, 0.020 mol) and $NH_4OAc$ (9.17 g, 0.119 mol) in xylene (130 mL) in a sealed reaction vessel was heated at 140° C. for 5 h. The reaction was cooled to rt. All solvents were removed in vacuo. The residue was taken up in ethyl acetate (300 mL) and partitioned with water (100 mL) and saturated $NaHCO_3$ (aq. 100 mL) carefully. The layers were separated and the aqueous layer was extracted with ethyl acetate (2×150 mL). The combined organic layers were washed with brine, dried over $MgSO_4$, and concentrated in vacuo. The resultant residue was dissolved in $CH_2Cl_2$ and loaded on a Biotage silica gel cartridge eluting with 25% ethyl acetate/$CH_2Cl_2$ to afford imidazole V-1d as a light yellow solid (3.63 g). $^1$H NMR (500 MHz, DMSO-$d_6$) δ ppm 12.17/ 11.93 (two bs, 1H), 7.69 (d, J=8.24, 2H), 7.54 (d, J=1.83, 1H), 7.50 (d, J=8.55, 2H), 3.59 (s, 3H), 3.44-3.34 (m, 1H), 3.28- 3.15 (m, 1H), 2.17-2.02 (m, 2H), 1.86-1.66 (m, 4H). LC/MS: Anal. Calcd. for $[M+H]^+$ $C_{16}H_{18}^{79}BrN_2O_2$: 349.06; found 349.13.

Example V-1

Step e

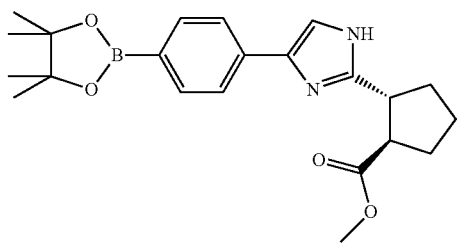 [SMILES: COC(=O)[C@@H]1CCC[C@H]1c1nc(-c2ccc(B3OC(C)(C)C(C)(C)O3)cc2)c[nH]1]

In a sealed reaction vessel, a mixture of bromide V-1d (1.8 g, 5.15 mmol), diboron pinacol ester (2.61 g, 10.3 mmol), and potassium acetate (1.29 g, 13.1 mmol) in 1,4-dioxane (30 mL) was added tetrakis(triphenylphosphine)palladium(0) (0.18 g, 0.16 mmol). The reaction vessel was thoroughly flushed with nitrogen, sealed and heated at 80° C. for 18 h. The volatile component was removed in vacuo, and the residue was taken up in $CH_2Cl_2$ (100 mL) and water (25 mL). The layers were separated and the aqueous layer was extracted with $CH_2Cl_2$ (2×100 mL). The combined organic layers was washed with saturated $NaHCO_3$ (aq), dried over $MgSO_4$, filtered, and concentrated in vacuo. The residue was loaded onto a Biotage silica gel cartridge and eluted with 25% ethyl acetate/$CH_2Cl_2$ to afford boronate V-1e as a white foam (1.9 g). LC/MS Anal. Calcd. for $[M+H]^+$ $C_{22}H_{30}BN_2O_4$: 397.23; found 397.33.

Example V-1

Step f

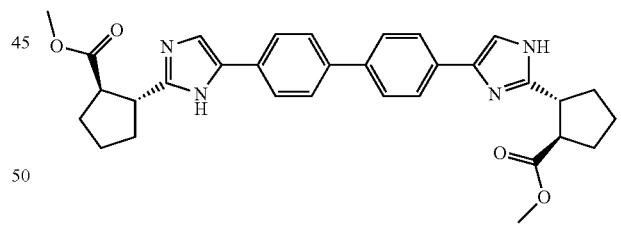

In a sealed reaction vessel, a mixture of bromide V-1d (1.2 g, 3.4 mmol), boronate V-1e (1.86 g, 4.7 mmol), and $NaHCO_3$ (0.862 g, 10.3 mmol) in 1,2-dimethoxy ethane (30 mL) and water (10 mL) was added tetrakis(triphenylphosphine)palladium(0) (0.12 g, 0.10 mmol). The reaction was thoroughly purged with nitrogen, sealed, and heated at 80° C. for 24 h. The volatile component was removed in vacuo, and the residue was taken up in 20% MeOH/$CHCl_3$ and washed with water. The layers were separated, and the aqueous layer was extracted with 20% MeOH/$CHCl_3$ (2×100 mL). The combined organic layer was washed with a saturated solution of $NaHCO_3$ (aq), dried over $MgSO_4$, filtered, and concentrated in vacuo. The residue was dissolved in minimum amount of 5% MeOH/$CHCl_3$ and loaded on a Biotage silica gel cartridge and eluted with 25% ethyl acetate/CH$_2$Cl$_2$ to afford V-1f as a light yellow solid (1.3 g). LC/MS Anal. Calcd. for [M+H]$^+$ C$_{32}$H$_{35}$N$_4$O$_4$: 539.27; found 539.40.

Example V-1

Step g

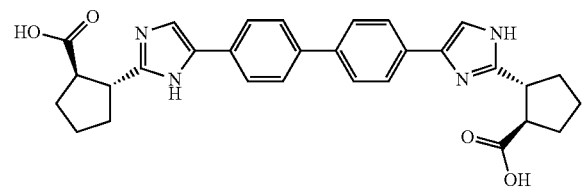 [SMILES: O=C(O)[C@@H]1CCC[C@H]1c1nc(-c2ccc(-c3ccc(-c4cnc([C@@H]5CCC[C@H]5C(=O)O)[nH]4)cc3)cc2)c[nH]1]

To a solution of V-1f (1.2 g, 2.2 mmol) in MeOH/H$_2$O was added 1 N NaOH (aq, 4.5 mL, 4.5 mmol), and the mixture was stirred at ~25° C. for 19 h. The reaction was cooled in an ice/water bath and made acidic with 1N HCl (aq, 6 mL, 6 mmol). The precipitate formed was filtered and washed with water to afford the HCl salt of acid V-1g as a tan solid (838.2 mg). $^1$H NMR (500 MHz, DMSO-d$_6$) δ ppm 12.31 (bs, 4H), 7.80 (d, J=8.24, 4H), 7.69 (d, J=8.24, 4H), 7.51 (s, 2H), 3.40 (app q, J=8.24, 2H), 3.16 (app q, J=8.44, 2H), 2.19-2.01 (m, 4H), 1.89-1.69 (m, 8H). LC/MS: Anal. Calcd. for [M+H]$^+$ C$_{30}$H$_{31}$N$_4$O$_4$: 511.23; found 511.15.

Example V-1

Step h

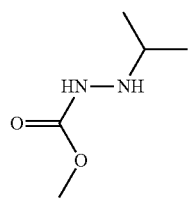

A solution of methyl carbazate (2.0 g, 22.2 mmol) and acetone (1.63 mL, 22.2 mmol) in MeOH (33 mL) was heated under nitrogen at 70° C. for 19 h. The reaction was cooled to ~25° C., and NaBH$_3$CN (1.4 g, 22.3 mmol) was added, followed by a dropwise addition of acetic acid (1 mL, 17.5 mmol). After stirring for 1 h at ~25° C. under nitrogen, all the volatile component was removed in vacuo. Water was added to the residue and the product was extracted with ethyl acetate (2×100 mL). The combined organic layer was washed with brine, dried over MgSO$_4$, filtered, and concentrated in vacuo to afford carbazate V-1h as a colorless oil which solidified to a white solid upon standing (2.6 g). $^1$H NMR (500 MHz, CDCl$_3$) δ ppm 6.44 (br s, 1H), 4.23 (br s, 1H), 3.69 (br s, 3H), 3.15 (app br s, 1H), 1.01 (d, J=6.41, 6H).

Example V-1

To a mixture of acid V-1g (0.100 g, 0.196 mmol), carbazate V-1h (0.155 g, 1.175 mmol), and N,N-diisopropylethylamine (0.150 mL, 0.859 mmol) in DMF (3 mL) was added HATU (0.164 g, 0.431 mmol). The reaction mixture was stirred at rt for 1.5 h, and then heated at 45° C. for 15 h. After it was allowed to cool to ambient condition, the mixture was diluted with MeOH (5 mL) and purified by reverse phase prep. HPLC (MeOH/water/TFA) to afford a white solid. The solid was re-purified by a different reverse phase prep. HPLC (acetonitrile/water/TFA) to afford the TFA salt of Example V-1 as a white solid (26.6 mg). $^1$H NMR (400 MHz, DMSO-d$_6$) δ ppm 14.38 (app br s, ~3H), 9.78/9.46 (two br s, 2H), 8.13 (br s, 2H), 8.03-7.83 (m, 8H), 4.66-4.46 (m, 2H), 3.91-3.72 (m, 2H), 3.68 (s, 2H), 3.58 (s, 4H), 3.51-1.48 (four overlapping m, 12H), 1.10-0.91 (m, 12H). LC/MS: Anal. Calcd. for [M+H]$^+$ C$_{40}$H$_{51}$N$_8$O$_6$: 739.39; found 739.45.

Intermediate 1-1: (tert-butyl (1S,1'S)-1,1'-(4,4'-(biphenyl-4,4'-diyl)bis(1H-imidazole-4,2-diyl))bis(2-methylpropane-1,1-diyl)dicarbamate) was prepared by employing the procedure described in U.S. Pat. Appl. Publ., 2008299075, 4 Dec. 2008.

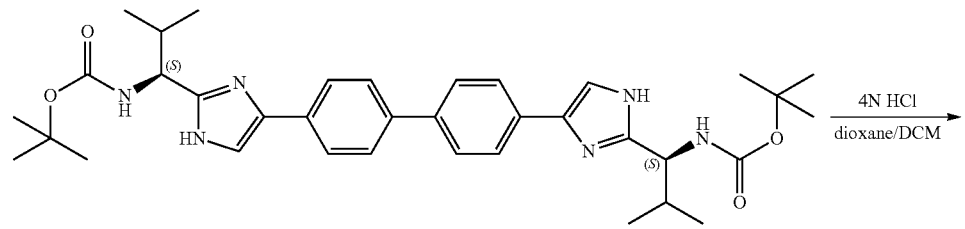

intermediate 1-1

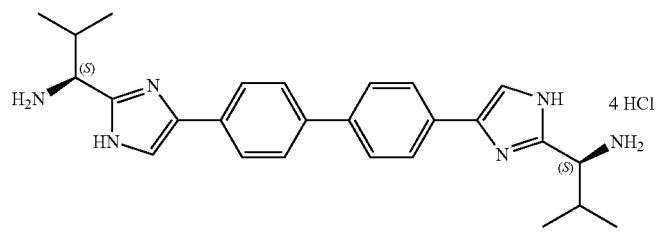

intermediate 1-2

Intermediate 1-2: (1S,1'S)-1,1'-(4,4'-(biphenyl-4,4'-diyl)bis(1H-imidazole-4,2-diyl))bis(2-methylpropan-1-amine), 4 HCl 4N HCl (16 mL, 64.0 mmol) in dioxane was added to a stirred partial solution of tert-butyl (1S,1'S)-1,1'-(4,4'-(biphenyl-4,4'-diyl)bis(1H-imidazole-4,2-diyl))bis(2-methylpropane-1,1-diyl)dicarbamate (1.42 g, 2.258 mmol) in DCM (5 mL) and the resultant suspension was stirred at rt for 1.5 h and then evaporated to dryness to afford the intermediate 1-2 as a yellow solid and isolated as 4 HCl salt (1.2 g, 93%). LC-MS: (retention time: 2.348 min, method P-1), MS m/z 429 (M+H)$^+$. $^1$H NMR (400 MHz, MeOD) δ ppm 8.11 (2H, br. s.), 7.95-8.03 (4H, m), 7.90 (4H, d, J=7.0 Hz), 4.56 (2H, br. s.), 2.64 (2H, br. s.), 1.27 (6H, d, J=5.8 Hz), 1.01 (6H, d, J=6.8 Hz).

Intermediate 1-3: (1R,1'R)-1,1'-(4,4'-(biphenyl-4,4'-diyl)bis(1H-imidazole-4,2-diyl))bis(2-methylpropan-1-amine) was prepared by following the procedure described in U.S. Pat. Appl. Publ., 2008299075, 4 Dec. 2008.

was prepared by following the procedure described in PCT Int. Appl., 2009020825, 12 Feb. 2009.

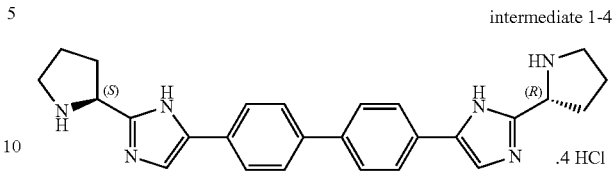

intermediate 1-4

Intermediate 1-5: (S)-2-methyl-1-(5-(4'-(2-((S)-pyrrolidin-2-yl)-1H-imidazol-5-yl)biphenyl-4-yl)-1H-imidazol-2-yl)propan-1-amine was prepared by following the procedure described in U.S. Pat. Appl. Publ., 2008299075, 4 Dec. 2008.

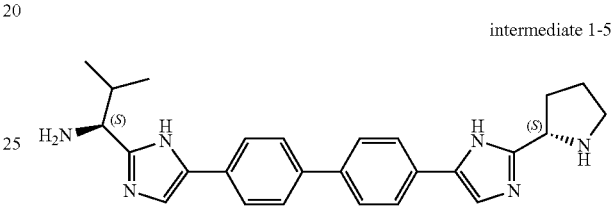

intermediate 1-5

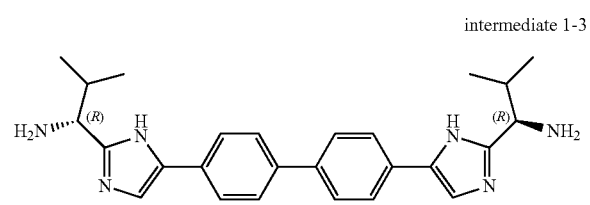

intermediate 1-3

Intermediate 1-4: 4-(2-((R)-pyrrolidin-2-yl)-1H-imidazol-5-yl)-4'-(2-((S)-pyrrolidin-2-yl)-1H-imidazol-S-yl)biphenyl General Methods for Amide Coupling:

Method 1: the below procedure represents the amide coupling using HATU as a reagent.

Example Y-19

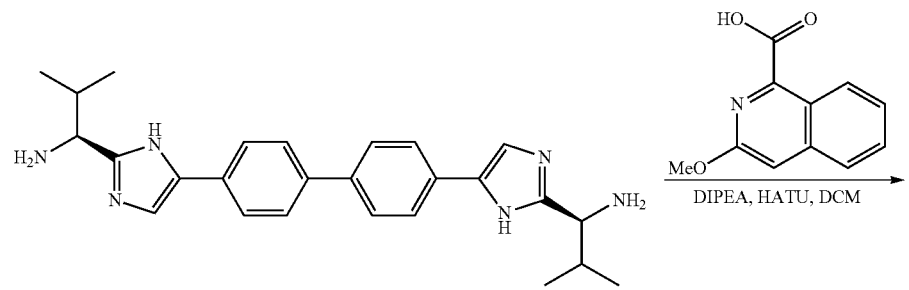

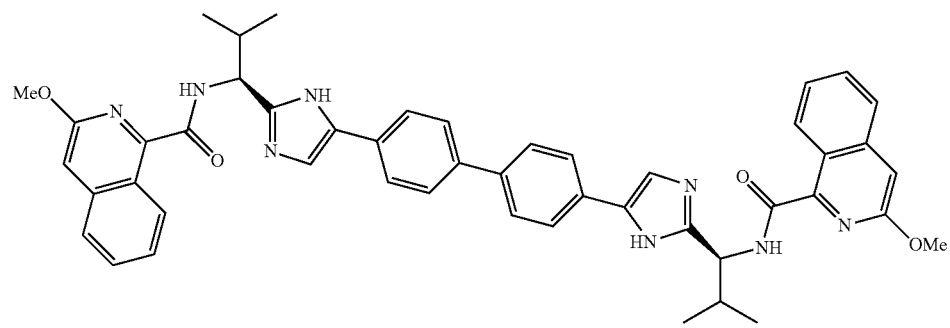

Y-19

To a mixture of 3-methoxyisoquinoline-1-carboxylic acid (19.46 mg, 0.096 mmol) in DCM (1.5 mL) was added DIPEA (0.053 mL, 0.305 mmol), (1S,1'S)-1,1'-(5,5'-(biphenyl-4,4'-diyl)bis(1H-imidazole-5,2-diyl))bis(2-methylpropan-1-amine), 4 HCl (25 mg, 0.044 mmol) and HATU (36.4 mg, 0.096 mmol). The mixture was stirred at rt for 1.5 h and diluted with 1 mL of MeOH, concentrated and purified by prep HPLC to afford compound Y-19 as a yellow glass. The product was isolated as bis-TFA salt (10.5 mg). LC-MS (retention time: 2.908 min, method P-1), m/z 799.52 $(M+H)^+$.

Method 2: the below procedure represents the amide coupling using HBTU as a reagent.

Example Y-20

HCl (80 mg, 0.139 mmol) and 5-methylthiophene-2-carboxylic acid (43.6 mg, 0.306 mmol) in DCM (2 mL) was added N-ethyl-N-isopropylpropan-2-amine (0.2 mL, 1.145 mmol) and HBTU (116 mg, 0.306 mmol). After stirring at rt for 1 h, the reaction mixture was diluted with MeOH (1 mL) and concentrated to dryness. The residue was purified by prep HPLC to afford compound Y-20 as bis-TFA salt (23.9 mg). LC-MS: retention time: 1.933 (method P-2); m/z 677 $(M+H)^+$. $^1$H NMR (400 MHz, MeOD) δ ppm 7.91 (2H, s), 7.86 (8H, s), 7.73 (2H, d, J=3.76 Hz), 6.87 (2H, dd, J=3.76, 1.00 Hz), 5.04 (2H, d, J=8.78 Hz), 2.42-2.55 (6H, m), 1.20 (6H, d, J=6.53 Hz), 0.99 (6H, d, J=6.78 Hz).

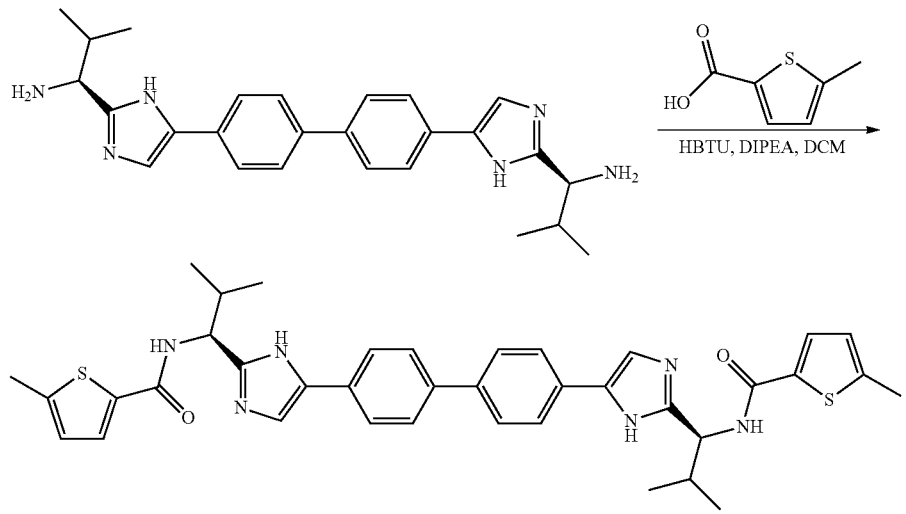

Y-20

To a mixture of (1S,1'S)-1,1'-(5,5'-(biphenyl-4,4'-diyl)bis(1H-imidazole-5,2-diyl))bis(2-methylpropan-1-amine), 4

Method 3: parallel synthesis of amide analogs were performed as following:

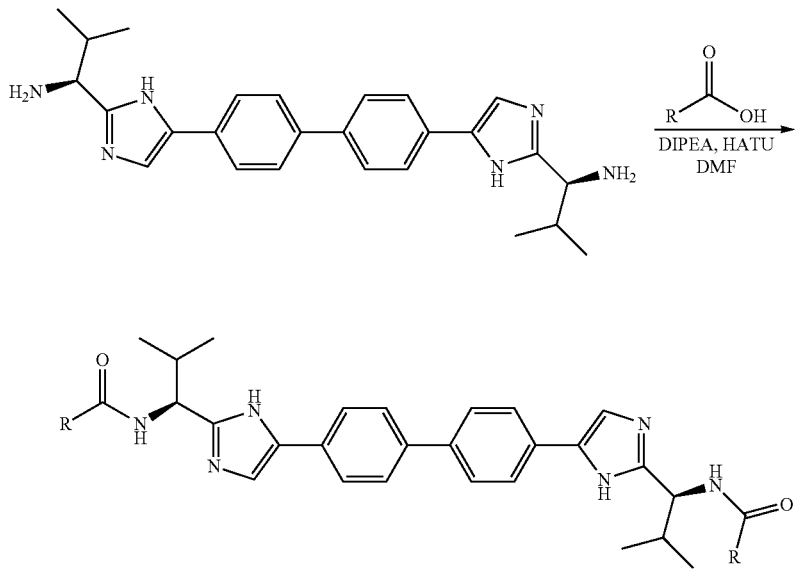

A stock solution of the (1S,1'S)-1,1'-(5,5'-(biphenyl-4,4'-diyl)bis(1H-imidazole-5,2-diyl))bis(2-methylpropan-1-amine), 4 HCl (660 mg, 1.15 mmol) and DIPEA (1.61 ml, 9.2 mmol) in DMF (11.5 ml) and a stock solution of the HATU (1.09 g, 2.87 mmol) in DMF (11.5 ml) were prepared and dispensed into each reaction vial. To a solution of a carboxylic acid (0.125 mmol) in 16×100 mm Wheaton vials were added 0.5 ml of the HATU solution. Capped vials were allowed to shake at room temp for 10 minutes before adding 0.5 ml of the (1S,1'S)-1,1'-(5,5'-(biphenyl-4,4'-diyl)bis(1H-imidazole-5,2-diyl))bis(2-methylpropan-1-amine)/DIPEA solution to each vial. Capped vials were allowed to shake at room temp for 18 h. Reaction mixtures were purified by prep HPLC to afford the corresponding amide analogs.

Method 4: parallel synthesis of carbamate analogs were performed as below:

A stock solution of the (2R,2'R)—N,N'-((1S,1'S)-1,1'-(5,5'-(biphenyl-4,4'-diyl)bis(1H-imidazole-5,2-diyl))bis(2-methylpropane-1,1-diyl))bis(2-amino-3-methylbutanamide), 4 HCl (460 mg, 600 mmol) and DIPEA (828 mL, 4.80 mmol) in DMF (12 mL) was prepared and dispensed into each reaction vial as: to each chloroformate (0.112 mmol) weighed into threaded 16×100 mm Wheaton tubes was added 1.0 mL of the (2R,2'R)—N,N'-((1S,1'S)-1,1'-(5,5'-(biphenyl-4,4'-diyl)bis(1H-imidazole-5,2-diyl))bis(2-methylpropane-1,1-diyl))bis(2-amino-3-methylbutanamide)/DIPEA stock solution. The capped vials were allowed to shake at room temp for 18 h. The reaction mixtures were purified by prep HPLC to afford the corresponding carbamate analogs (Examples S-245 to S-253 in Table 8).

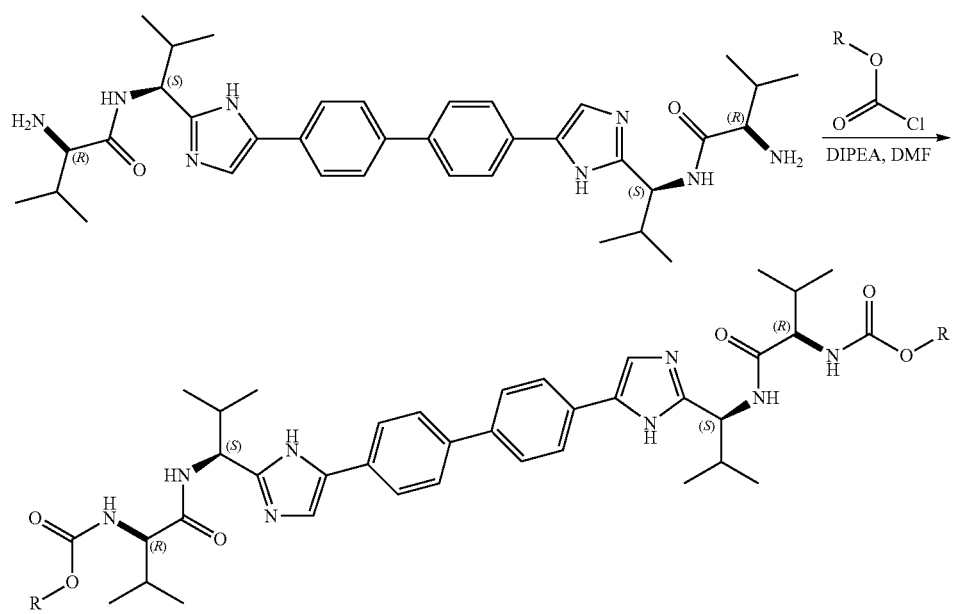

Method 5: parallel synthesis of urea analogs were performed as below:

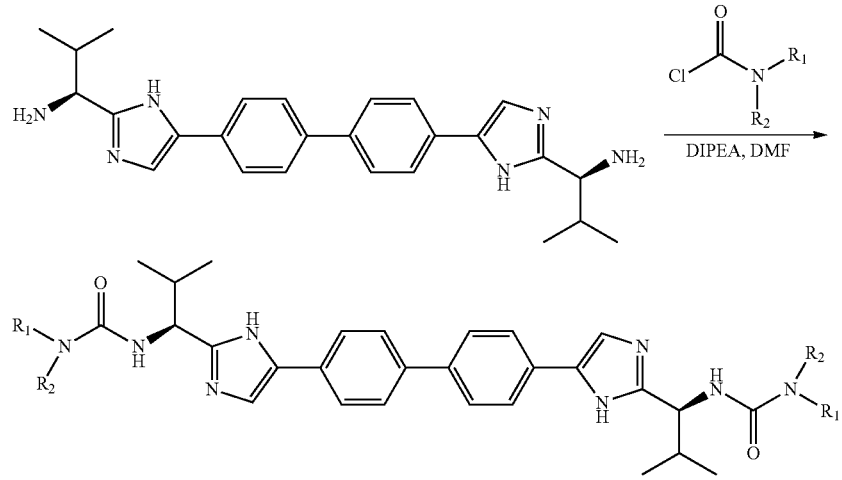

A stock solution of (1S,1'S)-1,1'-(5,5'-(biphenyl-4,4'-diyl)bis(1H-imidazole-5,2-diyl))bis(2-methylpropan-1-amine, 4 HCl (304 mg, 531 mmol) and DIPEA (558 µL, 3.2 mmol) in DMF (9 mL) was prepared and dispensed into each reaction vial. To each carbamyl chloride (0.129 mmol) weighed into threaded 16×100 mm Wheaton tubes was added 1.0 mL of the (1S,1'S)-1,1'-(5,5'-(biphenyl-4,4'-diyl)bis(1H-imidazole-5,2-diyl))bis(2-methylpropan-1-amine/DIPEA solution. The capped vials were allowed to shake at room temp for 18 h. The reaction mixtures were purified by prep HPLC to afford the corresponding urea analogs.

TABLE 2

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| S-1 | | PS-1 | 4.59 | 593.37 |
| S-2 | | PS-1 | 7.23 | 841.41 |
| S-3 | | PS-1 | 5.26 | 649.45 |
| S-4 | | PS-1 | 5.34 | 649.45 |
| S-5 | | PS-1 | 4.93 | 637.35 |
| S-6 | | PS-1 | 5.1 | 741.27 |
| S-7 | | PS-1 | 4.25 | 569.36 |
| S-8 | | PS-1 | 4.38 | 617.29 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| S-9 | 1-naphthylmethyl | PS-1 | 5.68 | 765.44 |
| S-10 | 2-naphthyl | PS-1 | 6.01 | 737.40 |
| S-11 | CHF$_2$ | PS-1 | 4.28 | 585.24 |
| S-12 | CH(Ph)$_2$ | PS-1 | 6.28 | 817.45 |
| S-13 | CH$_2$OMe (neopentyl-like) | PS-1 | 3.66 | 573.32 |
| S-14 | 2-thienyl | PS-1 | 4.93 | 649.27 |
| S-15 | pyrazin-2-yl (with methyl) | PS-1 | 4.09 | 641.30 |
| S-16 | 3,4-difluorophenyl | PS-1 | 5.57 | 709.31 |
| S-17 | 3-biphenyl (with methyl) | PS-1 | 6.46 | 789.44 |

TABLE 2-continued
N,N'-(1S,1'S)-1,1'-(5,5'-(biphenyl-4,4'-diyl)bis(1H-imidazole-5,2-diyl))bis(2-methylpropane-1,1-diyl)bis-amides
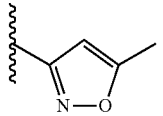 [SMILES: *c1cc(C)on1]
| Example | R | LCMS Method | Retention time (min) | Obs. MS Ion (M + H)+ |
|---|---|---|---|---|
| S-18 | 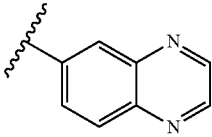 [SMILES: *c1ccc2nccnc2c1] | PS-1 | 4.76 | 647.32 |
| S-19 |  | PS-1 | 4.19 | 741.39 |
| S-20 | 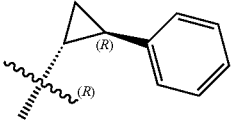 | PS-1 | 4.03 | 565.43 |
| S-21 | 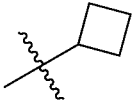 [SMILES: *C1CCC1] | PS-1 | 5.61 | 717.54 |
| S-22 | 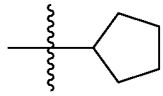 [SMILES: *C1CCCC1] | PS-1 | 4.49 | 593.46 |
| S-23 | 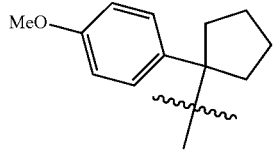 [SMILES: *C1(c2ccc(OC)cc2)CCCC1] | PS-1 | 4.87 | 621.51 |
| S-24 | 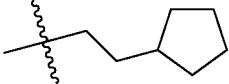 [SMILES: *CCC1CCCC1] | PS-1 | 6.5 | 833.63 |
| S-25 | 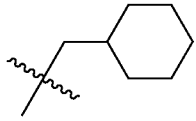 [SMILES: *CC1CCCCC1] | PS-1 | 5.91 | 677.58 |
| S-26 | 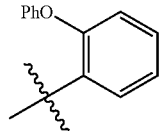 [SMILES: *c1ccccc1Oc1ccccc1] | PS-1 | 5.75 | 677.57 |
| S-27 |  | PS-1 | 6.55 | 821.55 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| S-28 | 4-MeO-C6H4- | PS-1 | 5.04 | 697.49 |
| S-29 | -CH2CN | PS-1 | 3.74 | 563.37 |
| S-30 | -CH2CH(Ph)2 | PS-1 | 6.18 | 845.61 |
| S-31 | Et | PS-1 | 3.72 | 541.41 |
| S-32 | -CH2CH2CH(CH3)2 | PS-1 | 5.25 | 625.51 |
| S-33 | Pr | PS-1 | 4.24 | 569.45 |
| S-34 | tert-Bu | PS-1 | 4.93 | 597.47 |
| S-35 | -CH2OPh | PS-1 | 5.24 | 697.46 |
| S-36 | Bn | PS-1 | 4.96 | 665.46 |
| S-37 | 2-F-C6H4-CH2- | PS-1 | 5.06 | 701.46 |
| S-38 | 2-Cl-C6H4-CH2- | PS-1 | 5.37 | 733.43 |
| S-39 | 2-Me-C6H4-CH2- | PS-1 | 5.3 | 693.52 |
| S-40 | 3-MeO-C6H4-CH2- | PS-1 | 4.96 | 725.51 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| S-41 | 3-methylbenzyl | PS-1 | 5.36 | 693.50 |
| S-42 | 4-methylbenzyl | PS-1 | 5.38 | 693.50 |
| S-43 | styryl/cinnamyl | PS-1 | 5.32 | 689.50 |
| S-44 | pent-4-yn-2-yl | PS-1 | 4.17 | 589.41 |
| S-45 | n-Bu | PS-1 | 4.77 | 597.49 |
| S-46 | 2-pyridyl-methyl | PS-1 | 4.78 | 639.42 |
| S-47 | 2-methyl-2-phenylpropyl | PS-1 | 5.87 | 721.54 |
| S-48 | 6-methylpyridin-2-yl | PS-1 | 5.25 | 667.45 |
| S-49 | Me | PS-1 | 3.38 | 513.37 |
| S-50 | cyclopropylmethyl | PS-1 | 4.39 | 593.44 |
| S-51 | 2-methoxyethyl | PS-1 | 3.55 | 601.44 |

TABLE 2-continued
N,N'-(1S,1'S)-1,1'-(5,5'-(biphenyl-4,4'-diyl)bis(1H-imidazole-5,2-diyl))bis(2-methylpropane-1,1-diyl)bis-amides
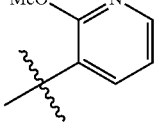
| Example | R | LCMS Method | Retention time (min) | Obs. MS Ion (M + H)+ |
|---|---|---|---|---|
| S-52 |  | PS-1 | 4.96 | 699.44 |
| S-53 |  | PS-1 | 4.59 | 649.36 |
| S-54 | 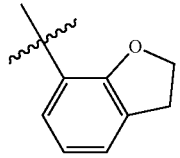 | PS-1 | 4.55 | 615.40 |
| S-55 | 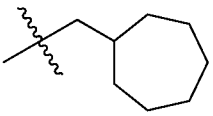 [SMILES: *CC1CCCCCC1] | PS-1 | 5.37 | 721.49 |
| S-56 | 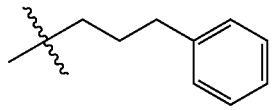 [SMILES: *CCCc1ccccc1] | PS-1 | 6.23 | 705.62 |
| S-57 | 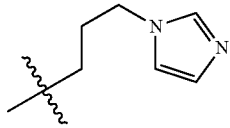 [SMILES: *CCCn1ccnc1] | PS-1 | 5.59 | 721.55 |
| S-58 | 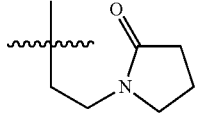 [SMILES: *CCN1CCCC1=O] | PS-1 | 3.88 | 701.56 |
| S-59 | 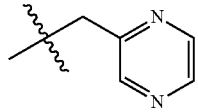 [SMILES: *Cc1cnccn1] | PS-1 | 3.27 | 707.54 |
| S-60 |  | PS-1 | 3.42 | 669.45 |

TABLE 2-continued
N,N'-(1S,1'S)-1,1'-(5,5'-(biphenyl-4,4'-diyl)bis(1H-imidazole-5,2-diyl))bis(2-methylpropane-1,1-diyl)bis-amides
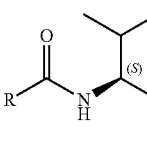
| Example | R | LCMS Method | Retention time (min) | Obs. MS Ion (M + H)+ |
|---|---|---|---|---|
| S-61 | 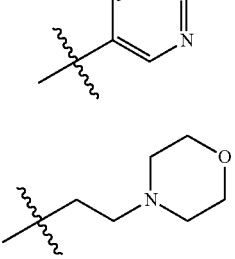 | PS-1 | 3.71 | 641.48 |
| S-62 | 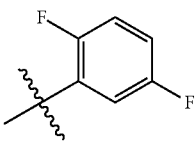 [SMILES: *c1cc(F)ccc1F] | PS-1 | 4.13 | 711.64 |
| S-63 | 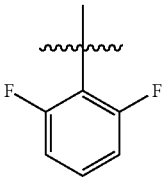 [SMILES: *c1c(F)cccc1F] | PS-1 | 3.12 | 709.36 |
| S-64 | 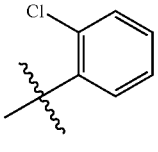 [SMILES: *c1ccccc1Cl] | PS-1 | 2.77 | 709.40 |
| S-65 | 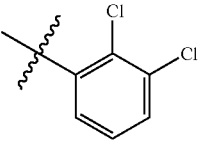 [SMILES: *c1cccc(Cl)c1Cl] | PS-1 | 2.89 | 705.31 |
| S-66 | 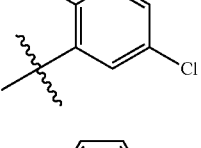 | PS-1 | 3.41 | 773.17 |
| S-67 | 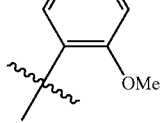 | PS-1 | 3.45 | 773.14 |
| S-68 |  | PS-1 | 2.96 | 697.47 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| S-69 | 2-CF3-phenyl | PS-1 | 3.2 | 773.40 |
| S-70 | 2-methylphenyl | PS-1 | 2.99 | 665.46 |
| S-71 | 2,4-dimethylphenyl | PS-1 | 3.42 | 693.52 |
| S-72 | 3-CN-phenyl | PS-1 | 2.84 | 687.45 |
| S-73 | 3-F-phenyl | PS-1 | 3.13 | 673.40 |
| S-74 | 3-Cl-phenyl | PS-1 | 3.47 | 705.23 |
| S-75 | 3,4-diCl-phenyl | PS-1 | 4.06 | 773.11 |
| S-76 | 3,5-diCl-phenyl | PS-1 | 4.2 | 773.17 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| S-77 | 3-methoxyphenyl | PS-1 | 3.03 | 697.45 |
| S-78 | 3,4-dimethoxyphenyl | PS-1 | 2.69 | 757.54 |
| S-79 | 3-(trifluoromethyl)phenyl | PS-1 | 3.83 | 773.40 |
| S-80 | 3-methylphenyl | PS-1 | 3.31 | 665.45 |
| S-81 | 4-cyanophenyl | PS-1 | 2.83 | 687.42 |
| S-82 | 4-fluorophenyl | PS-1 | 3.08 | 673.38 |
| S-83 | 4-chlorophenyl | PS-1 | 3.5 | 705.37 |
| S-84 | 4-(trifluoromethyl)phenyl | PS-1 | 3.86 | 773.36 |
| S-85 | 3-phenyl-5-methylisoxazol-4-yl | PS-1 | 3.25 | 799.56 |
| S-86 | naphthalen-1-yl | PS-1 | 3.43 | 737.51 |

TABLE 2-continued
N,N'-(1S,1'S)-1,1'-(5,5'-(biphenyl-4,4'-diyl)bis(1H-imidazole-5,2-diyl))bis(2-methylpropane-1,1-diyl)bis-amides
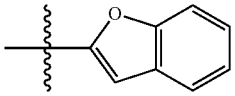 [SMILES: *c1cc2ccccc2o1]
| Example | R | LCMS Method | Retention time (min) | Obs. MS Ion (M + H)+ |
|---|---|---|---|---|
| S-87 | 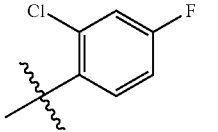 [SMILES: *c1ccc(F)cc1Cl] | PS-1 | 3.35 | 717.40 |
| S-88 | 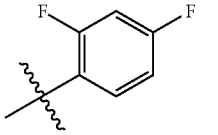 [SMILES: *c1ccc(F)cc1F] | PS-1 | 3.13 | 741.21 |
| S-89 | 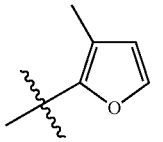 [SMILES: *c1occc1C] | PS-1 | 3.04 | 709.34 |
| S-90 | 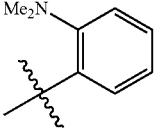 [SMILES: *c1ccccc1N(C)C] | PS-1 | 2.69 | 645.36 |
| S-91 | 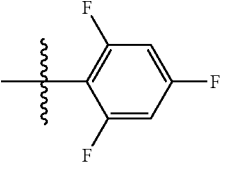 [SMILES: *c1c(F)cc(F)cc1F] | PS-1 | 2.16 | 723.52 |
| S-92 | 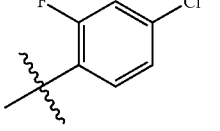 | PS-1 | 3.02 | 745.30 |
| S-93 | 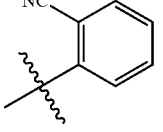 | PS-1 | 3.43 | 741.20 |
| S-94 | | PS-1 | 3.05 | 687.46 |

TABLE 2-continued
N,N'-(1S,1'S)-1,1'-(5,5'-(biphenyl-4,4'-diyl)bis(1H-imidazole-5,2-diyl))bis(2-methylpropane-1,1-diyl)bis-amides
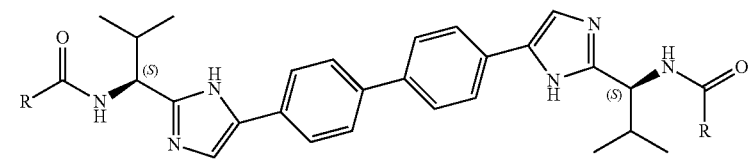
| Example | R | LCMS Method | Retention time (min) | Obs. MS Ion (M + H)+ |
|---|---|---|---|---|
| S-95 | | PS-1 | 4.04 | 799.54 |
| S-96 | | PS-1 | 2.37 | 675.35 |
| S-97 | | PS-1 | 3.16 | 701.40 |
| S-98 | | PS-1 | 3.26 | 673.38 |
| S-99 | | PS-1 | 2.54 | 701.43 |
| S-100 | | PS-1 | 1.97 | 619.29 |
| S-101 | | PS-1 | 3.68 | 757.61 |
| S-102 | | PS-1 | 3.66 | 781.34 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| S-103 | 5-(trifluoromethyl)pyridin-2-yl | PS-1 | 3.28 | 775.34 |
| S-104 | 5-methylisoxazol-4-yl | PS-1 | 2.47 | 647.32 |
| S-105 | 1-methyl-1H-imidazol-2-yl | PS-1 | 2.03 | 645.35 |
| P-55 | isobutyl | P-3 | 1.80 | 597.52 |
| P-56 | neopentyl | P-3 | 3.34 | 625.56 |
| P-57 | adamantan-1-ylmethyl | P-3 | 3.96 | 781.63 |
| P-58 | (tetrahydro-2H-pyran-4-yl)methyl | P-3 | 2.90 | 681.52 |
| P-59 | tetrahydro-2H-pyran-4-yl | P-3 | 2.78 | 653.47 |
| P-60 | adamantan-1-yl | P-3 | 3.90 | 753.58 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| P-61 | (S)-phenyl-sec-butyl | P-3 | 3.55 | 721.52 |
| P-62 | phenyl-isopropyl | P-3 | 3.35 | 693.54 |
| P-63 | 2-fluorophenyl-isopropyl | P-3 | 3.12 | 673.44 |
| P-64 | (R)-phenyl-isopropyl | P-3 | 3.38 | 693.47 |
| P-65 | t-butyl-O-(4-chlorophenyl) | P-3 | 3.72 | 821.49 |
| P-66 | (S)-tetrahydrofuran-2-yl | P-3 | 2.89 | 625.49 |
| P-67 | dimethyl-hydroxymethyl | P-3 | 2.92 | 629.50 |
| P-68 | 1,1-dimethylpropyl | P-3 | 3.36 | 625.43 |
| P-69 | dimethyl-methoxymethyl | P-3 | 3.00 | 629.47 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| P-70 | neopentyl-CH2OMe | P-3 | 3.16 | 657.50 |
| P-71 | C(CH3)2OH | P-3 | 2.81 | 601.45 |
| P-72 | CH2F-C(CH3)2- | P-3 | 3.11 | 633.44 |
| P-73 | 1-(fluoromethyl)cyclopropyl | P-3 | 2.97 | 629.23 |
| P-74 | 1-(methoxymethyl)cyclobutyl | P-3 | 3.20 | 681.33 |
| P-75 | (R)-PhCH(OMe)- | P-3 | 3.23 | 725.19 |
| P-76 | (3-methylisoxazol-5-yl)methyl | P-3 | 2.86 | 675.32 |
| P-77 | benzo[d]isoxazol-3-ylmethyl | P-3 | 3.15 | 747.29 |
| P-78 | thiophen-2-ylmethyl | P-3 | 3.11 | 677.26 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| P-79 | 4,4-difluorocyclohexyl | P-3 | 3.29 | 721.32 |
| P-80 | 1-(trifluoromethyl)cyclopentyl | P-3 | 3.61 | 757.31 |
| P-81 | neopentyl-methyl | P-3 | 3.56 | 653.40 |
| P-82 | 1-(4-fluorophenyl)cyclobutyl | P-3 | 3.71 | 781.35 |
| P-83 | 3,3-difluorocyclobutyl-methyl | P-3 | 3.10 | 665.31 |
| P-84 | 3-methyloxetan-3-yl | P-3 | 2.87 | 625.36 |
| P-85 | (S)-2-methoxy-1-phenylpropyl | P-3 | 3.38 | 725.35 |
| P-86 | 3-methoxyisoquinolin-1-yl-methyl | P-1 | 2.908 | 799.52 |
| P-87 | 3,3,3-trifluoro-2,2-dimethylpropyl | P-1 | 2.753 | 705.43 |
| P-88 | 1-(trifluoromethyl)cyclopropyl-methyl | P-1 | 2.695 | 701.42 |

TABLE 2-continued
N,N'-(1S,1'S)-1,1'-(5,5'-(biphenyl-4,4'-diyl)bis(1H-imidazole-5,2-diyl))bis(2-methylpropane-1,1-diyl)bis-amides
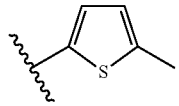 [SMILES: *c1ccc(C)s1]
| Example | R | LCMS Method | Retention time (min) | Obs. MS Ion (M + H)+ |
|---|---|---|---|---|
| P-89 | 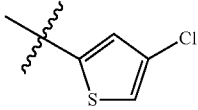 [SMILES: *c1cc(Cl)cs1] | P-1 | 2.448 | 677.38 |
| P-90 | 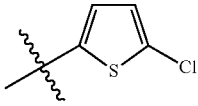 [SMILES: *c1ccc(Cl)s1] | P-1 | 2.032 | 717.31 |
| P-91 | 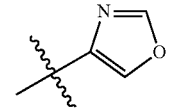 | P-1 | 2.552 | 717.31 |
| P-92 | 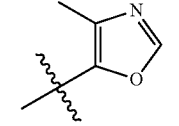 [SMILES: *c1ocnc1C] | P-1 | 2.238 | 619.35 |
| P-93 | 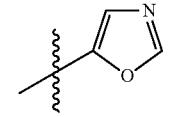 | P-1 | 2.483 | 647.39 |
| P-94 | 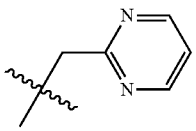 [SMILES: *Cc1ncccn1] | P-1 | 2.372 | 619.42 |
| P-95 | 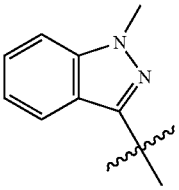 [SMILES: *c1nn(C)c2ccccc12] | P-1 | 2.177 | 669.24 |
| P-96 | 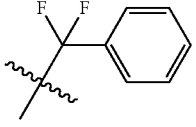 [SMILES: *C(F)(F)c1ccccc1] | P-1 | 2.671 | 745.29 |
| P-97 |  | P-1 | 2.681 | 737.21 |

TABLE 2-continued
N,N'-(1S,1'S)-1,1'-(5,5'-(biphenyl-4,4'-diyl)bis(1H-imidazole-5,2-diyl))bis(2-methylpropane-1,1-diyl)bis-amides
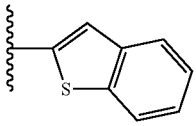 [SMILES: *c1cc2ccccc2s1]
| Example | R | LCMS Method | Retention time (min) | Obs. MS Ion (M + H)+ |
|---|---|---|---|---|
| P-98 | 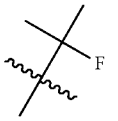 [SMILES: *C(C)(C)F] | P-1 | 2.978 | 749.16 |
| P-99 | 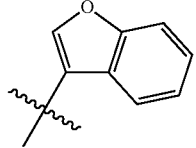 [SMILES: *c1coc2ccccc12] | P-1 | 2.313 | 605.90 |
| P-100 | 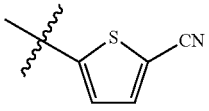 [SMILES: *c1ccc(C#N)s1] | P-1 | 2.77 | 717.18 |
| P-101 | 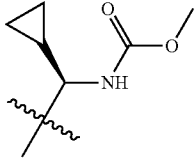 [SMILES: *[C@H](NC(=O)OC)C1CC1] | P-1 | 2.583 | 700.12 |
| P-102 | 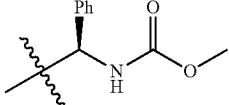 [SMILES: *[C@H](NC(=O)OC)c1ccccc1] | P-1 | 2.523 | 739.44 |
| P-103 | 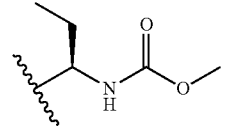 [SMILES: *[C@@H](CC)NC(=O)OC] | P-1 | 2.661 | 811.44 |
| P-104 | 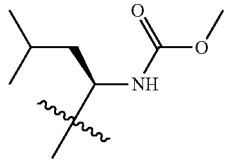 [SMILES: *[C@@H](CC(C)C)NC(=O)OC] | P-1 | 2.492 | 715.39 |
| P-105 | 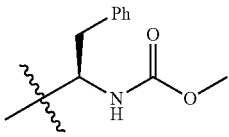 [SMILES: *[C@@H](Cc1ccccc1)NC(=O)OC] | P-1 | 2.785 | 771.50 |
| P-106 |  | P-1 | 2.780 | 839.50 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---------|---|-------------|----------------------|----------------------|
| P-107 | | P-1 | 2.721 | 771.51 |
| P-108 | | P-1 | 2.818 | 869.63 |
| P-109 | | P-1 | 2.641 | 689.40 |
| P-110 | | P-1 | 2.643 | 689.27 |
| P-111 | | P-3 | 3.626 | 677.26 |
| P-112 | | P-3 | 749.23 | 3.233 |
| P-113 | | P-3 | 765.16 | 3.546 |
| P-114 | | P-3 | 649.28 | 3.495 |
| P-115 | | P-3 | 621.31 | 3.286 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)⁺ |
|---|---|---|---|---|
| P-116 | | P-3 | 653.15 | 3.140 |
| P-117 | | P-3 | 657.77 | 3.251 |
| P-118 | | P-3 | 653.11 | 3.080 |
| P-119 | | P-3 | 733.10 | 3.143 |
| P-120 | | P-3 | 675.05 | 2.985 |
| P-121 | | P-3 | 675.32 | 2.888 |
| P-122 | | P-3 | 769.32 | 3.235 |
| P-123 | | P-3 | 625.30 | 3.080 |
| P-124 | | P-3 | 669.34 | 3.283 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| P-125 | 1-hydroxy-4,4-difluorocyclohexyl carbonyl | P-3 | 753.43 | 3.250 |
| P-126 | 1-methoxy-4,4-difluorocyclohexyl carbonyl | P-3 | 781.45 | 3.476 |
| P-127 | 1-(fluoromethyl)-4,4-difluorocyclohexyl carbonyl | P-3 | 785.44 | 3.458 |
| P-128 | 1-(hydroxymethyl)-4,4-difluorocyclohexyl carbonyl | P-3 | 781.45 | 3.268 |
| P-129 | difluorobicyclic carbonyl | P-3 | 773.42 | 3.541 |
| Y-21 | 5-(trifluoromethyl)thiophen-2-yl | YT-1 | 2.73 | 785.21 |
| Y-22 | 1-(3-fluoro-5-chlorophenyl)ethyl | YT-1 | 7.23 | 841.41 |
| Y-23 | 1-(3,5-difluorophenyl)ethyl | YT-1 | 2.76 | 709.10 |

TABLE 2-continued
N,N'-(1S,1'S)-1,1'-(5,5'-(biphenyl-4,4'-diyl)bis(1H-imidazole-5,2-diyl))bis(2-methylpropane-1,1-diyl)bis-amides
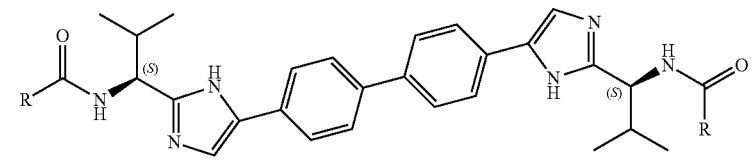
| Example | R | LCMS Method | Retention time (min) | Obs. MS Ion (M + H)⁺ |
|---------|---|-------------|----------------------|----------------------|
| Y-24 | 2-F, 5-Cl phenyl | YT-1 | 2.71 | 741.01 |
| Y-25 | tBu-pyrazole | YT-1 | 2.50 | 701.15 |
| Y-26 | C(CH₃)₂-NHBoc | YT-1 | 2.74 | 799.17 |
| Y-27 | C(CH₃)₂-O-CH₂CHF₂ | YT-1 | 2.49 | 730.88 |
| Y-28 | 3-F-thiophen-2-yl | YT-1 | 2.48 | 685.33 |
| Y-29 | C(CH₃)₂-O-iPr | YT-1 | 2.72 | 685.43 |
| Y-30 | 1-F-cyclohexyl | YT-1 | 2.71 | 685.54 |
| Y-31 | C(CH₃)₂-O-CH₂CF₃ | YT-2 | 3.20 | 765.37 |
| Y-32 | C(CH₃)₂-O-CH₂CH₂F | YT-2 | 2.87 | 693.44 |

TABLE 2-continued

N,N'-(1S,1'S)-1,1'-(5,5'-(biphenyl-4,4'-diyl)bis(1H-imidazole-5,2-diyl))bis(2-methylpropane-1,1-diyl)bis-amides

| Example | R | LCMS Method | Retention time (min) | Obs. MS Ion (M + H)+ |
|---|---|---|---|---|
| Y-33 | (2-fluorophenoxy-dimethyl-methyl) | YT-1 | 2.745 | 789.46 |

TABLE 3

(2S,2'S)-2,2'-(5,5'-(biphenyl-4,4'-diyl)bis(1H-imidazole-5,2-diyl))bis(pyrrolidine-2,1-diyl)bis-amides

| Example | R | LCMS method | Retention time (min) | Obs. MS Ion (M + H) |
|---|---|---|---|---|
| S-106 | Ph | PS-1 | 4.17 | 633.72 |
| S-107 | Bn | PS-1 | 4.57 | 661.89 |
| S-108 | Et | PS-1 | 3.41 | 537.72 |
| S-109 | cyclopropyl | PS-1 | 3.58 | 561.60 |
| S-110 | (cyclopropylmethyl) | PS-1 | 3.98 | 589.89 |
| S-111 | (tetrahydrofuran-2-yl) | PS-1 | 3.25 | 621.87 |
| S-112 | (isobutyl) | PS-1 | 2.44 | 595.86 |
| S-113 | Me | PS-1 | 2.99 | 509.73 |
| S-114 | (2-phenoxyphenyl-dimethyl-methyl) | PS-1 | 5.59 | 817.40 |

TABLE 3-continued
(2S,2'S)-2,2'-(5,5'-(biphenyl-4,4'-diyl)bis(1H-imidazole-5,2-diyl))bis(pyrrolidine-2,1-diyl)bis-amides
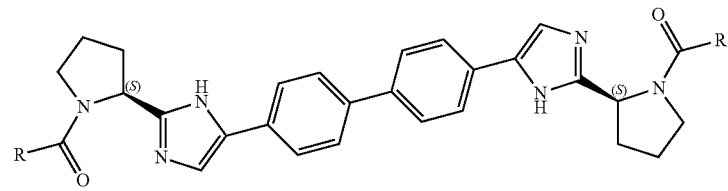
| Example | R | LCMS method | Retention time (min) | Obs. MS Ion (M + H) |
|---|---|---|---|---|
| S-115 | 2-(MeO₂C)phenyl | PS-1 | 4.56 | 749.34 |
| S-116 | 3-(OPh)phenyl | PS-1 | 5.49 | 817.39 |
| S-117 | 4-biphenyl | PS-1 | 5.52 | 785.40 |
| S-118 | 3-phenyl-5-methylisoxazol-4-yl | PS-1 | 4.76 | 795.38 |
| S-119 | 1-naphthyl | PS-1 | 4.97 | 733.39 |
| S-120 | 1H-indol-2-yl | PS-1 | 5.13 | 711.36 |
| S-121 | benzo[d][1,3]dioxol-5-yl | PS-1 | 4.01 | 721.32 |
| S-122 | benzofuran-2-yl | PS-1 | 4.98 | 713.32 |

TABLE 3-continued
(2S,2'S)-2,2'-(5,5'-(biphenyl-4,4'-diyl)bis(1H-imidazole-5,2-diyl))bis(pyrrolidine-2,1-diyl)bis-amides
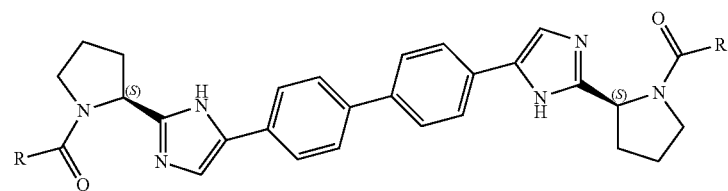
| Example | R | LCMS method | Retention time (min) | Obs. MS Ion (M + H) |
|---|---|---|---|---|
| S-123 | 2-quinolinyl | PS-1 | 4.41 | 735.36 |
| S-124 | 3-quinolinyl | PS-1 | 3.76 | 735.35 |
| S-125 | 4-quinolinyl | PS-1 | 3.48 | 735.37 |
| S-126 | 3-quinoxalinyl | PS-1 | 4.04 | 737.35 |
| S-127 | 2-cyanophenyl | PS-1 | 3.76 | 683.33 |
| S-128 | 3-biphenyl | PS-1 | 5.45 | 785.41 |
| S-129 | 4,5-dimethyl-2-phenyl-2H-triazolyl | PS-1 | 5.46 | 795.40 |
| S-130 | 2-(pyridin-3-yl)thiazol-4-yl | PS-1 | 3.66 | 801.31 |

TABLE 3-continued
(2S,2'S)-2,2'-(5,5'-(biphenyl-4,4'-diyl)bis(1H-imidazole-5,2-diyl))bis(pyrrolidine-2,1-diyl)bis-amides
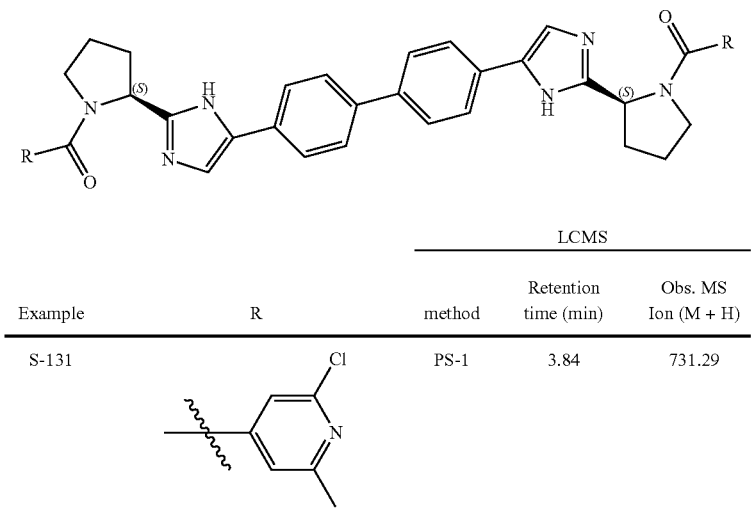
| Example | R | method | Retention time (min) | Obs. MS Ion (M + H) |
|---|---|---|---|---|
| S-131 | 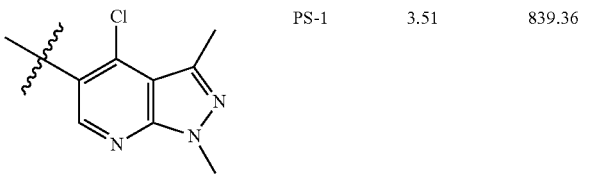 | PS-1 | 3.84 | 731.29 |
| S-132 | 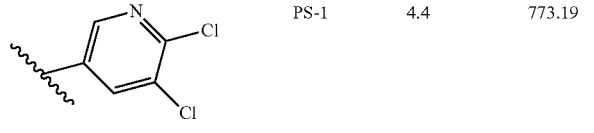 | PS-1 | 3.51 | 839.36 |
| S-133 | 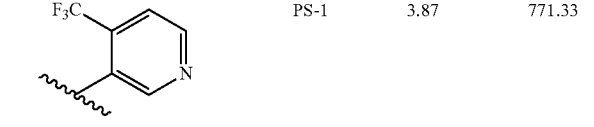 | PS-1 | 4.4 | 773.19 |
| S-134 | 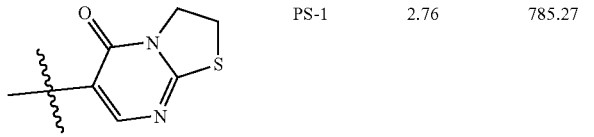 | PS-1 | 3.87 | 771.33 |
| S-135 | 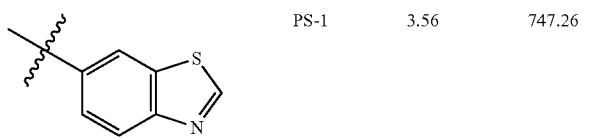 | PS-1 | 2.76 | 785.27 |
| S-136 | 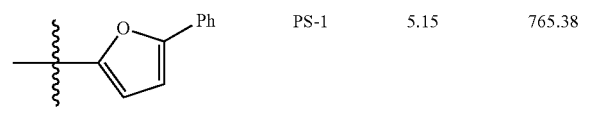 | PS-1 | 3.56 | 747.26 |
| S-137 | 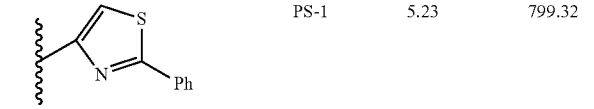 | PS-1 | 5.15 | 765.38 |
| S-138 |  | PS-1 | 5.23 | 799.32 |

TABLE 3-continued
(2S,2'S)-2,2'-(5,5'-(biphenyl-4,4'-diyl)bis(1H-imidazole-5,2-diyl))bis(pyrrolidine-2,1-diyl)bis-amides
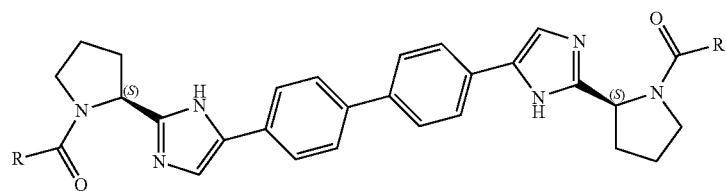
| Example | R | LCMS method | Retention time (min) | Obs. MS Ion (M + H) |
|---|---|---|---|---|
| S-139 | 7-(2,3-dihydrobenzofuranyl) | PS-1 | 4.15 | 717.36 |
| S-140 | 2-(trifluoromethyl)pyridin-5-yl | PS-1 | 4.23 | 771.27 |
| S-141 | benzothiazol-2-yl | PS-1 | 5.46 | 747.28 |
| S-142 | 1-methylindol-3-yl | PS-1 | 4.81 | 739.41 |
| S-143 | CH(CH₂-)CHPh₂ ... (Ph, Ph branched) | PS-1 | 6.02 | 841.48 |
| S-144 | naphthalen-1-ylmethyl-CH₂ | PS-1 | 5.39 | 761.42 |
| S-145 | naphthalen-2-ylmethyl-CH₂ | PS-1 | 5.38 | 761.43 |
| S-146 | CHPh₂ | PS-1 | 6.07 | 813.45 |

TABLE 3-continued
(2S,2'S)-2,2'-(5,5'-(biphenyl-4,4'-diyl)bis(1H-imidazole-5,2-diyl))bis(pyrrolidine-2,1-diyl)bis-amides
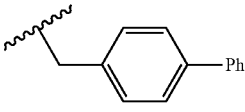
| Example | R | method | Retention time (min) | Obs. MS Ion (M + H) |
|---|---|---|---|---|
| S-147 | 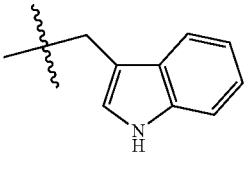 [SMILES: *Cc1c[nH]c2ccccc12] | PS-1 | 5.91 | 813.47 |
| S-148 | 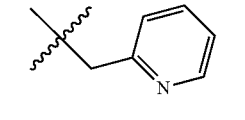 [SMILES: *Cc1ccccn1] | PS-1 | 4.43 | 739.41 |
| S-149 | 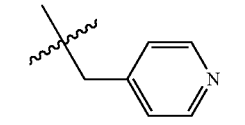 [SMILES: *Cc1ccncc1] | PS-1 | 3.43 | 663.36 |
| S-150 | 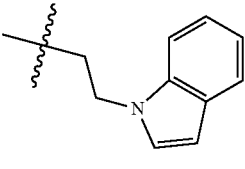 [SMILES: *CCn1ccc2ccccc21] | PS-1 | 3.15 | 663.36 |
| S-151 | 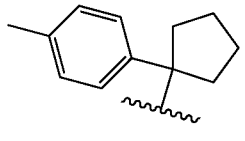 [SMILES: *C1(c2ccc(C)cc2)CCCC1] | PS-1 | 5.32 | 767.44 |
| S-152 | 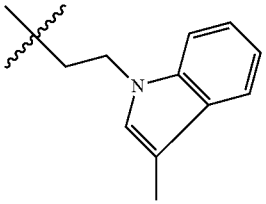 [SMILES: *CCn1cc(C)c2ccccc21] | PS-1 | 7.51 | 797.47 |
| S-153 | 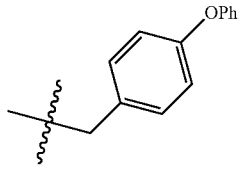 [SMILES: *Cc1ccc(Oc2ccccc2)cc1] | PS-1 | 5.78 | 795.46 |
| S-154 |  | PS-1 | 5.91 | 845.46 |

TABLE 3-continued (2S,2'S)-2,2'-(5,5'-(biphenyl-4,4'-diyl)bis(1H-imidazole-5,2-diyl))bis(pyrrolidine-2,1-diyl)bis-amides

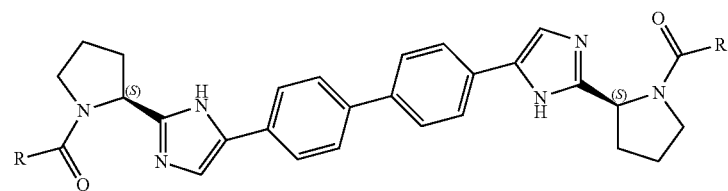

| Example | R | LCMS method | Retention time (min) | Obs. MS Ion (M + H) |
|---|---|---|---|---|
| S-155 | ![2-F-phenyl-cyclopentyl] | PS-1 | 6.51 | 805.43 |
| S-156 | ![2-Cl-4-F-phenyl-cyclopentyl] | PS-1 | 6.88 | 873.37 |
| S-157 | ![dihydrobenzofuran] | PS-1 | 4.66 | 717.37 |
| S-158 | ![4-MeO-phenyl-cyclopentyl] | PS-1 | 6.59 | 829.47 |
| S-159 | ![phenyl-cyclopropyl] | PS-1 | 5.43 | 713.74 |
| S-160 | ![dimethyl-cyclopropyl] | PS-1 | 3.91 | 589.63 |
| S-161 | ![(R,R)-phenyl-cyclopropyl] | PS-1 | 5 | 713.77 |
| S-162 | ![cyclobutyl-methyl] | PS-1 | 4.09 | 589.69 |
| S-163 | ![benzocyclobutenyl] | PS-1 | 4.92 | 685.77 |

TABLE 3-continued
(2S,2'S)-2,2'-(5,5'-(biphenyl-4,4'-diyl)bis(1H-imidazole-5,2-diyl))bis(pyrrolidine-2,1-diyl)bis-amides
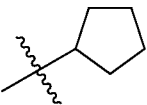 [SMILES: *C1CCCC1]
| Example | R | LCMS method | Retention time (min) | Obs. MS Ion (M + H) |
|---|---|---|---|---|
| S-164 | 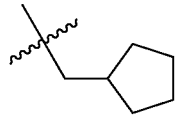 [SMILES: *CC1CCCC1] | PS-1 | 4.51 | 617.73 |
| S-165 | 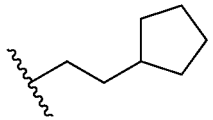 [SMILES: *CCC1CCCC1] | PS-1 | 5.05 | 645.78 |
| S-166 |  | PS-1 | 5.61 | 673.88 |
| S-167 | 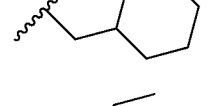 | PS-1 | 4.93 | 645.82 |
| S-168 | 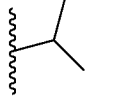 | PS-1 | 5.55 | 673.88 |
| S-169 | 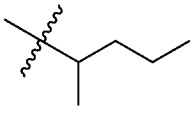 [SMILES: *C(C)CCC] | PS-1 | 4.24 | 593.78 |
| S-170 | 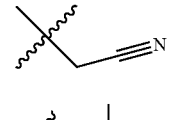 | PS-1 | 4.88 | 621.84 |
| S-171 | 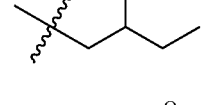 | PS-1 | 3.17 | 559.67 |
| S-172 | 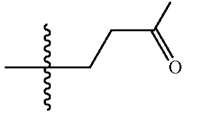 | PS-1 | 4.88 | 621.84 |
| S-173 | | PS-1 | 3.57 | 653.80 |

TABLE 3-continued
(2S,2'S)-2,2'-(5,5'-(biphenyl-4,4'-diyl)bis(1H-imidazole-5,2-diyl))bis(pyrrolidine-2,1-diyl)bis-amides
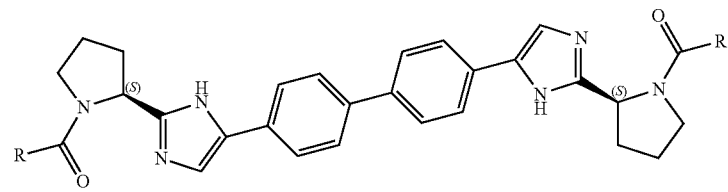
| Example | R | LCMS method | Retention time (min) | Obs. MS Ion (M + H) |
|---|---|---|---|---|
| S-174 | isobutyl-CH2- | PS-1 | 4.84 | 621.88 |
| S-175 | N-methylpyrrole | PS-1 | 4.24 | 639.82 |
| S-176 | cycloheptyl-CH- | PS-1 | 5.3 | 674.00 |
| S-177 | tert-butyl | PS-1 | 4.69 | 593.82 |
| S-178 | 2-fluorobenzyl | PS-1 | 4.71 | 697.94 |
| S-179 | pent-4-yn-1-yl | PS-1 | 3.86 | 585.75 |
| S-180 | n-pentyl | PS-1 | 4.38 | 593.87 |
| S-181 | hexyl branched | PS-1 | 4.98 | 621.92 |
| S-182 | 2-thienyl | PS-1 | 4.29 | 645.79 |
| S-183 | 3-thienyl | PS-1 | 4.13 | 645.78 |

TABLE 3-continued
(2S,2'S)-2,2'-(5,5'-(biphenyl-4,4'-diyl)bis(1H-imidazole-5,2-diyl))bis(pyrrolidine-2,1-diyl)bis-amides
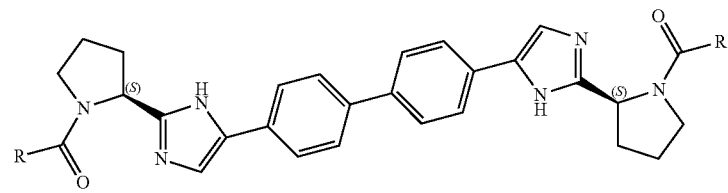
| Example | R | LCMS method | Retention time (min) | Obs. MS Ion (M + H) |
|---|---|---|---|---|
| S-184 | 2-pyridyl | PS-1 | 3.34 | 635.82 |
| S-185 | 3-pyridyl | PS-1 | 3.02 | 635.82 |
| S-186 | -C(CH₃)₂CH₂C(O)NH₂ | PS-1 | 2.69 | 623.87 |
| S-187 | pyridazinyl | PS-1 | 2.74 | 637.83 |
| S-188 | 2-methyl-3-pyridyl | PS-1 | 3.01 | 663.89 |
| S-189 | 3-methyl-2-furyl | PS-1 | 4.44 | 641.87 |
| S-190 | -C(CH₃)₂CH₂CH₃ | PS-1 | 6.05 | 649.52 |
| S-191 | 2,6-dimethyl-pyridyl | PS-1 | 3.69 | 663.91 |
| S-192 | -CH₂CH₂OCH₃ | PS-1 | 3.2 | 597.44 |
| S-193 | -C(CH₃)₂CH₂CF₃ | PS-1 | 4.09 | 645.38 |

TABLE 3-continued
(2S,2'S)-2,2'-(5,5'-(biphenyl-4,4'-diyl)bis(1H-imidazole-5,2-diyl))bis(pyrrolidine-2,1-diyl)bis-amides
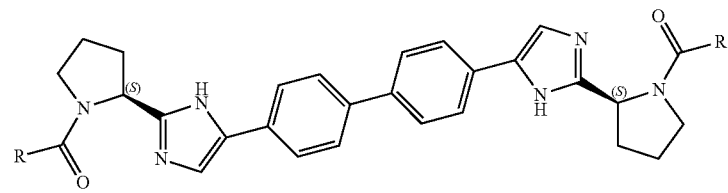
| Example | R | LCMS method | Retention time (min) | Obs. MS Ion (M + H) |
|---|---|---|---|---|
| S-194 | | PS-1 | 3.81 | 611.90 |
| S-195 | pyrimidinyl | PS-1 | 2.91 | 637.48 |
| S-196 | ethyl-morpholine | PS-1 | 2.8483 | 707.49 |
| S-197 | t-butyl-methyl | PS-1 | 5.05 | 621.57 |
| S-198 | 6-methoxyisoquinolin-1-yl | PS-1 | 2.568 | 795.34 |
| S-199 | 4-methoxyisoquinolin-1-yl | PS-1 | 2.608 | 795.41 |
| S-200 | 4-chloroisoquinolin-1-yl | PS-1 | 2.773 | 803.29 |
| S-201 | 5-methoxyisoquinolin-1-yl | PS-1 | 2.640 | 795.41 |

TABLE 3-continued
(2S,2'S)-2,2'-(5,5'-(biphenyl-4,4'-diyl)bis(1H-imidazole-5,2-diyl))bis(pyrrolidine-2,1-diyl)bis-amides
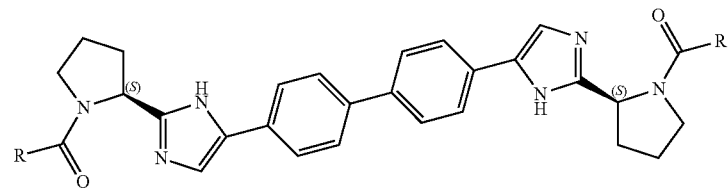
| Example | R | LCMS method | Retention time (min) | Obs. MS Ion (M + H) |
|---|---|---|---|---|
| S-202 | isoquinolin-1-yl | PS-1 | 2.681 | 735.43 |
| S-203 | isoquinolin-5-yl | PS-1 | 2.202 | 735.43 |
| S-204 | 3-chloro-6-methoxyisoquinolin-1-yl | PS-1 | 2.838 | 863.41 |
| S-205 | 2-phenylquinolin-4-yl | PS-1 | 3.021 | 754.50 |
| S-206 | 5-chloroisoquinolin-1-yl | PS-1 | 2.805 | 803.43 |
| P-136 | (4,4-difluorocyclohexyl)carbonyl | P-3 | 3.003 | 717.54 |

TABLE 4 dialkyl (1S, 1'S)-1,1'-(5,5'-(biphenyl-4,4'-diyl)bis(1H-imidazole-5,2-diyl))bis(2-methylpropane-1,1-diyl)bis-carbamates

| Example | R | LCMS Method | Retention time (min) | Obs. MS Ion (M + H) |
|---|---|---|---|---|
| S-207 | Et | PS-2 | 4.144 | 573.43 |
| S-208 | n-Pr | PS-3 | 3.005 | 601.46 |
| S-209 | n-Bu | PS-3 | 3.252 | 629.49 |
| S-210 | neopentyl | PS-3 | 2.943 | 657.63 |
| S-211 | isobutyl | PS-3 | 2.753 | 629.60 |
| S-212 | propargyl | PS-3 | 2.268 | 593.46 |
| S-213 | cyclopentylmethyl | PS-3 | 2.771 | 653.59 |
| S-214 | isopropylmethyl | PS-3 | 2.487 | 601.58 |
| S-215 | CH(CH3)Ph | PS-3 | 2.787 | 697.61 |

TABLE 5

(2S, 2'S)-dialkyl 2,2'-(5,5'-(biphenyl-4,4'-diyl)bis(1H-imidazole-5,2-diyl))dipyrrolidine-1-carboxylates

| Example | R | Method | Retention time (min) | Obs. MS Ion (M + H) |
|---|---|---|---|---|
| S-216 | Bn | PS-1 | 5.43 | 693.23 |
| S-217 | Et | PS-1 | 4.24 | 569.20 |
| S-218 | Pr | PS-1 | 4.76 | 597.22 |
| S-219 | Bu | PS-1 | 5.33 | 625.25 |
| S-220 | i-Pr | PS-1 | 4.68 | 597.25 |

TABLE 5-continued (2S, 2'S)-dialkyl 2,2'-(5,5'-(biphenyl-4,4'-diyl)bis(1H-imidazole-5,2-diyl))dipyrrolidine-1-carboxylates

| Example | R | LC-MS Method | Retention time (min) | Obs. MS Ion (M + H) |
|---|---|---|---|---|
| S-221 | *tert-butylmethyl* | PS-1 | 5.67 | 653.28 |
| S-222 | *isobutyl* | PS-1 | 5.28 | 625.24 |
| S-223 | Ph | PS-1 | 5.21 | 665.22 |
| S-224 | *propargyl-methyl* | PS-1 | 4.35 | 589.17 |
| S-225 | *cyclopentylmethyl* | PS-1 | 5.17 | 649.26 |
| S-226 | *2-naphthyl* | PS-1 | 6.27 | 765.25 |

TABLE 6

1,1'-(1S,1'S)-1,1'-(5,5'-(biphenyl-4,4'-diyl)bis(1H-imidazole-5,2-diyl))bis(2-methylpropane-1,1-diyl)bis(3,3-dialkylurea)

| Example | NR¹R² | LC-MS Method | Retention Time (min) | Obs. Mass ion (M + H)+ |
|---|---|---|---|---|
| S-227 | N(Ph)Ph | PS-1 | 6.65 | 819.28 |

TABLE 6-continued
1,1'-(1S,1'S)-1,1'-(5,5'-(biphenyl-4,4'-diyl)bis(1H-imidazole-5,2-diyl))bis(2-methylpropane-1,1-diyl)bis(3,3-dialkylurea)
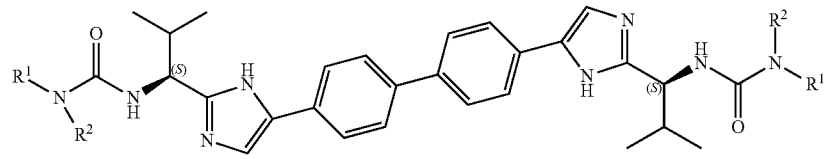
| Example | R¹N(R²)- group | LC-MS Method | Retention Time (min) | Obs. Mass ion (M + H)+ |
|---|---|---|---|---|
| S-228 | N,N-dimethyl | PS-1 | 3.89 | 571.22 |
| S-229 | N,N-diethyl | PS-1 | 4.85 | 627.28 |
| S-230 | N,N-diisopropyl | PS-1 | 6.15 | 683.33 |
| S-231 | morpholino | PS-1 | 3.83 | 655.22 |
| S-232 | pyrrolidinyl | PS-1 | 4.31 | 623.26 |
| S-233 | carbazol-9-yl | PS-1 | 7.83 | 815.24 |
| S-234 | piperidin-1-yl | PS-1 | 5.05 | 651.28 |
| S-235 | 4-methylpiperazin-1-yl | PS-1 | 4.03 | 681.33 |
| P-130 | 4,4-difluoropiperidin-1-yl | P-3 | 3.24 | 723.05 |

Example P-130

Scheme 8

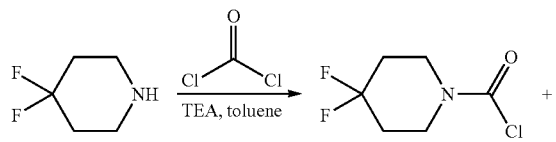

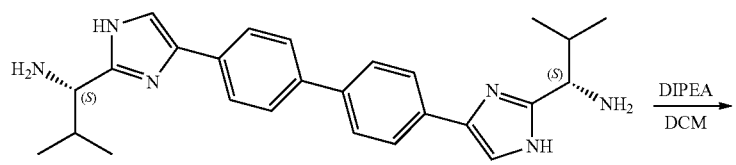

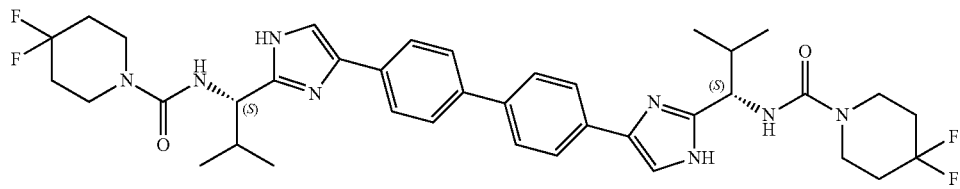

P-130

A solution of phosgene (3.17 mL, 6.00 mmol) in toluene was added to a stirred solution of 4,4-difluoropiperidine, HCl (315 mg, 2 mmol) and TEA (0.669 mL, 4.80 mmol) in THF (6 mL) at 0° C. The reaction mixture was warmed to rt and stirred at rt overnight. Ether was added and the reaction mixture was filtered through a plug of diatomaceous earth (Celite®) and washed with ether. The filtrate was evaporated to dryness to afford 4,4-difluoropiperidine-1-carbonyl chloride as a light yellow oil.

DIPEA (0.039 mL, 0.225 mmol) was added to a stirred mixture of (1S,1'S)-1,1'-(4,4'-(biphenyl-4,4'-diyl)bis(1H-imidazole-4,2-diyl))bis(2-methylpropan-1-amine), 4 HCl (47 mg, 0.082 mmol) and 4,4-difluoropiperidine-1-carbonyl chloride (33.0 mg, 0.180 mmol) in DCM (3 mL) and DMF (1 mL). The mixture was stirred at rt overnight, then evaporated to dryness. The residue was purified by prep HPLC to afford Example P-130 as a beige solid and isolated as bis-TFA salt. LCMS (method P-3): $R_t$=3.24 min, 723.05 [M+H]$^+$; $^1$H NMR (400 MHz, METHANOL-d$_4$) δ 7.91 (s, 2H), 7.90-7.86 (m, 8H), 4.80 (d, J=8.5 Hz, 2H), 3.71-3.54 (m, J=6.5, 5.0 Hz, 8H), 2.45-2.31 (m, 2H), 2.09-1.89 (m, 8H), 1.18 (d, J=6.5 Hz, 6H), 0.96 (d, J=6.8 Hz, 6H).

Example P-131

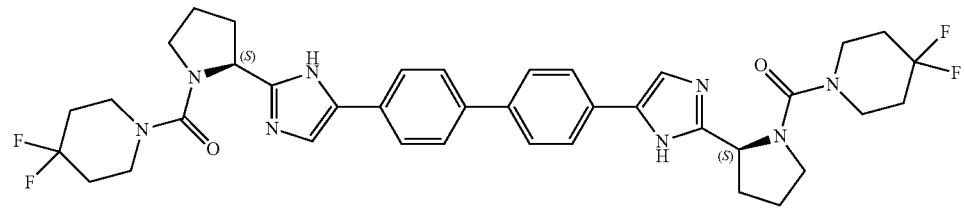

LCMS (method P-3): R$_t$=3.03 min, 719.32 [M+H]$^+$; $^1$H NMR (400 MHz, METHANOL-d$_4$) δ 7.89 (s, 2H), 7.89-7.84 (m, 8H), 5.35-5.25 (m, 2H), 3.88-3.79 (m, 2H), 3.69-3.60 (m, J=7.8, 7.8 Hz, 2H), 3.58-3.45 (m, 8H), 2.63-2.50 (m, 2H), 2.29-2.16 (m, J=6.0, 1.8 Hz, 2H), 2.15-2.03 (m, 8H), 2.02-1.88 (m, 4H).

TABLE 7

(2S,2'S)-2,2'-(5,5'-(biphenyl-4,4'-diyl)bis(1H-imidazole-5,2-diyl))bis(N,N-dialkylpyrrolidine-1-carboxamide)

| Example | -N(R¹)(R²) | Method | retention time (min) | Obs. MS Ion (M + H) |
|---|---|---|---|---|
| S-236 | N(Ph)(Ph) | PS-1 | 6.39 | 815.22 |
| S-237 | NMe₂ | PS-1 | 3.44 | 567.17 |
| S-238 | NEt₂ | PS-1 | 4.47 | 623.22 |
| S-239 | N(iPr)₂ | PS-1 | 5.56 | 679.26 |
| S-240 | morpholino | PS-1 | 3.28 | 651.19 |
| S-241 | pyrrolidinyl | PS-1 | 3.98 | 619.207 |
| S-242 | carbazol-9-yl | PS-1 | 6.84 | 811.21 |
| S-243 | piperidinyl | PS-1 | 4.69 | 647.23 |

TABLE 7-continued (2S,2'S)-2,2'-(5,5'-(biphenyl-4,4'-diyl)bis(1H-imidazole-5,2-diyl))bis(N,N-dialkylpyrrolidine-1-carboxamide)

| Example | -N(R¹)(R²) | Method | retention time (min) | Obs. MS Ion (M + H) |
|---|---|---|---|---|
| S-244 | N-methylpiperazinyl | PS-1 | 2.98 | 677.65 |
| P-131 | 4,4-difluoropiperidinyl | P-3 | 3.03 | 719.32 |

TABLE 8

| Example | R | method | Retention Time (min) | Obs. MS Ion (M + H) |
|---|---|---|---|---|
| S-245 | Bn | PS-1 | 7.15 | 895.63 |
| S-246 | i-Bu | PS-1 | 7.16 | 827.71 |
| S-247 | Et | PS-1 | 6.24 | 771.56 |
| S-248 | Pr | PS-1 | 6.74 | 799.61 |
| S-249 | Bu | PS-1 | 7.21 | 827.64 |
| S-250 | i-Pr | PS-1 | 6.68 | 799.62 |
| S-251 | cyclopentyl | PS-1 | 7.29 | 851.69 |
| S-252 | CH₂C(CH₃)₂C≡CH | PS-1 | 6.11 | 791.58 |
| S-253 | CH₂C(CH₃)₂C(CH₃)₃ | PS-1 | 7.53 | 855.67 |

Examples Y-34 to Y-37 and P-132 to P-134

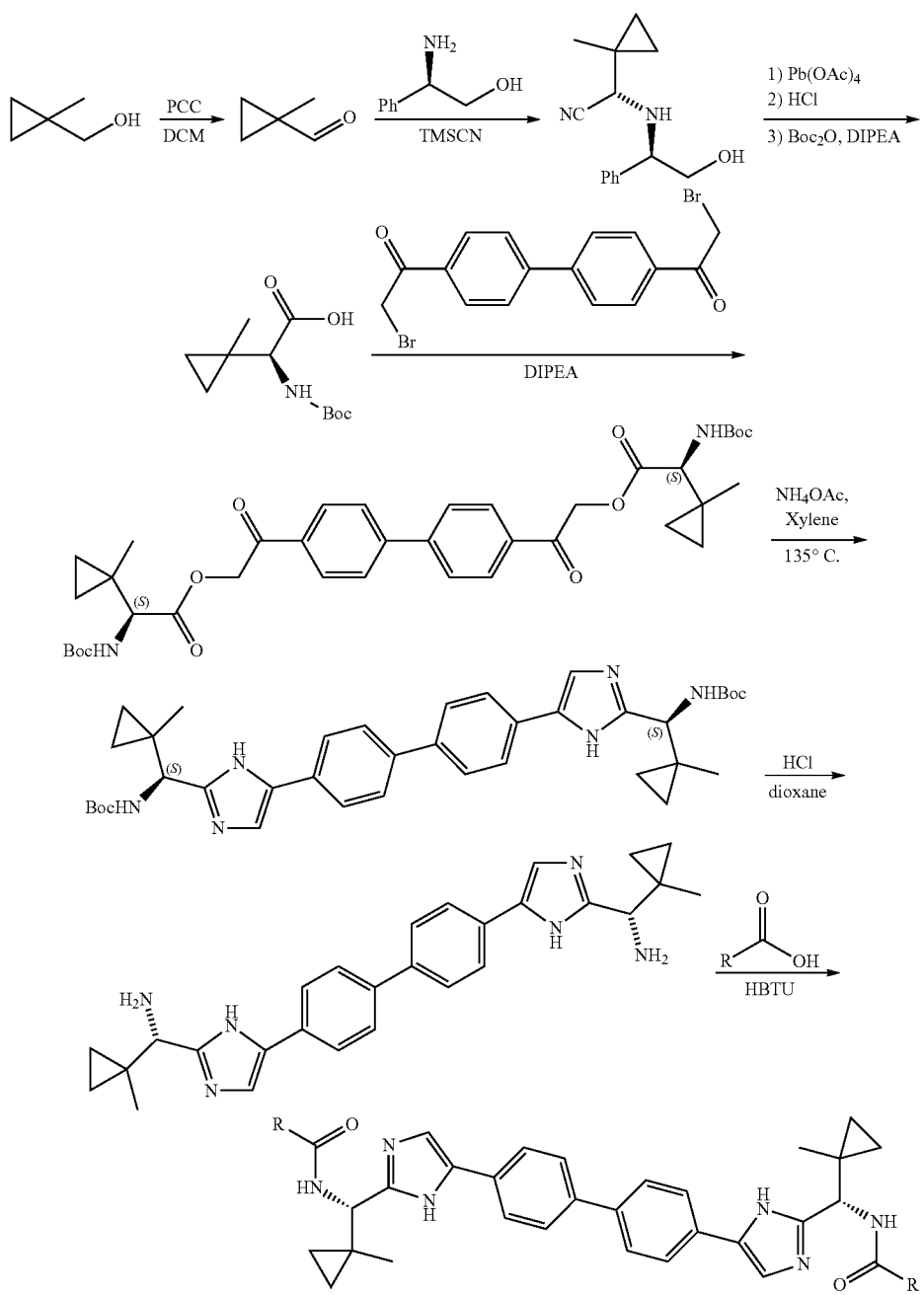

Scheme 9

To a mixture of (1-methylcyclopropyl)methanol (1.9 g, 22.06 mmol) in DCM (30 mL) and powdered molecular sieve 4 A (5 g) was added PCC (6.18 g, 28.7 mmol) portionwise in 30 min at 0° C. The reaction mixture was stirred at rt overnight. The reaction mixture was diluted with 60 mL of ether, stirred for 10 min and filtered through diatomaceous earth (Celite®)/silica gel and eluted with DCM/Ether (1:2). The filtrate was carefully concentrated to afford a pale brown oil which was directly used in the next step.

To a solution of 1-methylcyclopropanecarbaldehyde in MeOH (20 mL) was added (R)-2-amino-2-phenylethanol (3.23 g, 23.54 mmol) at rt under $N_2$ in 3 portions. The mixture was stirred at rt for 2 h and then cooled down with ice-water bath and added with trimethylsilyl cyanide (5.74 mL, 42.8 mmol) dropwise over 5 min. The mixture was stirred for 10 min, ice bath was removed and the reaction was stirred at rt overnight. The reaction mixture was concentrated and purified on a 40 g silica gel column (EtOAc/hexane: 0 to 100%) to afford (S)-2-((R)-2-hydroxy-1-phenylethylamino)-2-(1-methylcyclopropyl)acetonitrile. ¹H NMR (400 MHz, CHLOROFORM-d) δ 7.40-7.30 (m, 5H), 4.08 (dd, J=9.2, 4.1 Hz, 1H), 3.82 (dd, J=10.8, 4.0 Hz, 1H), 3.64 (t, J=10.0 Hz, 1H), 2.97 (s, 1H), 1.26 (s, 3H), 0.63-0.53 (m, 2H), 0.51-0.42 (m, 2H).

To a cold (0-5° C.) stirred solution of (S)-2-((R)-2-hydroxy-1-phenylethylamino)-2-(1-methylcyclopropyl)acetonitrile (1.1 g, 4.78 mmol) in MeOH (20 mL) and DCM (20 mL) was added lead tetraacetate (2.75 g, 6.21 mmol) in 5 portions. The reaction mixture was stirred at 0° C. for 10 min and then stirred at rt for 50 min. The reaction was quenched by addition of 20 ml of satd. NaHCO₃ and the solid was filtered. The filtrate was extracted with DCM (4×). The combined extracts were washed with NaHCO₃, brine, dried (MgSO₄), and removed the solvent to afford an oil which was refluxed in 20 ml of concentrated HCl for 20 h and cooled down. The clear top solution was decanted into another flask and concentrated to dryness to afford a white solid which was dissolved in 20 ml of MeOH and treated with TEA (1.997 mL, 14.33 mmol). The mixture was cooled in ice water, and BOC₂O (2.085 g, 9.55 mmol) was added in 5 portions. The reaction mixture was stirred at rt overnight (20 h). The solvent was removed and the residue was partitioned with 10 ml of 1 N NaOH and EtOAc/hexane (~1:5). The aqueous phase was acidified with ice cold 2 N HCl to adjust pH ~2, then extracted with EtOAc (3×). The combined extracts were washed with brine (2×), dried (MgSO₄). The solvent was removed to afford (S)-2-(tert-butoxycarbonylamino)-2-(1-methylcyclopropyl)acetic acid as a white solid. ¹H NMR (400 MHz, CHLOROFORM-d) δ 5.18 (br. S., 1H), 3.76 (br. S., 1H), 1.47 (s, 9H), 1.09 (s, 3H), 0.91-0.77 (m, 1H), 0.75-0.67 (m, 1H), 0.52-0.44 (m, 1H), 0.44-0.35 (m, 1H); [α]$_D$=80.95.

To a cold (0-5° C.) stirred solution of (S)-2-((tert-butoxycarbonyl)amino)-2-(1-methylcyclopropyl)acetic acid (0.81 g, 3.53 mmol) and DIPEA (0.679 mL, 3.89 mmol) in acetonitrile (10 mL) was added 1,1'-([1,1'-biphenyl]-4,4'-diyl)bis(2-bromoethanone) (0.700 g, 1.766 mmol) in 3 portions. The suspension was stirred in an ice bath for 0.5 h then stirred at rt for 18 h. The reaction mixture was diluted with EtOAc, washed with NH₄Cl, brine. The solvent was removed to afford the designated compound. LC/MS (Cond. YT-1): [M+Na]⁺ 715.37, R$_t$=3.16 min.

A mixture of (2S,2'S)-[1,1'-biphenyl]-4,4'-diylbis(2-oxoethane-2,1-diyl)bis(2-((tert-butoxycarbonyl)amino)-2-(1-methylcyclopropyl)acetate) (1.22 g, 1.761 mmol) and ammonium acetate (4.07 g, 52.8 mmol) in xylene (5 mL) was heated at 135° C. for 3 h in a sealed tube. The reaction mixture was cooled, diluted with EtOAc, washed with NaHCO₃, brine, dried (MgSO₄), concentrated and the residue was purified on a 25 g silica gel column (EtOAc/hexane 50 to 100%) to afford the product as a yellow solid. LC/MS (YT-1): [M+H]⁺ 653.49, R$_t$=2.33 min.

To a solution of di-tert-butyl((1S,1'S)-(5,5'-([1,1'-biphenyl]-4,4'-diyl)bis(1H-imidazole-5,2-diyl))bis((1-methylcyclopropyl)methylene))dicarbamate (0.64 g, 0.980 mmol) in DCM (5 mL) was added 4 M hydrogen chloride in dioxane (5 mL, 20.0 mmol) in ice bath. The reaction mixture was stirred at rt for 2 h and the solvent was removed to afford the product as a yellow solid. LC/MS (method YT-1): [M+H]⁺ 453.3, R$_t$=1.58 min.

Examples Y-34 to Y-37 and P-132 to P-134 (Table 9) were prepared by employing the standard amide coupling procedure.

TABLE 9

| Example | R | LC-MS Method | Retention Time (min) | Obs. Mass ion (M + H)+ |
|---|---|---|---|---|
| Y-34* | 4,4-difluorocyclohexyl carbonyl | YT-1 | 2.333 | 745.5 |
| Y-35 | pivaloyl (tert-butyl carbonyl) | YT-1 | 2.68 | 621.17 |
| Y-36 | 3-fluoro-2,2-dimethylpropanoyl | YT-1 | 2.380 | 629.50 |
| Y-37 | 3,3-difluorobicyclic carbonyl | YT-1 | 2.09 | 741.5 |

TABLE 9-continued

| Example | R | LC-MS Method | Retention Time (min) | Obs. Mass ion (M + H)+ |
|---|---|---|---|---|
| P-132 | | P-3 | 3.478 | 805.58 |
| P-133 | | P-3 | 3.536 | 773.57 |
| P-134 | | P-3 | 3.531 | 797.60 |

*$^1$H NMR of Y-34 (400 MHz, METHANOL-$d_4$): δ ppm 7.91 (2 H, s), 7.87 – 7.90 (4 H, m), 7.83 – 7.87 (4 H, m), 4.46 (2 H, s), 2.56 (2 H, t, J = 10.29 Hz), 2.06 – 2.20 (4 H, m), 1.67 – 2.01 (12 H, m), 1.19 (6 H, s), 0.84 – 0.94 (2 H, m), 0.65 – 0.77 (4 H, m), 0.50 – 0.64 (2 H, m).

Example P-135

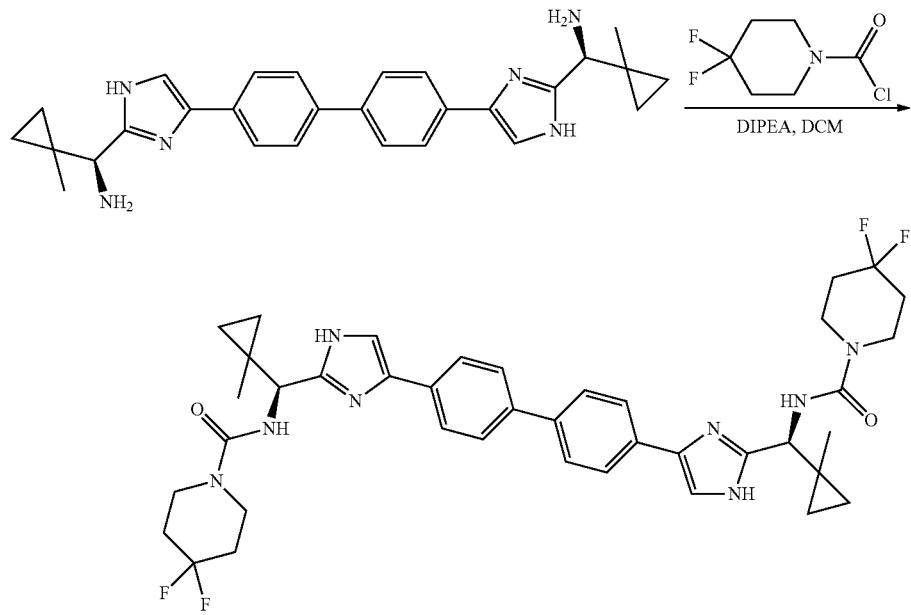

Example P-135

DIPEA (0.044 mL, 0.250 mmol) was added to a stirred partial solution of (1S,1'S)-(4,4'-([1,1'-biphenyl]-4,4'-diyl) bis(1H-imidazole-4,2-diyl))bis((1-methylcyclopropyl) methanamine), 4 HCl (54.5 mg, 0.091 mmol) and 4,4-difluoropiperidine-1-carbonyl chloride (36.8 mg, 0.200 mmol) in DCM (2 mL) and DMF (1 mL). The mixture was stirred at rt overnight. The reaction mixture was evaporated to dryness and purified by prep. HPLC to afford Example P-135 as a beige solid and isolated as bis-TFA salt. LCMS (method P-3): $R_t$=3.186 min, 747.55 [M+H]$^+$; $^1$H NMR (500 MHz, METHANOL-$d_4$) δ 7.89 (s, 2H), 7.89-7.86 (m, 8H), 3.65 (d, J=2.7 Hz, 8H), 2.08-1.96 (m, 8H), 1.19 (s, 6H), 0.93-0.87 (m, 2H), 0.79-0.73 (m, 2H), 0.73-0.67 (m, 2H), 0.60-0.53 (m, 2H).

Examples Y-38 to Y-39

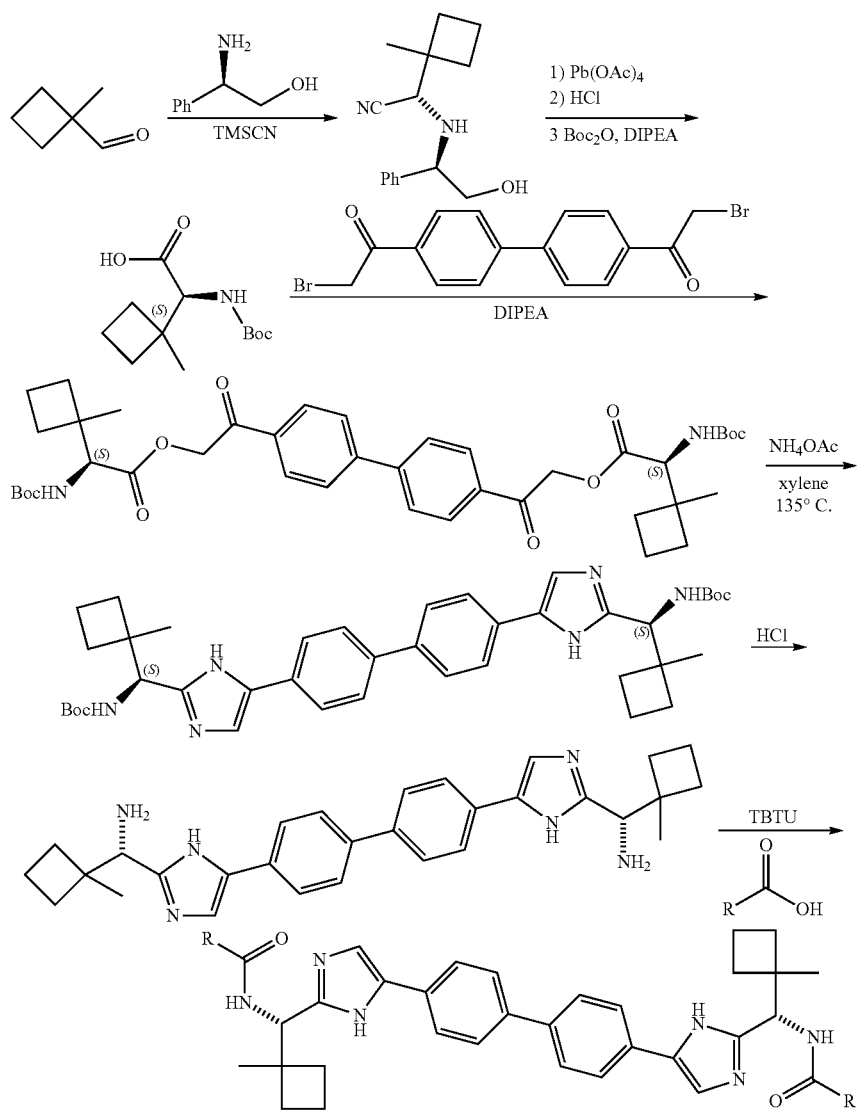

Scheme 10

To a solution of 1-methylcyclobutanecarbaldehyde (1 g, 10.19 mmol) in MeOH (20 mL) was added (R)-2-amino-2-phenylethanol (1.538 g, 11.21 mmol) at rt under $N_2$ in 3 portions. The resultant solution was stirred at rt for 1 h and then cooled to −20° C. and trimethylsilyl cyanide (2.73 mL, 20.38 mmol) was added dropwise over 5 min. Then the reaction mixture was warmed to rt and stirred at rt for 18 hr. The solvent was removed and the residue was purified on a 25 g silica gel column (MeOH/DCM: 0 to 24%) to afford the designated product (0.64 g).

To a cold (0-5° C.) stirred solution of (S)-2-(((R)-2-hydroxy-1-phenylethyl)amino)-2-(1-methylcyclobutyl)acetonitrile (0.64 g, 2.62 mmol) in MeOH (20 mL) and DCM (20 mL) was added lead tetraacetate (1.510 g, 3.41 mmol) in 5 portions. The reaction mixture was stirred at 0-5° C. for 5 min and allowed to warm to rt and stirred for 3.5 h. The reaction mixture was quenched with 20 ml of satd. $NaHCO_3$. The solid was filtered and the filtrate was extracted with DCM (4×). The combined extracts were washed with $NaHCO_3$, brine, dried ($MgSO_4$), and the solvent was removed to afford an oil which was refluxed in concentrated HCl (20 mL, 240 mmol) for 17 h. The reaction mixture was cooled down and the clear solution was decanted and concentrated to dryness to afford a brown solid which was dissolved in 20 mL of MeOH, added with TEA (1.095 mL, 7.86 mmol) and $Boc_2O$ (0.858 g, 3.93 mmol) in 5 portions in an ice bath then the reaction mixture was warmed to rt and stirred for 24 h at rt. The solvent was removed and the residue was dissolved in EtOAc and washed with ice chilled 1 N HCl (2×), brine (2×), dried (MgSO₄), the solvent was removed to afford the designated compound (0.61 g). ¹H NMR (400 MHz, CHLOROFORM-d) δ 4.97 (d, J=8.5 Hz, 1H), 4.40 (d, J=9.3 Hz, 1H), 2.43-2.22 (m, 1H), 2.20-2.06 (m, 1H), 2.04-1.90 (m, 1H), 1.91-1.79 (m, 1H), 1.80-1.60 (m, 2H), 1.46 (d, J=1.0 Hz, 9H), 1.15 (s, 3H); [α]$_D$=27.11.

To a cold (0-5° C.) stirred solution of (S)-2-((tert-butoxycarbonyl)amino)-2-(1-methylcyclobutyl)acetic acid (0.61 g, 2.507 mmol) and DIPEA (0.482 mL, 2.76 mmol) in acetonitrile (10 mL) was added 1,1'-([1,1'-biphenyl]-4,4'-diyl)bis(2-bromoethanone) (0.497 g, 1.254 mmol) in 3 portions in ice bath. The suspension was stirred in an ice bath for 0.5 h, then stirred at rt for 3 days. The volatile component was removed in vacuo and the residue was directly loaded on a 25 g silica gel column and eluted (EtOAc/hexane: 0 to 100%) to afford the product as a yellow solid (0.802 g). LC/MS (method YT-1): [M+H]⁺ 743.50, R$_t$=3.34 min. ¹H NMR (400 MHz, CHLOROFORM-d) δ 8.02 (d, J=8.3 Hz, 4H), 7.75 (d, J=8.5 Hz, 4H), 5.56 (d, J=16.3 Hz, 2H), 5.29 (d, J=16.3 Hz, 2H), 5.05 (d, J=9.0 Hz, 2H), 4.54 (d, J=9.3 Hz, 2H), 2.44-2.32 (m, 2H), 2.24-2.13 (m, 2H), 2.05-1.82 (m, 6H), 1.75-1.65 (m, 2H), 1.51-1.44 (m, 18H), 1.27 (s, 6H).

A mixture of (2S,2'S)[1,1'-biphenyl]-4,4'-diylbis(2-oxoethane-2,1-diyl)bis(2-((tert-butoxycarbonyl)amino)-2-(1-methylcyclobutyl)acetate) (0.802 g, 1.113 mmol) and ammonium acetate (2.57 g, 33.4 mmol) in xylene (5 ml) was heated in a sealed tube at 138° C. for 3 h and cooled to room temperature. The reaction mixture was diluted with EtOAc and washed with satd. NaHCO₃, brine, dried (MgSO₄). The solvent was removed and the residue was purified on a 40 g silica gel column (EtOAc/hexane: 50 to 100%) to afford a yellow foam (0.53 g). ¹H NMR (400 MHz, MeOD) δ 7.83-7.74 (m, 4H), 7.71-7.63 (m, 4H), 7.37 (s, 2H), 4.83 (s, 2H), 2.29 (q, J=9.0 Hz, 2H), 2.14 (quin, J=9.5 Hz, 2H), 2.01-1.87 (m, 2H), 1.86-1.74 (m, 2H), 1.77-1.54 (m, 4H), 1.51-1.39 (m, 18H), 1.24-1.11 (m, 6H). LC/MS (YT-1): [M+H]⁺ 681.45, R$_t$=2.44 min.

To a cold (0-5° C.) stirred suspension of di-tert-butyl((1S,1'S)-(5,5'-([1,1'-biphenyl]-4,4'-diyl)bis(1H-imidazole-5,2-diyl))bis((1-methylcyclobutyl)methylene))dicarbamate (0.12 g, 0.176 mmol) in DCM (3 mL) was added 4 N hydrogen chloride in dioxane (2 mL, 8.00 mmol). The reaction mixture was stirred at rt for 40 min, and the solvent was removed to afford a yellow solid. LC/MS (YT-1): [M+H]⁺ 481.45, R$_t$=2.30 min. This product was elaborated to Examples Y-38 to Y-39 by employing standard amide coupling procedure.

Example Y-38

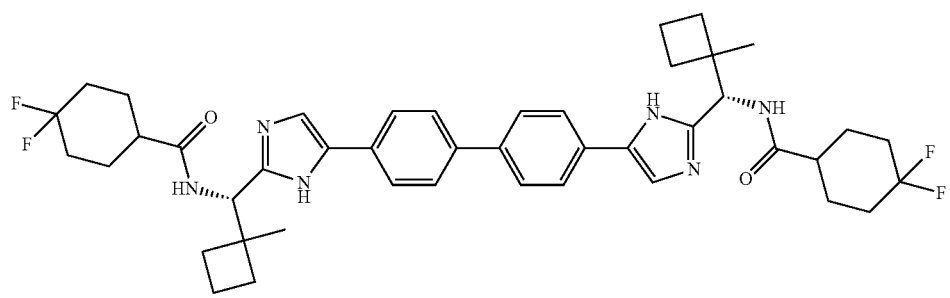 [SMILES: CC1([C@H](NC(=O)C2CCC(F)(F)CC2)c2ncc(-c3ccc(-c4ccc(-c5cnc([C@@H](NC(=O)C6CCC(F)(F)CC6)C6(C)CCC6)[nH]5)cc4)cc3)[nH]2)CCC1]

LC/MS (method YT-1): [M+H]⁺ 773.49, R$_t$=2.528 min; ¹H NMR (400 MHz, MeOD) δ 7.91 (s, 2H), 7.90-7.83 (m, 8H), 5.12 (s, 2H), 2.68-2.53 (m, 2H), 2.38-2.21 (m, 2H), 2.22-2.01 (m, 8H), 2.01-1.82 (m, 10H), 1.84-1.65 (m, 8H), 1.31 (s, 6H).

Example Y-39

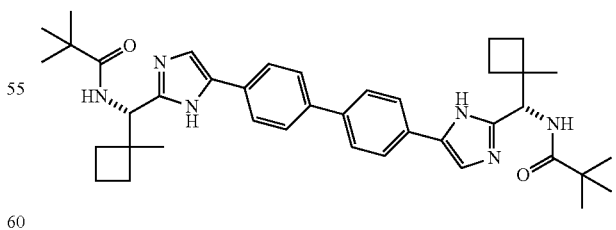

LC/MS (method YT-1): [M+H]⁺ 649.44, R$_t$=2.493 min; ¹H NMR (400 MHz, MeOD) δ 7.93 (s, 2H), 7.91-7.84 (m, 8H), 5.34-5.30 (m, 2H), 2.23 (dt, J=11.0, 8.1 Hz, 2H), 2.18-2.02 (m, 4H), 1.97-1.85 (m, 4H), 1.80-1.69 (m, 2H), 1.30 (s, 6H), 1.27 (s, 18H).

Examples Y-40 to Y-48

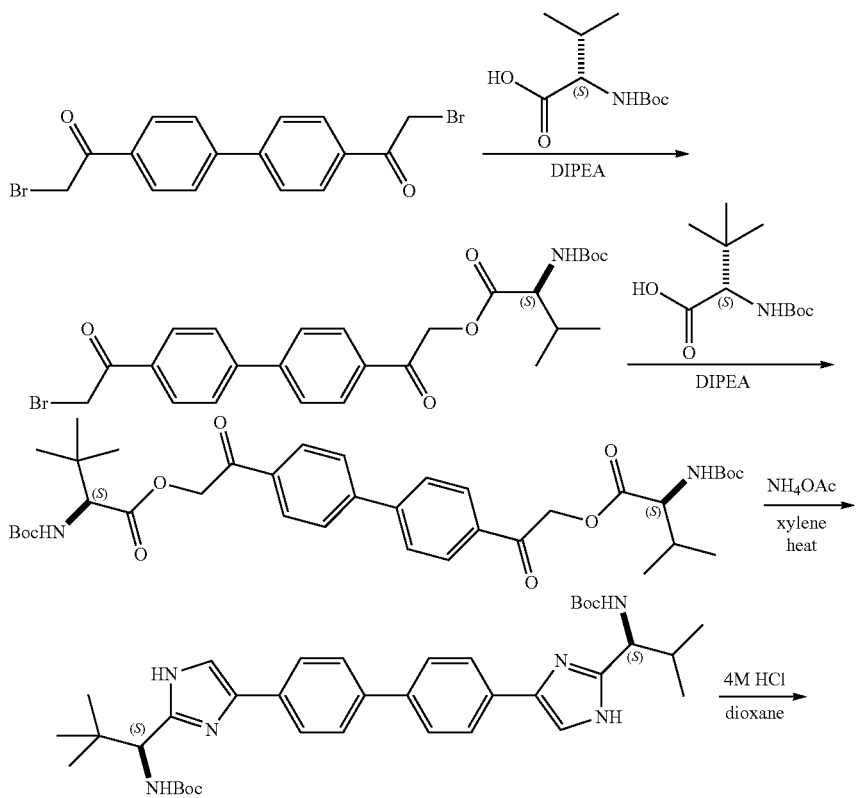

Example Y-40

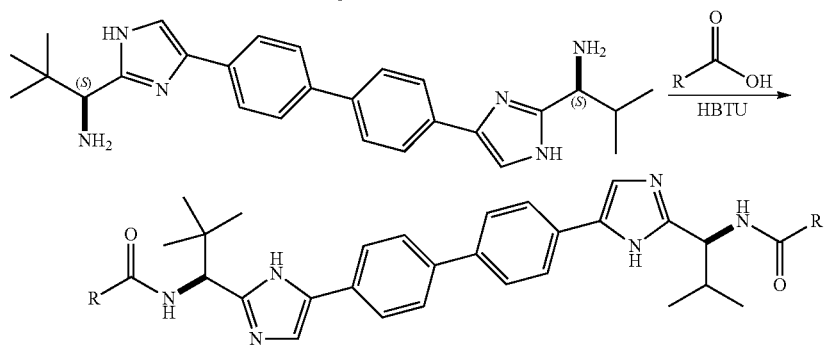

Examples Y-41 to Y-48

To a solution of 1,1'-(biphenyl-4,4'-diyl)bis(2-bromoethanone) (5 g, 12.6 mmol) and (S)-2-(tert-butoxycarbonylamino)-3-methylbutanoic acid (2.74 g, 12.62 mmol) in MeCN (40 mL), THF (100 mL) and DMF (100 mL) was added DIPEA (2.315 mL, 13.26 mmol) dropwise in 15 min. The reaction mixture was stirred at rt for 20 h and diluted with EtOAc, washed with ice cold satd. citric acid (2×), water, brine, dried (MgSO$_4$), and the residue was purified on a 160 g silica gel column (EtOAc/hex: 0 to 100%) to afford the product (2.8 g). LC-MS: retention time: 2.873 min (method YT-1); m/z 556.03 [M+Na]$^+$; $^1$H NMR (400 MHz, DMSO-d$_6$) δ ppm 8.07-8.19 (4H, m), 7.98 (4H, d, J=8.78 Hz), 7.26 (1H, d, J=8.53 Hz), 5.62-5.69 (1H, m), 5.51-5.57 (1H, m), 5.01 (2H, s), 4.01-4.10 (1H, m), 2.09-2.25 (1H, m), 1.41 (9H, s), 0.95-1.06 (6H, m).

To a solution of (S)-2-(4'-(2-bromoacetyl)biphenyl-4-yl)-2-oxoethyl 2-(tert-butoxycarbonylamino)-3-methylbutanoate (1.0 g, 1.878 mmol) and (S)-2-(tert-butoxycarbonylamino)-3,3-dimethylbutanoic acid (0.5 g, 2.162 mmol) in MeCN (5 mL) and DMF (5 mL) was added DIPEA (0.361 mL, 2.066 mmol) dropwise over 15 min. The reaction mixture was stirred at rt for 4 h and then diluted with EtOAc, washed with ice cold satd. citric acid (2×), water, brine, dried (MgSO$_4$), and purified on a 25 g silica gel column (EtOAc/ hexane: 20-100%) to afford the product (1.1 g) as a white solid. LC-MS: retention time=2.173 min (method YT-3); m/z 683.20 [M+H]⁺; ¹H NMR (400 MHz, CHLOROFORM-d) δ ppm 8.03 (4H, dd, J=8.53, 2.01 Hz), 7.76 (4H, d, J=8.28 Hz), 5.50-5.64 (2H, m), 5.27-5.39 (2H, m), 5.15 (1H, d, J=9.54 Hz), 5.06 (1H, d, J=9.54 Hz), 4.43 (1H, dd, J=9.16, 4.39 Hz), 4.28 (1H, d, J=9.79 Hz), 2.30-2.46 (1H, m), 1.47 (18H, s), 1.13 (9H, s), 1.09 (3H, d, J=6.78 Hz), 1.05 (3H, d, J=6.78 Hz).

A mixture of (S)-2-(4'-(2-((S)-2-(tert-butoxycarbonylamino)-3-methylbutanoyloxy)acetyl)biphenyl-4-yl)-2-oxoethyl 2-(tert-butoxycarbonylamino)-3,3-dimethylbutanoate (1.1 g, 1.611 mmol) and ammonium acetate (2.5 g, 32.4 mmol) was heated at 135° C. in a sealed tube for 5 h. The reaction mixture was cooled down and diluted with EtOAc, washed with ice cold NaHCO₃, brine, dried (MgSO₄). The solvent was removed and the residue was purified on a 40 g column (EtOAc/hexane: 20 to 100%) to afford Example Y-40 as a yellow solid (0.63 g). LC-MS: retention time=2.413 min (method YT-1); m/z 643.34 (M+H)⁺.

To a solution of Example Y-40 (0.62 g, 0.96 mmol) in DCM (3 mL) was added HCl in dioxane (5.00 mL, 20 mmol). The mixture was stirred at rt for 1.5 h and evaporated to dryness to afford the product (0.568 g) which was isolated as 4 HCl salt. LC-MS: retention time=2.338 min (method YT-1); m/z 443.16 (M+H)⁺.

To a mixture of (S)-1-(5-(4'-(2-((S)-1-amino-2-methylpropyl)-1H-imidazol-5-yl)biphenyl-4-yl)-1H-imidazol-2-yl)-2,2-dimethylpropan-1-amine, 4 HCl (50 mg, 0.085 mmol) and appropriate acid (2.2 equiv) in DCM (2 mL) was added DIPEA (0.2 mL, 1.145 mmol) and HBTU (71 mg, 0.187 mmol). The reaction mixture was stirred at rt for 50 min, then quenched with MeOH (1 mL), evaporated to dryness and the crude product was purified by prepHPLC to afford desired bis-amide products.

TABLE 10

| Example | R | LCMS Method | Retention time (min) | Obs. MS Ion (M + H)⁺ |
|---|---|---|---|---|
| Y-40 | (tert-butyl carbamate) | YT-1 | 2.413 | 643.33 |
| Y-41 | (pivaloyl) | YT-1 | 2.568 | 6.11.43 |
| Y-42 | (4,4-difluorocyclohexanecarbonyl) | YT-1 | 2.563 | 735.35 |

TABLE 10-continued

| Example | R | LCMS Method | Retention time (min) | Obs. MS Ion (M + H)⁺ |
|---|---|---|---|---|
| Y-43 | (2-chloro-6-fluorobenzoyl) | YT-1 | 2.475 | 755.17 |
| Y-44 | (5-chlorothiophene-2-carbonyl) | YT-1 | 2.648 | 731.13 |
| Y-45 | (5-cyanothiophene-2-carbonyl) | YT-1 | 2.578 | 713.17 |
| Y-46 | (3-chlorobenzoyl) | YT-1 | 2.600 | 719.18 |
| Y-47 | (6-trifluoromethylpyridine-3-carbonyl) | YT-1 | 2.587 | 789.15 |
| Y-48 | (3-fluoro-2,2-dimethylpropanoyl) | YT-1 | 2.452 | 619.48 |

Example Y-49 and Y-50
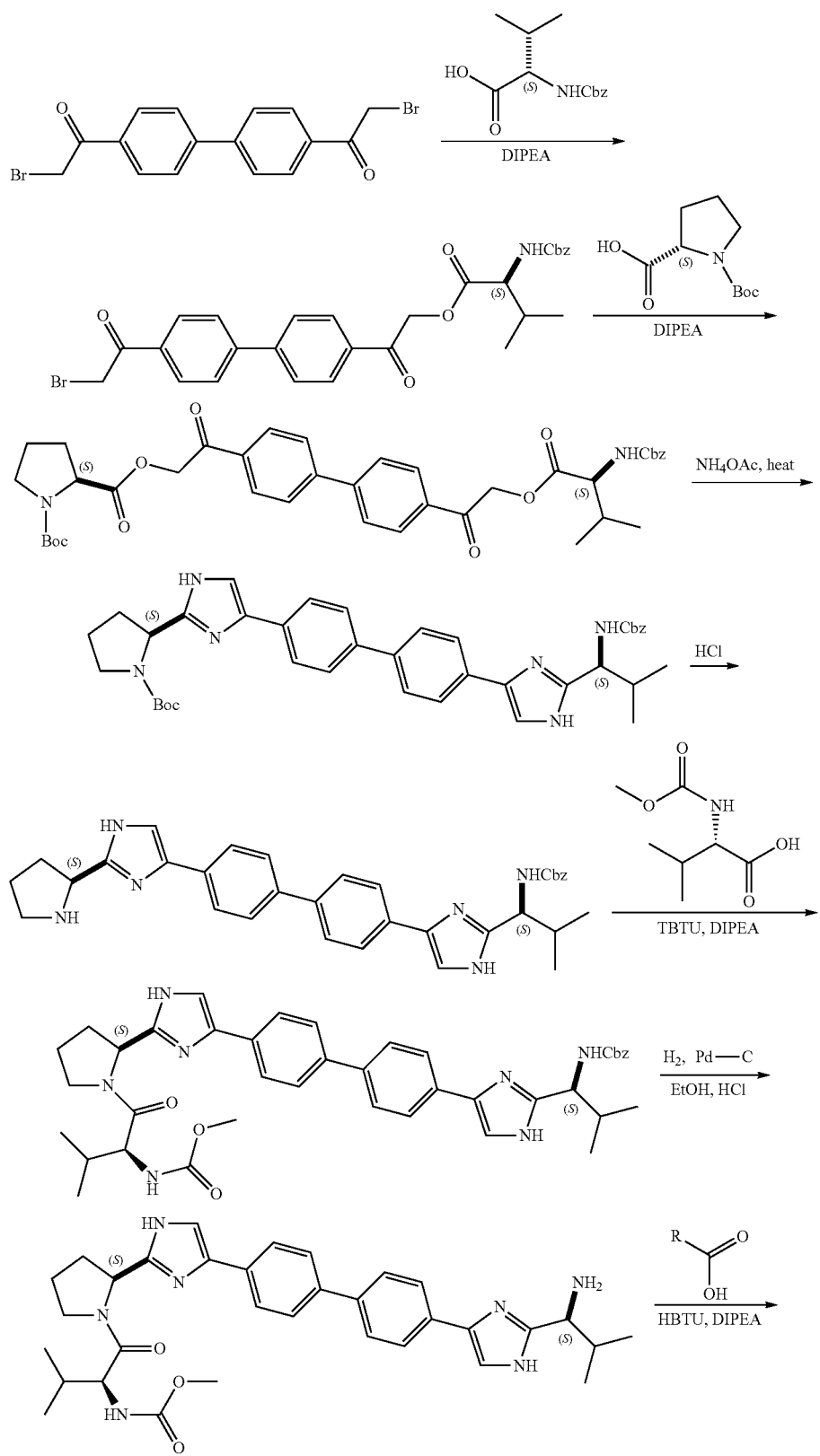
Scheme 12

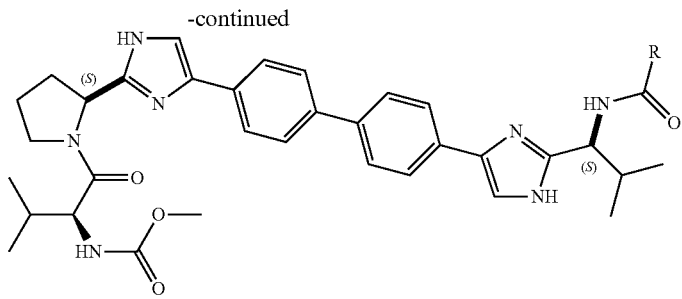

To a solution of 1,1'-(biphenyl-4,4'-diyl)bis(2-bromoethanone) (2.207 g, 5.57 mmol) and (S)-2-(benzyloxycarbonylamino)-3-methylbutanoic acid (1.4 g, 5.57 mmol) in MeCN (20 mL) and DMF (60 mL) was added DIPEA (1.022 mL, 5.85 mmol) dropwise over 20 min. The reaction mixture was stirred at rt for 20 h and diluted with EtOAc and washed with ice cold citric acid (2×), water, brine, dried (MgSO₄), and the residue was purified on a 80 g silica gel column (EtOAc/hex: 0 to 100%) to afford the product as a white solid (1.6 g). LC-MS: retention time: 2.988 min (method YT-1); m/z 590.01 (M+H)⁺. ¹H NMR (400 MHz, CHLOROFORM-d) δ ppm 8.09-8.15 (2H, m), 8.03 (2H, d, J=8.28 Hz), 7.72-7.82 (4H, m), 7.31-7.41 (5H, m), 5.56 (1H, d, J=16.31 Hz), 5.34 (1H, d, J=16.06 Hz), 5.15 (2H, s), 4.50 (2H, s), 4.46-4.57 (1H, m), 2.32-2.48 (1H, m, J=11.39, 6.79, 6.79, 6.65 Hz), 1.10 (3H, d, J=6.78 Hz), 1.05 (3H, d, J=7.03 Hz).

To a solution of (S)-2-(4'-(2-bromoacetyl)biphenyl-4-yl)-2-oxoethyl 2-(benzyloxycarbonylamino)-3-methylbutanoate (0.98 g, 1.730 mmol) and (S)-1-(tert-butoxycarbonyl)pyrrolidine-2-carboxylic acid (0.5 g, 2.323 mmol) in MeCN (10 mL) was added DIPEA (0.332 mL, 1.903 mmol) dropwise over 15 min. The reaction mixture was stirred at rt for 18 h, the solvent was removed and the residue was purified on a 25 g silica gel column (EtOAc/hexane: 20-100%) to afford the product as a pale yellow solid (1.05 g). LC-MS: retention time: 2.966 min (method YT-1); m/z 723.19 (M+Na)⁺.

A mixture of (S)-2-(2-(4'-(2-((S)-2-(benzyloxycarbonylamino)-3-methylbutanoyloxy)acetyl)biphenyl-4-yl)-2-oxoethyl) 1-tert-butyl pyrrolidine-1,2-dicarboxylate (1.05 g, 1.498 mmol) and ammonium acetate (2.5 g, 32.4 mmol) in a sealed tube was heated at 135° C. for 5 h. The reaction mixture was cooled down to ambient temperature, diluted with EtOAc and washed with ice cold NaHCO₃, brine, dried (MgSO₄). The solvent was removed and the residue was purified by silica gel chromatography (EtOAc/hexane: 20 to 100%) to afford the product as a yellow solid (0.643 g). LC-MS: retention time=2.373 min (method YT-1); m/z 661.30 (M+H)⁺.

To a solution of (S)-tert-butyl 2-(4-(4'-(2-((S)-1-(benzyloxycarbonylamino)-2-methylpropyl)-1H-imidazol-4-yl)biphenyl-4-yl)-1H-imidazol-2-yl)pyrrolidine-1-carboxylate (0.63 g, 0.953 mmol) in DCM (3 mL) was added HCl in dioxane (5 mL, 20.00 mmol). The mixture was stirred at rt for 1.5 h and evaporated to dryness to afford the product as a yellow solid (0.639 g). LC-MS: retention time: 2.265 min (method YT-1); m/z 561.21 (M+H)⁺.

To a mixture of benzyl(S)-2-methyl-1-(4-(4'-(2-((S)-pyrrolidin-2-yl)-1H-imidazol-4-yl)biphenyl-4-yl)-1H-imidazol-2-yl)propylcarbamate, 3 HCl (0.4 g, 0.597 mmol) and (S)-2-(methoxycarbonylamino)-3-methylbutanoic acid (0.125 g, 0.716 mmol) in DCM (5 mL) was added DIPEA (0.5 mL, 2.86 mmol) and HBTU (0.272 g, 0.716 mmol). The reaction mixture was stirred at rt for 2 h and directly purified on a 40 g siliga gel column (MeOH/DCM: 0 to 15%) to afford the coupled product as a yellow solid (0.29 g).

A mixture of the coupled product (0.29 g, 0.404 mmol) and 10% Pd—C (0.1 g, 0.94 mmol) in EtOH (5 mL) was purged with N₂. 4 N HCl in dioxane (2 ml, 8.00 mmol) was added and the reaction mixture was stirred under H₂ balloon overnight. The suspension was filtered and the filtrate was evaporated to afford the deprotected product (0.28 g). LC-MS: retention time: 2.250 min (method YT-1); m/z 584.14 (M+H)⁺.

Examples Y-49 and Y-50

To a mixture of methyl(S)-1-((S)-2-(4-(4'-(2-((S)-1-amino-2-methylpropyl)-1H-imidazol-4-yl)biphenyl-4-yl)-1H-imidazol-2-yl)pyrrolidin-1-yl)-3-methyl-1-oxobutan-2-ylcarbamate, 3 HCl (60 mg, 0.087 mmol) and 4,4-difluorocyclohexanecarboxylic acid (28.4 mg, 0.173 mmol) in DCM (2 mL) was added DIPEA (0.15 mL, 0.859 mmol) and HBTU (40 mg, 0.105 mmol). The reaction mixture was stirred at rt for 40 min, diluted with MeOH (1 mL). The solvent was removed and the residue was purified by prep-HPLC to afford Example Y-49 as bis-TFA salt (46.9 mg). Example Y-50 was prepared using the same method.

| Example | Structure | LC-MS method | Retention time (min) | Obs. MS Ion (M + H)⁺ |
|---|---|---|---|---|
| Y-49 | 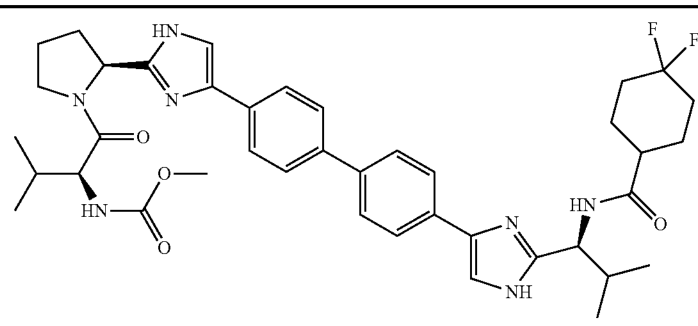 | YT-1 | 2.413 | 730.23 |

| Example | Structure | LC-MS method | Retention time (min) | Obs. MS Ion (M + H)+ |
|---|---|---|---|---|
| Y-50 | 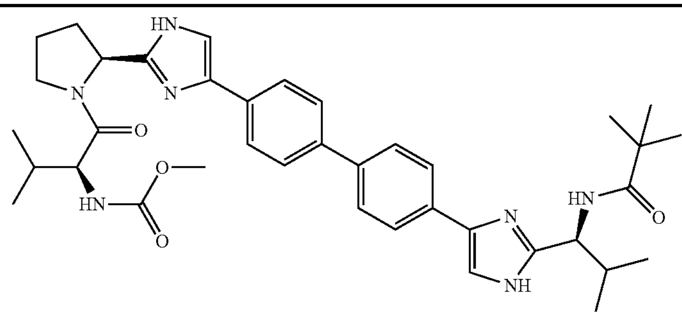 | YT-1 | 2.398 | 688.28 |
Examples Y-51 to Y-54
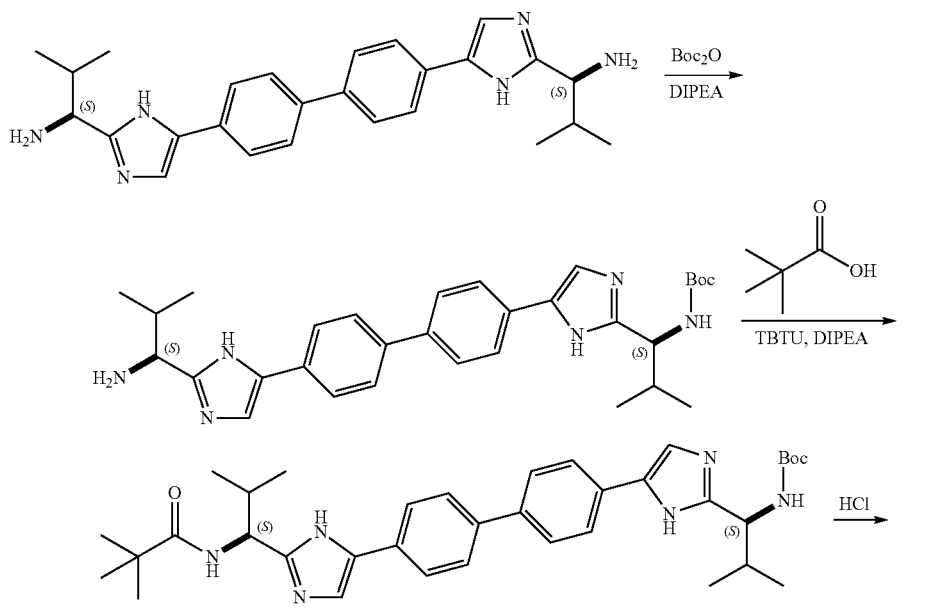
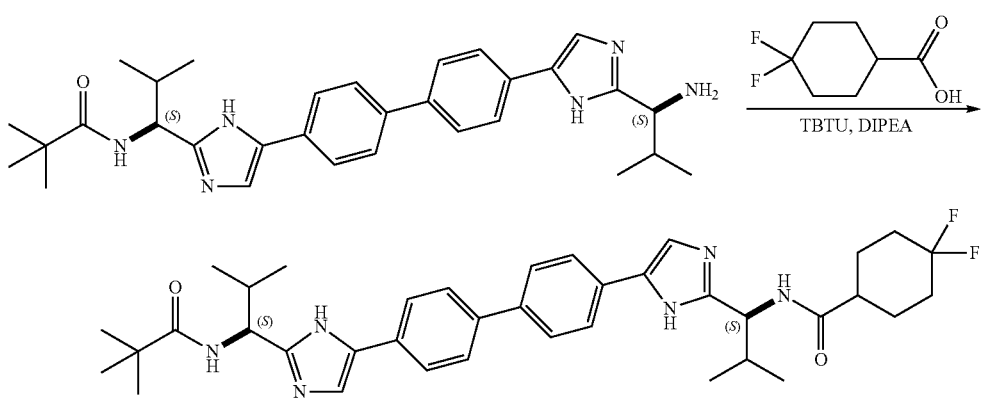

To a mixture of (1S,1'S)-1,1'-(5,5'-(biphenyl-4,4'-diyl)bis(1H-imidazole-5,2-diyl))bis(2-methylpropan-1-amine), 4 HCl (1.6 g, 2.79 mmol) in DCM (40 mL) and MeOH (40 mL) was added DIPEA (2.92 ml, 16.71 mmol). The mixture was stirred for 5 min until the solid dissolved. Boc$_2$O (0.608 g, 2.79 mmol) was added portionwise. The reaction mixture was stirred at rt for 4 h and diluted with EtOAc/DCM. The organic phase was washed with water, brine, dried (MgSO$_4$) and the residue was purified on a 80 g silica gel column (MeOH/DCM: 0 to 25%) to afford the product as a beige solid (0.8 g). $^1$H NMR (400 MHz, DMSO-d$_6$) δ ppm 7.78 (4H, d, J=8.03 Hz), 7.68 (4H, d, J=8.28 Hz), 7.51 (1H, s), 7.46 (1H, s), 6.84-6.98 (1H, m), 3.67 (1H, d, J=6.78 Hz), 1.88-2.11 (2H, m), 1.35 (9H, s), 0.88 (6H, d, J=6.78 Hz), 0.76 (3H, d, J=6.78 Hz), 0.72 (3H, d, J=6.78 Hz). LC/MS (YT 1): [M+H]$^+$ 529.23, R$_t$=2.363 min.

To a mixture of tert-butyl(S)-1-(5-(4'-(2-((S)-1-amino-2-methylpropyl)-1H-imidazol-5-yl)biphenyl-4-yl)-1H-imidazol-2-yl)-2-methylpropylcarbamate (0.46 g, 0.870 mmol) and pivalic acid (0.107 g, 1.044 mmol) in DCM (6 mL) was added HBTU (0.396 g, 1.044 mmol) and DIPEA (0.304 mL, 1.740 mmol). The reaction mixture was stirred at rt for 60 min and diluted with MeOH (0.5 mL). The volatile component was removed in vacuo and the residue was purified on a 25 g silica gel column (MeOH/DCM 0 to 15%) to afford Example Y-51 as a yellow solid (0.4 g). LC/MS (YT-1): M+H]$^+$ 613.29, R$_t$=2.547 min.

To a solution of Example Y-51 (0.4 g, 0.653 mmol) in DCM (3 mL) was added HCl/Dioxane (5 mL, 20.00 mmol). The mixture was stirred at rt for 1.5 h and evaporated to dryness to afford the product as a yellow solid (0.335 g). $^1$H NMR (400 MHz, MeOD) δ ppm 7.77-7.97 (10H, m), 4.84 (1H, d, J=9.03 Hz), 4.32 (1H, d, J=8.28 Hz), 2.34-2.54 (2H, m), 1.23 (9H, s), 1.18 (3H, d, J=6.53 Hz), 1.15 (3H, d, J=6.53 Hz), 0.98 (3H, s), 0.93 (3H, d, J=6.78 Hz). LC/MS (YT-1): [M+H]$^+$ 513.27, R$_t$=2.278 min.

To a mixture of N—((S)-1-(5-(4'-(2-((S)-1-amino-2-methylpropyl)-1H-imidazol-5-yl)biphenyl-4-yl)-1H-imidazol-2-yl)-2-methylpropyl)pivalamide, 3HCl (50 mg, 0.080 mmol) and 4,4-difluorocyclohexanecarboxylic acid (15 mg, 0.088 mmol) in DCM (2 mL) was added DIPEA (0.1 mL, 0.573 mmol) and HBTU (36.6 mg, 0.096 mmol). The reaction mixture was stirred at rt for 80 min and diluted with MeOH (1 mL), the volatile component was removed and the residue was purified by prepHPLC to afford Example Y-52: $^1$H NMR (400 MHz, MeOD) δ ppm 7.91 (2H, s), 7.83-7.90 (8H, m), 4.88 (1H, s), 4.86 (1H, d, J=2.01 Hz), 2.46-2.57 (1H, m), 2.30-2.46 (2H, m), 2.04-2.17 (2H, m), 1.83-1.97 (3H, m), 1.70-1.82 (3H, m), 1.24 (9H, s), 1.16 (6H, d, J=6.53 Hz), 0.97 (3H, d, J=6.78 Hz), 0.92 (3H, d, J=6.78 Hz).

Examples Y-53 and Y-54 were prepared by using the methods described in Example Y-52 from appropriate acids.

| Example | Structure | LCMS Method | Retention time (min) | Obs. MS Ion (M + H)$^+$ |
|---|---|---|---|---|
| Y-51 | 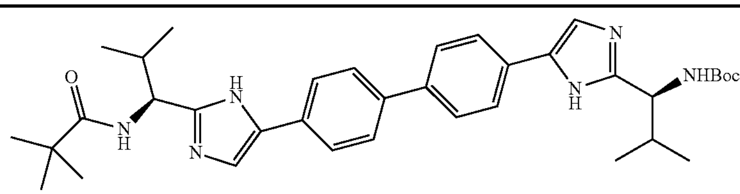 | YT-1 | 2.547 | 613.29 |
| Y-52 | 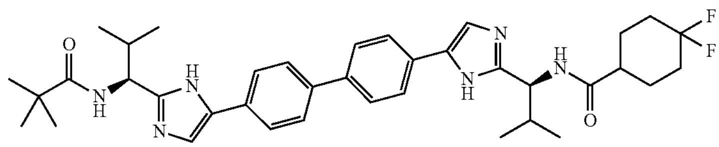 [SMILES: CC(C)[C@H](NC(=O)C1CCC(F)(F)CC1)c1ncc(-c2ccc(-c3ccc(-c4cnc([C@@H](NC(=O)C(C)(C)C)C(C)C)[nH]4)cc3)cc2)[nH]1] | YT-1 | 2.562 | 659.23 |
| Y-53 | 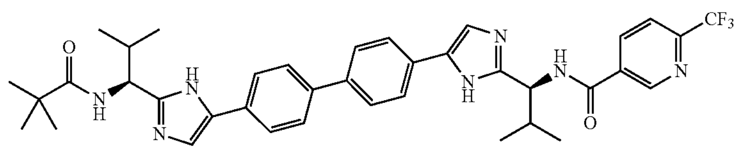 [SMILES: CC(C)[C@H](NC(=O)c1ccc(C(F)(F)F)nc1)c1ncc(-c2ccc(-c3ccc(-c4cnc([C@@H](NC(=O)C(C)(C)C)C(C)C)[nH]4)cc3)cc2)[nH]1] | YT-1 | 2.517 | 686.44 |
| Y-54 | 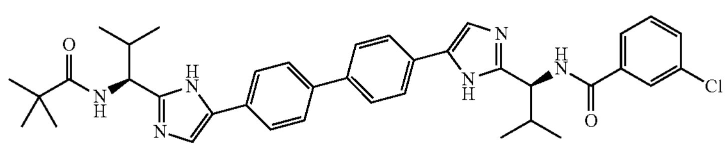 [SMILES: CC(C)[C@H](NC(=O)c1cccc(Cl)c1)c1ncc(-c2ccc(-c3ccc(-c4cnc([C@@H](NC(=O)C(C)(C)C)C(C)C)[nH]4)cc3)cc2)[nH]1] | YT-1 | 2.615 | 651.15 |

Examples Y-55 to Y-57

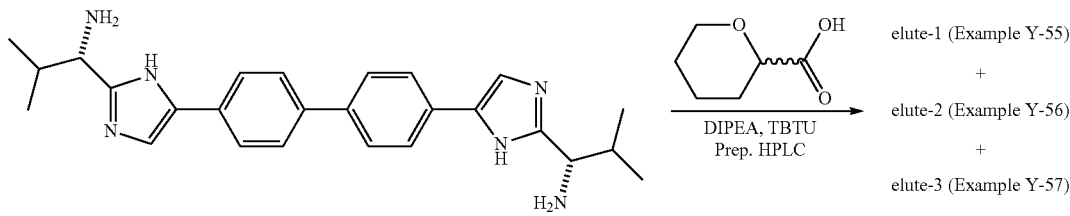 [SMILES: CC(C)[C@H](N)c1ncc(-c2ccc(-c3ccc(-c4cnc([C@@H](N)C(C)C)[nH]4)cc3)cc2)[nH]1 ; O=C(O)C1CCCCO1]

To a mixture of (1s,1'S)-1,1'-(5,5'-([1,1'-biphenyl]-4,4'-diyl)bis(1H-imidazole-5,2-diyl))bis(2-methylpropan-1-amine), 4 HCl (100 mg, 0.174 mmol) in DCM (2 mL) and tetrahydro-2H-pyran-2-carboxylic acid (55 mg, 0.423 mmol) was added DIPEA (0.2 mL, 1.145 mmol) and HBTU (141 mg, 0.372 mmol). The reaction mixture was stirred at rt for 90 min and quenched with MeOH (1 mL). The solvent was removed and the residue was purified by prepHPLC to afford three stereoisomeric products designated as elutes 1-3. Absolute stereochemistry was not assigned to elute-1 (Example Y-55) and elute-3 (Example Y-57). The second elute is the non-symmetrical stereoisomer (Example Y-56).

To a suspension of (1S,1'S)-1,1'-(5,5'-(biphenyl-4,4'-diyl)bis(1H-imidazole-5,2-diyl))bis(2-methylpropan-1-amine), 4 HCl (80 mg, 0.139 mmol) in DCM (3 mL) was added DIPEA (0.261 mL, 1.494 mmol) and 4-methylbenzene-1-sulfonyl chloride (58.4 mg, 0.306 mmol). The reaction mixture was stirred at rt for 1.5 h and quenched by addition of 1 mL of NH$_4$Cl and stirred for 20 min. The solvent was removed and the residue was purified by prepHPLC to afford Example Y-58 (53.3 mg). LCMS (method YT-1): [M+H]$^+$ 737.07, R$_t$=2.453 min. $^1$H NMR (400 MHz, MeOD) δ ppm 7.85-7.92 (4H, m), 7.70-7.81 (6H, m), 7.68 (4H, d, J=8.28 Hz), 7.22-7.38 (4H, m), 4.19-4.41 (2H, m), 2.25 (6H, s), 2.06-2.24 (2H, m, J=13.99, 6.93, 6.93, 6.78 Hz), 1.03 (6H, d, J=6.53 Hz), 0.81 (6H, d, J=6.78 Hz).

| Example | Structure | $^1$H NMR (400 MHz, MeOD) δ |
|---|---|---|
| Y-55 (elute-1) | (symmetrical diastereomer-1) | 7.93 (s, 2 H), 7.91-7.82 (m, 8 H), 4.95 (d, J = 9.0 Hz, 2 H), 4.12 (dd, J = 11.4, 3.1 Hz, 2 H), 3.94 (dd, J = 11.5, 2.3 Hz, 2 H), 3.65-3.52 (m, 2 H), 2.37 (dquin, J = 9.0, 6.7 Hz, 2H), 2.01-1.84 (m, 4 H), 1.69-1.50 (m, 6 H), 1.47-1.31 (m, 2 H), 1.13 (d, J = 6.8 Hz, 6 H), 0.95 (d, J = 6.5 Hz, 6 H) |
| Y-56 (elute-2) | 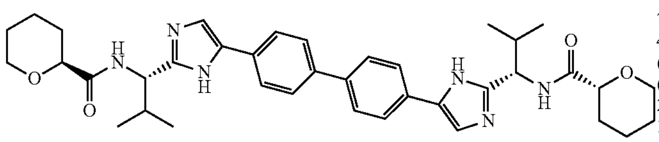 [SMILES: CC(C)[C@H](NC(=O)[C@@H]1CCCCO1)c1ncc(-c2ccc(-c3ccc(-c4cnc([C@@H](NC(=O)[C@H]5CCCCO5)C(C)C)[nH]4)cc3)cc2)[nH]1] | 7.93 (s, 2 H), 7.91-7.81 (m, 8 H), 4.99 (d, J = 8.8 Hz, 1 H), 4.13 (d, J = 11.5 Hz, 2 H), 3.97-3.84 (m, 2 H), 3.65-3.52 (m, 2 H), 2.36 (br. s., 2 H), 2.03 (d, J = 12.8 Hz, 1 H), 1.98-1.84 (m, 3H), 1.71-1.55 (m, 6H), 1.51-1.36 (m, 2 H), 1.13 (dd, J = 6.7, 1.6 Hz, 6 H), 1.00-0.86 (m, 6 H) |
| Y-57 (elute-3) | (symmetrical diastereomer-2) | 7.94-7.90 (m, 2 H), 7.90-7.81 (m, 8 H), 4.99 (d, J = 8.8 Hz, 2 H), 4.19-4.07 (m, 2 H), 3.90 (dd, J = 11.5, 2.5 Hz, 2 H), 3.63-3.52 (m, 2 H), 2.43-2.28 (m, 2 H), 2.09-1.99 (m, 2H), 1.94 (d, J = 4.8 Hz, 2 H), 1.73-1.55 (m, 6 H), 1.51-1.36 (m, 2 H), 1.13 (d, J = 6.8 Hz, 6 H), 0.96 (d, J = 6.8 Hz, 6 H) |

Example Y-58

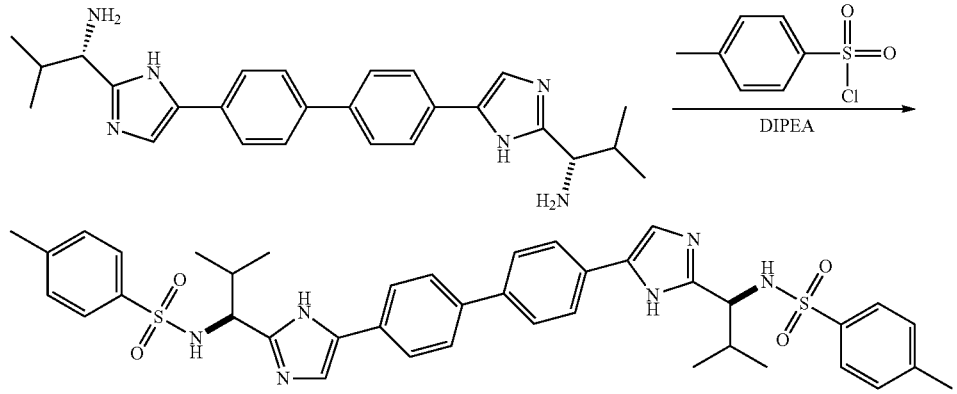

Y-58

Examples Y-59 to Y-61

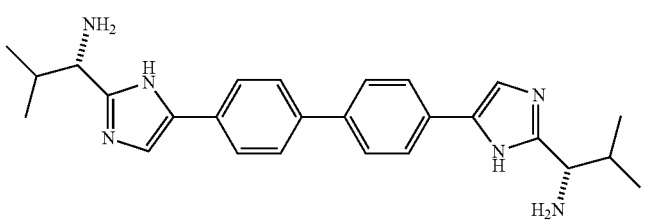 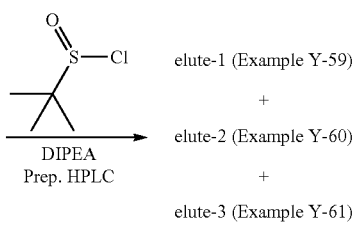

elute-1 (Example Y-59)
+
elute-2 (Example Y-60)
+
elute-3 (Example Y-61)

DIPEA
Prep. HPLC

To a cold (0-5° C.) stirred suspension of (1S,1'S)-1,1'-(5,5'-([1,1'-biphenyl]-4,4'-diyl)bis(1H-imidazole-5,2-diyl))bis(2-methylpropan-1-amine), 4 HCl (200 mg, 0.348 mmol) and DIPEA (0.486 mL, 2.79 mmol) in DCM (3 mL) was added 2-methylpropane-2-sulfinic chloride (0.095 mL, 0.766 mmol). The reaction mixture was allowed to warm to rt, stirred for 1 h and quenched with MeOH (1 mL) and evaporated to dryness. The residue was purified by prepHPLC to afford three stereoisomeric products (Examples Y-59, Y-60 and Y-61) listed in the table below:

| Example | structure | $^1$H NMR (400 MHz, MeOD) δ |
|---|---|---|
| Y-59 (elute-1) | (symmetrical diastereomer-1) | 7.99 (s, 2 H), 7.93-7.84 (m, 8 H), 4.51 (d, J = 8.8 Hz, 2 H), 2.51-2.35 (m, 2 H), 1.27 (s, 18 H), 1.21 (d, J = 6.5 Hz, 6 H), 0.97 (d, J = 6.8 Hz, 6 H). |
| Y-60 (elute-2) | 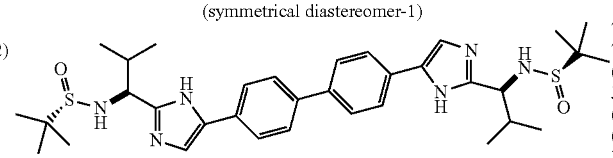 | 7.97 (s, 1 H), 7.96 (s, 1 H), 7.91-7.84 (m, 8 H), 4.52 (d, J = 8.8 Hz, 1 H), 4.40 (d, J = 8.8 Hz, 1 H), 2.50-2.33 (m, 2 H), 1.31 (s, 9 H), 1.26 (s, 9 H), 1.21 (d, J = 6.5 Hz, 3 H), 1.18 (d, J = 6.5 Hz, 3 H), 0.96 (t, J = 7.4 Hz, 6 H). |
| Y-61 (elute-3) | (symmetrical diastereomer-2) | 7.97 (s, 2H), 7.92-7.84 (m, 8H), 4.42 (d, J = 8.3 Hz, 2H), 2.39 (dq, J = 13.9, 7.0 Hz, 2H), 1.31 (s, 18H), 1.17 (d, J = 6.5 Hz, 6H), 0.97 (d, J = 6.8 Hz, 6H). |

Example L-1

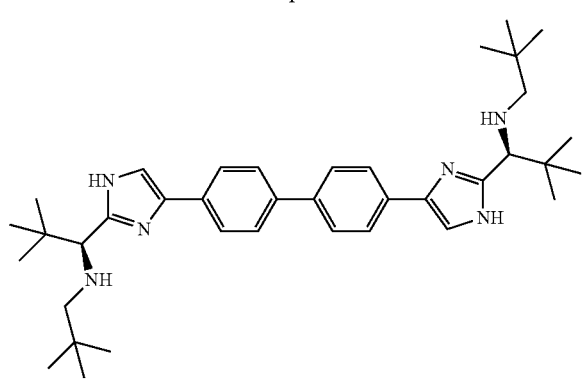

(1S,1'S)-1,1'-(4,4'-([1,1'-biphenyl]-4,4'-diyl)bis(1H-imidazole-4,2-diyl))bis(2,2-dimethylpropan-1-amine), 4 HCl (50 mg, 0.083 mmol), pivalaldehyde (0.020 mL, 0.183 mmol) and AcOH (10.45 µl, 0.183 mmol) were combined in CH$_2$Cl$_2$ (3 mL) and the resulting mixture was stirred for 5 min, followed by addition of NaCNBH$_4$ (20.86 mg, 0.332 mmol). MeOH was added to dissolve the solid material. The reaction mixture was stirred at rt for 2 hrs, then quenched by addition of sat. NaHCO$_3$ and the organic layer was separated. The aqueous layer was then extracted with DCM and the combined organic layers were dried (MgSO$_4$), filtered and concentrated. The residue was redissolved in methanol and purified by preparatory HPLC (MeOH/H$_2$O/TFA) to yield Example L-1 (30 mg, TFA salt) as a white solid. LC/MS (Cond. L-1): [M+H]$^+$ 597.6, R$_t$=2.438 min. $^1$H NMR (500 MHz, DMSO-d$_6$) ppm 8.12 (br. s., 2H), 7.92 (s, 8H), 3.83 (br. s., 2H), 2.37-2.24 (m, 4H), 1.02 (br. s., 18H), 0.89 (s, 18H).

Example L-2 (TFA salt) was prepared from (1S,1'S)-1,1'-(4,4'-([1,1'-biphenyl]-4,4'-diyl)bis(1H-imidazole-4,2-diyl))bis(2,2-dimethylpropan-1-amine), 4 HCl and appropriate starting materials, obtained from commercial sources, by employing the procedures described for the synthesis of Example L-1.

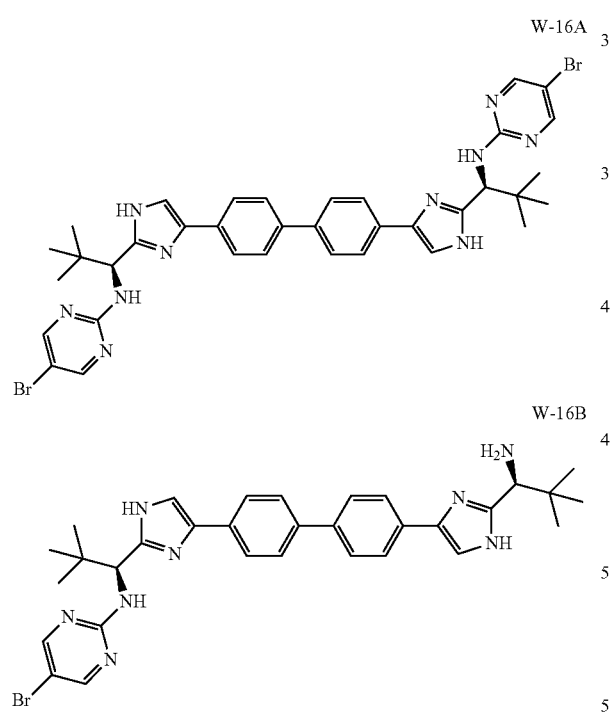

| Example | R | LC-MS Method | Retention Time (min) | Obs. Mass ion (M + H)+ |
|---|---|---|---|---|
| L-2 | cyclohexylmethyl | L-1 | 2.4 | 649.7 |

Example W-16A and W-16B

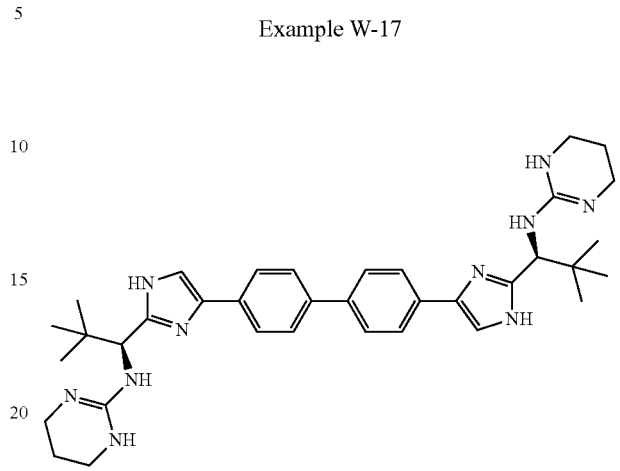

A light yellow cloudy solution of (1S,1'S)-1,1'-(4,4'-([1,1'-biphenyl]-4,4'-diyl)bis(1H-imidazole-4,2-diyl))bis(2,2-dimethylpropan-1-amine), 4 HCl (60 mg, 0.100 mmol), 5-bromo-2-fluoropyrimidine (42.3 mg, 0.239 mmol), and DIEA (0.122 mL, 0.697 mmol) in acetonitrile (1 mL) was heated in a microwave system at 65° C. for 2 h. The reaction mixture was purified by preparatory HPLC (MeOH/H₂O/TFA) to afford Example W-16B (11 mg, TFA salt) as a white solid, LC/MS (Cond. L-1): [M+H]+ 615.5, $R_t$=1.23 min; and Example W-16A (36 mg, TFA salt) as a white solid, LC/MS (Cond. L-1): [M+H]+ 771.4, $R_t$=1.512 min. ¹H NMR (400 MHz, MeOD-d₄) δ ppm 8.40 (4H, s), 7.79-7.93 (10H, m), 4.99-5.06 (2H, m), 1.21 (18H, s).

Example W-17

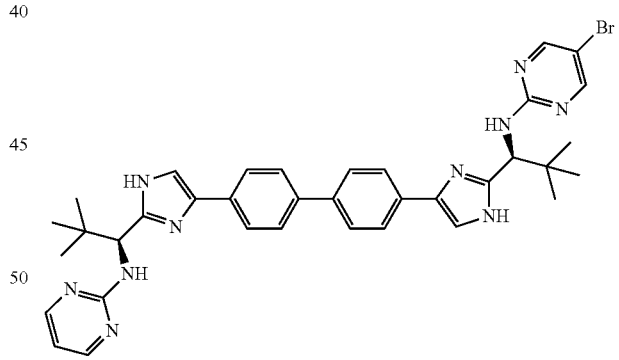

A vial containing Example W-16A (20 mg), 10% Pd/C (3.41 mg), and MeOH (1 mL) was placed in a Parr shaker under 30 psi H₂ for 3 h. The reaction mixture was filtered through a plug of diatomaceous earth (Celite®). The filtrate was purified by preparatory HPLC (MeOH/H₂O/TFA) to afford the TFA salt of Example W-17 (12 mg) as a white solid. LC/MS (Cond. L-1): [M+H]+ 621.4, $R_t$=1.105 min. ¹H NMR (400 MHz, MEOD-d₄) δ ppm 7.90-7.98 (6H, m), 7.82-7.90 (4H, m), 3.36-3.48 (8H, m), 1.96 (4H, quin, J=5.71 Hz), 1.13 (18H, s).

Example W-31

A vial containing Example W-16A (20 mg, 0.026 mmol), cyclohex-1-en-1-ylboronic acid (7.85 mg, 0.062 mmol), tetrakis(triphenylphosphine)palladium(0) (6.00 mg, 5.19 mmol), and DMA (1 mL) was heated in a microwave system at 100° C. for 2 h. The reaction mixture was filtered and the filtrate was concentrated then purified by preparatory HPLC (CH₃CN/H₂O/NH₄OAc) to afford Example W-31. LC/MS (Cond. L-1): [M+H]+ 691.6, $R_t$=1.6 min. ¹H NMR (500 MHz, MeOD-d₄) δ ppm 8.32 (2H, s), 8.28 (2H, d, J=4.88 Hz), 7.77 (4H, dd, J=8.39, 1.98 Hz), 7.68 (4H, d, J=8.54 Hz), 7.36 (2H, d, J=1.83 Hz), 6.62 (1H, t, J=4.88 Hz), 5.25 (1H, s), 5.18 (1H, s), 1.08 (18H, d, J=4.58 Hz).

Example L-3

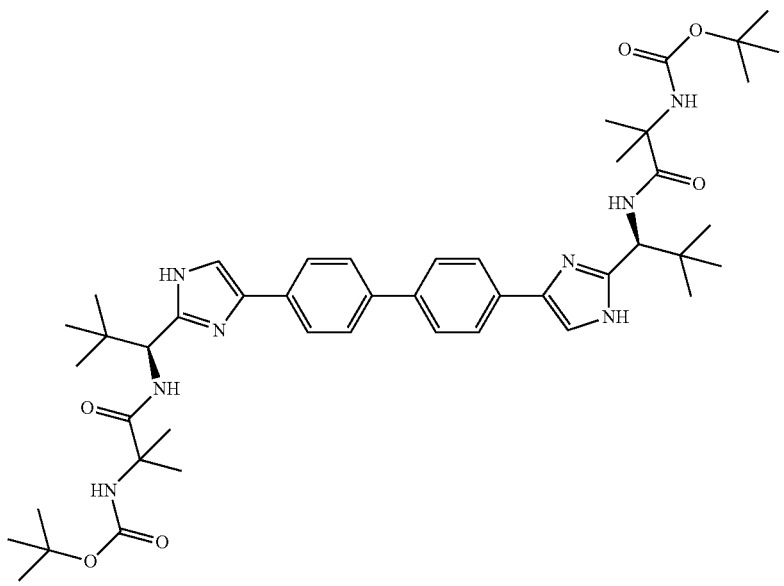 [SMILES: CC(C)(C)OC(=O)NC(C)(C)C(=O)N[C@H](c1nc(-c2ccc(-c3ccc(-c4c[nH]c([C@@H](NC(=O)C(C)(C)NC(=O)OC(C)(C)C)C(C)(C)C)n4)cc3)cc2)c[nH]1)C(C)(C)C]

(1S,1'S)-1,1'-(4,4'-([1,1'-biphenyl]-4,4'-diyl)bis(1H-imidazole-4,2-diyl))bis(2,2-dimethylpropan-1-amine), 4 HCl (50 mg, 0.083 mmol), 2-((tert-butoxycarbonyl)amino)-2-methylpropanoic acid (33.7 mg, 0.166 mmol) and DIEA (0.101 mL, 0.581 mmol) were combined in DMF (2 mL) and the resulting mixture was stirred for 5 min, followed by addition of HATU (66.3 mg, 0.174 mmol). The resulting solution was the stirred at rt for 2 h. The yellow solution was then purified by preparatory HPLC (MeOH/H$_2$O/TFA) to yield a white solid corresponding to the TFA salt of Example L-3 (40 mg). LC/MS (Cond. N-1): [M+H]$^+$ 827.0, R$_f$=3.74 min. $^1$H NMR (500 MHz, DMSO-d$_6$) ppm 8.19 (br. s., 2H), 8.01-7.83 (m, 8H), 5.22 (br. s., 2H), 1.46-1.21 (m, 30H), 0.96 (s, 18H).

The following examples were prepared from (1S,1'S)-1,1'-(4,4'-([1,1'-biphenyl]-4,4'-diyl)bis(1H-imidazole-4,2-diyl))bis(2,2-dimethylpropan-1-amine), 4 HCl and appropriate starting materials, by employing the procedures described for the synthesis of Example L-3. The resulting products were purified by preparatory HPLC (MeOH/H$_2$O/TFA or CH$_3$CN/H$_2$O/NH$_4$OAc) and obtained as their corresponding TFA salts or as free bases. For Example W-1, W-3, W-4, W-13, W-14, W-15, the cap synthesis was disclosed in patent application WO2009146347; for Example W-67, W-68, W-69, the cap synthesis was disclosed in patent application WO2011075439.

| Example | R | LC-MS Method | Retention Time (min) | Obs. Mass ion (M + H)+ | Salt Type |
|---|---|---|---|---|---|
| L-4 | ![Boc-NH-C(cyclopropyl)-C(O)-] | N-1 | 3.718 | 823.9 | 2 TFA |
| L-5 | ![C(O)-C(cyclopropyl)-NH-Boc] | N-1 | 3.8 | 852.0 | 2 TFA |

-continued
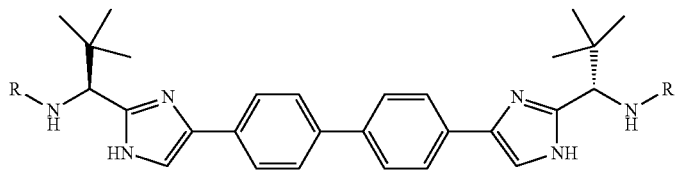
| Example | R | LC-MS Method | Retention Time (min) | Obs. Mass ion (M + H)+ | Salt Type |
|---|---|---|---|---|---|
| L-6 | | N-1 | 3.93 | 879.0 | 2 TFA |
| L-7 | | N-1 | 4.045 | 907.0 | 2 TFA |
| L-8* | | L-1 | 2.4 | 855.85 | 2 TFA |
| L-9 | | L-1 | 1.748 | 683.9 | 2 TFA |
| L-10 | | L-1 | 1.79 | 679.6 | 2 TFA |
| L-11 | | L-1 | 1.848 | 735.65 | 2 TFA |
| L-12 | | L-1 | 1.98 | 763.9 | 2 TFA |

-continued
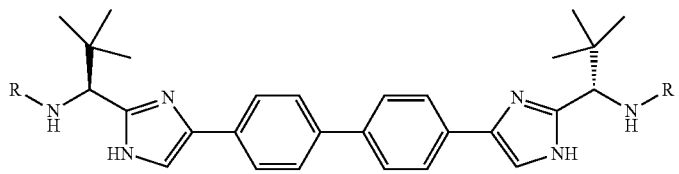
| Example | R | LC-MS Method | Retention Time (min) | Obs. Mass ion (M + H)+ | Salt Type |
|---|---|---|---|---|---|
| L-13 | | L-1 | 2.5 | 851.8 | 2 TFA |
| L-14 | | L-1 | 2.68 | 879.5 | 2 TFA |
| L-15 | | L-1 | 2.44 | 879.75 | 2 TFA |
| L-16 | | L-1 | 2.44 | 879.75 | Free Base |
| L-17 | | L-1 | 2.6 | 879.75 | Free Base |
| L-19* | | L-1 | 2.02 | 767.8 | 2 TFA |

-continued
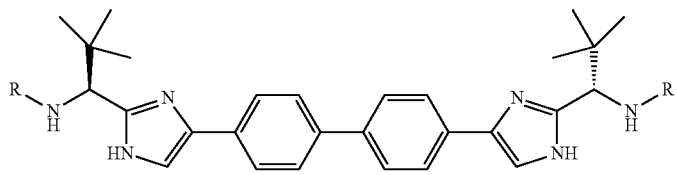
| Example | R | LC-MS Method | Retention Time (min) | Obs. Mass ion (M + H)+ | Salt Type |
|---|---|---|---|---|---|
| L-21 | | L-1 | 2.68 | 951.0 | Free Base |
| L-22* | | L-1 | 2.6 | 879.5 | Free Base |
| L-23 | | L-1 | 2.2 | 795.7 | Free Base |
| L-24 | | L-1 | 2.4 | 883.8 | Free Base |
| L-25 | | L-1 | 1.4 | 711.5 | Free Base |
| L-26 | | L-1 | 1.48 | 763.5 | Free Base |
| L-27 | | L-1 | 1.9 | 895.65 | Free Base |

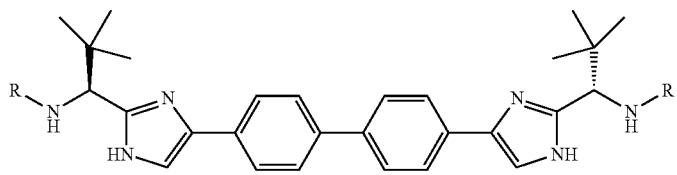
| Example | R | LC-MS Method | Retention Time (min) | Obs. Mass ion (M + H)+ | Salt Type |
|---|---|---|---|---|---|
| L-28 | | L-1 | 2.355 | 847.75 | Free Base |
| L-29 | | L-1 | 1.98 | 767.65 | Free Base |
| L-31 | | L-1 | 2.008 | 763.7 | Free Base |
| L-32* | | L-1 | 2.615 | 903.6 | Free Base |
| L-33 | | L-1 | 2.01 | 727.6 | Free Base |
| L-38 | | L-1 | 2.708 | 879.7 | Free Base |

-continued
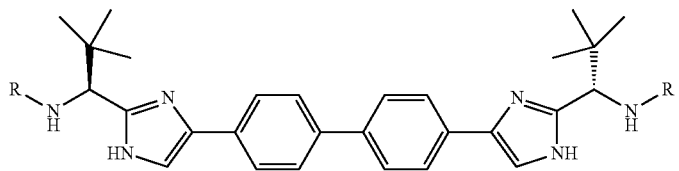
| Example | R | LC-MS Method | Retention Time (min) | Obs. Mass ion (M + H)+ | Salt Type |
|---|---|---|---|---|---|
| L-40 | | L-1 | 2.718 | 880.7 | Free Base |
| L-43 | | L-1 | 2.196 | 867.6 | Free Base |
| W-1 | | W-1 | 1.797 | 952.1 | Free Base |
| W-2 | | W-1 | 1.99 | 976.1 | Free Base |
| W-3 | | W-1 | 1.867 | 904.1 | Free Base |
| W-4 | | W-1 | 1.778 | 876.1 | Free Base |

-continued
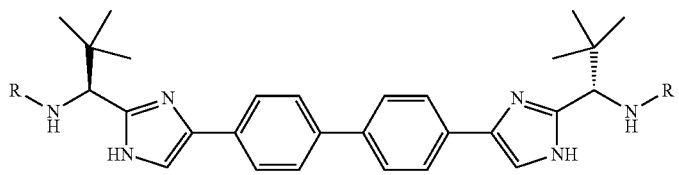
| Example | R | LC-MS Method | Retention Time (min) | Obs. Mass ion (M + H)+ | Salt Type |
|---|---|---|---|---|---|
| W-5 | | W-1 | 2.033 | 976.8 | Free Base |
| W-6 | | W-1 | 2.033 | 976.8 | Free Base |
| W-7 | | W-1 | 1.8 | 876.1 | Free Base |
| W-8 | | W-1 | 2.18 | 976.2 | Free Base |
| W-9 | | W-1 | 1.762 | 880.1 | Free Base |

-continued

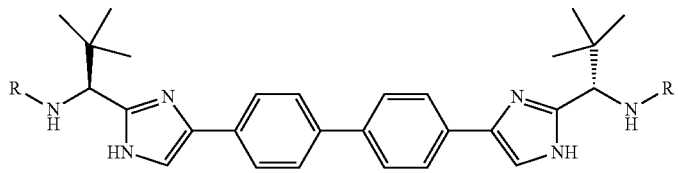

| Example | R | LC-MS Method | Retention Time (min) | Obs. Mass ion (M + H)+ | Salt Type |
|---|---|---|---|---|---|
| W-12 | | W-1 | 1.772 | 880.1 | Free Base |
| W-51 | | W-1 | 2.008 | 879.8 | Free Base |
| W-67 | | W-1 | 1.845 | 875.8 | Free Base |
| W-68 | | W-1 | 1.907 | 879.8 | Free Base |
| W-69 | | W-1 | 2.005 | 879.8 | Free Base |

*¹H NMR data:

Example L-8 ¹H NMR (400 MHz, DMSO-d₆) δ 12.44-11.94 (m, 3H), 7.84-7.63 (m, 8H), 7.54 (d, J = 1.8 Hz, 1H), 7.31 (br. s., 1H), 7.16-7.02 (m, 2H), 4.99-4.85 (m, 2H), 2.96-2.84 (m, 6H), 1.41 (s, 6H), 1.26 (s, 6H), 1.06 (br. s., 18H), 0.90 (s, 18H)

Example L-19 ¹H NMR (500 MHz, DMSO-d₆) δ 12.43-12.01 (m, 2H), 7.88-7.81 (m, 3H), 7.77 (d, J = 8.4 Hz, 1H), 7.73-7.67 (m, 4H), 7.65-7.58 (m, 1H), 7.39-7.25 (m, 2H), 5.03-4.83 (m, 2H), 3.74-3.54 (m, 5H), 3.31 (s, 8H), 3.01-2.91 (m, 6H), 1.48-1.25 (m, 4H), 1.16 (br. s., 4H), 0.89 (s, 18H)

Example L-22 ¹H NMR (500 MHz, DMSO-d₆) δ 12.50-11.90 (m, 2H), 7.80 (d, J = 7.3 Hz, 4H), 7.76-7.63 (m, 6H), 7.60-7.48 (m, 3H), 7.21-7.06 (m, 2H), 5.03-4.80 (m, 2H), 3.58 (br. s., 2H), 3.43 (br. s., 3H), 2.31-2.09 (m, 2H), 1.99-1.71 (m, 8H), 1.51-1.24 (m, 15H), 1.04-0.88 (m, 36H)

Example L-32 ¹H NMR (500 MHz, DMSO-d₆) δ 12.50-12.10 (m, 2H), 8.62-8.51 (m, 2H), 7.84 (d, J = 8.2 Hz, 3H), 7.78-7.63 (m, 5H), 7.62-7.56 (m, 2H), 7.43-7.27 (m, 2H), 5.39-5.19 (m, 2H), 4.93-4.82 (m, 2H), 1.47-1.36 (m, 6H), 1.13 (d, J = 9.8 Hz, 2H), 1.03 (br. s., 2H), 0.90 (s, 18H)

The following Examples were prepared from (1S,1'S)-(4,4'-([1,1'-biphenyl]-4,4'-diyl)bis(1H-imidazole-4,2-diyl))bis((1-methylcyclopropyl)methanamine), 4 HCl and appropriate starting materials, by employing the procedures described for the synthesis of Example L-3. The resulting products were purified by preparatory HPLC (CH$_3$CN/H$_2$O/NH$_4$OAc) and obtained as free bases.

The following examples were prepared from (1S,1'S)-1,1'-(4,4'-([1,1'-biphenyl]-4,4'-diyl)bis(1H-imidazole-4,2-diyl))bis(2,2-dimethylpropan-1-amine), 4 HCl and appropriate starting materials, by employing the procedures described for the synthesis of Example 30. The resulting products were purified by preparatory HPLC (CH$_3$CN/H$_2$O/NH$_4$OAc) and obtained as free bases with the exception of Example W-11, which was purified by preparatory HPLC (MeOH/H$_2$O/TFA) and obtained as its corresponding TFA salt.

| Example | R | LC-MS Method | Retention Time (min) | Obs. Mass ion (M + H)+ |
|---|---|---|---|---|
| L-30 | | L-1 | 2.22 | 763.6 |
| L-39 | | L-1 | 2.705 | 875.7 |
| L-42 | | L-1 | 2.453 | 899.55 |
| W-70 | | W-1 | 1.818 | 871.8 |
| W-71* | | W-1 | 1.908 | 875.8 |
| W-72 | | W-1 | 1.93 | 875.8 |

| Example | R | LC-MS Method | Retention Time (min) | Obs. Mass ion (M + H)+ |
|---|---|---|---|---|
| W-10 | | W-1 | 0.977 | 655.7 |
| W-18 | | W-1 | 1.582 | 721.5 |
| W-19 | | W-1 | 1.515 | 733.4 |
| W-20 | | W-1 | 1.348 | 701.5 |
| W-21 | | W-1 | 1.207 | 707.7 |
| W-22 | | W-1 | 1.382 | 779.6 |
| W-24* | | W-1 | 1.65 | 807.9 |

*Example W-71 $^1$H NMR (500 MHz, DMSO-d$_6$) δ ppm 12.28-11.89 (2 H, m), 8.16-8.10 (2 H, m), 7.86-7.35 (10 H, m), 4.72-4.62 (2 H, m), 4.28-4.27 (2 H, m), 3.66-3.65 (2 H, m), 2.85-2.84-3.40 (2 H, m), 2.37-2.14 (4 H, m), 1.41-1.31 (19 H, m), 1.10-0.97 (13 H, m), 0.76-0.30 (8 H, m).

| Example | R | LC-MS Method | Retention Time (min) | Obs. Mass ion (M + H)+ |
|---|---|---|---|---|
| W-25 | morpholine oxoacetyl | W-1 | 1.288 | 739.7 |
| W-26 | 4-fluoropiperidine oxoacetyl | W-1 | 1.500 | 771.8 |
| W-27 | (3)-fluoropyrrolidine oxoacetyl | W-1 | 1.433 | 743.7 |
| W-28 | 3,3-difluoroazetidine oxoacetyl | W-1 | 1.522 | 751.6 |
| W-32 | azepane oxoacetyl | W-1 | 1.56 | 763.5 |
| W-33 | N,N-diethyl oxoacetamide | W-1 | 1.42 | 711.6 |
| W-34 | 2,5-dihydropyrrole oxoacetyl | W-1 | 1.42 | 711.6 |
| W-35 | 4-methylpiperazine oxoacetyl | W-1 | 1.068 | 765.7 |
| W-36 | 2,2-dimethylmorpholine oxoacetyl | W-1 | 1.068 | 765.7 |
| W-37 | N-ethyl-N-(2,2,2-trifluoroethyl) oxoacetamide | W-1 | 1.938 | 819.25 |
| W-38 | (2)-methylpiperidine oxoacetyl | W-1 | 1.615 | 763.7 |
| W-60 | 4-(trifluoromethyl)piperidine oxoacetyl | W-1 | 2.043 | 871.44 |
| W-63 | 4,4-difluoropiperidinyl-oxetanyl | W-1 | 1.688 | 863.7 |
| W-66 | N-isopropyl-N-(2,2,2-trifluoroethyl) oxoacetamide | W-1 | 1.823 | 847.6 |

*Example W-24 ¹H NMR (500 MHz, DMSO-d₆) δ ppm 12.48, 12.18 (2 H, s), 9.10, 9.07, 9.05 (2 H, b), 7.87-7.41 (10 H, m), 5.01, 4.99, 4.93, 4.91 (2 H, s), 3.80-3.70 (2 H, m), 3.51-3.47 (6 H, m), 2.1-1.98 (8 H, m), 1.03-0.99 (18 H, m).

The following examples (bis-TFA) were prepared from (1S,1'S)-(4,4'-([1,1'-biphenyl]-4,4'-diyl)bis(1H-imidazole-4,2-diyl))bis((1-methylcyclopropyl)methanamine), 4 HCl and appropriate starting materials, by employing the procedures described for the synthesis of Example W-30. The resulting products were purified by preparatory HPLC (CH₃CN/H₂O/NH₄OAc) and obtained as free bases with the exception of Example W-39, which was purified by preparatory HPLC (MeOH/H₂O/TFA) and obtained as its corresponding TFA salt.

| Example | R | LC-MS Method | Retention Time (min) | Obs. Mass ion (M + H)+ |
|---|---|---|---|---|
| W-39* | [4,4-difluoropiperidinyl glyoxamide] | W-1 | 1.562 | 803.5 |
| W-57 | [azepanyl glyoxamide] | W-1 | 1.92 | 759.48 |
| W-58 | [N-isopropyl-N-cyclopropyl glyoxamide] | W-1 | 1.978 | 759.48 |
| W-59 | [4-trifluoromethylpiperidinyl glyoxamide] | W-1 | 2.003 | 867.36 |
| W-61 | [2,6-dimethylmorpholinyl glyoxamide] | W-1 | 1.893 | 791.43 |

| Example | R | LC-MS Method | Retention Time (min) | Obs. Mass ion (M + H)+ |
|---|---|---|---|---|
| W-62 | [oxetane-spiro-4,4-difluoropiperidinyl glyoxamide] | W-1 | 1.615 | 859.6 |
| W-66 | [N-(2,2,2-trifluoroethyl)-N-isopropyl glyoxamide] | W-1 | 1.777 | 843.6 |
| W-73 | [2-methylpiperidinyl glyoxamide] | W-1 | 1.602 | 764.5 |

(Mixture of 3 diastereomers)

*Example W-39 $^1$H NMR (500 MHz, MeOH-d$_4$) δ ppm 7.96-7.88 (10 H, m), 4.70-4.15 (2 H, s), 3.82-3.80 (4 H, m), 3.75-3.73 (4 H, m), 2.16-2.07 (8 H, m), 1.20 (6 H, s), 0.98 (2 H, m), 0.81 (2 H, m), 0.70-0.67 (4 H, m).

Example W-13

Diastereomer 1

Example W-14

Diastereomer 2

Example W-15

Diastereomer 3

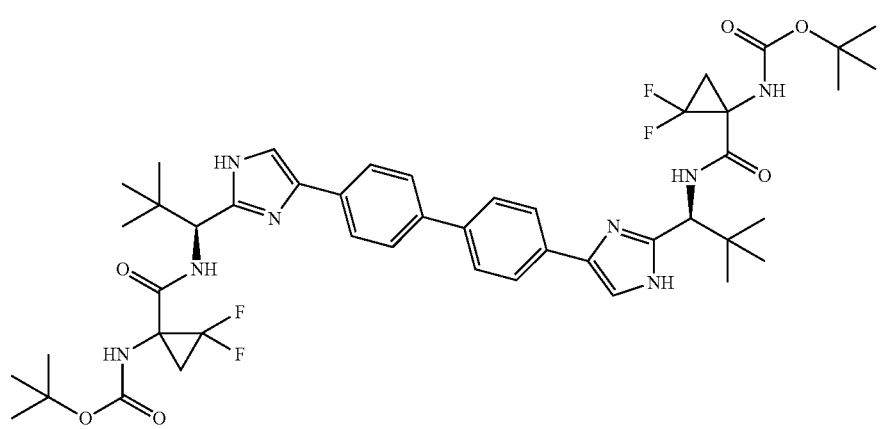 [SMILES: CC(C)(C)OC(=O)NC1(C(=O)N[C@H](c2nc(-c3ccc(-c4ccc(-c5c[nH]c([C@@H](NC(=O)C6(NC(=O)OC(C)(C)C)CC6(F)F)C(C)(C)C)n5)cc4)cc3)c[nH]2)C(C)(C)C)CC1(F)F]

To a slurry of (1S,1'S)-1,1'-(4,4'4-([1,1'-biphenyl]-4,4'-diyl)bis(1H-imidazole-4,2-diyl))bis(2,2-dimethylpropan-1-amine), 4 HCl (40 mg, 0.066 mmol), 1-((tert-butoxycarbonyl)amino)-2,2-difluorocyclopropanecarboxylic acid (15.75 mg, 0.066 mmol), HATU (63.1 mg, 0.166 mmol) in DCM (1 mL) was added DIEA (0.081 mL, 0.465 mmol). The reaction mixture was stirred for at rt for 18 h. The reaction mixture was purified by preparatory HPLC (MeOH/H$_2$O/TFA) to afford the product as a mixture of diastereomers. LC/MS (Cond. W-1): [M+H]$^+$ 896.0, R$_t$=1.96 min. The diastereomers were separated by Chiral SFC Kromasil DMB, 21.2×250 mm, 5 µm (15% IPA (w/0.1% DEA)/85% CO$_2$) to yield in the order of elution Example W-13, Example W-14 and Example W-15.

Example W-23A

Diastereomer 1

Example W-23B

Diastereomer 2

Example W-23C

Diastereomer 3

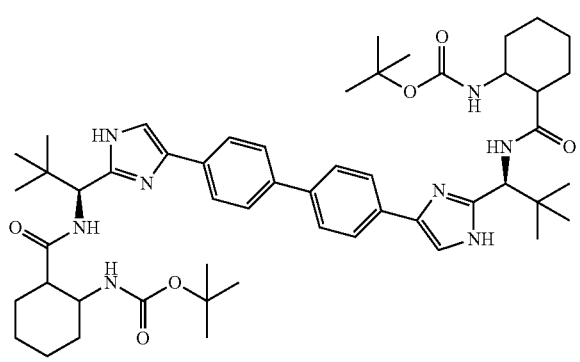 [SMILES: CC(C)(C)OC(=O)NC1CCCCC1C(=O)N[C@H](c1nc(-c2ccc(-c3ccc(-c4c[nH]c([C@@H](NC(=O)C5CCCCC5NC(=O)OC(C)(C)C)C(C)(C)C)n4)cc3)cc2)c[nH]1)C(C)(C)C]

To a slurry of (1S,1'S)-1,1'-(4,4'-([1,1'-biphenyl]-4,4'-diyl)bis(1H-imidazole-4,2-diyl))bis(2,2-dimethylpropan-1-amine), 4 HCl (500 mg, 0.830 mmol), cis-2-((tert-butoxycarbonyl)amino)cyclohexanecarboxylic acid (414 mg, 1.701 mmol), HATU (663 mg, 1.743 mmol) in DCM (15 mL) was added DIEA (1.015 mL, 5.81 mmol). The reaction mixture was stirred for at rt for 18 h. The reaction mixture was purified by preparatory HPLC (MeOH/H$_2$O/TFA) to afford a mixture of diastereomers. LC/MS (Cond. W-1): [M+H]$^+$ 908.0, R$_t$=1.832 min. The diastereomers were separated by ChiralPak IC, 30×250 mm, 5 µm (30% EtOH (w/0.1% DEA)/70% CO$_2$) to yield in the order of elution Example W-23 A, Example W-23 B and Example W-23 C.

Example W-40A

Diastereomer 1

Example W-40B

Diastereomer 2

Example W-40C

Diastereomer 3

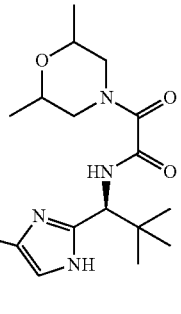

To a solution of (1S,1'S)-1,1'-(4,4'-([1,1'-biphenyl]-4,4'-diyl)bis(1H-imidazole-4,2-diyl))bis(2,2-dimethylpropan-1-amine), 4 HCl (35 mg, 0.058 mmol), 2-(trans-2,6-dimethylmorpholino)-2-oxoacetic acid (23.47 mg, 0.119 mmol), HATU (46.4 mg, 0.122 mmol) in DCM (1 mL) was added DIEA (0.071 mL, 0.407 mmol). The reaction mixture was stirred for at rt for 15 h. The reaction mixture was purified by preparatory HPLC (MeOH/H$_2$O/TFA) to afford the product (30 mg) as a mixture of diastereomers. LC/MS (Cond. W-1): [M+H]$^+$ 795.7, R$_t$=1.427 min. Three diastereomers were separated by ChiralCel SFC OD-H (30% MeOH (w/0.1% DEA)/70% CO$_2$) to yield in the order of elution Example W-40 A, Example W-40 B and Example W-40 C.

Example W-30

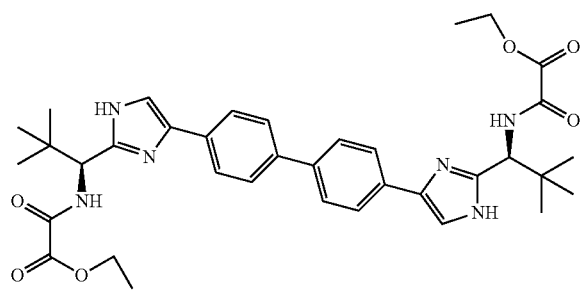 [SMILES: CCOC(=O)C(=O)N[C@H](c1nc(-c2ccc(-c3ccc(-c4c[nH]c([C@@H](NC(=O)C(=O)OCC)C(C)(C)C)n4)cc3)cc2)c[nH]1)C(C)(C)C]

To a slurry of (1S,1'S)-1,1'-(4,4'-([1,1'-biphenyl]-4,4'-diyl)bis(1H-imidazole-4,2-diyl))bis(2,2-dimethylpropan-1- amine), 4 HCl (150 mg, 0.249 mmol), 2-ethoxy-2-oxoacetic acid (61.5 mg, 0.510 mmol), HATU (199 mg, 0.523 mmol) in DCM (5 mL) was added DIEA (0.304 mL, 1.743 mmol). The reaction mixture was stirred for at rt for 18 h. The solvent was removed and the residue was purified by preparatory HPLC ($CH_3CN/H_2O/NH_4OAc$) to afford Example W-30: LC/MS (Cond. W-1): [M+H]$^+$ 657.6, $R_t$=1.447 min. $^1$H NMR (500 MHz, MEOD-$d_4$) δ ppm 7.95 (2H, s), 7.85-7.92 (8H, m), 5.19 (2H, s), 4.40 (4H, q, J=7.09 Hz), 1.39 (6H, t, J=7.17 Hz), 1.15 (18H, s).

Example W-11

To a slurry of (1S,1'S)-1,1'-(4,4'-([1,1'-biphenyl]-4,4'-diyl)bis(1H-imidazole-4,2-diyl))bis(2,2-dimethylpropan-1-amine), 4 HCl (100 mg, 0.166 mmol), 2-oxo-2-(piperidin-1-yl)acetic acid (56.3 mg, 0.340 mmol), HATU (133 mg, 0.349 mmol) in DCM (3 mL) was added DIEA (0.203 mL, 1.162 mmol). The reaction mixture was stirred for at rt for 18 h. The solvent was removed and the residue was purified by preparatory HPLC (MeOH/$H_2O$/TFA) to afford Example W-11 (95 mg, TFA salt) LC/MS (Cond. W-1): [M+H]$^+$ 735.8, $R_t$=1.518 min. $^1$H NMR (500 MHz, MeOD-$d_4$) δ ppm 7.94-7.97 (2H, m), 7.86-7.93 (8H, m), 5.04 (2H, s), 3.44-3.68 (8H, m), 1.59-1.78 (12H, m), 1.10-1.24 (18H, m).

Example W-41

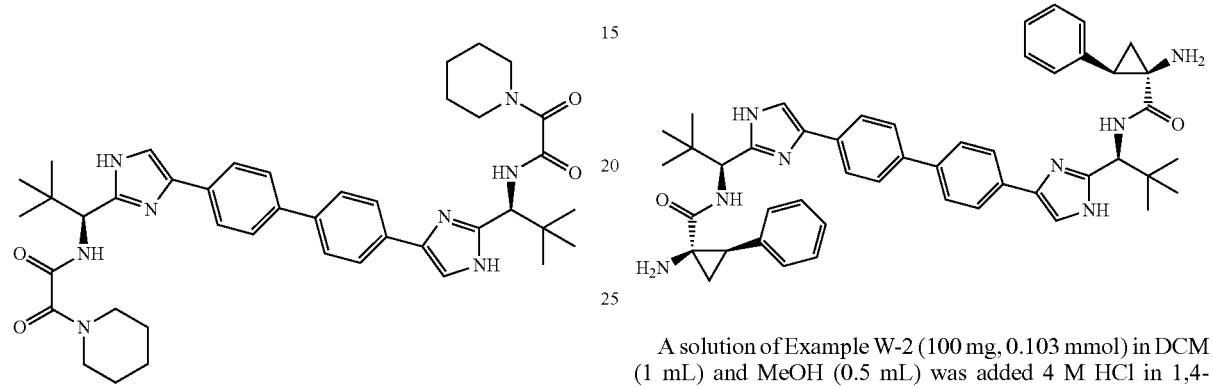

A solution of Example W-2 (100 mg, 0.103 mmol) in DCM (1 mL) and MeOH (0.5 mL) was added 4 M HCl in 1,4-dioxane (1.025 mL). The reaction mixture was stirred at rt for 3 h, then concentrated to yield Example W-41 (94 mg, HCl salt). LC/MS (Cond. W-1): [M+H]$^+$ 775.8, $R_t$=1.508 min.

Example W-41A-B

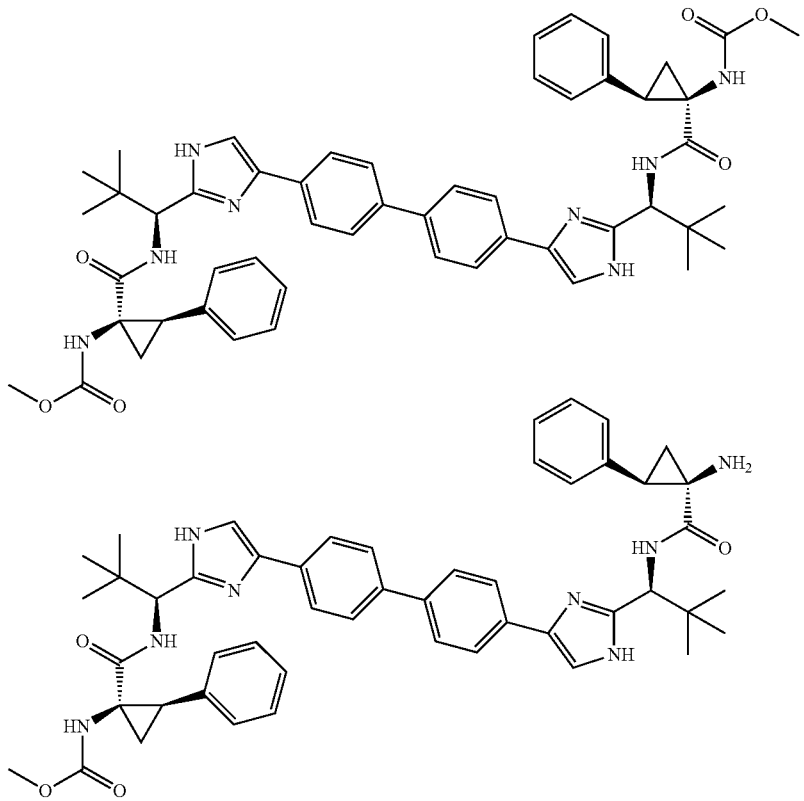

To a mixture Example W-41 (50 mg, 0.054 mmol) in CH$_2$Cl$_2$ (5 mL) at 4° C. was added DIPEA (0.095 mL) and methyl chloroformate (0.034 mL). The reaction mixture was stirred at rt for 1 hour. A solution of 2 M ammonia in MeOH (2 mL) was added and the reaction mixture was stirred at rt for 3 h, then concentrated and the residue was purified preparatory HPLC (MeOH/H$_2$O/TFA) to afford Example W-41A (44 mg, TFA salt) as a white solid. LC/MS (Cond. W-1): [M+H]$^+$ 891.9, R$_t$=1.8 min. $^1$H NMR (500 MHz, MeOD-d$_4$) δ ppm 7.98 (2H, s), 7.86-7.96 (8H, m), 7.24-7.35 (5H, m), 7.15-7.22 (5H, m), 5.19 (2H, br. s.), 3.54 (6H, br. s.), 2.89-3.05 (2H, m), 1.98 (2H, dd, J=9.62, 5.83 Hz), 1.78 (2H, dd, J=7.96, 5.91 Hz), 1.16-1.12 (18H, s); and Example W-41B. LC/MS (Cond. W-1): [M+H]$^+$ 833.8, R$_t$=1.67 min.

Example W-42

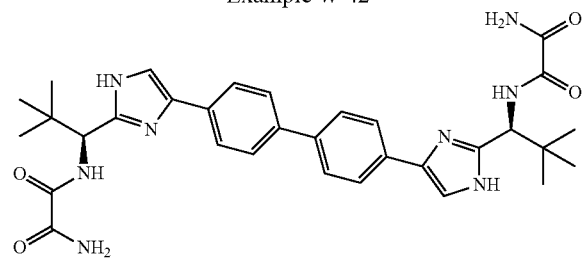

To a light yellow slurry of (1S,1'S)-1,1'-(4,4'-([1,1'-biphenyl]-4,4'-diyl)bis(1H-imidazole-4,2-diyl))bis(2,2-dimethylpropan-1-amine), 4 HCl (50 mg, 0.083 mmol) and DIEA (0.145 mL, 0.830 mmol) in DCM (5 mL) at 4° C. was added methyl chloroformate (0.040 mL, 0.415 mmol) dropwise. The reaction mixture was stirred at rt for 1 hour. A solution of 2 M ammonia in MeOH (2 mL) was added and the reaction mixture was stirred at rt for 3 h, then concentrated and the residue was purified preparatory HPLC (CH$_3$CN/H$_2$O/NH$_4$OAc) to afford Example W-42 (24 mg). LC/MS (Cond. W-1): [M+H]$^+$ 599.5, R$_t$=1.208 min.

Example W-43A

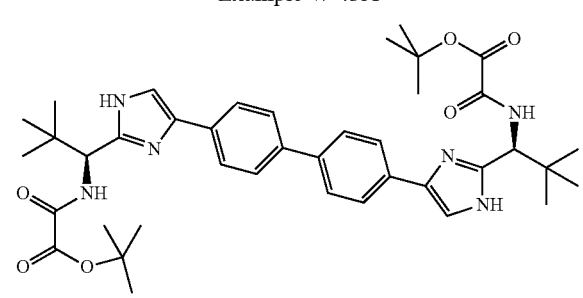

Example W-43B

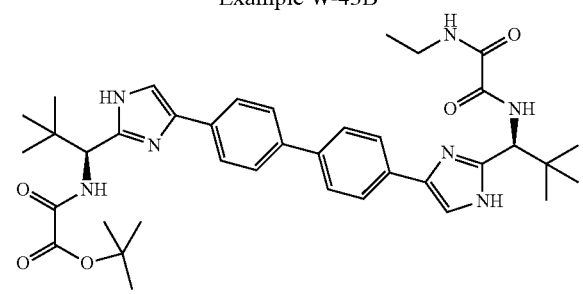

To a solution of (1S,1'S)-1,1'-(4,4'-([1,1'-biphenyl]-4,4'-diyl)bis(1H-imidazole-4,2-diyl))bis(2,2-dimethylpropan-1-amine), 4 HCl (702 mg, 1.166 mmol), 2-(tert-butoxy)-2-oxoacetic acid (358 mg, 2.45 mmol), HATU (953 mg, 2.507 mmol) in DCM (20 mL) was added DIEA (1.426 mL, 8.16 mmol). The reaction mixture was stirred for at rt for 3.5 h. The solvent was removed and the residue was purified by a preparatory HPLC (CH$_3$CN/H$_2$O/NH$_4$OAc) to provide Example W-43A (619 mg), LC/MS (Cond. W-1): [M+H]$^+$ 713.7, R$_t$=1.665 min, $^1$H NMR (500 MHz, MeOD-d$_4$) δ ppm 7.83 (3H, br. s.), 7.63-7.76 (5H, m), 7.45 (1H, br. s.), 7.40 (1H, br. s.), 5.06 (2H, s), 1.59 (18H, s), 0.97-1.11 (18H, m); and Example W-43B (45 mg), LC/MS (Cond. W-1): [M+H]$^+$ 683.6, R$_t$=1.425 min.

Example W-44

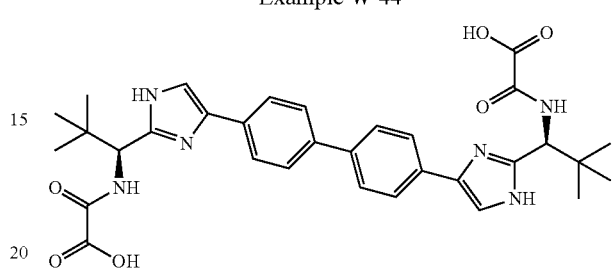

To a solution of Example W-43A (35.5 mg) in DCM (5 mL) at ice bath was added TFA (0.038 mL). The resulting solution was stirred at rt for 2 h. The volatile was removed in vacuo to afford Example W-44 (40 mg, TFA salt) as a white solid. LC/MS (Cond. W-1): [M+H]$^+$ 601.4, R$_t$=1.162 min.

Example W-45

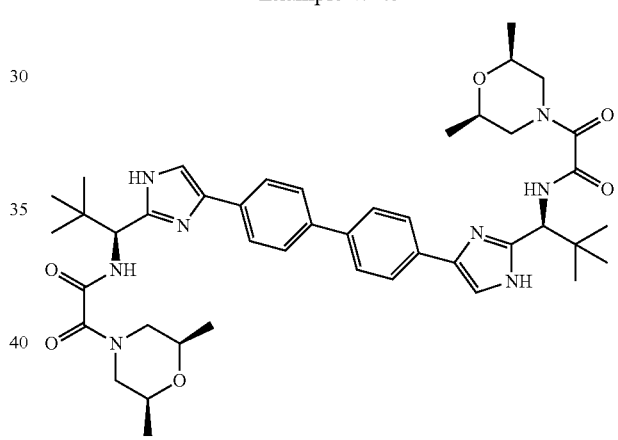

To a solution of Example W-44 (30 mg, 0.036 mmol), cis-2,6-dimethylmorpholine (8.76 mg, 0.076 mmol), HATU (28.9 mg, 0.076 mmol) in DCM (1 mL) was added DIEA (0.044 mL, 0.253 mmol). The resulting solution was stirred at rt overnight. The volatile was removed in vacuo and the residue was purified by a preparatory HPLC (CH$_3$CN/H$_2$O/NH$_4$OAc) system to yield W-45. LC/MS (Cond. W-1): [M+H]$^+$ 795.9, R$_t$=1.43 min.

Example W-46A

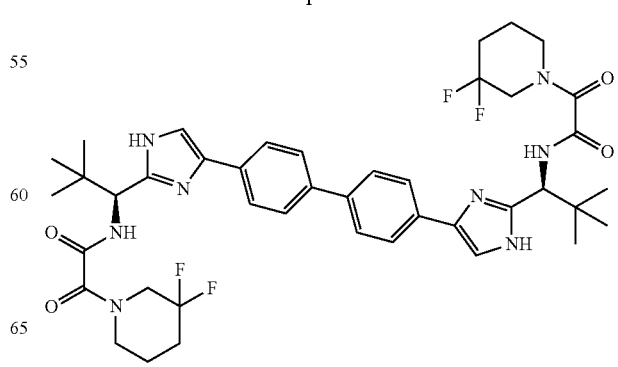

To a solution of Example W-44 (50 mg, 0.060 mmol), 3,3-difluoropiperidine/HCl (39.0 mg, 0.247 mmol), HATU (71.1 mg, 0.187 mmol) in DCM (2 mL) was added DIEA (0.105 mL, 0.603 mmol). The reaction mixture was stirred at rt overnight. Then 2 M ammonia in MeOH (2 mL) was added and the reaction mixture was stirred at rt for 3 h. The volatile component was removed in vacuo and the residue was purified by a preparatory HPLC (CH$_3$CN/H$_2$O/NH$_4$OAc) system to yield Example W-46A (14 mg), LC/MS (Cond. W-1): [M+H]$^+$ 807.6, R$_t$=1.535 min.

Example W-47 to W-50 were synthesized by employing the method described in Example W-45 and using a commercially available amine.

| Example | R | LC-MS Method | Retention Time (min) | Obs. Mass ion (M + H)+ |
|---|---|---|---|---|
| W-47 | ![structure] | W-1 | 1.687 | 819.5 |
| W-48 | ![structure] | W-1 | 1.39 | 785.6 |
| W-49 | ![structure] | W-1 | 1.65 | 763.8 |
| W-50 | ![structure] | W-1 | 1.34 | 707.6 |

*Example W-47: $^1$H NMR (500 MHz, DMSO-d$_6$) δ ppm 12.48-12.14 (2 H, m), 9.25-8.96 (2 H, m), 7.87-7.41 (10 H, m), 5.01-4.91 (2 H, m), 4.70-4.15 (4 H, m), 3.80-3.70 (2 H, m), 3.51-3.40 (4 H, m), 1.17-1.15 (6 H, m), 0.99-0.96 (18 H, m).
Example W-49: $^1$H NMR (500 MHz, DMSO-d$_6$) δ ppm 12.50-12.26 (2 H, m), 9.06-8.90 (2 H, m), 7.85-7.40 (10 H, m), 5.01-4.93 (2 H, m), 4.23-4.21 (2 H, m), 1.24-1.23 (12 H, m), 1.00-0.99 (18 H, m), 0.77-0.47 (10 H, m).

Example L-18

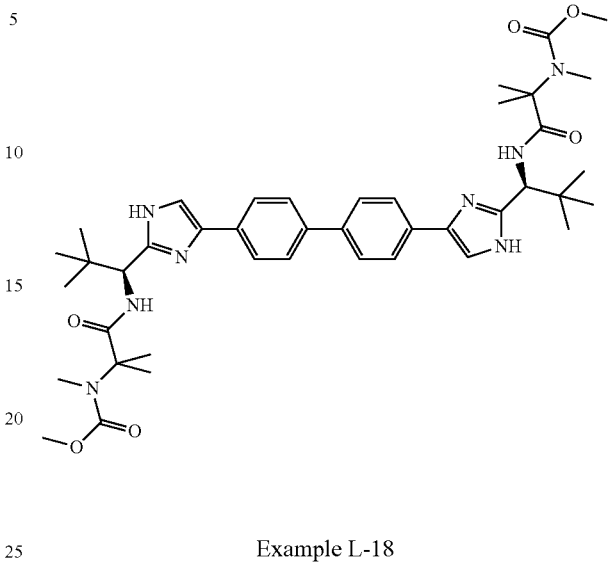

Example L-18

Step a

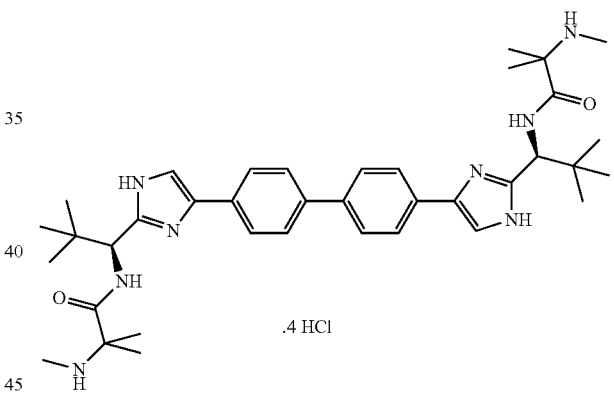

.4 HCl

HCl (4 N in dioxanes) (0.292 mL, 1.169 mmol) was added to a solution of Example L-8 (100 mg, 0.117 mmol) in DCM (5 mL) and the resulting suspension was stirred at rt for 3 h. The solvent was removed under reduced pressure and a beige solid corresponding to Example L-18 step a (90 mg) was isolated. LC/MS (Cond. L-1): [M+H]$^+$ 655.65, R$_t$=1.576 min.

To a mixture Example L-18 step a in CH$_2$Cl$_2$ (1.5 mL) was added DIPEA (0.061 mL, 0.350 mmol) and methyl chloroformate (3.9 μL, 0.050 mmol). The mixture was stirred at room temperature for 1 hour. Ammonia (2 mL, 4.0 mmol, 2 M in MeOH) was added and the mixture was stirred at room temperature for 3 hours. The reaction mixture was concentrated under vacuum and the residue was purified by preparatory HPLC (CH$_3$CN/H$_2$O/NH$_4$OAc) to yield a white solid corresponding to Example L-18 (40 mg). $^1$H NMR (500 MHz, DMSO-d$_6$) δ 12.01 (br. s., 2H), 7.81 (br. s., 4H), 7.69 (br. s., 4H), 7.57 (br. s., 1H), 7.13 (d, J=9.2 Hz, 2H), 4.85 (d, J=8.2 Hz, 2H), 3.25 (br. s., 6H), 2.95 (s, 6H), 1.40 (s, 6H), 1.29 (s, 6H), 0.91 (s, 18H). LC-MS (Cond. L-1): [M+H]$^+$ 771.7, R$_t$=2.01 min.

Example L-20

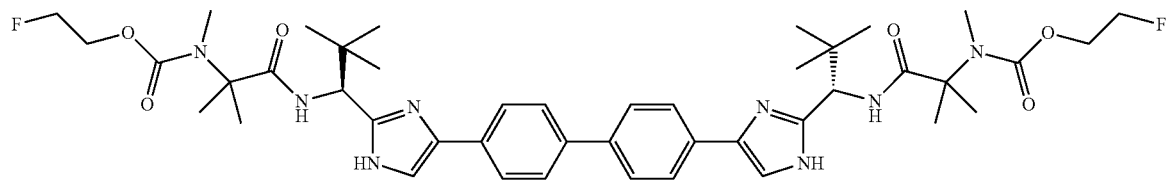 [SMILES: CN(C(=O)OCCF)C(C)(C)C(=O)N[C@H](c1nc(-c2ccc(-c3ccc(-c4c[nH]c([C@@H](NC(=O)C(C)(C)N(C)C(=O)OCCF)C(C)(C)C)n4)cc3)cc2)c[nH]1)C(C)(C)C]

Example L-20 (bis-TFA) was prepared by employing the procedures described for the synthesis of Example L-18. LC-MS (Cond. L-1): [M+H]$^+$ 835.7, $R_t$=2.14 min.

Example L-41

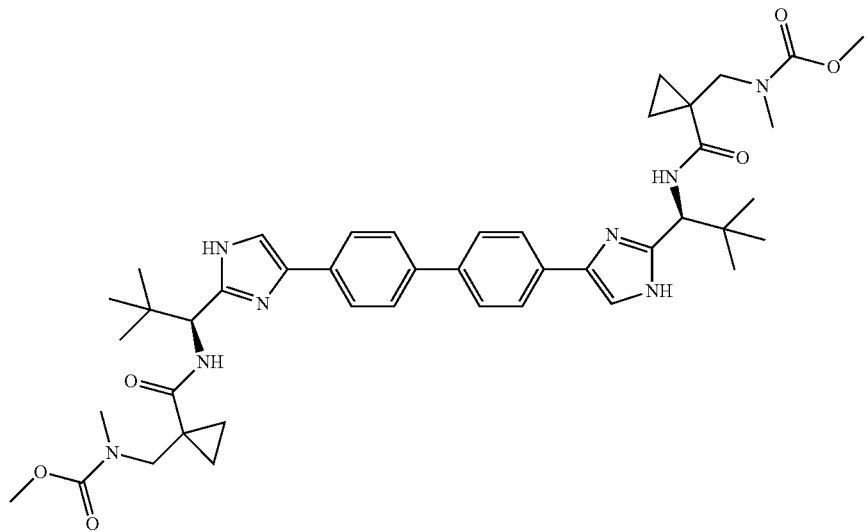

Example L-41 (bis-TFA) was prepared from Example L-40 and appropriate starting materials, obtained from commercial sources, by employing the procedures described for the synthesis of Example L-18. LC-MS (Cond. L-2): [M+H]$^+$ 795.65, $R_t$=1.268 min.

Example Q-1

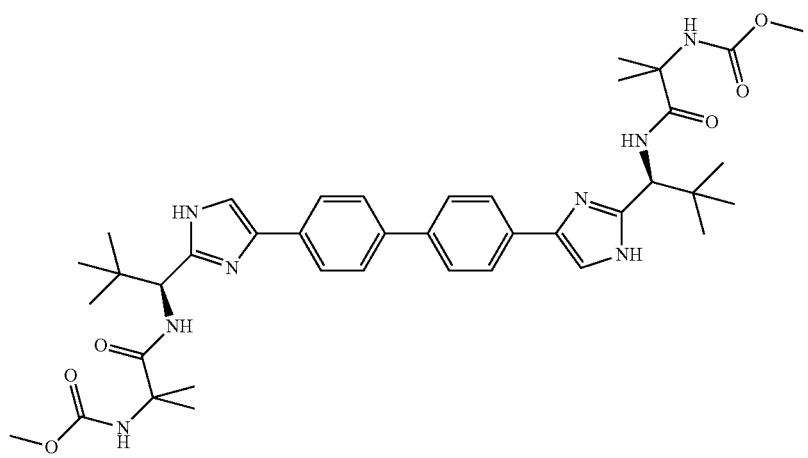

Example Q-1

Step a

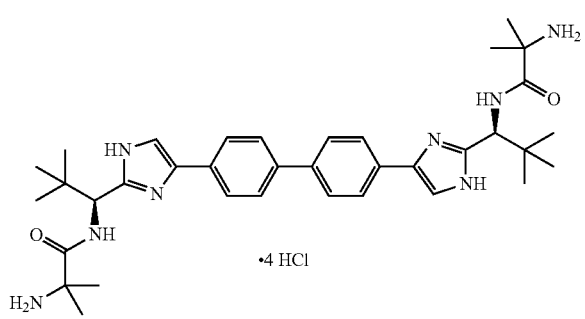 [SMILES: CC(C)(N)C(=O)N[C@H](c1nc(-c2ccc(-c3ccc(-c4c[nH]c([C@@H](NC(=O)C(C)(C)N)C(C)(C)C)n4)cc3)cc2)c[nH]1)C(C)(C)C]

To a suspension of Example L1 (320 mg, 0.387 mmol) in CH₂Cl₂ (4 mL) was added HCl (3 mL, 12.00 mmol) (4 N in dioxane). The mixture was stirred at room temperature for 1 hour. The mixture was concentrated. The residue was dissolved in MeOH and triturated with Et₂O to give Example Q-1 Step a as a light yellow solid. LC/MS (Cond. P-2): [M+H]⁺ 627.63, $R_t$=1.64 min. ¹H NMR (500 MHz, MeOD-d₄) δ ppm 7.99-8.06 (6H, m), 7.90 (4H, d, J=8.51 Hz), 5.38 (2H, s), 1.81 (6H, s), 1.75 (6H, s), 1.16 (18H, s).

To a mixture of Example Q-1 Step a (40 mg, 0.052 mmol) in CH₂Cl₂ (2 mL) was added DIPEA (0.063 mL, 0.362 mmol) and methyl chloroformate (0.012 mL, 0.155 mmol). The mixture was stirred at room temperature for 1 hour.

Then ammonia (2 mL) (2 M in MeOH) was added and the mixture was stirred at room temperature for 3 hours. The reaction mixture was then concentrated and purified by prep HPLC (MeOH/H₂O/TFA) to yield Example Q-1 (0.03 g) as a white solid. LC/MS (Cond. P-2): [M+H]⁺ 743.58, $R_t$=1.767 min. ¹H NMR (400 MHz, MeOD-d₄) δ ppm 7.93 (2H, s), 7.89 (8H, s), 5.10 (2H, s), 3.66 (6H, s), 1.50 (6H, s), 1.44 (6H, s), 1.11 (18H, s).

Example Q-2 to Q-6 (bis-TFA) were prepared from N,N'-((1S,1'S)-(4,4'-([1,1'-biphenyl]-4,4'-diyl)bis(1H-imidazole-4,2-diyl))bis(2,2-dimethylpropane-1,1-diyl))bis(2-amino-2-methylpropanamide), 4 HCl and appropriate starting materials, obtained from commercial sources, by employing the procedures described for the synthesis of Example Q-1.

| Example | R | LC-MS Method | Retention Time (min) | Obs. Mass ion (M + H)+ |
|---|---|---|---|---|
| Q-2 | ethyl carbonate | P-2 | 1.848 | 771.53 |
| Q-3 | isopropyl carbonate | P-2 | 1.91 | 799.57 |
| Q-4 | 2-fluoroethyl carbonate | P-2 | 1.768 | 807.6 |
| Q-5 | neopentyl carbonate | P-2 | 2.01 | 823.72 |
| Q-6 | cyclohexyl carbonate | P-2 | 2.075 | 880.68 |

Example Q-7

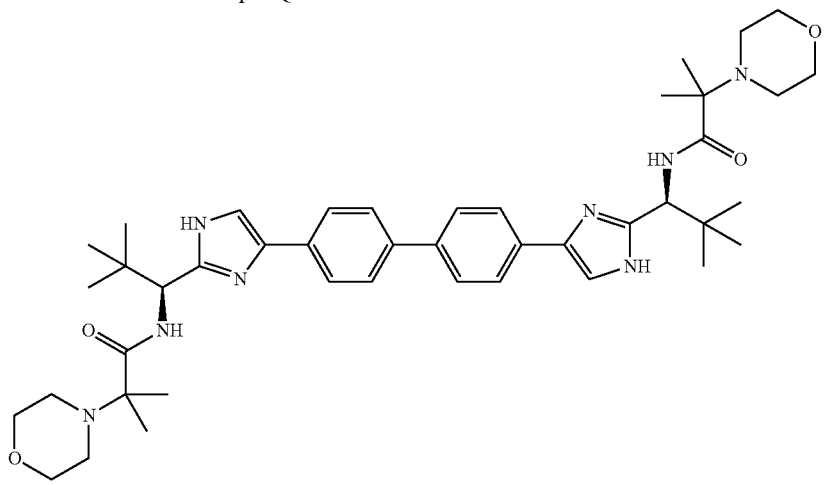

To a solution of morpholine (1.2 mL, 13.77 mmol) in BuOH (3 mL) was added 2-bromo-2-methylpropanoic acid (1 g, 5.99 mmol) and TEA (1.085 mL, 7.78 mmol). The resulting mixture was stirred at 80° C. for 24 h. The mixture was cooled to room temperature, NaOH (0.240 g, 5.99 mmol) was added, and the mixture was stirred at room temperature for 1 hour. The mixture was then evaporated to dryness and the product sodium 2-methyl-2-morpholinopropanoate was used without further purification.

(1S,1'S)-1,1'-(4,4'-([1,1'-biphenyl]-4,4'-diyl)bis(1H-imidazole-4,2-diyl))bis(2,2-dimethylpropan-1-amine), 4 HCl (50 mg), sodium 2-methyl-2-morpholinopropanoate (64.8 mg) and DIEA (0.101 mL) were combined in DMF (10 mL) and the resulting mixture was stirred for 5 min, followed by addition of HATU (66.3 mg, 0.174 mmol). The resulting solution was the stirred at rt for 2 h. The reaction mixture was concentrated and purified by prep. HPLC (MeOH/H$_2$O/TFA) to yield Example Q-7 as a white solid (18 mg). LC/MS (Cond. P-2): [M+H]$^+$ 767.57, R$_t$=1.657 min.

Example P-137

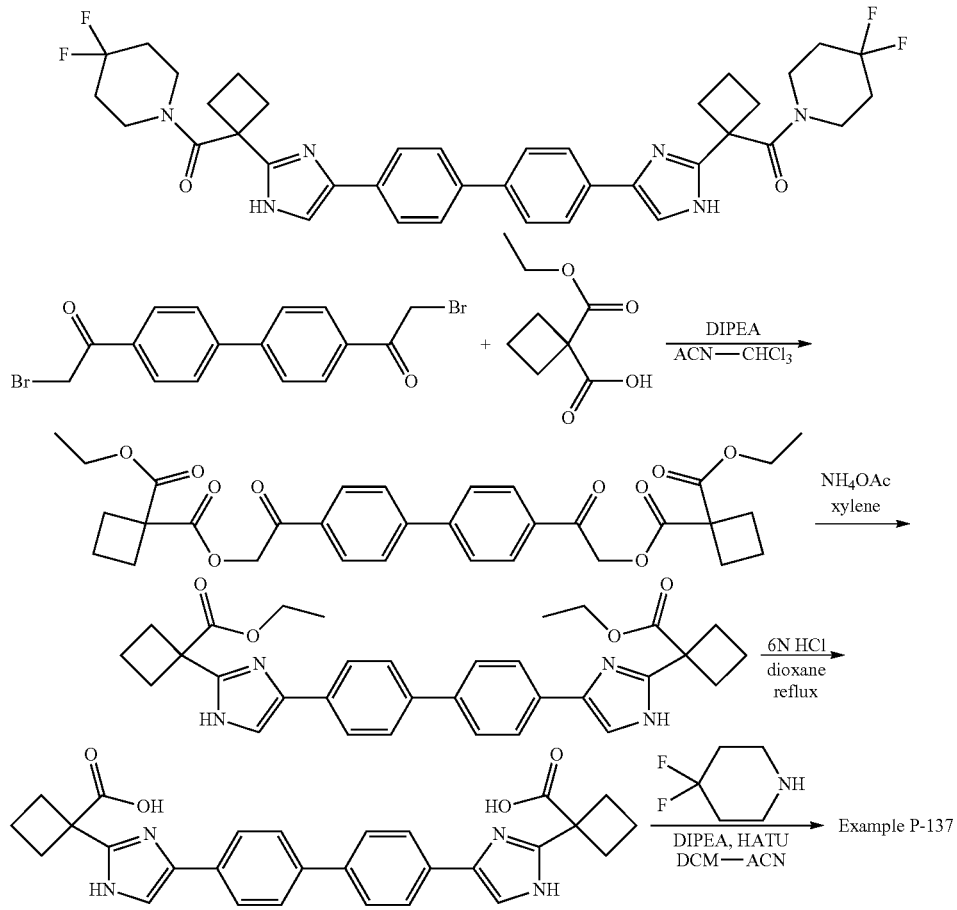

Neat DIPEA (0.384 mL) was added to a stirred solution of 1,1'-([1,1'-biphenyl]-4,4'-diyl)bis(2-bromoethanone) (396 mg) and 1-(ethoxycarbonyl)cyclobutanecarboxylic acid (362 mg) in acetonitrile (4 mL) and CHCl$_3$ (4 mL). The suspension was stirred at rt overnight and evaporated to dryness and then purified by silica FCC (0-1% MeOH in DCM) to afford O'1,O1-([1,1'-biphenyl]-4,4'-diylbis(2-oxoethane-2,1-diyl)) 1-diethyl bis(cyclobutane-1,1-dicarboxylate) as a beige solid (0.576 g). $^1$H NMR (500 MHz, CDCl$_3$) ppm 8.01-8.06 (4H, m), 7.74-7.79 (4H, m), 5.43 (4H, s), 4.27 (4H, q, J=7.12 Hz), 2.71-2.81 (4H, m), 2.60-2.70 (4H, m), 1.93-2.17 (4H, m), 1.26-1.38 (6H, m). In a sealed tube, a stirred suspension of O'1,O1-([1,1'-biphenyl]-4,4'-diylbis(2-oxoethane-2,1-diyl)) 1-diethyl bis(cyclobutane-1,1-dicarboxylate) (0.576 g) and ammonium acetate (1.535 g) in xylene (5 mL) was heated to 135° C. for 3 h. The reaction mixture was diluted with DCM and washed with sat. NaHCO$_3$, water, sat. NaCl and dried over anhydrous Na$_2$SO$_4$, filtered and concentrated to afford an orange solid which was purified by silica gel FCC (3-5% MeOH in DCM) to afford diethyl 1,1'-(4,4'-(biphenyl-4,4'-diyl)bis(1H-imidazole-4,2-diyl))dicyclobutanecarboxylate as a yellow-orange solid (0.217 g).

A stirred suspension of diethyl 1,1'-(4,4'-([1,1'-biphenyl]-4,4'-diyl)bis(1H-imidazole-4,2-diyl))dicyclobutanecarboxylate (217 mg, 0.403 mmol) and HCl (4.03 mL, 24.17 mmol) in dioxane (5 mL) was heated to reflux for 3 h. The resultant yellow solution was evaporated to dryness to afford 1,1'-(4,4'-([1,1'-biphenyl]-4,4'-diyl)bis(1H-imidazole-4,2-diyl))dicyclobutanecarboxylic acid, 2 HCl as a yellow solid (55.5 mg). LC/MS (Cond. P-2): [M+H]$^+$ 483.3, R$_t$=1.73 min.

Neat DIPEA (0.112 mL, 0.640 mmol) was added to a stirred partial solution of 1,1'-(4,4'-([1,1'-biphenyl]-4,4'-diyl)bis(1H-imidazole-4,2-diyl))dicyclobutanecarboxylic acid, 2 HCl (55.5 mg, 0.1 mmol) and 4,4-difluoropiperidine, HCl (34.7 mg, 0.220 mmol) in DCM (1 mL) and acetonitrile (1 mL). The mixture was stirred at rt overnight. The crude reaction mixture was evaporated and purified by prep. HPLC (MeOH/H$_2$O/TFA) to afford Example P-137 (bis-TFA) as a white solid. LC/MS (Cond. P-3): [M+H]$^+$ 689.43, R$_t$=3.173 min.

Example P-138

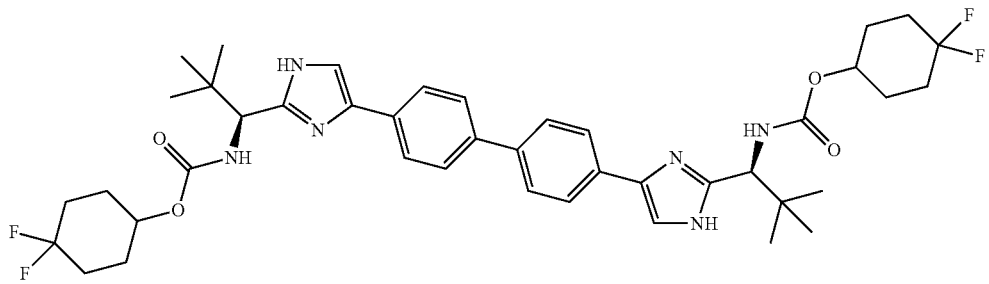 [SMILES: CC(C)(C)[C@H](NC(=O)OC1CCC(F)(F)CC1)c1nc(-c2ccc(-c3ccc(-c4c[nH]c([C@@H](NC(=O)OC5CCC(F)(F)CC5)C(C)(C)C)n4)cc3)cc2)c[nH]1]

Neat DIPEA (0.040 mL) was added to a stirred partial solution of (1S,1'S)-1,1'-(4,4'-([1,1'-biphenyl]-4,4'-diyl)bis(1H-imidazole-4,2-diyl))bis(2,2-dimethylpropan-1-amine), 4 HCl (50.2 mg) and 4,4-difluorocyclohexyl carbonochloridate (0.40 mL, 0.20 mmol) in DCM (1 mL), acetonitrile (1 mL) and DMF (0.5 mL). The mixture was stirred at rt overnight. The crude mixture was evaporated to dryness and then purified by prep. HPLC (MeOH/H$_2$O/TFA) to afford Example P-138 as a beige solid and was isolated as bis-TFA salt form (26 mg). $^1$H NMR (400 MHz, MeOD-d$_4$) δ ppm 7.95 (2H, s), 7.84-7.93 (8H, m), 4.73-4.85 (2H, m), 4.00 (2H, s), 2.09-1.78 (16H, m), 1.14 (18H, s).

Example Y-84

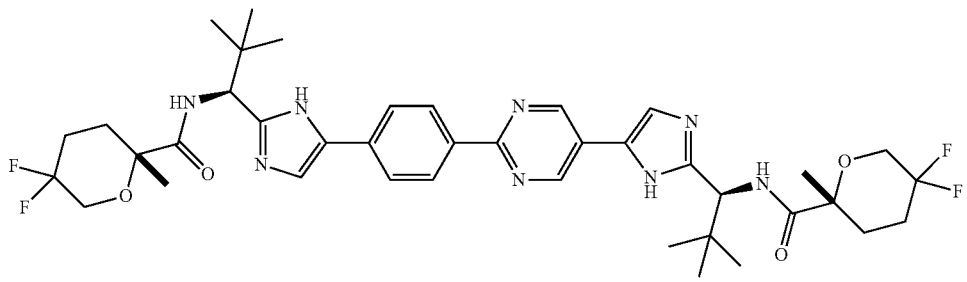

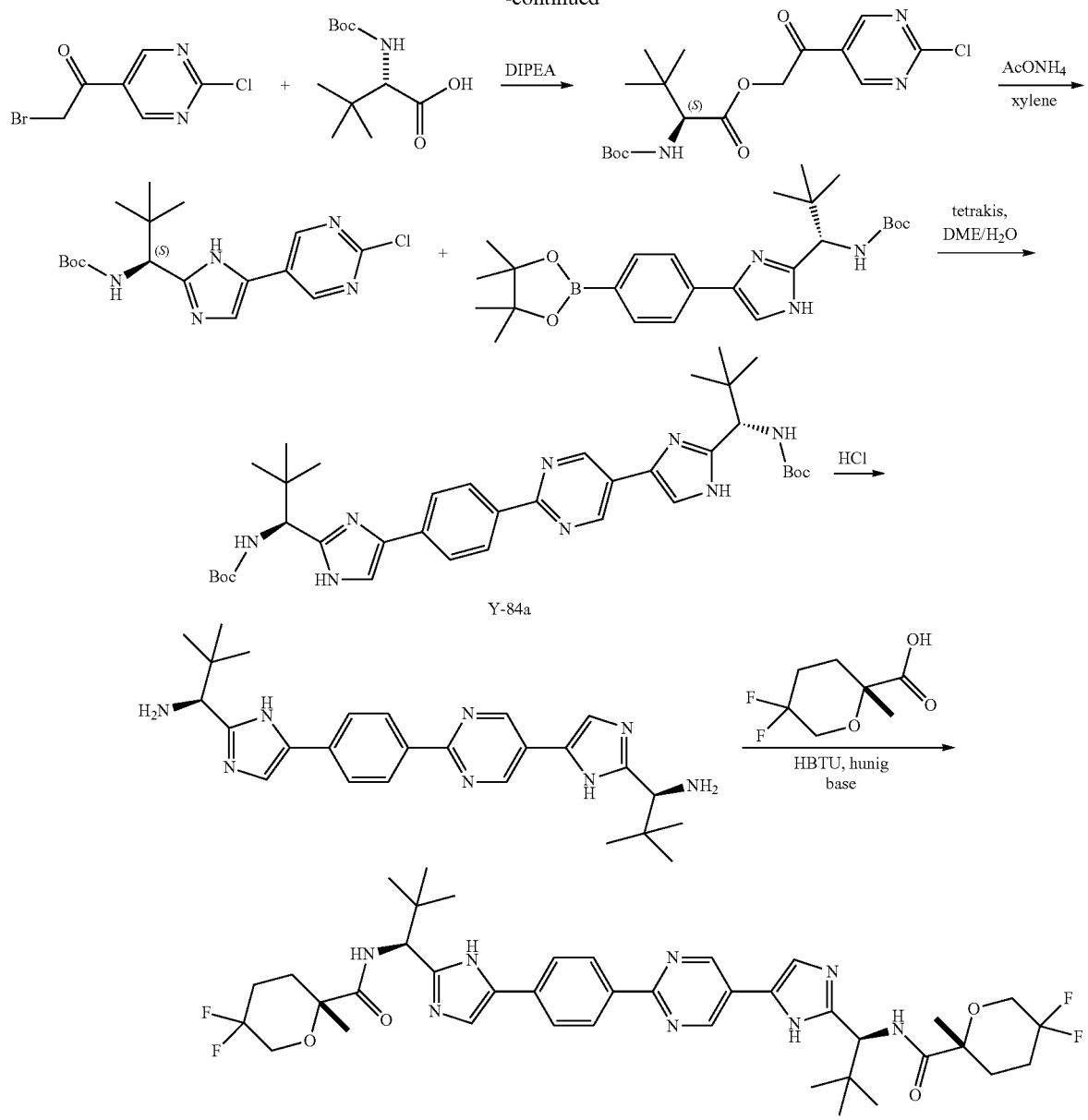

To a solution of (S)-2-((tert-butoxycarbonyl)amino)-3,3-dimethylbutanoic acid (1.8 g, 7.78 mmol) and DIPEA (1.4 mL, 8.02 mmol) in acetonitrile (25 mL) was added (S)-2-((tert-butoxycarbonyl)amino)-3,3-dimethylbutanoic acid (1.8 g, 7.78 mmol) in ice bath. The suspension was stirred at rt for 2 h. The reaction mixture was diluted with EtOAc and washed with satd. aq. NaHCO$_3$, NH$_4$Cl, brine, water, dried (MgSO$_4$), and concentrated to afford (S)-2-(2-chloropyrimidin-5-yl)-2-oxoethyl 2-((tert-butoxycarbonyl)amino)-3,3-dimethylbutanoate. The crude product was used in the next step without purification.

A mixture of (S)-2-(2-chloropyrimidin-5-yl)-2-oxoethyl 2-((tert-butoxycarbonyl)amino)-3,3-dimethylbutanoate (2.5 g, 6.48 mmol) and acetic acid, ammonia salt (5 g, 64.9 mmol) in xylene (20 mL) was charged in a sealed vial and heated in 138° C. bath for 5 h. The reaction mixture was diluted with EtOAc and washed with satd. NaHCO$_3$, brine, dried (MgSO$_4$), concentrated and purified by silica gel flash chromatography to afford (S)-tert-butyl (1-(4-(2-chloropyrimidin-5-yl)-1H-imidazol-2-yl)-2,2-dimethylpropyl)carbamate (0.25 g, 6.5%). LC/MS (Cond. Y-1): [M+H]$^+$ 366.2, R$_t$=2.596 min.

To a solution of (S)-tert-butyl (1-(4-(2-chloropyrimidin-5-yl)-1H-imidazol-2-yl)-2,2-dimethylpropyl)carbamate (0.25 g, 0.683 mmol) and (S)-tert-butyl (2,2-dimethyl-1-(4-(4-(4,4,5,5-tetramethyl-1,3,2-dioxaborolan-2-yl)phenyl)-1H-imidazol-2-yl)propyl)carbamate (0.622 g, 1.367 mmol) in DME (10 mL) and water (4 mL) was added sodium bicarbonate (0.3 g, 3.57 mmol). The reaction mixture was degassed, refiled with N$_2$ and tetrakis(triphenylphosphine)palladium(0) (0.04 g, 0.035 mmol) was added, degassed and refilled with N$_2$. The reaction mixture was heated to 80° C. for 16 hours under N$_2$. The reaction mixture was diluted with EtOAc and washed with NaHCO$_3$ (2×), brine, dried (MgSO$_4$), concentrated and purified on silica gel flash chromatography to afford the product Y-84a (0.16 g, 35%). LC/MS (Cond. Y-1): [M+H]$^+$ 659.45, R$_t$=2.95 min.

To a solution of Y-84a (0.16 g, 0.243 mmol) in DCM (3 mL) was added hydrogen chloride/dioxane (2 mL, 8.00 mmol) in icebath. The reaction mixture was stirred at rt for 2 h. removed the solvents to afford (S)-1-(4-(2-(4-(24S)-1-amino-2,2-dimethylpropyl)-1H-imidazol-4-yl)phenyl)pyrimidin-5-yl)-1H-imidazol-2-yl)-2,2-dimethylpropan-1-amine tetrahydrochloride as a yellow solid. LC/MS (Cond. Y-1): [M+H]$^+$ 459, R$_t$=2.625 min.

To a suspension of (S)-1-(5-(2-(4-(2-((S)-1-amino-2,2-dimethylpropyl)-1H-imidazol-5-yl)phenyl)pyrimidin-5-yl)-1H-imidazol-2-yl)-2,2-dimethylpropan-1-amine, 4 HCl (0.040 g, 0.066 mmol) and (R)-5,5-difluoro-2-methyltetrahydro-2H-pyran-2-carboxylic acid (0.030 g, 0.165 mmol) in DCM (1 mL) was added DIPEA (0.12 mL, 0.687 mmol) and HBTU (0.06 g, 0.158 mmol) at 0° C. The reaction mixture was stirred for 1 h, diluted with MeOH (1 mL), removed the solvent and purified by HPLC to afford (R)—N—((S)-1-(5-(2-(4-(2-((S)-1-((R)-5,5-difluoro-2-methyltetrahydro-2H-pyran-2-carboxamido)-2,2-dimethylpropyl)-1H-imidazol-5-yl)phenyl)pyrimidin-5-yl)-1H-imidazol-2-yl)-2,2-dimethylpropyl)-5,5-difluoro-2-methyltetrahydro-2H-pyran-2-carboxamide, 2 TFA) as Example Y-84. LC/MS (Cond. Y-1): [M+H]$^+$ 783.45, R$_t$=2.889 min.

7.03 (dd, J=9.9, 8.9 Hz, 2H), 5.24-5.15 (m, 4H), 1.20 (s, 6H), 1.15 (s, 18H), 1.13-1.05 (m, 6H).

Example N-124B (stereoisomer-2): LC/MS (Cond. N-1): [M+H]$^+$ 845.65, RT=3.648 min. $^1$H NMR (400 MHz, METHANOL-d$_4$) ppm 7.96 (s, 1H), 7.94 (s, 1H), 7.92-7.82 (m, 8H), 7.47 (dt, J=15.1, 7.5 Hz, 1H), 7.47 (dt, J=15.1, 7.6 Hz, 1H), 7.37-7.25 (m, 2H), 7.22-6.98 (m, 4H), 5.24-5.16 (m, 3H), 5.04-4.99 (m, 1H), 1.27-1.06 (m, 30H).

Example N-124C (stereoisomer-3): LC/MS (Cond. N-1): [M+H]$^+$ 845.65, RT=3.648 min. $^1$H NMR (400 MHz, METHANOL-d$_4$) ppm 7.95-7.83 (m, 10H), 7.49 (td, J=7.5, 1.8 Hz, 2H), 7.37-7.28 (m, 2H), 7.19 (td, J=7.5, 1.0 Hz, 2H), 7.07 (dd, J=10.0, 9.0 Hz, 1H), 7.07 (dd, J=11.2, 7.7 Hz, 1H), 5.21 (s, 2H), 4.98 (s, 2H), 1.25 (s, 6H), 1.22-1.13 (m, 18H), 1.09 (s, 6H).

Example N-124

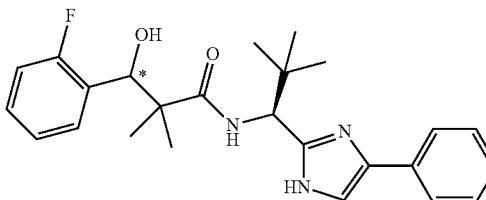

N-124A to N-124C

Three Diastereomers

Example N-124A to N-124C (TFA salt) were prepared in a similar fashion starting from (1S,1'S)-1,1'-(4,4'-(biphenyl-4,4'-diyl)bis(1H-imidazole-4,2-diyl))bis(2,2-dimethylpropan-1-amine), 4 HCl and Cap N-9 according to the procedure described for the preparation Example N-28. The three diastereomers were separated by prepHPLC (Water Sunfire 30×100 mm column, 20 min gradient from 0-55% B. A=H$_2$O/CH$_3$CN/TFA 90:10:0.1, B=CH$_3$CN/H$_2$O/TFA 90:10:0.1). Example N-124A (stereoisomer-1): LC/MS (Cond. N-1): [M+H]$^+$ 845.65, RT=3.648 min. $^1$H NMR (400 MHz, METHANOL-d$_4$) ppm 7.94 (s, 2H), 7.93-7.85 (m, 8H), 7.45 (td, J=7.5, 1.5 Hz, 2H), 7.34-7.23 (m, 2H), 7.16-7.08 (m, 2H), Example N-125

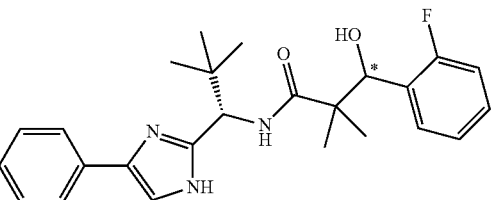

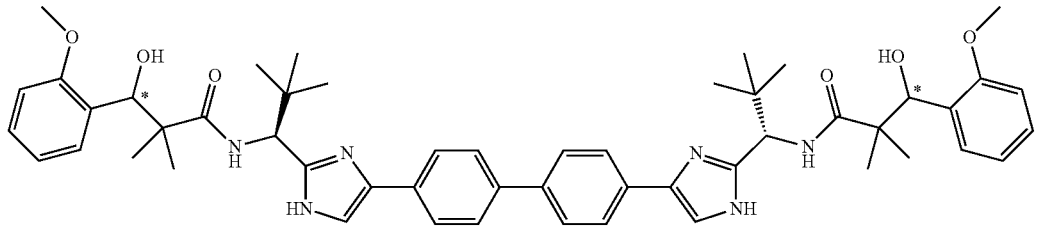 [SMILES: COc1ccccc1C(O)C(C)(C)C(=O)N[C@H](c1nc(-c2ccc(-c3ccc(-c4c[nH]c([C@@H](NC(=O)C(C)(C)C(O)c5ccccc5OC)C(C)(C)C)n4)cc3)cc2)c[nH]1)C(C)(C)C]

N-125A to N-125C

Three Diastereomers

Example N-125A to N-125C (TFA salt) were prepared in a similar fashion starting from (1S,1'S)-1,1'-(4,4'-(biphenyl-4,4'-diyl)bis(1H-imidazole-4,2-diyl))bis(2,2-dimethylpropan-1-amine), 4 HCl and Cap N-10 according to the procedure described for the preparation Example N-28. The three diastereomers were separated by prepHPLC (Water Sunfire 30×100 mm column, 20 min gradient from 0-52% B. A=H₂O/CH₃CN/TFA 90:10:0.1, B=CH₃CN/H₂O/TFA 90:10:0.1).

Example N-125A (stereoisomer-1): ¹H NMR (400 MHz, METHANOL-d₄) ppm 8.02-7.83 (m, 10H), 7.33 (dd, J=7.7, 1.6 Hz, 2H), 7.30-7.18 (m, 2H), 7.01-6.82 (m, 4H), 5.36 (s, 2H), 5.18-5.08 (m, 2H), 3.88-3.70 (m, 6H), 1.22-1.05 (m, 30H).

Example N-125B (stereoisomer-2): ¹H NMR (400 MHz, METHANOL-d₄) ppm 8.00-7.83 (m, 10H), 7.34 (dd, J=7.7, 1.6 Hz, 1H), 7.38 (dd, J=7.7, 1.6 Hz, 1H), 7.30-7.20 (m, 2H), 7.03-6.79 (m, 4H), 5.37 (d, J=3.5 Hz, 2H), 5.15 (s, 1H), 4.98 (s, 1H), 3.81 (s, 3H), 3.82 (s, 3H), 1.27-1.12 (m, 24H), 1.10-1.00 (m, 6H).

Example N-125C (stereoisomer-3): ¹H NMR (400 MHz, METHANOL-d₄) ppm 7.97-7.81 (m, 10H), 7.38 (dd, J=7.7, 1.6 Hz, 2H), 7.31-7.19 (m, 2H), 7.04-6.90 (m, 4H), 5.37 (s, 2H), 5.01-4.93 (m, 2H), 3.89-3.73 (m, 6H), 1.23 (s, 6H), 1.20-1.12 (m, 18H), 1.09-1.00 (m, 6H).

Example N-126

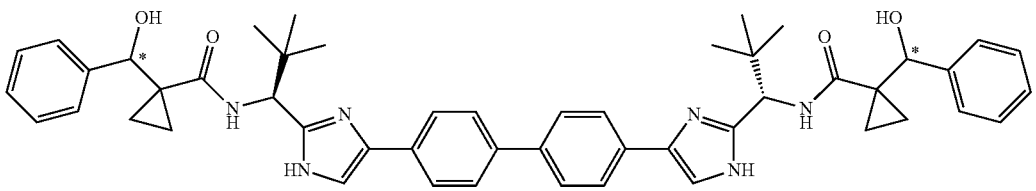 [SMILES: CC(C)(C)[C@H](NC(=O)C1(C(O)c2ccccc2)CC1)c1nc(-c2ccc(-c3ccc(-c4c[nH]c([C@@H](NC(=O)C5(C(O)c6ccccc6)CC5)C(C)(C)C)n4)cc3)cc2)c[nH]1]

N-126A to N-126C

Three Diastereomers

Example N-126A to N-126C (TFA salt) were prepared in a similar fashion starting from (1S,1'S)-1,1'-(4,4'-(biphenyl-4,4'-diyl)bis(1H-imidazole-4,2-diyl))bis(2,2-dimethylpropan-1-amine), 4 HCl and Cap N-11 according to the procedure described for the preparation Example N-28. The three diastereomers were separated by prepHPLC (Water Sunfire 30×100 mm column, 20 min gradient from 5-45% B. A=H₂O/CH₃CN/TFA 90:10:0.1, B=CH₃CN/H₂O/TFA 90:10:0.1).

Example N-126A (stereoisomer-1): LC/MS (Cond. N-1): [M+H]⁺ 805.6, RT=3.538 min. ¹H NMR (400 MHz, METHANOL-d₄) ppm 7.93-7.80 (m, 10H), 7.42 (d, J=7.3 Hz, 4H), 7.34-7.21 (m, 6H), 5.07-5.04 (m, 2H), 4.94 (s, 2H), 1.17-1.08 (m, 22H), 0.95-0.86 (m, 2H), 0.74-0.67 (m, 2H).

Example N-126B (stereoisomer-2): LC/MS (Cond. N-1): [M+H]⁺ 805.6, RT=3.604 min. ¹H NMR (400 MHz, METHANOL-d₄) ppm 7.95-7.79 (m, 10H), 7.58 (d, J=8.0 Hz, 2H), 7.46-7.34 (m, 4H), 7.34-7.20 (m, 4H), 5.06 (s, 1H), 4.97-4.92 (m, 1H), 4.76-4.71 (m, 1H), 4.59 (s, 1H), 1.58-1.48 (m, 1H), 1.14-1.05 (m, 11H), 1.00-0.82 (m, 13H), 0.75-0.65 (m, 1H).

Example N-126B (stereoisomer-3): LC/MS (Cond. N-1): [M+H]⁺ 805.6, RT=3.638 min. ¹H NMR (400 MHz, METHANOL-d₄) ppm 7.94-7.81 (m, 10H), 7.58 (d, J=7.8 Hz, 4H), 7.44-7.35 (m, 4H), 7.33-7.25 (m, 2H), 4.75-4.70 (m, 2H), 4.58 (s, 2H), 1.60-1.50 (m, 2H), 1.01-0.84 (m, 24H).

Example N-127

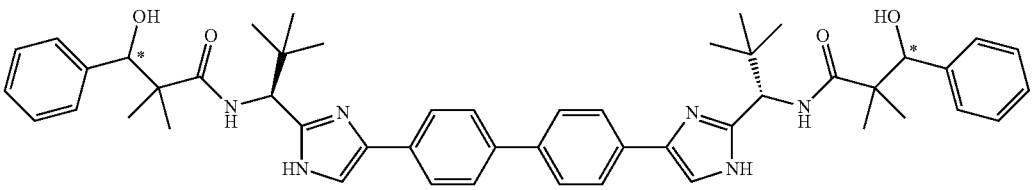 [SMILES: CC(C)(C(=O)N[C@H](c1nc(-c2ccc(-c3ccc(-c4c[nH]c([C@@H](NC(=O)C(C)(C)C(O)c5ccccc5)C(C)(C)C)n4)cc3)cc2)c[nH]1)C(C)(C)C)C(O)c1ccccc1]

N-127A to N-127C

Three Diastereomers

Example N-127A to N-127C (TFA salt) were prepared in a similar fashion starting from (1S,1'S)-1,1'-(4,4'-(biphenyl-4,4'-diyl)bis(1H-imidazole-4,2-diyl))bis(2,2-dimethylpropan-1-amine), 4 HCl and 3-hydroxy-2,2-dimethyl-3-phenylpropanoic acid according to the procedure described for the preparation Example N-28. The three diastereomers were separated by prepHPLC (Water Sunfire 30×100 mm column, 20 min gradient from 10-50% B. A=H₂O/CH₃CN/TFA 90:10:0.1, B=CH₃CN/H₂O/TFA 90:10:0.1).

Example N-127A (stereoisomer-1): LC/MS (Cond. N-1): [M+H]⁺ 809.7, RT=3.576 min. ¹H NMR (400 MHz, METHANOL-d₄) ppm 8.01-7.83 (m, 10H), 7.37-7.20 (m, 10H), 5.25-5.17 (m, 2H), 4.82 (s, 2H), 1.21 (s, 6H), 1.18-1.01 (m, 24H).

Example N-127B (stereoisomer-2): LC/MS (Cond. N-1): [M+H]⁺ 809.7, RT=3.365 min. ¹H NMR (400 MHz, METHANOL-d₄) ppm 7.98-7.81 (m, 10H), 7.40-7.15 (m, 10H), 5.22-5.16 (m, 1H), 5.00-4.92 (m, 1H), 4.79 (d, J=7.3 Hz, 2H), 1.29-1.01 (m, 30H).

Example N-127C (stereoisomer-3): LC/MS (Cond. N-1): [M+H]⁺ 809.7, RT=3.656 min. ¹H NMR (400 MHz, METHANOL-d₄) ppm 8.00-7.83 (m, 10H), 7.42-7.18 (m, 10H), 4.99 (t, J=2.5 Hz, 2H), 4.79 (s, 2H), 1.32-1.02 (m, 30H).

Example N-128

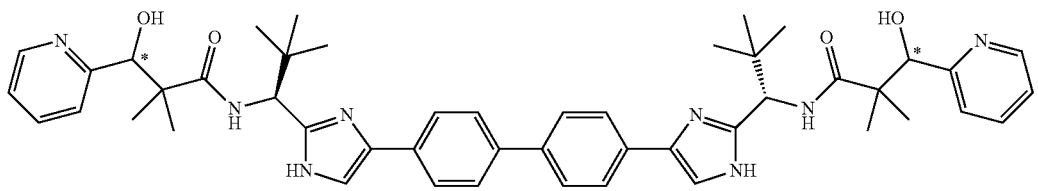 [SMILES: CC(C)(C(=O)N[C@H](c1nc(-c2ccc(-c3ccc(-c4c[nH]c([C@@H](NC(=O)C(C)(C)C(O)c5ccccn5)C(C)(C)C)n4)cc3)cc2)c[nH]1)C(C)(C)C)C(O)c1ccccn1]

N-128A and N-128B

Two Diastereomers

Example N-128A and N-128B were prepared in a similar fashion starting from (1S,1'S)-1,1'-(4,4'-(biphenyl-4,4'-diyl)bis(1H-imidazole-4,2-diyl))bis(2,2-dimethylpropan-1-amine), 4 HCl and Cap N-12A or N-12B according to the procedure described for the preparation Example N-28.

Example N-128A (stereoisomer-1): LC/MS (Cond. N-1): [M+H]$^+$ 811.53, RT=2.995 min. $^1$H NMR (400 MHz, METHANOL-d$_4$) ppm 8.39 (br. s., 2H), 7.84 (br. s., 4H), 7.72 (br. s., 6H), 7.54 (br. s., 2H), 7.47 (br. s., 2H), 7.39 (br. s., 2H), 7.18 (br. s., 2H), 5.08-4.99 (m, 3H), 4.79 (s, 2H), 1.31 (s, 7H), 1.12 (s, 7H), 1.06 (s, 20H).

Example N-128B (stereoisomer-2): LC/MS (Cond. N-1): [M+H]$^+$ 811.53, RT=2.975 min. $^1$H NMR (400 MHz, METHANOL-d$_4$) ppm 8.53-8.38 (m, 2H), 7.84-7.64 (m, 10H), 7.47-7.36 (m, 4H), 7.27 (ddd, J=7.5, 5.0, 1.0 Hz, 2H), 5.04 (s, 2H), 4.90 (br. s., 2H), 1.18 (d, J=3.5 Hz, 12H), 1.10-0.95 (m, 18H).

Example N-129

Diastereomer Mixture

Example N-129 was prepared in a similar fashion starting from (1S,1'S)-1,1'-(4,4'-(biphenyl-4,4'-diyl)bis(1H-imidazole-4,2-diyl))bis(2,2-dimethylpropan-1-amine), 4 HCl and Cap N-13 according to the procedure described for the preparation Example N-28. LC/MS (Cond. N-1): [M+H]$^+$ 818.3, RT=3.256 min.

Example N-130

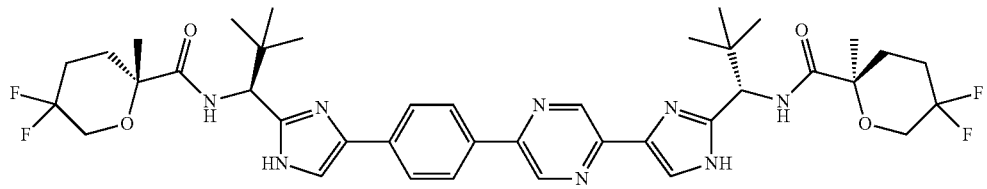

Example N-130 was prepared according to the procedure described for the preparation of Example N-104. LC/MS (Cond. N-1): [M+H]$^+$ 783.45, RT=3.591 min. $^1$H NMR (400 MHz, METHANOL-d$_4$) ppm 9.10 (br. s., 1H), 9.05 (br. s., 1H), 8.12 (d, J=8.5 Hz, 2H), 7.86 (br. s., 2H), 7.76 (s, 1H), 7.47 (s, 1H), 5.16-5.00 (m, 2H), 3.86 (td, J=12.7, 6.5 Hz, 2H), 3.80-3.59 (m, 2H), 2.32-2.17 (m, 2H), 2.17-2.02 (m, 2H), 1.98-1.74 (m, 4H), 1.58-1.47 (m, 6H), 1.04-0.92 (m, 18H).

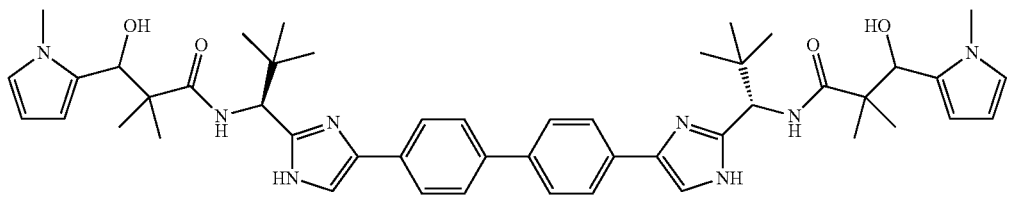 [SMILES: Cn1cccc1C(O)C(C)(C)C(=O)N[C@H](c1nc(-c2ccc(-c3ccc(-c4c[nH]c([C@@H](NC(=O)C(C)(C)C(O)c5cccn5C)C(C)(C)C)n4)cc3)cc2)c[nH]1)C(C)(C)C]

Example N-131

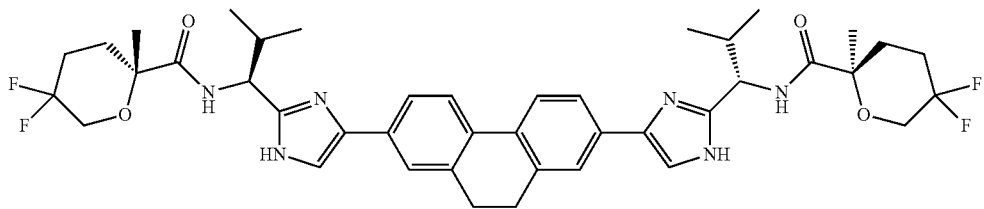 [SMILES: CC(C)[C@H](NC(=O)[C@@]1(C)CCC(F)(F)CO1)c1nc(-c2ccc3c(c2)CCc2cc(-c4c[nH]c([C@@H](NC(=O)[C@@]5(C)CCC(F)(F)CO5)C(C)C)n4)ccc2-3)c[nH]1]

Example N-131 was prepared according to the procedure described for the preparation of Example N-74. LC/MS (Cond. N-1): [M+H]+ 779.4, RT=3.563 min. $^1$H NMR (400 MHz, METHANOL-$d_4$) ppm 8.01 (d, J=8.0 Hz, 2H), 7.95-7.87 (m, 2H), 7.76-7.63 (m, 4H), 4.99-4.94 (m, 2H), 3.97-3.81 (m, 2H), 3.70 (td, J=13.9, 7.0 Hz, 2H), 3.01 (s, 4H), 2.41 (dquin, J=9.8, 6.6 Hz, 2H), 2.24-2.06 (m, 4H), 2.02-1.76 (m, 4H), 1.50 (s, 6H), 1.21-1.08 (m, 6H), 0.98-0.86 (m, 6H).

Example N-132

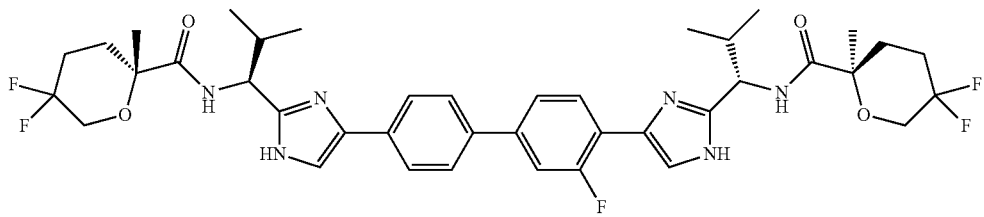 [SMILES: CC(C)[C@H](NC(=O)[C@@]1(C)CCC(F)(F)CO1)c1nc(-c2ccc(-c3ccc(-c4c[nH]c([C@@H](NC(=O)[C@@]5(C)CCC(F)(F)CO5)C(C)C)n4)c(F)c3)cc2)c[nH]1]

Example N-132 was prepared according to the procedure described for the preparation of Example N-77. LC/MS (Cond. N-1): [M+H]+ 771.4, RT=3.508 min. $^1$H NMR (400 MHz, METHANOL-$d_4$) δ ppm 7.97 (t, J=8.2 Hz, 1H), 7.84-7.76 (m, J=8.5 Hz, 2H), 7.75-7.65 (m, J=8.5 Hz, 2H), 7.60-7.39 (m, 4H), 4.90-4.81 (m, 2H), 3.93-3.79 (m, 2H), 3.78-3.60 (m, 2H), 2.34-2.19 (m, 4H), 2.16-2.01 (m, 2H), 1.91-1.71 (m, 4H), 1.55-1.46 (m, 6H), 1.04 (d, J=6.5 Hz, 6H), 0.93-0.80 (m, 6H).

Example N-133

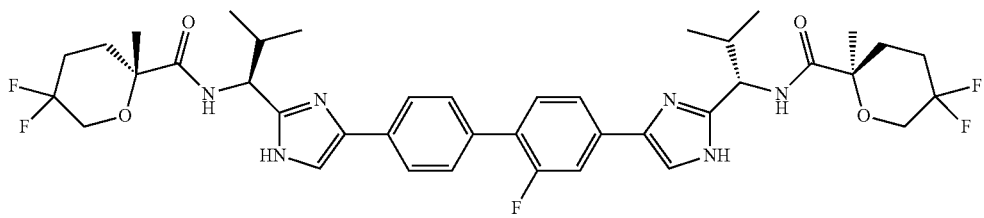 [SMILES: CC(C)[C@H](NC(=O)[C@@]1(C)CCC(F)(F)CO1)c1nc(-c2ccc(-c3ccc(-c4c[nH]c([C@@H](NC(=O)[C@@]5(C)CCC(F)(F)CO5)C(C)C)n4)cc3F)cc2)c[nH]1]

Example N-133 was prepared according to the procedure described for the preparation of Example N-77. LC/MS (Cond. N-1): [M+H]+ 771.4, RT=3.493. $^1$H NMR (400 MHz, METHANOL-$d_4$) δ ppm 8.01-7.91 (m, 2H), 7.91-7.83 (m, 2H), 7.82-7.76 (m, 2H), 7.76-7.64 (m, 3H), 5.01-4.93 (m, 2H), 3.95-3.79 (m, 2H), 3.77-3.61 (m, 2H), 2.49-2.35 (m, 2H), 2.25-2.05 (m, 4H), 2.02-1.77 (m, 4H), 1.57-1.39 (m, 6H), 1.22-1.07 (m, 6H), 1.01-0.83 (m, 6H).

Example N-134

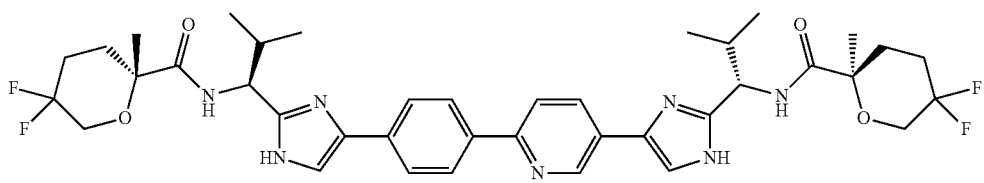 [SMILES: CC(C)[C@H](NC(=O)[C@@]1(C)CCC(F)(F)CO1)c1nc(-c2ccc(-c3ccc(-c4c[nH]c([C@@H](NC(=O)[C@@]5(C)CCC(F)(F)CO5)C(C)C)n4)cn3)cc2)c[nH]1]

Example N-134 was prepared according to the procedure described for the preparation of Example N-101. LC/MS (Cond. N-1): [M+H]+ 754.4, RT=3.384 min. ¹H NMR (400 MHz, METHANOL-d₄) ppm 9.07 (dd, J=2.4, 0.6 Hz, 1H), 8.34-8.24 (m, 3H), 8.17-8.11 (m, 1H), 8.05-7.98 (m, 2H), 7.94-7.89 (m, 2H), 5.00-4.94 (m, 2H), 3.96-3.81 (m, 2H), 3.80-3.64 (m, 2H), 2.49-2.34 (m, 2H), 2.26-2.07 (m, 4H), 2.04-1.78 (m, 4H), 1.50 (s, 6H), 1.21-1.11 (m, 6H), 0.99-0.87 (m, 6H).

The following examples (bis-TFA) were prepared from (1S,1'S)-1,1'-(4,4'-([1,1'-biphenyl]-4,4'-diyl)bis(1H-imidazole-4,2-diyl))bis(2,2-dimethylpropan-1-amine), 4 HCl and appropriate starting materials, by employing the procedures described for the synthesis of Example L-3.

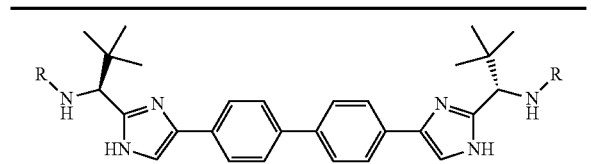

| Example | R | LC-MS Method | Retention Time (min) | Obs. Mass ion (M + H)+ |
|---|---|---|---|---|
| N-118 | 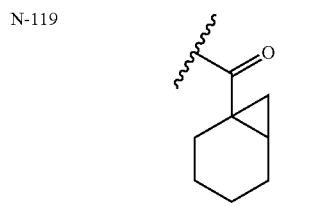 | N-1 | 3.711 | 701.72 |
| N-119 | | N-1 | 3.8 | 701.7 |
| | (diastereomeric mixture) | | | |
| N-120 | | N-1 | 3.47 | 721.5 |
| N-121 | | N-1 | 3.83 | 773.53 |
| N-122 | | N-1 | 3.71 | 801.62 |
| | (diastereomeric mixture) | | | |
| N-123 | | N-1 | 3.84 | 729.69 |
| P-139 | | P-3 | 3.288 | 836.43 |
| P-141 | | P-3 | 3.7 | 889.47 |
| P-146 | | P-3 | 3.55 | 861.53 |
| P-148 | | P-3 | 3.32 | 887.49 |

| Example | R | LC-MS Method | Retention Time (min) | Obs. Mass ion (M + H)+ |
|---|---|---|---|---|
| P-149* | (4,4-difluoro-1-hydroxycyclohexyl dimethyl ketone group) | P-3 | 3.58 | 865.54 |
| P-150* | (4,4-difluorocyclohexyl dimethyl ketone group) | P-3 | 3.8 | 833.49 |
| P-152 | (difluoro bicyclic methyl ketone group) | P-3 | 3.691 | 829.32 |
| P-153 | (tetrahydropyran-2-yl dimethyl ketone group, diastereomeric mixture) | P-3 | 3.645 | 765.46 |
| P-154* | (2-methyl-5,5-dimethyl-1,3-dioxane ketone group) | P-3 | 3.351 | 769.37 |
| P-155* | (4,4-difluorotetrahydropyranyl dimethyl ketone group, diastereomeric mixture) | P-3 | 3.551 | 837.44 |
| Y-62 | (norbornene ketone group) | YT-1 | 2.7 | 725.65 |
| Y-65 | (pyrazolyl cyclopropyl ketone group) | YT-1 | 2.26 | 729.4 |
| Y-67A* | (4,4-difluoro-2-methyltetrahydropyran ketone, single symmetrical diastereomer 1) | YT-1 | 2.45 | 781.4 |
| Y-67B* | (4,4-difluoro-2-methyltetrahydropyran ketone, single symmetrical diastereomer 2) | YT-1 | 2.68 | 781.4 |
| Y-70 | (spiro cyclopropyl-difluorocyclohexyl ketone, diastereomeric mixture) | YT-1 | 2.718 | 801.45 |

*¹H NMR:

Example P-149: ¹H NMR (500 MHz, METHANOL-d₄) δ 7.93 (s, 2 H), 7.92-7.84 (m, 8 H), 4.96-4.92 (m, 2 H), 2.27-2.08 (m, 4 H), 2.00-1.88 (m, 4 H), 1.87-1.73 (m, 6 H), 1.64 (d, J = 12.4 Hz, 2 H), 1.33-1.27 (m, 6 H), 1.18 (s, 6 H), 1.15 (s, 18 H).

Example P-150: ¹H NMR (500 MHz, METHANOL-d₄) δ 7.95 (s, 2 H), 7.92-7.87 (m, 8 H), 5.19 (t, J = 3.8 Hz, 2 H), 2.06 (d, J = 3.7 Hz, 4 H), 1.91-1.81 (m, 2 H), 1.81-1.67 (m, 4 H), 1.62 (t, J = 14.0 Hz, 4 H), 1.37 (t, J = 12.9 Hz, 4 H), 1.24 (s, 6 H), 1.22-1.19 (m, 6 H), 1.13 (s, 18 H).

Example P-154: ¹H NMR (500 MHz, METHANOL-d₄) δ 7.98 (s, 2 H), 7.93-7.86 (m, 8 H), 5.33 (s, 2 H), 3.67-3.60 (m, 2 H), 3.58-3.50 (m, 4 H), 3.42 (d, J = 11.3 Hz, 2 H), 1.51 (s, 6 H), 1.17 (s, 6 H), 1.15-1.08 (m, 18 H), 0.79 (s, 6 H).

Example P-155: ¹H NMR (500 MHz, METHANOL-d₄) δ 7.96 (s, 2 H), 7.93-7.83 (m, 8 H), 5.19 (d, J = 7.3 Hz, 2 H), 5.12 (d, J = 6.9 Hz, 1 H), 4.14-4.03 (m, 1 H), 4.03-3.92 (m, 1 H), 3.78-3.54 (m, 4 H), 2.33-2.16 (m, 2 H), 2.16-1.85 (m, 4 H), 1.80-1.59 (m, 2 H), 1.33 (s, 3 H), 1.25 (d, J = 6.9 Hz, 6 H), 1.19-1.09 (m, 21 H).

Example Y-67A: ¹H NMR (400 MHz, METHANOL-d₄) δ 8.01-7.75 (m, 10 H), 5.19 (s, 2 H), 4.04-3.81 (m, 4 H), 2.27-2.13 (m, 4 H), 2.10-1.87 (m, 4 H), 1.46 (s, 6 H), 1.11 (s, 18 H).

Example Y-67B: ¹H NMR (400 MHz, METHANOL-d₄) δ 7.98 (s, 2 H), 7.94-7.85 (m, 8 H), 5.30-5.21 (m, 2 H), 4.02-3.90 (m, 2 H), 3.89-3.78 (m, 2 H), 2.28-1.98 (m, 6 H), 1.97-1.85 (m, 2 H), 1.56 (s, 6 H), 1.11 (s, 18 H).

The following examples were prepared from (1S,1'S)-1,1'-(4,4'-([1,1'-biphenyl]-4,4'-diyl)bis(1H-imidazole-4,2-diyl)) bis(2,2-dimethylpropan-1-amine), 4 HCl and appropriate starting materials, by employing the standard amide coupling procedure.

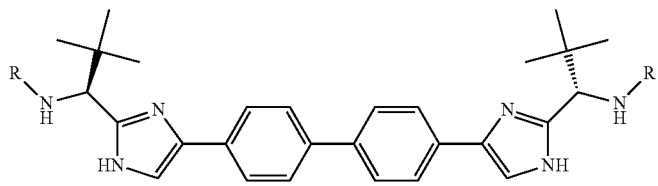
| Example | R | LCMS Method | Retention time (min) | Obs. MS Ion (M + H)+ |
|---|---|---|---|---|
| Y-71 | ![structure with cyclohexyl-CHF2] | YT-1 | 2.92 | 777.55 |
| Y-72 | ![2-hydroxyphenyl ketone] | YT-1 | 2.77 | 697.4 |
| Y-73 | ![2-(trifluoromethoxy)phenyl acetyl] | YT-1 | 2.88 | 861.56 |
| Y-74 | ![2-oxabicyclic] | YT-1 | 2.82 | 733.5 |
| Y-75 | ![methyl-difluoro-tetrahydropyran] | YT-1 | 2.789 | 781.45 |
| Y-76 | ![fluoro-methylenecyclohexyl] | YT-3 | 2.13 | 737.45 |
| Y-77 | ![methyl-difluoro-tetrahydrofuran] | YT-1 | 2.72 | 753.45 |

-continued
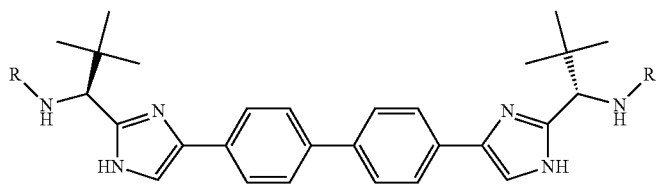
| Example | R | LCMS Method | Retention time (min) | Obs. MS Ion $(M + H)^+$ |
|---|---|---|---|---|
| S-254 | 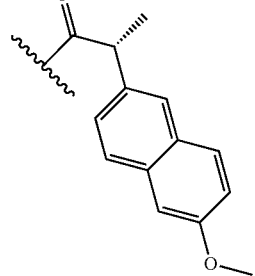 | CA-2 | 4.8408 | 881.79 |
| S-255 | 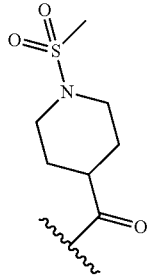 [SMILES: *C(=O)C1CCN(S(C)(=O)=O)CC1] | PS-2 | 2.6892 | 835.75 |
| S-256 | 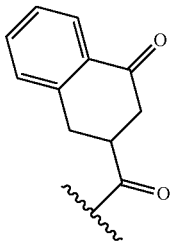 [SMILES: *C(=O)C1CC(=O)c2ccccc2C1] | PS-2 | 3.1417 | 801.74 |
| S-257 | 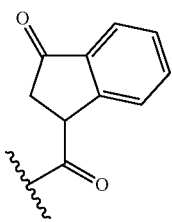 [SMILES: *C(=O)C1CC(=O)c2ccccc21] | PS-3 | 4.3325 | 773.72 |
| S-258 | 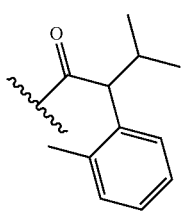 [SMILES: *C(=O)C(c1ccccc1C)C(C)C] | PS-2 | 3.98 | 805.82 |

-continued
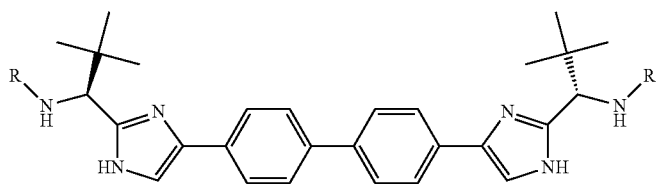
| Example | R | LCMS Method | Retention time (min) | Obs. MS Ion (M + H)+ |
|---|---|---|---|---|
| S-260 | | PS-3 | 4.9975 | 881.96 |
| S-261 | | PS-3 | 4.8708 | 701.67 |
| S-263 | | PS-3 | 4.4317 | 893.86 |
| S-264 | | PS-2 | 3.4092 | 879.87 |
| S-265 | | PS-3 | 4.2167 | 863.74 |

-continued
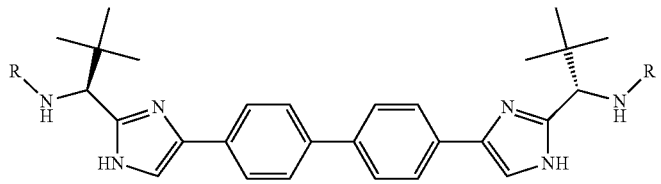
| Example | R | LCMS Method | Retention time (min) | Obs. MS Ion (M + H)+ |
|---|---|---|---|---|
| S-266 | 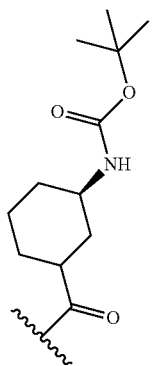 [SMILES: *C(=O)C1CCC[C@@H](NC(=O)OC(C)(C)C)C1] | PS-3 | 4.66 | 907.78 |
| S-267 | 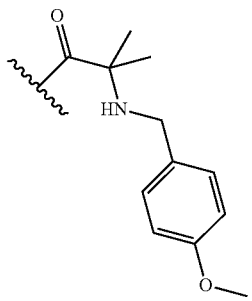 [SMILES: *C(=O)C(C)(C)NCc1ccc(OC)cc1] | PS-3 | 4.7242 | 867.90 |
| S-268 | 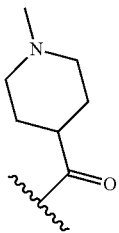 [SMILES: *C(=O)C1CCN(C)CC1] | PS-3 | 3.88 | 707.65 |
| S-269 | 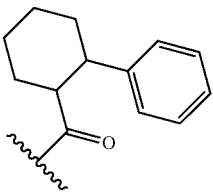 [SMILES: *C(=O)C1CCCCC1c1ccccc1] | PS-3 | 5.0058 | 829.90 |

-continued
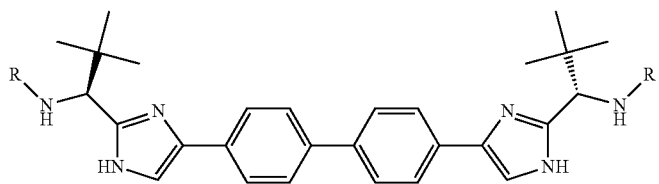
| Example | R | LCMS Method | Retention time (min) | Obs. MS Ion (M + H)+ |
|---|---|---|---|---|
| S-270 | 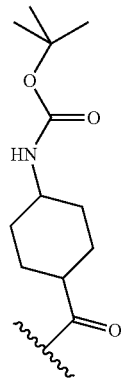 [SMILES: *C(=O)C1CCC(NC(=O)OC(C)(C)C)CC1] | PS-3 | 4.7108 | 907.96 |
| S-271 | 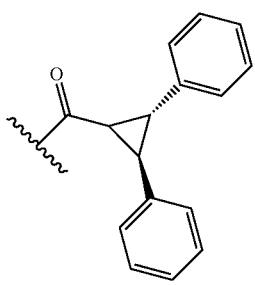 [SMILES: *C(=O)C1[C@H](c2ccccc2)[C@H]1c1ccccc1] | PS-3 | 4.9242 | 895.74 |
| S-272 | 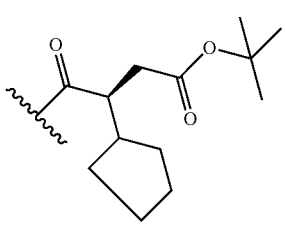 [SMILES: *C(=O)[C@@H](CC(=O)OC(C)(C)C)C1CCCC1] | PS-2 | 3.58 | 906.15 |
| S-273 | 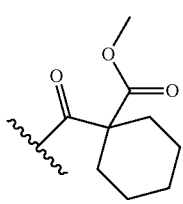 [SMILES: *C(=O)C1(C(=O)OC)CCCCC1] | PS-2 | 3.6275 | 793.83 |
| S-274 | 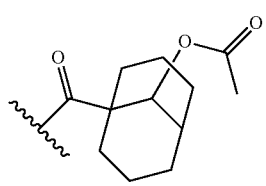 [SMILES: *C(=O)C12CCCC(CCC1)C2OC(C)=O] | PS-2 | 3.7392 | 873.40 |

-continued
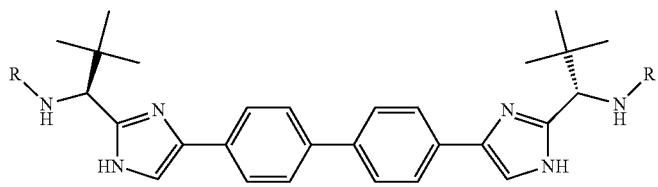
| Example | R | LCMS Method | Retention time (min) | Obs. MS Ion (M + H)+ |
|---|---|---|---|---|
| S-275 | 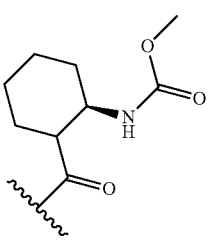 [SMILES: *C(=O)C1CCCC[C@H]1NC(=O)OC] | PS-2 | 2.8483 | 823.89 |
| S-276 | 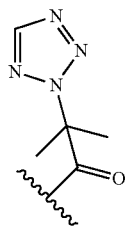 [SMILES: *C(=O)C(C)(C)n1ncnn1] | PS-2 | 3.0083 | 733.70 |
| S-277 | 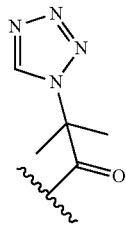 [SMILES: *C(=O)C(C)(C)n1cnnn1] | PS-2 | 2.7717 | 733.70 |
| S-278 | 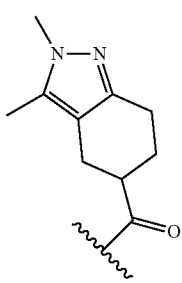 [SMILES: *C(=O)C1CCc2nn(C)c(C)c2C1] | PS-3 | 4.33 | 809.84 |
| S-279 | 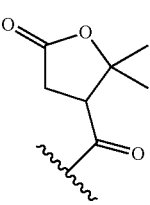 [SMILES: *C(=O)C1CC(=O)OC1(C)C] | PS-2 | 2.5642 | 737.66 |

-continued
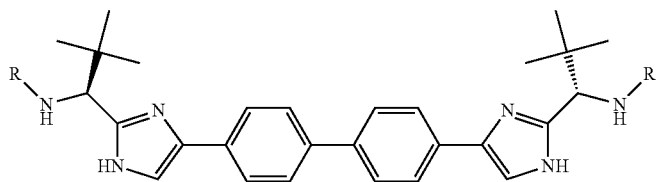
| Example | R | LCMS Method | Retention time (min) | Obs. MS Ion (M + H)+ |
|---|---|---|---|---|
| S-280 | | PS-2 | 3.6075 | 865.88 |
| S-281 | | PS-3 | 4.8808 | 681.9 |
| S-282 | | PS-2 | 3.5392 | 765.9 |
| S-283 | | PS-2 | 2.7842 | 827.85 |
| S-284 | | PS-2 | 3.3283 | 669.77 |
| S-285 | | PS-3 | 4.9458 | 837.99 |

-continued
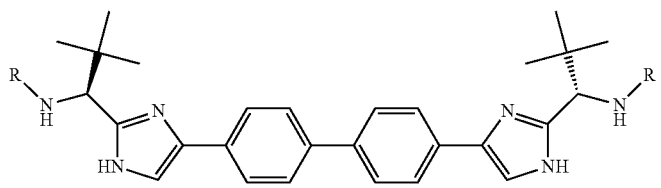
| Example | R | LCMS Method | Retention time (min) | Obs. MS Ion $(M + H)^+$ |
|---|---|---|---|---|
| S-286 | 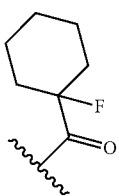 [SMILES: *C(=O)C1(F)CCCCC1] | PS-2 | 3.6767 | 713.83 |
| S-287 | 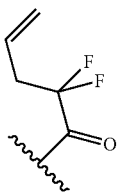 [SMILES: *C(=O)C(F)(F)CC=C] | PS-2 | 3.3975 | 693.77 |
| S-288 | 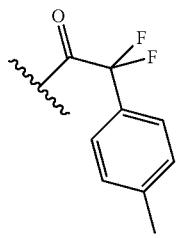 [SMILES: *C(=O)C(F)(F)c1ccc(C)cc1] | PS-2 | 3.7358 | 793.81 |
| S-289 | 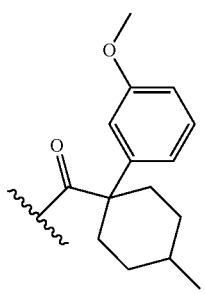 [SMILES: *C(=O)C1(c2cccc(OC)c2)CCC(C)CC1] | PS-2 | 4.2 | 918.19 |
| S-290 | 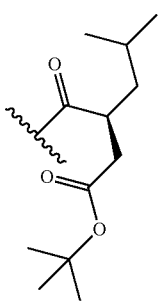 [SMILES: *C(=O)[C@H](CC(=O)OC(C)(C)C)CC(C)C] | PS-3 | 4.9758 | 881.17 |

-continued
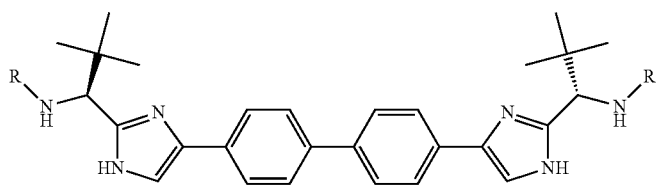
| Example | R | LCMS Method | Retention time (min) | Obs. MS Ion (M + H)+ |
|---|---|---|---|---|
| S-291 | | PS-2 | 3.12 | 881.77 |
| S-292 | | PS-2 | 3.4933 | 826.09 |
| S-293 | | PS-2 | 3.1925 | 789.99 |
| S-294 | | PS-2 | 3.7742 | 902.11 |
| S-295 | | PS-2 | 3.3692 | 846.07 |

-continued
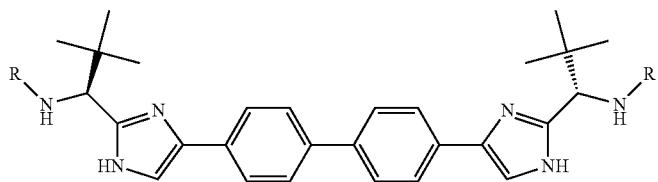
| Example | R | LCMS Method | Retention time (min) | Obs. MS Ion (M + H)+ |
|---|---|---|---|---|
| S-296 | | PS-2 | 3.5025 | 879.09 |
| S-297 | | PS-2 | 2.5508 | 763.96 |
| S-298 | | PS-3 | 4.9058 | 725.82 |
| S-299 | | PS-2 | 3.73 | 842.9 |
| S-301 | | PS-2 | 4.1092 | 833.97 |
| S-302 | | PS-2 | 3.7225 | 709.94 |
| S-303 | | PS-3 | 4.785 | 857.87 |
| S-304 | | PS-2 | 3.4692 | 795.99 |
| S-305 | | PS-2 | 2.9325 | 820.08 |
| P-156 | | P-3 | 3.56 | 897.56 |
diastereomer mix.

-continued
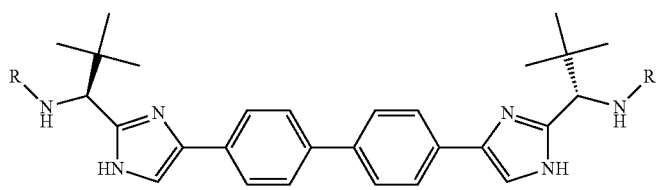
| Example | R | LCMS Method | Retention time (min) | Obs. MS Ion (M + H)+ |
|---|---|---|---|---|
| P-157 | | P-3 | 3.71 | 917.54 |
| P-158 | | P-3 | 3.19 | 797.43 |
| P-159 | | P-3 | 3.626 | 809.47 |
| P-160 | | P-3 | 3.688 | 793.57 |
| P-161 | diastereomer mix. | P-3 | 3.17 | 717.33 |
| P-162 | diastereomer mix. | P-3 | 3.286 | 781.45 |
| P-163 | | P-3 | 3.196 | 813.55 |

-continued
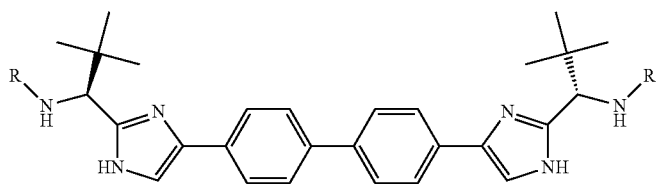
| Example | R | LCMS Method | Retention time (min) | Obs. MS Ion $(M + H)^+$ |
| --- | --- | --- | --- | --- |
| P-164 | | P-3 | 3.475 | 781.4 |
| P-165 | | P-3 | 3.405 | 753.36 |
| P-166 | diastereomer mix. | P-3 | 3.575 | 781.36 |
| P-167 | | P-3 | 3.871 | 837.74 |
| P-168 | diastereomer mix. | P-3 | 4.218 | 825.5 |
| P-169 | | P-3 | 3.361 | 733.63 |
| P-170 | | P-3 | 3.416 | 817.69 |

-continued

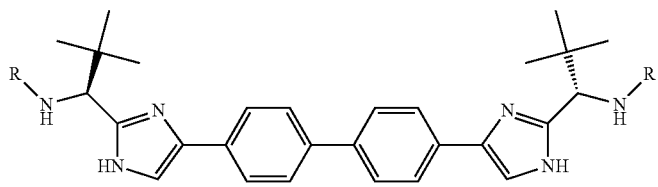

| Example | R | LCMS Method | Retention time (min) | Obs. MS Ion $(M + H)^+$ |
|---|---|---|---|---|
| P-171 | (2-hydroxycyclopentyl carbonyl) | P-3 | 3.141 | 681.56 |
| P-172 | (difluoro(phenylthio)acetyl) | P-3 | 3.711 | 829.49 |
| P-173 | (tetrahydrothiopyran-2-ylcarbonyl) diastereomer mix. | P-3 | 3.463 | 713.49 |
| P-174 | (2-(cyclohexylamino)-2-methylpropanoyl) | P-3 | 3.216 | 791.73 |
| P-175 | (2-(tert-butylamino)-2-methylpropanoyl) | P-3 | 2.988 | 739.63 |
| P-176 | (2-methyltetrahydropyran-2-ylcarbonyl) | P-3 | 3.433 | 709.54 |
| P-177 | (2-(hydroxymethyl)tetrahydropyran-2-ylcarbonyl) diastereomer mix. | P-3 | 3.206 | 741.48 |
| P-178 | (2-(fluoromethyl)tetrahydropyran-2-ylcarbonyl) diastereomer mix. | P-3 | 3.306 | 745.5 |

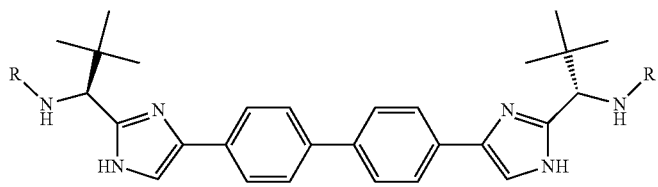

| Example | R | LCMS Method | Retention time (min) | Obs. MS Ion (M + H)+ |
|---|---|---|---|---|
| P-179 | (F, F, O, tetrahydropyran, C=O) diastereomer mix. | P-3 | 3.386 | 781.53 |
| P-180 | (HO, tetrahydropyran, C=O) symmetrical homodimer | P-3 | 3.01 | 741.48 |
| P-181 | (HO, tetrahydropyran, C=O) unsymmetrical heterodimer | P-3 | 3.116 | 741.48 |
| P-182 | (HO, tetrahydropyran, C=O) symmetrical homodimer | P-3 | 3.248 | 741.48 |
| P-183 | (MeO, tetrahydropyran, C=O) diastereomer mix. | P-3 | 3.26 | 769.51 |

The following examples (bis-TFA) were prepared from (1S,1'S)-(4,4'-([1,1'-biphenyl]-4,4'-diyl)bis(1H-imidazole-4,2-diyl))bis((1-methylcyclopropyl)methanamine), 4 HCl and appropriate starting materials, by employing the procedures described for the synthesis of Example L-3.

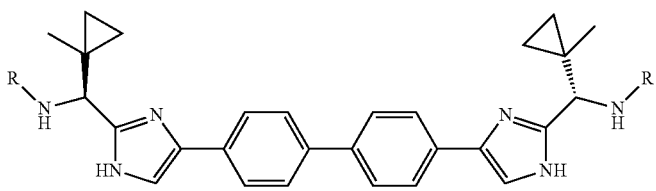
| Example | R | LC-MS Method | Retention Time (min) | Obs. Mass ion (M + H)+ |
|---|---|---|---|---|
| P-140 | | P-3 | 3.41 | 797.5 |
| P-142* | | P-3 | 3.445 | 809.48 |
| P-143 | | P-3 | 3.17 | 657.3 |
| P-144 | | P-3 | 3.568 | 861.46 |
| P-145* | | P-3 | 3.29 | 805.3 |
| P-147 | | P-3 | 3.46 | 857.37 |
| P-151* | | P-3 | 3.3 | 777.42 |
| P-152 | | P-3 | 3.596 | 825.24 |
| Y-63 | | YT-1 | 2.15 | 653.4 |

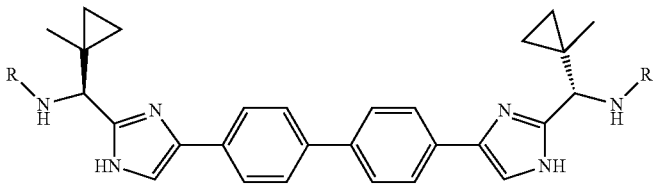

| Example | R | LC-MS Method | Retention Time (min) | Obs. Mass ion (M + H)+ |
|---|---|---|---|---|
| Y-64 | HF₂C-O-C(CH₃)₂-C(=O)- | YT-1 | 2.3 | 753.4 |
| Y-66 | pyrazol-1-yl-cyclopropyl-C(=O)- | YT-1 | 2.19 | 725.54 |

*¹H NMR:
Example P-142: ¹H NMR (500 MHz, METHANOL-d₄) δ 7.92 (s, 2 H), 7.91-7.84 (m, 8 H), 4.99-4.94 (m, 2 H), 4.65-4.58 (m, 2 H), 4.52 (s, 2 H), 2.31 (dd, J = 12.9, 4.8 Hz, 4 H), 2.09-1.85 (m, 8 H), 1.79-1.63 (m, 4 H), 1.25-1.17 (m, 6 H), 0.85 (dt, J = 9.9, 5.1 Hz, 2 H), 0.75-0.52 (m, 6 H).
Example P-145: ¹H NMR (500 MHz, METHANOL-d₄) δ 7.95-7.92 (m, 2 H), 7.91-7.84 (m, 8 H), 4.78 (t, J = 2.8 Hz, 2 H), 3.78 (d, J = 11.3 Hz, 2 H), 3.70 (d, J = 11.3 Hz, 2 H), 2.32-2.19 (m, 4 H), 2.08-1.86 (m, 8 H), 1.70 (ddd, J = 14.3, 10.8, 4.0 Hz, 2 H), 1.64-1.54 (m, 2 H), 1.24-1.16 (m, 6 H), 0.97-0.87 (m, 2 H), 0.79-0.72 (m, 2 H), 0.69-0.56 (m, 4 H).
Example P-151: ¹H NMR (500 MHz, METHANOL-d₄) δ 7.96-7.92 (m, 2 H), 7.91-7.83 (m, 8 H), 4.83-4.78 (m, 2 H), 2.21-1.97 (m, 12 H), 1.88-1.76 (m, 4 H), 1.26-1.14 (m, 6 H), 0.88 (dt, J = 9.8, 4.9 Hz, 2 H), 0.74 (dt, J = 10.0, 5.0 Hz, 2 H), 0.69-0.57 (m, 4 H).

The following examples (bis-TFA) were prepared from (1S,1'S)-(4,4'-([1,1'-biphenyl]-4,4'-diyl)bis(1H-imidazole-4,2-diyl))bis((1-methylcyclopropyl)methanamine), 4 HCl and appropriate starting materials, by employing the standard amide coupling procedure.

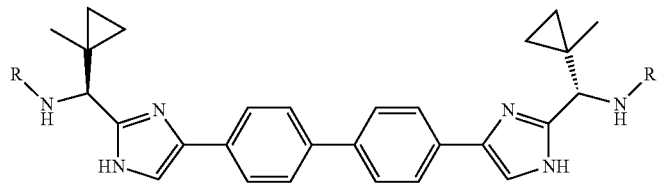

| Example | R | LCMS Method | Retention time (min) | Obs. MS Ion (M + H)⁺ |
|---|---|---|---|---|
| Y-81 | 2-methyl-5,5-difluoro-tetrahydropyran-2-carbonyl | YT-1 | 2.703 | 777.45 |
| Y-82 | 2-methyl-4,4-difluoro-tetrahydropyran-2-carbonyl | YT-1 | 2.699 | 777.35 |

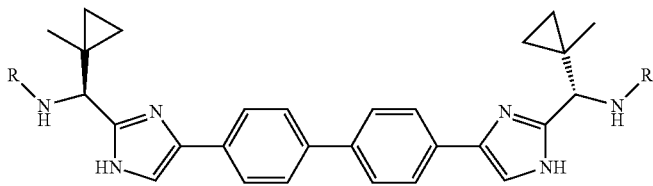
| Example | R | LCMS Method | Retention time (min) | Obs. MS Ion (M + H)+ |
|---|---|---|---|---|
| Y-83 | | YT-1 | 2.663 | 749.4 |
| P-187 | | P-3 | 3.321 | 705.51 |
The following examples (bis-TFA) were prepared from (1S,1'S)-1,1'-(4,4'-(biphenyl-4,4'-diyl)bis(1H-imidazole-4,2-diyl))bis(2-methylpropan-1-amine), 4HCl and appropriate starting materials, by employing the standard amide coupling procedure.
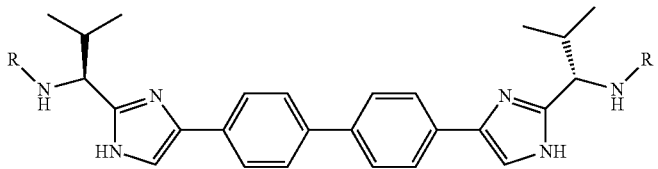
| Example | R | LCMS Method | Retention time (min) | Obs. MS Ion (M + H)+ |
|---|---|---|---|---|
| Y-78 | | YT-1 | 2.698 | 753.5 |
| Y-79 | | YT-1 | 2.721 | 753.4 |
| Y-80 | | YT-1 | 2.52 | 725.50 |

-continued
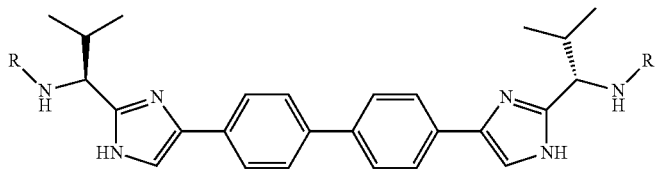
| Example | R | LCMS Method | Retention time (min) | Obs. MS Ion (M + H)+ |
|---|---|---|---|---|
| P-184 | | P-3 | 3.3 | 681.49 |
The following examples (bis-TFA) were prepared from 4,4'-bis(2-((S)-pyrrolidin-2-yl)-1H-imidazol-5-yl)-1,1'-biphenyl, 4 HCl and appropriate starting materials, by employing the standard amide coupling procedure.
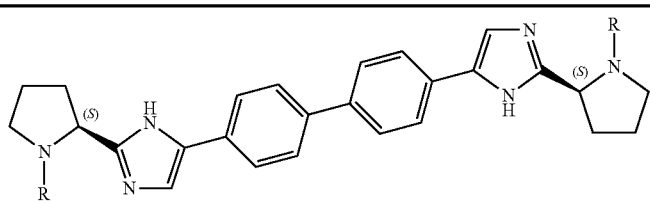
| Example | R | LCMS Method | Retention time (min) | Obs. MS Ion (M + H)+ |
|---|---|---|---|---|
| P-185 | | P-3 | 3.075 | 749.49 |
| P-186 | | P-3 | 3.035 | 749.48 |
Example Y-68
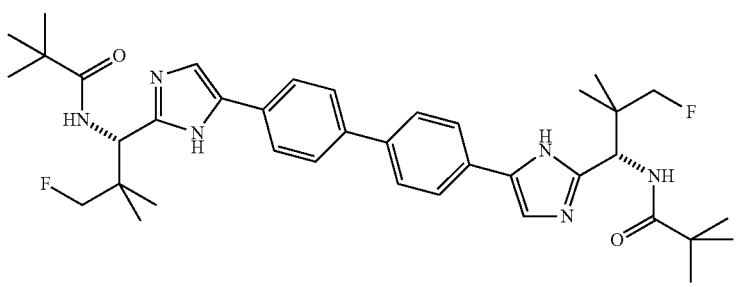

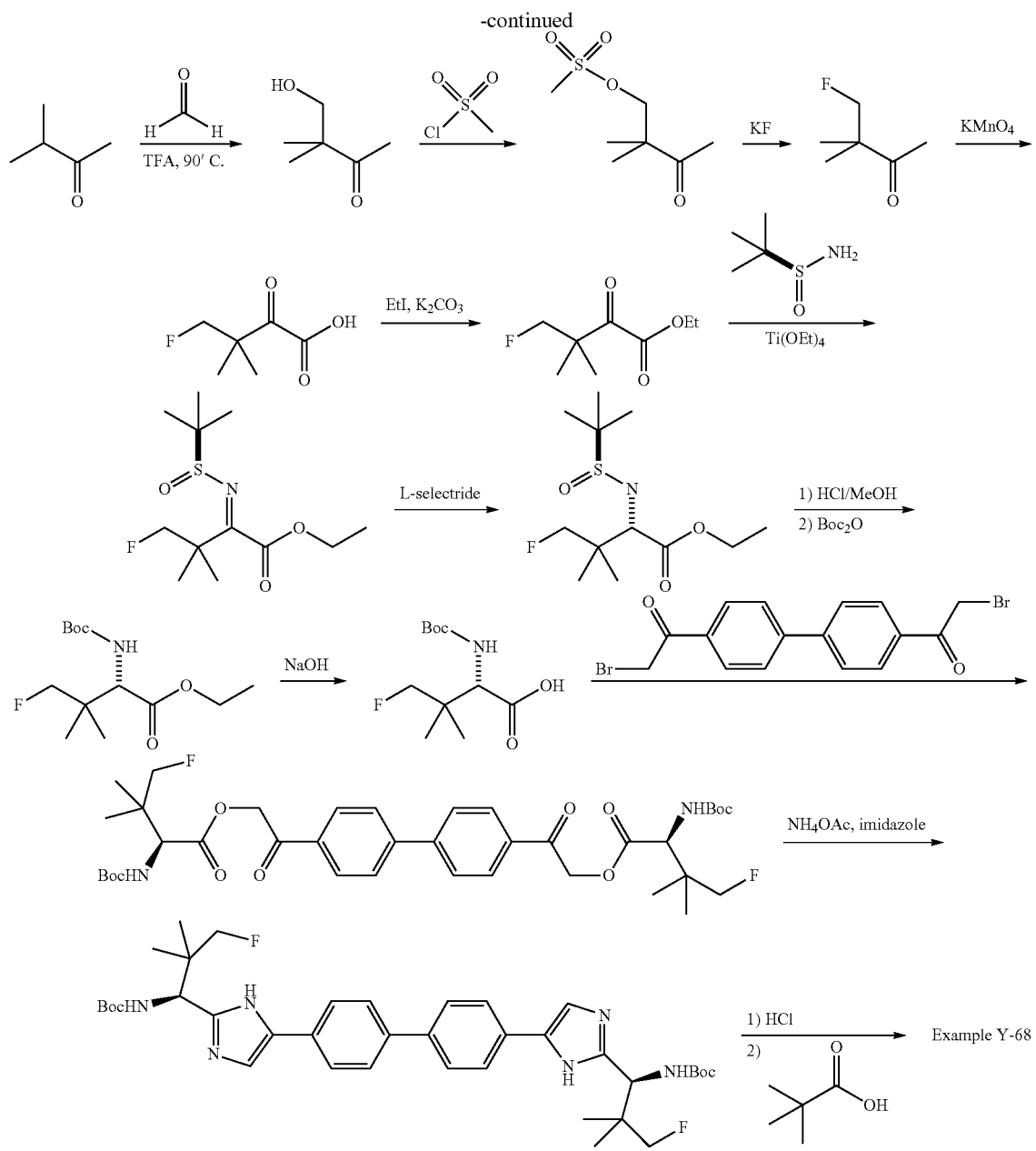

A reaction mixture of 3-methylbutan-2-one (20 g, 232 mmol), paraformaldehyde (6.97 g, 232 mmol) in TFA (20 mL) was heated in a sealed vial at 90° C. for 8 h. The reaction mixture was cooled down and the volatile solvent was removed. The residue was carefully poured into sat. NaHCO$_3$, and extracted with EtOAc. The organic phase was washed with water, sat. NaCl, dried (MgSO$_4$), filtered and concentrated to yield an oil. The crude product was dissolved in MeOH (60 mL) and cooled in an ice bath, then 1 N NaOH (180 mL) was added and the mixture was stirred in the ice bath for 1.5 h. MeOH was removed and the aqueous phase was extracted with DCM. The organic phase was washed with water, sat. NaCl, dried (MgSO$_4$), filtered and concentrated to yield 4-hydroxy-3,3-dimethylbutan-2-one (9.7 g). $^1$H NMR (400 MHz, CDCl$_3$) δ ppm 3.57 (2H, s), 2.18 (3H, s), 1.18 (6H, s).

To a solution of 4-hydroxy-3,3-dimethylbutan-2-one (9.7 g, 84 mmol) and DIPEA (16.04 mL, 92 mmol) in DCM (50 mL) cooled to 0° C. was dropwise added methanesulfonyl chloride (7.16 mL, 92 mmol). The reaction mixture was stirred at rt for 18 h. The reaction mixture was diluted with EtOAc and washed with sat. NaHCO$_3$, sat. NaCl, dried (MgSO$_4$), filtered and concentrated to yield 2,2-dimethyl-3-oxobutyl methanesulfonate (14.6 g). $^1$H NMR (400 MHz, CDCl$_3$) δ ppm 4.21 (2H, s), 3.04 (3H, s), 2.21 (3H, s), 1.25 (6H, s).

A suspension of KF (8.73 g, 150 mmol) in tetraethylene glycol (80 mL) was charged to a three neck flask equipped with distillation apparatus, under reduced pressure. The reaction mixture was heated to 160° C. and 2,2-dimethyl-3-oxobutyl methanesulfonate (14.6 g, 75 mmol) in tetraethylene glycol (80 mL) was added slowly over 80 min. The product 4-fluoro-3,3-dimethylbutan-2-one was collected as a solid (4.1 g). ¹H NMR (400 MHz, CDCl₃) δ ppm 4.47 (1H, s), 4.35 (1H, s), 2.21 (3H, d, J=0.50 Hz), 1.19 (6H, d, J=1.76 Hz).

To a vigorous stirring mixture of 4-fluoro-3,3-dimethylbutan-2-one (4.1 g, 34.7 mmol) in water (50 mL) and NaOH (7 mL, 70.0 mmol) cooled in an ice-acetone bath was added portionwise potassium permanganate (9.87 g, 62.5 mmol). The inner temperature was controlled between −3 to 2° C. during the addition process. Upon the completion of the addition, the reaction mixture was stirred in the ice-acetone bath for 6 hrs and then allowed to warm up. EtOH (5 mL) was added and the reaction mixture was stirred for another 15 min. The reaction mixture was filtered and the solid was washed with water (~80 mL). The filtration was acidified with 6 N HCl, and extracted with EtOAc. The combined extracts were washed with 1N HCl, sat. NaCl, dried (Na₂SO₄), filtered and concentrated to yield 4-fluoro-3,3-dimethyl-2-oxobutanoic acid (2.3 g).

To a solution of 4-fluoro-3,3-dimethyl-2-oxobutanoic acid (2.3 g, 15.53 mmol) in DMF (30 mL) was added iodoethane (1.880 mL, 23.29 mmol) and K₂CO₃ (5.36 g, 38.8 mmol). The reaction mixture was stirred at rt for 18 h. The reaction mixture was diluted with EtOAc and stirred for 10 min. The solid was filtered. The filtration was partitioned between EtOAc and water. The organic phase was washed water, sat. NaCl, and concentrated. The residue was diluted with hexane (~100 mL) and washed with water (2×30 mL), dried over MgSO₄, filtered and concentrated to yield ethyl 4-fluoro-3,3-dimethyl-2-oxobutanoate (2.3 g).

To a solution of ethyl 4-fluoro-3,3-dimethyl-2-oxobutanoate (2.3 g, 13.05 mmol) in THF (20 mL) was added (S)-2-methylpropane-2-sulfinamide (1.899 g, 15.67 mmol) and tetraethoxytitanium (5.91 mL, 26.1 mmol). The reaction mixture was heated at 65° C. for 6 h. The reaction mixture was cooled down, diluted with EtOAc and sat. NaCl (40 mL) and stirred at rt for 0.5 h. The solid was filtered and washed with water and EtOAc. The filtrate was separated and the organic layer was washed with water, sat. NaCl, dried (MgSO₄) and purified by flash chromatography (EtOAc/hexane) to afford (S)-ethyl 2-(tert-butylsulfinylimino)-4-fluoro-3,3-dimethylbutanoate (1.1 g). ¹H NMR (400 MHz, CDCl₃) δ ppm 4.46-4.53 (1H, m), 4.28-4.42 (3H, m), 1.59 (3H, s), 1.21-1.31 (15H, m).

To a solution of (S)-ethyl 2-(tert-butylsulfinylimino)-4-fluoro-3,3-dimethylbutanoate (1.1 g, 3.94 mmol) in THF (8 mL) was added L-Selectride/THF (5.12 mL, 5.12 mmol) via a syringe pump at 6 mL/h rate at −78° C. The reaction mixture was stirred at −78° C. for 4 h after the completion of addition. The reaction was quenched by addition of aq. NH₄Cl at −78° C., diluted with EtOAc and washed with water, brine, dried (MgSO₄), concentrated and purified on silica gel chromatography (EtOAc/hexane) to afford (S)-ethyl 2-((S)-1,1-dimethylethylsulfinamido)-4-fluoro-3,3-dimethylbutanoate (0.38 g). ¹H NMR (400 MHz, MeOD-d₄) δ ppm 4.20-4.44 (4H, m), 3.99 (1H, s), 1.35 (3H, t, J=7.15 Hz), 1.13 (6H, dd, J=15.81, 2.01 Hz).

To a solution of (S)-ethyl 2-((S)-1,1-dimethylethylsulfinamido)-4-fluoro-3,3-dimethylbutanoate (0.38 g, 1.350 mmol) in MeOH (10 mL) was added HCl/dioxane (1.350 mL, 5.40 mmol). The reaction mixture was stirred at rt for 30 min and concentrated to afford (S)-ethyl 2-amino-4-fluoro-3,3-dimethylbutanoate/HCl as a white solid (0.29 g).

To a solution of (S)-ethyl 2-amino-4-fluoro-3,3-dimethylbutanoate/HCl (0.29 g, 1.357 mmol) in MeOH (5 mL) was added TEA (0.4 mL, 2.87 mmol) and Boc₂O (0.58 g, 2.66 mmol). The reaction mixture was stirred for 2 h at rt and concentrated. The residue was redissolved in THF (10 mL) and treated with NaOH (8 mL, 16.00 mmol), MeOH (20 mL) and stirred for 1 h. The reaction mixture was diluted with water (4 mL) and extracted with EtOAc/hexane (1/2). The aqueous layer was acidified with cold 1 N HCl and extracted with EtOAc. The organic phase was washed with water, brine, dried (MgSO₄) and concentrated to afford (S)-2-(tert-butoxycarbonylamino)-4-fluoro-3,3-dimethylbutanoic acid (0.3 g). ¹H NMR (400 MHz, CDCl₃) δ ppm 12.06 (1H, br. s.), 4.06-4.36 (3H, m), 1.38-1.46 (15H, m).

To a solution of (S)-2-((tert-butoxycarbonyl)amino)-4-fluoro-3,3-dimethylbutanoic acid (0.3 g, 1.203 mmol) and DIPEA (0.230 mL, 1.318 mmol) in acetonitrile (5 mL) was added 1,1'-([1,1'-biphenyl]-4,4'-diyl)bis(2-bromoethanone) (0.23 g, 0.581 mmol). The suspension was stirred at rt for 18 h. The reaction mixture was diluted with EtOAc and washed with sat. NaHCO₃, brine, water, dried (MgSO₄) and concentrated to afford a pale white solid. The product was purified on silica gel chromatography (EtOAc/hexane) to afford (2S,2'S)-[1,1'-biphenyl]-4,4'-diylbis(2-oxoethane-2,1-diyl)bis (2-((tert-butoxycarbonyl)amino)-4-fluoro-3,3-dimethylbutanoate) (0.3 g). LC/MS (Cond. YT-1): [M+Na]⁺ 755.35, R_f=3.384 min.

A mixture of (2S,2'S)-[1,1'-biphenyl]-4,4'-diylbis(2-oxoethane-2,1-diyl)bis(2-((tert-butoxycarbonyl)amino)-4-fluoro-3,3-dimethylbutanoate) (0.31 g, 0.423 mmol), ammonium acetate (0.8 g, 10.38 mmol) and 1H-imidazole (0.1 g, 1.469 mmol) in toluene (5 mL) was heated to 110° C. for 6 h. The reaction mixture was cooled down, and diluted with EtOAc. The organic extraction was washed with sat. NaHCO₃, brine, dried (MgSO₄) and concentrated. The product was purified on silica gel chromatography to yield tert-butyl (1S,1'S)-1,1'-(5,5'-(biphenyl-4,4'-diyl)bis(1H-imidazole-5,2-diyl))bis(3-fluoro-2,2-dimethylpropane-1,1-diyl)dicarbamate (0.21 g). LC/MS (Cond. YT-1): [M+H]⁺ 693.4, R_f=2.486 min.

To a solution of di-tert-butyl((1S,1'S)-(5,5'-([1,1'-biphenyl]-4,4'-diyl)bis(1H-imidazole-5,2-diyl))bis(3-fluoro-2,2-dimethylpropane-1,1-diyl))dicarbamate (0.21 g, 0.303 mmol) in DCM (2 mL) was added hydrogen chloride/dioxane (2.0 mL, 8.0 mmol). The reaction mixture was stirred at rt for 2 h and concentrated to afford (1S,1'S)-1,1'-(5,5'-([1,1'-biphenyl]-4,4'-diyl)bis(1H-imidazole-5,2-diyl))bis(3-fluoro-2,2-dimethylpropan-1-amine), 4 HCl (0.04 g) as a yellow solid. LC/MS (Cond. YT-1): [M+H]⁺ 493.4, R_f=1.84 min.

To a mixture of (1S,1'S)-1,1'-(5,5'-([1,1'-biphenyl]-4,4'-diyl)bis(1H-imidazole-5,2-diyl))bis(3-fluoro-2,2-dimethylpropan-1-amine), 4 HCl (0.04 g, 0.063 mmol) in DCM (1 mL) and acetonitrile (1 mL) was added pivalic acid (20 mg), DIPEA (0.1 mL, 0.573 mmol) and HBTU (0.052 g, 0.138 mmol). The reaction mixture was stirred at rt for 0.5 h, then concentrated. The residue was dissolved in MeOH and purified on prepHPLC (MeOH/H₂O/TFA) to yield TFA salt of Example Y-68 (10 mg). LC/MS (Cond. YT-1): [M+H]⁺ 661.4, R_f=2.238 min. ¹H NMR (400 MHz, MeOD-d₄) δ ppm 7.94 (2H, s), 7.83-7.91 (8H, m), 5.35-5.44 (2H, m), 4.44-4.52 (1H, m), 4.33-4.43 (2H, m), 4.15-4.31 (1H, m), 1.26 (18H, s), 1.08-1.18 (12H, m).

Example Y-69

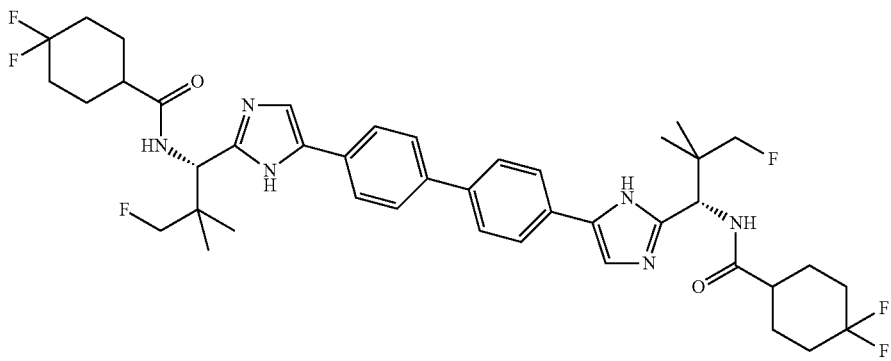 [SMILES: CC(C)(CF)[C@H](NC(=O)C1CCC(F)(F)CC1)c1ncc(-c2ccc(-c3ccc(-c4cnc([C@@H](NC(=O)C5CCC(F)(F)CC5)C(C)(C)CF)[nH]4)cc3)cc2)[nH]1]

Example Y-69 was synthesized from appropriate precursor by employing the method described in Example Y-68. LC/MS (Cond. YT-1): [M+H]$^+$ 785.35, R$_t$=2.428 min. $^1$H NMR (400 MHz, MeOD-d$_4$) δ ppm 7.75-7.96 (10H, m), 5.23 (2H, br. s.), 4.45 (1H, br. s.), 4.29-4.42 (2H, m), 4.25 (1H, br. s.), 2.49-2.65 (2H, m), 2.09 (4H, br. s.), 1.91 (2H, br. s.), 1.83 (4H, br. s.), 1.72 (3H, s), 1.75 (3H, s), 1.14 (12H, d, J=8.03 Hz).

Example L-34

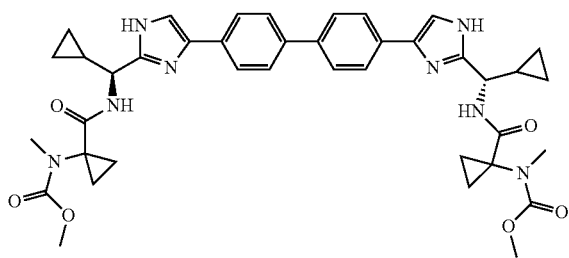 [SMILES: COC(=O)N(C)C1(C(=O)N[C@H](c2nc(-c3ccc(-c4ccc(-c5c[nH]c([C@@H](NC(=O)C6(N(C)C(=O)OC)CC6)C6CC6)n5)cc4)cc3)c[nH]2)C2CC2)CC1]

Step a

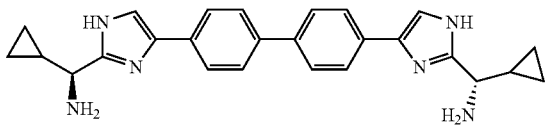 [SMILES: N[C@H](c1nc(-c2ccc(-c3ccc(-c4c[nH]c([C@@H](N)C5CC5)n4)cc3)cc2)c[nH]1)C1CC1]

HCl salt of Example L-34 step a was synthesized by following the methods described in Example Y-68 starting from commercial available (S)-2-((tert-butoxycarbonyl)amino)-2-cyclopropylacetic acid. A solution of 1-((methoxycarbonyl)(methyl)amino)cyclopropanecarboxylic acid (24.89 mg, 0.144 mmol), Example L-34 step a (40 mg, 0.070 mmol) and DIEA (0.086 mL, 0.491 mmol) in DMF (1.5 mL) was treated with HATU (56.0 mg, 0.147 mmol), the resulting solution was stirred at rt for 3 h, and then purified on prep HPLC (CH$_3$CN/H$_2$O/NH$_4$OAc) to yield Example L-34 (32 mg). LC/MS (Cond. L-1): [M+H]$^+$ 735.55, R$_t$=1.63 min. $^1$H NMR (500 MHz, DMSO-d$_6$) δ ppm 11.96 (2H, br. s.), 8.01-7.63 (12H, m), 4.56 (2H, br. s.), 3.62 (3H, s), 3.65 (3H, s), 2.84-3.03 (6H, m), 1.28-1.51 (6H, m), 1.15 (4H, br. s.), 0.48 (4H, d, J=8.24 Hz), 0.35 (4H, d, J=17.09 Hz).

Example L-35 to L-37 were synthesized by following the methods described in Example L-34.

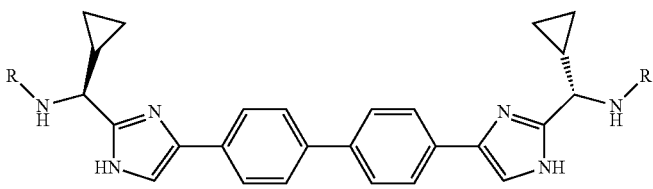

| Example | R | LC-MS Method | Retention Time (min) | Obs. Mass ion (M + H)+ |
|---|---|---|---|---|
| L-35 | ![structure with O, N-ethyl, CF3] | L-1 | 1.906 | 787.5 |

-continued
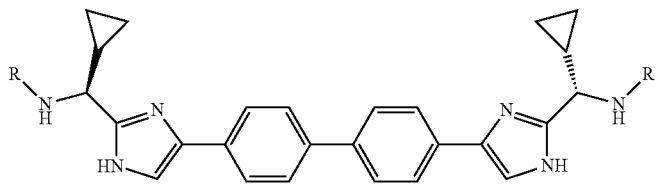
| Example | R | LC-MS Method | Retention Time (min) | Obs. Mass ion (M + H)+ |
|---|---|---|---|---|
| L-36 | | L-1 | 1.798 | 731.65 |
| L-37 | | L-1 | 1.783 | 775.33 |
Example W-51 to W-56, W-64 and W-65 were synthesized by following the methods described in Example L-34.
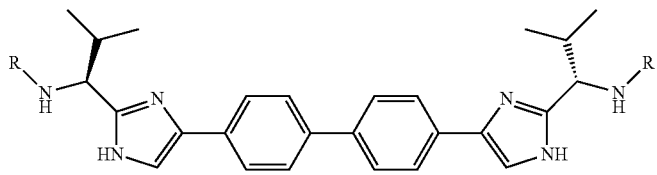
| Example | R | LC-MS Method | Retention Time (min) | Obs. Mass ion (M + H)+ |
|---|---|---|---|---|
| W-51 | | W-1 | 1.517 | 779.5 |
| W-52 | | W-1 | 1.532 | 735.7 |

-continued

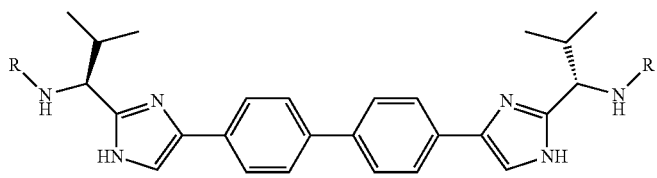

| Example | R | LC-MS Method | Retention Time (min) | Obs. Mass ion (M + H)+ |
|---|---|---|---|---|
| W-53 | | W-1 | 1.69 | 843.6 |
| W-54 | | W-1 | 1.383 | 767.6 |
| W-55 | | W-1 | 1.562 | 735.6 |
| W-56 | | W-1 | 1.635 | 791.5 |
| W-64 | | W-1 | 1.59 | 835.7 |
| W-65 | | W-1 | 1.748 | 819.6 |

The following examples were prepared from (1S,1'S)-1,1'-(4,4'-([1,1'-biphenyl]-4,4'-diyl)bis(1H-imidazole-4,2-diyl))bis(2-methylpropan-1-amine), 4HCl, and appropriate starting materials (caps), by employing the procedures described for the synthesis of Example L-3. The resulting products were purified by preparatory HPLC (either MeOH/H$_2$O/TFA or CH$_3$CN/H$_2$O/NH$_4$OAc) and obtained as their corresponding TFA salts or as free bases.

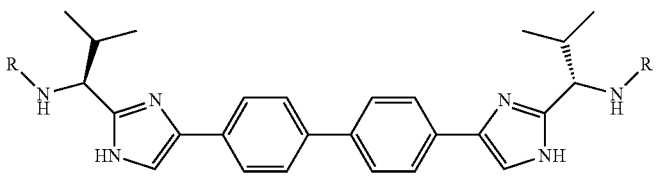
| Example | R | LC-MS Method | Retention Time (min) | Obs. Mass ion (M + H)+ | Salt |
|---|---|---|---|---|---|
| W-74 | | W-2 | 1.99 | 847.6 | Free base |
| W-89 | | W-2 | 1.82 | 847.7 | Free base |
| W-97 | | W-2 | 1.49 | 855.8 | Free base |
| W-100 | | W-2 | 1.60 | 855.8 | Free base |
| W-161 | | W-2 | 1.26 | 795.7 | Free base |
| W-164 | | W-2 | 2.04 | 737.6 | Free base |
| W-172 | | W-2 | 1.34 | 621.4 | Free base |
| W-176 | | W-2 | 1.64 | 709.4 | Free base |

-continued

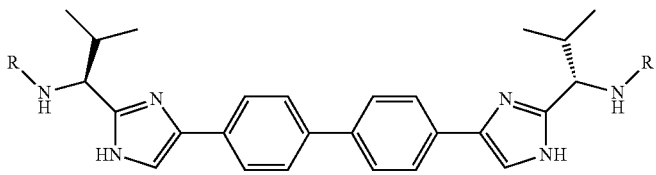

| Example | R | LC-MS Method | Retention Time (min) | Obs. Mass ion (M + H)+ | Salt |
|---|---|---|---|---|---|
| W-181 | 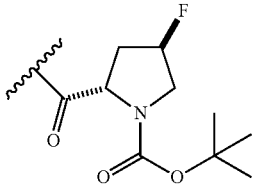 [SMILES: *C(=O)[C@@H]1C[C@@H](F)CN1C(=O)OC(C)(C)C] | W-2 | 1.94 | 859.5 | Free base |

The following examples were prepared from (1S,1'S)-1,1'-(4,4'-([1,1'-biphenyl]-4,4'-diyl)bis(1H-imidazole-4,2-diyl))bis(2,2-dimethylpropan-1-amine), 4 HCl and appropriate starting materials (caps), by employing the procedures described for the synthesis of Example L-3. The resulting products were purified by preparatory HPLC (either MeOH/H$_2$O/TFA or CH$_3$CN/H$_2$O/NH$_4$OAc) and obtained as their corresponding TFA salts or as free bases. Example W-80, W-102, and W-103 were made by methods described separately.

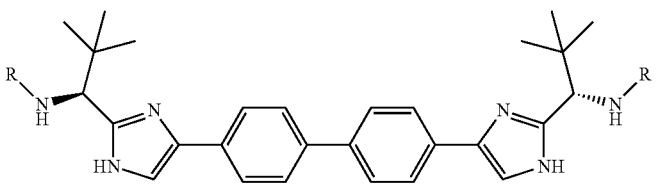

| Example | R | LC-MS Method | Retention Time (min) | Obs. Mass ion (M + H)+ | Salt |
|---|---|---|---|---|---|
| W-76* | 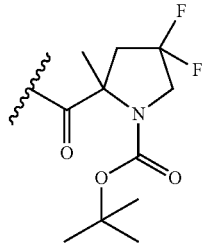 Diastereomer 1 | W-2 | 2.20 | 952.5 | Free base |
| W-77* | 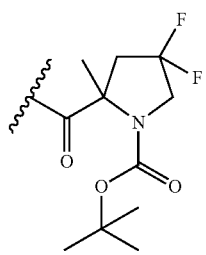 Diastereomer 2 | W-2 | 2.20 | 952.5 | Free base |

-continued
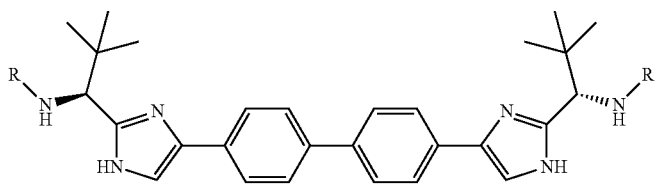
| Example | R | LC-MS Method | Retention Time (min) | Obs. Mass ion (M + H)+ | Salt |
|---|---|---|---|---|---|
| W-78* | 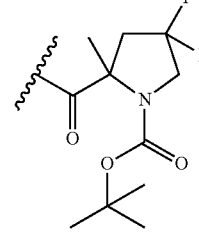 Diastereomer 3 | W-2 | 2.20 | 952.5 | Free base |
| W-79 | 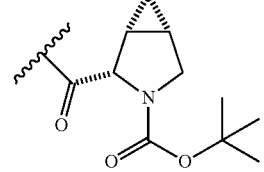 | W-2 | 2.00 | 876.5 | Free base |
| W-80 | 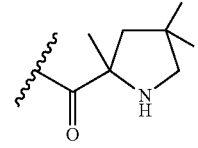 Diastereomeric mixture | W-2 | 1.68 | 751.5 | 4 HCl salt |
| W-81 | 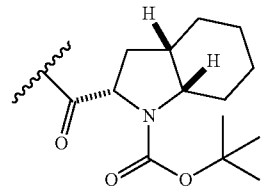 | W-1 | 1.93 | 480.5 (1/2 M + H) | Free base |
| W-82# | 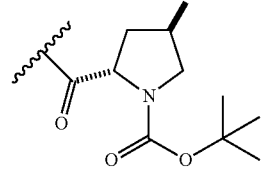 | W-1 | 1.56 | 887.7 | Free base |
| W-83 |  | W-1 | 1.56 | 887.7 | Free base |

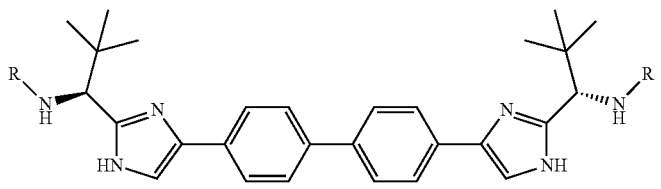
| Example | R | LC-MS Method | Retention Time (min) | Obs. Mass ion (M + H)+ | Salt |
|---|---|---|---|---|---|
| W-84 | | W-1 | 1.66 | 490.5 (1/2 M + H) | Free base |
| W-85 | | W-2 | 2.00 | 904.7 | Free base |
| W-86 | | W-2 | 1.78 | 851.9 | Free base |
| W-87 | | W-2 | 1.78 | 851.9 | Free base |
| W-88 | | W-2 | 1.96 | 923.8 | Free base |
| W-91 | | W-2 | 1.91 | 875.8 | Free Base |

-continued
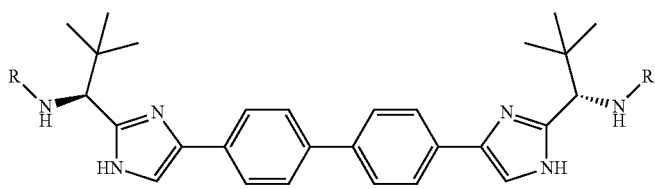
| Example | R | LC-MS Method | Retention Time (min) | Obs. Mass ion (M + H)+ | Salt |
|---|---|---|---|---|---|
| W-92** | [azabicycloheptane carbonyl] | W-2 | 1.20 | 703.7 | 4 HCl salt |
| W-93 | [4,4-dimethyl-N-Boc-pyrrolidinyl carbonyl] | W-2 | 2.05 | 908.8 | Free base |
| W-94 | [spiro cyclopropane N-Boc-pyrrolidinyl carbonyl] | W-2 | 1.98 | 903.8 | Free base |
| W-96 | [4-OH N-Boc-pyrrolidinyl carbonyl] | W-2 | 1.58 | 883.8 | Free base |
| W-98 | [4-OH N-Boc-pyrrolidinyl carbonyl] | W-2 | 1.64 | 883.8 | Free base |
| W-114*** | [4-OMe N-Boc-pyrrolidinyl carbonyl] | W-2 | 1.84 | 911.8 | Free base |

-continued
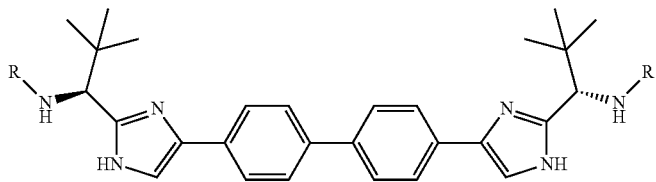
| Example | R | LC-MS Method | Retention Time (min) | Obs. Mass ion (M + H)+ | Salt |
|---|---|---|---|---|---|
| W-115 | | W-2 | 1.70 | 911.8 | Free base |
| W-116# | | W-2 | 1.64 | 911.8 | Free base |
| W-117**** | | W-2 | 1.61 | 819.9 | 2 TFA salt |
| W-118**** | | W-2 | 1.89 | 876.0 | 2 TFA salt |
| W-120 | | W-2 | 1.94 | 879.9 | Free base |
| W-121 | | W-2 | 2.00 | 904.0 | Free base |

-continued
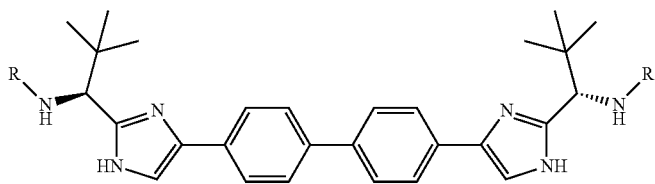
| Example | R | LC-MS Method | Retention Time (min) | Obs. Mass ion (M + H)+ | Salt |
|---|---|---|---|---|---|
| W-122 | | W-2 | 1.50 | 737.8 | Free base |
| W-123 | | W-2 | 1.28 | 681.7 | Free base |
| W-124 | | W-2 | 1.50 | 709.7 | Free base |
| W-125 | | W-2 | 1.15 | 689.7 | Free base |
| W-126 | | W-2 | 1.64 | 741.8 | 2 TFA salt |
| W-127 | | W-2 | 1.75 | 846.6 | Free base |
| W-128 | | W-2 | 1.29 | 761.9 | Free base |
| W-129 | | W-2 | 1.26 | 653.7 | Free base |
| W-130 | | W-2 | 1.40 | 709.8 | Free base |

-continued
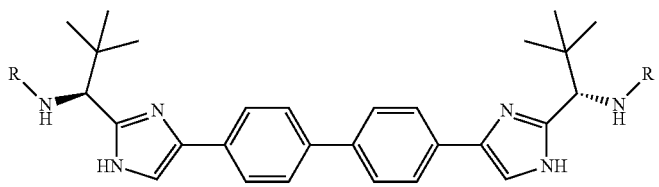
| Example | R | LC-MS Method | Retention Time (min) | Obs. Mass ion (M + H)+ | Salt |
|---|---|---|---|---|---|
| W-131 | | W-2 | 1.30 | 681.8 | Free base |
| W-132 | | W-2 | 1.66 | 912.1 | Free base |
| W-134 | | W-2 | 1.26 | 709.8 | Free base |
| W-149 | | W-2 | 1.64 | 755.5 | Free base |
| W-150 | | W-2 | 1.67 | 865.6 | Free base |
| W-159 | | W-2 | 1.19 | 713.6 | Free base |
| W-160 | | W-2 | 1.31 | 823.7 | Free base |
| W-163 | Diastereomeric mixture | W-2 | 2.08 | 765.7 | Free base |

-continued
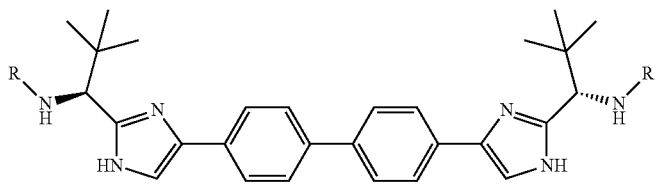
| Example | R | LC-MS Method | Retention Time (min) | Obs. Mass ion (M + H)+ | Salt |
|---|---|---|---|---|---|
| W-165 | Diastereomer 1 | W-2 | 2.08 | 765.7 | Free base |
| W-167 | Diastereomer 2 | W-2 | 2.08 | 765.7 | Free base |
| W-168 | Diastereomer 3 | W-2 | 2.08 | 765.7 | Free base |
| W-169 |  | W-2 | 1.26 | 681.7 | Free base |
| W-170 |  | W-2 | 1.24 | 681.7 | Free base |
| W-171 |  | W-2 | 1.35 | 649.5 | Free base |
| W-173 |  | W-2 | 1.44 | 705.5 | Free base |
| W-175 |  | W-2 | 1.24 | 737.6 | Free base |
| W-178 |  | W-2 | 1.68 | 737.5 | Free base |

-continued
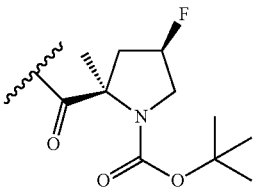 [SMILES: *C(=O)[C@@]1(C)C[C@@H](F)CN1C(=O)OC(C)(C)C]
| Example | R | LC-MS Method | Retention Time (min) | Obs. Mass ion (M + H)+ | Salt |
|---|---|---|---|---|---|
| W-184# | 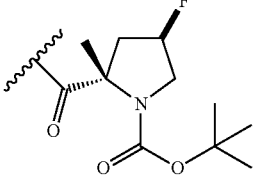 | W-2 | 1.78 | 916.5 | Free base |
| W-185# | 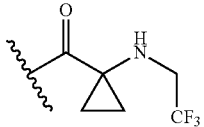 | W-2 | 1.94 | 916.5 | Free base |
| L-96 | 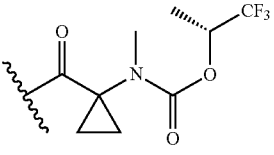 [SMILES: *C(=O)C1(N(C)C(=O)O[C@H](C)C(F)(F)F)CC1] | PS-2 | 3.421 | 787.38 | Free Base |
| L-44 | 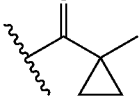 | PS-2 | 3.60 | 931.42 | Free Base |
| L-45 | 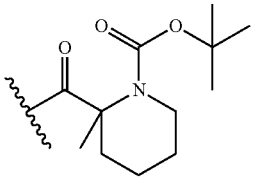 [SMILES: *C(=O)C1(C)CCCCN1C(=O)OC(C)(C)C] | PS-2 | 3.07 | 621.38 | Free Base |
| L-46a | 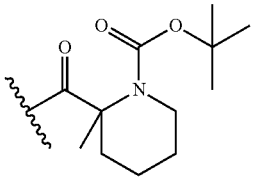 [SMILES: *C(=O)C1(C)CCCCN1C(=O)OC(C)(C)C] | L-1 | 2.83 | 907.80 | Free Base |
| L-46b |  | L-1 | 2.82 | 907.82 | Free Base |

-continued

| Example | R | LC-MS Method | Retention Time (min) | Obs. Mass ion (M + H)+ | Salt |
|---|---|---|---|---|---|
| L-46c | | L-1 | 2.82 | 907.82 | Free Base |
| L-47 | | PS-2 | 3.30 | 881.50 | Free Base |
| L-48 | | PS-2 | 3.53 | 931.42 | Free Base |
| L-49 | | PS-2 | 3.65 | 979.54 | Free Base |
| L-50 | | PS-2 | 3.40 | 791.41 | Free Base |
| L-51 | | PS-2 | 3.73 | 843.44 | Free Base |
| L-52 | | PS-2 | 3.54 | 815.41 | Free Base |

-continued

| Example | R | LC-MS Method | Retention Time (min) | Obs. Mass ion (M + H)+ | Salt |
|---|---|---|---|---|---|
| L-53 | | PS-2 | 3.57 | 677.45 | Free Base |
| L-54 | | PS-2 | 2.76 | 681.41 | Free Base |
| L-55 | | PS-2 | 3.73 | 911.53 | Free Base |
| L-56 | | PS-2 | 2.67 | 657.41 | Free Base |
| L-57 | | PS-2 | 3.36 | 903.54 | Free Base |
| L-58a | Diaastereomer 1 | L-1 | 2.29 | 693.50 | Free Base |
| L-58b | Diaastereomer 2 | L-1 | 2.29 | 693.50 | Free Base |

-continued
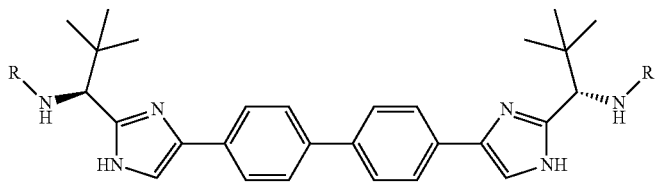
| Example | R | LC-MS Method | Retention Time (min) | Obs. Mass ion (M + H)+ | Salt |
|---|---|---|---|---|---|
| L-58c | Diaastereomer 3 | L-1 | 2.29 | 639-50 | Free Base |
| L-59 | | PS-2 | 2.47 | 771.38 | Free Base |
| L-60 | | PS-3 | 4.80 | 939.56 | Free Base |
| L-61 | | PS-2 | 3.31 | 883.50 | Free Base |
| L-62 | | PS-2 | 3.78 | 819.44 | Free Base |
| L-63 | | PS-2 | 3.40 | 851.51 | Free Base |
| L-64 | | PS-2 | 2.85 | 653.37 | Free Base |

-continued

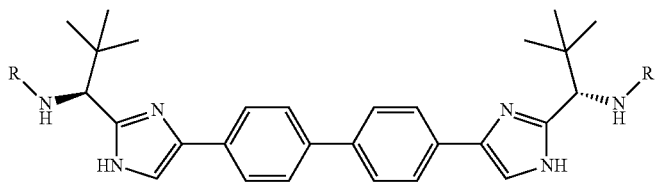

| Example | R | LC-MS Method | Retention Time (min) | Obs. Mass ion (M + H)+ | Salt |
|---|---|---|---|---|---|
| L-65 | (tetrahydrofuran-2-yl carbonyl) | PS-2 | 2.92 | 653.37 | Free Base |
| L-66a | (CF3, OH, methyl, carbonyl) Diaastereomer 1 | L-1 | 2.09 | 737.33 | 2 TFA |
| L-66b | (CF3, OH, methyl, carbonyl) Diaastereomer 2 | L-1 | 2.17 | 737.33 | 2 TFA |
| L-66c | (CF3, OH, methyl, carbonyl) Diaastereomer 3 | L-1 | 2.23 | 737.33 | 2 TFA |
| L-67 | (bicyclic oxa carbonyl) | PS-2 | 2.65 | 677.37 | Free Base |
| L-68 | (morpholinyl with CF3 ethyl, carbonyl) | PS-2 | 3.27 | 847.40 | Free Base |
| L-69 | (2-methyltetrahydrofuran-2-yl carbonyl) Mixture of diastereomers | L-1 | 2.29 | 681.55 | 2 TFA |

-continued
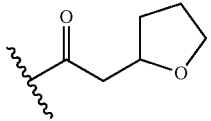
| Example | R | LC-MS Method | Retention Time (min) | Obs. Mass ion (M + H)+ | Salt |
|---|---|---|---|---|---|
| L-70 | 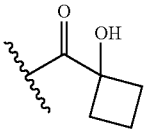<br>Mixture of diastereomers | L-1 | 2.28 | 681.60 | 2 TFA |
| L-71 | 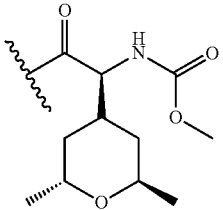 [SMILES: *C(=O)[C@@H](NC(=O)OC)C1C[C@@H](C)O[C@H](C)C1] | PS-2 | 2.83 | 653.37 | Free Base |
| L-72 | 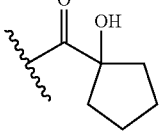 | PS-2 | 2.51 | 911.53 | Free Base |
| L-73 | 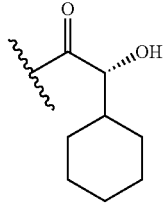 [SMILES: *C(=O)[C@H](O)C1CCCCC1] | PS-2 | 3.94 | 681.41 | Free Base |
| L-74 | 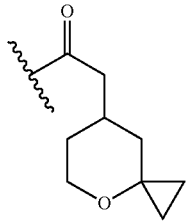 | PS-2 | 3.46 | 737.47 | Free Base |
| L-75 | <br>Mixture of diastereomers | PS-2 | 3.05 | 761.47 | Free Base |

-continued

| Example | R | LC-MS Method | Retention Time (min) | Obs. Mass ion (M + H)+ | Salt |
|---|---|---|---|---|---|
| L-76 | | PS-2 | 3.30 | 685.44 | Free Base |
| L-77 | | PS-2 | 3.46 | 737.47 | Free Base |
| L-78 | | PS-2 | 2.65 | 657.41 | Free Base |
| L-79 | | PS-2 | 2.56 | 681.33 | Free Base |
| L-80 | | PS-2 | 2.76 | 629.37 | Free Base |
| L-81 | | PS-2 | 2.79 | 709.29 | Free Base |
| L-82 | | PS-2 | 2.75 | 657.41 | Free Base |
| L-83 | | PS-2 | 2.82 | 713.39 | Free Base |

-continued

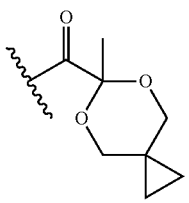 [SMILES: *C(=O)C1(C)OCC2(CC2)CO1]

| Example | R | LC-MS Method | Retention Time (min) | Obs. Mass ion (M + H)+ | Salt |
|---|---|---|---|---|---|
| L-84 | 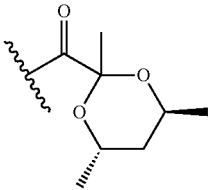 [SMILES: *C(=O)C1(C)O[C@@H](C)C[C@H](C)O1] | PS-2 | 3.04 | 765.43 | Free Base |
| L-85 | 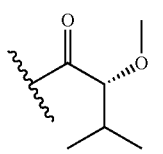 [SMILES: *C(=O)[C@H](OC)C(C)C] | PS-2 | 3.44 | 769.46 | Free Base |
| L-86 | 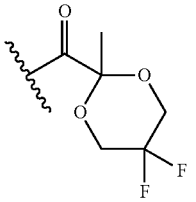 [SMILES: *C(=O)C1(C)OCC(F)(F)CO1] | PS-2 | 2.29 | 685.75 | Free Base |
| L-87 | 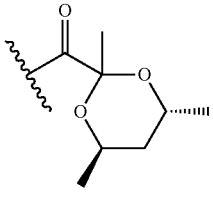 [SMILES: *C(=O)C1(C)O[C@H](C)C[C@@H](C)O1] | PS-2 | 3.01 | 785.36 | Free Base |
| L-88 | 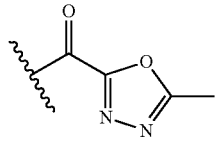 [SMILES: *C(=O)c1nnc(C)o1] | PS-2 | 3.37 | 769.46 | Free Base |
| L-89 |  | PS-2 | 2.65 | 677.32 | Free Base |

*Examples W-76, W-77 and W-78 were separated from a mixture of diastereomers by preparatory HPLC
**Example W-92 was prepared by employing the same procedures as described for the synthesis of Example W-80.
***Example W-114 was isolated as a minor product during purification of W-115.
****Examples W-117 and W-118 were prepared by employing the same procedures as described for the synthesis of Example W-109 and W-107, except for using Example W-92 as the starting material.

\# The following examples were characterized by proton NMR:

Example W-82

¹H NMR (500 MHz, DMSO-$d_6$) δ 12.53-11.93 (m, 1H), 8.36-7.21 (m, 6H), 5.51-5.08 (m, 1H), 5.02-4.78 (m, 1H), 4.63-4.35 (m, 1H), 3.83-3.40 (m, 2H), 2.44-1.82 (m, 2H), 1.54-1.20 (m, 9H), 1.11-0.85 (m, 9H)

Example W-116

¹H NMR (500 MHz, DMSO-$d_6$) δ 12.52-11.81 (m, 1H), 8.22-7.14 (m, 5H), 5.58-5.13 (m, 1H), 5.03-4.76 (m, 1H), 4.35-4.24 (m, 1H), 4.13-4.10 (m, 1H), 3.31-3.16 (m, 1H), 2.36-1.68 (m, 2H), 1.54-1.10 (m, 12H), 1.05-0.87 (m, 9H)

Example W-184

¹H NMR (500 MHz, DMSO-$d_6$) δ 12.04 (br. s., 1H), 8.08-7.09 (m, 5H), 5.29-4.70 (m, 2H), 3.95-3.54 (m, 3H), 2.23-1.82 (m, 2H), 1.72-1.28 (m, 12H), 0.92 (br. s., 9H)

Example W-185

¹H NMR (500 MHz, CD$_3$OD) δ 7.88-7.65 (m, 4H), 7.47-7.31 (m, 1H), 5.44-5.16 (m, 1H), 5.14-4.98 (m, 1H), 4.13-3.73 (m, 2H), 2.63-2.24 (m, 2H), 1.80-1.58 (m, 3H), 1.39 (s, 3H), 1.13 (s, 9H), 1.07-0.98 (m, 9H)

Example L-66a

¹H NMR (500 MHz, DMSO-$d_6$) δ 8.46 (br. s., 2H), 8.02-7.81 (m, 9H), 7.61 (br. s., 2H), 5.20 (br. s., 2H), 1.57 (s, 6H), 1.28-1.21 (m, 2H), 0.97 (s, 19H); ¹⁹F NMR (471 MHz, DMSO-$d_6$) δ −74.09 (s, 3F), −78.19 (br. s., 3F).

Example L-66b

¹H NMR (500 MHz, DMSO-$d_6$) δ 8.43 (br. s., 2H), 8.12 (br. s., 2H), 8.02-7.81 (m, 8H), 7.62 (br. s., 1H), 7.51 (br. s., 1H), 5.20 (br. s., 2H), 1.57 (s, 3H), 1.48 (s, 3H), 1.29-1.20 (m, 2H), 0.97 (br. s., 9H), 0.95 (br. s., 9H); ¹⁹F NMR (471 MHz, DMSO-$d_6$) δ −74.10 (br. s., 6F), −78.19 (br. s., 3F), −78.34 (br. s., 3F)

Example L-66c

¹H NMR (500 MHz, DMSO-$d_6$) δ 8.43 (d, J=19.2 Hz, 2H), 7.87 (br. s., 9H), 7.49 (br. s., 2H), 5.19 (br. s., 2H), 1.47 (s, 6H), 1.39 (br. s., 2H), 0.94 (br. s., 18H); ¹⁹F NMR (471 MHz, DMSO-$d_6$) δ −74.02 (br. s., 3F), −78.36 (br. s., 3F)

Example L-96

¹H NMR (500 MHz, DMSO-$d_6$) δ 12.45-12.08 (m, 2H), 8.29-8.19 (m, 2H), 7.85 (d, J=8.2 Hz, 3H), 7.78-7.65 (m, 5H), 7.59-7.36 (m, 2H), 4.94-4.75 (m, 2H), 3.49-3.42 (m, 2H), 3.37 (d, J=4.3 Hz, 2H), 3.24-3.12 (m, 2H), 1.17-1.08 (m, 2H), 1.05-0.98 (m, 4H), 0.94 (s, 18H)

The following examples were prepared from (1S,1'S)-(4,4'-([1,1'-biphenyl]-4,4'-diyl)bis(1H-imidazole-4,2-diyl))bis(cyclopropylmethanamine), 4 HCl and appropriate starting materials, by employing the procedures described for the synthesis of Example L-34. The resulting products were purified by preparatory HPLC (MeOH/H$_2$O/TFA or CH$_3$CN/H$_2$O/NH$_4$OAc) and obtained as their corresponding TFA salts or as free bases.

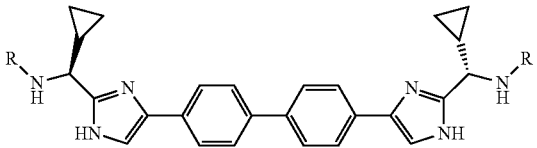

| Example | R | LC-MS Method | Retention Time (min) | Obs. Mass ion (M + H)+ | Salt Type |
|---|---|---|---|---|---|
| L-90 | 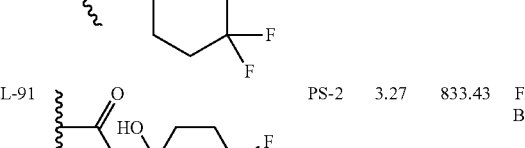 | PS-2 | 2.81 | 717.35 | Free Base |
| L-91 | 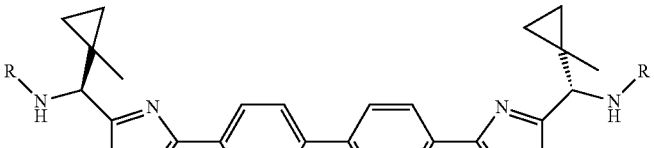 | PS-2 | 3.27 | 833.43 | Free Base |

The following Examples were prepared from (1S,1'S)-(4,4'-([1,1'-biphenyl]-4,4'-diyl)bis(1H-imidazole-4,2-diyl))bis((1-methylcyclopropyl)methanamine), 4HCl and appropriate starting materials (caps), by employing the procedures described for the synthesis of Example L-3. The resulting products were purified by preparatory HPLC (either MeOH/H$_2$O/TFA or CH$_3$CN/H$_2$O/NH$_4$OAc) and obtained as their corresponding TFA salts or as free bases.

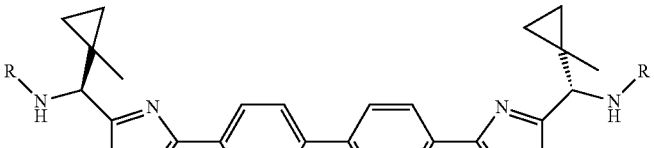

| Example | R | LC-MS Method | Retention Time (min) | Obs. Mass ion (M + H)+ | Salt |
|---|---|---|---|---|---|
| W-75 | | W-2 | 2.04 | 871.6 | Free base |

-continued

| Example | R | LC-MS Method | Retention Time (min) | Obs. Mass ion (M + H)+ | Salt |
|---|---|---|---|---|---|
| W-90 | | W-2 | 1.86 | 871.8 | Free base |
| W-95 | | W-2 | 1.84 | 879.8 | Free base |
| W-99 | | W-2 | 1.66 | 879.8 | Free base |
| W-162 | | W-2 | 1.25 | 819.7 | Free base |
| W-165 | | W-2 | 2.15 | 761.6 | Free base |
| W-174 | | W-2 | 1.32 | 645.4 | Free base |
| W-176 | | W-2 | 1.65 | 733.4 | Free base |

-continued

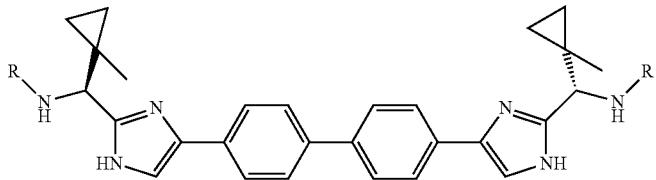

| Example | R | LC-MS Method | Retention Time (min) | Obs. Mass ion (M + H)+ | Salt |
|---|---|---|---|---|---|
| W-182 | 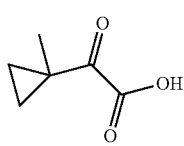 | W-2 | 1.95 | 883.2 | Free base |
| L-92 | 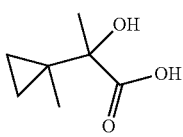 | PS-2 | 3.44 | 927.39 | Free Base |

Example L-93

Diastereomer 1

Example L-93

Diastereomer 2

Example L-93

Diastereomer 3

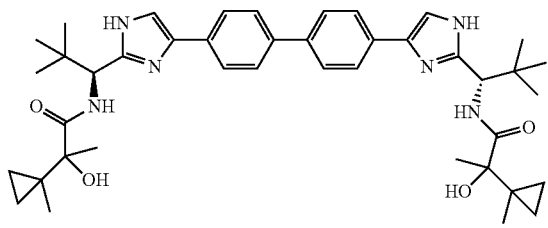

Example L-93

Step a

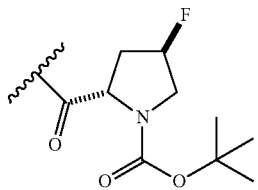

1-(1-methylcyclopropyl)ethanone (5 g, 50.9 mmol), NaOH (10.19 mL, 102 mmol) and H$_2$O (150 mL) were charged in a 500 ml Erlenmyer flask and cooled in acetone-ice bath. After the inner temperature reached −4° C., KMnO$_4$ (14.49 g, 92 mmol) was added portionwise with vigorous stirring. The inner temperature was kept at −3 to 1° C. during the addition process, which lasted 60 min. The reaction mixture was then stirred in the bath for 6 h and warmed up in the process (the inner temperature reached 16° C.). EtOH (10 ml) was added and stirring continued for another 15 min. The reaction mixture was filtered to remove the solids and washed with water (~100 ml). The filtrate was acidified with cold 6 N HCl in an ice cold bath to pH<2. The mixture was extracted with EtOAc (4×100 ml and 3×50 ml) and the combined extracts were washed with 1N HCl (10 ml)), brine (3×15 ml), dried (Na$_2$SO$_4$) and concentrated to give a clear oil that solidified upon standing under vacuum and corresponded to Example L-93 Step a (3.71 g). $^1$H NMR (400 MHz, CDCl$_3$) δ 10.21 (br. s., 1H), 1.84-1.78 (m, 2H), 1.36 (s, 3H), 1.09-1.04 (m, 2H); $^{13}$C NMR (101 MHz, CDCl$_3$) δ 197.0, 162.1 (br. s., 1C), 26.8, 20.5 (s, 2C), 19.2.

Example L-93

Step b

Racemate

MeMgCl (3 M in THF) (21.23 mL, 63.7 mmol) was added dropwise to a solution of Example L-92 Step a (3.71 g, 29.0 mmol) in THF (40 mL) at 0° C. The resulting solution was then stirred at rt for 24 h. The reaction mixture was then cooled to 0° C. and carefully quenched with 6N HCl (~15 mL). The organic solvent was removed under reduced pressure and the aqueous' layer was extracted with Et₂O (4×50 mL). The combined organic layers were washed with brine, dried (MgSO₄), filtered and concentrated under vacuum to give a white solid. The residue was then recrystallized from hot n-heptanes to give Example L-93 Step b (3.15 g) as off-white crystals. ¹H NMR (500 MHz, CDCl₃) δ 1.39 (s, 3H), 1.16 (s, 3H), 0.83-0.73 (m, 2H), 0.37-0.31 (m, 1H), 0.31-0.25 (m, 1H); ¹³C NMR (126 MHz, CDCl₃) δ 180.6, 75.9, 21.9, 21.9, 20.7, 10.7, 9.4.

Example L-93

Step c

Racemate

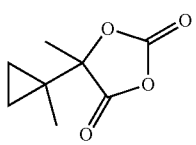

N-methylpiperidine (0.843 mL, 6.94 mmol) was added to a stirred solution of Example L-92 Step b (0.5 g, 3.47 mmol) in THF (10 mL) at rt. After 10 min, CCl₃OCOCl (0.502 mL, 4.16 mmol) was added dropwise at 0° C. and the resulting mixture was stirred at rt for 12 h. A white precipitate formed. The solvent was removed under reduced pressure and the residue was taken up in hexanes. The solid was filtered off and washed with hexanes. The hexanes solution was then concentrated under reduced pressure to give a yellowish oil which corresponded to Example L-93 Step c (0.47 g) and was used without further purification. ¹H NMR (400 MHz, CDCl₃) δ 1.67 (s, 3H), 1.25 (s, 3H), 0.88-0.80 (m, 1H), 0.75 (dt, J=9.6, 4.6 Hz, 1H), 0.59-0.47 (m, 2H); ¹³C NMR (101 MHz, CDCl₃) δ 168.6, 147.7, 89.2, 20.2, 19.7, 19.2, 10.9, 9.5.

Example L-93 step c (116 mg, 0.681 mmol) (in 0.5 mL DCM) was added to a solution of (1S,1'S)-1,1'-(4,4'-([1,1'-biphenyl]-4,4'-diyl)bis(1H-imidazole-4,2-diyl))bis(2,2-dimethylpropan-1-amine), 4 HCl (200 mg, 0.332 mmol) and DIEA (0.348 mL, 1.992 mmol) in DCM (2.0 mL) and acetonitrile (2.0 mL) and the mixture was stirred at rt for 2 h. Sample was concentrated under reduced pressure and the residue was purified by preparatory HPLC (Solvent A: 05% MeCN/95% water/10 mM NH₄Ac; Solvent B: 95% MeCN/5% water/10 mM NH₄Ac; Column: Sunfire Prep MS C18 30×100 mm S10; Wavelength: 220 nM; Flow rate: 30 ml/min; Gradient: 0% B to 80% B over 15 min. with a 5 min hold time) to afford three diastereomeric products (Example L-93a, Example L-93b and Example L-93c) listed in the table below:

| Example | Structure | LC-MS Method | Retention Time (min) | Obs. Mass ion (M + H)+ |
|---|---|---|---|---|
| L-93a* | Symmetrical diastereomer 1 | L-1 | 2.26 | 709.65 |
| L-93b* | Asymmetrical diastereomer | L-1 | 2.30 | 709.65 |

-continued

| Example | Structure | LC-MS Method | Retention Time (min) | Obs. Mass ion (M + H)+ |
|---|---|---|---|---|
| L-93c | 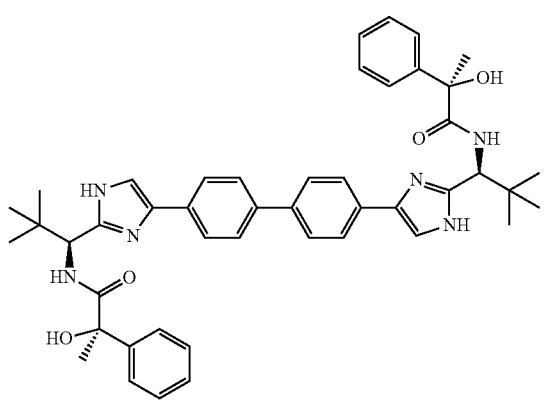 [SMILES: CC(C)(C)[C@H](NC(=O)[C@](C)(O)c1ccccc1)c1nc(-c2ccc(-c3ccc(-c4c[nH]c([C@@H](NC(=O)[C@](C)(O)c5ccccc5)C(C)(C)C)n4)cc3)cc2)c[nH]1] Symmetrical diastereomer 2 | L-1 | 2.37 | 709.65 |

*Example L-93a $^1$H NMR (500 MHz, DMSO-d$_6$) δ 12.46-12.03 (m, 2H), 7.83 (d, J = 8.2 Hz, 3H), 7.78-7.64 (m, 6H), 7.60-7.53 (m, 1H), 7.61-7.31 (m, 1H), 5.44 (s, 2H), 4.92-4.79 (m, 2H), 3.32 (s, 7H), 1.23 (s, 6H), 0.92 (br. s., 18H), 0.65 (d, J = 5.2 Hz, 2H), 0.61-0.54 (m, 2H), 0.09-0.02 (m, 2H), −0.05 (s, 2H).
*Example L-93b $^1$H NMR (500 MHz, DMSO-d$_6$) δ 12.49-12.05 (m, 2H), 7.83 (d, J = 7.3 Hz, 3H), 7.78-7.62 (m, 6H), 7.60-7.29 (m, 2H), 5.56-5.33 (m, 2H), 4.84 (t, J = 10.8 Hz, 2H), 3.32 (br. s., 6H), 1.22 (d, J = 9.6 Hz, 6H), 0.96-0.85 (m, 18H), 0.81 (br. s., 1H), 0.74 (d, J = 4.6 Hz, 1H), 0.65 (d, J = 3.6 Hz, 1H), 0.58 (d, J = 3.8 Hz, 1H), 0.20-0.09 (m, 2H), 0.08-0.02 (m, 1H), −0.05 (dd, J = 8.7, 4.7 Hz, 1H).

Example L-94

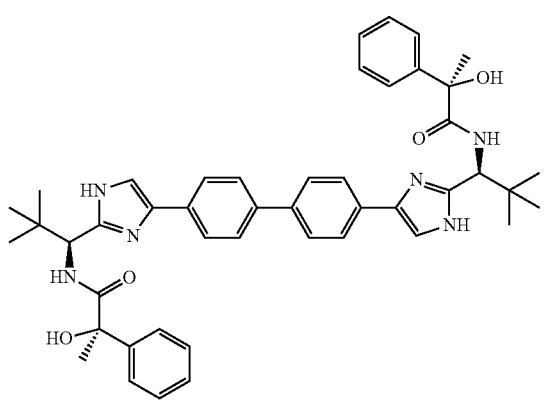 [SMILES: CC(C)(C)[C@H](NC(=O)[C@](C)(O)c1ccccc1)c1nc(-c2ccc(-c3ccc(-c4c[nH]c([C@@H](NC(=O)[C@](C)(O)c5ccccc5)C(C)(C)C)n4)cc3)cc2)c[nH]1]

Neat 1,1′-carbonyldiimidazole (50.3 mg, 0.301 mmol) was added to a solution of (R)-2-hydroxy-2-phenylpropanoic acid (50.0 mg, 0.301 mmol) in THF (2 mL) and the mixture was stirred at rt overnight. Solvent was removed under reduced pressure and the residue was taken up in DMF (1.5 mL). The resulting solution was then treated with DIPEA (0.074 mL, 0.421 mmol) and (1S,1'S)-1,1′-(4,4′-([1,1′-biphenyl]-4,4′-diyl)bis(1H-imidazole-4,2-diyl))bis(2,2-dimethylpropan-1-amine), 4 HCl (59.8 mg, 0.099 mmol) and the mixture was stirred at rt for 2 h. The crude material was purified via preparative LC/MS (Column: Waters XBridge C18, 19×200 mm, 5 μm; Mobile Phase A: water with 20-mM ammonium acetate; Mobile Phase B: 95:5 acetonitrile:water with 20-mM ammonium acetate; Gradient: 35-75% B over 20 minutes, then a 5-minute hold at 100% B; Flow: 20 mL/min.) Fractions containing the desired product were combined and dried via centrifugal evaporation yielding a solid corresponding to Example L-94 (1.5 mg). LC/MS (Cond. PS-2): [M+H]$^+$ 753.41, R$_t$=2.99 min. $^1$H NMR (400 MHz, DMSO-d$_6$) δ 7.81 (br. s., 3H), 7.69 (br. s., 5H), 7.57-7.47 (m, 6H), 7.29-7.10 (m, 6H), 6.44 (s, 2H), 4.79 (br. s., 2H), 1.70 (s, 6H), 0.94 (s, 18H).

Example L-95

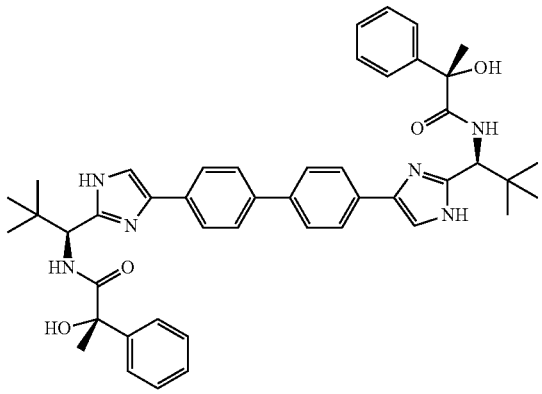 [SMILES: CC(C)(C)[C@H](NC(=O)[C@@](C)(O)c1ccccc1)c1nc(-c2ccc(-c3ccc(-c4c[nH]c([C@@H](NC(=O)[C@@](C)(O)c5ccccc5)C(C)(C)C)n4)cc3)cc2)c[nH]1]

Example L-95 was prepared by employing the procedures described for the synthesis of Example L-94 starting from (S)-2-hydroxy-2-phenylpropanoic acid. LC/MS (Cond. PS-2): [M+H]$^+$ 756.41, R$_t$=3.18 min. $^1$H NMR (500 MHz, DMSO-d$_6$) δ 7.98-7.82 (m, 5H), 7.77-7.66 (m, 5H), 7.59 (br. s., 5H), 7.40-7.22 (m, 7H), 6.41 (br. s., 2H), 4.86-4.73 (m, 2H), 1.61 (br. s., 6H), 0.73 (br. s., 18H).

Example W-80

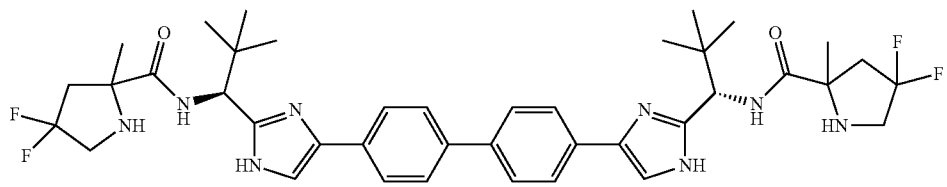 [SMILES: CC1(C(=O)N[C@H](c2nc(-c3ccc(-c4ccc(-c5c[nH]c([C@@H](NC(=O)C6(C)CC(F)(F)CN6)C(C)(C)C)n5)cc4)cc3)c[nH]2)C(C)(C)C)CC(F)(F)CN1]

To a solution of W-77 in MeOH (0.25 mL) was added 4 M HCl in 1,4-dioxane (0.126 mL, 0.505 mmol). The formed light yellow solution was stirred at rt for 2 h. Removed the volatiles in vacuo. The residue was triturated with ether, filtered, washed with ether and dried under vacuo to afford W-80 (4 HCl salt) as a light yellow solid (22 mg).

Example W-101

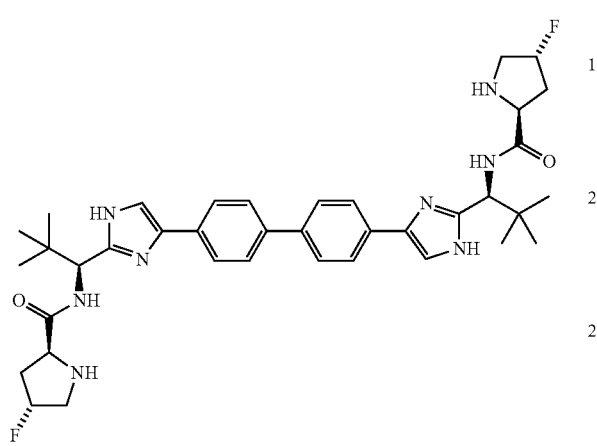

Example W-101 was prepared as the 4 HCl salt from Example W-181 according to the procedure described for the synthesis of Example W-80.

Example W-102

Method W-A

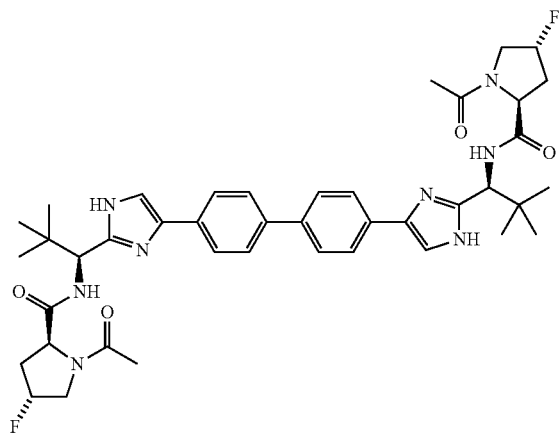 [SMILES: CC(=O)N1C[C@H](F)C[C@H]1C(=O)N[C@H](c1nc(-c2ccc(-c3ccc(-c4c[nH]c([C@@H](NC(=O)[C@@H]5C[C@@H](F)CN5C(C)=O)C(C)(C)C)n4)cc3)cc2)c[nH]1)C(C)(C)C]

To a mixture of (2S,2'S,4R,4'R)—N,N'-((1S,1'S)-(4,4'-([1,1'-biphenyl]-4,4'-diyl)bis(1H-imidazole-4,2-diyl))bis(2,2-dimethylpropane-1,1-diyl))bis(4-fluoropyrrolidine-2-carboxamide), 4 HCl (Example W-101, 50 mg, 0.060 mmol) in $CH_2Cl_2$ (1 mL) at 4° C. was added DIPEA (0.105 mL, 0.600 mmol) and Acetic anhydride (0.045 mL, 0.480 mmol). The formed mixture (it turned into a clear solution in 10 min) was stirred at room temperature for 1 hour. 2 M ammonia in MeOH (1.000 mL, 2 mmol) was added and stirred at rt for 3 h. The Solvents were evaporated by blowing N2 and the residue was taken up in 1 mL of MeOH and purified by prep-HPLC ($CH_3CN/H_2O/NH_4OAc$) to afford the desired product Example W-102 (30 mg white solid, 62% yield) as free base.

Example W-103

Method W-B

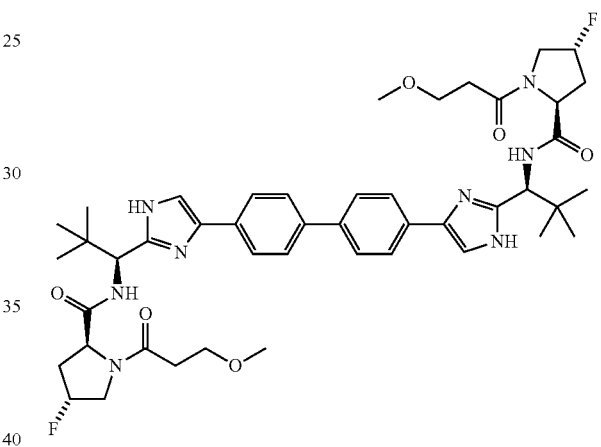

To a mixture of (2S,2'S,4R,4'R)—N,N'-((1S,1'S)-(4,4'-([1,1'-biphenyl]-4,4'-diyl)bis(1H-imidazole-4,2-diyl))bis(2,2-dimethylpropane-1,1-diyl))bis(4-fluoropyrrolidine-2-carboxamide), 4 HCl (50 mg, 0.060 mmol) in DMF (1 mL) at 4° C. was added DIPEA (0.105 mL, 0.600 mmol), O-(7-Azabenzotriazol-1-yl)-N,N,N',N'-tetramethyluronium hexafluorophosphate (47.9 mg, 0.126 mmol) and 2-ethoxyacetic acid (0.012 mL, 0.126 mmol). The formed solution was stirred at room temperature for 2 h and purified by prep-HPLC ($CH_3CN/H_2O/NH_4OAc$) to afford the desired product Example W-103 (28 mg white solid, 54% yield) as free base.

The Examples in the following table were prepared by employing the same methods as described either in Example W-102 (Method W-A), or in Example W-103 (Method W-B), except for Example W-101, which was prepared by the same method as described in Example W-80.

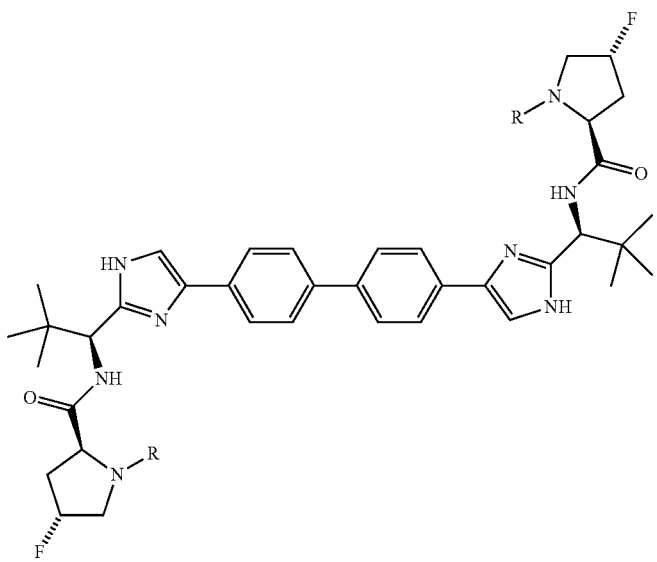
| Example | R | LC-MS Method | Retention Time (min) | Obs. Mass ion (M + H)+ | Salt | Method |
| --- | --- | --- | --- | --- | --- | --- |
| W-104 | ![cyclopropyl ketone] | W-2 | 1.57 | 823.7 | Free base | A |
| W-105 | ![tert-butyl ketone] | W-2 | 1.76 | 855.8 | Free base | A |
| W-106 | ![neopentyl ketone] | W-2 | 1.92 | 884.7 | Free base | A |
| W-107 | ![isopropyl ester] | W-2 | 1.79 | 859.7 | Free base | A |
| W-108 | ![2-fluoroethyl ester] | W-2 | 1.63 | 867.7 | Free base | A |

-continued
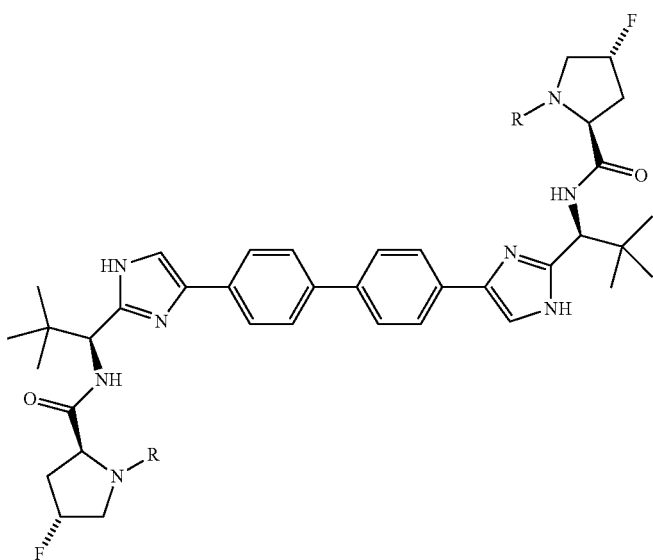
| Example | R | LC-MS Method | Retention Time (min) | Obs. Mass ion (M + H)+ | Salt | Method |
|---|---|---|---|---|---|---|
| W-109 | methyl ester | W-2 | 1.57 | 803.7 | Free base | A |
| W-110 | 2-methoxyethyl ester | W-2 | 1.57 | 891.7 | Free base | A |
| W-111 | cyclopentyl ester | W-2 | 1.92 | 911.8 | Free base | A |
| W-119 | 1-methylcyclopropyl ester | W-2 | 1.68 | 883.8 | Free base | A |

Example W-112 and Example W-113

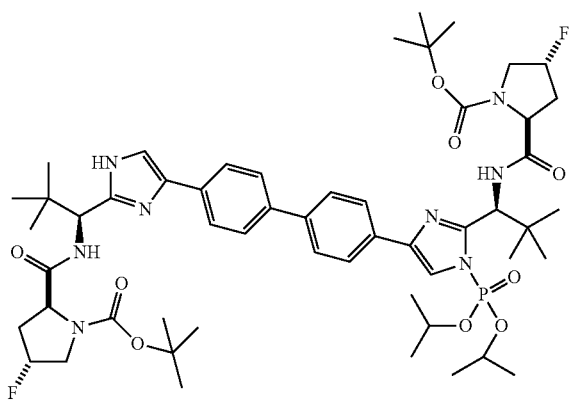

To an ice cooled solution of (3R,3'R,5S,5'S)-di-tert-butyl 5,5'-(((((1S,1'S)-(4,4'-([1,1'-biphenyl]-4,4'-diyl)bis(1H-imi- dazole-4,2-diyl))bis(2,2-dimethylpropane-1,1-diyl))bis (azanediyl))bis(carbonyl))bis(3-fluoropyrrolidine-1-car- boxylate) (50 mg, 0.056 mmol) in tetrahydrofuran was added DIPEA (24.61 µl, 0.141 mmol) and diisopropyl phosphoro- chloridate (23.74 mg, 0.118 mmol). The formed mixture (it turned into a clear solution in 10 min) was stirred at room temperature for 1 h. Transferred the content to a vial, sealed it, and heated to 80° C. in a microwave system for 2 h. Purifica- tion by prep-HPLC(CH$_3$CN/H$_2$O/NH$_4$OAc) to afforded two fractions corresponding to Example W-112 (4.4 mg) as a white solid and to Example W-113 (5.4 mg) as a white solid.

Example W-112: LC/MS (Cond. W-3): ½[M+H]+ 526.5, Rt=3.25 min.

Example W-113: LC/MS (Cond. W-3): ½[M+H]+ 608.6, Rt=3.39 min.

Example W-135

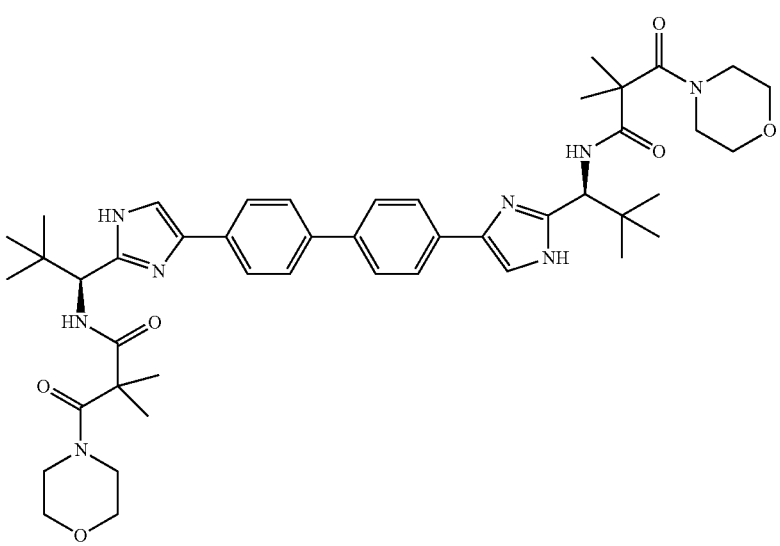 [SMILES: CC(C)(C(=O)N[C@H](c1nc(-c2ccc(-c3ccc(-c4c[nH]c([C@@H](NC(=O)C(C)(C)C(=O)N5CCOCC5)C(C)(C)C)n4)cc3)cc2)c[nH]1)C(C)(C)C)C(=O)N1CCOCC1]

-continued

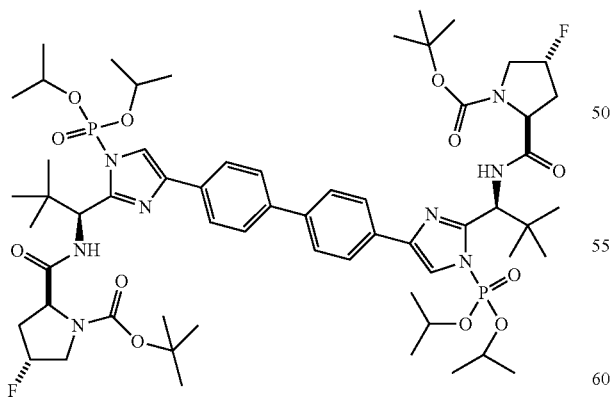

Example W-135

Step A

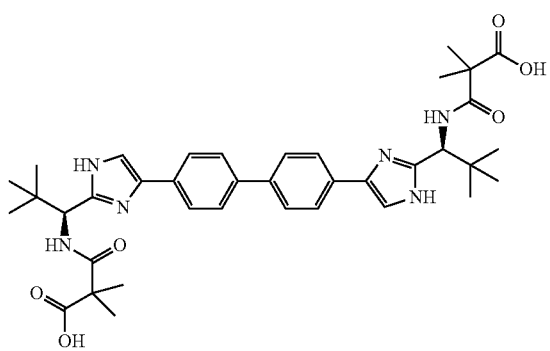 [SMILES: CC(C)(C(=O)O)C(=O)N[C@H](c1nc(-c2ccc(-c3ccc(-c4c[nH]c([C@@H](NC(=O)C(C)(C)C(=O)O)C(C)(C)C)n4)cc3)cc2)c[nH]1)C(C)(C)C]

To a solution of Example W-126, 2 TFA (1.27 g, 1.311 mmol), water (12.00 mL) in MeOH (12 mL) and THF (12.00 mL) was added a premade solution of LiOH monohydrate (0.275 g, 6.55 mmol) in water (12.00 mL). The formed thick paste was heated to gentle reflux for 2 h. An aliquot was taken and purified by prep-HPLC (CH₃CN/H₂O/NH₄OAc) for characterization, to afford Example W-133 Step A. The rest of the mixture was evaporated in vacuo, diluted with DMF (10 mL), acidified by 2 ml 2 M HCl with stirring. Removed the volatiles under high vacuum. The residual gum was taken up into 15.8 mL DMA. The formed 0.083 M stock solution was used for future couplings.

To a vial containing morpholine (15.21 mg, 0.175 mmol) and HATU (66.4 mg, 0.175 mmol) was added 0.083 stock solution Example W-135 Step A 2 HCl (1.002 mL, 0.083 mmol) in DMA and DIEA (0.145 mL, 0.831 mmol). The formed light yellow solution was stirred at rt for 3 h. The mixture was then urified by prep-HPLC (CH₃CN—H₂O—NH₄OAc) to afford Example W-135 (41 mg, 59% yield) as a white solid.

Examples W-136 to W-158 in the following table were prepared by employing the procedures described for the synthesis of Example W-135. The resulting products were purified by preparatory HPLC (either MeOH/H₂O/TFA or CH₃CN/H₂O/NH₄OAc) and obtained as their corresponding TFA salts or as free bases.

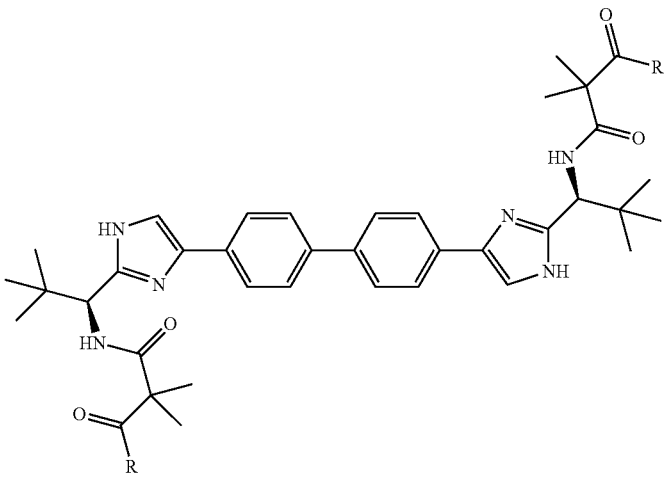

| Example | R | LC-MS Method | Retention Time (min) | Obs. Mass ion (M + H)+ | Salt |
|---|---|---|---|---|---|
| W-136 | piperidine-4-OH | W-2 | 1.22 | 851.9 | Free base |
| W-137 | 4-OH-piperidine with CH₂N(CH₃)₂ | W-2 | 1.27 | 809.9 | Free base |
| W-138 | N(CH₃)₂ | W-2 | 1.28 | 739.8 | Free base |
| W-139 | NHCH₂CF₃ | W-2 | 1.56 | 847.8 | Free base |
| W-140 | N(CH₃)(cyclopropyl) | W-2 | 1.40 | 791.9 | Free base |

-continued
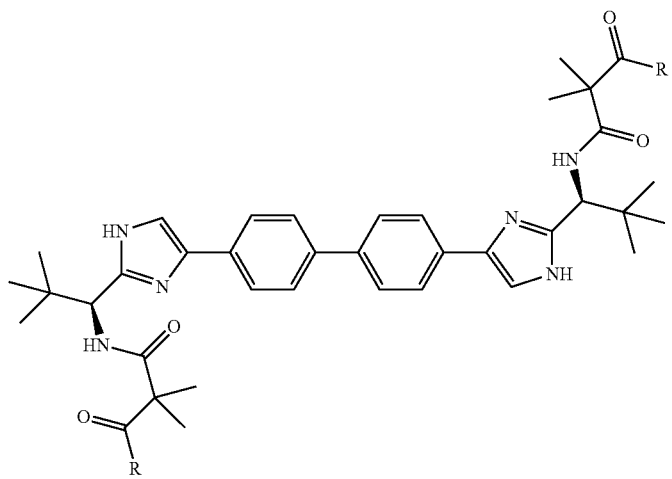
| Example | R | LC-MS Method | Retention Time (min) | Obs. Mass ion (M + H)+ | Salt |
|---|---|---|---|---|---|
| W-141 | 4,4-difluoropiperidinyl | W-2 | 1.58 | 891.9 | Free base |
| W-142 | 4-fluoropiperidinyl | W-2 | 1.45 | 856.0 | Free base |
| W-143 | 4-methoxypiperidinyl | W-2 | 1.38 | 880.0 | Free base |
| W-144 | 3-hydroxyazetidinyl | W-2 | 1.17 | 795.9 | Free base |
| W-145 | 8-oxa-3-azabicyclo[3.2.1]octyl | W-2 | 1.34 | 876.0 | Free base |
| W-146* | 4,4-difluoropiperidinyl / dimethylamino | W-2 | 1.58 | 817.0 | Free base |

-continued
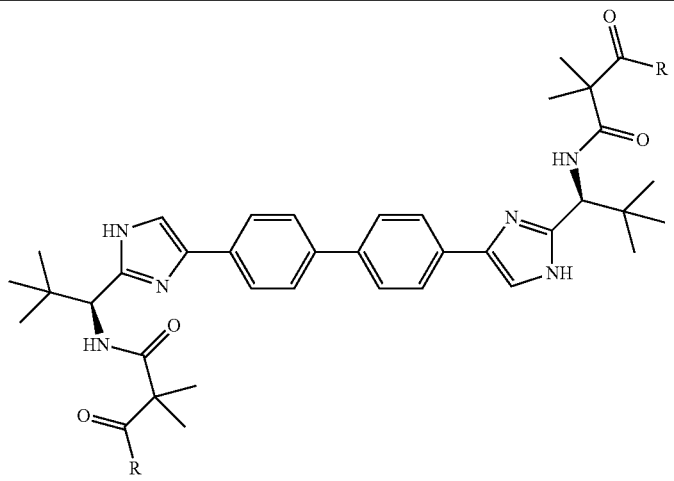
| Example | R | LC-MS Method | Retention Time (min) | Obs. Mass ion (M + H)+ | Salt |
|---|---|---|---|---|---|
| W-147** | [piperidine with F, and dimethylamine] | W-2 | 1.45 | 798.0 | Free base |
| W-148 | [2-methylpiperidine] | W-2 | 1.61 | 848.0 | Free base |
| W-151 | [(3R)-3-hydroxypyrrolidine] | W-2 | 1.20 | 823.7 | Free base |
| W-152 | [(3S)-3-hydroxypyrrolidine] | W-2 | 1.73 | 823.7 | Free base |
| W-153 | [3-azabicyclo[3.1.0]hexane] | W-2 | 1.50 | 815.7 | Free base |
| W-154 | [2,6-dimethylmorpholine] | W-2 | 1.51 | 879.8 | Free base |
| W-155 | [bicyclo[1.1.1]pentylamine] | W-2 | 1.71 | 815.8 | Free base |

-continued

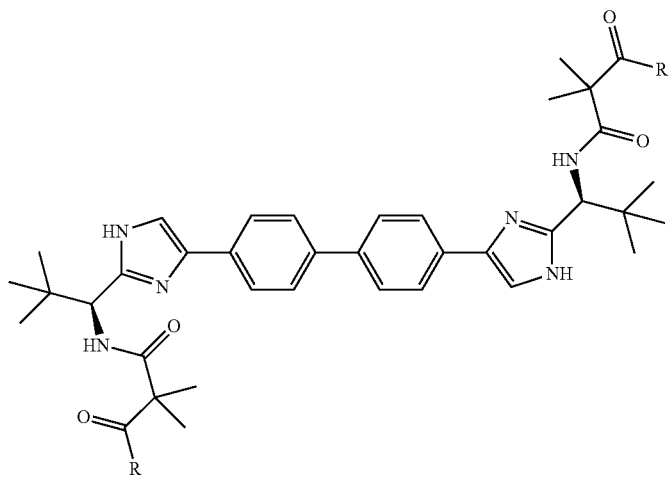

| Example | R | LC-MS Method | Retention Time (min) | Obs. Mass ion (M + H)+ | Salt |
|---|---|---|---|---|---|
| W-156 | (N-ethyl-N-(cyclopropylmethyl)amino) | W-2 | 1.68 | 847.8 | Free base |
| W-157 | (N-ethyl-N-(2-methoxyethyl)amino) | W-2 | 1.48 | 855.8 | Free base |
| W-158 | (N-ethyl-N-(2-cyanoethyl)amino) | W-2 | 1.50 | 845.7 | Free base |

*W-146 was isolated as a minor product during purification of Example W-141.
**W-147 was isolated as a minor product during purification of Example W-142.

Example W-179

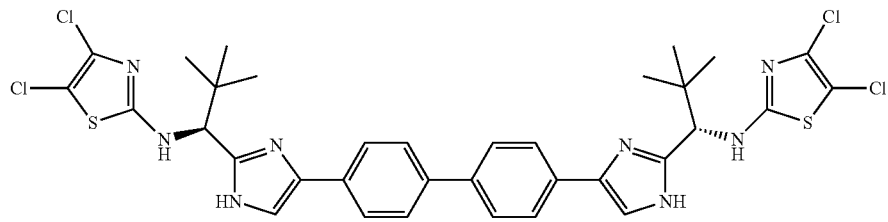 [SMILES: CC(C)(C)[C@H](Nc1nc(Cl)c(Cl)s1)c1nc(-c2ccc(-c3ccc(-c4c[nH]c([C@@H](Nc5nc(Cl)c(Cl)s5)C(C)(C)C)n4)cc3)cc2)c[nH]1]

To a vial containing (1S,1'S)-1,1'-(4,4'-([1,1'-biphenyl]-4,4'-diyl)bis(1H-imidazole-4,2-diyl))bis(2,2-dimethylpropan-1-amine), 4 HCl (50 mg, 0.083 mmol), 4,5-dichloro-2-fluorothiazole (57.1 mg, 0.332 mmol), N,N-Di-iso-propylethylamine (0.110 mL, 0.664 mmol) and DMA (1 mL) was heated in a microwave system at 65° C. for 4 h. Purified by prep-HPLC (CH₃CN—H₂O—NH₄OAc) to afford the desired product as a white solid. LC/MS (Cond. W-2): [M+H]+ 761.2, Rt=2.25 min.

The following Examples in the table were made by the same method as described in Example W-179. The resulting products were purified by preparatory HPLC (CH₃CN/H₂O/NH₄OAc) and obtained as their corresponding free bases.

| Example | Ar | LC-MS Method | Retention Time (min) | Obs. Mass ion (M + H)+ | Salt |
|---|---|---|---|---|---|
| W-180 | (thiazole with CF₃ and Cl) | W-2 | 2.22 | 827.2 | Free base |
| W-183 | (benzothiazole) | W-2 | 2.25 | 723.3 | Free base |

Example W-186

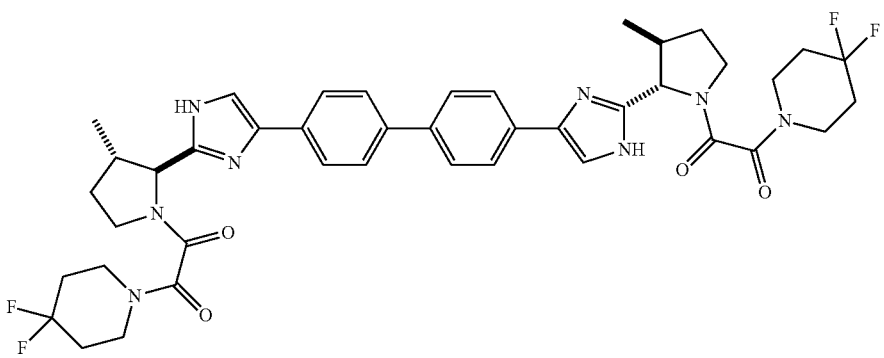

To a mixture of 4,4'-bis(2-((2S,3S)-3-methylpyrrolidin-2-yl)-1H-imidazol-4-yl)-1,1'-biphenyl, 4 HCl (15 mg, 0.025 mmol), 2-(4,4-difluoropiperidin-1-yl)-2-oxoacetic acid (10.17 mg, 0.053 mmol), HATU (20.01 mg, 0.053 mmol) in DMA (0.5 mL) was added DIEA (0.031 mL, 0.175 mmol). The formed light yellow solution was stirred at rt for 2 h. The reaction mixture was directly purified by a preparatory HPLC (CH₃CN/H₂O/NH₄OAc) system to yield Example W-186. LC/MS (Cond. W-2): [M+H]⁺ 803.4, R$_t$=1.66 min.

Example W-187

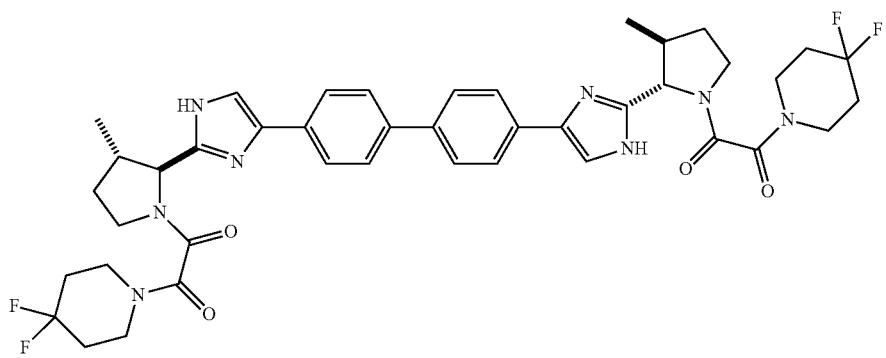

Example W-187 was isolated and identified as an atropisomer of Example W-186 during the purification of the latter. LC/MS (Cond. W-2): [M+H]$^+$ 803.4, $R_t$=1.66 min.

Example W-188

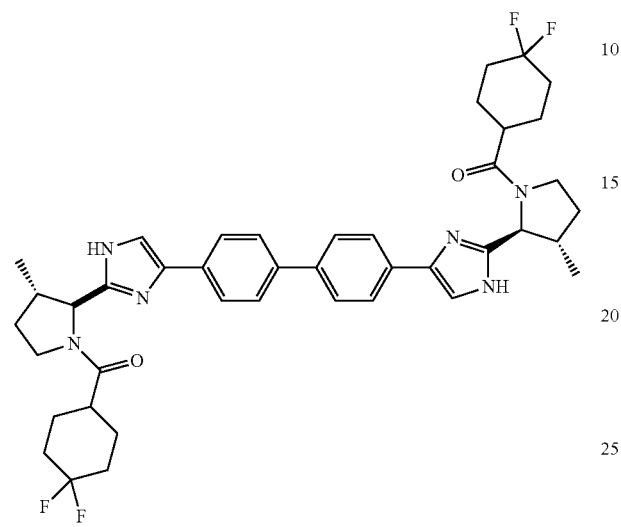

Example W-188 was prepared by the same method as described in the synthesis of Example W-186, except using 4,4-difluorocyclohexanecarboxylic acid instead. LC/MS (Cond. W-2): [M+H]$^+$ 745.5, $R_t$=1.54 min.

Example W-189

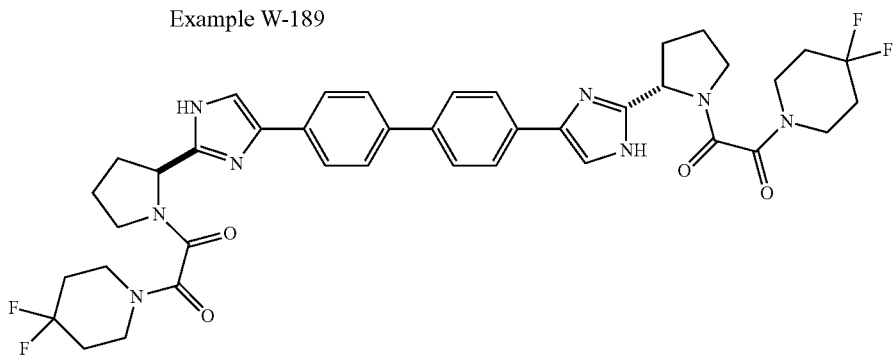

To a mixture of 4,4'-bis(2-((S)-pyrrolidin-2-yl)-1H-imidazol-4-yl)-1,1'-biphenyl, 4 HCl (30 mg, 0.053 mmol), 2-(4,4-difluoropiperidin-1-yl)-2-oxoacetic acid (21.33 mg, 0.110 mmol), HATU (42.0 mg, 0.110 mmol) in DMA (1 mL) was added DIEA (0.064 mL, 0.368 mmol). The formed light yellow solution was stirred at rt for 2 h. The reaction mixture was directly purified by a preparatory HPLC (CH$_3$CN/H$_2$O/ NH$_4$OAc) system to yield Example W-189. LC/MS (Cond. W-2): [M+H]$^+$ 775.3, $R_t$=1.46 min.

Example B1

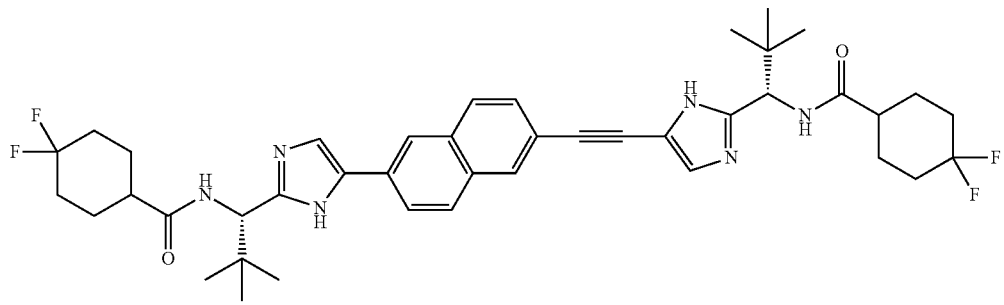 [SMILES: CC(C)(C)[C@H](NC(=O)C1CCC(F)(F)CC1)c1ncc(C#Cc2ccc3cc(-c4cnc([C@@H](NC(=O)C5CCC(F)(F)CC5)C(C)(C)C)[nH]4)ccc3c2)[nH]1]

Example B1

Step a

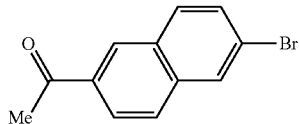

To a solution of 2-bromonaphthalene (25 g, 121 mmol) and AlCl₃ (19.32 g, 145 mmol) in nitrobenzene (227 mL) was added AcCl (10.78 mL, 152 mmol) at 10° C. The reaction mixture was heated to 40° C. for 18 h. Then the reaction mixture was cooled to rt and poured into ice containing con. HCl (400 mL). The reaction mixture was extracted with EtOAc and washed with 1.5; N HCl solution, brine, dried over Na₂SO₄ and concentrated. The crude was purified by column chromatography (Silica gel 60-120, 3-5% EtOAc/petroleum ether) to obtain bromide B-1a (11 g) as light brown solid. $^1$H NMR (CDCl₃), δ=7.26 ppm, 400 MHz): δ 8.43 (s, 1H), 8.08-8.04 (m, 2H), 7.84 (d, J=8.8, 1H), 7.81 (d, J=8.8, 1H), 7.64 (dd, J=8.8, 2.0, 1H), 2.72 (s, 3H).

Example B1

Step b

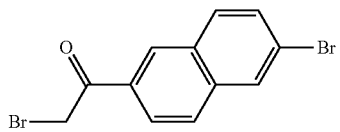 [SMILES: O=C(CBr)c1ccc2cc(Br)ccc2c1]

To a solution of bromide B-1a (5.0 g, 20.07 mmol) in DCM (150 mL) was added Br₂ (0.827 mL, 16.06 mmol) in dioxane (50 mL) over 10 minutes at 10° C. and the reaction mixture was stirred at 10° C. for 2 h. The reaction mixture was quenched with 10% NaHCO₃ and extracted with DCM. The organic layer was dried over Na₂SO₄ and concentrated to obtain crude dibromide B-1b (7.0 g) as a yellow solid. $^1$H NMR (CDCl₃), δ=7.26 ppm, 400 MHz): δ 8.48 (s, 1H), 8.07-8.04 (m, 2H), 7.85 (d, J=8.8, 1H), 7.84 (d, J=8.8, 1H), 7.66 (dd, J=8.8, 2.0, 1H), 4.55 (s, 2H).

Example B1

Step c

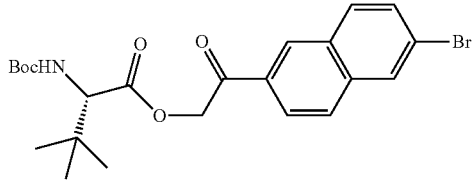 [SMILES: CC(C)(C)OC(=O)N[C@H](C(=O)OCC(=O)c1ccc2cc(Br)ccc2c1)C(C)(C)C]

To a solution of dibromide B-1b (7.0 g, 21.34 mmol) and (S)-2-((tert-butoxycarbonyl)amino)-3,3-dimethylbutanoic acid (4.94 g, 21.34 mmol) in ACN was added DIPEA (7.45 mL, 42.7 mmol) dropwise at 0° C. and the reaction mixture was stirred at rt for 5 h. Then the reaction mixture was concentrated and the crude was diluted with EtOAc. The organic layer was washed with 10% NaHCO₃, brine, dried over Na₂SO₄, filtered and concentrated. The crude was purified by Combiflash Isco (Silica gel, 120 g, Redisep, EtOAc:petroleum ether, 20:80) to obtain ketoester B-1c (9.2 g) as a yellow solid. LC/MS (Condition B-10): R$_f$=2.43 min. $^1$H NMR (CDCl3, δ=7.26 ppm, 400 MHz): δ 8.40 (s, 1H), 8.06 (d, J=1.6, 1H), 7.99 (dd, J=8.8, 1.6, 1H), 7.83 (d, J=8.8, 2H), 7.65 (dd, J=8.8, 1.6, 1H), 5.60 (d, J=16.0, 1H), 5.4 (d, J=16.0, 1H), 5.13 (d, J=9.2, 1H), 4.27 (d, J=9.6, 1H), 1.46 (s, 9H), 1.12 (s, 9H). LC/MS: Anal. Calcd. for [M–H]⁻ C₂₃H₂₇BrNO₅: 477.38; found 478.0.

Example B1

Step d

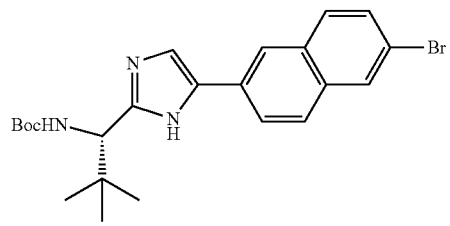 [SMILES: CC(C)(C)OC(=O)N[C@H](c1ncc(-c2ccc3cc(Br)ccc3c2)[nH]1)C(C)(C)C]

A reaction mixture of ketoester B-1c (9.2 g, 19.23 mmol) and NH₄OAc (14.82 g, 192 mmol) in xylene (75 mL) was heated at 130° C. for 18 h. Then the reaction mixture was cooled to rt and volatile components were evaporated. Then the residue was diluted with DCM and washed with 10% NaHCO₃. The organic layer was dried over Na₂SO₄, filtered and concentrated. The crude was purified by Combiflash Isco (Silica gel, 120 g, Redisep, MeOH:CHCl₃, 2:98) to obtain bromide B-1d (6 g) as a yellow solid. LC/MS (Condition B-10): R$_f$=2.34 min. $^1$H NMR (CDCl₃, δ=7.26 ppm, 400 MHz): δ 10.05 (br s, 1H), 8.15 (br s, 1H), 7.94 (br s, 1H), 7.86-7.40 (m, 4H), 7.16 (br s, 1H), 5.68 (d, J=7.6, 1H), 4.65 (br s, 1H), 1.44 (s, 9H), 1.08 (s, 9H). LC/MS: Anal. Calcd. for [M+H]⁺ C₂₃H₂₈BrN₃O₂: 458.14; found 458.2.

Example B1

Step e

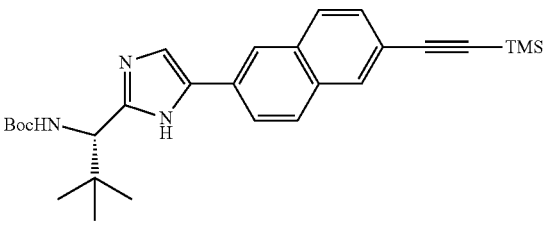 [SMILES: CC(C)(C)OC(=O)N[C@H](c1ncc(-c2ccc3cc(C#C[Si](C)(C)C)ccc3c2)[nH]1)C(C)(C)C]

To a solution of bromide B-1d (2.0 g, 4.36 mmol) and DIPEA (5.33 mL, 30.5 mmol) in DMF (20 mL) was added trimethylsilylacetylene (6.12 mL, 43.6 mmol), CuI (0.415 g, 2.182 mmol) and Pd(TPP)₂Cl₂ (1.102 g, 1.571 mmol) under N₂. After stirring for 10 minutes at rt, the reaction mixture was heated at 90° C. for 12 h. Then the reaction mixture was diluted with EtOAc, washed with saturated NH₄Cl, water and brine. The organic layer was filtered through diatomaceous earth (Celite®) and dried over Na₂SO₄, filtered and concentrated. The crude was purified by Combiflash Isco (Silica gel, 40 g, Redisep, EtOAc:petroleum ether, 20:80) to obtain trimethylsilyl alkyne B-1e (850 mg) as a yellow solid. LC/MS (Condition B-10): $R_t$=2.72 min. ¹H NMR (CDCl₃, δ=7.26 ppm, 400 MHz): δ 9.28 (br s, 1H), 8.22 (br s, 1H), 7.95 (br s, 1H), 7.78-7.00 (m, 5H), 5.52 (br s, 1H), 4.53 (br s, 1H), 1.43 (s, 9H), 1.07 (s, 9H), 0.28/0.25 (s, 9H). LC/MS: Anal. Calcd. for [M-Boc]⁻ C₂₃H₂₈N₃Si: 374.21; found 374.2.

Example B1

Step f

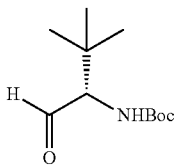

To a solution of (S)-tert-butyl (1-hydroxy-3,3-dimethylbutan-2-yl)carbamate (10 g, 46.0 mmol) in DCM (50 mL) was added Dess-Martin periodinane (39.0 g, 92 mmol) portion wise at 0° C. and the reaction mixture was stirred at rt for 2 h. The reaction mixture was quenched with 10% NaHCO₃, diluted with DCM. The organic layer was separated and washed with 10% NaHCO₃. Then the organic layer was filtered through diatomaceous earth (Celite®), washed with DCM. The combined filtrate was dried over Na₂SO₄ and concentrated. The crude was dissolved in diethyl ether and again filtered through diatomaceous earth (Celite®), washed with diethyl ether. The combined filtrate was concentrated and dried to obtain aldehyde B-1f (10 g) as a white solid. ¹H NMR (CDCl₃, δ=7.26 ppm, 400 MHz): δ 9.82 (s, 1H), 5.13 (br s, 1H), 4.17 (d, J=8.4, 1H), 1.44 (s, 9H), 1.04 (s, 9H).

Example B1

Step g

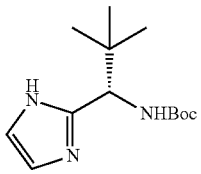 [SMILES: CC(C)(C)OC(=O)N[C@H](c1ncc[nH]1)C(C)(C)C]

To a solution of aldehyde B-1f (10 g, 46.4 mmol) in MeOH (150 mL) was added glyoxal hydrate (4 mL, 46.4 mmol) and the reaction mixture was stirred for 10 minutes at 10° C. Then NH₄OH (6 mL, 154 mmol) was added and the reaction mixture was stirred at 10° C. for 24 h. The volatile components were evaporated and the resulting residue was dissolved in EtOAc. The organic layer was washed with water, brine, dried with Na₂SO₄ and concentrated. The crude was purified by Combiflash Isco (Silica gel, 120 g, Redisep, MeOH:CHCl₃, 2:98) to obtain imidazole B-1g (9.5 g) as a white solid. LC/MS (Condition B-10): $R_t$=1.36 min. ¹H NMR (CDCl₃, δ=7.26 ppm, 400 MHz): δ 10.21 (br s, 1H), 7.00-6.86 (m, 2H), 5.64 (d, J=10.0, 1H), 4.62 (d, J=10.0, 1H), 1.42 (s, 9H), 0.99 (s, 9H). LC/MS: Anal. Calcd. for [M+H]⁺ C₁₃H₂₄N₃O₂: 254.18; found 254.2.

Example B1

Step h

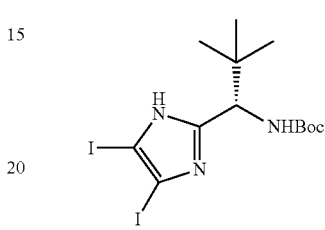

To a solution of imidazole B-1g (7.6 g, 30.0 mmol) in DCM (250 mL) was added NIS (13.50 g, 60.0 mmol) at 0° C. and stirred for 2 h while warming to rt. The organic layer was washed with 10% NaHCO₃, brine, dried over Na₂SO₄, filtered and concentrated. The crude was purified by Combiflash Isco (Silica gel, 120 g, Redisep, EtOAc/petroleum ether, 10:90) to obtain diiodide B-1h (13 g) as a white solid. LC/MS (Condition B-10): $R_t$=1.89 min. ¹H NMR (MeOD, δ=3.34 ppm, 400 MHz): δ 4.51 (br s, 1H), 1.45 (s, 9H), 0.94 (s, 9H). LC/MS: Anal. Calcd. for [M+H]⁺ C₁₃H₂₂I₂N₃O₂: 506.13; found 506.0.

Example B1

Step i

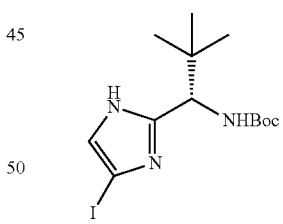

To a solution of diiodide B-1h (13 g, 25.7 mmol) in EtOH (62 mL) and water (62 mL) was added Na₂SO₃ (64.9 g, 515 mmol) and the reaction mixture was refluxed for 17 h. Then the volatile components were evaporated and the resulting residue was dissolved in EtOAc. The organic layer was washed with water, brine, and dried over Na₂SO₄, filtered and concentrated. The crude was purified by Combiflash Isco (Silica gel, 120 g, Redisep, EtOAc/petroleum ether, 10:90) to obtain iodide B-1i (6 g) as a white solid. LC/MS (Condition B-10): $R_t$=1.71 min. ¹H NMR (CDCl₃, δ=7.26 ppm, 400 MHz): δ 10.57 (br s, 1H), 6.89 (s, 1H), 5.70 (d, J=9.6, 1H), 4.57 (d, J=9.6, 1H), 1.42 (s, 9H), 0.98 (s, 9H). LC/MS: Anal. Calcd. for [M+H]⁺ C₁₃H₂₃IN₃O₂: 380.08; found 380.0.

Example B1

Step j-1 & j-2

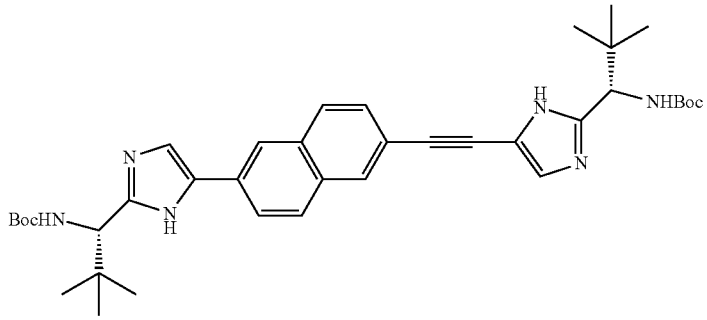

B1 j-1

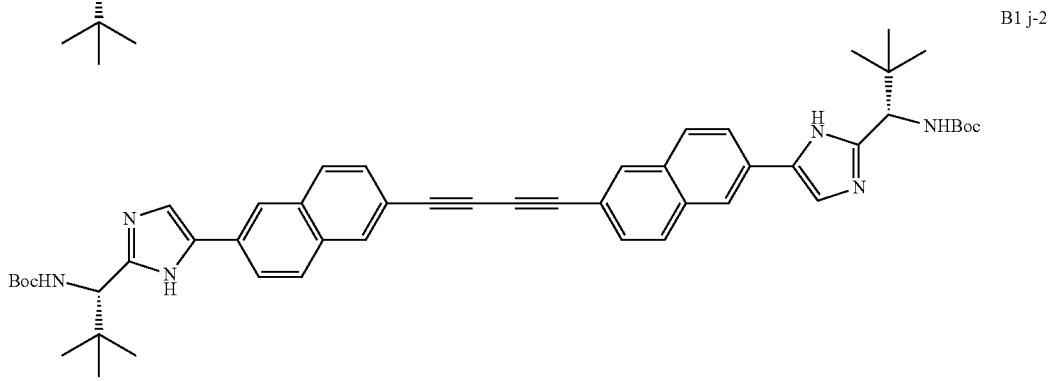

B1 j-2

To a solution of trimethylsilyl alkyne B-1e (700 mg, 1.472 mmol) and iodide B-1i (614 mg, 1.619 mmol) in DMF (50 mL) was added TEA (0.615 mL, 4.41 mmol), CuI (28.0 mg, 0.147 mmol) and Pd(TPP)$_2$Cl$_2$ (103 mg, 0.147 mmol). Then the reaction mixture was heated to 70° C., slowly added 1 M TBAF in THF (1.472 mL, 1.472 mmol) and stirred at 70° C. for 10 h. The reaction mixture was concentrated and diluted with EtOAc, washed with 10%, saturated NH$_4$Cl and brine. The organic layer was filtered through diatomaceous earth (Celite®), the filtrate was dried over Na$_2$SO$_4$, filtered and concentrated. The residue was purified by reverse phase HPLC (ACN/water/NH$_4$OAc) to obtain carbamate B-1j-1 (380 mg) as a light brown solid. LC/MS (Condition B-9): R$_t$=2.21 min. $^1$H NMR (MeOD, δ=3.34 ppm, 400 MHz): δ 8.18 (br s, 1H), 8.01 (s, 1H), 7.89-7.87 (m, 3H), 7.55 (dd, J=8.8, 1.6, 1H), 7.52 (br s, 1H), 7.34 (br s, 1H), 4.67 (s, 1H), 4.58 (s, 1H), 1.47 (s, 18H), 1.02/0.99 (s, 18H). LC/MS: Anal. Calcd. for [M−H]$^-$ C$_{38}$H$_{49}$N$_6$O$_4$: 653.39; found 653.3. The symmetric dimer B-1j-2 (130 mg) was also isolated as a light brown solid. LC/MS (Condition B-9): R$_t$=2.10 min. $^1$H NMR (MeOD, δ=3.34 ppm, 400 M Hz): δ 8.21 (br s, 2H), 8.11 (s, 2H), 7.94-7.87 (m, 6H), 7.57 (dd, J=8.4, 1.2, 2H), 7.55 (br s, 2H), 4.68 (s, 2H), 1.47 (s, 18H), 1.03 (s, 18H). LC/MS: Anal. Calcd. for [M+H]$^+$ C$_{50}$H$_{52}$N$_6$O$_4$: 805.44; found 805.4.

Example B1

Step k

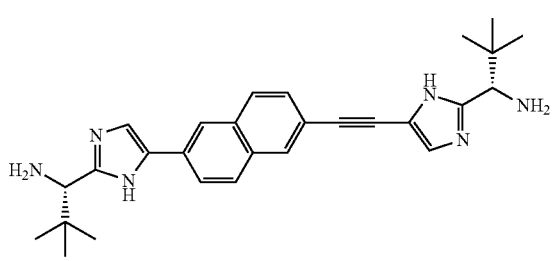 [SMILES: CC(C)(C)[C@H](N)c1ncc(C#Cc2ccc3cc(-c4cnc([C@@H](N)C(C)(C)C)[nH]4)ccc3c2)[nH]1]

To a solution of carbamate B-1j-1 (200 mg, 0.305 mmol) in MeOH (10 mL) was added 4 N HCl in MeOH (20 mL) at 0° C. and the reaction mixture was stirred at rt for 12 h. Then the reaction mixture was concentrated and dried to obtain HCl salt of B-1k (210 mg) as a pale yellow solid. LC/MS (Condition B-10): R$_t$=1.44 min. $^1$H NMR (MeOD, δ=3.34 ppm, 400 MHz): δ 8.47 (br s, 1H), 8.16-8.14 (m, 2H), 8.04-8.01 (m, 3H), 7.67-7.66 (m, 2H), 4.73 (s, 1H), 4.36 (s, 1H), 1.23 (s, 9H), 1.14 (s, 9H). LC/MS: Anal. Calcd. for [M+H]$^+$ C$_{28}$H$_{35}$N$_6$: 455.28; found 455.3.

Example B1

To a solution of amine B-1k (4HCl) (80 mg, 0.152 mmol) and 4,4-difluorocyclohexanecarboxylic acid (52.3 mg, 0.318 mmol) in DMF (5 mL) was added DIPEA (0.106 mL, 0.607 mmol) at 0° C. followed by HATU (118 mg, 0.311 mmol). The reaction mixture was stirred at rt for 2 h, then the volatile components were removed. The resulting residue was dissolved in DCM, washed with saturated NH$_4$Cl, 10% NaHCO$_3$, brine, dried over Na$_2$SO$_4$ and concentrated. The crude was purified by reverse phase HPLC (ACN/water/TFA) to afford TFA salt of Example B1 (80 mg) as a white solid. HPLC (Condition B-1 and B-2): >97% homogeneity index. LC/MS (Condition B-10): R$_t$=2.06 min. $^1$H NMR (MeOD, δ=3.34 ppm, 400 MHz): δ 8.29 (br s, 1H), 8.17 (br s, 1H), 8.06 (d, J=8.8, 1H), 8.01 (d, J=8.8, 1H), 7.99 (s, 1H), 7.89 (dd, J=8.8, 2.0, 1H), 7.68 (dd, J=8.4, 1.6, 1H), 7.64 (s, 1H), 4.99-4.80 (obscured, 2H), 2.63-2.55 (m, 2H), 2.19-2.08 (m, 4H), 2.00-1.72 (m, 12H), 1.17 (s, 9H), 1.09 (s, 9H). LC/MS: Anal. Calcd. for [M−H]$^-$ C$_{42}$H$_{49}$N$_6$O$_2$: 745.39; found 745.4.

Example B2-5A

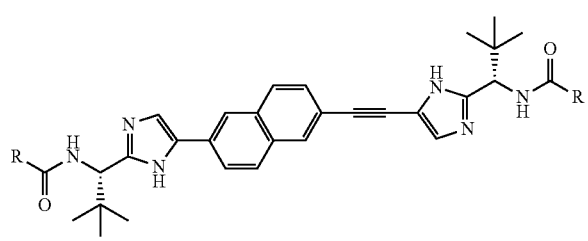

Example B2-5A (TFA salt) were prepared in a similar fashion from HCl salt of B-1k and pivalic acid/3-chlorobenzoic acid/2-(4,4-difluoropiperidin-1-yl)-2-oxoacetic acid/1-((methoxycarbonyl)(methyl)amino)cyclopropanecarboxylic acid/2-(4,4-difluoro-1-hydroxycyclohexyl)-2-methylpropanoic acid according to the procedure described for Example B1.

| Example # | R | LC & LC/MS data |
|---|---|---|
| B2 | *tert-butyl* | LC (Condition B-1 and B-2): >95% homogeneity index. LC/MS (Condition B-10): $R_t$ = 2.08 min. LC/MS: Anal. Calcd. for [M − H]⁻ $C_{38}H_{49}N_6O_2$: 621.4; found 621.3. |
| B3 | *3-chlorophenyl* | LC (Condition B-1 and B-2): >96% homogeneity index. LC/MS (Condition B-10): $R_t$ = 2.33 min. LC/MS: Anal. Calcd. for [M − H]⁻ $C_{42}H_{39}Cl_2N_6O_2$: 729.26; found 729.2. |
| B4 | *4,4-difluoropiperidinyl oxoacetyl* | LC (Condition B-1 and B-2): >98% homogeneity index. LC/MS (Condition B-14): $R_t$ = 1.97 min. LC/MS: Anal. Calcd. for [M + H]⁺ $C_{42}H_{49}F_4N_8O_4$: 805.37; found 805.6. |
| B5 | *1-((methoxycarbonyl)(methyl)amino)cyclopropyl* | LC (Condition B-1 and B-2): >98% homogeneity index. LC/MS (Condition B-14): $R_t$ = 1.95 min. LC/MS: Anal. Calcd. for [M − H]⁻ $C_{42}H_{51}N_8O_6$: 763.40; found 763.4. |
| B5A | *2-(4,4-difluoro-1-hydroxycyclohexyl)-2-methylpropyl* | LC (Condition B-1 and B-2): >95% homogeneity index. LC/MS (Condition B-17): $R_t$ = 2.45 min. LC/MS: Anal. Calcd. for [M − H]⁻ $C_{48}H_{61}F_4N_6O_4$: 861.48; found 861.4. |

Example B5B

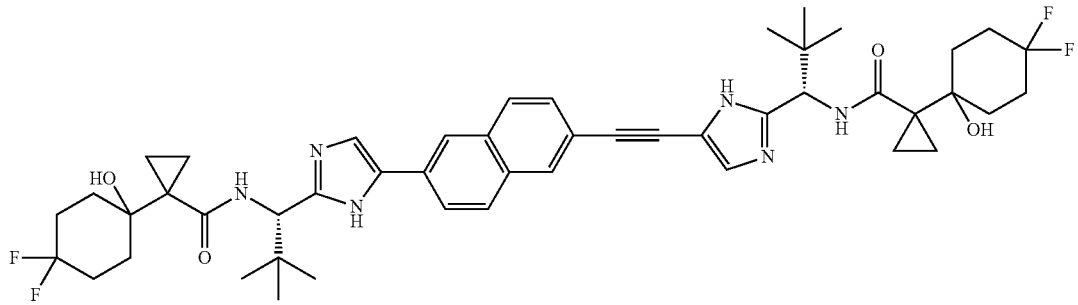 [SMILES: CC(C)(C)[C@H](NC(=O)C1(C2(O)CCC(F)(F)CC2)CC1)c1ncc(C#Cc2ccc3cc(-c4cnc([C@@H](NC(=O)C5(C6(O)CCC(F)(F)CC6)CC5)C(C)(C)C)[nH]4)ccc3c2)[nH]1]

To a solution of amine B-1k (4HCl) (20 mg, 0.033 mmol) and 1-(4,4-difluoro-1-hydroxycyclohexyl)cyclopropanecarboxylic acid (15.40 mg, 0.070 mmol) in DMF (5 mL) was added, DIPEA (0.023 mL, 0.133 mmol) at 0° C. followed by BOP (30.2 mg, 0.068 mmol). After being stirred for 2 h at room temperature, the volatile components were removed under reduced pressure. The resulting residue was dissolved in DCM (50 mL), washed with saturated NH₄Cl solution (50 mL), 10% NaHCO₃ solution (50 mL), brine (25 mL), dried over Na₂SO₄ and concentrated in vacuo. The crude was purified by reverse phase HPLC (ACN/water/TFA) to afford TFA salt of B5B (5.2 mg) as a white solid. HPLC (Condition B-1 and B-2): >97% homogeneity index. LC/MS (Condition B-18): $R_t$=2.31 min. LC/MS: Anal. Calcd. For [M+H]⁺ $C_{48}H_{59}F_4N_6O_4$: 859.45; found 859.4.

Example B6

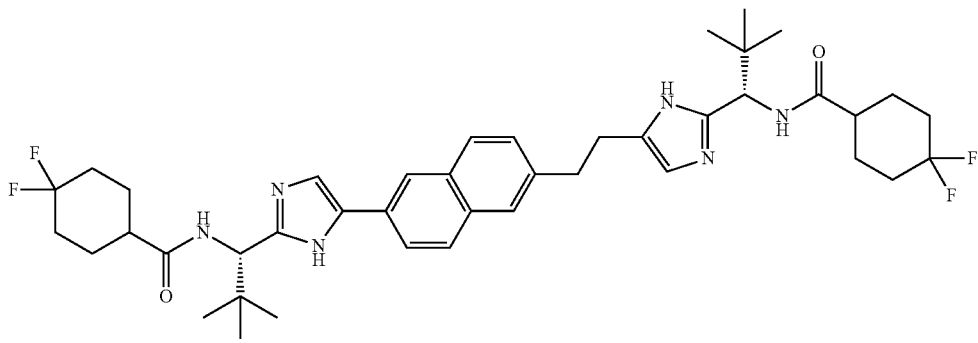 [SMILES: CC(C)(C)[C@H](NC(=O)C1CCC(F)(F)CC1)c1ncc(CCc2ccc3cc(-c4cnc([C@@H](NC(=O)C5CCC(F)(F)CC5)C(C)(C)C)[nH]4)ccc3c2)[nH]1]

To a solution of Example B1 (25 mg, 0.033 mmol) in MeOH (5 mL) was added Pd/C (17.81 mg, 0.017 mmol) and the reaction mixture was stirred at rt for 2 h under $H_2$. The reaction mixture was filtered through diatomaceous earth (Celite®) and washed with MeOH. The filtrate was concentrated and the crude was purified by reverse phase HPLC (ACN/water/TFA) to afford TFA salt of Example B6 (20 mg) as an off-white solid. HPLC (Condition B-1 and B-2): >97% homogeneity index. LC/MS (Condition B-10): $R_t$=2.00 min. $^1$H NMR (MeOD, δ=3.34 ppm, 400 MHz): δ 8.20 (br s, 1H), 7.92 (d, J=8.4, 1H), 7.89 (d, J=8.4, 1H), 7.84 (br s, 1H), 7.79 (dd, J=8.4, 1.6, 1H), 7.64 (br s, 1H), 7.44 (dd, J=8.4, 1.6, 1H), 7.14 (s, 1H), 4.94 (s, 1H), 4.72 (s, 1H), 3.21-3.12 (m, 4H), 2.61-2.50 (m, 2H), 2.15-2.00 (m, 4H), 1.90-1.62 (m, 12H), 1.13 (s, 9H), 1.00 (s, 9H). LC/MS: Anal. Calcd. for [M+H]$^+$ $C_{42}H_{55}F_4N_6O_2$: 751.42; found 751.4.

Example B7-9

Step a

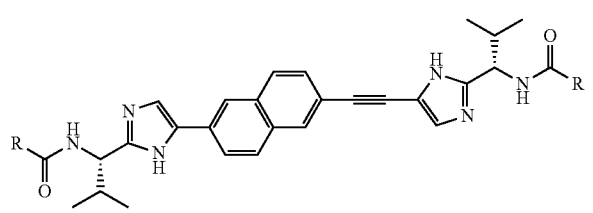

Bromide B7-9a was prepared in a similar fashion from dibromide B-1b and (S)-2-((tert-butoxycarbonyl)amino)-3-methylbutanoic acid according to the procedure described for the preparation of bromide B-1d. LC/MS (Condition B-9): $R_t$=1.83 min. LC/MS: Anal. Calcd. for [M+H]$^+$ $C_{22}H_{27}BrN_3O_2$: 444.12; found 444.0.

Example B7-9

Step b

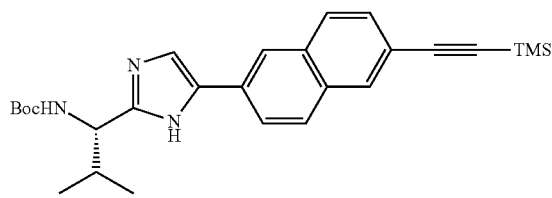

Trimethylsilyl alkyne B7-9b was prepared in a similar fashion from bromide B7-9a according to the procedure described for the preparation of trimethylsilyl alkyne B-1e. LC/MS (Condition B-9): $R_t$=2.19 min. LC/MS: Anal. Calcd. for [M+H]$^+$ $C_{27}H_{36}N_3O_2Si$: 462.25; found 462.2.

Example B7-9

Step c

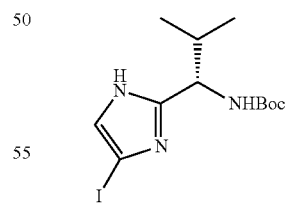

Iodide B7-9c was prepared in a similar fashion starting from (S)-tert-butyl (1-hydroxy-3-methylbutan-2-yl)carbamate according to the procedure described for the preparation of iodide B-1i. LC/MS (Condition B-13): $R_t$=1.84 min. $^1$H NMR (CDCl$_3$, δ=7.26 ppm, 400 MHz): δ 10.29 (br s, 1H), 6.97 (s, 1H), 5.34 (br s, 1H), 4.28 (br s, 1H), 2.38-2.32 (m, 1H), 1.42 (s, 9H), 0.99 (d, J=6.8, 3H), 0.85 (d, J=6.4, 3 H). LC/MS: Anal. Calcd. for [M+H]$^+$ $C_{12}H_{21}IN_3O_2$: 366.06; found 366.2.

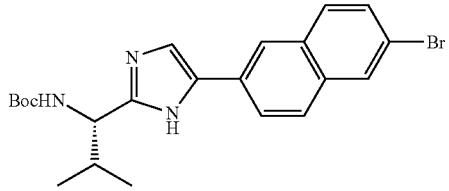 [SMILES: CC(C)[C@H](NC(=O)OC(C)(C)C)c1ncc(-c2ccc3cc(Br)ccc3c2)[nH]1]

Example B7-9

Example B7-9 (TFA salt) were prepared in a similar fashion starting from trimethylsilyl alkyne B7-9b and iodide B7-9c according to the procedure described for the preparation Example B1-3.

| Example # | R | LC & LC/MS data |
|---|---|---|
| B7 | 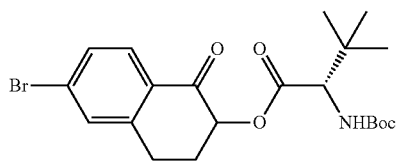 (4,4-difluorocyclohexyl) | LC (Condition B-1 and B-5): >96% homogeneity index. LC/MS (Condition B-9): $R_t$ = 1.78 min. LC/MS: Anal. Calcd. for $[M + H]^+$ $C_{40}H_{47}F_4N_6O_2$: 719.36; found 719.2. |
| B8 | (tert-butyl) | LC (Condition B-1 and B-4): >96% homogeneity index. LC/MS (Condition B-9): $R_t$ = 1.77 min. LC/MS: Anal. Calcd. for $[M + H]^+$ $C_{36}H_{47}N_6O_2$: 595.37; found 595.2. |
| B9 | (3-chlorophenyl) | LC (Condition B-1 and B-8): >96% homogeneity index. LC/MS (Condition B-9): $R_t$ = 1.96 min. LC/MS: Anal. Calcd. For $[M + H]^+$ $C_{40}H_{37}Cl_2N_6O_2$: 704.66; found 704.0. |

Example B10

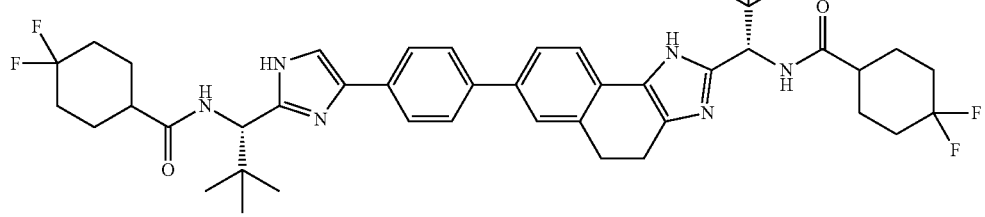

Example B10

Step a

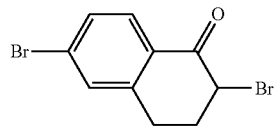

To a solution of 6-bromo-3,4-dihydronaphthalen-1(2H)-one (2.0 g, 8.89 mmol) in DCM (100 mL) was added HBr (0.048 mL, 0.400 mmol) at 0° C. followed by $Br_2$ (0.494 mL, 9.60 mmol) in 5 mL of DCM over 10 minutes. After stirring at rt for 2 h, the reaction mixture was quenched with 10% $NaHCO_3$ and extracted with DCM. The organic layer was dried over $Na_2SO_4$, filtered, concentrated and dried to obtain dibromide B-10a (2.7 g) as a brown solid. LC/MS (Condition B-10): Rt=2.05 min. LC/MS: Anal. Calcd. for $[M+H]^+$ $C_{10}H_8Br_2O$: 304.98; found 305.0.

Example B10

Step b

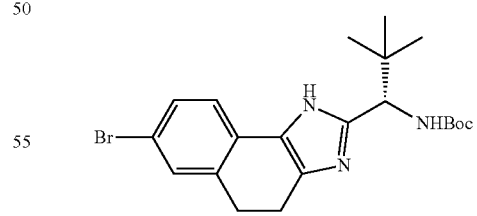

To a solution of dibromide B-10a (2.7 g, 8.88 mmol) and (S)-2-((tert-butoxycarbonyl)amino)-3,3-dimethylbutanoic acid (2.054 g, 8.88 mmol) in ACN (50 mL) was added DIPEA (3.10 mL, 17.76 mmol) drop wise at 0° C. and the reaction mixture was stirred at 0° C. for 10 minutes then heated to 50° C. for 10 h, the volatile components were removed. The resulting residue was dissolved in EtOAc and washed with 10% $NaHCO_3$, brine, dried over $Na_2SO_4$, filtered and concentrated. The crude was purified by Combiflash Isco (Silica gel, 120 g, Redisep, EtOAc/petroleum ether, 25:75) to obtain ketoester B-10b (1.9 g) as a mixture of two diastereomers. LC/MS (Condition B-10): $R_t$=2.37 min. LC/MS: Anal. Calcd. for $[M-H_2O]^-$ $C_{21}H_{27}BrNO_5$: 453.35; found 454.0.

Example B10

Step c

A mixture of ketoester B-10b (3.8 g, 8.36 mmol), $NH_4OAc$ (3.22 g, 41.8 mmol) and TEA (1.749 mL, 12.55 mmol) in xylene (50 mL) was heated at 130° C. for 18 h. After cooling to rt, the volatile components were removed. Then the residue was diluted with DCM, washed with 10% $NaHCO_3$ solution, dried over $Na_2SO_4$, filtered and concentrated. The crude was purified by Combiflash Isco (Silica gel, 120 g, Redisep, $MeOH/CHCl_3$, 2:95) to obtain bromide B-10c (3.4 g) as a brown solid. $^1$H NMR (CDCl$_3$, δ=7.26 ppm, 400 MHz): δ 10.51/9.45 (br s, 1H), 7.54-6.53 (m, 3H), 5.65-5.57 (m, 1H), 4.60-4.48 (m, 1H), 2.90-2.42 (m, 4H), 1.44 (s, 9H), 1.01 (s, 9H).

Example B10

Step d

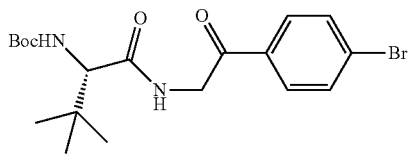 [SMILES: CC(C)(C)OC(=O)N[C@H](C(=O)NCC(=O)c1ccc(Br)cc1)C(C)(C)C]

To a solution of 2-amino-1-(4-bromophenyl)ethanone hydrochloride (10 g, 39.9 mmol) and (S)-2-((tert-butoxycarbonyl)amino)-3,3-dimethylbutanoic acid (10.16 g, 43.9 mmol) in DMF (150 mL) was added HATU (16.70 g, 43.9 mmol) followed by DIPEA (20.91 mL, 120 mmol) at 0° C. and the reaction mixture was stirred at rt for 2 h. Water (500 mL) was added and the reaction mixture was extracted with EtOAc. The organic layer was washed with saturated NH$_4$Cl, 10% NaHCO$_3$, water and brine. The organic layer was dried over Na$_2$SO$_4$ and concentrated. The crude was purified by flash chromatography (Silica gel 60-120, 0.6% MeOH in DCM) to yield ketoamide B-10d (18 g) as off-white solid. LC/MS (Condition B-12): R$_t$=2.09 min. $^1$H NMR (CDCl$_3$, δ=7.26 ppm, 400 MHz): δ 7.89-7.82 (m, 2H), 7.67-7.63 (m, 2H), 6.65 (m, 1H), 5.57 (br s, 1H), 4.86-4.60 (m, 2H), 3.97 (d, J=9.2, 1H), 1.44 (s, 9H), 1.03 (s, 9H). LC/MS: Anal. Calcd. for [M+H]$^+$ C$_{19}$H$_{28}$BrN$_2$O$_4$: 428.33; found 428.1.

Example B10

Step e

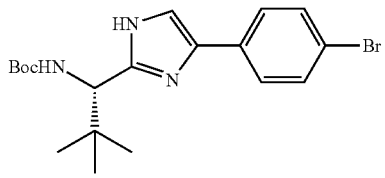 [SMILES: CC(C)(C)OC(=O)N[C@H](c1nc(-c2ccc(Br)cc2)c[nH]1)C(C)(C)C]

A mixture of NH$_4$OAc (16.23 g, 211 mmol) and ketoamide B-10d (18 g, 42.1 mmol) in xylene (125 mL) was heated at 130° C. for overnight. The volatile components were evaporated. The resulting residue was diluted with EtOAc, washed with 10% NaHCO$_3$, water and brine. The organic layer was dried over Na$_2$SO$_4$ and concentrated under reduced pressure. The residue was purified by flash chromatography (Silica gel 60-120, 1% MeOH in CHCl$_3$) to yield bromide B-10e (10.5 g) as an off-white solid. LC/MS (Condition B-14): R$_t$=2.09 min. $^1$H NMR (CDCl$_3$, δ=7.26 ppm, 400 MHz): δ 10.23 (br s, 1H), 7.59 (d, J=8.4, 2H), 7.45 (d, J=8.4, 2H), 7.03 (s, 1H), 5.67 (d, J=9.2, 1H), 4.61 (d, J=9.2, 1H), 1.43 (s, 9H), 1.03 (s, 9H). LC/MS: Anal. Calcd. for [M+H]$^+$ C$_{19}$H$_{22}$BrN$_3$O$_2$: 408.12; found 408.2.

Example B10

Step f

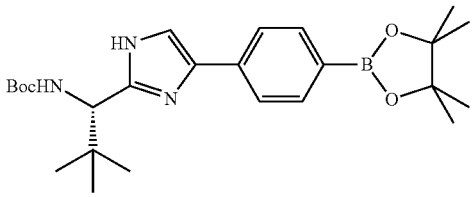 [SMILES: CC(C)(C)OC(=O)N[C@H](c1nc(-c2ccc(B3OC(C)(C)C(C)(C)O3)cc2)c[nH]1)C(C)(C)C]

A mixture of bromide B-10e (3.0 g, 7.35 mmol), bis(pinacolato)diboron (2.99 g, 11.76 mmol) and KOAc (2.163 g, 22.04 mmol) in 1,4-dioxane (30 mL) was purged with N$_2$ for 10 minutes. Then PdCl$_2$(dppf) (0.269 g, 0.367 mmol) was added and the reaction mixture was heated at 100° C. for overnight. The reaction mixture was filtered through diatomaceous earth (Celite®) and washed with. The filtrate was concentrated and the resulting residue was diluted with EtOAc. The organic layer was washed with water, brine, dried over Na$_2$SO$_4$ and concentrated to yield boronate B-10f (3.5 g) as a dark brown solid. LC/MS (Condition B-10): R$_t$=2.14 min. LC/MS: Anal. Calcd. for [M+H]$^+$ C$_{25}$H$_{39}$BN$_3$O$_4$: 456.3; found 456.4.

Example B10

Step g-1 & g-2

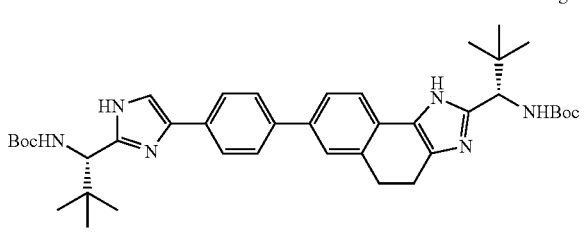

B10 g-1

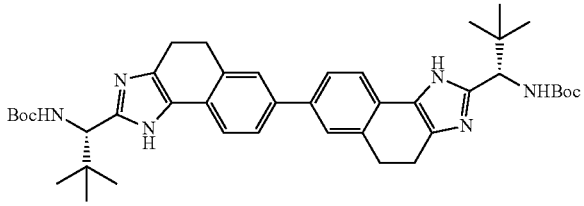

B10 g-2

To a solution of bromide B-10c (1.7 g, 3.91 mmol) in MeOH (40 mL) was added boronate B-10f (1.782 g, 3.91 mmol) followed by K$_2$CO$_3$ (1.082 g, 7.83 mmol) and Pd(Ph$_3$P)$_4$ (0.226 g, 0.196 mmol). The reaction mixture was heated at 65° C. for 12 h. The volatile components were removed and the resulting residue was dissolved in EtOAc and washed with water. The organic layer was separated and the aqueous layer was extracted with EtOAc. The combined organic layer was washed with brine, dried over Na$_2$SO$_4$ and concentrated. The crude was purified by reverse phase HPLC (ACN/water/NH$_4$OAc) to afford carbamate B-10g-1 (1.0 g) as a brown solid. HPLC (Condition B-1 and B-2):

>93% homogeneity index. LC/MS (Condition B-10): $R_t$=2.22 min. $^1$H NMR (MeOD, δ=3.34 ppm, 400 MHz): δ 7.76 (m, 2H), 7.70-7.68 (m, 2H), 7.55-7.54 (m, 3H), 7.39 (br s, 1H), 4.66 (s, 1H), 4.62 (s, 1H), 3.15 (t, J=8.0, 2H), 2.90 (t, J=8.0, 2H), 1.47 (s, 18H), 1.01 (s, 18H). LC/MS: Anal. Calcd. for [M−H]$^-$ $C_{40}H_{53}N_6O_4$: 681.42; found 681.4. The symmetric dimer B-10g-2 (600 mg) was also isolated as a brown solid. HPLC (Condition B-5 and B-6): >96% homogeneity index. LC/MS (Condition B-10): $R_t$=2.26 min. $^1$H NMR (MeOD, δ=3.34 ppm, 400 MHz): δ 7.51 (br s, 6H), 4.61 (s, 2H), 3.13 (t, J=8.0, 4H), 2.88 (t, J=8.0, 4H), 1.47 (s, 18H), 1.01 (s, 18H). LC/MS: Anal. Calcd. for [M−H]$^-$ $C_{42}H_{55}N_6O_4$: 707.44; found 707.4.

Example B10

Step h

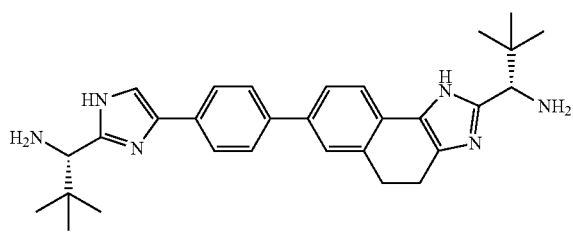 [SMILES: CC(C)(C)[C@H](N)c1nc(-c2ccc(-c3ccc4c(c3)CCc3nc([C@@H](N)C(C)(C)C)[nH]c3-4)cc2)c[nH]1]

HCl salt of amine B-10h (40 mg) was prepared according to the procedure described in Example B1 step k. LC/MS (Condition B-11): $R_t$=1.44 min. $^1$H NMR (MeOD, δ=3.34 ppm, 400 MHz): δ 7.98-7.91 (m, 3H), 7.83-7.76 (m, 3H), 7.70-7.64 (m, 2H), 4.63 (s, 1H), 4.61 (s, 1H), 3.35-3.20 (obscured, 2H), 3.09 (br s, 2H), 1.19 (s, 9H), 1.18 (s, 9H). LC/MS: Anal. Calcd. for [M+H]$^+$ $C_{30}H_{39}N_6$: 483.32; found 483.4.

Example B10

TFA salt of Example B10 (26.6 mg) was prepared according to the procedure described in Example B1. HPLC (Condition B-1 and B-2): >98% homogeneity index. LC/MS (Condition B-12): $R_t$=2.16 min. $^1$H NMR (MeOD, δ=3.34 ppm, 400 MHz): δ 7.89-7.83 (m, 5H), 7.72-6.99 (m, 3H), 4.94 (s, 1H), 4.89 (s, 1H), 3.31-3.27 (m, 2H), 3.08-3.04 (m, 2H), 2.64-2.57 (m, 2H), 2.18-2.04 (m, 4H), 1.98-1.75 (m, 12H), 1.16 (s, 9H), 1.15 (s, 9H). LC/MS: Anal. Calcd. for [M+H]$^+$ $C_{44}H_{55}F_4N_6O_2$: 775.42; found 775.4.

Example B11-13A (TFA salt) were prepared in a similar fashion from HCl salt of amine B-10h and appropriate acids according to the procedure described for Example B10.

| Example # | R | LC & LC/MS data |
|---|---|---|
| B11 | (tert-butyl group) | LC (Condition B-1 and B-2): >98% homogeneity index. LC/MS (Condition B-12): $R_t$ = 2.21 min. LC/MS: Anal. Calcd. for [M + H]$^+$ $C_{40}H_{55}N_6O_2$: 651.43; found 651.9. |
| B12 | (3-chlorophenyl dimethyl) | LC (Condition B-1 and B-2): >97% homogeneity index. LC/MS (Condition B-12): $R_t$ = 2.26 min. LC/MS: Anal. Calcd. for [M + H]$^+$ $C_{44}H_{45}Cl_2N_6O_2$: 760.77; found 760.5. |
| B13 | (piperidine amide) | LC (Condition B-1 and B-2): >96% homogeneity index. LC/MS (Condition B-12): $R_t$ = 1.96 min. LC/MS: Anal. Calcd. for [M + H]$^+$ $C_{44}H_{56}N_8O_4$: 761.44; found 761.4. |
| B13A | (tert-butyl, 4,4-difluoro-1-hydroxycyclohexyl) | LC (Condition B-2 and B-8): >91% homogeneity index. LC/MS (Condition B-17): $R_t$ = 2.48 min. LC/MS: Anal. Calcd. For [M − H]$^-$ $C_{50}H_{65}F_4N_6O_4$: 889.51; found 889.4. |

Example B13B

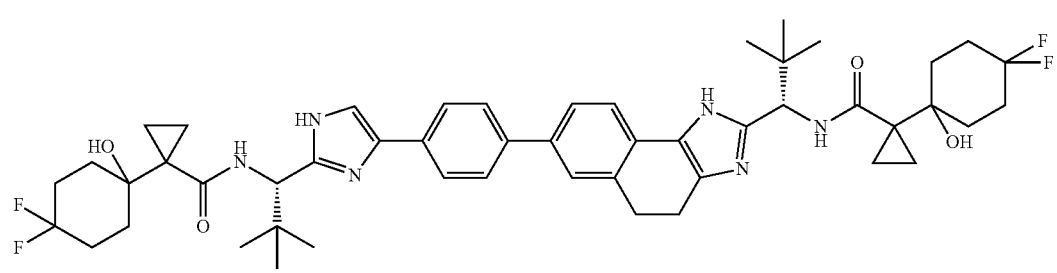 [SMILES: CC(C)(C)[C@H](NC(=O)C1(C2(O)CCC(F)(F)CC2)CC1)c1nc(-c2ccc(-c3ccc4c(c3)CCc3nc([C@@H](NC(=O)C5(C6(O)CCC(F)(F)CC6)CC5)C(C)(C)C)[nH]c3-4)cc2)c[nH]1]

Example B13B (TFA salt) was prepared in a similar fashion from HCl salt of amine B-10h and 1-(4,4-difluoro-1-hydroxycyclohexyl)cyclopropanecarboxylic acid according to the procedure described for Example B5B. HPLC (Condition B-1 and B-2): >97% homogeneity index. LC/MS (Condition B-18): $R_t$=2.33 min. $^1$H NMR (MeOD, δ=3.34 ppm, 400 MHz): δ 7.86-7.81 (m, 5H), 7.71-7.65 (m, 3H), 4.91 (s, 2H), 3.32-3.28 (m, 2H), 3.07-3.02 (m, 2H), 2.28-2.17 (m, 4H), 1.99-1.86 (m, 8H), 1.65-1.54 (m, 4H), 1.16 (s, 9H), 1.15 (s, 9H), 1.09-1.02 (m, 2H), 0.98-0.90 (m, 6H). LC/MS: Anal. Calcd. For [M+H]$^+$ $C_{50}H_{63}F_4N_6O_4$: 887.48; found 887.4.

Example B14-16

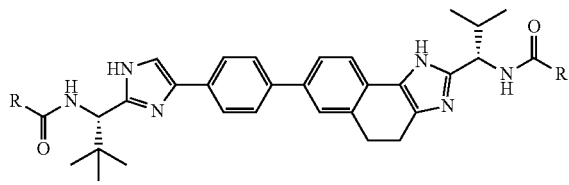

Example B14-16

Step a

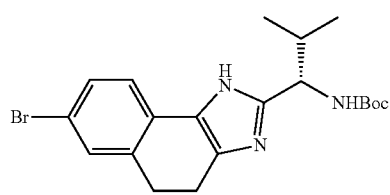 [SMILES: CC(C)[C@H](NC(=O)OC(C)(C)C)c1nc2c([nH]1)-c1ccc(Br)cc1CC2]

Bromide B14-16a was prepared in a similar fashion from dibromide B-10a and (S)-2-((tert-butoxycarbonyl)amino)-3-methylbutanoic acid according to the procedure described for the preparation of bromide B-10c. LC/MS (Condition B-10): $R_t$=2.05 min. LC/MS: Anal. Calcd. for [M+H]$^+$ $C_{20}H_{27}BN_3O_2$: 420.12; found 420.2.

Example B14-16

Step b

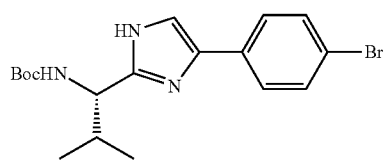 [SMILES: CC(C)[C@H](NC(=O)OC(C)(C)C)c1nc(-c2ccc(Br)cc2)c[nH]1]

Bromide B14-16b was prepared in a similar fashion from 2-amino-1-(4-bromophenyl)ethanone hydrochloride and (S)-2-((tert-butoxycarbonyl)amino)-3-methylbutanoic acid according to the procedure described for the preparation of bromide B-10e. LC/MS (Condition B-9): $R_t$=1.62 min. LC/MS: Anal. Calcd. for [M+H]$^+$ $C_{18}H_{25}BrN_3O_2$: 394.11; found 394.2.

Example B14-16

Step c

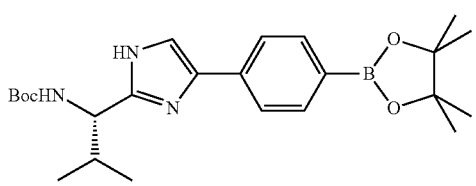 [SMILES: CC(C)[C@H](NC(=O)OC(C)(C)C)c1nc(-c2ccc(B3OC(C)(C)C(C)(C)O3)cc2)c[nH]1]

Boronate B14-16c was prepared in a similar fashion from bromide B14-16b according to the procedure described for the preparation of boronate B-10f. LC/MS (Condition B-9): $R_t$=1.83 min. LC/MS: Anal. Calcd. for [M+H]$^+$ $C_{24}H_{37}BN_3O_4$: 442.28; found 442.2.

Example B14-16

Step d

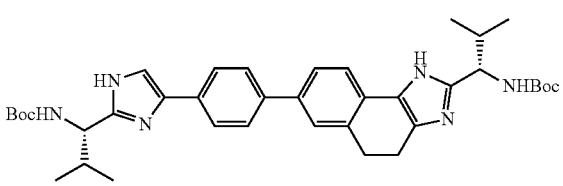 [SMILES: CC(C)[C@H](NC(=O)OC(C)(C)C)c1nc(-c2ccc(-c3ccc4c(c3)CCc3nc([C@@H](NC(=O)OC(C)(C)C)C(C)C)[nH]c3-4)cc2)c[nH]1]

Carbamate B14-16d was prepared in a similar fashion starting from bromide B14-16a and boronate B14-16c according to the procedure described for the preparation carbamate B-10g. LC/MS (Condition B-10): $R_t$=2.02 min. LC/MS: Anal. Calcd. for [M−H]$^-$ $C_{38}H_{49}N_6O_4$: 653.39; found 653.4.

Example B14-16

Example B14-16 (TFA salt) were prepared in a similar fashion starting from carbamate B14-16d according to the procedure described for the preparation Example B10-12.

| Example # | R | LC & LC/MS data |
|---|---|---|
| B14 | ![cyclohexyl-4,4-difluoro] | LC (Condition B-1 and B-2): >96% homogeneity index. LC/MS (Condition B-12): $R_t$ = 1.87 min. LC/MS: Anal. Calcd. for [M + H]$^+$ $C_{42}H_{51}F_4N_6O_2$: 747.39; found 747.7. |
| B15 | ![tert-butyl] | LC (Condition B-1 and B-2): >95% homogeneity index. LC/MS (Condition B-12): $R_t$ = 2.34 min. LC/MS: Anal. Calcd. for [M + H]$^+$ $C_{38}H_{51}N_6O_2$: 623.4; found 623.8. |
| B16 | ![3-chlorophenyl] | LC (Condition B-1 and B-2): >96% homogeneity index. LC/MS (Condition B-12): $R_t$ = 2.09 min. LC/MS: Anal. Calcd. for [M + H]$^+$ $C_{42}H_{41}Cl_2N_6O_2$: 732.71; found 732.5. |

Example B17

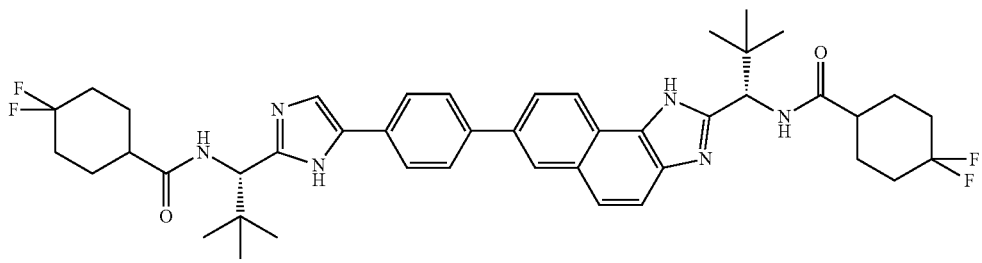 [SMILES: CC(C)(C)[C@H](NC(=O)C1CCC(F)(F)CC1)c1ncc(-c2ccc(-c3ccc4c(ccc5nc([C@@H](NC(=O)C6CCC(F)(F)CC6)C(C)(C)C)[nH]c54)c3)cc2)[nH]1]

Example B17

Step a

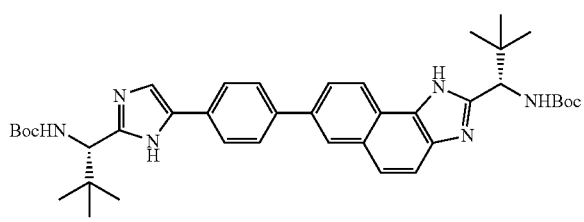 [SMILES: CC(C)(C)OC(=O)N[C@H](c1ncc(-c2ccc(-c3ccc4c(ccc5nc([C@@H](NC(=O)OC(C)(C)C)C(C)(C)C)[nH]c54)c3)cc2)[nH]1)C(C)(C)C]

To a solution of carbamate B-10g-1 (400 mg, 0.586 mmol) in THF (75 mL) was added DDQ (266 mg, 1.171 mmol) in THF (10 mL) and the reaction mixture was stirred at 70° C. for 2 h. The reaction mixture was cooled to rt and then diluted with EtOAc. The organic layer was washed with water, saturated Na$_2$CO$_3$, dried over Na$_2$SO$_4$ and concentrated. The crude was purified by reverse phase HPLC (ACN/water/NH$_4$OAc) to afford carbamate B-17a (280 mg) as a brown solid. HPLC (Condition B-2): >97% homogeneity index. LC/MS (Condition B-10): R$_t$=2.24 min. $^1$H NMR (MeOD, δ=3.34 ppm, 400 MHz): δ 8.47 (m, 1H), 8.28 (d, J=1.2, 1H), 7.96 (dd, J=8.4, 2.0, 1H), 7.88-7.81 (m, 5H), 7.72 (d, J=8.8, 1H), 7.49 (s, 1H), 4.90-4.80 (obscured, 1H), 4.68 (s, 1H), 1.47 (s, 18H), 1.09 (s, 9H), 1.04 (s, 9H). LC/MS: Anal. Calcd. for [M−H]$^-$ C$_{40}$H$_{51}$N$_6$O$_4$: 679.4; found 679.4.

Example B17

Step b

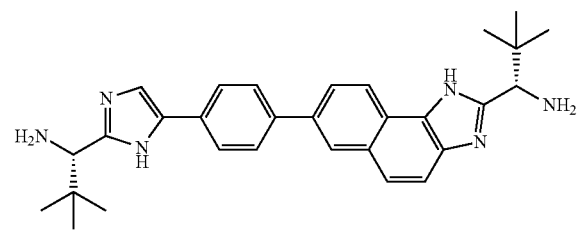 [SMILES: CC(C)(C)[C@H](N)c1ncc(-c2ccc(-c3ccc4c(ccc5nc([C@@H](N)C(C)(C)C)[nH]c54)c3)cc2)[nH]1]

HCl salt of amine B-17b (230 mg) was prepared according to the procedure described in Example B1 step k. LC/MS (Condition B-10): R$_t$=1.49 min. $^1$H NMR (MeOD, δ=3.34 ppm, 400 MHz): δ 8.64 (d, J=8.4, 1H), 8.43 (br s, 1H), 8.12-8.01 (m, 7H), 7.87 (d, J=8.8, 1H), 4.77 (s, 1H), 4.70 (s, 1H), 1.26 (s, 9H), 1.24 (s, 9H). LC/MS: Anal. Calcd. for [M+H]$^+$ C$_{30}$H$_{37}$N$_6$: 481.65; found 481.3.

Example B17

TFA salt of Example B17 (64 mg) was prepared according to the procedure described in Example B1. HPLC (Condition B-1 and B-2): >99% homogeneity index. LC/MS (Condition B-12): R$_t$=2.61 min. $^1$H NMR (MeOD, δ=3.34 ppm, 400 MHz): δ 8.56 (d, J=8.0, 1H), 8.46 (br s, 1H), 8.14 (dd, J=8.8, 2.0, 1H), 8.10 (d, J=8.8, 1H), 8.02 (d, J=8.8, 2H), 7.93 (s, 1H), 7.91 (d, J=8.8, 2H), 7.84 (d, J=8.8, 1H), 5.13 (s, 1H), 4.95 (s, 1H), 2.68-2.55 (m, 2H), 2.20-2.02 (m, 4H), 2.00-1.70 (m, 12H), 1.21 (s, 9H), 1.17 (s, 9H). LC/MS: Anal. Calcd. for [M+H]$^+$ C$_{44}$H$_{53}$F$_4$N$_6$O$_2$: 773.41; found 773.8.

Example B18-19

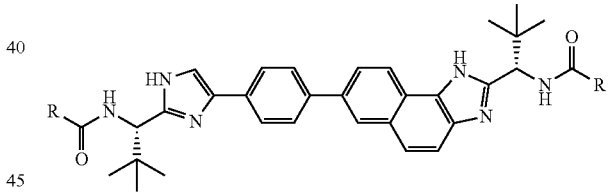

Example B18-19 (TFA salt) were prepared from HCL salt of amine B-17b and appropriate acids according to the procedure described for Example B17.

| Example # | R | LC & LC/MS data |
|---|---|---|
| B18 | *tert*-butyl | LC (Condition B-1 and B-2): >99% homogeneity index. LC/MS (Condition B-12): R$_t$ = 2.06 min. LC/MS: Anal. Calcd. for [M − H]$^-$ C$_{40}$H$_{51}$N$_6$O$_2$: 647.42; found 648.0. |
| B19 | 3-chlorophenyl (with methyl) | LC (Condition B-1 and B-5): >99% homogeneity index. LC/MS (Condition B-12): R$_t$ = 2.23 min. LC/MS: Anal. Calcd. for [M + H]$^+$ C$_{44}$H$_{43}$Cl$_2$N$_6$O$_2$: 758.75; found 758.6. |

Example B20-22

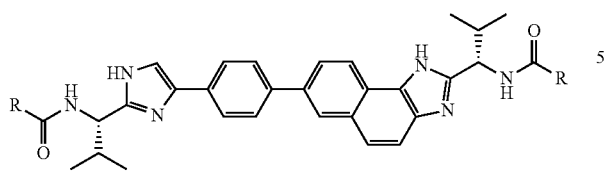

Example B20-22 (TFA salt) were prepared in a similar fashion starting from carbamate B14-16d according to the procedure described for the preparation Example B17-19.

| Example # | R | LC & LC/MS data |
|---|---|---|
| B20 | 4,4-difluorocyclohexyl | LC (Condition B-1 and B-2): >97% homogeneity index. LC/MS (Condition B-12): $R_t$ = 1.88 min. LC/MS: Anal. Calcd. for $[M + H]^+$ $C_{42}H_{49}F_4N_6O_2$: 745.38; found 745.8. |
| B21 | tert-butyl | LC (Condition B-1 and B-2): >97% homogeneity index. LC/MS (Condition B-12): $R_t$ = 2.34 min. LC/MS: Anal. Calcd. for $[M + H]^+$ $C_{38}H_{49}N_6O_2$: 621.38; found 621.5. |
| B22 | 3-chlorophenyl | LC (Condition B-1 and B-2): >96% homogeneity index. LC/MS (Condition B-12): $R_t$ = 2.09 min. LC/MS: Anal. Calcd. for $[M + H]^+$ $C_{42}H_{39}Cl_2N_6O_2$: 730.7; found 730.3. |

Example B23

Step a

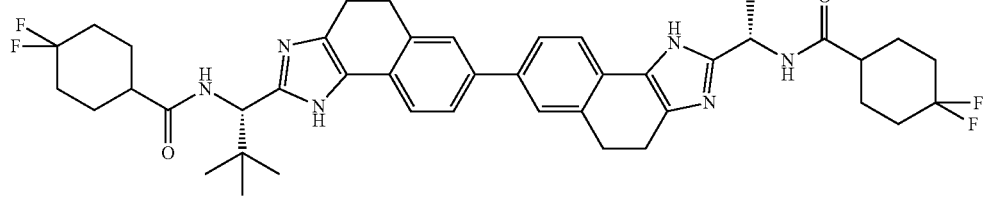

HCl salt of amine B-23a (70 mg) was prepared according to the procedure described in Example B1 step k. LC/MS (Condition B-10): $R_t$=1.47 min. $^1$H NMR (MeOD, δ=3.34 ppm, 400 MHz): δ 7.78 (d, J=8.0, 2H), 7.68 (br s, 2H), 7.67 (d, J=8.0, 2H), 4.59 (s, 1H), 3.37-3.25 (obscured, 4H), 3.10-3.05 (m, 4H), 1.21 (s, 9H). LC/MS: Anal. Calcd. for $[M+H]^+$ $C_{32}H_{41}N_6$: 509.33; found 509.4.5

Example B23

Example B23 (45.7 mg) was prepared according to the procedure described in Example B1. HPLC (Condition B-1 and B-3): >95% homogeneity index. LC/MS (Condition B-13): $R_t$=2.13 min. $^1$H NMR (MeOD, δ=3.34 ppm, 400 MHz): δ 7.69 (br s, 6H), 4.97-4.80 (obscured, 2H), 3.28 (t, J=8.0, 4H), 3.05 (t, J=8.4, 4H), 2.65-2.57 (m, 2H), 2.19-2.08 (m, 4H), 1.99-1.68 (m, 12H), 1.16 (s, 18H). LC/MS: Anal. Calcd. for $[M-H]^-$ $C_{46}H_{55}F_4N_6O_2$: 799.44; found 799.4.

Example B24

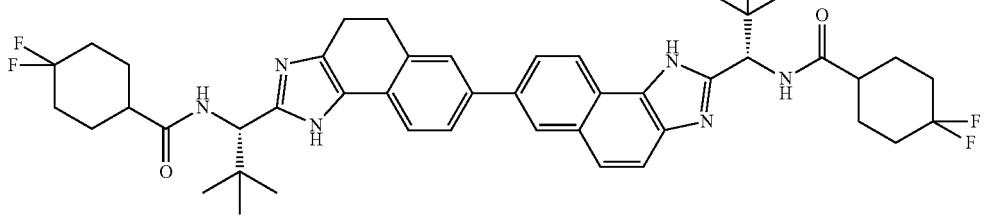

Example B24

Step a-1 & a-2

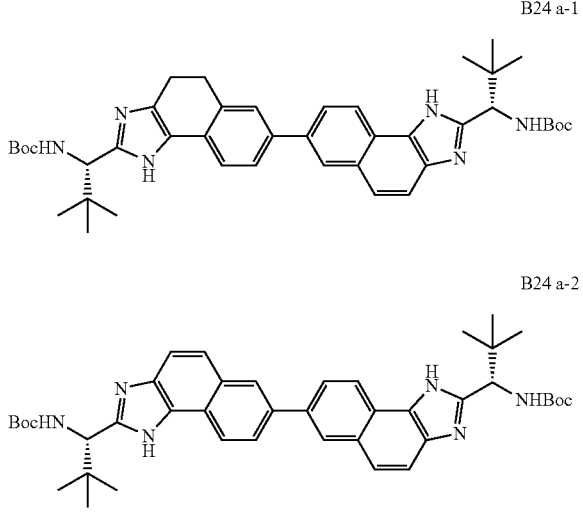

A reaction mixture of carbamate B-10g-2 (300 mg, 0.423 mmol) and DDQ (96 mg, 0.423 mmol) in THF was heated at 70° C. for 2 h. The reaction mixture was cooled to rt and diluted with EtOAc. The organic layer was washed with water, saturated $Na_2CO_3$, dried over $Na_2SO_4$ and concentrated. The crude was purified by reverse phase HPLC (ACN/water/$NH_4OAc$) to afford free base of carbamate B-24a-1 (73 mg) as an off-white solid. HPLC (Condition B-2 and B-7): >94% homogeneity index. LC/MS (Condition B-12): $R_t$=2.62 min. $^1H$ NMR (MeOD, δ=3.34 ppm, 400 MHz): δ 8.58 (br s, 1H), 8.24 (s, 1H), 7.93 (dd, J=8.8, 1.6, 1H), 7.79 (d, J=8.8, 2H), 7.75-7.52 (m, 3H), 4.90-4.80 (obscured, 1H), 4.63 (s, 1H), 3.19 (t, J=8.0, 2H), 2.92 (t, J=8.0, 2H), 1.47 (s, 18H), 1.09 (s, 9H), 1.03 (s, 9H). LC/MS: Anal. Calcd. for [M−H]⁻ $C_{42}H_{53}N_6O_4$: 705.42; found 705.9. The symmetric dimer B-24a-2 (79 mg) was also isolated as an off-white solid. HPLC (Condition B-1 and B-2): >99% homogeneity index. LC/MS (Condition B-12): $R_t$=2.23 min. $^1H$ NMR (MeOD, δ=3.34 ppm, 400 MHz): δ 8.52 (br s, 2H), 8.40 (s, 2H), 8.10 (dd, J=8.8, 2.0, 2H), 7.87 (d, J=8.8, 2H), 7.75 (d, J=8.8, 2H), 4.90-4.80 (obscured, 1H), 1.47 (br s, 18H), 1.10 (br s, 18H). LC/MS: Anal. Calcd. for [M−H]⁻ $C_{42}H_{51}N_6O_4$: 703.41; found 703.9.

Step b

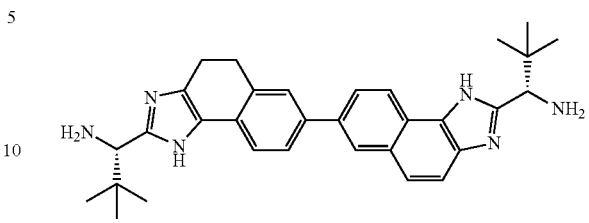

HCl salt of amine B-24b (60 mg) was prepared according to the procedure described in Example B1 step k. LC/MS (Condition B-10): $R_t$=1.52 min. $^1H$ NMR (MeOD, δ=3.34 ppm, 400 MHz): δ 8.59 (br d, 1H), 8.36 (br s, 1H), 8.04 (br d, 1H), 7.97 (d, J=8.4, 1H), 7.87-7.79 (m, 4H), 4.69 (s, 1H), 4.61 (s, 1H), 3.52-3.32 (obscured, 2H), 3.14 (br s, 2H), 1.23 (s, 18H). LC/MS: Anal. Calcd. for [M+H]⁺ $C_{32}H_{39}N_6$: 506.68; found 507.4.

Example B24

Example B24 (51.2 mg) was prepared according to the procedure described in Example B1. HPLC (Condition B-2): >99% homogeneity index. LC/MS (Condition B-12): $R_t$=2.14 min. $^1H$ NMR (MeOD, δ=3.34 ppm, 400 MHz): δ 8.55 (d, J=8.8, 1H), 8.43 (d, J=1.2, 1H), 8.12 (dd, J=8.8, 1.6, 1H), 8.08 (d, J=8.8, 1H), 7.85-7.20 (m, 3H), 7.75 (d, J=8.0, 1H), 5.13 (s, 1H), 4.92-4.85 (obscured, 1H), 3.35-3.29 (obscured, 2H), 3.10-3.06 (m, 2H), 2.67-2.58 (m, 2H), 2.20-2.11 (m, 4H), 1.98-1.73 (m, 12H), 1.17 (s, 9H), 1.15 (s, 9H). LC/MS: Anal. Calcd. for [M−H]⁻ $C_{46}H_{53}F_4N_6O_2$: 797.95; found 798.1.

Example B25

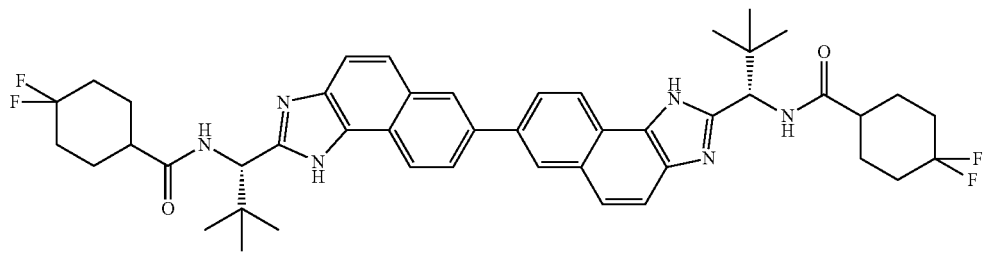 [SMILES: CC(C)(C)[C@H](NC(=O)C1CCC(F)(F)CC1)c1nc2ccc3cc(-c4ccc5c(ccc6nc([C@@H](NC(=O)C7CCC(F)(F)CC7)C(C)(C)C)[nH]c65)c4)ccc3c2[nH]1]

Example B25

Step a

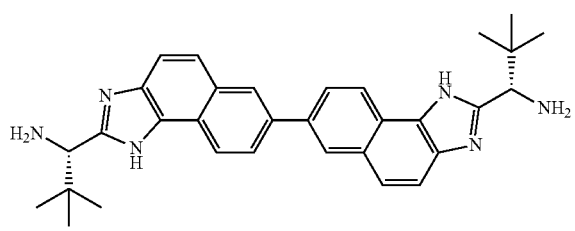 [SMILES: CC(C)(C)[C@H](N)c1nc2ccc3cc(-c4ccc5c(ccc6nc([C@@H](N)C(C)(C)C)[nH]c65)c4)ccc3c2[nH]1]

HCl salt of amine B-25a (60 mg) was prepared according to the procedure described in Example B1 step k. LC/MS (Condition B-10): $R_t$=1.61 min. $^1H$ NMR (MeOD, δ=3.34 ppm, 400 MHz): δ 8.69 (d, J=8.0, 2H), 8.55 (s, 2H), 8.25 (d, J=8.0, 2H), 8.11 (d, J=8.4, 2H), 7.89 (d, J=8.4, 2H), 4.75 (s, 2H), 1.27 (s, 18H). LC/MS: Anal. Calcd. for [M+H]⁺ $C_{32}H_{36}N_6$: 505.3; found 505.4.

Example B25

Example B25 (53 mg) was prepared according to the procedure described in Example B1. HPLC (Condition B-1 and B-8): >98% homogeneity index. LC/MS (Condition B-11): $R_t$=2.09 min. ¹H NMR (MeOD, δ=3.34 ppm, 400 MHz): δ 8.60 (d, J=8.8, 2H), 8.58 (d, J=1.6, 2H), 8.29 (dd, J=8.8, 1.6, 2H), 8.15 (d, J=8.8, 2H), 7.86 (d, J=8.8, 2H), 5.14 (s, 2H), 2.72-2.61 (m, 2H), 2.19-2.05 (m, 4H), 2.04-1.64 (m, 12H), 1.22 (s, 18H). LC/MS: Anal. Calcd. for [M–H]⁻ $C_{46}H_{51}F_4N_6O_2$: 795.41; found 795.7.

Example B26 tin (3.65 mL, 10.71 mmol) under $N_2$. Then $Pd(PPh_3)_2Cl_2$ (0.251 g, 0.357 mmol) was added. The reaction mixture was heated at 100° C. for 16 h then cooled to rt and diluted with DCM and 1.5 N HCl. The organic layer was separated and the aqueous layer was extracted with DCM. The combined organic layer was dried over $Na_2SO_4$ and concentrated. The crude was purified by Combiflash Isco (Silica gel, 12 g, Redisep, 0.5% MeOH in $CHCl_3$) and the resulting product was washed with petroleum ether to yield 1,1'-(anthracene-2,6-diyl)diethanone (600 mg) as a yellow solid. ¹H NMR ($CDCl_3$, δ=7.26 ppm, 400 MHz): δ 8.67 (s, 2H), 8.61 (s, 2H), 8.44-8.04 (m, 4H), 2.78 (s, 6H).

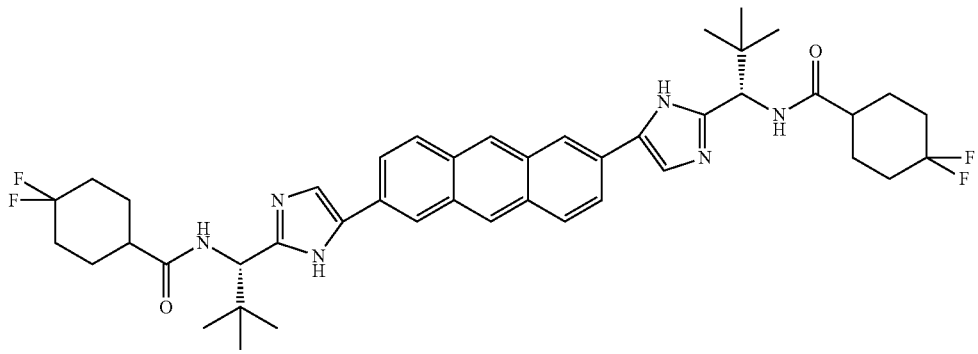 [SMILES: CC(C)(C)[C@H](NC(=O)C1CCC(F)(F)CC1)c1ncc(-c2ccc3cc4cc(-c5cnc([C@@H](NC(=O)C6CCC(F)(F)CC6)C(C)(C)C)[nH]5)ccc4cc3c2)[nH]1]

Example B26

Example B26

Step a

Step b

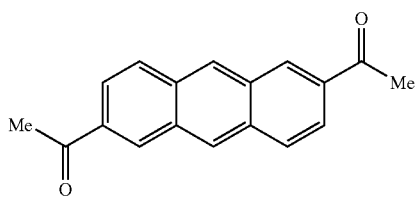 [SMILES: CC(=O)c1ccc2cc3cc(C(C)=O)ccc3cc2c1]

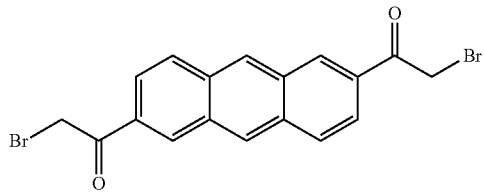 [SMILES: O=C(CBr)c1ccc2cc3cc(C(=O)CBr)ccc3cc2c1]

To a solution of 2,6-dibromoanthracene (1.2 g, 3.57 mmol) in 1,4-dioxane (20 mL) was added 1-ethoxyvinyltri-n-butyl- To a solution of 1,1'-(anthracene-2,6-diyl)diethanone (500 mg, 1.906 mmol) in 1,4-dioxane was added $Br_2$ (0.187 mL, 3.62 mmol) and the reaction mixture was stirred at rt for 3 h. Then the reaction mixture was added with water and extracted with DCM. The combined organic layer was dried over $Na_2SO_4$ and concentrated under reduced pressure to yield dibromide B-26b (800 mg) as a yellow solid.

Example B26

Step c-1 & c-2

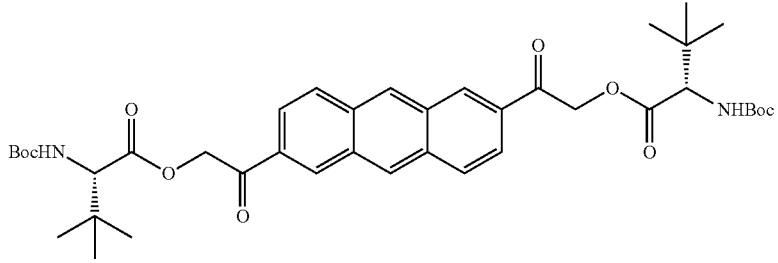
B26 c-1

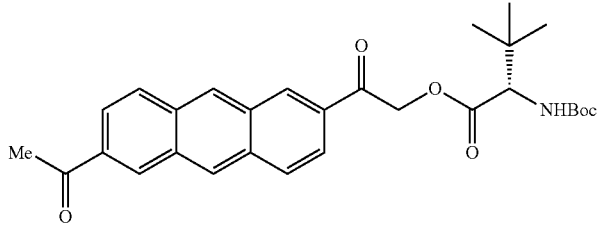
B26 c-2

To a solution of dibromide B-26b (700 mg, 1.666 mmol) and (S)-2-((tert-butoxycarbonyl)amino)-3,3-dimethylbutanoic acid (848 mg, 3.67 mmol) in ACN (25 mL) was added DIPEA (1.164 mL, 6.67 mmol) at 0° C. The reaction mixture was stirred at rt for 4 h. Then the reaction mixture was added with water and extracted with EtOAc. The organic layer was washed with 10% NaHCO$_3$ and brine. The organic layer was dried over Na$_2$SO$_4$ and concentrated. The crude was purified by Combiflash Isco (Silica gel, 24 g, Redisep, 22% EtOAc in petroleum ether) to yield a mixture of diketoester B-26c-1 (53%) & monoketoester B-26c-2 (20%) (650 mg). B-26c-1: LC/MS (Condition B-10): R$_t$=2.55 min. L C/MS: Anal. Calcd. for [M−H]⁻ C$_{40}$H$_{51}$N$_2$O$_{10}$: 719.36; found: 719.2. B-26c-2: R$_t$=2.31 min. LC/MS: Anal. Calcd. for [M−H]⁻ C$_{29}$H$_{32}$NO$_6$: 490.23; found: 490.2.

Example B26

Step d-1 & d-2

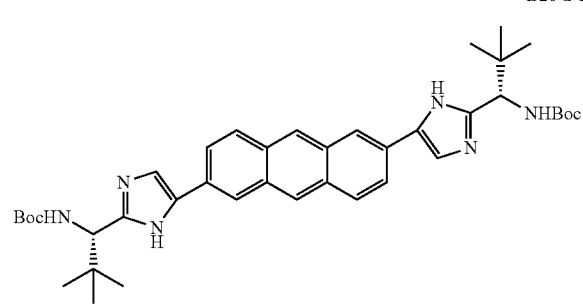
B26 d-1

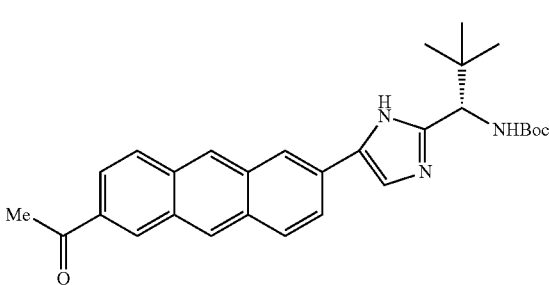
B26 d-2

A reaction mixture of diketoester B-26c-1 & monoketoester B-26c-2 (650 mg, 0.902 mmol) and NH$_4$OAc (1.39 g, 18.03 mmol) in xylene was heated at 130° C. for 18 h. Then the volatile components were removed. The residue was dissolved in DCM and washed with water. The aqueous layer was extracted with DCM. The combined organic layer was dried over Na$_2$SO$_4$ and concentrated. The crude was purified by reverse phase HPLC purification (ACN/water/NH$_4$OAc) to yield carbamate B26d-1 (100 mg) as a yellow solid. LC/MS (Condition B-10): R$_t$=2.29 min. $^1$H NMR (MeOD, δ=3.34 ppm, 400 MHz): δ 8.44 (s, 2H), 8.32 (br s, 2H) 8.05 (d, J=8.8, 2H), 7.83 (d, J=8, 2H), 7.53 (s, 2H), 4.70 (s, 2H), 1.48 (s, 18H), 1.04 (s, 18H). LC/MS: Anal. Calcd. for [M−H]⁻ C$_{40}$H$_{51}$N$_6$O$_4$: 679.41; found: 679.4. Carbamate B26d-2 (54 mg) was also isolated as a yellow solid. LC/MS (Condition B-13): R$_t$=2.13 min. $^1$H NMR (MeOD, δ=3.34 ppm, 400 MHz): δ 8.82 (s, 1H), 8.68 (s, 1H), 4.51 (s, 1H), 8.41 (br s, 1H), 8.13 (d, J=8.8, 1H), 8.09 (d, J=9.2, 1 H), 7.98 (dd, J=8.8, 1.6, 1H), 7.96-7.88 (m, 1H), 7.59 (br s, 1H), 4.70 (s, 1H), 2.78 (s, 3H), 1.47 (s, 9H), 1.04 (s, 9H). LC/MS: Anal. Calcd. For [M+H]⁺ C$_{29}$H$_{34}$N$_3$O$_3$: 472.25; found: 472.2.

Example B26

Step e

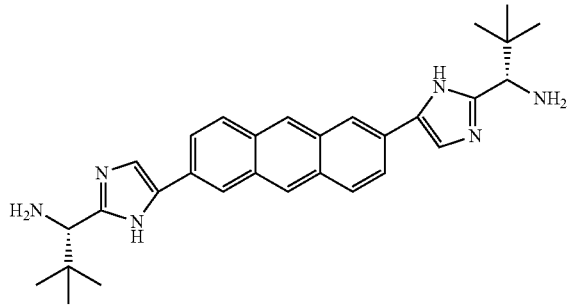 [SMILES: CC(C)(C)[C@H](N)c1ncc(-c2ccc3cc4cc(-c5cnc([C@@H](N)C(C)(C)C)[nH]5)ccc4cc3c2)[nH]1]

HCl salt of amine B-26e (100 mg) was prepared according to the procedure described in Example B1 step k. LC/MS (Condition B-13): $R_t$=1.85 min. $^1$H NMR (MeOD, δ=3.34 ppm, 400 MHz): δ 8.60 (s, 4H), 8.19 (d, J=8.8, 2H), 8.03 (s, 2H), 7.95 (dd, J=8.8, 1.6, 2H), 4.58 (s, 2H), 1.23 (s, 18H). LC/MS: Anal. Calcd. for [M+H]$^+$ $C_{30}H_{37}N_6$: 481.3; found: 481.2.

Example B26

Example B26 (32 mg) was prepared according to the procedure described in Example B1. HPLC (Condition B-6 and B-8): >93% homogeneity index. LC/MS (Condition B-12): $R_t$=2.71 min. $^1$H NMR (MeOD, δ=3.34 ppm, 400 MHz): δ 8.64 (s, 2H), 8.50 (d, J=0.4, 2H), 8.24 (d, J=9.2, 2H), 8.03 (s, 2H), 7.86 (dd, J=9.03, 1.6, 2H), 5.01 (s, 2H), 2.68-2.57 (m, 2H), 2.21-2.07 (m, 4H), 2.02-1.71 (m, 12H), 1.17 (s, 18H). LC/MS: Anal. Calcd. for [M+H]$^+$ $C_{44}H_{53}F_4N_6O_2$: 773.41; found: 773.5.

Example B27

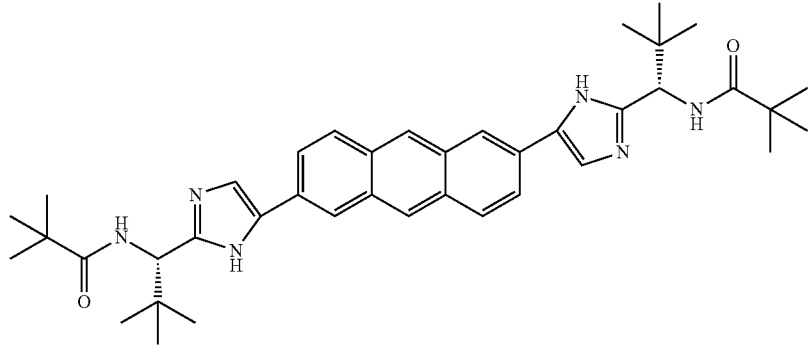 [SMILES: CC(C)(C)C(=O)N[C@H](c1ncc(-c2ccc3cc4cc(-c5cnc([C@@H](NC(=O)C(C)(C)C)C(C)(C)C)[nH]5)ccc4cc3c2)[nH]1)C(C)(C)C]

Example B27 (TFA salt) was prepared in a similar fashion from HCl salt of amine B-26e and pivalic acid according to the procedure described for Example B26. HPLC (Condition B-1 and B-2): >92% homogeneity index. LC/MS (Condition B-10): $R_t$=2.18 min. LC/MS: Anal. Calcd. for [M−H]$^-$ $C_{40}H_{51}N_6O_2$: 647.42; found: 647.4.

Example B28

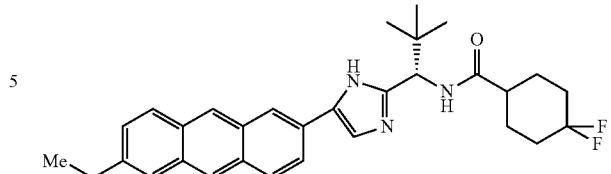

Example B28

Step a

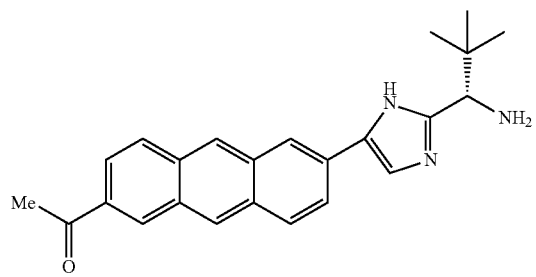 [SMILES: CC(=O)c1ccc2cc3cc(-c4cnc([C@@H](N)C(C)(C)C)[nH]4)ccc3cc2c1]

HCl salt of amine B-28a (60 mg) was prepared according to the procedure described in Example B1 step k. LC/MS (Condition B-13): $R_t$=1.93 min. $^1$H NMR (D$_2$O, δ=4.79 ppm, 400 MHz): δ 7.73-7.34 (m, 7H), 7.18-7.15 (m, 2H), 4.90-4.40 (obscured, 1H), 2.29 (s, 3H), 1.13 (s, 9H). LC/MS: Anal. Calcd. For [M+H]$^+$ $C_{24}H_{26}N_3O$: 372.2; found: 372.2.

Example B28

Example B28 (36 mg) was prepared according to the procedure described in Example B1. HPLC (Condition B-1 and B-2): >99% homogeneity index. LC/MS (Condition B-12): $R_t$=3.22 min. $^1$H NMR (MeOD, δ=3.34 ppm, 400 MHz): δ 8.85 (s, 1H), 8.77 (s, 1H), 8.61 (s, 1H), 8.47 (s, 1H), 8.27 (d, J=8.8, 1H), 8.15 (d, J=8.8, 1H), 8.05 (s, 1H), 8.02 (dd, J=8.8, 1.6, 1H), 7.84 (dd, J=8.8, 2.0, 1H), 4.99 (s, 1H), 2.79 (s, 3H), 2.68-2.56 (m, 1H), 2.21-2.04 (m, 2H), 1.99-1.69 (m, 6H), 1.18 (s, 9H). LC/MS: Anal. Calcd. for [M+H]$^+$ $C_{31}H_{34}F_2N_3O_2$: 518.25; found: 518.1.

Example B29-31

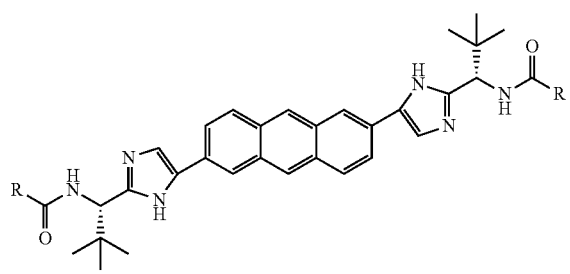

Example B29-31 (TFA salt) were prepared in a similar fashion starting from dibromide B-26b and (S)-2-((tert-butoxycarbonyl)amino)-3-methylbutanoic acid according to the procedure described for the preparation Example B26.

| Example # | R | LC & LC/MS data |
|---|---|---|
| B29 | ![cyclohexyl-difluoro] | LC (Condition B-1 and B-2): >94% homogeneity index. LC/MS (Condition B-12): $R_t$ = 1.91 min. LC/MS: Anal. Calcd. for $[M + H]^+$ $C_{42}H_{49}F_4N_6O_2$: 745.38; found: 745.8. |
| B30 | ![tert-butyl-methyl] | LC (Condition B-1 and B-8): >94% homogeneity index. LC/MS (Condition B-10): $R_t$ = 1.96 min. LC/MS: Anal. Calcd. for $[M - H]^-$ $C_{38}H_{47}N_6O_2$: 619.38; found: 619.4. |
| B31 | ![methyl-chlorophenyl] | LC (Condition B-1 and B-8): >98% homogeneity index. LC/MS (Condition B-10): $R_t$ = 2.22 min. LC/MS: Anal. Calcd. for $[M - H]^-$ $C_{42}H_{37}Cl_2N_6O_2$: 727.24; found: 727.2. |

Example B32

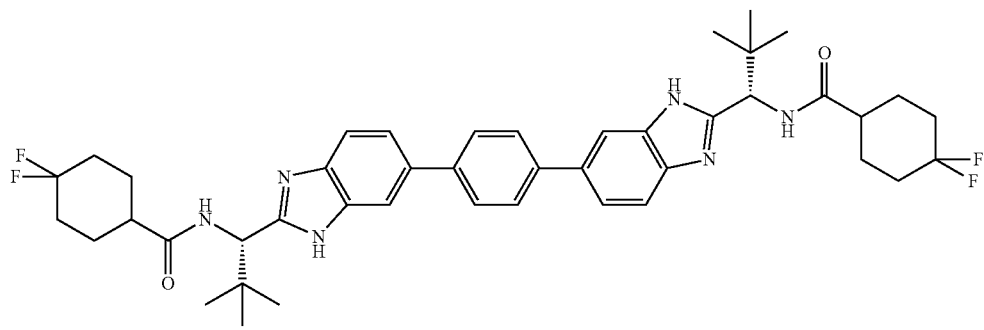 [SMILES: CC(C)(C)[C@H](NC(=O)C1CCC(F)(F)CC1)c1nc2ccc(-c3ccc(-c4ccc5nc([C@@H](NC(=O)C6CCC(F)(F)CC6)C(C)(C)C)[nH]c5c4)cc3)cc2[nH]1]

Example B32

Step a

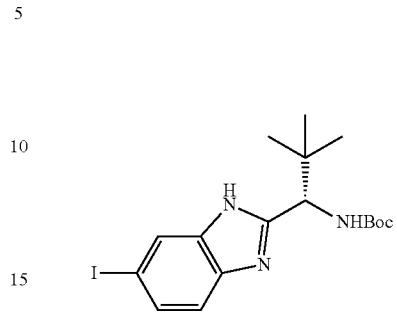

HATU (16.25 g, 42.7 mmol) was added to a stirred solution of 4-iodobenzene-1,2-diamine (10 g, 42.7 mmol), (S)-2-((tert-butoxycarbonyl)amino)-3,3-dimethylbutanoic acid (9.88 g, 42.7 mmol) and DIPEA (14.93 mL, 85 mmol) in DMF (120 mL) at 0° C. and the reaction mixture was stirred at rt for 12 h. The reaction mixture was diluted with water and EtOAc. The organic layer was washed with water, 10% $NaHCO_3$ solution, brine, dried over $Na_2SO_4$ and concentrated to yield (S)-tert-butyl (1-((2-amino-5-iodophenyl)amino)-3,3-dimethyl-1-oxobutan-2-yl)carbamate (20 g). LC/MS (Condition B-10): $R_t$=1.94 min. LC/MS: Anal. Calcd. for $[M+H]^+$ $C_{17}H_{27}IN_3O_3$: 448.10; found 448.2.

AcOH (150 mL) was added to the mixture of crude carbamate (20 g, 44.7 mmol) and the reaction mixture was heated at 65° C. for 12 h. The volatile components were removed; the resulting residue was dissolved in EtOAc and neutralized with 10% NaOH. The organic layer was separated and washed with water, brine, dried over $Na_2SO_4$ and concentrated. The crude was purified by flash chromatography (Silica gel 60-120, 15% EtOAc in petroleum ether) to yield iodide B-32a (16 g) as an off-white solid. LC/MS (Condition B-10): $R_t$=1.97 min. $^1$H NMR (MeOD, δ=3.34 ppm, 400 MHz): δ 7.91 (s, 1H), 7.54 (d, J=8.4, 1.6, 1H), 7.37 (d, J=8.4, 1H), 4.69 (br s, 1H), 1.47 (s, 9H), 1.03 (s, 9H). LC/MS: Anal. Calcd. for $[M+H]^+$ $C_{17}H_{25}IN_3O_2$: 430.09; found 430.0.

Example B32

Step b-1 & b-2 & b-3

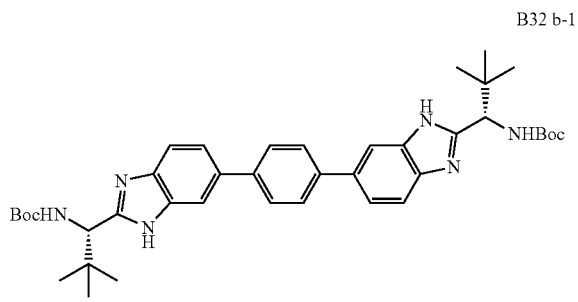

B32 b-1

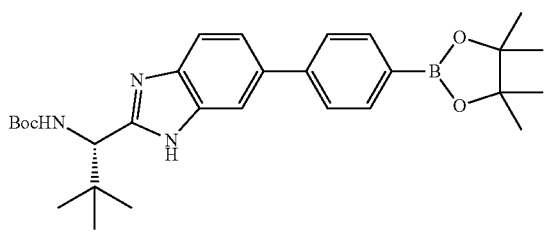

B32 b-2

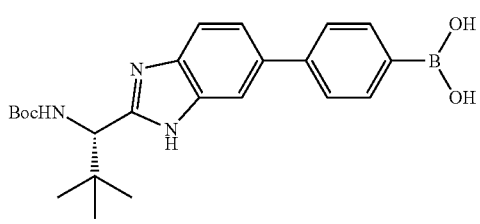

B32 b-3

To a solution of iodide B-32a (2 g, 4.66 mmol) in MeOH (20 mL) was added 1,4-bis(4,4,5,5-tetramethyl-1,3,2-dioxaborolan-2-yl)benzene (3.08 g, 9.32 mmol) and the reaction mixture was purged with $N_2$ for 10 minutes. Then $K_2CO_3$ (2.58 g, 18.64 mmol) was added followed by $Pd(Ph_3P)_4$ (0.538 g, 0.466 mmol) and the reaction mixture was purged with $N_2$ for further 10 minutes. Then the reaction mixture was heated to 85° C. for 2 h under microwave condition. The volatile components were removed and the resulting residue was dissolved in EtOAc. The organic layer was washed with water and the aqueous layer was back extracted with EtOAc. The combined organic layer was washed with brine, dried over $Na_2SO_4$ and concentrated. The crude was purified by reverse phase HPLC (ACN/water/$NH_4OAc$) to afford carbamate B32b-1 (325 mg) as a pale yellow solid. HPLC (Condition B-1 and B-2): >96% homogeneity index. LC/MS (Condition B-12): $R_t$=2.19 min. $^1$H NMR (MeOD, δ=3.34 ppm, 400 MHz): δ 7.85 (s, 2H), 7.79 (s, 4H), 7.69-7.60 (m, 4H), 4.76 (br s, 2H), 1.47 (br s, 18H), 1.07 (s, 18H). LC/MS: Anal. Calcd. for [M−H]$^-$ $C_{40}H_{51}N_6O_4$: 680.88; found 679.8. The boronic ester B32b-2 and boronic acid B32b-3 (500 mg) were also isolated as a mixture. B32b-2: LC/MS (Condition B-10): $R_t$=2.25 min. LC/MS: Anal. Calcd. for [M+H]$^+$ $C_{29}H_{41}BN_3O_4$: 506.31; found 506.4; B32b-3: $R_t$=1.66 min. LC/MS: Anal. Calcd. for [M+H]$^+$ $C_{23}H_{31}BN_3O_4$: 424.23; found 424.2.

Example B32

Step c

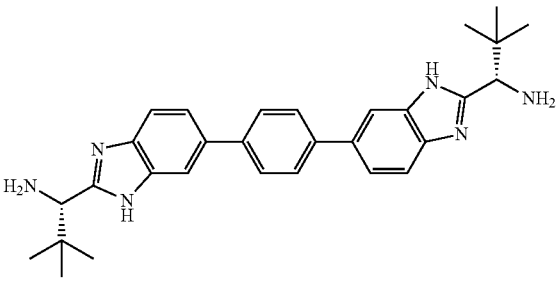 [SMILES: CC(C)(C)[C@H](N)c1nc2ccc(-c3ccc(-c4ccc5nc([C@@H](N)C(C)(C)C)[nH]c5c4)cc3)cc2[nH]1]

HCl salt of amine B-32c (225 mg) was prepared according to the procedure described in Example B1 step k. LC/MS (Condition B-10): $R_t$=1.44 min. $^1$H NMR (MeOD, δ=3.34 ppm, 400 MHz): δ 8.12 (s, 2H), 7.94 (s, 4H), 7.89 (s, 4H), 4.78 (s, 2H), 1.25 (s, 18H). LC/MS: Anal. Calcd. for [M+H]$^+$ $C_{30}H_{37}N_6$: 481.3; found 481.4.

Example B32

Example B32 (53.9 mg) was prepared according to the procedure described in Example B1. HPLC (Condition B-1 and B-2): >98% homogeneity index. LC/MS (Condition B-12): $R_t$=2.10 min. $^1$H NMR (MeOD, δ=3.34 ppm, 400 MHz): δ 8.35-8.20 (m, 2H), 7.93 (dd, J=8.4, 1.6, 2H), 7.88 (br s, 4H), 7.86 (d, J=8.4, 2H), 4.99 (s, 2H), 2.68-2.60 (m, 2H), 2.19-2.06 (m, 4H), 2.02-1.63 (m, 12H), 1.20 (s, 18H). LC/MS: Anal. Calcd. for [M−H]$^-$ $C_{44}H_{51}F_4N_6O_2$: 771.41; found 771.9.

Example B33-34

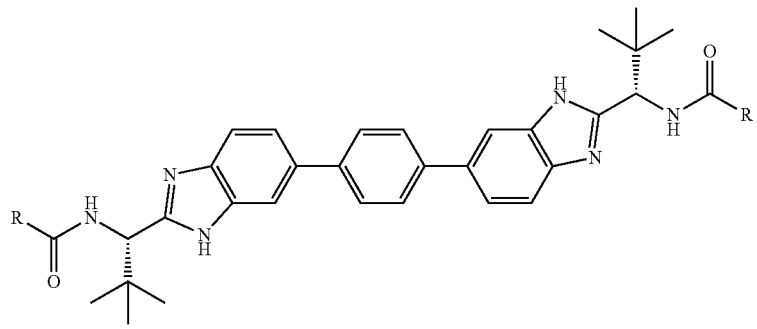

Example B33-34 (TFA salt) were prepared in a similar fashion starting from amine B-32c and appropriate acids according to the procedure described for Example B32.

| Example # | R | LC & LC/MS data |
|---|---|---|
| B33 | 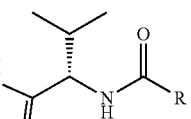 | LC (Condition B-1 and B-8): >94% homogeneity index. LC/MS (Condition B-12): $R_t$ = 2.12 min. LC/MS: Anal. Calcd. for [M – H]⁻ $C_{40}H_{51}N_6O_2$: 647.42; found: 647.8. |
| B34 | 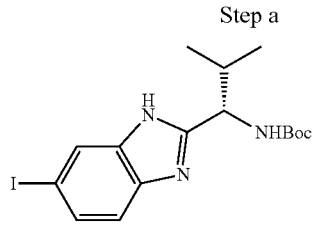 | LC (Condition B-1 and B-2): >96% homogeneity index. LC/MS (Condition B-12): $R_t$ = 2.29 min. LC/MS: Anal. Calcd. for [M – H]⁻ $C_{44}H_{41}Cl_2N_6O_2$: 756.75; found: 756.7. |

Example B35-37

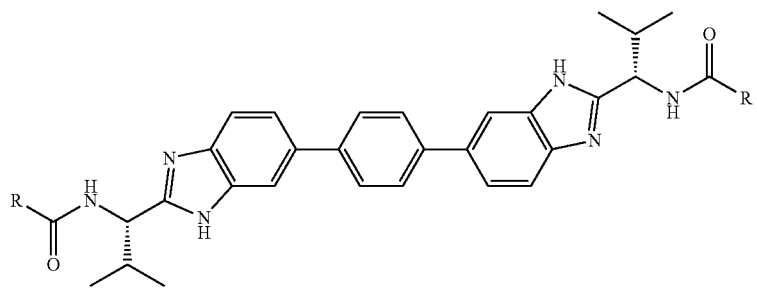

To a stirred solution of B35-37a (1 g, 2.408 mmol) and 1,4-bis(4,4,5,5-tetramethyl-1,3,2-dioxaborolan-2-yl)benzene (0.397 g, 1.204 mmol) in toluene/EtOH/H₂O (15 mL, 1:1:1) was added Cs₂CO₃ (3.14 g, 9.63 mmol) under N₂. Then PdCl₂(dppf)-DCM adduct (0.197 g, 0.241 mmol) was added and the resulting mixture was heated at 105° C. for 16 h. After cooling to rt, the solid was filtered and the solid was purified by reverse phase HPLC (ACN/water/NH₄OAc) to give carbamate B35-37b (80 mgas an off-white solid. HPLC (Condition B-1 and B-2): >98% homogeneity index. LC/MS (Condition B-12): $R_t$=2.81 min. LC/MS: Anal. Calcd. for [M+H]⁺ $C_{38}H_{49}N_6O_4$: 653.27; found 653.4.

Example B35-37

Example B35-37 (TFA salt) were prepared in a similar fashion starting from carbamate B35-37b and appropriate acids according to the procedure described for Example B32.

Example B35-37

Step a

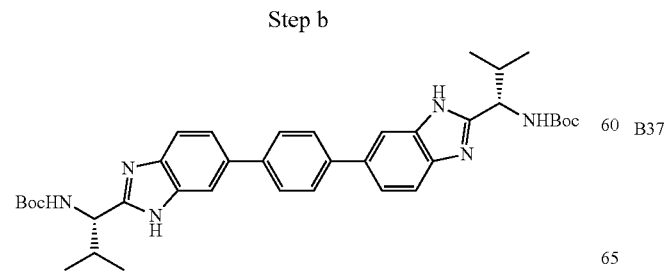

The iodide B35-37a was prepared in a similar fashion starting from 4-iodobenzene-1,2-diamine and (S)-2-((tert-butoxycarbonyl)amino)-3-methylbutanoic acid according to the procedure described for iodide B-32a.

Example B35-37

Step b

| Example # | R | LC & LC/MS data |
|---|---|---|
| B35 | 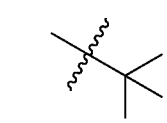 [SMILES: *C(C)(C)C] | LC (Condition B-1 and B-2): >98% homogeneity index. LC/MS (Condition B-13): $R_t$ = 2.02 min. LC/MS: Anal. Calcd. for [M + H]⁺ $C_{42}H_{49}F_4N_6O_2$: 745.38; found: 745.4. |
| B36 | | LC (Condition B-1 and B-2): >99% homogeneity index. LC/MS (Condition B-13): $R_t$ = 2.01 min. LC/MS: Anal. Calcd. for [M + H]⁺ $C_{38}H_{49}N_6O_2$: 621.38; found: 621.4. |
| B37 | | LC (Condition B-1 and B-2): >99% homogeneity index. LC/MS (Condition B-10): $R_t$ = 2.11 min. LC/MS: Anal. Calcd. for [M + H]⁺ $C_{42}H_{39}Cl_2N_6O_2$: 730.7; found: 730.2. |

Example B38

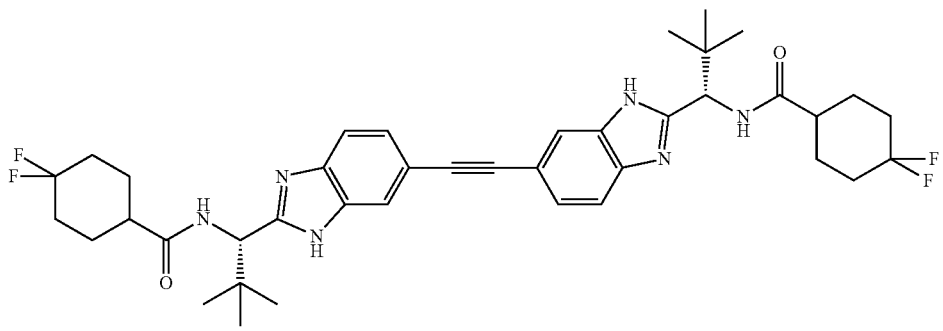 [SMILES: CC(C)(C)[C@H](NC(=O)C1CCC(F)(F)CC1)c1nc2ccc(C#Cc3ccc4nc([C@@H](NC(=O)C5CCC(F)(F)CC5)C(C)(C)C)[nH]c4c3)cc2[nH]1]

Example B38

Step a

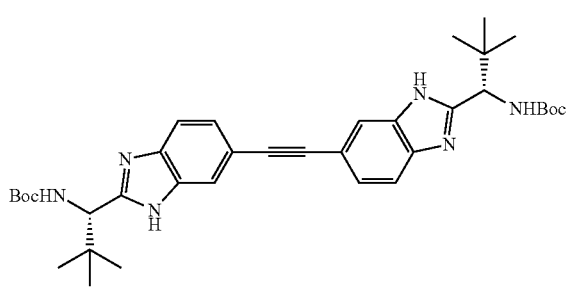 [SMILES: CC(C)(C)OC(=O)N[C@H](c1nc2ccc(C#Cc3ccc4nc([C@@H](NC(=O)OC(C)(C)C)C(C)(C)C)[nH]c4c3)cc2[nH]1)C(C)(C)C]

To a solution of iodide B32a (1 g, 2.329 mmol) and Pd(TPP)$_4$ (0.269 g, 0.233 mmol) in DMF (10 mL) was added bis(trimethylstannyl)acetylene (0.410 g, 1.165 mmol) under N$_2$ and the reaction mixture was heated at 90° C. for 12 h. The reaction mixture was filtered through diatomaceous earth (Celite®) and the filtrate was concentrated. The residue was dissolved in EtOAc, washed with water and brine. The organic layer was dried over Na$_2$SO$_4$ and concentrated. The crude was purified by combiflash Isco (Silica gel, 40 g, 3% MeOH in CHCl$_3$) to yield carbamate B38a (320 mg) as a white solid. LC (Condition B-2 and B-8): >98% homogeneity index. LC/MS (Condition B-12): R$_t$=2.40 min. $^1$H NMR (DMSO-d$_6$, δ=2.50 ppm, 400 MHz): δ 12.38/12.34 (s, 2H), 7.61/7.52 (d, J=8.4, 2H), 7.40-7.30 (m, 2H), 7.03 (d, J=9.6, 2H), 4.68 (d, J=8.8, 2H), 1.39 (s, 18H), 0.96 (s, 18H). LC/MS: Anal. Calcd. for [M+H]$^+$ C$_{36}$H$_{49}$N$_6$O$_4$: 629.37; found 629.3.

Example B38

Step b

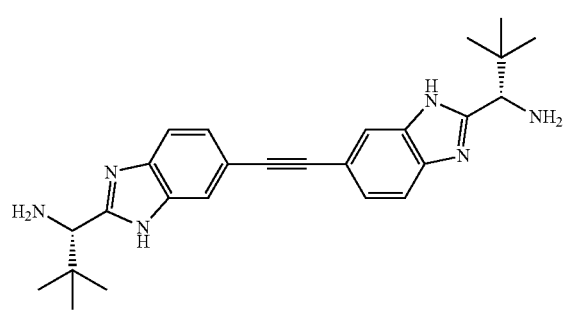

HCl salt of amine B-38b (230 mg) was prepared according to the procedure described in Example B1 step k. $^1$H NMR (MeOD, δ=3.34 ppm, 400 MHz): δ 7.91 (s, 2H), 7.74 (d, J=8.4, 2H), 7.61 (dd, J=8.4, 1.1, 2H), 4.57 (s, 2H), 1.18 (s, 18H).

Example B38

Example B38 (72 mg) was prepared according to the procedure described in Example B1. LC (Condition B-1 and B-2): >99% homogeneity index. LC/MS (Condition B-13): R$_t$=2.03 min. $^1$H NMR (MeOD, δ=3.34 ppm, 400 MHz): δ 7.94 (s, 2H), 7.77 (d, J=8.8, 2H), 7.72 (dd, J=8.8, 1.2, 2H), 4.97 (s, 2H), 2.65-2.58 (m, 2H), 2.18-2.03 (m, 4H), 1.97-1.67 (m, 12H), 1.16 (s, 18H). LC/MS: Anal. Calcd. for [M+H]$^+$ C$_{40}$H$_{49}$F$_4$N$_6$O$_2$: 721.38; found 721.4.

Example B39-41B

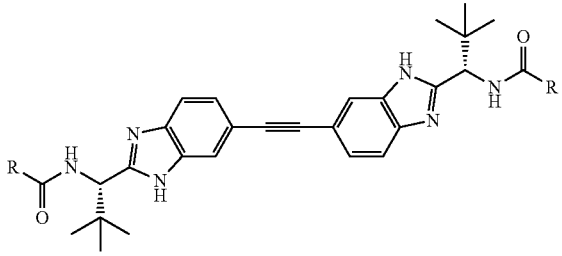

Example B39-41B (TFA salt) were prepared in a similar fashion starting from iodide B-38b and appropriate acids according to the procedure described for Example B38.

| Example # | R | LC & LC/MS data |
|---|---|---|
| B39 | ![tBu] | LC (Condition B-1 and B-2): >98% homogeneity index. LC/MS (Condition B-12): R$_t$ = 3.62 min. LC/MS: Anal. Calcd. for [M − H]$^-$ C$_{36}$H$_{47}$N$_6$O$_2$: 595.38; found 595.5. |

-continued

| Example # | R | LC & LC/MS data |
|---|---|---|
| B40 | 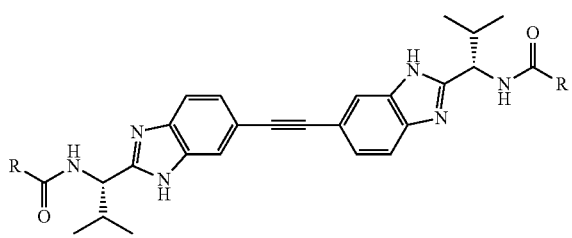 (3-chlorophenyl) | LC (Condition B-1 and B-2): >98% homogeneity index. LC/MS (Condition B-13): $R_t$ = 2.14 min. LC/MS: Anal. Calcd. for $[M + H]^+$ $C_{40}H_{39}Cl_2N_6O_2$: 706.67; found 706.2. |
| B41 | (4,4-difluoropiperidinyl carbonyl) | LC (Condition B-1 and B-2): >95% homogeneity index. LC/MS (Condition B-12): $R_t$ = 1.97 min. LC/MS: Anal. Calcd. for $[M + H]^+$ $C_{40}H_{46}F_4N_8O_4$: 779.36; found 779.4. |
| B41A | (1-(4,4-difluorocyclohexyl)-1-hydroxy-2-methylpropyl) | LC (Condition B-1 and B-5): >96% homogeneity index. LC/MS (Condition B-17): $R_t$ = 2.39 min. LC/MS: Anal. Calcd. for $[M - H]^-$ $C_{46}H_{59}F_4N_6O_4$: 835.46; found 835.4. |
| B41B | (cyclopropyl-(4,4-difluorocyclohexyl)-hydroxymethyl) | HPLC (Condition B-1 and B-2): >97% homogeneity index. LC/MS (Condition B-13): $R_t$ = 2.11 min. LC/MS: Anal. Calcd. For $[M - H]^-$ $C_{46}H_{55}F_4N_6O_4$: 831.43; found 831.2 |

Example B42-44

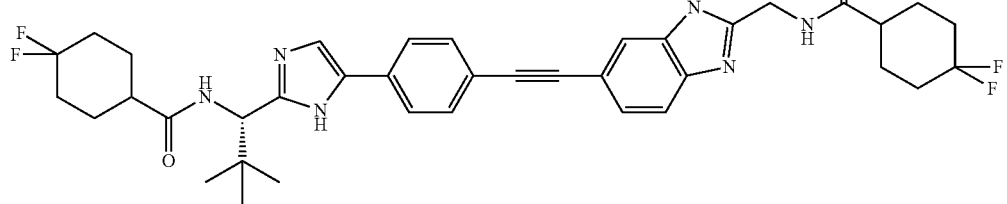

Example B42-44 (TFA salt) were prepared in a similar fashion starting from iodide B35-37a and bis(trimethylstannyl)acetylene according to the procedure described for Example B38-40.

| Example # | R | LC & LC/MS data |
|---|---|---|
| B42 | 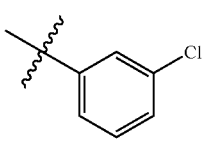 (4,4-difluorocyclohexyl) | LC (Condition B-1 and B-2): >99% homogeneity index. LC/MS (Condition B-12): $R_t$ = 2.40 min. LC/MS: Anal. Calcd. for $[M - H]^-$ $C_{38}H_{43}F_4N_6O_2$: 691.35; found 691.5. |
| B43 | (tert-butyl) | LC (Condition B-1 and B-2): >99% homogeneity index. LC/MS (Condition B-12): $R_t$ = 1.96 min. LC/MS: Anal. Calcd. for $[M - H]^-$ $C_{34}H_{43}N_6O_2$: 567.35; found 567.8. |
| B44 | (3-chlorophenyl) | LC (Condition B-1 and B-2): >99% homogeneity index. LC/MS (Condition B-12): $R_t$ = 2.11 min. LC/MS: Anal. Calcd. for $[M + H]^+$ $C_{38}H_{35}Cl_2N_6O_2$: 678.62; found 678.1. |

Example B45-46

Example B45

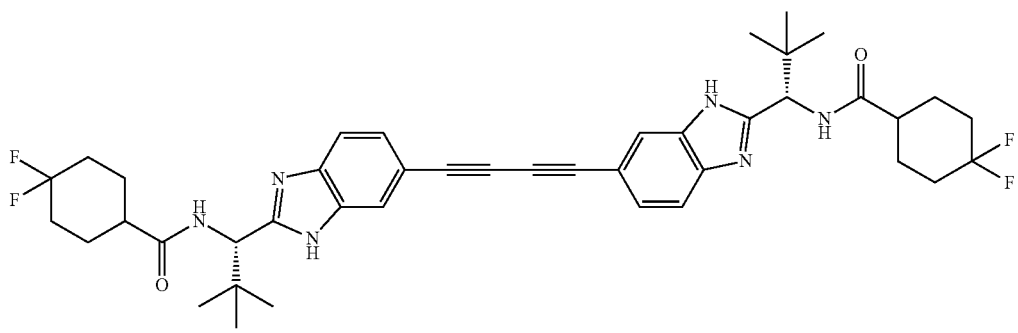 [SMILES: CC(C)(C)[C@H](NC(=O)C1CCC(F)(F)CC1)c1nc2ccc(C#CC#Cc3ccc4nc([C@@H](NC(=O)C5CCC(F)(F)CC5)C(C)(C)C)[nH]c4c3)cc2[nH]1]

Example B46

Example B45-46

Step a

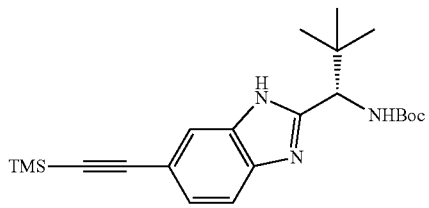 [SMILES: CC(C)(C)OC(=O)N[C@H](c1nc2ccc(C#C[Si](C)(C)C)cc2[nH]1)C(C)(C)C]

To a solution of iodide B-32a (2 g, 4.66 mmol) in DMF (20 mL) was added DIPEA (5.70 mL, 32.6 mmol) followed by trimethylsilylacetylene (6.54 mL, 46.6 mmol), CuI (0.444 g, 2.329 mmol) and Pd(PPh$_3$)$_2$Cl$_2$ (1.177 g, 1.677 mmol) under N$_2$. The reaction mixture was stirred at rt for 10 minutes and heated at 90° C. for 12 h. Then the reaction mixture was filtered through diatomaceous earth (Celite®). The filtrate was diluted with EtOAc, washed with water, saturated NH$_4$Cl and brine. The organic layer was dried over Na$_2$SO$_4$ and concentrated. The crude was purified by Combiflash Isco (Silica gel, 12 g, Redisep, 3% MeOH in CHCl$_3$) to yield trimethylsilylalkyne B45-46a (860 mg) as a brown solid. LC/MS (Condition B-10): R$_t$=2.26 min. LC/MS: Anal. Calcd. for [M+H]$^+$ C$_{22}$H$_{34}$N$_3$O$_2$Si: 400.23; found 400.2.

Example B45-46

Step b

To a solution of trimethylsilylalkyne B45-46a (944 mg, 2.312 mmol) and bromide B-10e (840 mg, 2.102 mmol) in DMF (20 mL) was added TEA (0.879 mL, 6.31 mmol), CuI (40.0 mg, 0.210 mmol) and Pd(PPh$_3$)$_2$Cl$_2$ (148 mg, 0.210 mmol) and the reaction mixture was heated at 70° C. Then TBAF (1 M in THF) (2.102 mL, 2.102 mmol) was added and the reaction mixture was heated at 70° C. for 14 h. Then the reaction mixture was filtered through diatomaceous earth (Celite®) and the filtrate was concentrated. The residue was dissolved in EtOAc and washed with water, saturated NH$_4$Cl and brine. The organic layer was dried over Na$_2$SO$_4$ and concentrated. The crude was purified by Combiflash Isco (Silica gel, 24 g, Redisep, 3% MeOH/CHCl$_3$) to yield a mixture of carbamate B-45b and B-46b (70:30, respectively).

Example B45-46

Step c

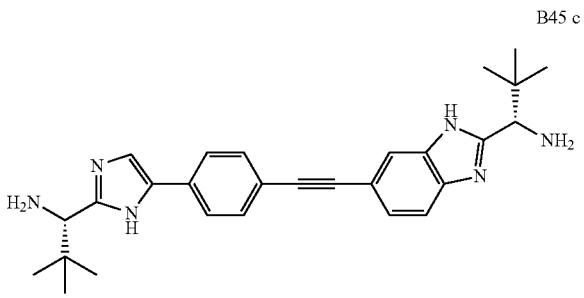

B45 c

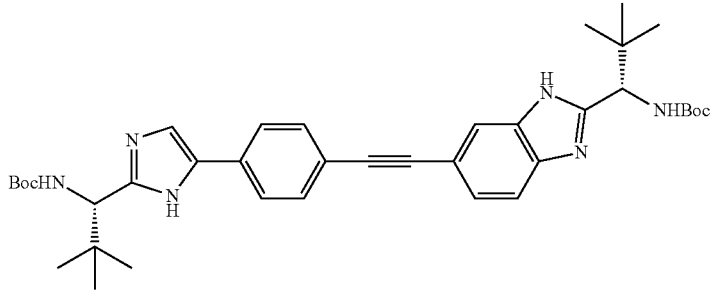

B45 b

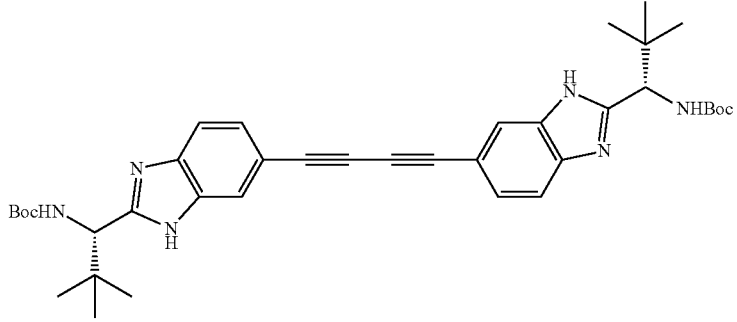

B46 b

-continued

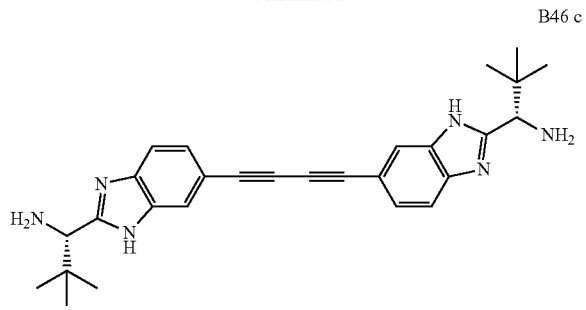

B46c

HCl salt of amine B-45c and B-46c were prepared according to the procedure described in Example B1 step k.

Example B45-46

Example B45 and B46 were prepared according to the procedure described in Example B1 and separated by prepHPLC. Example B45: LC (Condition B-1 and B-2): >95% homogeneity index. LC/MS (Condition 15): $R_f$=2.15 min. $^1$H NMR (MeOD, δ=3.34 ppm, 400 MHz): δ 7.92 (s, 1H), 7.90-7.89 (m, 1H), 7.82-7.78 (m, 2H), 7.76-7.70 (m, 3H), 7.68/7.65 (d, J=1.6, 1H), 4.99 (s, 1H), 4.93 (s, 1H), 2.65-2.56 (m, 2H), 2.18-2.04 (m, 4H), 1.96-1.68 (m, 12H), 1.15 (s, 9H), 1.14 (s, 9H). LC/MS: Anal. Calcd. for [M+H]$^+$ $C_{42}H_{51}F_4N_6O_2$: 747.39; found 747.4. Example B46: LC (Condition B-1 and B-5): >91% homogeneity index. LC/MS (Condition B-13): $R_f$=2.13 min. $^1$H NMR (MeOD, δ=3.34 ppm, 400 MHz): δ 7.91 (s, 2H), 7.73 (d, J=8.4, 2H), 7.64 (dd, J=8.4, 1.2, 2H), 4.97 (s, 2H), 2.66-2.56 (m, 2H), 2.18-2.06 (m, 4H), 1.99-1.65 (m, 12H), 1.15 (s, 18H). LC/MS: Anal. Calcd. for [M−H]$^-$ $C_{42}H_{47}F_4N_6O_2$: 743.38; found 743.4.

Example B47-50

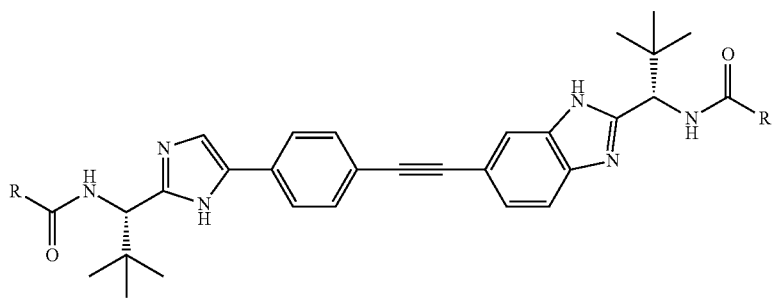

Example B47-48

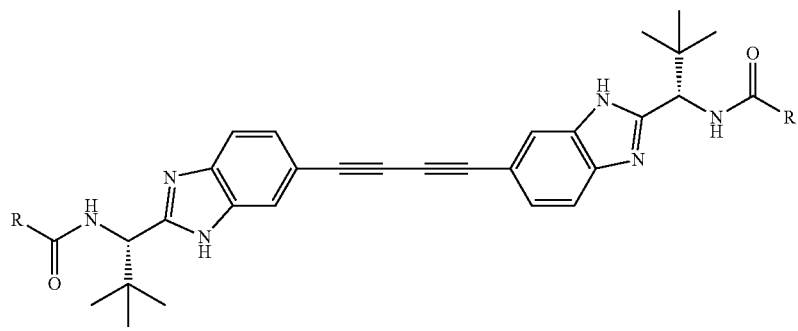

Example B49-50

Example B47-50 (TFA salt) were prepared in a similar fashion starting from mixture of amine B-45c and amine B-46c according to the procedure described for Example B45-46.

| Example # | R | LC & LC/MS data |
|---|---|---|
| B47 | *tert-butyl group* | LC (Condition B-1 and B-2): >94% homogeneity index. LC/MS (Condition 15): $R_t$ = 2.13 min. LC/MS: Anal. Calcd. for $[M + H]^+$ $C_{38}H_{51}N_6O_2$: 623.40; found 623.4. |
| B48 | *3-chlorophenyl group* | LC (Condition B-1 and B-2): >91% homogeneity index. LC/MS (Condition 15): $R_t$ = 2.22 min. LC/MS: Anal. Calcd. for $[M + H]^+$ $C_{42}H_{41}Cl_2N_6O_2$: 732.71; found 732.2. |

Example B48A

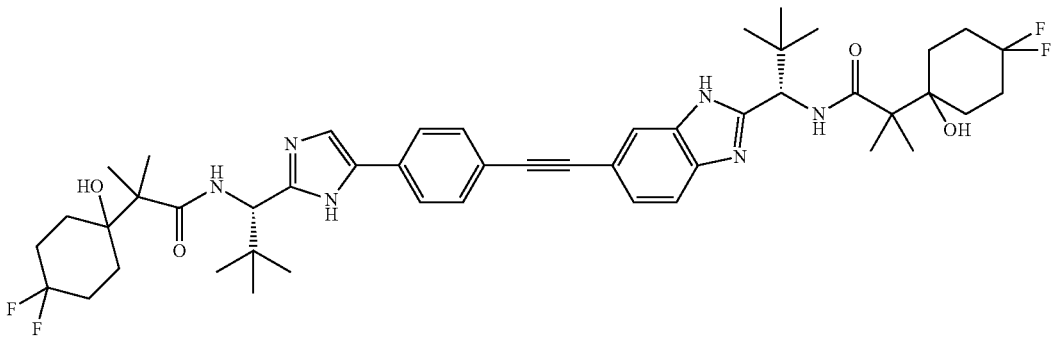 [SMILES: CC(C)(C)[C@H](NC(=O)C(C)(C)C1(O)CCC(F)(F)CC1)c1ncc(-c2ccc(C#Cc3ccc4nc([C@@H](NC(=O)C(C)(C)C5(O)CCC(F)(F)CC5)C(C)(C)C)[nH]c4c3)cc2)[nH]1]

Example B48A (TFA salt) was prepared in a similar fashion starting from pure amine B-45c and the appropriate acid according to the procedure described for Example B45-46. HPLC (Condition B-1 and B-2): >97% homogeneity index. LC/MS (Condition B-15): $R_t$=2.25 min. $^1$H NMR (MeOD, δ=3.34 ppm, 400 MHz): δ 7.89 (s, 1H), 7.87 (s, 1H), 7.78 (d, J=8.4, 2H), 7.72 (d, J=8.4, 2H), 7.71 (d, J=8.8, 1H), 7.64 (d, J=8.8, 1H), 4.95 (s, 1H), 4.91 (s, 1H), 2.28-2.05 (m, 4H), 1.97-1.60 (m, 12H), 1.29 (s, 3H), 1.27 (s, 3H), 1.20 (s, 3H), 1.18 (s, 3H), 1.14 (s, 18H). LC/MS: Anal. Calcd. for $[M-H]^-$ $C_{48}H_{61}F_4N_6O_4$: 861.48; found 861.4.

Example B48B

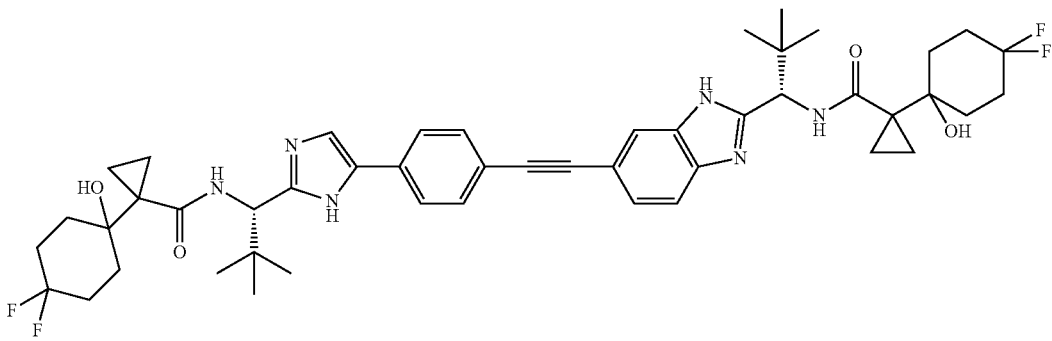 [SMILES: CC(C)(C)[C@H](NC(=O)C1(C2(O)CCC(F)(F)CC2)CC1)c1ncc(-c2ccc(C#Cc3ccc4nc([C@@H](NC(=O)C5(C6(O)CCC(F)(F)CC6)CC5)C(C)(C)C)[nH]c4c3)cc2)[nH]1]

Example B48B (TFA salt) was prepared in a similar fashion starting from pure amine B-45c the appropriate acid according to the procedure described for Example B5B. (Condition B-1 and B-2): >98% homogeneity index. LC/MS (Condition B-18): $R_t$=2.12 min. LC/MS: Anal. Calcd. for $[M-H]^-$ $C_{48}H_{57}F_4N_6O_4$: 857.45; found 857.2.

| Example # | R | LC & LC/MS data |
|---|---|---|
| B49 | | LC (Condition B-1 and B-2): >91% homogeneity index. LC/MS (Condition B-13): $R_t$ = 2.14 min. LC/MS: Anal. Calcd. for $[M - H]^-$ $C_{38}H_{47}N_6O_2$: 619.38; found 619.4. |
| B50 | | LC (Condition 5 and 6): >95% homogeneity index. LC/MS (Condition B-13): $R_t$ = 2.25 min. LC/MS: Anal. Calcd. for $[M - H]^-$ $C_{42}H_{37}Cl_2N_6O_2$: 728.7; found 728.2. |

Example B51

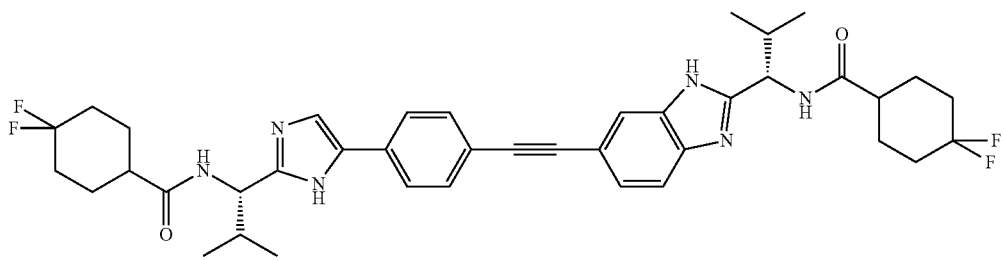 [SMILES: CC(C)[C@H](NC(=O)C1CCC(F)(F)CC1)c1ncc(-c2ccc(C#Cc3ccc4nc([C@@H](NC(=O)C5CCC(F)(F)CC5)C(C)C)[nH]c4c3)cc2)[nH]1]

Example B51

Step a

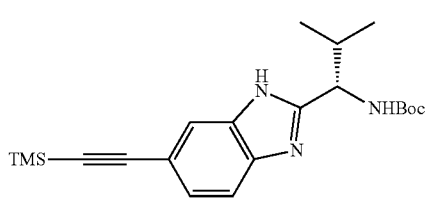 [SMILES: CC(C)[C@H](NC(=O)OC(C)(C)C)c1nc2ccc(C#C[Si](C)(C)C)cc2[nH]1]

To a stirred solution of iodide B35-37a (500 mg, 1.29 mmol) in DMF (10 mL) was added DIPEA (2.94 mL, 16.86 mmol) and CuI (0.092 g, 0.482 mmol) under $N_2$. Then trimethylsilylacetylene (1.689 mL, 12.04 mmol) was added followed by $Pd(PPh_3)_2Cl_2$ (0.5 g, 0.71 mmol) and the reaction mixture was stirred at 90° C. for 12 h. Then the reaction was diluted with EtOAc and washed with saturated $NH_4Cl$, brine. The organic layer was dried over $Na_2SO_4$ and concentrated. The crude was purified by Combiflash Isco (Silica gel, 24 g, Redisep, 30% EtOAc/petroleum ether) to give trimethylsilylalkyne B-51a (0.7 g) as a yellow solid. LC/MS (Condition B-10): $R_t$=2.12 min. LC/MS: Anal. Calcd. for $[M+H]^+$ $C_{21}H_{32}N_3O_2Si$: 386.22; found 386.2.

Example B51

Step b-1 & b-2

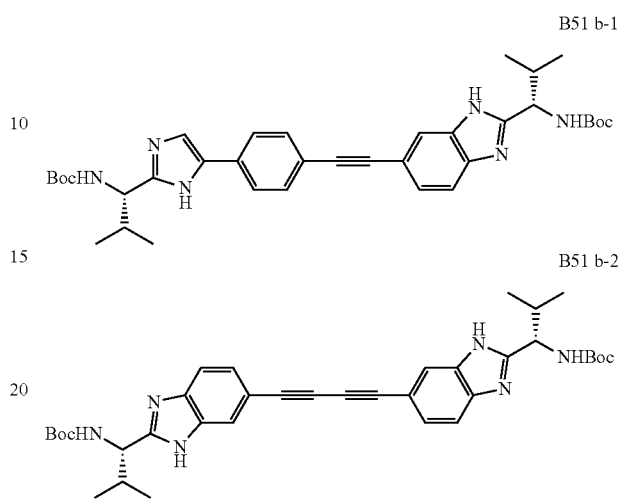

To a stirred solution of trimethylsilylalkyne B-51a (0.7 g, 1.815 mmol) and bromide B14-16b (0.716 g, 1.815 mmol) in DMF (15 mL) was added TEA (0.759 mL, 5.45 mmol) followed by CuI (0.035 g, 0.182 mmol) and $Pd(PPh_3)_2Cl_2$ (0.127 g, 0.182 mmol) under $N_2$. TBAF (1 M in THF) (0.475 g, 1.815 mmol) was added slowly at 70° C. and the reaction mixture was stirred at 70° C. for 12 h. Then the reaction was diluted with EtOAc and washed with saturated $NH_4Cl$ (brine. The organic layer was dried over $Na_2SO_4$ and concentrated. The crude was purified by reverse phase HPLC (ACN/water/$NH_4OAc$) to give carbamate B51b-1 (0.17 g) as pale yellow solid. LC/MS (Condition B-12): $R_t$=2.17 min. LC/MS: Anal. Calcd. for $[M+H]^+$ $C_{36}H_{47}N_6O_4$: 627.36; found 627.3. Carbamate B51b-2 (50 mg, 0.083 mmol) was also isolated as an off-white solid. LC/MS (Condition B-12): $R_t$=2.15 min. LC/MS: Anal. Calcd. for $[M+H]^+$ $C_{36}H_{45}N_6O_4$: 625.34; found 625.3.

Example B51

Example B51 (TFA salt) was prepared in a similar fashion starting from carbamate B51b-1 according to the procedure described for Example B45-46. HPLC (Condition B-1 and B-2): >99% homogeneity index. LC/MS (Condition B-12): $R_t$=2.04 min. LC/MS: Anal. Calcd. for $[M+H]^+$ $C_{40}H_{47}F_4N_6O_2$: 719.36; found 719.3.

Example B52

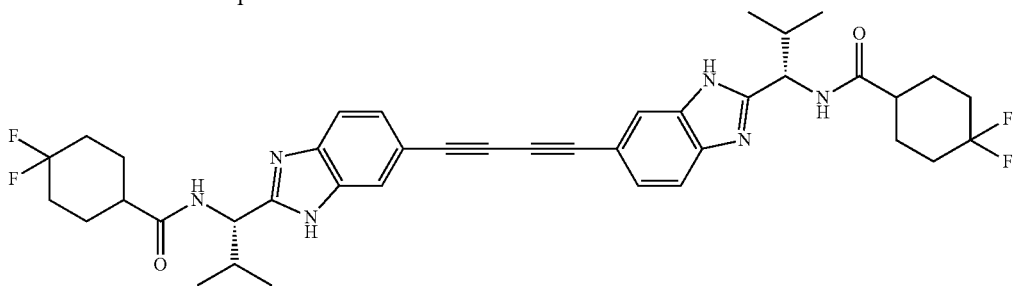

Example B52 (TFA salt) was prepared in a similar fashion starting from carbamate B51b-2 according to the procedure described for Example B45-46. HPLC (Condition B-1 and B-2): >98% homogeneity index. LC/MS (Condition B-14): $R_t$=2.17 min. LC/MS: Anal. Calcd. for $[M-H]^-$ $C_{40}H_{43}F_4N_6O_2$: 715.35; found 715.2.

Example B53

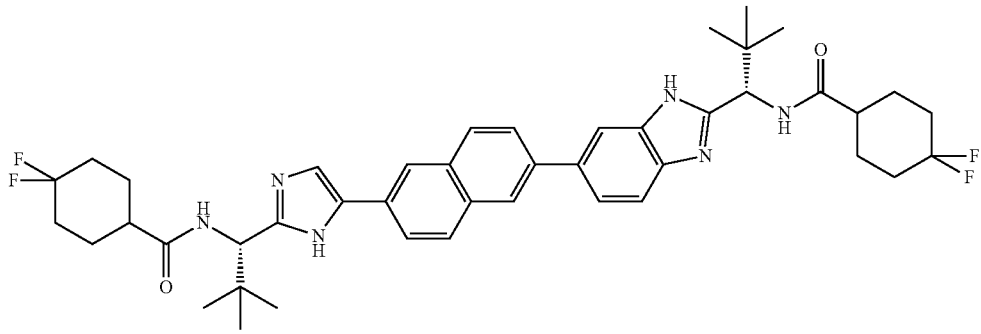 [SMILES: CC(C)(C)[C@H](NC(=O)C1CCC(F)(F)CC1)c1ncc(-c2ccc3cc(-c4ccc5nc([C@@H](NC(=O)C6CCC(F)(F)CC6)C(C)(C)C)[nH]c5c4)ccc3c2)[nH]1]

Example B53
Step a

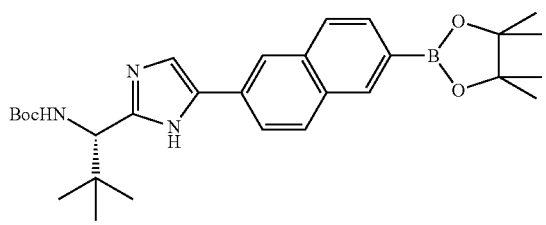 [SMILES: CC(C)(C)OC(=O)N[C@H](c1ncc(-c2ccc3cc(B4OC(C)(C)C(C)(C)O4)ccc3c2)[nH]1)C(C)(C)C]

Example B53
Step b

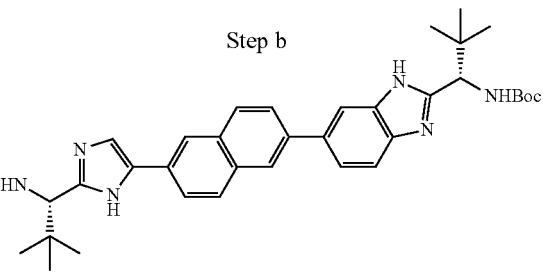

To a solution of bromide B-1d (2.0 g, 4.36 mmol) in 1,4-dioxane (20 mL) was added bis(pinacolato)diboron (1.773 g, 6.98 mmol) and KOAc (1.285 g, 13.09 mmol), followed by PdCl$_2$(dppf) (0.160 g, 0.218 mmol) under N$_2$ and the reaction mixture was heated to 100° C. for 3 h under microwave condition. The volatile components were removed and the resulting residue was dissolved in EtOAc and washed with water. The organic layer was separated and the aqueous layer was extracted with EtOAc. The combined the organic layer was washed with brine, dried over Na$_2$SO$_4$ and concentrated. The residue was washed with 5% EtOAc/petroleum ether to obtain boronate B-53a (2.2 g) as a brown solid. LC/MS (Condition B-10): $R_t$=2.39 min. Anal. Calcd. for $[M+H]^+$ $C_{29}H_{41}BN_3O_4$: 506.31; found 506.4.

To a solution of iodide B-32a (1 g, 2.329 mmol) in MeOH (15 mL) was added boronate B-53a (1.177 g, 2.329 mmol) and K$_2$CO$_3$ (0.966 g, 6.99 mmol), followed by Pd(Ph$_3$P)$_4$ (0.135 g, 0.116 mmol) under N$_2$ and the reaction mixture was heated at 80° C. for 14 h. The volatile components were removed and the resulting residue was dissolved in EtOAc and washed with water. The organic layer was separated and the aqueous layer was extracted with EtOAc. The combined organic layer was washed with brine, dried over Na$_2$SO$_4$ and concentrated. The crude was purified by reverse phase HPLC (ACN/water/NH$_4$OAc) to afford carbamate B-53b (170 mg) as an off-white solid. HPLC (Condition B-1 and B-2): >95% homogeneity index. LC/MS (Condition B-12): $R_t$=2.21 min. $^1$H NMR (MeOD, δ=3.34 ppm, 400 MHz): δ 8.21 (br s, 1H), 8.12 (br s, 1H), 8.02-7.83 (m, 5H), 7.74-7.46 (m, 3H), 4.76 (s, 1H), 4.68 (s, 1H), 1.47 (s, 18H), 1.07 (s, 9H), 1.03 (s, 9H). LC/MS: Anal. Calcd. for $[M-H]^-$ $C_{40}H_{51}N_6O_4$: 679.88; found 680.8.

Example B53

Step c

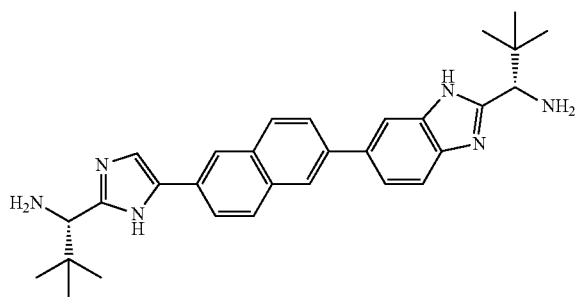 [SMILES: CC(C)(C)[C@H](N)c1ncc(-c2ccc3cc(-c4ccc5nc([C@@H](N)C(C)(C)C)[nH]c5c4)ccc3c2)[nH]1]

HCl salt of amine B-53c was prepared according to the procedure described in Example B1 step k. LC/MS (Condition B-10): R$_t$=1.56 min. $^1$H NMR (MeOD, δ=3.34 ppm, 400 MHz): δ 8.52 (s, 1H), 8.29 (s, 1H), 8.19-8.13 (m, 4H), 8.02-7.88 (m, 4H), 4.78 (s, 1H), 4.65 (s, 1H), 1.26 (s, 9H), 1.24 (s, 9H). LC/MS: Anal. Calcd. for [M−H]$^−$ C$_{30}$H$_{35}$N$_6$: 479.3; found 479.2.

Example B53

Example B53 was prepared according to the procedure described in Example B1. HPLC (Condition B-1): >97% homogeneity index. LC/MS (Condition B-10): R$_t$=2.02 min. $^1$H NMR (MeOD, δ=3.34 ppm, 400 MHz): δ 8.34 (br s, 1H), 8.29 (br s, 1H), 8.16 (d, J=8.8, 1H), 8.13 (d, J=8.8, 1H), 8.10 (br s, 1H), 8.01-7.97 (m, 3H), 7.91-7.86 (m, 2H), 5.01 (s, 1H), 4.98 (s, 1H), 2.64-2.57 (m, 2H), 2.18-2.05 (m, 4H), 1.99-1.70 (m, 12H), 1.20 (s, 9H), 1.18 (s, 9H). LC/MS: Anal. Calcd. for [M−H]$^−$ C$_{44}$H$_{51}$F$_4$N$_6$O$_2$: 771.41; found 771.4.

Example B54

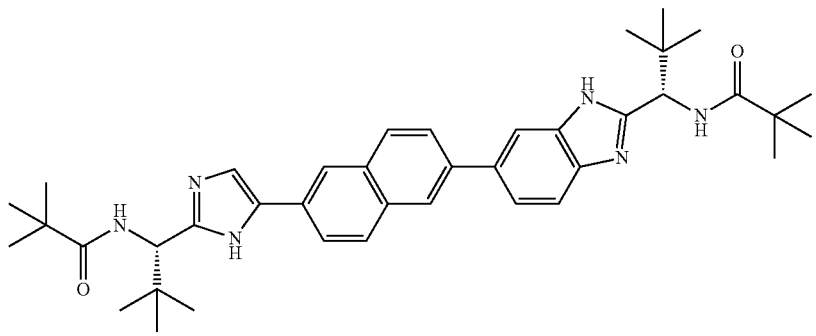 [SMILES: CC(C)(C)C(=O)N[C@H](c1ncc(-c2ccc3cc(-c4ccc5nc([C@@H](NC(=O)C(C)(C)C)C(C)(C)C)[nH]c5c4)ccc3c2)[nH]1)C(C)(C)C]

Example B54 (TFA salt) was prepared in a similar fashion starting from HCl salt of amine B-53c and pivalic acid according to the procedure described for Example B53. HPLC (Condition B-1): >97% homogeneity index. LC/MS (Condition B-10): R$_t$=2.08 min. LC/MS: Anal. Calcd. for [M−H]$^−$ C$_{40}$H$_{51}$N$_6$O$_2$: 647.42; found 647.4.

Example B55

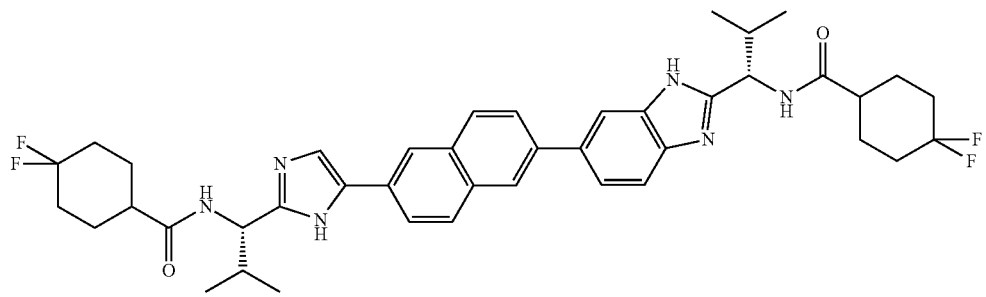 [SMILES: CC(C)[C@H](NC(=O)C1CCC(F)(F)CC1)c1ncc(-c2ccc3cc(-c4ccc5nc([C@@H](NC(=O)C6CCC(F)(F)CC6)C(C)C)[nH]c5c4)ccc3c2)[nH]1]

Example B55 (TFA salt) was prepared in a similar fashion starting from bromide B7-9a and iodide B35-37a according to the procedure described for Example B53. HPLC (Condition B-1 and B-2): >96% homogeneity index. LC/MS (Condition B-12): $R_t$=2.02 min. LC/MS: Anal. Calcd. for [M+H]$^+$ $C_{42}H_{49}F_4N_6O_2$: 745.38; found 745.2.

Example B56

Step c

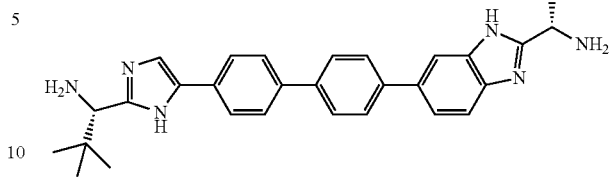

Example B56

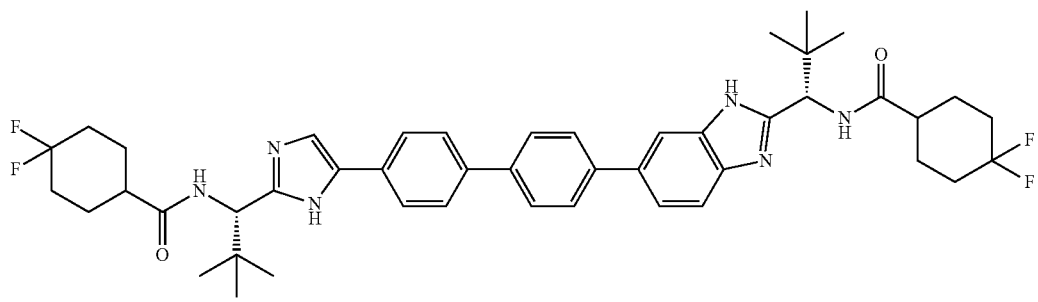 [SMILES: CC(C)(C)[C@H](NC(=O)C1CCC(F)(F)CC1)c1ncc(-c2ccc(-c3ccc(-c4ccc5nc([C@@H](NC(=O)C6CCC(F)(F)CC6)C(C)(C)C)[nH]c5c4)cc3)cc2)[nH]1]

Example B56

Step a

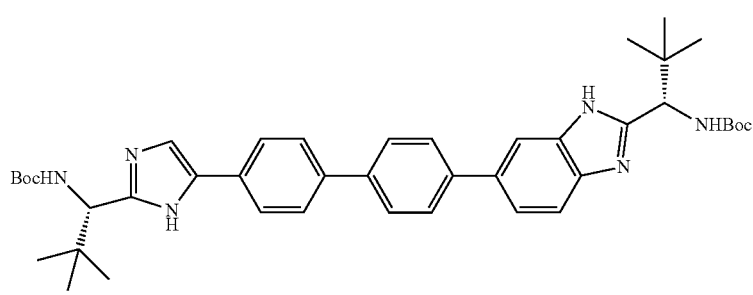 [SMILES: CC(C)(C)OC(=O)N[C@H](c1ncc(-c2ccc(-c3ccc(-c4ccc5nc([C@@H](NC(=O)OC(C)(C)C)C(C)(C)C)[nH]c5c4)cc3)cc2)[nH]1)C(C)(C)C]

To a solution of bromide B-10e (285 mg, 0.698 mmol) in MeOH (15 mL) was added boronic ester B32b-2 & 32b-3 (353 mg, 0.698 mmol) and $K_2CO_3$ (193 mg, 1.396 mmol), followed by Pd(Ph$_3$P)$_4$ (40.3 mg, 0.035 mmol) under $N_2$. The reaction mixture was heated at 80° C. for 14 h. The volatile components were removed and the resulting residue was dissolved in EtOAc and washed with water. The organic layer was separated and the aqueous layer was extracted with EtOAc. The combined organic layer was washed with brine, dried over $Na_2SO_4$ and concentrated. The crude was purified by reverse phase HPLC (ACN/water/NH$_4$OAc) to afford carbamate B-56a (245 mg) as an off-white solid. HPLC (Condition B-1 and B-2): >95% homogeneity index. LC/MS (Condition B-10): $R_t$=2.18 min. $^1$H NMR (MeOD, δ=3.34 ppm, 400 MHz): δ 7.87-7.72 (m, 9H), 7.69-7.58 (m, 2H), 7.40 (s, 1H), 4.76 (s, 1H), 4.67 (s, 1H), 1.47 (br s, 18H), 1.07 (s, 9H), 1.01 (s, 9H). LC/MS: Anal. Calcd. for [M–H]$^-$ $C_{42}H_{53}N_6O_4$: 705.42; found 705.4.

HCl salt of amine B-56b was prepared according to the procedure described in Example B1 step k. LC/MS (Condition B-10): $R_t$=1.62 min. $^1$H NMR (MeOD, δ=3.34 ppm, 400 MHz): δ 8.10 (s, 1H), 8.04 (br s, 1H), 8.01 (d, J=8.4, 2H), 7.91 (d, J=8.4, 2H), 7.87-7.82 (m, 6H), 4.74 (s, 1H), 4.64 (s, 1H), 1.24 (s, 9H), 1.23 (s, 9H). LC/MS: Anal. Calcd. for [M–H]$^-$ $C_{32}H_{37}N_6$: 505.32; found 505.3.

Example B56

Example B56 was prepared according to the procedure described in Example B1. HPLC (Condition B-1 and B-2): >99% homogeneity index. LC/MS (Condition B-12): $R_t$=2.19 min. $^1$H NMR (MeOD, δ=3.34 ppm, 400 MHz): δ 8.00 (s, 1H), 7.92-7.82 (m, 11H), 5.00 (s, 1H), 4.94 (s, 1H), 2.64-2.55 (m, 2H), 2.19-2.04 (m, 4H), 2.00-1.65 (m, 12H), 1.19 (s, 9H), 1.16 (s, 9H). LC/MS: Anal. Calcd. for [M+H]$^+$ $C_{46}H_{55}F_4N_6O_2$: 799.42; found 799.4.

Example B57

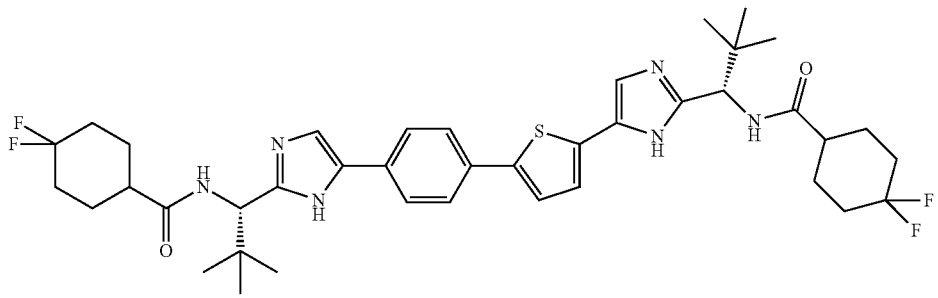 [SMILES: CC(C)(C)[C@H](NC(=O)C1CCC(F)(F)CC1)c1ncc(-c2ccc(-c3ccc(-c4cnc([C@@H](NC(=O)C5CCC(F)(F)CC5)C(C)(C)C)[nH]4)s3)cc2)[nH]1]

Example B57

Step a

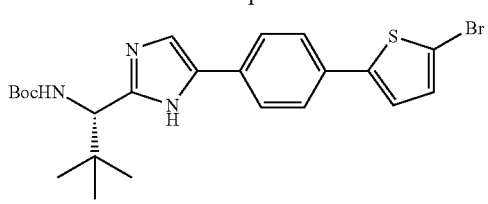

To a solution of boronate B-10f (2 g, 4.39 mmol) in MeOH (5 mL) was added 2,5-dibromothiophene (1.063 g, 4.39 mmol) and K$_2$CO$_3$ (1.821 g, 13.18 mmol), followed by Pd(Ph$_3$P)$_4$ (0.254 g, 0.220 mmol) under N$_2$ and the reaction mixture was heated at 80° C. for 14 h. The volatile components were removed and the resulting residue was dissolved in EtOAc and washed with water. The organic layer was separated and the aqueous layer was extracted with EtOAc. The combined organic layer was washed with brine, dried over Na$_2$SO$_4$ and concentrated. The crude was purified by Combiflash Isco (Silica gel, 24 g, Redisep, EtOAc/petroleum ether, 25:75) to obtain carbamate B-57a (750 mg) as a yellow solid. LC/MS (Condition B-10): R$_t$=2.33 min. $^1$H NMR (MeOD, δ=3.34 ppm, 400 MHz): δ 7.79-7.62 (m, 2H), 7.61 (d, J=8.4, 2H), 7.43-7.37 (m, 1H), 7.22 (d, J=4.0, 1H), 7.12 (d, J=4.0, 1H), 4.64 (s, 1H), 1.47 (s, 9H), 1.00 (s, 9H). LC/MS: Anal. Calcd. for [M+H]$^+$ C$_{23}$H$_{29}$BrN$_3$O$_2$S: 491.46; found 492.2.

Example B57

Step b-1 & b-2

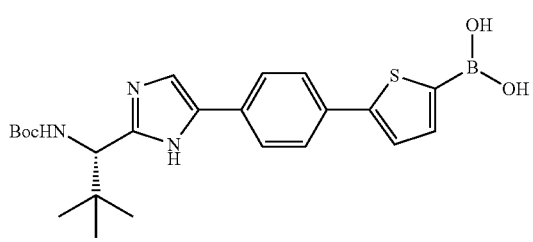

To a solution of carbamate B-57a (600 mg, 1.223 mmol) in 1,4-dioxane (20 mL) was added bis(pinacolato)diboron (652 mg, 2.57 mmol) and K$_2$CO$_3$ (516 mg, 5.26 mmol), followed by Pd(Ph$_3$P)$_4$ (70.7 mg, 0.061 mmol) under N$_2$. The reaction mixture was heated to 90° C. for 12 h under microwave condition. The volatile components were removed and the resulting residue was dissolved in EtOAc and washed with water. The organic layer was separated and the aqueous layer was extracted with EtOAc. The combined organic layer was washed with brine, dried over Na$_2$SO$_4$ and concentrated. The residue was washed with 5% EtOAc/petroleum ether to obtain a mixture of boronate ester B57b-1 (21%) & boronic acid B57b-2 (840 mg). B57b-1: LC/MS (Condition B-10): R$_t$=2.32 min. Anal. Calcd. for [M+H]$^+$ C$_{29}$H$_{41}$BN$_3$O$_4$S: 538.28; found 538.3. B57b-2: R$_t$=1.67 min. Anal. Calcd. for [M+H]$^+$ C$_{23}$H$_{31}$BN$_3$O$_4$S: 456.21; found 456.2.

Example B57

Step c

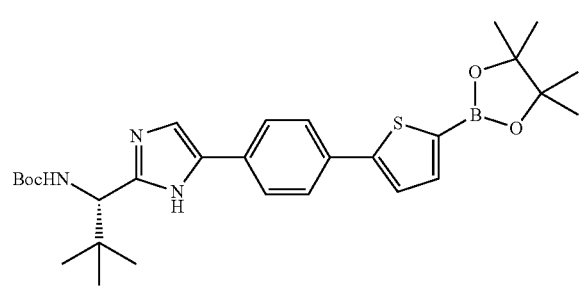

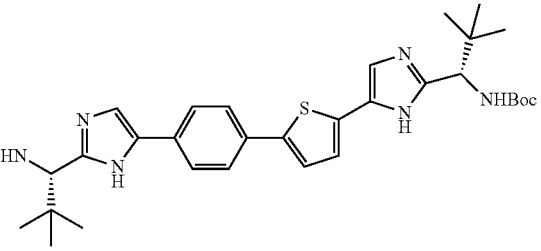

To a solution of mixture of boronate ester B57b-1 & boronic acid B57b-2 (850 mg, 1.581 mmol) in MeOH (15 mL) was added iodide B-1i (600 mg, 1.581 mmol) and $K_2CO_3$ (437 mg, 3.16 mmol), followed by $Pd(Ph_3P)_4$ (91 mg, 0.079 mmol) under $N_2$. The reaction mixture was heated at 80° C. for 14 h. Then the volatile components ware removed and the resulting residue was dissolved in EtOAc and washed with water. The organic layer was separated and the aqueous layer was extracted with EtOAc. The combined organic layer was washed with brine, dried over $Na_2SO_4$ and concentrated. The crude was purified by reverse phase HPLC (ACN/water/$NH_4OAc$) to afford B-57c (120 mg) as an off-white solid. HPLC (Condition B-1 and B-2): >95% homogeneity index. LC/MS (Condition B-12): $R_t$=2.22 min. $^1$H NMR (MeOD, δ=3.34 ppm, 400 MHz): δ 7.75-7.71 (m, 2H), 7.68 (d, J=8.4, 2H), 7.39 (br s, 1H), 7.37 (d, J=3.6, 1H), 7.9 (br s, 1H), 7.7 (d, J=3.6, 1H), 4.65 (s, 1H), 4.63 (s, 1H), 1.47 (s, 18H), 1.01 (s, 9H), 1.00 (s, 9H). LC/MS: Anal. Calcd. for [M+H]$^+$ $C_{36}H_{51}N_6O_4S$: 663.36; found 663.2.

Example B57

Step d

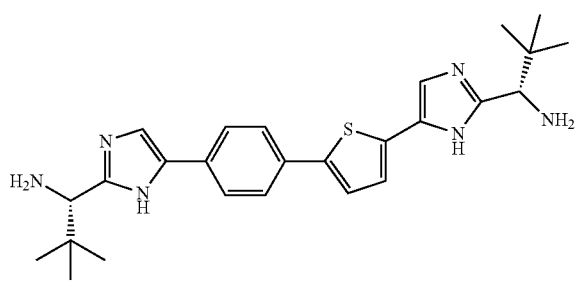 [SMILES: CC(C)(C)[C@H](N)c1ncc(-c2ccc(-c3ccc(-c4cnc([C@@H](N)C(C)(C)C)[nH]4)s3)cc2)[nH]1]

HCl salt of amine B-57d was prepared according to the procedure described in Example B1 step k. LC/MS (Condition B-10): $R_t$=1.50 min. $^1$H NMR (MeOD, δ=3.34 ppm, 400 MHz): δ 8.04 (br s, 1H), 7.93 (d, J=8.0, 2H), 7.83 (d, J=8.0, 2H), 7.70 (s, 1H), 7.53 (s, 1H), 7.49 (s, 1H), 4.68 (s, 1H), 4.42 (s, 1H), 1.21 (s, 9H), 1.17 (s, 9H). LC/MS: Anal. Calcd. for [M+H]$^+$ $C_{26}H_{35}N_6S$: 463.26; found 463.2.

Example B57

Example B57 was prepared according to the procedure described in Example B1. HPLC (Condition B-1 and B-2): >99% homogeneity index. LC/MS (Condition B-12): $R_t$=2.12 min. $^1$H NMR (DMSO-d$_6$, δ=2.50 ppm, 400 MHz): δ 14.40 (m, 2H), 8.32 (br s, 1H), 8.19-8.02 (m, 2H), 7.85-7.77 (m, 4H), 7.60 (br s, 2H), 7.38 (br s, 1H), 4.91-4.82 (m, 2H), 2.60-2.45 (obscured, 2H), 2.10-1.99 (m, 2H), 1.95-1.67 (m, 8H), 1.61-1.49 (m, 4H), 1.02 (s, 9H), 0.97 (s, 9H). LC/MS: Anal. Calcd. for [M+H]$^+$ $C_{40}H_{51}F_4N_6O_2S$: 755.37; found 755.4.

Example B58

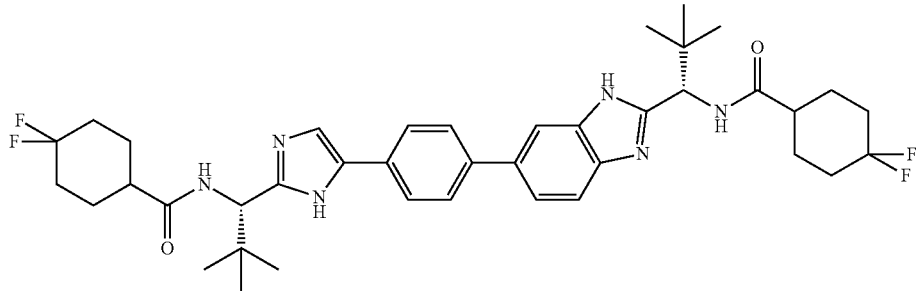 [SMILES: CC(C)(C)[C@H](NC(=O)C1CCC(F)(F)CC1)c1ncc(-c2ccc(-c3ccc4nc([C@@H](NC(=O)C5CCC(F)(F)CC5)C(C)(C)C)[nH]c4c3)cc2)[nH]1]

Example B58

Step a

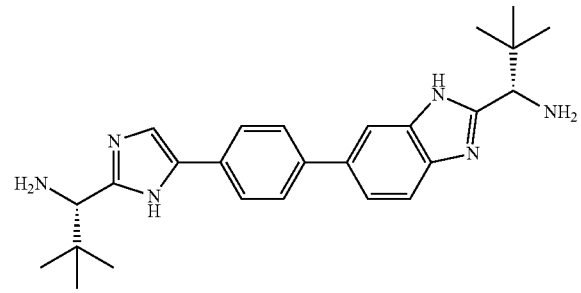 [SMILES: CC(C)(C)[C@H](N)c1ncc(-c2ccc(-c3ccc4nc([C@@H](N)C(C)(C)C)[nH]c4c3)cc2)[nH]1]

To a solution of boronate B-10f (2 g, 4.39 mmol), iodide B-32a (1.885 g, 4.39 mmol) and $K_2CO_3$ (1.821 g, 13.18 mmol) in MeOH (25 mL) was added $Pd(PPh_3)_4$ (0.254 g, 0.220 mmol) under $N_2$. The reaction mixture was heated at 80° C. for overnight. The reaction mixture was filtered through diatomaceous earth (Celite®) and washed with EtOAc. The filtrate was concentrated and the residue was redissolved in EtOAc, washed with water and brine. The organic layer was dried over $Na_2SO_4$ and concentrated. The crude was purified by Combiflash Isco (Silica gel, 40 g, 2.5% MeOH/CHCl$_3$) and reverse phase HPLC (ACN/water/$NH_4OAc$) to yield carbamate B-58a (225 mg) as a pale yellow solid. HPLC (Condition B-1 and B-2): >96% homogeneity index. LC/MS (Condition B-12): $R_t$=2.20 min. $^1$H NMR (MeOD, δ=3.34 ppm, 400 MHz): δ 7.81 (s, 1H), 7.79 (d, J=8.4, 2H), 7.72 (d, J=8.4, 2H), 7.64 (d, J=8.4, 1H), 7.58 (dd, J=8.4, 1.2, 1H), 7.41 (s, 1H), 4.75 (s, 1H), 4.67 (s, 1H), 1.47 (br s, 18H), 1.07 (s, 9H), 1.02 (s, 9H). LC/MS: Anal. Calcd. for [M+H]$^+$ $C_{36}H_{51}N_6O_4$: 631.39; found 631.4.

Example B58

Step b

HCl salt of amine B-58b was prepared according to the procedure described in Example B1 step k. LC/MS (Condition B-13): $R_t$=1.81 min. $^1$H NMR (MeOD, δ=3.34 ppm, 400 MHz): δ 8.07 (s, 1H), 8.01 (s, 1H), 8.00 (d, J=8.0, 2H), 7.89 (d, J=8.0, 2H), 7.83 (d, J=8.4, 1H), 7.78 (d, J=8.4, 1H), 4.72 (s, 1H), 4.57 (s, 1H), 1.23 (s, 9H), 1.21 (s, 9H). LC/MS: Anal. Calcd. for [M+H]$^+$ $C_{26}H_{35}N_6$: 431.28; found 431.2.

Example B58

Example B58 was prepared according to the procedure described in Example B1. HPLC (Condition B-1 and B-2): >98% homogeneity index. LC/MS (Condition B-14): $R_t$=2.04 min. $^1$H NMR (DMSO-$d_6$, δ=2.50 ppm, 400 MHz): δ 7.23 (s, 1H), 7.13-7.04 (m, 7H), 4.21 (s, 1H), 4.16 (s, 1H), 1.88-1.76 (m, 2H), 1.38-1.22 (m, 4H), 1.19-0.86 (m, 12H), 0.38 (s, 9H), 0.35 (s, 9H). LC/MS: Anal. Calcd. for [M+H]$^+$ $C_{40}H_{51}F_4N_6O_2$: 723.39; found 723.4.

Example B58A

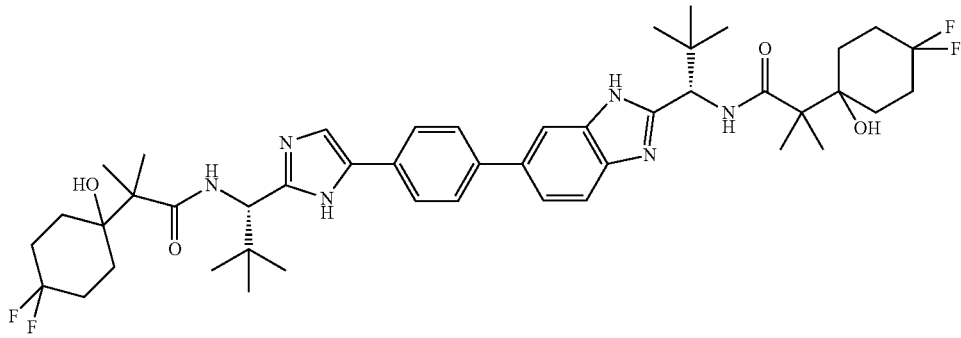 [SMILES: CC(C)(C)[C@H](NC(=O)C(C)(C)C1(O)CCC(F)(F)CC1)c1ncc(-c2ccc(-c3ccc4nc([C@@H](NC(=O)C(C)(C)C5(O)CCC(F)(F)CC5)C(C)(C)C)[nH]c4c3)cc2)[nH]1]

Example B58A (TFA salt) was prepared according to the procedure described in Example B1. HPLC (Condition B-1 and B-2): >96% homogeneity index. LC/MS (Condition B-17): $R_t$=2.40 min. LC/MS: Anal. Calcd. for [M+H]$^+$ $C_{46}H_{63}F_4N_6O_4$: 839.48; found 839.4.

Example B58B

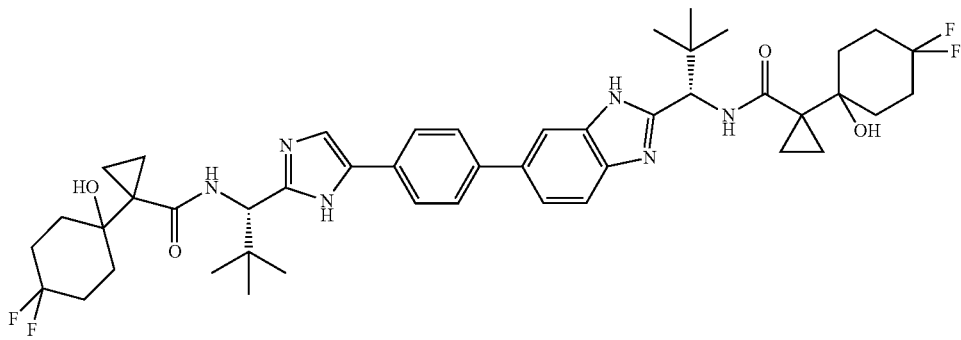 [SMILES: CC(C)(C)[C@H](NC(=O)C1(C2(O)CCC(F)(F)CC2)CC1)c1ncc(-c2ccc(-c3ccc4nc([C@@H](NC(=O)C5(C6(O)CCC(F)(F)CC6)CC5)C(C)(C)C)[nH]c4c3)cc2)[nH]1]

Example B B58B (TFA salt) was prepared according to the procedure described in Example B5B. HPLC (Condition B-1 and B-2): >98% homogeneity index. LC/MS (Condition B-18): $R_t$=2.06 min. LC/MS: Anal. Calcd. for [M-H]$^-$ $C_{46}H_{57}F_4N_6O_4$: 833.45; found 833.2.

Example B59

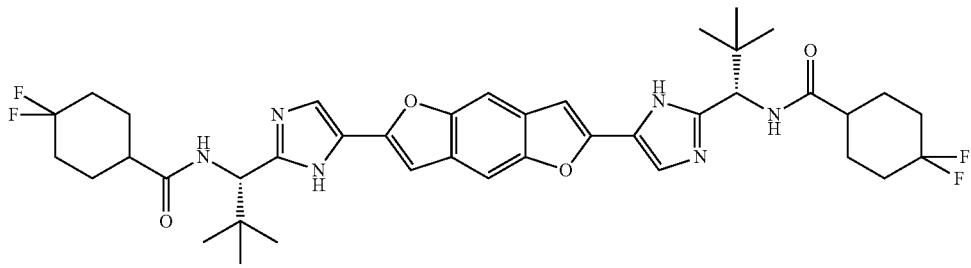 [SMILES: CC(C)(C)[C@H](NC(=O)C1CCC(F)(F)CC1)c1ncc(-c2cc3cc4oc(-c5cnc([C@@H](NC(=O)C6CCC(F)(F)CC6)C(C)(C)C)[nH]5)cc4cc3o2)[nH]1]

Example B59

Step a

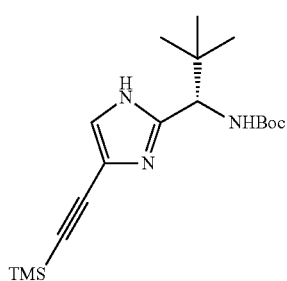 [SMILES: CC(C)(C)OC(=O)N[C@H](c1nc(C#C[Si](C)(C)C)c[nH]1)C(C)(C)C]

To a solution of iodide B-1i (1 g, 2.64 mmol) in DMF (20 mL) was added DIPEA (3.22 mL, 18.46 mmol) followed by trimethylsilylacetylene (3.70 mL, 26.4 mmol), CuI (0.100 g, 0.527 mmol) and Pd(PPh$_3$)$_2$Cl$_2$ (0.555 g, 0.791 mmol) under N$_2$. The reaction mixture was stirred at rt for 10 minutes and heated at 90° C. for 12 h. Then the reaction mixture was concentrated. The residue was diluted with EtOAc and filtered through diatomaceous earth (Celite®). The filtrate was washed with water, saturated NH$_4$Cl and brine. The organic layer was dried over Na$_2$SO$_4$ and concentrated. The crude was purified by Combiflash Isco (Silica gel, 40 g, Redisep, 20% EtOAc in petroleum ether) to yield trimethylsilylalkyne B-59a (720 mg) as a brown solid. LC/MS (Condition B-13): R$_t$=2.16 min. $^1$H NMR (MeOD, δ=3.34 ppm, 400 MHz): δ 7.23 (br s, 1H), 4.52 (s, 1H), 1.44 (s, 9H), 0.94 (s, 9H), 0.23 (s, 9H). LC/MS: Anal. Calcd. for [M+H]$^+$ C$_{18}$H$_{32}$N$_3$O$_2$Si: 350.22; found 350.2.

Example B59

Step b

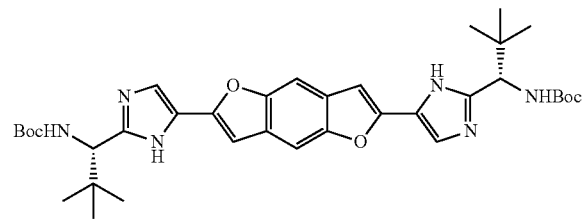 [SMILES: CC(C)(C)OC(=O)N[C@H](c1ncc(-c2cc3cc4oc(-c5cnc([C@@H](NC(=O)OC(C)(C)C)C(C)(C)C)[nH]5)cc4cc3o2)[nH]1)C(C)(C)C]

A solution of trimethylsilylalkyne B-59a (660 mg, 1.888 mmol) and 2,5-diiodobenzene-1,4-diol (342 mg, 0.944 mmol) in DMF (20 mL) was purged N$_2$ for 5 minutes. Then TEA (0.790 mL, 5.66 mmol), CuI (36.0 mg, 0.189 mmol) and Pd(PPh$_3$)$_2$Cl$_2$ (133 mg, 0.189 mmol) were added and the reaction mixture was heated to 70° C. followed by the addition of TBAF (1 M in THF) (1.888 mL, 1.888 mmol) and the reaction mixture was stirred at 70° C. for overnight. The solvents were removed. The residue was dissolved in EtOAc and filtered through diatomaceous earth (Celite®). The filtrate was washed with water, 10% NaHCO$_3$ and brine. The organic layer was dried over Na$_2$SO$_4$ and concentrated. The crude was purified by Combiflash Isco (Silica gel, 24 g, Redisep, 2% MeOH/CHCl$_3$) and reverse phase HPLC (ACN/water/NH$_4$OAc) to yield carbamate B-59b (190 mg) as an off-white solid. HPLC (Condition B-7): >92% homogeneity index. LC/MS (Condition B-12): R$_t$=2.18 min. $^1$H NMR (MeOD, δ=3.34 ppm, 400 MHz): δ 7.62 (s, 2H), 7.49 (s, 2H), 7.05 (s, 2H), 4.66 (s, 2H), 1.47 (s, 18H), 1.01 (s, 18H). LC/MS: Anal. Calcd. for [M+H]$^+$ C$_{36}$H$_{49}$N$_6$O$_6$: 661.36; found 661.3.

Example B59

Step c

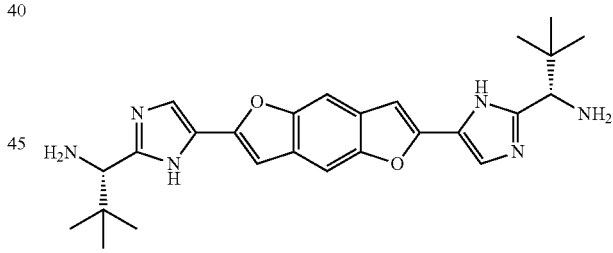

HCl salt of amine B-59c (was prepared according to the procedure described in Example B1 step k. LC/MS (Condition B-14): R$_t$=1.98 min. $^1$H NMR (MeOD, δ=3.34 ppm, 400 MHz): δ 7.96 (s, 2H), 7.79 (s, 2H), 7.39 (s, 2H), 4.56 (s, 2H), 1.19 (s, 18H). LC/MS: Anal. Calcd. for [M+H]$^+$ C$_{26}$H$_{33}$N$_6$O$_2$: 461.26; found 461.4.

Example B59

Example B59 was prepared according to the procedure described in Example B1. HPLC (Condition B-1 and B-2): >92% homogeneity index. LC/MS (Condition B-12): R$_t$=2.07 min. $^1$H NMR (MeOD, δ=3.34 ppm, 400 MHz): δ 7.92 (s, 2H), 7.82 (s, 2H), 7.38 (s, 2H), 4.98 (s, 2H), 2.64-2.55 (m, 2H), 2.18-2.07 (m, 4H), 1.97-1.70 (m, 12H), 1.13 (s, 18H). LC/MS: Anal. Calcd. for [M+H]$^+$ C$_{40}$H$_{49}$F$_4$N$_6$O$_4$: 753.37; found 753.3.

Example B60

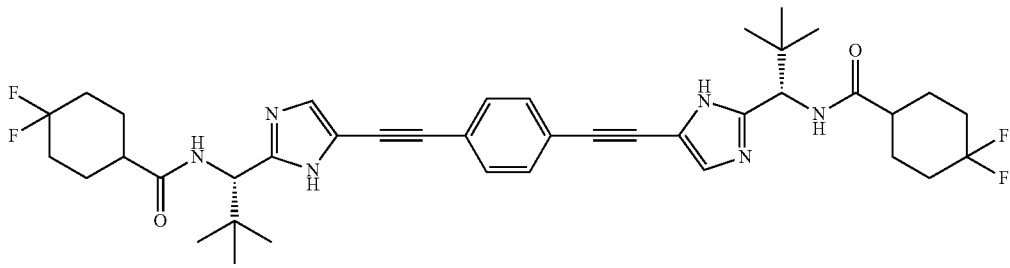 [SMILES: CC(C)(C)[C@H](NC(=O)C1CCC(F)(F)CC1)c1ncc(C#Cc2ccc(C#Cc3cnc([C@@H](NC(=O)C4CCC(F)(F)CC4)C(C)(C)C)[nH]3)cc2)[nH]1]

Example B60

Step a

Example B60

Step b

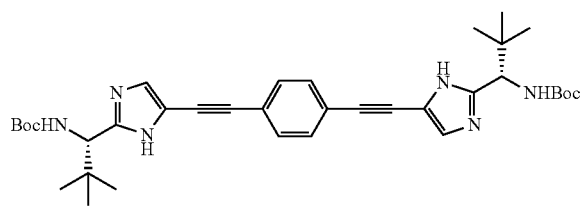 [SMILES: CC(C)(C)OC(=O)N[C@H](c1ncc(C#Cc2ccc(C#Cc3cnc([C@@H](NC(=O)OC(C)(C)C)C(C)(C)C)[nH]3)cc2)[nH]1)C(C)(C)C]

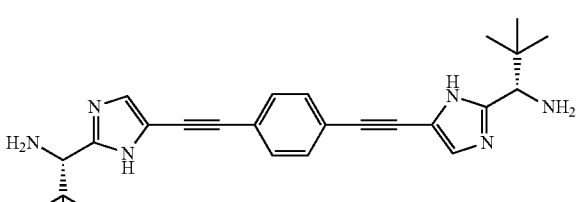

To a stirred solution of trimethylsilylalkyne B-59a (0.5 g, 1.430 mmol) and 1,4-diiodobenzene (0.236 g, 0.715 mmol) in DMF (15 mL) was added TEA (0.598 mL, 4.29 mmol) and CuI (0.027 g, 0.143 mmol). The reaction mixture was purged with $N_2$ for 30 minutes and added with $Pd(PPh_3)_2Cl_2$ (0.100 g, 0.143 mmol). Then the reaction mixture was heated to 70° C. followed by the addition of TBAF (1M in THF) (0.374 g, 1.430 mmol) and the reaction mixture was stirred at 70° C. for 12 h. The residue was diluted with EtOAc and filtered through diatomaceous earth (Celite®). The filtrate was washed with water, saturated $NH_4Cl$ and brine. The organic layer was dried over $Na_2SO_4$ and concentrated. The crude was purified by reverse phase HPLC (ACN/water/$NH_4OAc$) to give carbamate B-60a (0.12 g) as a pale yellow solid. HPLC (Condition B-1 and B-2): >95% homogeneity index. LC/MS (Condition B-10): $R_t$=2.06 min. $^1$H NMR (MeOD, δ=3.34 ppm, 400 MHz): δ 7.50 (s, 4H), 7.35 (s, 2H), 4.56 (s, 2H), 1.46 (br s, 18H), 0.97 (s, 18H). LC/MS: Anal. Calcd. for [M+H]$^+$ $C_{36}H_{49}N_6O_4$: 629.8; found 630.5.

HCl salt of amine B-60b (was prepared according to the procedure described in Example B1 step k. LC/MS (Condition B-10): $R_t$=1.47 min. $^1$H NMR (MeOD, δ=3.34 ppm, 400 MHz): δ 7.74 (s, 2H), 7.59 (br s, 4H), 4.43 (s, 2H), 1.12 (s, 18H). LC/MS: Anal. Calcd. for [M+H]$^+$ $C_{26}H_{33}N_6$: 429.27; found 429.3.

Example B60

Example B60 was prepared according to the procedure described in Example B1. HPLC (Condition B-1 and B-2): >95% homogeneity index. LC/MS (Condition B-12): $R_t$=2.09 min. $^1$H NMR (MeOD, δ=3.34 ppm, 400 MHz): δ 7.69 (s, 2H), 7.62 (br s, 4H), 4.81 (s, 2H), 2.61-2.52 (m, 2H), 2.18-2.07 (m, 4H), 1.95-1.70 (m, 12H), 1.09 (s, 18H). LC/MS: Anal. Calcd. for [M+H]$^+$ $C_{40}H_{49}F_4N_6O_2$; 721.38; found 721.3.

Example B61

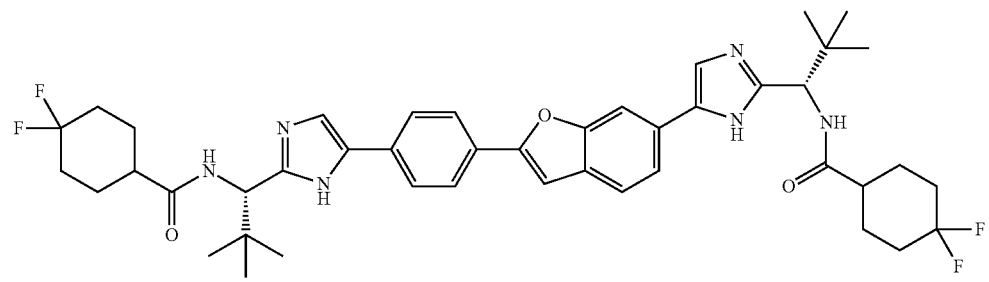 [SMILES: CC(C)(C)[C@H](NC(=O)C1CCC(F)(F)CC1)c1ncc(-c2ccc(-c3cc4ccc(-c5cnc([C@@H](NC(=O)C6CCC(F)(F)CC6)C(C)(C)C)[nH]5)cc4o3)cc2)[nH]1]

Example B61

Step a

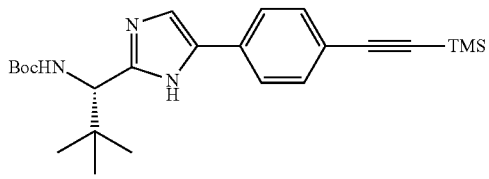 [SMILES: CC(C)(C)OC(=O)N[C@H](c1ncc(-c2ccc(C#C[Si](C)(C)C)cc2)[nH]1)C(C)(C)C]

To a solution of bromide B-10e (1.5 g, 3.67 mmol) in DMF (10 mL) was added CuI (0.140 g, 0.735 mmol) followed by DIPEA (4.49 mL, 25.7 mmol). The reaction mixture was purged with $N_2$ for 20 minutes. Then a trimethylsilylacetylene (5.15 mL, 36.7 mmol) was added followed by $PdCl_2(TPP)_2$ (770 mg, 1.09 mmol). The reaction mixture was heated at 90° C. for 12 h. The reaction was diluted with EtOAc and washed with saturated $NH_4Cl$ and brine. The organic layer was dried over $Na_2SO_4$, filtered and evaporated. The crude was purified on flash chromatography (Silica gel, 60-120, 20% EtOAc/petroleum ether) to give trimethylsilylalkyne B-61a (0.7 g) as a yellow solid. LC/MS (Condition B-14): $R_t$=2.25 min. $^1H$ NMR (MeOD, δ=3.34 ppm, 400 MHz): δ 7.67 (d, J=8.4, 2H), 7.45-7.40 (m, 3H), 4.63 (s, 1H), 1.45 (s, 9H), 0.98 (s, 9H), 0.25 (s, 9H). LC/MS: Anal. Calcd. for [M−H]⁻ $C_{24}H_{34}N_3O_2Si$: 424.25; found 424.2.

Example B61

Step b

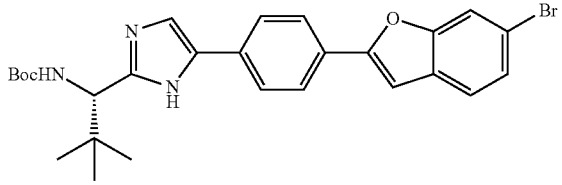 [SMILES: CC(C)(C)OC(=O)N[C@H](c1ncc(-c2ccc(-c3cc4ccc(Br)cc4o3)cc2)[nH]1)C(C)(C)C]

To a solution of 5-bromo-2-iodophenol (0.48 g, 1.64 mmol) and trimethylsilylalkyne B-61a (0.7 g, 1.64 mmol) in isopropyl acetate (10 mL) was added $Pd(OAc)_2$ (7.63 mg, 0.03 mmol) and TPP (0.029 g, 0.060 mmol) followed by CuI (1.24 mg, 0.060 mmol). The reaction mixture was purged with $N_2$ for 20 minutes and then DIPEA (1.51 mL, 8.2 mmol) was added. Then the reaction mixture was heated to 60° C. followed by the addition of TBAF (1 M in THF) (1.64 mL, 1.64 mmol) and the reaction mixture was stirred at 60° C. for 8 h. Then the reaction was quenched with water and diluted with EtOAc. The organic layer was washed with saturated $NH_4Cl$, dried over $Na_2SO_4$, filtered and evaporated. The crude was purified by Combiflash Isco (Silica gel, 40 g, Redisep, 40% EtOAc/petroleum ether) to give bromide B-61b (0.5 g) as a pale yellow solid. LC/MS (Condition B-14): $R_t$=2.30 min. $^1H$ NMR (DMSO-$d_6$, δ=2.50 ppm, 400 MHz): δ 11.90 (br s, 1H), 7.94-7.75 (m, 5H), 7.66-7.58 (m, 2H), 7.48-7.39 (m, 2H), 6.77 (d, J=10.0, 1H), 4.56 (d, J=10.0, 1H), 1.40 (s, 9H), 0.93 (s, 9H). LC/MS: Anal. Calcd. for [M+H]⁺ $C_{27}H_{31}BrN_3O_3$: 524.15; found 524.2.

Example B61

Step c

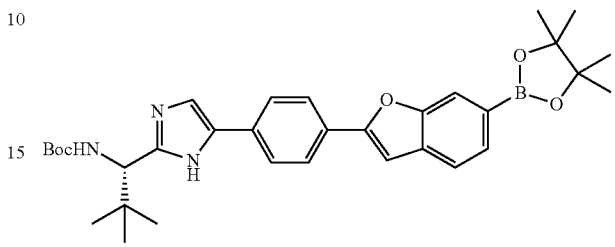

To a solution of bromide B-61b (0.5 g, 1.907 mmol) and bis(pinacolato)diboron (0.7363 g, 1.43 mmol) in 1,4-dioxane (15 mL) was added KOAc (0.0.28 g, 2.86 mmol) and the reaction mixture was purged with $N_2$ for 20 minutes. The $PdCl_2(dppf)$ (0.035 g, 0.045 mmol) was added and the reaction mixture was heated at 100° C. for 12 h. After cooling to rt, the reaction mixture was passed through diatomaceous earth (Celite®) and evaporated. The resulting residue was dissolved in EtOAc and washed with water and brine, dried over $Na_2SO_4$, filtered and evaporated. The crude was purified on Combiflash Isco (Neutral $Al_2O_3$, 40 g, Redisep, 15% EtOAc/petroleum ether) to give boronate B-61c (0.38 g) as a yellow solid. LC/MS (Condition B-16): $R_t$=1.44 min. $^1H$ NMR (MeOD, δ=3.34 ppm, 400 MHz): δ 7.97 (d, J=8.8, 2H), 7.90 (d, J=0.4, 1H), 7.83 (d, J=8.8, 2H), 7.66-7.59 (m, 2H), 7.45 (s, 1H), 7.22 (d, J=0.8, 1H), 4.66 (s, 1H), 1.47 (s, 9H), 1.22 (s, 12H), 1.01 (s, 9H). LC/MS: Anal. Calcd. for [M+H]⁺ $C_{33}H_{43}BN_3O_5$: 572.32; found 572.5.

Example B61

Step d

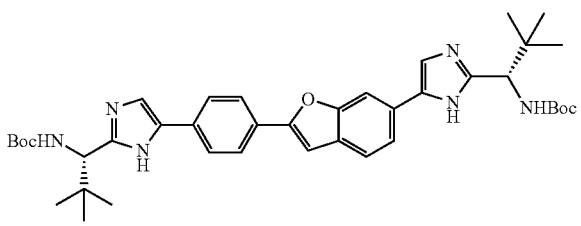 [SMILES: CC(C)(C)OC(=O)N[C@H](c1ncc(-c2ccc(-c3cc4ccc(-c5cnc([C@@H](NC(=O)OC(C)(C)C)C(C)(C)C)[nH]5)cc4o3)cc2)[nH]1)C(C)(C)C]

To a stirred solution of boronate B-61c (0.38 g, 0.66 mmol) and iodide B-1i (0.22 g, 0.66 mmol) in toluene (5 mL) and EtOH (5 mL) and water (5 mL) was added $Na_2CO_3$ (0.17 g, 1.75 mmol) under $N_2$. Then $PdCl_2(dppf)$-DCM adduct (0.0480 g, 0.058 mmol) was added and the reaction mixture was heated at 85° C. for 12 h. Then the reaction was diluted with EtOAc and washed with brine, filtered through diatomaceous earth (Celite®) and washed with EtOAc. The combined filtrate was evaporated. The resulting crude was purified on Combiflash Isco (Silica gel, 40 g, Redisep, 40% EtOAc/petroleum ether) to give carbamate B-61d (0.4 g) as a brown solid. HPLC (Condition B-1 and B-2): >97% homogeneity index. LC/MS (Condition B-14): $R_t$=2.18 min. $^1H$ NMR (MeOD, δ=3.34 ppm, 400 MHz): δ 7.96-7.78 (m, 5H), 7.61 (br s, 2H), 7.45 (br s, 1H), 7.41 (br s, 1H), 7.21 (s, 1H), 4.66 (br s, 2H), 1.47 (s, 18H), 1.01 (s, 18H). LC/MS: Anal. Calcd. for [M−H]⁻ 696.878 $C_{40}H_{51}N_6O_5$: 695.4; found 695.3.

Example B61

Step e

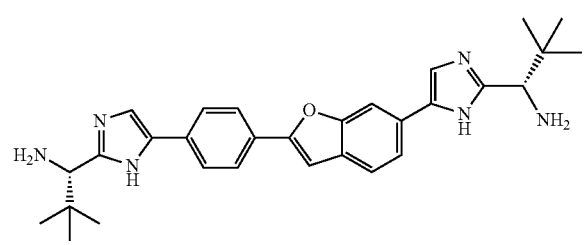 [SMILES: CC(C)(C)[C@H](N)c1ncc(-c2ccc(-c3cc4ccc(-c5cnc([C@@H](N)C(C)(C)C)[nH]5)cc4o3)cc2)[nH]1]

HCl salt of amine B-61e was prepared according to the procedure described in Example B1 step k. LC/MS (Condition B-16): $R_t$=0.88 min. ¹H NMR (MeOD, δ=3.34 ppm, 400 MHz): δ 8.19-7.92 (m, 7H), 7.84-7.70 (m, 2H), 7.44 (br s, 1H), 4.77 (s, 1H), 4.73 (s, 1H), 1.22 (s, 9H), 1.21 (s, 9H). LC/MS: Anal. Calcd. for [M+H]⁺ $C_{30}H_{37}N_6O$: 497.3; found 497.47.

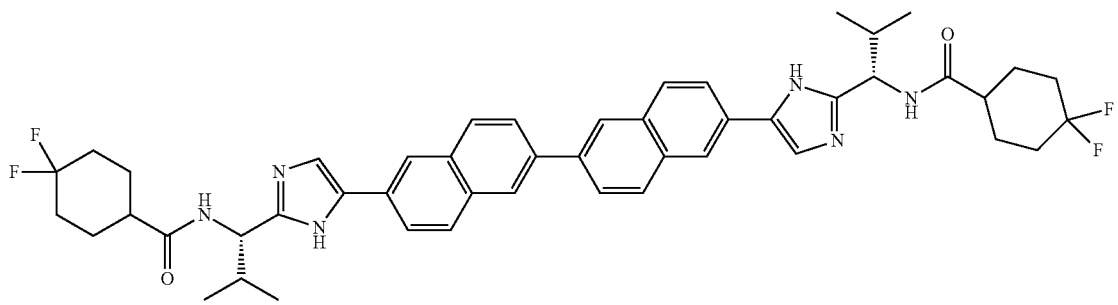 [SMILES: CC(C)[C@H](NC(=O)C1CCC(F)(F)CC1)c1ncc(-c2ccc3cc(-c4ccc5cc(-c6cnc([C@@H](NC(=O)C7CCC(F)(F)CC7)C(C)C)[nH]6)ccc5c4)ccc3c2)[nH]1]

Example B61

Example B61 was prepared according to the procedure described in Example B1. HPLC (Condition B-1 and B-2): >94% homogeneity index. LC/MS (Condition B-14): $R_t$=2.10 min. ¹H NMR (MeOD, δ=3.34 ppm, 400 MHz): δ 7.95 (d, J=8.4, 2H), 7.89-7.77 (m, 3H) 7.62 (br s, 2H), 7.45 (s, 1H), 7.41 (s, 1H), 7.22 (s, 1H), 5.02 (s, 1H), 5.01 (s, 1H), 2.52-2.48 (m, 2H), 2.18-2.04 (m, 4H), 2.00-1.70 (m, 12H), 1.05 (s, 9H), 1.04 (s, 9H). LC/MS: Anal. Calcd. for [M−H]⁻ $C_{44}H_{51}F_4N_6O_3$: 787.40; found 787.3.

Example B62-63

Example B62-63 (TFA salt) were prepared in a similar fashion from amine B-61e and appropriate acids according to the procedure described for Example B61.

| Example # | R | LC & LC/MS data |
|---|---|---|
| B62 | *tert-butyl group* | LC (Condition B-1 and B-2): >97% homogeneity index. LC/MS (Condition B-12): $R_t$ = 2.16 min. LC/MS: Anal. Calcd. for [M + H]⁺ $C_{40}H_{53}N_6O_3$: 665.41; found 665.9. |
| B63 | *Me–N(cyclopropyl)–C(=O)OMe group* | LC (Condition B-1 and B-2): >97% homogeneity index. LC/MS (Condition B-12): $R_t$ = 1.98 min. LC/MS: Anal. Calcd. for [M + H]⁺ $C_{44}H_{55}N_8O_7$: 807.41; found 807.8. |

Example B64

Example B64

Step a

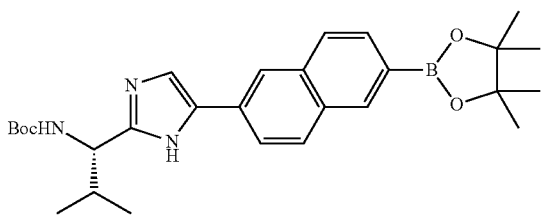 [SMILES: CC(C)[C@H](NC(=O)OC(C)(C)C)c1ncc(-c2ccc3cc(B4OC(C)(C)C(C)(C)O4)ccc3c2)[nH]1]

A solution of bromide B7-9a (1 g, 2.250 mmol) in 1,4-dioxane (20 mL) was purged with $N_2$ for 5 minutes. Then bis(pinacolato)diboron (0.571 g, 2.250 mmol) was added followed by KOAc (0.663 g, 6.75 mmol) and $PdCl_2$(dppf) (0.082 g, 0.113 mmol). Then the reaction mixture was heated at 100° C. for 24 h. The volatile component was removed and the resulting crude was dissolved in EtOAc and water and filtered through diatomaceous earth (Celite®). The filtrate was collected and the aqueous layer was separated. The organic phase was washed with brine, dried over $Na_2SO_4$ and concentrated. The resulting residue was washed with petroleum ether to obtain boronate ester B-64a (443 mg). LC/MS (Condition B-10): $R_t$=2.19 min. LC/MS: Anal. Calcd. for $[M+H]^+$ $C_{28}H_{39}BN_3O_4$: 492.3; found 492.2.

water/$NH_4OAc$) to get carbamate B-64b (42 mg) as an off-white solid. HPLC (Condition B-1 and B-2): >91% homogeneity index. LC/MS (Condition B-12): $R_t$=2.27 min. $^1H$ NMR (MeOD, δ=3.34 ppm, 400 MHz): δ 8.22 (br s, 4H), 8.03-7.93 (m, 6H), 7.87 (dd, J=8.4, 1.2, 2H), 7.50 (s, 2H), 4.60 (s, 1H), 4.58 (s, 1H), 2.22-2.17 (m, 2H), 1.48 (s, 18H), 1.05 (d, J=6.4, 6H), 0.92 (d, J=6.8, 6 H). LC/MS: Anal. Calcd. for $[M+H]^+$ $C_{44}H_{53}N_6O_4$: 729.41; found 729.5.

Example B64

Step b

Example B64

Step c

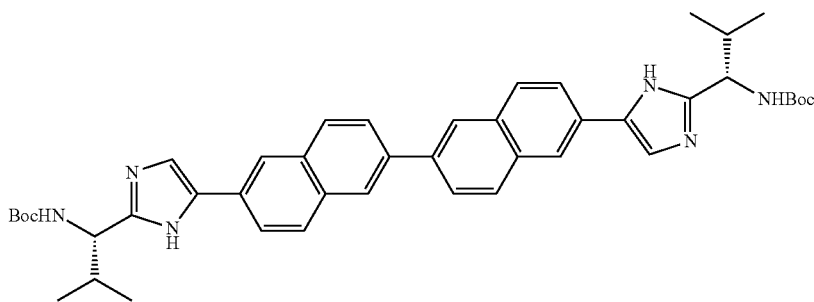 [SMILES: CC(C)[C@H](NC(=O)OC(C)(C)C)c1ncc(-c2ccc3cc(-c4ccc5cc(-c6cnc([C@@H](NC(=O)OC(C)(C)C)C(C)C)[nH]6)ccc5c4)ccc3c2)[nH]1]

A solution of iodide B7-9c (300 mg, 0.675 mmol) and boronate ester B-64a (398 mg, 0.810 mmol) in MeOH (25 mL) was purged with $N_2$ for 10 minutes. Then $K_2CO_3$ (280 mg, 2.025 mmol) was added followed by $Pd(Ph_3P)_4$ (78 mg,

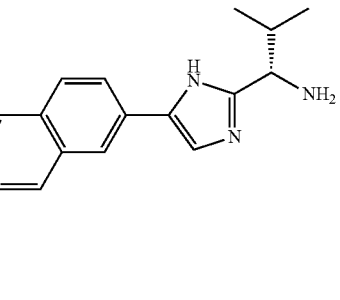

0.068 mmol). The reaction mixture was stirred at 85° C. for overnight. The volatile component was removed and the resulting crude was dissolved in EtOAc, water and filtered through diatomaceous earth (Celite®). The filtrate was washed with brine, dried over $Na_2SO_4$ and concentrated. The crude was purified by flash chromatography (Silica gel 60-120, 3-5% MeOH/DCM) and reverse phase HPLC (ACN/

HCl salt of amine 64c was prepared according to the procedure described in Example B1 step k. LC/MS (Condition B-12): $R_t$=1.84 min. $_1H$ NMR (MeOD, δ=3.34 ppm, 400 MHz): δ 8.51 (s, 2H), 8.39 (s, 2H), 8.25-7.99 (m, 10H), 4.67 (s, 1H), 4.65 (s, 1H), 2.74-2.68 (m, 2H), 1.31 (d, J=6.4, 6H), 1.05 (d, J=6.0, 6 H). LC/MS: Anal. Calcd. for $[M+H]^+$ $C_{34}H_{36}N_6$: 529.30; found 529.2. (MeOD,

Example B64

Example B64 (16 mg) was prepared according to the procedure described in Example B1. HPLC (Condition B-1 and B-2): >95% homogeneity index. LC/MS (Condition B-12): $R_t$=2.13 min. $^1$H NMR (MeOD, δ=3.34 ppm, 400 MHz): δ 8.38 (s, 2H), 8.34 (s, 2H), 8.17 (d, J=8.4, 2H), 8.13 (d, J=8.4, 2H), 8.09 (dd, J=8.4, 1.6, 2H), 7.99 (s, 2H), 7.89 (dd, J=8.8, 1.6, 2H), 4.93 (s, 1H), 4.91 (s, 1H), 2.58-2.50 (m, 2H), 2.45-2.34 (m, 2H), 2.20-1.98 (m, 4H), 2.00-1.72 (m, 12H), 1.19 (d, J=6.4, 6H), 1.01 (d, J=6.8, 6 H). Calcd. for [M+H]$^+$ $C_{48}H_{53}F_4N_6O_2$: 821.41; found 821.4.

Example B65

To a stirred solution of trimethylsilylalkyne B-59a (0.5 g, 1.430 mmol) and 2,6-dibromonaphthalene (0.409 g, 1.430 mmol) in DMF (10 mL) was added CuI (0.054 g, 0.286 mmol), TEA (0.598 mL, 4.29 mmol) under $N_2$. Then $Pd(PPh_3)_2Cl_2$ (0.301 g, 0.429 mmol) was added and the reaction mixture was heated to 70° C. Then TBAF (1 M in THF) (0.374 g, 1.430 mmol) was added and the reaction mixture was stirred at 70° C. for 12 h. Then the reaction mixture was diluted with EtOAc and washed with saturated $NH_4Cl$, brine, dried over $Na_2SO_4$, filtered and evaporated. The crude was purified by reverse phase HPLC (ACN/water/$NH_4OAc$) to give free base of carbamate B65a-1 (0.08 g) as a pale yellow solid. HPLC (Condition B-1 and B-2): >96% homogeneity index. LC/MS (Condition B-14): $R_t$=2.16 min. $^1$H NMR (MeOD, δ=3.34 ppm, 400 MHz): δ 8.02 (s, 2H), 7.85 (m, 2H), 7.57 (m, 2H), 7.34 (br s, 2H), 4.56 (s, 2H), 1.45 (s, 18H), 0.96 (s, 18H). LC/MS: Anal. Calcd. for [M−H]$^−$ $C_{40}H_{49}N_6O_4$: 677.39; found 677.2. Carbamate B65a-2 (0.02 g, 0.036 mmol, 2.53%) was also isolated as a pale yellow solid. LC/MS (Condition B-14): $R_t$=2.16 min. $^1$H NMR (MeOD, δ=3.34 ppm, 400 MHz): δ 7.42 (s, 2H), 4.53 (s, 2H), 1.45 (s, 18H), 0.95 (s, 18H). LC/MS: Anal. Calcd. for [M−H]$^−$ $C_{30}H_{43}N_6O_4$: 551.34; found 551.3.

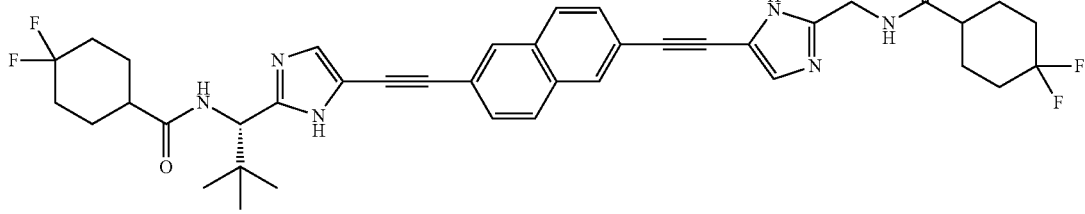

Example B65

Step a-1 & a-2

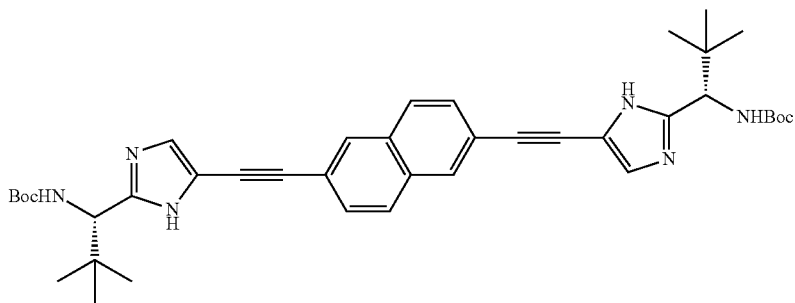

B65 a-1

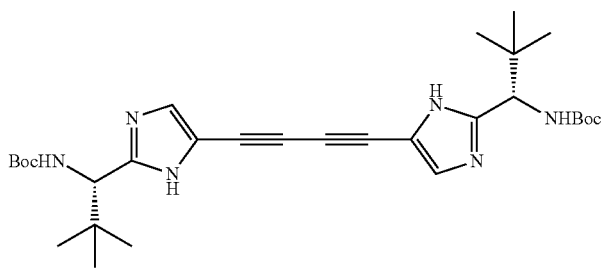

B65 a-2

Example B65

Step b

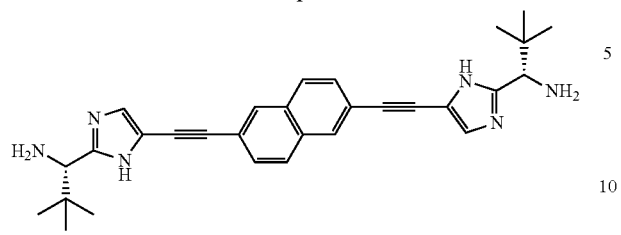

HCl salt of amine B-65b (0.07 g) was prepared according to the procedure described in Example B1 step k. LC/MS (Condition B-14): $R_t$=1.99 min. $^1$H NMR (MeOD, δ=3.34 ppm, 400 MHz): δ 8.09 (s, 2H), 7.91 (d, J=8.4, 2H), 7.67 (s, 2H), 7.61 (d, J=8.4, 2H), 4.36 (s, 2H), 1.12 (s, 18H). LC/MS: Anal. Calcd. for [M−H]$^-$ $C_{30}H_{33}N_6$: 477.28; found 477.2

Example B65

Example B65 (0.038 g) was prepared according to the procedure described in Example B1. HPLC (Condition B-1 and B-2): >97% homogeneity index. LC/MS (Condition B-12): $R_t$=2.13 min. $^1$H NMR (MeOD, δ=3.34 ppm, 400 MHz): δ 8.17 (br s, 2H), 7.97 (d, J=8.8, 2H), 7.76 (s, 2H), 7.67 (d, J=8.8, 2H), 4.86 (s, 2H), 2.64-2.54 (m, 2H), 2.19-2.05 (m, 4H), 1.98-1.70 (m, 12H), 1.11 (s, 18H). LC/MS: Anal. Calcd. for [M+H]$^+$ $C_{44}H_{51}F_4N_6O_2$: 771.39; found 771.8.

Example B66

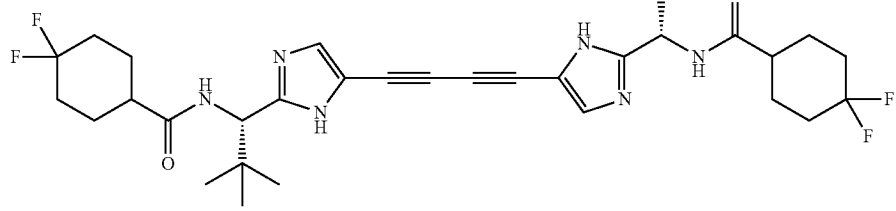

Example B66

Step a

HCl salt of amine B-66a (0.017 g) was prepared according to the procedure described in Example B1 step k. LC/MS (Condition 16): $R_t$=0.71 min. $^1$H NMR (MeOD, δ=3.34 ppm, 400 MHz): δ 7.55 (s, 2H), 4.20 (s, 2H), 1.08 (s, 18H). LC/MS: Anal. Calcd. for [M+H]$^+$ $C_{20}H_{29}N_6$: 353.24; found 353.35.

Example B66

Example B66 (0.010 g) was prepared according to the procedure described in Example B1. HPLC (Condition B-1 and B-5): >98% homogeneity index. LC/MS (Condition B-12): $R_t$=1.94 min. $^1$H NMR (MeOD, δ=3.34 ppm, 400 MHz): δ 7.67 (s, 2H), 4.82 (s, 2H), 2.57-2.48 (m, 2H), 2.18-2.04 (m, 4H), 1.96-1.68 (m, 12H), 1.04 (s, 18H). LC/MS: Anal. Calcd. for [M+H]$^+$ $C_{34}H_{45}F_4N_6O_2$: 645.35; found 645.7.

Example B67

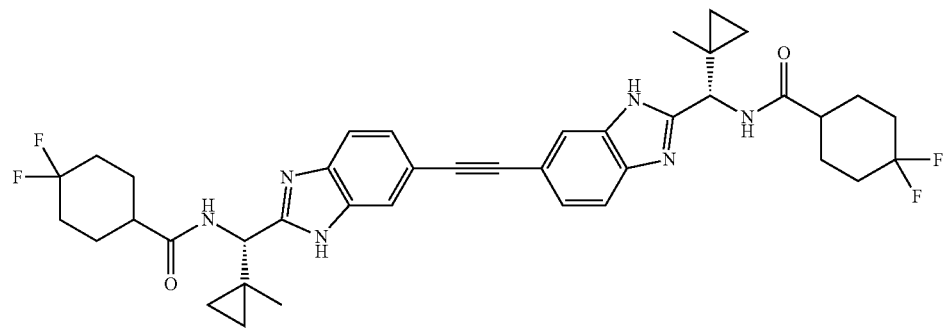 [SMILES: CC1([C@H](NC(=O)C2CCC(F)(F)CC2)c2nc3ccc(C#Cc4ccc5nc([C@@H](NC(=O)C6CCC(F)(F)CC6)C6(C)CC6)[nH]c5c4)cc3[nH]2)CC1]

Example B67

Step a

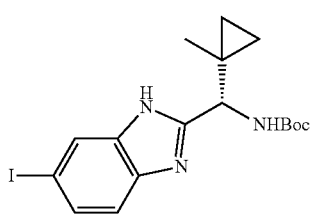 [SMILES: CC(C)(C)OC(=O)N[C@H](c1nc2ccc(I)cc2[nH]1)C1(C)CC1]

HATU (1.658 g, 4.36 mmol) was added to a stirred solution of 4-iodobenzene-1,2-diamine (1.021 g, 4.36 mmol), (S)-2-((tert-butoxycarbonyl)amino)-2-(1-methyl cyclopropyl) acetic acid (1 g, 4.36 mmol) and DIPEA (1.524 mL, 8.72 mmol) in DMF (20 mL) at 0° C. and stirred at room temperature for overnight. Water (50 mL) was added to the reaction mixture and extracted with EtOAc (50 mL). The organic layer was washed with water (50 mL), 10% NaHCO$_3$ solution (50 mL) and brine (50 mL). The organic layer was dried over Na$_2$SO$_4$ and concentrated under reduced pressure to yield a crude mixture of (S)-tert-butyl (2-((2-amino-4-iodophenyl)amino)-1-(1-methylcyclopropyl)-2-oxoethyl)carbamate (1.9 g, 4.27 mmol) and (S)-tert-butyl (2-((2-amino-5-iodophenyl)amino)-1-(1-methylcyclopropyl)-2-oxoethyl)carbamate as a brown solid. LC/MS (Condition B-13): R$_t$=2.03 min. LC/MS: Anal. Calcd. for [M+H]$^+$ C$_{17}$H$_{25}$IN$_3$O$_3$: 446.09; found 446.0. The crude mixture of (S)-tert-butyl (2-((2-amino-4-iodophenyl)amino)-1-(1-methylcyclopropyl)-2-oxoethyl)carbamate (1.9 g, 4.27 mmol) and (S)-tert-butyl (2-((2-amino-5-iodophenyl)amino)-1-(1-methylcyclopropyl)-2-oxoethyl)carbamate was dissolved in AcOH (20 mL) and heated at 65° C. for overnight. AcOH was removed under reduced pressure; the resulting crude residue was dissolved with EtOAc (100 mL) and neutralized with 10% NaOH solution. The organic layer was separated, and the aqueous layer was extracted again with EtOAc (100 mL). The combined organic layer was washed with water (200 mL) and brine (100 mL), dried over Na$_2$SO$_4$ and concentrated under reduced pressure. The crude material was purified by Combiflash Isco (Silica gel, 40 g, Redisep, 25% EtOAc/petroleum ether) to yield carbamate B-67a (1.25 g) as a brown solid. LC/MS (Condition B-13): R$_t$=2.03 min. $^1$H NMR (DMSO-d$_6$, δ=2.50 ppm, 400 MHz): δ 12.28/12.19 (s, 1H), 7.94/7.83 (s, 1H), 7.47-7.26 (m, 3H), 4.42/4.39 (s, 1H), 1.40 (br s, 9H), 0.98 (s, 3H), 0.78-0.76 (m, 1H), 0.60-0.58 (m, 1H), 0.34-0.30 (m, 2H). LC/MS: Anal. Calcd. for [M+H]$^+$ C$_{17}$H$_{231}$N$_3$O$_2$: 428.08; found 428.0.

Example B67

Step b

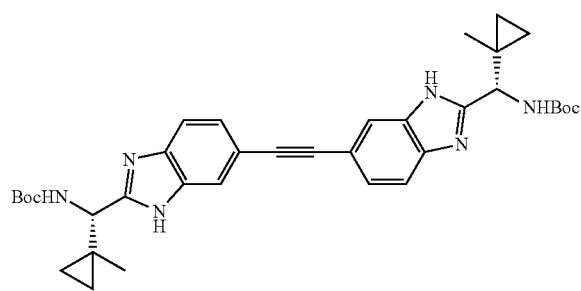 [SMILES: CC(C)(C)OC(=O)N[C@H](c1nc2ccc(C#Cc3ccc4nc([C@@H](NC(=O)OC(C)(C)C)C5(C)CC5)[nH]c4c3)cc2[nH]1)C1(C)CC1]

Nitrogen was purged through a solution of carbamate B-67a (900 mg, 2.106 mmol) and Pd(TPP)$_4$ (243 mg, 0.211 mmol) for 5 minutes. Bis(trimethystannyl)acetylene (370 mg, 1.053 mmol) was added and the reaction mixture was then heated in a sealed tube at 90° C. for overnight. The reaction mixture was filtered through celite pad and the filter cake was washed with EtOAc (100 mL). The filtrate was washed with water (2×100 mL) and brine (50 mL). The organic layer was dried over Na$_2$SO$_4$ and concentrated under reduced pressure. The residue was purified by Combiflash Isco ((Silica gel, 40 g, Redisep, 3.5% MeOH/CHCl$_3$) followed by chiral SFC(CO$_2$/0.5% diethyl amine in MeOH) to yield carbamate B-67b (230 mg) as a brown solid. LC/MS (Condition B-17): R$_t$=2.14 min. $^1$H NMR (DMSO-d$_6$, δ=2.50 ppm, 400 MHz): δ 12.30/12.28 (s, 2H), 7.77-7.52 (m, 4H), 7.39-7.24 (m, 4H), 4.43 (br s, 2H), 1.46 (br s, 18H), 1.01 (s, 6H), 0.82-0.78 (m, 2H), 0.62-0.58 (m, 2H), 0.39-0.22 (m, 4H). LC/MS: Anal. Calcd. for [M+H]$^+$ C$_{36}$H$_{45}$N$_6$O$_4$: 625.34; found 625.4.

Example B67

Step c

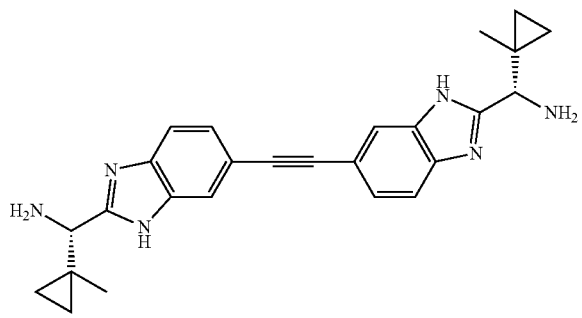 [SMILES: CC1([C@H](N)c2nc3ccc(C#Cc4ccc5nc([C@@H](N)C6(C)CC6)[nH]c5c4)cc3[nH]2)CC1]

HCl/MeOH (4 N) (5 mL, 0.128 mmol) was added to a solution of carbamate B-67b (80 mg, 0.128 mmol) in MeOH (2 mL) at 0° C. and stirred at room temperature for overnight. The reaction mixture was concentrated under reduced pressure and co-evaporated with DCM (3×10 mL) to yield HCl salt of amine B-67c (73.0 mg) as a brown solid. LC/MS (Condition B-17): R$_t$=1.64 min. $^1$H NMR (MeOD, δ=3.34 ppm, 300 MHz): δ 7.82 (br s, 2H), 7.65 (d, J=8.0, 2H), 7.49 (d, J=8.0, 2H), 4.14 (br s, 2H), 1.15-1.08 (m, 2H), 1.06 (s, 6H), 0.88-0.81 (m, 2H), 0.78-0.67 (m, 4H). LC/MS: Anal. Calcd. for [M+H]$^+$ C$_{26}$H$_{29}$N$_6$: 425.24; found 425.2.

Example B67

HATU (100 mg, 0.262 mmol) was added to a solution of amine B-67c (4HCl) (73 mg, 0.128 mmol), 4,4-difluorocyclohexanecarboxylic acid (44.1 mg, 0.269 mmol) and DIPEA (0.089 mL, 0.512 mmol) in DMF (3 mL) at 0° C. and stirred at room temperature for 2 h. The reaction mixture was diluted with EtOAc (2×20 mL), washed with saturated NH$_4$Cl solution (20 mL), 10% NaHCO$_3$ solution (20 mL), water (20 mL) and brine (20 mL). The organic layer was dried over Na$_2$SO$_4$ and concentrated under reduced pressure. The crude was purified by preparative HPLC (ACN/water/TFA) to yield TFA salt of Example B-67 (50 mg) as a white solid. HPLC (Condition B-1 and B-2): >98% homogeneity index. LC/MS (Condition B-17): R$_t$=2.14 min. $^1$H NMR (MeOD, δ=3.34 ppm, 400 MHz): δ 7.92 (s, 2H), 7.75 (d, J=8.8, 2H), 7.69 (dd, J=8.8, 1.6, 2H), 4.61 (s, 2H), 2.66-2.54 (m, 2H), 2.20-2.08 (m, 4H), 2.06-1.93 (m, 4H), 1.91-1.70 (m, 8H), 1.17 (s, 6H), 0.99-0.94 (m, 2H), 0.78-0.74 (m, 2H), 0.67-0.58 (m, 4H). LC/MS: Anal. Calcd. for [M+H]$^+$ C$_{40}$H$_{45}$F$_4$N$_6$O$_2$: 717.35; found 717.2.

Example B68

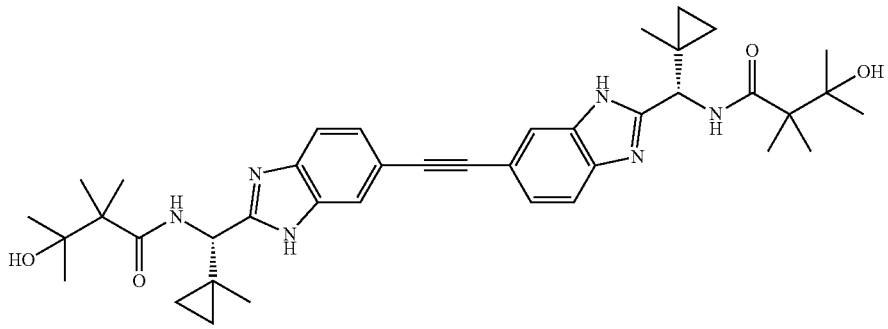 [SMILES: CC1([C@H](NC(=O)C(C)(C)C(C)(C)O)c2nc3ccc(C#Cc4ccc5nc([C@@H](NC(=O)C(C)(C)C(C)(C)O)C6(C)CC6)[nH]c5c4)cc3[nH]2)CC1]

Example B-68 (TFA salt) was prepared according to the procedure described in Example B-67. HPLC (Condition B-1 and B-2): >98% homogeneity index. LC/MS (Condition B-19): R$_t$=2.00 min. LC/MS: Anal. Calcd. for [M+H]$^+$ C$_{40}$H$_{53}$N$_6$O$_4$: 681.41; found 681.1.

Example B69

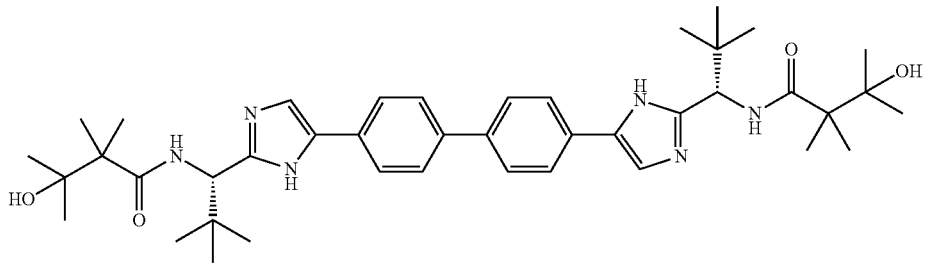 [SMILES: CC(C)(C)[C@H](NC(=O)C(C)(C)C(C)(C)O)c1ncc(-c2ccc(-c3ccc(-c4cnc([C@@H](NC(=O)C(C)(C)C(C)(C)O)C(C)(C)C)[nH]4)cc3)cc2)[nH]1]

To (1S,1'S)-1,1'-(5,5'-([1,1'-biphenyl]-4,4'-diyl)bis(1H-imidazole-5,2-diyl))bis(2,2-dimethylpropan-1-amine)tetrahydrochloride (75 mg, 0.124 mmol) was added 3-hydroxy-2,2,3-trimethylbutanoic acid (38.2 mg, 0.261 mmol) in DMF (3 mL) followed by DIPEA (0.174 mL, 0.996 mmol) at 0° C. Then HATU (97 mg, 0.255 mmol) was added and stirred from 0° C. to RT for 6 h. The crude was dissolved in EtOAc (50 mL), washed with saturated NH$_4$Cl (25 mL), 10% NaHCO$_3$ (25 mL), brine (25 mL), dried over Na$_2$SO$_4$ and concentrated under reduced pressure. The crude material was purified by reverse phase HPLC (ACN/water/TFA) to get TFA salt of Example B-69 (30 mg) as a white solid. HPLC (Condition B-1 and B-2): >97% homogeneity index. LC/MS (Condition B-12): R$_t$=2.13 min. $^1$H NMR (MeOD, δ=3.34 ppm, 400 MHz): δ 7.92-7.85 (m, 10H), 4.94 (s, 2H), 1.28 (s, 18H), 1.16 (s, 12H), 1.15 (s, 12H). LC/MS: Anal. Calcd. for [M+H]$^+$ C$_{42}$H$_{61}$N$_6$O$_4$: 713.47; found 713.3.

Example B70-72

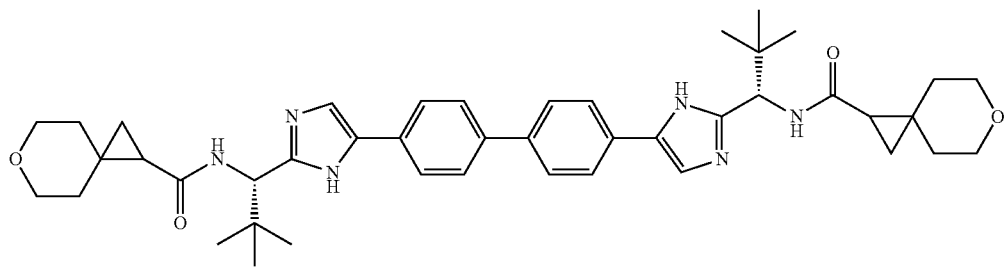 [SMILES: CC(C)(C)[C@H](NC(=O)C1CC12CCOCC2)c1ncc(-c2ccc(-c3ccc(-c4cnc([C@@H](NC(=O)C5CC56CCOCC6)C(C)(C)C)[nH]4)cc3)cc2)[nH]1]

Example B70

Diastereomer-1

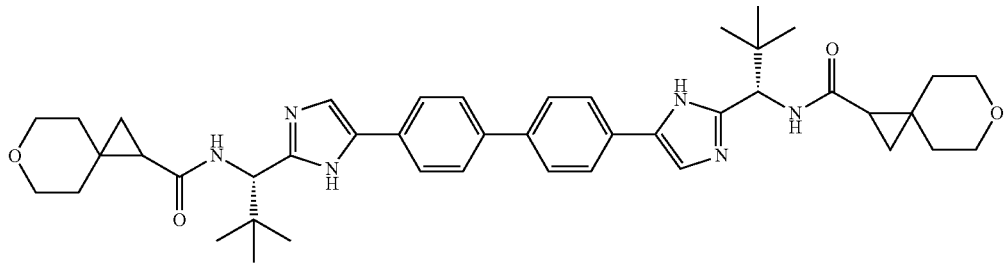 [SMILES: CC(C)(C)[C@H](NC(=O)C1CC12CCOCC2)c1ncc(-c2ccc(-c3ccc(-c4cnc([C@@H](NC(=O)C5CC56CCOCC6)C(C)(C)C)[nH]4)cc3)cc2)[nH]1]

Example B71

Diastereomer-2

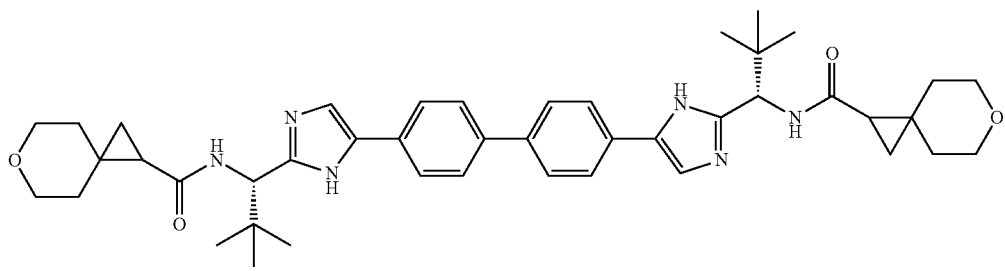 [SMILES: CC(C)(C)[C@H](NC(=O)C1CC12CCOCC2)c1ncc(-c2ccc(-c3ccc(-c4cnc([C@@H](NC(=O)C5CC56CCOCC6)C(C)(C)C)[nH]4)cc3)cc2)[nH]1]

Example B72

Diastereomer-3

Example B-70-72 was prepared according to the procedure described in Example B-69. The crude material was purified by reverse phase HPLC (ACN/water/TFA) to get TFA salt of Example B-70 (15.3 mg, white solid, diastereomer-1) and Example B-72 (19.6 mg, white solid, diastereomer-3). The impure Example B-71 (84 mg, TFA salt, diastereomer-2) was repurified by SFC ($CO_2$/0.3% diethyl amine in MeOH) to get the free base of Example B-71 (32.88 mg, white solid). Example B-70 (diastereomer-1): LC (Condition B-1 and B-2): >96% homogeneity index. LC/MS (Condition B-15): $R_t$=1.90 min. LC/MS: Anal. Calcd. for [M–H]⁻ $C_{44}H_{55}N_6O_4$: 731.44; found 731.2. Example B-71 (diastereomer-2): LC (Condition B-1 and B-2): >98% homogeneity index. LC/MS (Condition B-15): $R_t$=1.92 min. LC/MS: Anal. Calcd. for [M–H]⁻ $C_{44}H_{55}N_6O_4$: 731.44; found 731.2. Example B-72 (diastereomer-3): LC (Condition B-1 and B-2): >97% homogeneity index. LC/MS (Condition B-15): $R_t$=1.91 min. LC/MS: Anal. Calcd. for [M–H]⁻ $C_{44}H_{55}N_6O_4$: 731.44; found 731.2.

Example B73-75

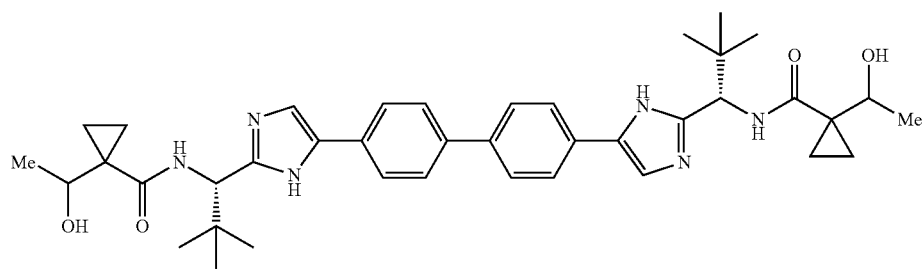 [SMILES: CC(O)C1(C(=O)N[C@H](c2ncc(-c3ccc(-c4ccc(-c5cnc([C@@H](NC(=O)C6(C(C)O)CC6)C(C)(C)C)[nH]5)cc4)cc3)[nH]2)C(C)(C)C)CC1]

Example B73

Diastereomer-1

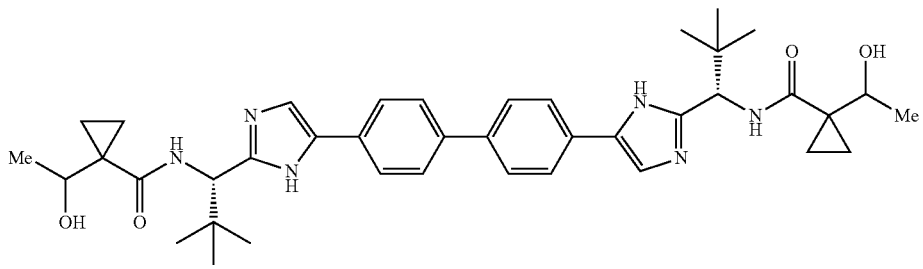 [SMILES: CC(O)C1(C(=O)N[C@H](c2ncc(-c3ccc(-c4ccc(-c5cnc([C@@H](NC(=O)C6(C(C)O)CC6)C(C)(C)C)[nH]5)cc4)cc3)[nH]2)C(C)(C)C)CC1]

Example B74

Diastereomer-2

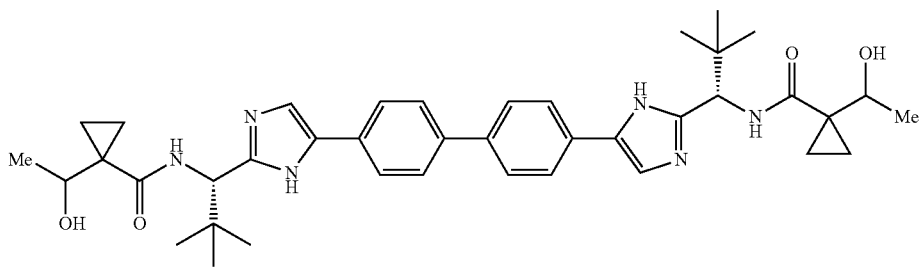 [SMILES: CC(O)C1(C(=O)N[C@H](c2ncc(-c3ccc(-c4ccc(-c5cnc([C@@H](NC(=O)C6(C(C)O)CC6)C(C)(C)C)[nH]5)cc4)cc3)[nH]2)C(C)(C)C)CC1]

Example B75

Diastereomer-3

Example B-73-75 was prepared according to the procedure described in Example B-69. The crude material was purified by reverse phase HPLC (NH$_4$OAc/acetonitrile/water) to get a mixture of three diastereomers. These three diastereomers were repurified by SFC(CO$_2$/0.3% diethyl amine in MeOH) to get Example B-73 (diastereomer-1, 15 mg, off-white solid, free base), Example B-74 (diastereomer-2, 25 mg, off-white solid, free base) and Example B-75 (diastereomer-3, 10 mg, off-white solid, free base). Example B-73 (diastereomer-1): LC (Condition B-1 and B-2): >97% homogeneity index. LC/MS (Condition B-19): R$_f$=1.97 min. LC/MS: Anal. Calcd. for [M−H]$^-$ C$_{40}$H$_{51}$N$_6$O$_4$: 679.41; found 678.9. Example B-74 (diastereomer-2): LC (Condition B-1 and B-2): >96% homogeneity index. LC/MS (Condition B-19): R$_f$=1.95 min. LC/MS: Anal. Calcd. for [M+H]$^+$ C$_{40}$H$_{53}$N$_6$O$_4$: 681.41; found 680.9. Example B-75 (diastereomer-3): LC (Condition B-1 and B-2): >98% homogeneity index. LC/MS (Condition B-24): R$_f$=1.33 min. $^1$H NMR (MeOD, δ=3.34 ppm, 400 MHz): δ 7.92-7.69 (m, 8H), 7.37 (s, 2H), 5.03 (s, 2H), 3.50-3.42 (m, 2H), 1.35 (d, J=6.0, 6H), 1.26-1.21 (m, 2H), 1.0 (s, 18H), 0.99-0.94 (m, 2H), 0.92-0.87 (m, 2H), 0.60-0.53 (m, 2H). LC/MS: Anal. Calcd. for [M+H]$^+$ C$_{40}$H$_{53}$N$_6$O$_4$: 681.41; found 681.4.

Example B76-78

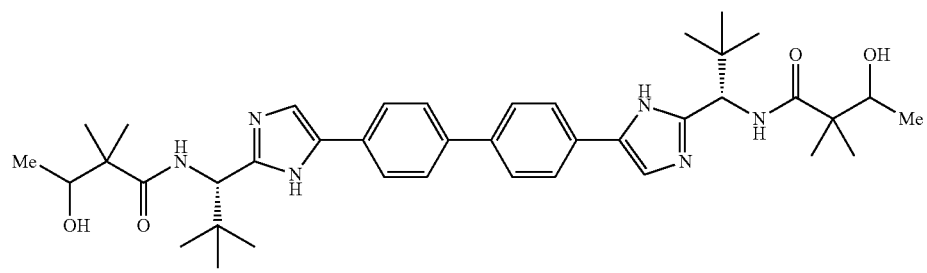 [SMILES: CC(O)C(C)(C)C(=O)N[C@H](c1ncc(-c2ccc(-c3ccc(-c4cnc([C@@H](NC(=O)C(C)(C)C(C)O)C(C)(C)C)[nH]4)cc3)cc2)[nH]1)C(C)(C)C]

Example B76

Diastereomer-1

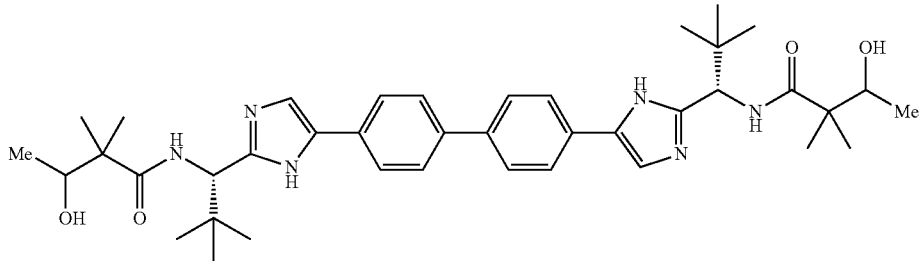 [SMILES: CC(O)C(C)(C)C(=O)N[C@H](c1ncc(-c2ccc(-c3ccc(-c4cnc([C@@H](NC(=O)C(C)(C)C(C)O)C(C)(C)C)[nH]4)cc3)cc2)[nH]1)C(C)(C)C]

Example B77

Diastereomer-2

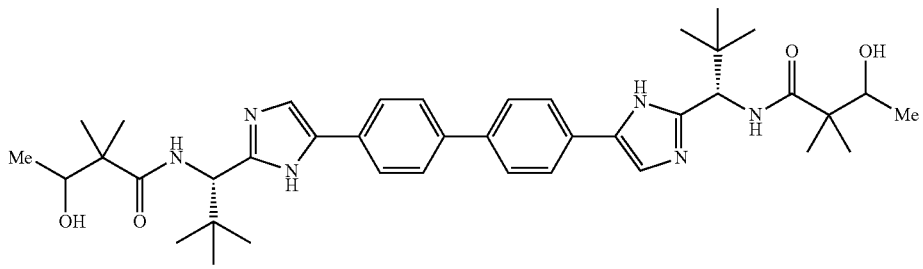 [SMILES: CC(O)C(C)(C)C(=O)N[C@H](c1ncc(-c2ccc(-c3ccc(-c4cnc([C@@H](NC(=O)C(C)(C)C(C)O)C(C)(C)C)[nH]4)cc3)cc2)[nH]1)C(C)(C)C]

Example B78

Diastereomer-3

Example B-76-78 was prepared according to the procedure described in Example B-69. The crude material was purified by reverse phase HPLC (NH$_4$OAc/acetonitrile/water) to get a mixture of three diastereomers. These three diastereomers were repurified by normal phase chiral HPLC to get Example B-76 (diastereomer-1, 25 mg, pale yellow solid, free base), Example B-77 (diastereomer-2, 30 mg, white solid, acetate salt) and Example B-78 (diastereomer-3, 40 mg, pale yellow solid, acetate salt). Example B-76 (diastereomer-1): LC (Condition B-1 and B-2): >98% homogeneity index. LC/MS (Condition B-19): R$_t$=2.03 min. LC/MS: Anal. Calcd. for [M−H]$^-$ C$_{40}$H$_{55}$N$_6$O$_4$: 683.44; found 682.9. Example B-77 (diastereomer-2): LC (Condition B-1 and B-2): >98% homogeneity index. LC/MS (Condition B-24): R$_t$=1.40 min. LC/MS: Anal. Calcd. for [M−H]$^-$ C$_{40}$H$_{55}$N$_6$O$_4$: 683.44; found 683.4. Example B-78 (diastereomer-3): LC (Condition B-1 and B-2): >96% homogeneity index. LC/MS (Condition B-19): R$_t$=2.03 min. LC/MS: Anal. Calcd. for [M+H]$^+$ C$_{40}$H$_{57}$N$_6$O$_4$: 685.44; found 685.0.

Example B79-81

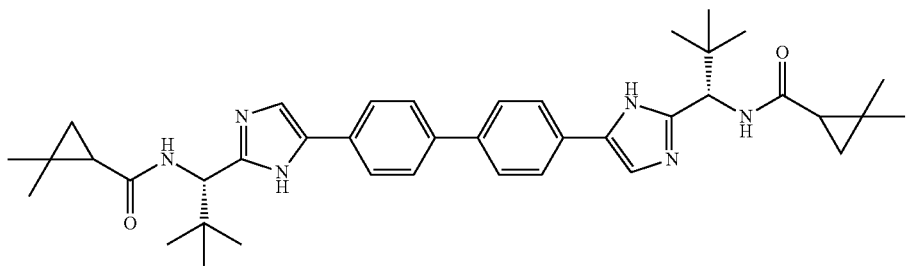

Example B79

Diastereomer-1

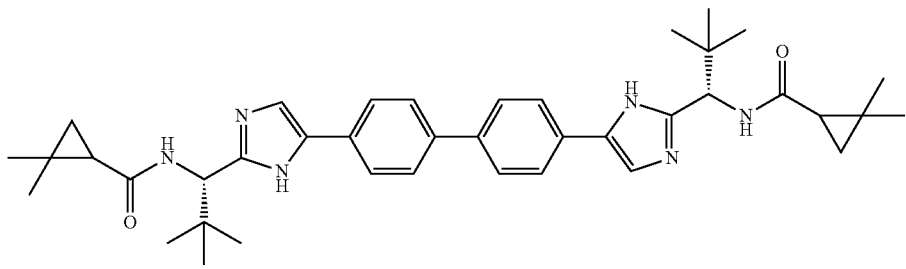

Example B80

Diastereomer-2

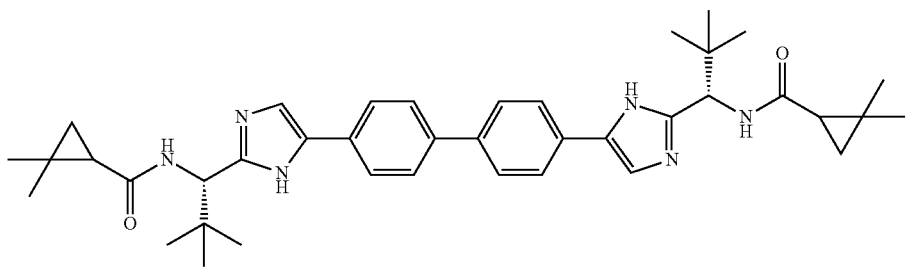

Example B81

Diastereomer-3

Example B79-81 was prepared according to the procedure described in Example B-69. The crude material was purified by reverse phase HPLC (TFA/acetonitrile/water) to get a mixture of three diastereomers. These three diastereomers were repurified by SFC(CO$_2$/0.3% diethyl amine in MeOH) to get Example B-79 (22 mg, diastereomer-1, TFA salt), Example B-80 (42 mg, diastereomer-2, TFA salt) and impure Example B-81 containing diethylamine (67 mg, diastereomer-3, TFA salt). Therefore the impure Example B-81 (diastereomer-3) was dissolved in EtOAc (50 mL) and washed with 10% NaHCO$_3$ (25 mL), brine (25 mL), dried over Na$_2$SO$_4$ and concentrated under reduced pressure. The crude material was lyophilized (acetonitrile and water) to get the Example B-81 (15 mg, diastereomer-3, free base). Example B-79 (diastereomer-1): LC (Condition B-1 and B-2): >98% homogeneity index. LC/MS (Condition B-12): R$_f$=1.95 min. LC/MS: Anal. Calcd. for [M+H]$^+$ C$_{40}$H$_{53}$N$_6$O$_2$: 649.42; found 649.1. Example B-80 (diastereomer-2): LC (Condition B-1 and B-2): >98% homogeneity index. LC/MS (Condition B-12): R$_f$=1.99 min. LC/MS: Anal. Calcd. for [M+H]$^+$ C$_{40}$H$_{53}$N$_6$O$_2$: 649.42; found 649.1. Example B-81 (diastereomer-3): LC (Condition B-1 and B-2): >94% homogeneity index. LC/MS (Condition B-12): R$_f$=2.10 min. LC/MS: Anal. Calcd. for [M+H]$^+$ C$_{40}$H$_{53}$N$_6$O$_2$: 649.42; found 649.1.

Example B82-83

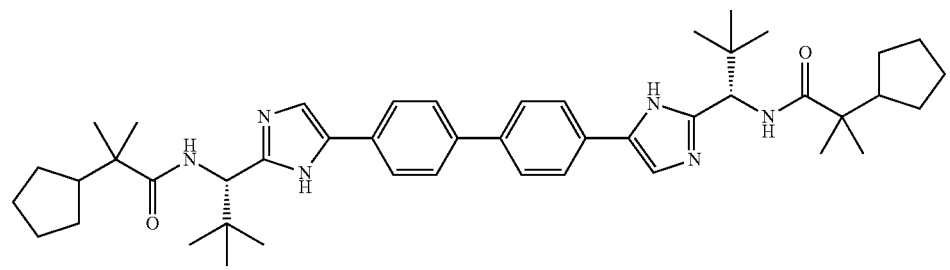 [SMILES: CC(C)(C(=O)N[C@H](c1ncc(-c2ccc(-c3ccc(-c4cnc([C@@H](NC(=O)C(C)(C)C5CCCC5)C(C)(C)C)[nH]4)cc3)cc2)[nH]1)C(C)(C)C)C1CCCC1]

Example B82

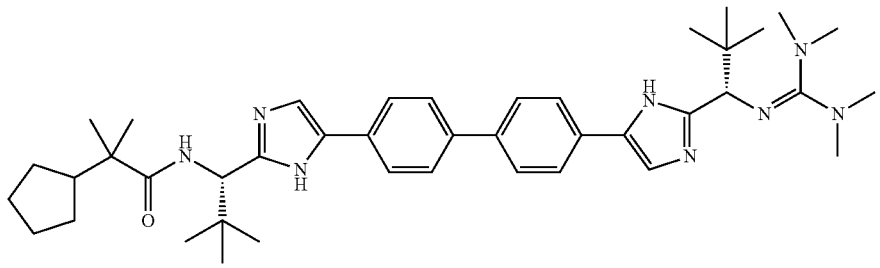 [SMILES: CN(C)C(=N[C@H](c1ncc(-c2ccc(-c3ccc(-c4cnc([C@@H](NC(=O)C(C)(C)C5CCCC5)C(C)(C)C)[nH]4)cc3)cc2)[nH]1)C(C)(C)C)N(C)C]

Example B83

To (1S,1'S)-1,1'-(5,5'-([1,1'-biphenyl]-4,4'-diyl)bis(1H-imidazole-5,2-diyl))bis(2,2-dimethylpropan-1-amine)tetrahydrochloride (90 mg, 0.149 mmol) was added 2-cyclopentyl-2-methylpropanoic acid (49.0 mg, 0.314 mmol) in DCM:DMF (1:1, 4 mL). Then DIPEA (0.209 mL, 1.195 mmol) was added at 0° C. followed by HATU (116 mg, 0.306 mmol). The reaction mixture was stirred from 0° C. to RT for 7 h. The reaction mixture was quenched with saturated NH$_4$Cl (25 mL) and the crude was extracted with EtOAc (50 mL). The organic layer was separated and washed with 10% NaHCO$_3$ (25 mL), brine (25 mL), dried over Na$_2$SO$_4$ and concentrated under reduced pressure. The crude material was purified by reverse phase HPLC (ACN/water/TFA) to get TFA salt of Example B-82 (38 mg) and TFA salt of Example B-83 (17 mg). Example B-82: LC (Condition B-1 and B-2): >93% homogeneity index. LC/MS (Condition B-18): R$_t$=2.61 min. LC/MS: Anal. Calcd. for [M−H]$^-$ C$_{46}$H$_{63}$N$_6$O$_2$: 731.51; found 731.4. Example B-83: LC (Condition B-1 and B-2): >95% homogeneity index. LC/MS (Condition B-18): R$_t$=2.24 min. LC/MS: Anal. Calcd. for [M+H]$^+$ C$_{42}$H$_{61}$N$_8$O: 693.49; found 693.4.

Example B84-85

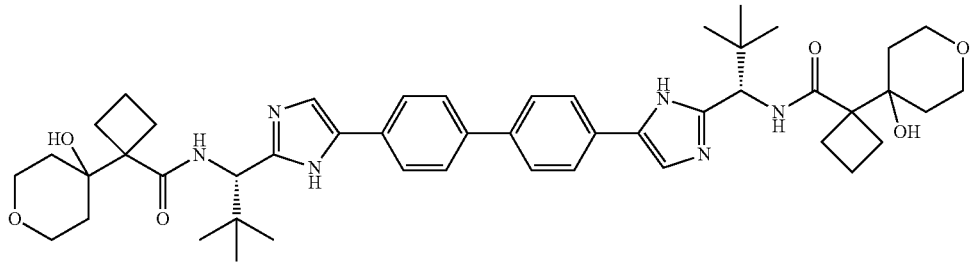 [SMILES: CC(C)(C)[C@H](NC(=O)C1(C2(O)CCOCC2)CCC1)c1ncc(-c2ccc(-c3ccc(-c4cnc([C@@H](NC(=O)C5(C6(O)CCOCC6)CCC5)C(C)(C)C)[nH]4)cc3)cc2)[nH]1]

Example B84

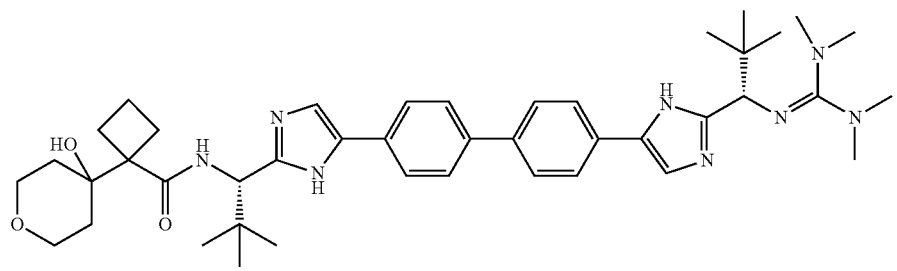 [SMILES: CN(C)C(=N[C@H](c1ncc(-c2ccc(-c3ccc(-c4cnc([C@@H](NC(=O)C5(C6(O)CCOCC6)CCC5)C(C)(C)C)[nH]4)cc3)cc2)[nH]1)C(C)(C)C)N(C)C]

Example B85

Example B-84 (12 mg, TFA salt) and Example B-85 (6 mg, TFA salt) were prepared according to the procedure described in Example B-82-83. Example B-84: LC (Condition B-1 and B-2): >97% homogeneity index. LC/MS (Condition B-12): $R_t$=1.84 min. LC/MS: Anal. Calcd. for $[M+H]^+$ $C_{48}H_{65}N_6O_6$: 821.49; found 821.2. Example B-85: LC (Condition B-1 and B-2): >97% homogeneity index. LC/MS (Condition B-12): $R_t$=1.74 min. LC/MS: Anal. Calcd. for $[M+H]^+$ $C_{43}H_{61}N_8O_3$: 737.47; found 737.1.

Example B86-87

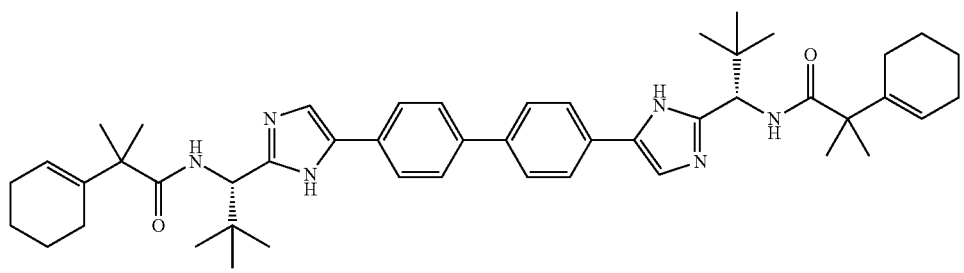 [SMILES: CC(C)(C(=O)N[C@H](c1ncc(-c2ccc(-c3ccc(-c4cnc([C@@H](NC(=O)C(C)(C)C5=CCCCC5)C(C)(C)C)[nH]4)cc3)cc2)[nH]1)C(C)(C)C)C1=CCCCC1]

Example B86

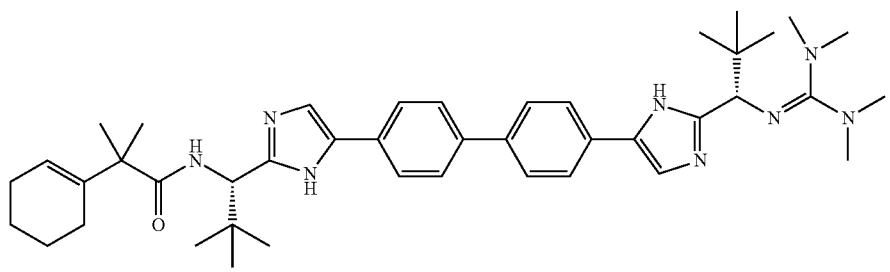 [SMILES: CN(C)C(=N[C@H](c1ncc(-c2ccc(-c3ccc(-c4cnc([C@@H](NC(=O)C(C)(C)C5=CCCCC5)C(C)(C)C)[nH]4)cc3)cc2)[nH]1)C(C)(C)C)N(C)C]

Example B87

Example B-86 (30 mg, TFA salt) and Example B-87 (5 mg, TFA salt) were prepared according to the procedure described in Example B-82-83. Example B-86: LC (Condition B-1 and B-2): >97% homogeneity index. LC/MS (Condition B-13): $R_t$=2.40 min. LC/MS: Anal. Calcd. for $[M-H]^-$ $C_{48}H_{63}N_6O_2$: 755.51; found 755.4. Example B-87: LC (Condition B-2): >92% homogeneity index. LC/MS (Condition B-13): $R_t$=2.06 min. LC/MS: Anal. Calcd. for $[M]^+$ $C_{43}H_{61}N_8O$: 705.50; found 705.4.

Example B88-89

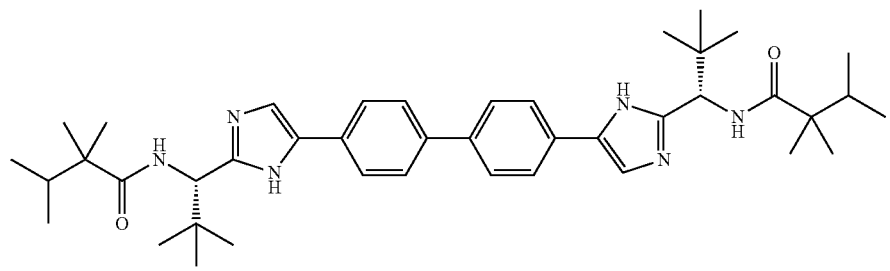 [SMILES: CC(C)C(C)(C)C(=O)N[C@H](c1ncc(-c2ccc(-c3ccc(-c4cnc([C@@H](NC(=O)C(C)(C)C(C)C)C(C)(C)C)[nH]4)cc3)cc2)[nH]1)C(C)(C)C]

Example B88

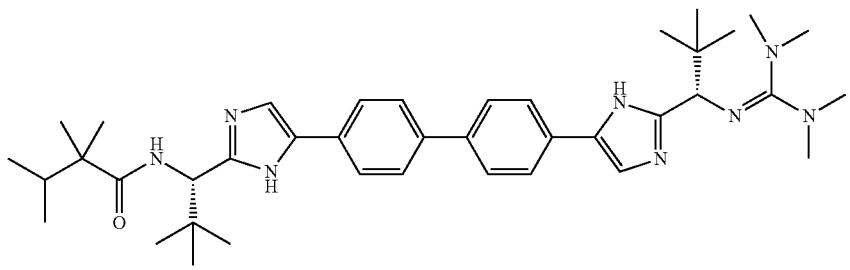 [SMILES: CC(C)C(C)(C)C(=O)N[C@H](c1ncc(-c2ccc(-c3ccc(-c4cnc([C@@H](N=C(N(C)C)N(C)C)C(C)(C)C)[nH]4)cc3)cc2)[nH]1)C(C)(C)C]

Example B89

Example B-88 (18 mg, free base) and Example B-89 (2 mg, free base) were prepared according to the procedure described in Example B-82-83. Example B-88: LC (Condition B-1 and B-2): >96% homogeneity index. LC/MS (Condition B-27): $R_t$=1.80 min. LC/MS: Anal. Calcd. for [M+H]$^+$ $C_{42}H_{61}N_6O_2$: 681.48; found 681.6. Example B-89: LC (Condition B-1 and B-2): >97% homogeneity index. LC/MS (Condition B-27): $R_t$=1.56 min. LC/MS: Anal. Calcd. for [M+H]$^+$ $C_{40}H_{59}N_8O$: 667.94; found 668.4.

Example B90-147

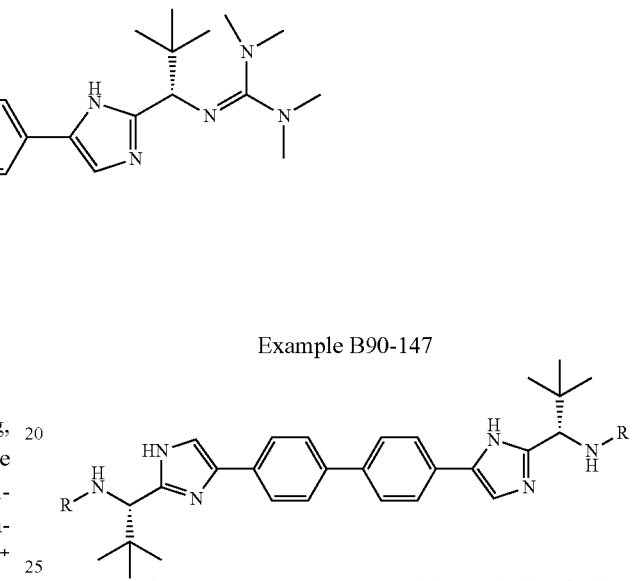

Example B-90-147 were prepared in a similar fashion starting from (1S,1'S)-1,1'-(5,5'-([1,1'-biphenyl]-4,4'-diyl)bis(1H-imidazole-5,2-diyl))bis(2,2-dimethylpropan-1-amine)tetrahydrochloride and appropriate acids according to the procedure described for Example B-69.

| Example | R | Salt Type | LC & LC/MS data |
|---|---|---|---|
| B90* | 2-hydroxy-2-methyl-1-(1-hydroxycyclobutyl) group | TFA | LC (Condition B-1 and B-2): >97% homogeneity index. LC/MS (Condition B-15): $R_t$ = 2.14 min. LC/MS: Anal. Calcd. for [M + H]$^+$ $C_{44}H_{61}N_6O_4$: 737.47; found 737.4. |
| B91 | 2-methyl-2-cyclohexyl-propanoyl | TFA | LC (Condition B-1 and B-2): >96% homogeneity index. LC/MS (Condition B-15): $R_t$ = 2.75 min. LC/MS: Anal. Calcd. for [M − H]$^-$ $C_{48}H_{67}N_6O_2$: 759.54; found 759.4. |
| B92 | (tetrahydropyran-4-ylidene)acetyl | Acetate | LC (Condition B-1 and B-2): >94% homogeneity index. LC/MS (Condition B-12): $R_t$ = 1.86 min. LC/MS: Anal. Calcd. for [M + H]$^+$ $C_{42}H_{53}N_6O_4$: 705.41; found 705.1. |
| B93 | (tetrahydropyran-4-yl)acetyl | Free base | LC (Condition B-1 and B-2): >97% homogeneity index. LC/MS (Condition B-15): $R_t$ = 1.85 min. LC/MS: Anal. Calcd. for [M − H]$^-$ $C_{42}H_{55}N_6O_4$: 707.44; found 707.2. |

-continued

| Example | R | Salt Type | LC & LC/MS data |
|---|---|---|---|
| B94 | (structure) | TFA | LC (Condition B-1): >88% homogeneity index. LC/MS (Condition B-15): $R_t$ = 2.21 min. LC/MS: Anal. Calcd. for $[M + H]^+$ $C_{42}H_{57}N_6O_4$: 709.54; found 709.4. |
| B95 | (structure) | TFA | LC (Condition B-1 and B-2): >95% homogeneity index. LC/MS (Condition B-15): $R_t$ = 2.32 min. LC/MS: Anal. Calcd. for $[M - H]^-$ $C_{50}H_{67}N_6O_4$: 815.53; found 815.4. |
| B96 | (structure) | TFA | LC (Condition B-1 and B-2): >96% homogeneity index. LC/MS (Condition B-12): $R_t$ = 2.13 min. LC/MS: Anal. Calcd. for $[M + H]^+$ $C_{50}H_{65}F_4N_6O_4$: 889.49; found 889.1. |
| B97* | (structure) | TFA | LC (Condition B-1 and B-2): >93% homogeneity index. LC/MS (Condition B-12): $R_t$ = 2.15 min. LC/MS: Anal. Calcd. for $[M + H]^+$ $C_{46}H_{61}N_6O_4$: 761.47; found 761.1. |
| B98 | (structure) | Free base | LC (Condition B-1 and B-2): >97% homogeneity index. LC/MS (Condition B-15): $R_t$ = 2.08 min. LC/MS: Anal. Calcd. for $[M + H]^+$ $C_{46}H_{65}N_6O_4$: 765.5; found 765.4. |
| B99 | (structure) | TFA | LC (Condition B-1 and B-2): >98% homogeneity index. LC/MS (Condition B-37): $R_t$ = 1.63 min. LC/MS: Anal. Calcd. for $[M + H]^+$ $C_{46}H_{61}N_6O_6$: 793.46; found 793.6. |
| B100 | (structure) | TFA | LC (Condition B-1 and B-2): >97% homogeneity index. LC/MS (Condition B-21): $R_t$ = 1.97 min. LC/MS: Anal. Calcd. for $[M + H]^+$ $C_{46}H_{59}F_2N_6O_4$: 797.45; found 797.4. |
| B101 | (structure) | TFA | LC (Condition B-1 and B-2): >91% homogeneity index. LC/MS (Condition B-19): $R_t$ = 2.15 min. LC/MS: Anal. Calcd. for $[M - H]^-$ $C_{46}H_{55}N_6O_4$: 755.44; found 754.9. |
| B102 | (structure) | TFA | LC (Condition B-1 and B-2): >92% homogeneity index. LC/MS (Condition B-19): $R_t$ = 2.10 min. LC/MS: Anal. Calcd. for $[M + H]^+$ $C_{46}H_{61}N_6O_4$: 761.47; found 761.0. |

-continued

| Example | R | Salt Type | LC & LC/MS data |
|---|---|---|---|
| B103 | | TFA | LC (Condition B-2): >91% homogeneity index. LC/MS (Condition B-13): $R_t$ = 2.31 min. LC/MS: Anal. Calcd. for [M − H]$^-$ $C_{48}H_{63}N_6O_2$: 755.51; found 755.4. |
| B104 | | TFA | LC (Condition B-1 and B-2): >95% homogeneity index. LC/MS (Condition B-12): $R_t$ = 2.09 min. LC/MS: Anal. Calcd. for [M + H]$^+$ $C_{44}H_{61}N_6O_4$: 737.47; found 737.2. |
| B105 | | TFA | LC (Condition 1 and 5): >99% homogeneity index. LC/MS (Condition 18): $R_t$ = 2.72 min. LC/MS: Anal. Calcd. For [M + H]$^+$ $C_{48}H_{61}N_6O_2$: 753.47; found 753.4 |
| B106 | | TFA | LC (Condition B-1 and B-2): >92% homogeneity index. LC/MS (Condition B-15): $R_t$ = 2.29 min. LC/MS: Anal. Calcd. for [M − H]$^-$ $C_{48}H_{57}F_6N_6O_2$: 863.45; found 863.2. |
| B107 | | TFA | LC (Condition B-1 and B-4): >95% homogeneity index. LC/MS (Condition B-15): $R_t$ = 1.95 min. LC/MS: Anal. Calcd. for [M + H]$^+$ $C_{36}H_{45}N_6O_4$: 625.34; found 625.2. |
| B108 | | TFA | LC (Condition B-1 and B-2): >95% homogeneity index. LC/MS (Condition B-15): $R_t$ = 1.96 min. LC/MS: Anal. Calcd. for [M − H]$^-$ $C_{44}H_{59}N_6O_4$: 735.47; found 735.2. |
| B109 | | TFA | LC (Condition B-1 and B-2): >97% homogeneity index. LC/MS (Condition B-15): $R_t$ = 1.96 min. LC/MS: Anal. Calcd. for [M + H]$^+$ $C_{40}H_{49}N_6O_4$: 677.37; found 677.2. |
| B110* | | TFA | LC (Condition B-1 and B-2): >96% homogeneity index. LC/MS (Condition B-23): $R_t$ = 1.77 min. LC/MS: Anal. Calcd. for [M + H]$^+$ $C_{42}H_{57}N_6O_4$: 709.44; found 709.6. |
| B111 | | Free base | LC (Condition B-1 and B-2): >95% homogeneity index. LC/MS (Condition B-21): $R_t$ = 2.13 min. LC/MS: Anal. Calcd. for [M + H]$^+$ $C_{42}H_{55}F_2N_6O_2$: 713.43; found 713.4. |
| B112 (Mixture of three diastereomers) | | Free base | LC (Condition B-1 and B-2): >92% homogeneity index. LC/MS (Condition B-19): $R_t$ = 2.16 min. LC/MS: Anal. Calcd. for [M − H]$^-$ $C_{40}H_{49}F_2N_6O_2$: 683.40; found 682.8. |

-continued

| Example | R | Salt Type | LC & LC/MS data |
|---|---|---|---|
| B113 | (2,2-dimethyl-3-fluoro-3-methylbutanoyl group) | Free base | LC (Condition B-1 and B-2): >93% homogeneity index. LC/MS (Condition B-27): $R_t$ = 1.73 min. LC/MS: Anal. Calcd. for $[M - H]^-$ $C_{42}H_{57}F_2N_6O_2$: 715.46; found 715.4. |
| B114 | (1-(prop-1-en-2-yl)cyclopropanecarbonyl group) | Free base | LC (Condition B-1 and B-2): >96% homogeneity index. LC/MS (Condition B-19): $R_t$ = 2.37 min. LC/MS: Anal. Calcd. for $[M + H]^+$ $C_{42}H_{53}N_6O_2$: 673.42; found 672.9. |
| B115 | (2,3-dimethyl-2-methylbut-3-enoyl group) | Free base | LC (Condition B-1 and B-2): >97% homogeneity index. LC/MS (Condition B-19): $R_t$ = 2.38 min. LC/MS: Anal. Calcd. for $[M + H]^+$ $C_{42}H_{57}N_6O_2$: 677.45; found 677.0. |
| B116 | (2-(cyclopent-1-en-1-yl)-2-methylpropanoyl group) | TFA | LC (Condition B-5 and B-6): >95% homogeneity index. LC/MS (Condition B-17): $R_t$ = 2.74 min. LC/MS: Anal. Calcd. for $[M + H]^+$ $C_{46}H_{61}N_6O_2$: 729.48; found 729.4. |
| B117 | (2-(1-hydroxycyclopentyl)-2-methylpropanoyl group) | TFA | LC (Condition B-1 and B-2): >98% homogeneity index. LC/MS (Condition B-25): $R_t$ = 2.07 min. LC/MS: Anal. Calcd. for $[M - H]^-$ $C_{46}H_{63}N_6O_4$: 763.5; found 763.4. |
| B118 | (1,2,5-oxadiazol-3-ylcarbonyl group) | TFA | LC (Condition B-1 and B-2): >92% homogeneity index. LC/MS (Condition B-25): $R_t$ = 1.82 min. LC/MS: Anal. Calcd. For $[M - H]^-$ $C_{34}H_{35}N_{10}O_4$: 647.29; found 647.2. |
| B119 | (2-chloropyridin-3-ylcarbonyl group) | TFA | LC (Condition B-2): >98% homogeneity index. LC/MS (Condition B-28): $R_t$ = 2.32 min. LC/MS: Anal. Calcd. For $[M + H]^+$ $C_{40}H_{41}Cl_2N_8O_2$: 735.27; found 735.3. |
| B120 | (6-chloropyridin-2-ylcarbonyl group) | TFA | LC (Condition B-5): >96% homogeneity index. LC/MS (Condition B-28): $R_t$ = 2.99 min. LC/MS: Anal. Calcd. For $[M + H]^+$ $C_{40}H_{41}Cl_2N_8O_2$: 735.27; found 735.3. |
| B121 | (2-chloropyridin-4-ylcarbonyl group) | TFA | LC (Condition B-2): >97% homogeneity index. LC/MS (Condition B-28): $R_t$ = 2.62 min. LC/MS: Anal. Calcd. For $[M + H]^+$ $C_{40}H_{41}Cl_2N_8O_2$: 735.27; found 735.3. |
| B122 | (pyridin-4-ylcarbonyl group) | TFA | LC/MS (Condition B-28): $R_t$ = 2.12 min. LC/MS: Anal. Calcd. For $[M + H]^+$ $C_{40}H_{43}N_8O_2$: 667.34; found 667.4. |

-continued

| Example | R | Salt Type | LC & LC/MS data |
|---|---|---|---|
| B123 | (5-methyl-pyridin-2-yl carbonyl via 5-position; acyl attached at pyridine 3-position with 6-Me) | TFA | LC (Condition B-2): >98% homogeneity index. LC/MS (Condition B-28): $R_t$ = 2.24 min. LC/MS: Anal. Calcd. For $[M + H]^+$ $C_{42}H_{47}N_8O_2$: 695.37; found 695.4. |
| B124 | 2,6-dimethoxypyridin-3-yl carbonyl | TFA | LC (Condition B-5): >96% homogeneity index. LC/MS (Condition B-28): $R_t$ = 3.08 min. LC/MS: Anal. Calcd. For $[M + H]^+$ $C_{44}H_{51}N_8O_6$: 787.39; found 787.4. |
| B125 | 5-methylpyrazin-2-yl carbonyl | TFA | LC (Condition B-2): >96% homogeneity index. LC/MS (Condition B-28): $R_t$ = 2.45 min. LC/MS: Anal. Calcd. For $[M + H]^+$ $C_{40}H_{45}N_{10}O_2$: 697.36; found 697.4. |
| B126 | furan-3-yl carbonyl | Free base | LC (Condition B-2): >97% homogeneity index. LC/MS (Condition B-28): $R_t$ = 2.42 min. LC/MS: Anal. Calcd. For $[M + H]^+$ $C_{38}H_{41}N_6O_4$: 645.31; found 645.4. |
| B127 | 3-chlorothiophen-2-yl carbonyl | TFA | LC (Condition B-2): >94% homogeneity index. LC/MS (Condition B-28): $R_t$ = 3.08 min. LC/MS: Anal. Calcd. For $[M + H]^+$ $C_{38}H_{39}Cl_2N_6O_2S_2$: 745.19; found 745.2. |
| B128 | 1-methyl-1H-imidazol-5-yl carbonyl | TFA | LC (Condition B-4): >98% homogeneity index. LC/MS (Condition B-28): $R_t$ = 1.91 min. LC/MS: Anal. Calcd. For $[M + H]^+$ $C_{38}H_{45}N_{10}O_2$: 673.36; found 673.4 |
| B129 | 5-isopropyl-1H-pyrazol-3-yl carbonyl | TFA | LC (Condition B-2): >95% homogeneity index. LC/MS (Condition B-28): $R_t$ = 2.44 min. LC/MS: Anal. Calcd. For $[M + H]^+$ $C_{42}H_{53}N_{10}O_2$: 729.43; found 729.5. |
| B130 | 1-methyl-1H-pyrazol-3-yl carbonyl | TFA | LC (Condition B-2): >95% homogeneity index. LC/MS (Condition B-28): $R_t$ = 2.19 min. LC/MS: Anal. Calcd. For $[M + H]^+$ $C_{38}H_{45}N_{10}O_2$: 673.36; found 673.4. |
| B131 | 1-methyl-1H-pyrazol-4-yl carbonyl | TFA | LC (Condition B-2): >97% homogeneity index. LC/MS (Condition B-28): $R_t$ = 1.96 min. LC/MS: Anal. Calcd. For $[M + H]^+$ $C_{38}H_{45}N_{10}O_2$: 673.36; found 673.4. |

-continued

| Example | R | Salt Type | LC & LC/MS data |
|---------|---|-----------|-----------------|
| B132 | | TFA | LC (Condition B-2): >96% homogeneity index. LC/MS (Condition B-28): $R_t$ = 2.39 min. LC/MS: Anal. Calcd. For $[M + H]^+$ $C_{34}H_{37}N_{10}O_2S_2$: 681.25; found 681.3. |
| B133 | | TFA | LC (Condition B-2): >99% homogeneity index. LC/MS (Condition B-28): $R_t$ = 2.50 min. LC/MS: Anal. Calcd. For $[M + H]^+$ $C_{36}H_{41}N_{10}O_2S_2$: 709.28; found 709.3. |
| B134 | | TFA | LC (Condition B-4): >97% homogeneity index. LC/MS (Condition B-28): $R_t$ = 1.64 min. LC/MS: Anal. Calcd. For $[M + H]^+$ $C_{36}H_{47}N_8O_4$: 655.36; found 655.4. |
| B135 | | TFA | LC (Condition B-30 and B-31): >95.6% homogeneity index. LC/MS (Condition B-29): $R_t$ = 2.35 min. LC/MS: Anal. Calcd. $[M + H]^+$ $C_{44}H_{60}N_6O_4$: 737.47; found 737.6. |
| B136 | | Free base | LC (Condition B-33 and B-35): >96.6% homogeneity index. LC/MS (Condition B-21): $R_t$ = 2.36 min. LC/MS: Anal. Calcd. for $[M - H]^-$ $C_{44}H_{59}N_6O_2$: 703.47; found 703.4 |
| B137 | | Free base | LC (Condition B-32 and B-35): >97.9% homogeneity index. LC/MS (Condition B-21): $R_t$ = 2.38 min. LC/MS: Anal. Calcd. for $[M - H]^-$ $C_{44}H_{55}N_6O_2$: 699.44; found 700.2 |
| B138 | | Free base | LC (Condition B-30 and B-35): >97.8% homogeneity index. LC/MS (Condition B-34): $R_t$ = 2.16 min. LC/MS: Anal. Calcd. for $[M + H]^+$ $C_{44}H_{55}N_6O_2$: 681.4; found 681.4 |
| B139 | | Free base | LC (Condition B-30 and B-31): >96.7% homogeneity index. LC/MS (Condition B-29): $R_t$ = 2.30 min. LC/MS: Anal. Calcd. for $[M + H]^+$ $C_{40}H_{53}F_4N_6O_2$: 725.4; found 725.5 |
| B140 | | TFA | LC (Condition B-30 and B-35): >99% homogeneity index. LC/MS (Condition B-29): $R_t$ = 2.28 min. LC/MS: Anal. Calcd. for $[M + H]^+$ $C_{40}H_{49}F_4N_6O_2$: 721.4; found 721.5 |
| B141 | | TFA | LC (Condition B-30 and B-35): >99% homogeneity index. LC/MS (Condition B-29): $R_t$ = 2.24 min. LC/MS: Anal. Calcd. for $[M + H]^+$ $C_{40}H_{49}N_6O_2$: 645.4; found 645.5 |
| B142 | | TFA | LC (Condition B-30 and B-35): >98% homogeneity index. LC/MS (Condition B-29): $R_t$ = 2.30 min. LC/MS: Anal. Calcd. for $[M + H]^+$ $C_{42}H_{53}N_6O_2$: 673.4; found 673.5 |

-continued

| Example | R | Salt Type | LC & LC/MS data |
|---|---|---|---|
| B143 | (1-ethylcyclopropyl carbonyl) | TFA | LC (Condition B-5 and B-36): >95% homogeneity index. LC/MS (Condition B-13): $R_t$ = 3.03 min. LC/MS: Anal. Calcd. for $[M + H]^+ C_{40}H_{53}N_6O_2$: 649.4; found 649.4 |
| B144 | (1-ethoxycyclopropyl carbonyl) | TFA | LC (Condition B-31 and B-32): >95% homogeneity index. LC/MS (Condition B-29): $R_t$ = 2.24 min; LC/MS: Anal. Calcd. for $[M + H]^+ C_{40}H_{53}N_6O_4$: 681; found 681.5 |
| B145 (Diastereomer 1) | (2-ethoxypropanoyl) | TFA | LC (Condition B-30 and B-31): >96% homogeneity index. LC/MS (Condition B-34): $R_t$ = 2.30 min; LC/MS: Anal. Calcd. for $[M + H]^+ C_{38}H_{53}N_6O_4$: 657.4; found 657.4 |
| B146 (Diastereomer 2) | (2-ethoxypropanoyl) | TFA | LC (Condition B-30 and B-31): >99% homogeneity index. LC/MS (Condition B-34): $R_t$ = 2.27 min; LC/MS: Anal. Calcd. for $[M - H]^- C_{40}H_{51}N_6O_4$: 655.4; found 655.2 |
| B147 (Diastereomer 3) | (2-ethoxypropanoyl) | TFA | LC (Condition B-30 and B-31): >99% homogeneity index. LC/MS (Condition B-34): $R_t$ = 2.25 min; LC/MS: Anal. Calcd. for $[M - H]^- C_{40}H_{51}N_6O_4$: 655.4; found 655.2 |

*B90: $^1$H NMR (MeOD, δ = 3.34 ppm, 400 MHz): δ 7.92-7.86 (m, 10H), 4.96 (s, 2H), 2.45-2.32 (m, 4H), 2.17-2.08 (m, 4H), 1.98-1.92 (m, 2H), 1.66-1.62 (m, 2H), 1.28 (s, 6H), 1.25 (s, 6H), 1.12 (s, 18H).

*B97: $^1$H NMR (MeOD, δ = 3.34 ppm, 400 MHz): δ 7.91-7.88 (m, 10H), 5.87 (br s, 2H), 5.15 (s, 2H), 4.25 (dd, J = 5.2, 2.4 4H), 3.87-3.81 (m, 2H), 3.77-3.71 (m, 2H), 2.17-2.11 (m, 2H), 2.06-1.99 (m, 2H), 1.37 (s, 6H), 1.36 (s, 6H), 1.09 (s, 18H).

*B110: $^1$H NMR (MeOD, δ = 3.34 ppm, 400 MHz): δ 7.78 (d, J = 8.4, 4H), 7.70 (d, J = 8.4, 4H), 7.36 (s, 2H), 4.95 (s, 2H), 1.34 (s, 6H), 1.23 (s, 6H), 1.07 (s, 18H), 1.06-1.02 (m, 2H), 0.93-0.84 (m, 6H).

Example B148

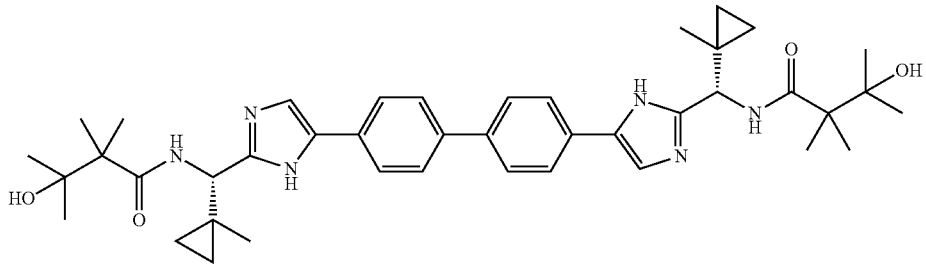 [SMILES: CC1([C@H](NC(=O)C(C)(C)C(C)(C)O)c2ncc(-c3ccc(-c4ccc(-c5cnc([C@@H](NC(=O)C(C)(C)C(C)(C)O)C6(C)CC6)[nH]5)cc4)cc3)[nH]2)CC1]

HATU (61.3 mg, 0.161 mmol) was added to a stirring solution of (1S,1'S)-(5,5'-([1,1'-biphenyl]-4,4'-diyl)bis(1H-imidazole-5,2-diyl))bis((1-methylcyclopropyl)methanamine)tetrahydrochloride (48 mg, 0.080 mmol), 3-hydroxy-2,2,3-trimethylbutanoic acid (29.3 mg, 0.201 mmol) and DIPEA (0.056 mL, 0.321 mmol) in DMF (2 mL) at 0° C. and the reaction mixture was stirred at room temperature for 2 h. The reaction mixture was diluted with EtOAc (40 mL), washed with saturated NH₄Cl solution (20 mL), 10% NaHCO₃ solution (20 mL), water (20 mL) and brine (20 mL). The organic layer was dried over Na₂SO₄ and concentrated under reduced pressure. The crude was purified by preparative HPLC (ACN/water/TFA) to yield TFA salt of Example B-148 (17.5 mg) as a white solid. LC (Condition B-1 and B-2): >98% homogeneity index. LC/MS (Condition B-19): $R_t$=2.06 min. LC/MS: Anal. Calcd. for $[M+H]^+ C_{42}H_{57}N_6O_4$: 709.44; found 708.9.

Example B149

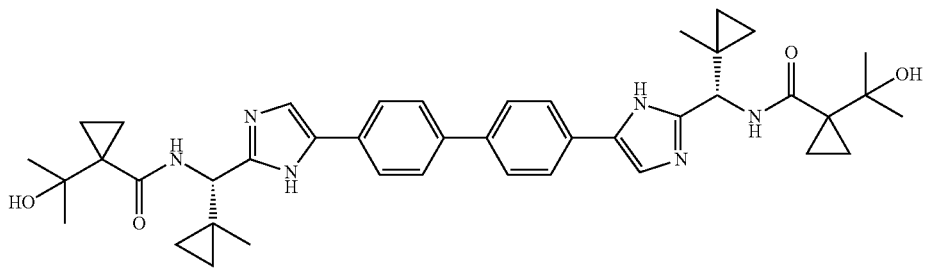 [SMILES: CC1([C@H](NC(=O)C2(C(C)(C)O)CC2)c2ncc(-c3ccc(-c4ccc(-c5cnc([C@@H](NC(=O)C6(C(C)(C)O)CC6)C6(C)CC6)[nH]5)cc4)cc3)[nH]2)CC1]

Example B-149 (23 mg, TFA salt) was prepared according to the procedure described in Example B-148. LC (Condition B-1 and B-2): >93% homogeneity index. LC/MS (Condition B-26): $R_t$=1.54 min. LC/MS: Anal. Calcd. for $[M+H]^+$ $C_{42}H_{53}N_6O_4$: 705.41; found 704.9.

Preparation of Intermediate Acids

Cap-1: 1-methoxycyclobutanecarboxylic acid

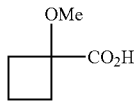

Cap-1 was prepared by following the procedure described in Organometallics, 6 (10), 2079-85; 1987.

Cap-2: 4-fluorobicyclo[2.2.2]octane-1-carboxylic acid0

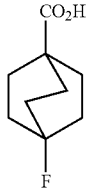

Cap-2 was prepared by following the procedure described in Journal of Organic Chemistry, 57 (10), 2850-5, 1992.

Cap-3: 1-(fluoromethyl)cyclopropanecarboxylic acid

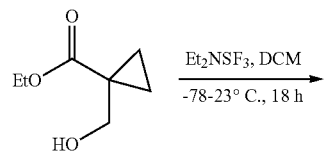

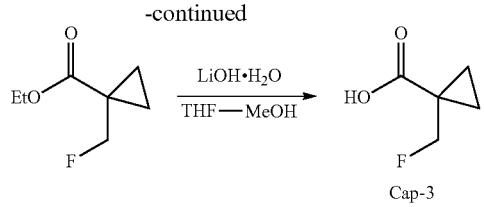

Neat (diethylamino)sulfurtrifluoride (419 mg, 2.60 mmol) was added to a cold stirred (−78° C.) solution of ethyl 1-(hydroxymethyl)cyclopropanecarboxylate (288 mg, 2 mmol) in DCM and the mixture was warmed to rt and stirred at rt overnight. The reaction mixture was cooled and quenched with ice cold satd. NaHCO₃. The organic layer was separated and washed with 1 N HCl, water, brine and dried (MgSO₄). Evaporation of DCM gave a light-brown oil (258 mg) which was dissolved in THF and MeOH and treated with lithium hydroxide hydrate (126 mg, 3.00 mmol) in water. The homogeneous mixture was stirred at rt overnight and then acidified and extracted with ether to afford Cap-3 as a light brown oil. ¹H NMR (400 MHz, CHLOROFORM-d) δ 4.53 (d, J=46.9 Hz, 2H), 1.51-1.45 (m, 2H), 1.13-1.07 (m, 2H).

Cap-4: 3-fluoro-2,2-dimethylpropanoic acid

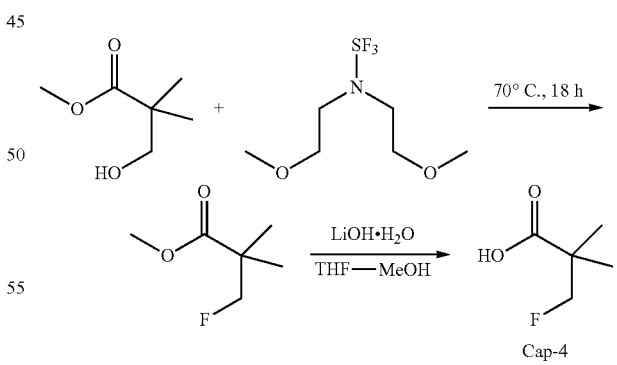

A neat stirred mixture of methyl 3-hydroxy-2,2-dimethylpropanoate (0.264 g, 2 mmol) and [bis(2-methoxyethyl)amino]sulfurtrifluoride (0.531 g, 2.400 mmol) was heated in a capped vial at 70° C. for 18 h. The reaction mixture was cooled and quenched with ice and DCM was added. The organic layer was washed with 1 N HCl, water, brine and dried (MgSO₄). Evaporation of DCM gave light-brown oil (258 mg) which was dissolved in THF and MeOH and treated with lithium hydroxide hydrate (0.126 g, 3.00 mmol) in water. The homogeneous mixture was stirred at rt overnight and acidified with 1 N HCl and extracted with EtOAc, washed with water, brine and dried (MgSO$_4$). Evaporation of the solvent afforded Cap-4 as a light brown oil: $^1$H NMR (400 MHz, CHLOROFORM-d) δ 4.43 (d, J=47.1 Hz, 2H), 1.28 (d, J=1.0 Hz, 6H).

Cap-5: 4,4-difluoro-1-methylcyclohexanecarboxylic acid

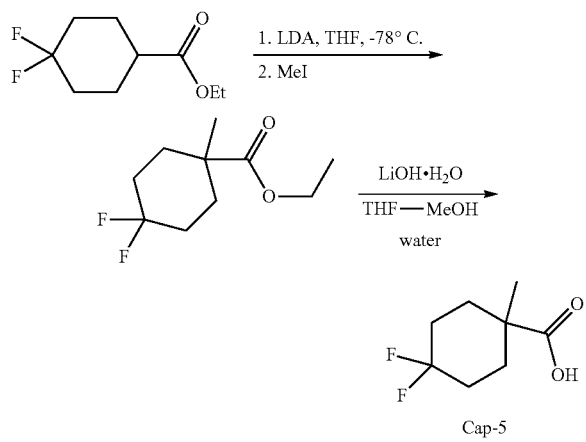

A solution of n-butyl lithium (1.250 mL, 2.000 mmol) was added to a cold (–78° C.) solution of diisopropylamine (0.283 mL, 2.000 mmol) in THF under nitrogen and the mixture was stirred at –78° C. 1 h. A solution of ethyl 4,4-difluorocyclohexanecarboxylate (192 mg, 1 mmol) in THF (1 mL) was added at –78° C. The reaction mixture was stirred at –78° C. for 1 h and then gradually warm to –20° C. over 2 h. Then neat iodomethane (0.138 mL, 2.200 mmol) was added at –78° C. and the mixture was allowed to warm to rt and stirred at rt overnight. The reaction was quenched with satd. NH$_4$Cl and extracted with EtOAc and the organic phase was washed with water, brine, dried (Na$_2$SO$_4$). Evaporation of the solvent afforded ethyl 4,4-difluoro-1-methylcyclohexanecarboxylate (222 mg) as a light brown oil which was dissolved in EtOH and was added a solution of KOH (112 mg, 2.000 mmol) in water (2.00 mL). The reaction mixture was heated to reflux overnight, then cooled and acidified and extracted with EtOAc to afford Cap-5 as a light brown solid. $^1$H NMR (400 MHz, CHLOROFORM-d) δ 2.26-2.17 (m, 2H), 2.07-1.95 (m, 2H), 1.94-1.83 (m, 2H), 1.63-1.54 (m, 2H), 1.31 (s, 3H).

Cap-6: 4,4-difluoro-1-(hydroxymethyl)cyclohexanecarboxylic acid

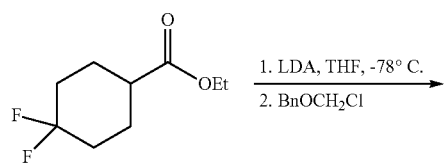

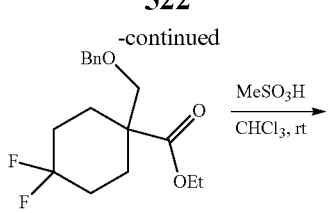

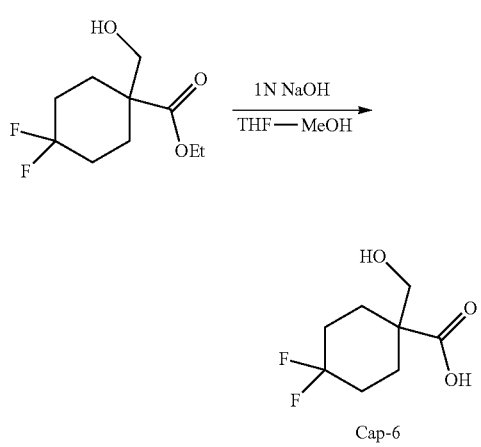

A solution of butyllithium (2.000 mL, 2.80 mmol) was added to a cold (–78° C.) solution of diisopropylamine (0.396 mL, 2.80 mmol) in THF (5 mL) under N$_2$ and the mixture was stirred at –78° C. for 1 h. A solution of ethyl 4,4-difluorocyclohexanecarboxylate (384 mg, 2 mmol) in THF (2 mL) was added at –78° C. and the mixture was stirred for 1 h and then gradually warmed to –20° C. over 2 h and then re-cooled to –78° C. Neat ((chloromethoxy)methyl)benzene (0.226 mL, 2.200 mmol) was added and the mixture was allowed to warm to rt over 2 h. The reaction was quenched with satd. NH$_4$Cl and extracted with EtOAc and washed with water, brine, dried (Na$_2$SO$_4$). Evaporation of the solvent afforded a light yellow oil which was purified by silica gel FCC (1:1 DCM-hexanes) to afford 1-((benzyloxy)methyl)-4,4-difluorocyclohexanecarboxylate as a colorless oil.

Neat methanesulfonic acid (1.102 mL, 16.97 mmol) was added to a stirred solution of ethyl 1-((benzyloxy)methyl)-4, 4-difluorocyclohexanecarboxylate (106 mg, 0.339 mmol) in DCM (2 mL) and the mixture was stirred at rt for 2 h. The reaction mixture was washed with water, satd. NaHCO$_3$, brine and dried (MgSO$_4$) to afford ethyl 4,4-difluoro-1-(hydroxymethyl)cyclohexanecarboxylate as an oil. $^1$H NMR (400 MHz, CHLOROFORM-d) δ 4.25 (q, J=7.3 Hz, 2H), 3.67 (s, 2H), 2.28-2.17 (m, 2H), 2.08-1.93 (m, 2H), 1.86-1.80 (m, 2H), 1.67-1.56 (m, 2H), 1.31 (t, J=1.0 Hz, 3H).

1 N NaOH (0.994 mL, 0.994 mmol) was added to a solution of ethyl 4,4-difluoro-1-(hydroxymethyl)cyclohexanecarboxylate (73.6 mg, 0.331 mmol) in THF (1 mL) and MeOH (1 mL) and the mixture was stirred at rt for 3-4 h. The reaction mixture was acidified and extracted with EtOAC, washed with brine and dried (MgSO$_4$). Evaporation of the solvent afforded Cap-6 as a beige solid. $^1$H NMR (400 MHz, CHLOROFORM-d) δ 3.74 (s, 2H), 2.30-2.20 (m, J=13.3 Hz, 2H), 2.13-1.85 (m, 4H), 1.71-1.60 (m, 2H).

Cap-7:
4,4-difluoro-1-(fluoromethyl)cyclohexanecarboxylic acid

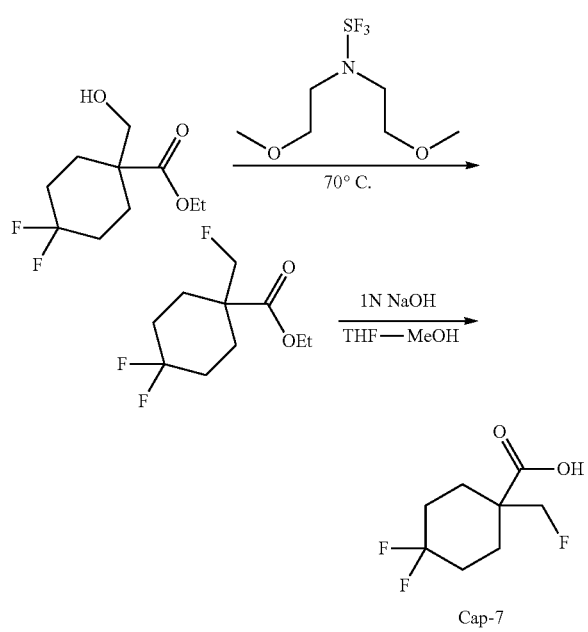

A neat stirred mixture of Deoxo-Fluor® (196 mg, 0.887 mmol) and ethyl 4,4-difluoro-1-(hydroxymethyl)cyclohexanecarboxylate (98.6 mg, 0.444 mmol) was heated at 70° C. overnight. The reaction was cooled to rt and quenched with ice and extracted with DCM, washed with satd. NaHCO$_3$, water, brine and dried (MgSO$_4$). Evaporation of DCM gave a light brown oil which was purified by silica gel FCC (1:3 hexanes:DCM) to afford ethyl 4,4-difluoro-1-(fluoromethyl) cyclohexanecarboxylate as a clear oil. $^1$H NMR (400 MHz, CHLOROFORM-d) δ 4.42 (d, J=47.2 Hz, 2H), 4.25 (q, J=7.0 Hz, 2H), 2.33-2.19 (m, 2H), 2.15-2.01 (m, 2H), 2.01-1.81 (m, 2H), 1.69-1.56 (m, 2H), 1.31 (t, J=7.0 Hz, 3H).

1 N NaOH (0.994 mL, 0.994 mmol) was added to a solution of ethyl 4,4-difluoro-1-(fluoromethyl)cyclohexanecarboxylate (73.6 mg, 0.331 mmol) in THF (1 mL) and MeOH (1 ml) and the mixture was stirred at rt for 3-4 h. The reaction mixture was acidified and extracted with EtOAc, washed with brine and dried (MgSO$_4$). Evaporation of the solvent afforded Cap-7 as a beige solid. $^1$H NMR (400 MHz, CHLOROFORM-d) δ 4.38 (d, J=47.1 Hz, 2H), 2.30-2.16 (m, 2H), 2.11-1.98 (m, 2H), 1.96-1.76 (m, 2H), 1.65-1.51 (m, 2H).

Cap-8: 4,4-difluoro-1-(methoxymethyl)cyclohexanecarboxylic acid

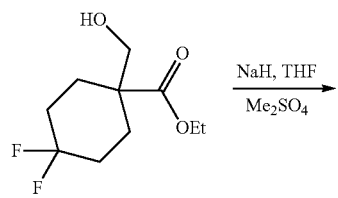

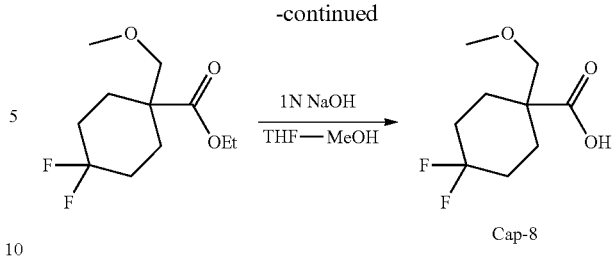

NaH (60%, 29.4 mg, 0.736 mmol) was added to a cold (0° C.) solution of ethyl 4,4-difluoro-1-(hydroxymethyl)cyclohexanecarboxylate (109 mg, 0.490 mmol) in THF (2 mL) and the mixture was allowed to warm to rt over 30 min. Then neat dimethyl sulfate (0.070 mL, 0.736 mmol) was added and the mixture was stirred at rt overnight. Excess Me$_2$SO$_4$ was quenched with TEA, acidified with 1N HCl and extracted with EtOAc to afford a light brown oil which was purified by silica gel FCC (DCM) to afford ethyl 4,4-difluoro-1-(methoxymethyl)cyclohexanecarboxylate as a clear oil (47 mg). Ethyl ester was saponified as described for Cap-7 synthesis (1 N NaOH, MeOH-THF) to afford Cap-8 as a white solid: $^1$H NMR (400 MHz, CHLOROFORM-d) δ 3.47 (s, 2H), 3.39 (s, 3H), 2.25 (br. d, J=13.1 Hz, 2H), 2.10-1.95 (m, 3H), 1.69-1.55 (m, 3H).

Cap-9:
4,4-difluoro-1-hydroxycyclohexanecarboxylic acid

Cap-10:
4,4-difluoro-1-methoxycyclohexanecarboxylic acid

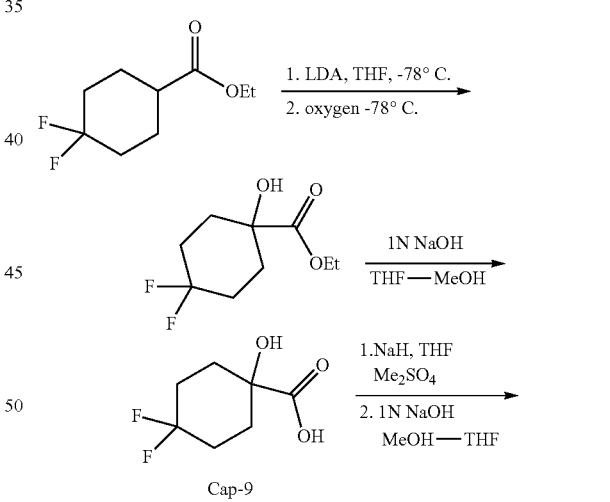

A solution of butyllithium (1.600 mL, 4.00 mmol) was added to cold (−78° C.) solution of diisopropylamine (0.565 mL, 4.00 mmol) in THF (5 mL) under nitrogen and the mixture was stirred at −78° C. 1 h. A solution of ethyl 4,4- difluorocyclohexanecarboxylate (384 mg, 2 mmol) in THF (2 mL) was added at −78° C. and the mixture was stirred for 1 h. The mixture was gradually warmed to −20° C. over 2 h and then recooled to −78° C. and connected to a balloon of oxygen and stirred at −78° C. for 1 h. The reaction mixture was added satd. NaHSO$_3$ solution (5 mL) and allowed to warm to rt and stirred at rt overnight. The reaction mixture was diluted with ether and organic layer separated, washed with water, brine, dried (Na$_2$SO$_4$). Evaporation of the solvent afforded a light yellow oil which was purified by silica gel FCC (DCM) to afford ethyl 4,4-difluoro-1-hydroxycyclohexanecarboxylate as a colorless oil (143 mg). $^1$H NMR (400 MHz, CHLOROFORM-d) δ 4.28 (q, J=7.3 Hz, 2H), 2.23 (br. s, 1H), 2.19-1.99 (m, 6H), 1.83-1.73 (m, 2H), 1.33 (t, J=1.0 Hz, 3H).

1 N NaOH (0.382 mL, 0.382 mmol) was added to a solution of ethyl 4,4-difluoro-1-hydroxycyclohexanecarboxylate (26.5 mg, 0.127 mmol) in THF (0.5 mL) and methanol (0.5 mL) and the mixture was stirred at rt overnight. The reaction mixture was acidified with 2 N HCl and extracted with EtOAc, washed with brine and dried (MgSO$_4$). Evaporation of the solvent afforded Cap-9 as a white solid. $^1$H NMR (400 MHz, CHLOROFORM-d) δ 2.21-2.01 (m, 5H), 1.92-1.87 (m, J=6.8, 3.2, 3.2 Hz, 2H), 1.86-1.79 (m, J=6.7, 3.1 Hz, 2H).

NaH (60%, 2.2 equiv) was added to a cold (0° C.) stirred solution of 4,4-difluoro-1-hydroxycyclohexanecarboxylic acid (1 equiv) in THF (2 mL) and the mixture was allowed to warm rt (30 min). Then neat dimethyl sulfate (2.4 equiv) was added at 0° C. and the mixture was allowed to warm rt and stirred at rt overnight. Excess Me$_2$SO$_4$ was quenched with TEA and the reaction mixture was acidified with 1 N HCl, extracted with ether to afford methyl 4,4-difluoro-1-methoxycyclohexanecarboxylate which was saponified (1 N NaOH, THF-MeOH) to afford Cap-10 as a beige semi-solid. $^1$H NMR (400 MHz, CHLOROFORM-d) δ 3.36 (s, 3H), 2.17-1.98 (m, 8H).

Cap-11: 3,3-difluoro-2,2-dimethylpropanoic acid

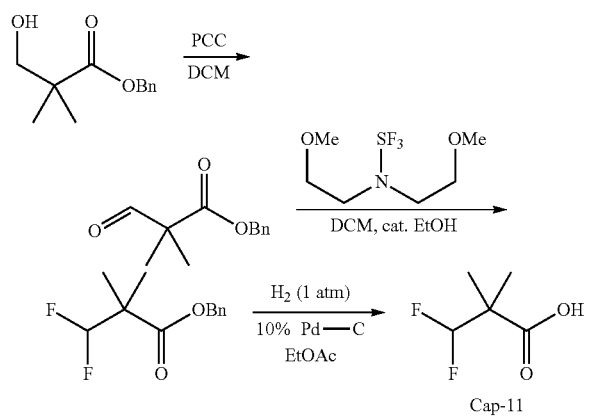

PCC (808 mg, 3.75 mmol) was added to a solution of benzyl 3-hydroxy-2,2-dimethylpropanoate (521 mg, 2.5 mmol) in DCM (5 mL) containing powdered 4 Å molecular seives (~0.5 g) and the mixture was stirred at rt overnight. The reaction mixture was filtered through a plug of silica gel and eluted with DCM to afford benzyl 2,2-dimethyl-3-oxopropanoateas as an oil.

Deoxo-Fluor® (0.789 ml, 4.28 mmol) was added to a solution of benzyl 2,2-dimethyl-3-oxopropanoate (401 mg, 1.944 mmol) in DCM (5 mL) followed by addition of a catalytic amount of EtOH (0.034 mL, 0.583 mmol). The resulting solution was stirred at rt overnight. The reaction was quenched with sat. NaHCO$_3$ and the mixture was extracted with DCM (2×). The combined organic layers were washed with water, brine and dried (MgSO$_4$), filtered and dried to afford a yellow-orange oil which was purified by silica gel FCC (2:1 hexanes-DCM) to afford benzyl 3,3-difluoro-2,2-dimethylpropanoate as a colorless oil (340 mg).

A stirred suspension of benzyl 3,3-difluoro-2,2-dimethylpropanoate (340 mg, 1.49 mmol) and 10% Pd—C (42 mg, 0.04 mmol) in EtOAc (20 mL) was hydrogenated under balloon pressure overnight. The suspension was filtered and the filtrate was evaporated to dryness to afford Cap-11 as a white solid (205 mg). $^1$H NMR (400 MHz, chloroform-d) δ 6.01 (t, J=1.0 Hz, 1H), 2.07 (br. s, 1H), 1.34 (t, J=1.0 Hz, 6H).

Cap-12:
5,5-difluorooctahydropentalene-2-carboxylic acid

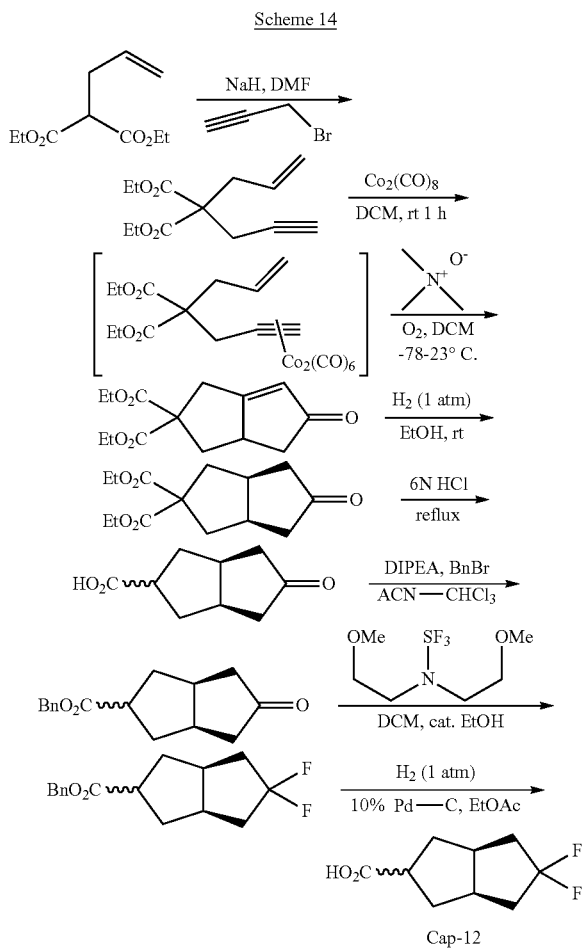

NaH (60%, 0.480 g) was added to a cold (0° C.) solution of diethyl 2-allylmalonate (2.002 g) in DMF (10 mL) and the mixture was allowed to warm to rt over 30 min. Then a solution of 3-bromoprop-1-yne (1.487 g) in DMF (3 mL) was added dropwise at 0° C. and the mixture was allowed to warm to rt and stirred at rt overnight. The reaction mixture was diluted with ether and then quenched with sat. NH$_4$Cl, washed with water, brine and dried (Na$_2$SO$_4$). The crude product was purified by silica gel FCC (1:1 DCM-hexane) to afford diethyl 2-allyl-2-(prop-2-ynyl)malonate as a clear oil.

Neat dicobolt octacarbonyl (718 mg, 2.100 mmol) was added to a stirred solution of diethyl 2-allyl-2-(prop-2-yn-1-yl)malonate (477 mg, 2 mmol) in DCM (25 mL) under $N_2$ and the mixture was stirred at rt for 1 h. In-situ formed eneyne-$Co_2(CO)_6$ complex was diluted with DCM (25 mL) and neat trimethylamine N-oxide (451 mg) was added in one portion at −78° C. under balloon of $O_2$. The reaction mixture was warmed to rt and stirred at rt overnight. The reaction mixture was evaporated to dryness and then purified by silica gel FCC (0-3% MeOH in DCM) to afford diethyl 5-oxo-3,3a,4,5-tetrahydropentalene-2,2(1H)-dicarboxylate as a light brown oil. $^1$H NMR (400 MHz, chloroform-d) δ 5.95 (br. s., 1H), 4.35-4.15 (m, 4H), 3.44-3.32 (m, 1H), 3.32-3.21 (m, 1H), 3.12 (br. s., 1H), 2.81 (dd, J=12.7, 7.7 Hz, 1H), 2.65 (dd, J=17.8, 6.3 Hz, 1H), 2.15 (d, J=17.6 Hz, 1H), 1.75 (t, J=12.8 Hz, 1H), 1.37-1.18 (m, 6H).

A stirred suspension of diethyl 5-oxo-3,3a,4,5-tetrahydropentalene-2,2(1H)-dicarboxylate (322 mg, 1.209 mmol) and 10% Pd—C (129 mg, 0.121 mmol) in EtOH (40 mL) was hydrogenated under balloon pressure overnight. The suspension was filtered and the filtrate was evaporated to dryness to afford diethyl 5-oxohexahydropentalene-2,2(1H)-dicarboxylate as a clear oil.

A stirred mixture of diethyl 5-oxohexahydropentalene-2,2 (1H)-dicarboxylate (0.651 g, 2.426 mmol) and 6 N HCl (10 ml, 60.0 mmol) was heated to reflux for 3-4 h and then evaporated to dryness to afford endo/exo mixture of 5-oxooctahydropentalene-2-carboxylic acid as a viscous oil which was used in the next step without further purification.

Neat (bromomethyl)benzene (531 mg) was added to a stirred mixture of 5-oxooctahydropentalene-2-carboxylic acid (435 mg) and DIPEA (0.542 mL) in acetonitrile (2.5 mL) and $CHCl_3$ (2.5 mL) and the mixture was stirred at rt overnight. Reaction mixture was evaporated to dryness and purified by silica gel FCC (0-1% MeOH in DCM) to afford benzyl 5-oxooctahydropentalene-2-carboxylate which was isolated as an endo/exo isomeric mixture.

Neat Deoxo-Fluor® (0.771 mL) was added to a cold (0° C.) solution of benzyl 5-oxooctahydropentalene-2-carboxylate (450 mg) in DCM (6 mL) followed by addition of EtOH (0.031 mL). The resulting yellowish solution was stirred at rt overnight. The reaction was quenched with sat. $NaHCO_3$ and the mixture was extracted with DCM (2×). The combined organic layers were washed with water, brine and dried ($MgSO_4$), filtered and dried to give a yellow-orange oil. The residue was purified by silica gel FCC (1:1 hexanes-DCM) to afford endo/exo mixture of benzyl 5,5-difluorooctahydropentalene-2-carboxylate as a colorless oil (262 mg).

A stirred suspension of 10% Pd—C (12.53 mg) in a solution of benzyl 5,5-difluorooctahydropentalene-2-carboxylate (33 mg) in EtOAc (5 mL) was hydrogenated under balloon pressure for 2-3 h. The suspension was filtered and evaporated to dryness to afford a mixture of endo/exo isomers of Cap-12 as a white semi-solid. $^1$H NMR (400 MHz, chloroform-d) δ 3.04-2.93 (m, 1H), 2.88-2.76 (m, 2H), 2.40-2.26 (m, 2H), 2.15-2.04 (m, 2H), 1.87-1.71 (m, 4H).

Cap-13: 6,6-difluorospiro[3.3]heptane-2-carboxylic acid

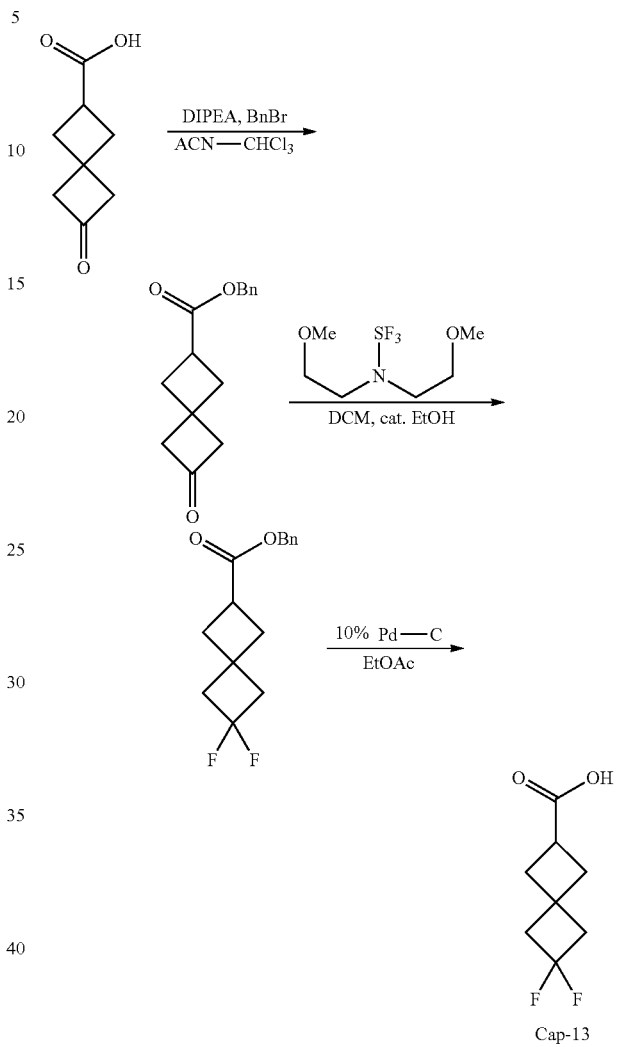

A solution of (bromomethyl)benzene (564 mg) in $CHCl_3$ (1 mL) was added to a stirred solution of 6-oxospiro[3.3] heptane-2-carboxylic acid (462 mg) and DIPEA (0.576 mL) in acetonitrile (2 mL) and $CHCl_3$ (2 mL) and the mixture was stirred at rt overnight. The reaction mixture was evaporated to dryness and then purified by silica gel FCC (1:1 DCM:hexanes) to afford benzyl 6-oxospiro[3.3]heptane-2-carboxylate as a clear oil.

Deoxo-Fluor® (1.456 g) was added to a cold (0° C.) solution of benzyl 6-oxospiro[3.3]heptane-2-carboxylate (0.670 g) in DCM (6 mL) followed by addition of EtOH (0.048 mL). The resulting solution was stirred at rt overnight. The reaction was quenched with sat. $NaHCO_3$ and extracted with DCM (2×). The combined organic layers were washed with water, brine and dried ($MgSO_4$), filtered and evaporated to provide a yellow-orange oil, which was purified by silica gel FCC (1:1 hexanes-DCM) to afford benzyl 6,6-difluorospiro[3.3]heptane-2-carboxylate as a colorless oil (619 mg).

A stirred suspension of 10% Pd—C (40.6 mg) in an EtOAc (10 mL) solution of benzyl 6,6-difluorospiro[3.3]heptane-2-carboxylate (203 mg) was hydrogenated under balloon pressure for 2 h. The suspension was filtered and the filtrate was evaporated to dryness to afford Cap-13 as a clear viscous oil. $^1$H NMR (400 MHz, CHLOROFORM-d) δ 3.18-3.08 (m, 1H), 2.69-2.55 (m, 4H), 2.52-2.37 (m, 4H).

Cap-14: 8,8-difluorobicyclo[3.2.1]octane-3-endo-carboxylic acid

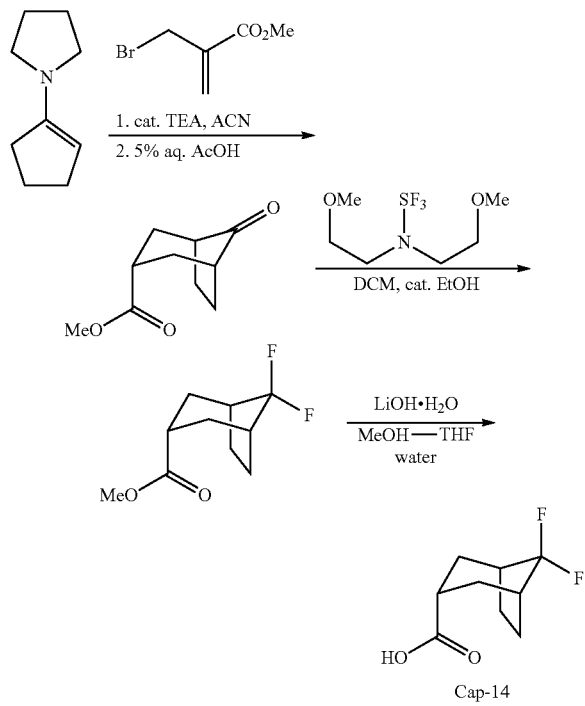

A solution of methyl 2-(bromomethyl)acrylate (531 mg) in acetonitrile (3 mL) was added dropwise to a stirred solution of 1-(cyclopent-1-en-1-yl)pyrrolidine (407 mg) in acetonitrile (3 mL) followed by a few drops of TEA and then mixture was heated to reflux for 5 h. Hydrolysis of iminium ion intermediate was accomplished by addition of 5% aq. AcOH (2 mL) followed by refluxing the mixture for 0.5 h. The solvent was evaporated and the residue was extracted with ether, washed with 1 N HCl, satd. NaHCO$_3$, water, brine and then dried (Na$_2$SO$_4$). Evaporation of ether afforded an oil which was purified by silica gel FCC (0-2% MeOH in DCM) to afford methyl 8-oxobicyclo[3.2.1]octane-3-endo-carboxylate as a clear oil.

Deoxo-Fluor® (411 mg) was added to a cold (0° C.) solution of methyl 8-oxobicyclo[3.2.1]octane-3-endo-carboxylate (141 mg) in DCM (2 mL) followed by addition of EtOH (0.014 mL). The resulting solution was stirred at rt overnight. The reaction was quenched with sat. NaHCO3 and the mixture was extracted with DCM (2×). The combined organic layers was washed with water, brine and dried (MgSO$_4$), filtered and dried to give an oil which was purified by silica gel FCC (1:1 hexanes-DCM) to afford 8,8-difluorobicyclo[3.2.1]octane-3-endo-carboxylate as a colorless oil (98 mg).

A stirred solution of methyl 8,8-difluorobicyclo[3.2.1]octane-3-endo-carboxylate (98 mg) and lithium hydroxide monohydrate (60.4 mg) in THF (1 mL), MeOH (1 mL) and water (1 mL) was sonicated for 2 h. The volatile component was evaporated and the aqueous residue was acidified with 2 N HCl and extracted with EtOAc to afford Cap-14 as a white solid. $^1$H NMR (500 MHz, CHLOROFORM-d) δ ppm 2.65-2.76 (1H, m), 2.32 (2H, dd, J=6.26, 3.66 Hz), 2.09 (2H, t, J=12.74 Hz), 1.95-2.03 (2H, m), 1.83-1.92 (2H, m), 1.52-1.62 (2H, m).

Cap-15: 8,8-difluorobicyclo[3.2.1]octane-3-exo-carboxylic acid

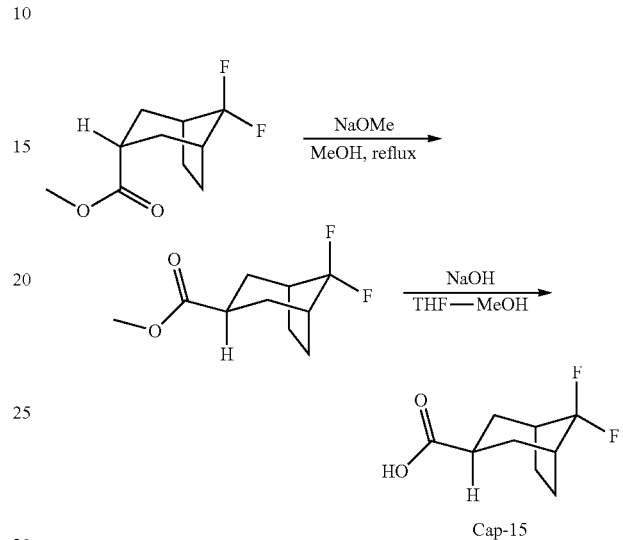

A solution of sodium methoxide (0.5 ml, 0.250 mmol) in MeOH was added to a stirred solution of methyl 8,8-difluorobicyclo[3.2.1]octane-3-endo-carboxylate (67.7 mg) in MeOH (4 mL) and the mixture was heated at 70° C. for 1 h. The reaction was cooled and acidified with 5% aq. AcOH and extracted with ether to afford methyl 8,8-difluorobicyclo[3.2.1]octane-3-exo-carboxylate which was saponified as described for Cap-14 synthesis (1 N NaOH, THF-MeOH) to afford Cap-15 as a white solid. $^1$H NMR (400 MHz, CHLOROFORM-d) δ 2.77-2.64 (m, J=11.9, 6.1, 6.1 Hz, 1H), 2.32 (dd, J=6.3, 3.5 Hz, 2H), 2.15-2.04 (m, 2H), 2.03-1.95 (m, 2H), 1.94-1.84 (m, 2H), 1.62-1.54 (m, 2H).

Cap Y-1: (1R,5S,6r)-3,3-difluorobicyclo[3.1.0]hexane-6-carboxylic acid

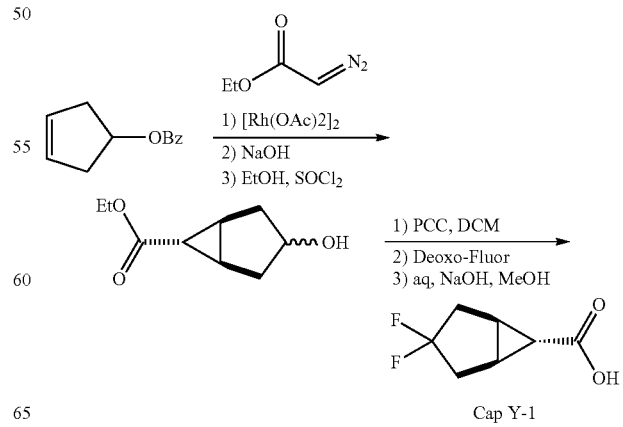

To a solution of cyclopent-3-en-1-yl benzoate (1.6 g) and rhodium(II) acetate dimer (0.225 g) in DCM (20 mL) was added a solution of ethyl 2-diazoacetate (3.53 mL) in 20 mL DCM via syringe pump at a rate of 0.8 mL/h. Another portion of neat ethyl 2-diazoacetate (4.0 mL) was added via syringe pump at a rate of 0.2 mL/h. After the addition, the reaction mixture was concentrated and purified on a 80 g silica gel column (EtOAc/hexane 0 to 25%) to retrieve an isomeric mixture of product.

The above product was dissolved in 5 mL of THF, 20 mL of MeOH and 30 mL of 2 N NaOH. The mixture was stirred for one day and partially concentrated. The residue was acidified, extracted with EtOAc (2×). The combined extract was washed with water, brine, dried (MgSO$_4$) and evaporated to dryness. The residue was dissolved in EtOH (30 mL) and added SOCl$_2$ (1 mL, 13.70 mmol) in an ice bath. The resultant clear solution was stirred at rt for 2 days, the solvent was removed and the residue was purified on a 25 g silica gel column (MeOH/DCM 0 to 25%) to afford the product.

To a solution of (1R,5S,6r)-ethyl 3-hydroxybicyclo[3.1.0] hexane-6-carboxylate (0.59 g) in DCM (20 mL) was added molecular sieve (1.5 g, powdered), then PCC (0.971 g) was added in three portions. The reaction mixture was stirred at rt for 3 h, filtered through silica gel (topped with diatomaceous earth (Celite®) and eluted with EtOAc/hexane 5 to 100%), and concentrated to afford the product as a viscous oil (0.5 g). $^1$H NMR (400 MHz, CHLOROFORM-d) δ 4.16 (q, J=7.3 Hz, 2H), 2.73-2.59 (m, 2H), 2.34-2.24 (m, 2H), 2.19 (td, J=3.5, 1.6 Hz, 2H), 1.33-1.19 (m, 4H).

To a solution of (1R,5S,6r)-ethyl 3-oxobicyclo[3.1.0]hexane-6-carboxylate (0.5 g) in DCM (5 mL) was added Deoxo-Fluor® (1.206 mL), followed by addition of EtOH (0.052 mL). The resulting solution was stirred at rt for 16 h. Another portion of Deoxo-Fluor® (0.3 mL) was added and the reaction mixture was stirred for another day, and another portion of Deoxo-Fluor® (0.5 mL) was added and the reaction mixture was stirred at rt for 7 h. The reaction mixture was partitioned between satd. NaHCO$_3$ and ether. The organic phase was washed with satd. NaHCO$_3$, water, satd. NaCl and dried over anhydrous MgSO$_4$, filtered and removed the solvent to yield a yellow oil (0.5 g). $^1$H NMR (400 MHz, CHLOROFORM-d) δ 4.13 (q, J=7.0 Hz, 2H), 2.54-2.37 (m, 2H), 2.35-2.21 (m, 2H), 1.96 (quin, J=3.3 Hz, 2H), 1.66 (q, J=3.0 Hz, 1H), 1.30-1.24 (m, 3H).

To a solution of ethyl 3,3-difluorobicyclo[3.1.0]hexane-6-carboxylate (0.5 g) in THF (10 mL) and MeOH (10 mL) was added 1 N sodium hydroxide (7.89 mL). The reaction mixture was stirred at rt for 18 h, concentrated and diluted with EtOAc, washed with 1 N HCl, brine, dried (Na$_2$SO$_4$). Removal of the solvent afforded Cap Y-1 as a brown solid (0.43 g). $^1$H NMR (400 MHz, chloroform-d) δ 2.57-2.40 (m, 2H), 2.39-2.25 (m, 2H), 2.07-2.02 (m, J=3.2, 3.2, 3.2 Hz, 2H), 1.69 (q, J=3.0 Hz, 1H).

Cap Y-2: (1R,3s,5S)-6,6-difluorobicyclo[3.1.0]hexane-3-carboxylic acid

Cap Y-3: (1R,3r,5S)-6,6-difluorobicyclo[3.1.0]hexane-3-carboxylic acid

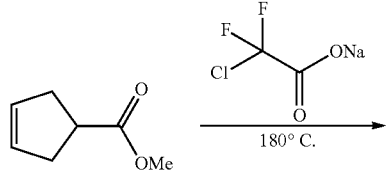

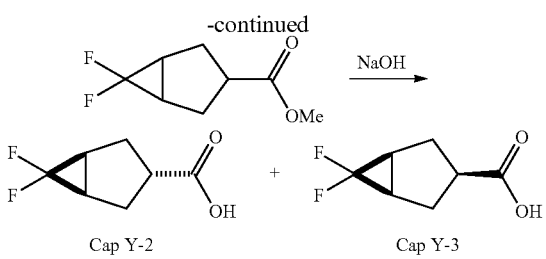

Cap Y-2

Cap Y-3

To a solution of methyl cyclopent-3-enecarboxylate (0.41 g) in diglyme (6 mL) was added a solution of sodium 2-chloro-2,2-difluoroacetate (2.5 g, 16.40 mmol) in 15 mL of diglyme via syringe pump at 0.5 mL/h in a 180° C. bath. Then another portion of sodium 2-chloro-2,2-difluoroacetate (2.5 g) in 18 mL of diglyme was added at a rate of 1.0 mL/h. The solution was cooled down after the addition and the reaction mixture was diluted with ether, washed with water (3×), brine and dried (MgSO$_4$) and the solvent was removed. The residue was dissolved in MeOH (5 mL) and 1 N NaOH (15 mL) was added and the mixture was stirred for 24 h. The reaction mixture was extracted with ether (2×) and the aqueous layer was acidified with 6 N HCl and extracted with EtOAc (2×). The combined EtOAc extracts were washed with 1 N HCl, water (2×), brine, dried (MgSO$_4$). The trans- and cis-isomers were separated by silica gel chromatography.

Cap Y-2: $^1$H NMR (400 MHz, CHLOROFORM-d) δ 3.08-2.78 (m, 1H), 2.47-2.19 (m, 4H), 2.05 (d, J=13.8 Hz, 2H).

Cap-Y-3: $^1$H NMR (400 MHz, CHLOROFORM-d) δ 3.31-3.16 (m, 1H), 2.50-2.40 (m, 2H), 2.40-2.28 (m, 2H), 2.10-1.98 (m, 2H).

Cap Y-4: 2-(2-fluoroethoxy)-2-methylpropanoic acid

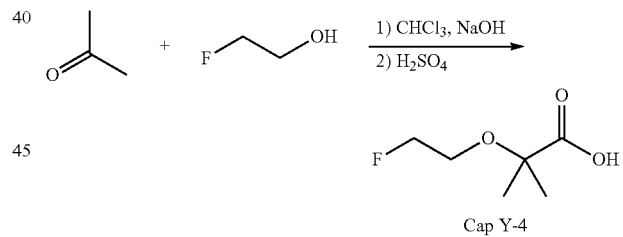

Cap Y-4

To a cold (0-5° C.) stirred solution of 2-fluoroethanol (2 g) in acetone (60 mL) was added NaOH (5.0 g) followed by chloroform (10 mL) dropwise over 10 min. The reaction mixture was stirred in an ice bath for 1 h and then stirred at rt for 16 h. The solid was filtered and washed with MeOH. The filtrate was concentrated and the residue was diluted with EtOAc, washed with ice-cold 1 N HCl, brine and dried (MgSO$_4$). The crude product was dissolved in sulfuric acid (30 mL) and heated at 60° C. for 4 h and cooled down. The reaction mixture was extracted with EtOAc and washed with water, brine, dried (MgSO$_4$). The solvent was removed and the residue was purified on a 25 g silica gel column (MeOH/DCM) to afford Cap Y-4: $^1$H NMR (400 MHz, CHLOROFORM-d) δ 4.73-4.59 (m, 1H), 4.59-4.45 (m, 1H), 3.81-3.68 (m, 2H), 1.51 (s, 6H).

Cap Y-5 to Cap Y-7 were prepared according to the procedure described for the synthesis of Cap Y-4.

Cap Y-5: 2-(2,2-difluoroethoxy)-2-methylpropanoic acid

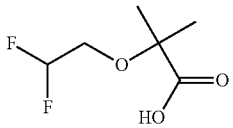

¹H NMR (400 MHz, CHLOROFORM-d) δ ppm 5.75-6.15 (1H, m), 3.74 (2H, td, J=13.49, 4.14 Hz), 1.53 (6H, s).

Cap Y-6: 2-methyl-2-(2,2,2-trifluoroethoxy)propanoic acid

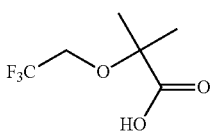

¹H NMR (400 MHz, CHLOROFORM-d) δ 3.94 (q, J=8.4 Hz, 2H), 1.54 (s, 6H).

Cap Y-7: 2-(2-fluorophenoxy)-2-methylpropanoic acid

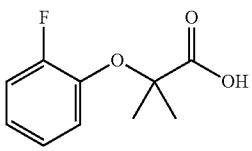

¹H NMR (400 MHz, CHLOROFORM-d) δ 7.18-7.00 (m, 4H), 1.59 (s, 6H).

Cap N-1: 2-(4,4-difluorocyclohexyl)acetic acid

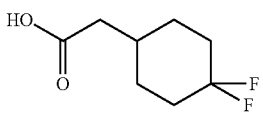

To a solution of ethyl 2-(4-oxocyclohexyl)acetate (0.4 g) in DCM (5 mL) was added Deoxo-Fluor® (0.881 mL) and EtOH (0.038 mL). The reaction mixture was stirred at rt for 16 h and then diluted with sat. NaHCO₃ and EtOAc. The organic phase was washed with water, sat. NaCl and dried over anhydrous Na₂SO₄, filtered and dried to yield ethyl 2-(4,4-difluorocyclohexyl)acetate (0.4 g). To a solution of ethyl 2-(4,4-difluorocyclohexyl)acetate in THF/MeOH (2 mL) was added 1N NaOH (1 mL), and the reaction mixture was stirred at rt for 16 h. The reaction mixture was concentrated, then diluted with EtOAc and acidified with 1N HCl. The organic phase was washed with sat. NaCl, dried over anhydrous Na₂SO₄, filtered and concentrated to yield 2-(4,4-difluorocyclohexyl) acetic acid as a yellow solid. ¹H NMR (400 MHz, DMSO-d₆) ppm 12.13 (1H, br. s.), 2.06-2.28 (3H, m), 1.92-2.03 (1H, m), 1.72-1.91 (4H, m), 1.31-1.48 (1H, m), 1.10-1.31 (2H, m).

Cap N-2: 3,3-difluorocyclopentanecarboxylic acid

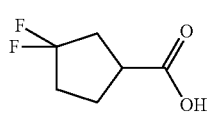

To a solution of racemic 3-oxocyclopentanecarboxylic acid (1.28 g) in DCM (5 mL) was added (S)-1-phenylethanol (1.281 g), DCC (2.061 g) and DMAP (0.122 g) in DCM (5 mL) slowly at 0° C., and the reaction mixture was stirred at rt for 16 h. Then the reaction mixture was diluted with EtOAc, filtered off the solid, and the filtrate was washed with sat. NaHCO₃, water, citric acid, water, sat. NaCl and dried over anhydrous Na₂SO₄, concentrated to yield the crude product. The crude product was purified by silica chromatography to afford a diastereomeric mixture of (S)-1-phenylethyl 3-oxocyclopentanecarboxylate (1 g). LC/MS (Cond. N-1): [M+Na]⁺ 255.15, RT=3.245 min. ¹H NMR (400 MHz, CHLOROFORM-d) ppm 7.27-7.40 (5H, m), 5.91 (1H, qd, J=6.61, 2.26 Hz), 3.06-3.24 (1H, m), 2.43-2.52 (2H, m), 2.27-2.41 (2H, m), 2.13-2.25 (2H, m), 1.56 (3H, dd, J=6.53, 1.00 Hz).

To a solution of (S)-1-phenylethyl 3-oxocyclopentanecarboxylate (1 g) in DCM was added Deoxo-Fluor® (1.746 mL) and EtOH (0.075 mL). The reaction mixture was stirred at rt for 16 hrs, then diluted with sat. NaHCO₃ and EtOAc. The organic phase was washed with water, sat. NaCl and dried over anhydrous Na₂SO₄, filtered and dried to yield a yellow oil. The crude product was purified by silica gel chromatography to yield (S)-1-phenylethyl 3,3-difluorocyclopentanecarboxylate. LC/MS (Cond. N-1): [M+Na]⁺ 277.16, RT=3.8 min. ¹H NMR (400 MHz, CHLOROFORM-d) ppm 7.29-7.41 (5H, m), 5.91 (1H, q, J=6.69 Hz), 2.97-3.12 (1H, m), 2.30-2.51 (2H, m), 1.96-2.26 (4H, m), 1.53-1.58 (3H, m). The two diastereomers were separated by chiral column chromatography (ChiralCel OJ-H, 4.6×100 mm, 5 μm, Mobile Phase: 90% Heptane/0.1% DEA/10% EtOH, Flow Rate: 1.0 mL/min): diastereomer-1: R_t=3.58 min; diastereomer-2: R_t=4.06 min.

To a solution of (S)-1-phenylethyl 3,3-difluorocyclopentanecarboxylate (diastereomer-1 or diastereomer-2, 0.15 g) in ethanol (5 mL) was added 10% Pd—C. The reaction mixture was stirred at rt under H₂ for 16 h. The reaction mixture was filtered and the filtrate was concentrated to afford corresponding enantiomers of 3,3-difluorocyclopentanecarboxylic acid. ¹H NMR (400 MHz, METHANOL-d₄) ppm 2.97-3.08 (1H, m), 2.28-2.41 (2H, m), 1.93-2.23 (4H, m).

Cap W-1

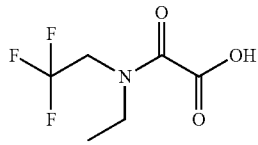

Cap W-1

Step a

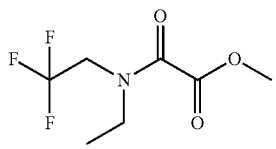

To a solution of N-ethyl-2,2,2-trifluoroethanamine, HCl (211 mg, 1.290 mmol) and N,N-diiso-propylethylamine (0.674 mL, 3.87 mmol) in DCM (5 mL) at 0° C. was added a solution of methyl oxalyl chloride (0.124 mL, 1.290 mmol) in DCM (5 mL) dropwise. The reaction mixture was stirred at rt for 1 h, then added water (50 mL). The organic layer was separated and washed with 1 N HCl and brine, dried over MgSO$_4$, filtered, evaporated in vacuo to afford Cap W-1 Step a (239 mg) as a colorless oil.

To a solution of this oil in MeOH (4 mL) and THF (4 mL) was added a solution of lithium hydroxide monohydrate (94 mg) in water (4 mL). The reaction mixture was stirred at rt for 1.5 h. The solution was then acidified with 2 M HCl (2 mL). The volatile was removed. The remaining aqueous layer was saturated with NaCl, extracted with EtOAc. The combined organic layers were washed with brine, dried over MgSO$_4$, filtered, evaporated to yield Cap W-1 (219 mg). $^1$H NMR (500 MHz, MeOD-d$_4$) δ ppm 4.18 (2H, q, J=9.14 Hz), 3.51-3.61 (2H, m), 1.24-1.31 (3H, m).

Cap W-2

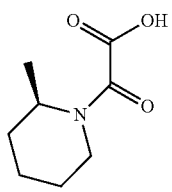

Cap W-2 was prepared by employing the procedures described for the synthesis of Cap W-1, using appropriate starting materials.

Cap W-3

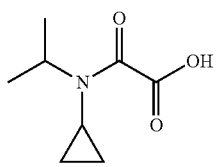

Cap W-3 was prepared by employing the procedures described for the synthesis of Cap W-1 starting from N-isopropylcyclopropanamine. LC/MS (Cond. W-1): [M+H]$^+$ 172.1, R$_t$=0.76 min.

Cap W-4

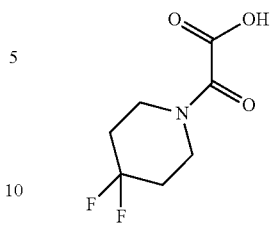

Cap W-4 was prepared by employing the procedures described for the synthesis of Cap W-1 starting from 4,4-difluoropiperidine/HCl salt. $^1$H NMR (500 MHz, CDCl$_3$) δ ppm 7.99 (1H, br. s.), 3.97-4.11 (2H, m), 3.72-3.90 (2H, m), 2.12 (4H, dtt, J=18.69, 12.57, 12.57, 6.23, 6.23 Hz).

Cap W-5

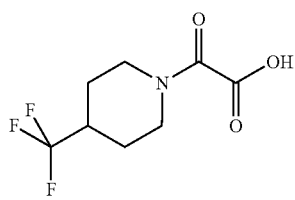 [SMILES: O=C(O)C(=O)N1CCC(C(F)(F)F)CC1]

To a solution of methyl 2-oxo-2-(4-(trifluoromethyl)piperidin-1-yl)acetate (1.00 g, 4.18 mmol) in MeOH and THF was added a solution of LiOH (8.36 mmol) in water. The reaction mixture was stirred at rt for 1.5 h, then acidified with 2 M HCl. Removed volatiles in vacuo. The remaining aqueous layer was saturated with NaCl, extracted with EtOAc. The combined organic layers were washed with brine, dried over MgSO$_4$, filtered, and evaporated to yield Cap W-5 (806 mg). LC/MS (Cond. W-1): [M+H]$^+$ 226.1, R$_t$=0.743 min.

Cap W-6

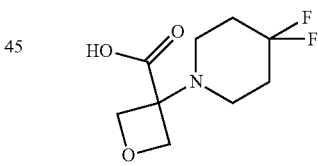

Cap W-6

Step a

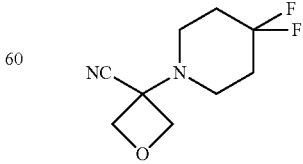

To a solution of oxetan-3-one (290 mg, 4.02 mmol) and 4,4-difluoropiperidine, HCl (1268 mg, 8.05 mmol) in acetic acid (4 mL) was added trimethylsilyl cyanide (1.073 mL, 8.05 mmol). The reaction mixture was heated at 60° C. for 5 h, diluted with DCM (20 mL), and poured into sat. Na₂CO₃ (40 mL). The separated organic layer was washed with 1M NaOH and brine, dried over MgSO₄, filtered, evaporated in vacuo. The residual oil was purified by flash silica chromatography to afford the desired product Cap W-6 Step a (410 mg). ¹H NMR (400 MHz, CDCl₃) δ ppm 4.84 (2H, d, J=6.53 Hz), 4.67 (2H, d, J=6.53 Hz), 2.54 (4H, t, J=5.65 Hz), 2.02-2.22 (4H, m).

A reaction mixture of Cap W-6 Step a (481 mg, 2.379 mmol) and sodium hydroxide in water (19.0 ml, 95 mmol) was heated at 100° C. for 12 h, cooled down and diluted with water (20 mL), extracted with ether (20 mL). The separated aqueous layer was cooled with ice and acidified with con. HCl to pH=4, then saturated with NaCl, extracted with EtOAc. The combined organic layer was washed with brine, dried over MgSO₄, filtered, evaporated to yield Cap W-6 as a white solid (167 mg). ¹H NMR (400 MHz, MeOD-d₄) δ ppm 4.79 (2H, d, J=6.53 Hz), 4.61 (2H, d, J=6.53 Hz), 2.64 (4H, t, J=5.65 Hz), 1.93-2.14 (4H, m).

Cap W-7

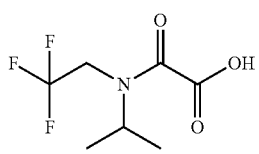

Cap W-7 was prepared by employing the procedures described for the synthesis of Cap W-1 starting from N-(2,2,2-trifluoroethyl)propan-2-amine, HCl. LC/MS (Cond. W-1): [M+H]⁺ 214.1, R_f=0.645 min.

Cap W-8

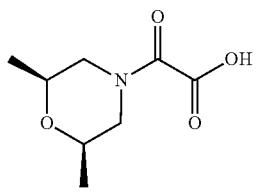

Cap W-8 was prepared by employing the procedures described for the synthesis of Cap W-1 starting from cis-2,6-dimethylmorpholine. ¹H NMR (500 MHz, MeOD-d₄) δ ppm 4.23-4.33 (1H, m), 3.54-3.71 (3H, m), 2.89-2.98 (1H, m), 2.51 (1H, dd, J=13.08, 10.72 Hz), 1.22 (3H, d, J=6.15 Hz), 1.15-1.20 (3H, m).

Cap W-9

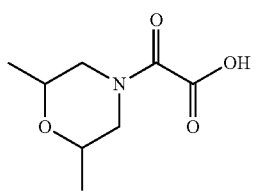

Trans

Cap W-9

Step a

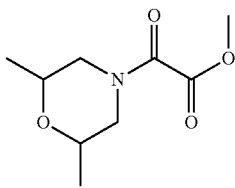

Trans

To a solution of 2,6-dimethylmorpholine (mixture of cis and trans, 5.08 mL, 40 mmol) and N,N-diisopropylethylamine (15.33 mL, 88 mmol) in DCM (50 mL) with ice bath was added a solution of methyl oxalyl chloride (3.84 mL, 40.0 mmol) in DCM (50 mL) dropwise. The reaction mixture was stirred at rt for 30 min, then quenched with water. The separated organic layer was washed with 1 N HCl and brine, dried over MgSO₄, filtered, evaporated. The residual oil was purified by a Biotage system (240 g silica gel cartridge), eluted with gradient 30%~60% acetone-hexanes to afford Cap W-9 Step a (Cis) as the first eluting peak (major) product, and Cap W-9 Step a (Trans) as the second eluting (minor) product. Cap W-9 Step a (Cis): ¹H NMR (500 MHz, CDCl₃) δ ppm 4.34-4.38 (1H, m), 3.90 (3H, s), 3.61-3.64 (2H, m), 3.50-3.54 (1H, m), 2.87-2.92 (1H, m), 2.46-2.51 (1H, m), 1.20-1.24 (6H, m).

Cap W-9 Step a (Trans): ¹H NMR (500 MHz, CDCl₃) δ ppm 4.02-4.12 (2H, m), 3.90 (3H, s), 3.77 (1H, dd, J=13.08, 3.47 Hz), 3.52 (1H, dd, J=13.24, 3.31 Hz), 3.30 (1H, dd, J=13.24, 6.46 Hz), 3.19 (1H, dd, J=13.24, 5.67 Hz), 1.20-1.30 (6H, m).

To a solution of Cap W-9 Step a (Trans) (1.49 g) in MeOH and THF was added a premade solution of lithium hydroxide monohydrate (0.621 g) in water. The reaction mixture was stirred at rt for 1.5 h. The solution was concentrated then acidified with 2M HCl. The aqueous layer was saturated with NaCl, extracted with EtOAc. The combined organic layers were washed with brine, dried over MgSO₄, filtered, evaporated to yield Cap W-9 (Trans) (1.43 g). ¹H NMR (500 MHz, MeOD-d₄) δ ppm 4.00-4.09 (2H, m), 3.70 (1H, dd, J=13.16, 3.39 Hz), 3.60 (1H, dd, J=13.32, 3.39 Hz), 3.22-3.32 (2H, m), 1.21 (6H, d, J=6.46 Hz).

Cap W-10

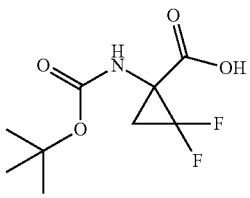 [SMILES: CC(C)(C)OC(=O)NC1(C(=O)O)CC1(F)F]

Cap W-10

Step a

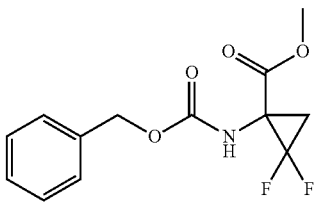 [SMILES: COC(=O)C1(NC(=O)OCc2ccccc2)CC1(F)F]

A 3-neck flask containing methyl 2-(benzyloxycarbonylamino)acrylate (6.80 g, 28.9 mmol), sodium fluoride (0.121 g, 2.89 mmol) and toluene (150 mL) was heated to gentle reflux. A solution of trimethylsilyl 2,2-difluoro-2-(fluorosulfonyl)acetate (14.24 mL, 72.3 mmol) in toluene (150 mL) was added dropwise over 4 h. The reaction mixture was heated for another 3 hours, then cooled to rt, quenched with sat. Na$_2$CO$_3$ at 0° C. The separated aqueous layer was extracted with EtOAc. The combined organic layer was washed with brine, dried over MgSO$_4$, filtered, concentrated in vacuo. The residue was purified by silica gel chromatography to afford Cap W-10 Step a (7.95 g). $^1$H NMR (400 MHz, CDCl$_3$) δ ppm 7.32-7.47 (5H, m), 5.54 (1H, br. s.), 5.17 (2H, s), 3.68-3.89 (3H, m), 2.56-2.84 (1H, m), 1.98 (1H, br. s.).

Cap W-10

Step b

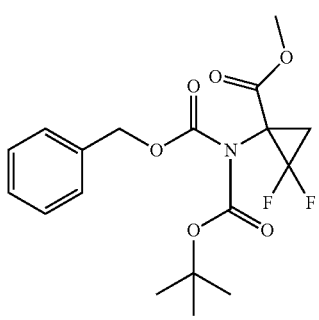 [SMILES: COC(=O)C1(N(C(=O)OCc2ccccc2)C(=O)OC(C)(C)C)CC1(F)F]

A solution of Cap W-10 Step a (7.12 g, 24.96 mmol), di-t-butyl dicarbonate (6.54 g, 30.0 mmol), and 4-dimethylaminopyridine (0.610 g, 4.99 mmol) in THF was stirred at rt for 18 h. The reaction mixture was quenched with water, stirred at rt for 30 min, and extracted with EtOAc. The separated aqueous layer was saturated with NaCl, and extracted with EtOAc. The combined organic layers were washed with brine, dried over MgSO$_4$, filtered, and concentrated. The residue was purified by silica gel chromatography to afford Cap W-10 Step b (9.44 g) as a viscous oil. LC/MS (Cond. W-1): [M+Na]$^+$ 408.12, R$_t$=2.077 min.

A mixture of Cap W-10 Step b (9.44 g, 24.50 mmol), 3 M sodium hydroxide (40.8 mL, 122 mmol) in MeOH and THF was stirred at rt for 18 h, and then concentrated in vacuo. The remaining solution was diluted with water (50 mL), filtered and the filtrate was then extracted with ether. The aqueous layer was acidified while stirring with 2 N HCl to pH 2, and extracted with EtOAc. The combined organic layers were washed with brine, dried over MgSO$_4$, filtered, and concentrated to yield Cap W-10 (5.43 g). $^1$H NMR (400 MHz, MEOD-d$_4$) δ ppm 2.39-2.59 (1H, m), 1.73-1.93 (1H, m), 1.43-1.52 (9H, m).

Cap W-11

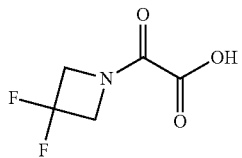

Cap W-11

Step a

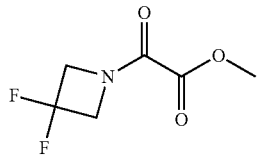

To a solution of 3,3-difluoroazetidine, HCl (0.775 g, 5.98 mmol) in DCM (5 mL) at 0° C. was added triethylamine (0.834 mL, 5.98 mmol) followed by dropwise addition of methyl 2-chloro-2-oxoacetate (0.806 g, 6.58 mmol) in DCM (5 mL). The reaction was stirred at rt for 18 h. The reaction solution was washed with 1 N HCl (2×25 mL), sat. NaHCO$_3$ (2×25 mL) and then dried (MgSO$_4$), filtered, and concentrated to yield Cap W-11 Step a (1.015 g) as a white crystalline solid. $^1$H NMR (500 MHz, CDCl$_3$) δ ppm 4.84 (2H, td, J=11.67, 1.98 Hz), 4.46 (2H, td, J=11.83, 1.98 Hz), 3.88 (3H, s).

To a solution of Cap W-11 Step a (0.850 g, 4.75 mmol) in EtOH (5 mL) at 0° C. was added 22.5% aq. KOH (1.183 mL, 4.75 mmol). The reaction was stirred for 1 hr then acidified with conc. HCl. The resulting mixture was concentrated and the solid was washed with DCM. The filtrate was concentrated to yield Cap W-11 (0.205 g). $^1$H NMR (500 MHz, DMSO-d$_6$) δ ppm 14.08 (1H, br. s.), 4.82 (2H, td, J=12.44, 0.76 Hz), 4.41 (2H, td, J=12.44, 0.76 Hz).

Cap W-12

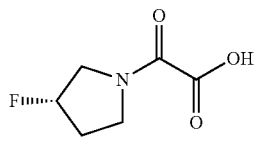 [SMILES: O=C(O)C(=O)N1CC[C@H](F)C1]

Cap W-12 (S)-2-(3-fluoropyrrolidin-1-yl)-2-oxoacetic acid was prepared by employing the procedures described for the synthesis of Cap W-10 starting from (S)-3-fluoropyrrolidine, HCl. $^1$H NMR (500 MHz, DMSO-d$_6$) δ ppm 14.08 (1H, br. s.), 5.36 (1H, d, J=53.10 Hz), 3.46-3.93 (4H, m), 2.12-2.22 (2H, m).

Cap W-13

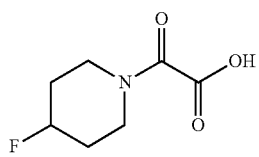 [SMILES: O=C(O)C(=O)N1CCC(F)CC1]

Cap W-13 was prepared by employing the procedures described for the synthesis of Cap W-10 starting from 4-fluoropiperidine, HCl. $^1$H NMR (500 MHz, CDCl$_3$) δ ppm 7.62 (1H, br. s.), 4.93 (1H, d, J=47.90 Hz), 4.36-4.46 (1H, m), 4.02-4.11 (1H, m), 3.79-3.89 (1H, m), 3.45-3.53 (1H, m), 1.78-2.09 (4H, m).

Cap W-14

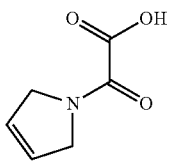

Cap W-14 was prepared by employing the procedures described for the synthesis of Cap W-10 starting from 2,5-dihydro-1H-pyrrole. $^1$H NMR (400 MHz, MeOD-d$_4$) δ ppm 5.77-6.00 (2H, m), 4.50-4.60 (2H, m), 4.18-4.36 (2H, m).

Cap W-15

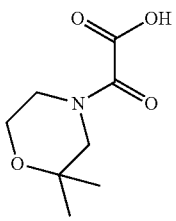

Cap W-15 was prepared by employing the procedures described for the synthesis of Cap W-10 starting from 2,2-dimethylmorpholine. $^1$H NMR (500 MHz, MEOD-d$_4$) δ ppm 3.70-3.84 (2H, m), 3.56-3.63 (1H, m), 3.47-3.54 (1H, m), 3.45 (1H, s), 3.36 (1H, s), 1.20-1.30 (6H, m).

Cap L-1

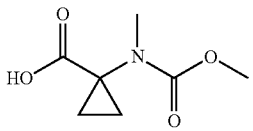

Cap L-1
Step a

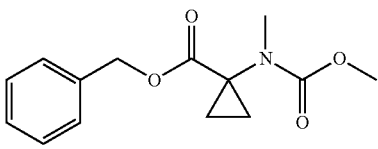 [SMILES: COC(=O)N(C)C1(C(=O)OCc2ccccc2)CC1]

Methyl chloroformate (0.127 mL, 1.644 mmol) was added to a solution of benzyl 1-(methylamino)cyclopropanecarboxylate, TFA (0.35 g, 1.096 mmol) and DIEA (0.574 mL, 3.29 mmol) in CH$_2$Cl$_2$ (5 mL). The resulting solution was stirred at rt for 2 h. The mixture was diluted with CH$_2$Cl$_2$ (15 mL) and then washed with NaHCO$_3$ and brine, dried (MgSO$_4$) and concentrated. The residue was purified with silica gel chromatography to yield Cap L-1 step a (180 mg). LC/MS (Cond. L-1): [M+H]$^+$ 264.2, R$_f$=2.58 min. $^1$H NMR (400 MHz, CDCl$_3$) ppm 7.43-7.28 (m, 5H), 5.15 (s, 2H), 3.75-3.56 (m, 3H), 3.00-2.87 (m, 3H), 1.76-1.56 (m, 2H), 1.26 (br. s., 2H).

Cap L-1 step a (180 mg) was dissolved in MeOH (5 mL) and charged with 10% Pd/C (36.4 mg). The suspension was flushed with N$_2$, and stirred at rt under H$_2$ for 16 h. The reaction mixture was filtered and the solvent was removed under reduced pressure to yield Cap L-1 (100 mg). $^1$H NMR (500 MHz, CDCl$_3$) 10.65 (br. s., 1H), 3.70 (s, 3H), 2.93 (d, J=5.2 Hz, 3H), 1.85-1.41 (m, 2H), 1.40-1.09 (m, 2H).

Cap L-2

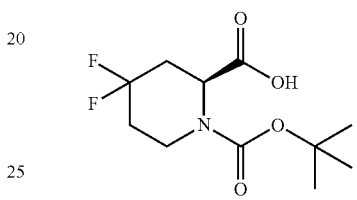

Cap L-2
Step a

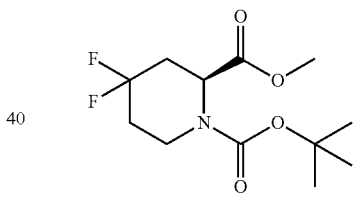

Deoxo-Fluor® (0.473 mL, 2.57 mmol) was added to a solution of (S)-1-tert-butyl 2-methyl 4-oxopiperidine-1,2-dicarboxylate (300 mg, 1.166 mmol) in DCM (5 mL), followed by the addition of EtOH (0.020 mL) and the resulting solution was stirred at room temperature for 16 h.

The reaction mixture was diluted with DCM (10 mL) and washed with sat. NaHCO$_3$ (20 mL), water (20 mL) and brine (20 mL), dried (MgSO$_4$) and concentrated. The residue was purified with silica gel chromatography to yield Cap L-2 Step a (201 mg). $^1$H NMR (500 MHz, CDCl$_3$) δ ppm 5.15-4.81 (m, 1H), 4.24-4.01 (m, 1H), 3.76 (br. s., 3H), 3.38-3.12 (m, 1H), 2.72 (br. s., 1H), 2.27-1.97 (m, 2H), 1.97-1.77 (m, 1H), 1.54-1.39 (m, 9H).

A solution of LiOH (34.3 mg, 1.432 mmol) in water (3.00 mL) was added to a solution of (S)-1-tert-butyl 2-methyl 4,4-difluoropiperidine-1,2-dicarboxylate (200 mg) in THF (3 mL) and the resulting mixture was stirred at rt for 3 h. The reaction mixture was diluted with water and washed with EtOAc. The aqueous layer was then acidified with 1 N HCl and extracted with EtOAc. The combined organic layers were washed with brine, dried (MgSO$_4$), filtered and concentrated to yield Cap L-2. $^1$H NMR (500 MHz, DMSO-d$_6$) δ ppm 13.00 (br. s., 1H), 4.90-4.69 (m, 1H), 4.19-3.91 (m, 1H), 3.22-2.98 (m, 1H), 2.49-2.14 (m, 2H), 1.98 (dd, J=12.2, 3.5 Hz, 1H), 1.48-1.33 (m, 9H).

Cap L-3

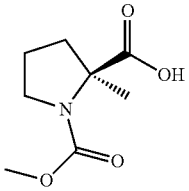

(S)-2-Methylpyrrolidine-2-carboxylic acid (0.5 g, 3.87 mmol) and $Na_2CO_3$ (0.240 g) were dissolved in 1 N NaOH (3.87 mL, 3.87 mmol) and the solution was cooled to 0° C. Methyl chloroformate (0.315 mL) was added dropwise and the solution was stirred at room temperature for 2 h. The reaction mixture was diluted with water and washed with $Et_2O$. The organic layer was acidified with 1 N HCl and extracted with $CH_2Cl_2$. The combined organic layers were dried ($MgSO_4$), filtered and concentrated to give Cap L-3 (0.41 g). $^1H$ NMR (500 MHz, DMSO-$d_6$) δ ppm 12.43 (s, 1H), 3.55 (s, 3H), 3.48-3.37 (m, 2H), 2.16-1.99 (m, 1H), 1.96-1.80 (m, 3H), 1.43 (m, 3H).

Cap L-4

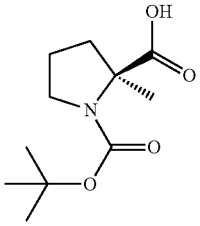 [SMILES: CC(C)(C)OC(=O)N1CCC[C@@]1(C)C(=O)O]

To a stirred solution of (S)-2-methylpyrrolidine-2-carboxylic acid (0.42 g, 3.25 mmol) and $BOC_2O$ (0.906 mL, 3.90 mmol) in DCM (10 mL) was added $Et_3N$ (0.680 mL, 4.88 mmol) and the resulting suspension was stirred at room temperature for 16 h. The reaction was partitioned between water and EtOAc. The organic layer was removed. The aqueous layer was mixed with EtOAc (10 mL) and the pH of the biphasic mixture was acidified with 10% $KHSO_4$. The layers were separated and the aqueous layer was extracted with EtOAc. The combined organic layers were dried ($MgSO_4$), and concentrated to Cap L-4 (0.57 g) as a white solid. $^1H$ NMR (500 MHz, DMSO-$d_6$) ppm 12.36 (s, 1H), 3.45-3.28 (m, 2H), 2.13-1.98 (m, 1H), 1.91-1.74 (m, 3H), 1.40 (s, 3H), 1.39-1.29 (m, 9H).

Cap L-5

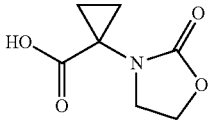

A mixture of ethyl 1-((2-hydroxyethyl)amino)cyclopropanecarboxylate (0.180 g, 1.039 mmol) and CDI (0.177 g, 1.091 mmol) in THF (5 mL) was stirred at room temperature for 15 h, then heated to reflux for 15 h. The solvent was removed and the residue was purified with silica gel chromatography to yield ethyl 1-(2-oxooxazolidin-3-yl)cyclopropanecarboxylate (0.2 g). A solution of LiOH (0.048 g) in water (3 mL) was added to a solution of ethyl 1-(2-oxooxazolidin-3-yl)cyclopropanecarboxylate (0.2 g, 1.004 mmol) in THF (5 mL) and the resulting mixture was stirred vigorously at rt for 16 h. The reaction mixture was then diluted with water and washed with EtOAc. The aqueous layer was then acidified with 1N HCl and extracted with EtOAc. The combined organic layers were dried ($MgSO_4$), filtered and concentrated to yield Cap L-5 (60 mg). $^1H$ NMR (500 MHz, DMSO-$d_6$) ppm 12.83 (br. s., 1H), 4.30-4.20 (m, 2H), 3.65-3.56 (m, 2H), 1.41-1.33 (m, 2H), 1.25-1.19 (m, 2H).

Cap L-6

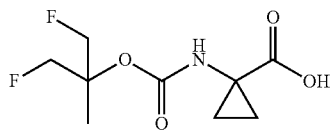 [SMILES: CC(CF)(CF)OC(=O)NC1(C(=O)O)CC1]

Cap L-6

Step a

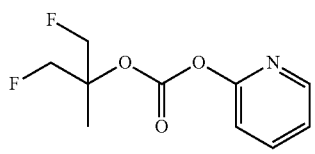 [SMILES: CC(CF)(CF)OC(=O)Oc1ccccn1]

To a suspension of NaH (0.200 g, 5.00 mmol) in THF (5 mL) was added 1,3-difluoro-2-methylpropan-2-yl pyridin-2-yl carbonate (0.5 g, 4.54 mmol). After stirring 1 h, the solution was transferred to a solution of dipyridin-2-yl carbonate (0.982 g, 4.54 mmol) in THF (5 mL) through a cannula. The formed slurry was stirred at rt overnight. It was diluted with EtOAc, washed with brine, dried over $MgSO_4$, filtered, concentrated to give Cap L-6 Step a as an oily residue.

Benzyl 1-aminocyclopropanecarboxylate, HCl (118 mg) and Cap L-6 Step a (180 mg) were combined in DCM (5 mL) in the presence of DIEA (0.136 mL) and the resulting solution was stirred at rt for 16 h. The solvent was removed under reduced pressure and the residue was purified with silica gel to yield Cap L-6 Step b (150 mg). $^1H$ NMR (500 MHz, $CDCl_3$) δ ppm 7.43-7.28 (m, 5H), 5.58 (br. s., 1H), 5.13 (s, 2H), 4.72-4.42 (m, 4H), 1.56 (br. s., 2H), 1.46 (br. s., 3H), 1.19 (d, J=1.7 Hz, 2H).

Cap L-6

Step b

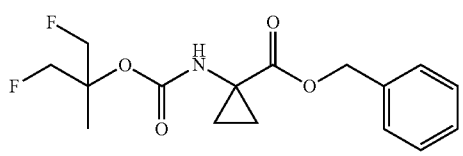 [SMILES: CC(CF)(CF)OC(=O)NC1(C(=O)OCc2ccccc2)CC1]

Cap L-6 Step b (150 mg) was dissolved in MeOH (5 mL) and charged with 10% Pd/C (24.4 mg). The reaction mixture was stirred under $H_2$ at rt for 16 h. The catalyst was filtered and the volatiles were removed to yield Cap L-6 (105 mg). $^1H$ NMR (500 MHz, DMSO-d$_6$) δ ppm 12.28 (br. s., 1H), 7.84 (br. s., 1H), 4.73-4.49 (m, 4H), 1.39 (br. s., 3H), 1.27 (d, J=2.8 Hz, 2H), 0.96 (br. s., 2H).

Cap L-7

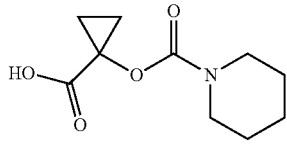

Cap L-7

Step a

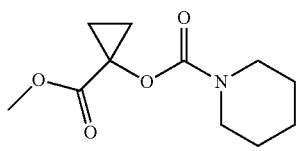 [SMILES: COC(=O)C1(OC(=O)N2CCCCC2)CC1]

Piperidine-1-carbonyl chloride (1.599 mL) was added to a solution of methyl 1-hydroxycyclopropanecarboxylate (1 mL) and DIEA (3.04 mL) in DCM (15 mL). The resulting solution was stirred at rt for 2 h, then diluted with DCM and the organic layer was washed with 1N HCl, water and brine, dried (MgSO$_4$), filtered and concentrated. The residue was purified with silica gel to yield Cap L-7 Step a (0.75 g).

A solution of LiOH (0.158 g, 6.60 mmol) in water (5 mL) was added to a solution of 1-(methoxycarbonyl)cyclopropyl piperidine-1-carboxylate (0.75 g) in THF (10 mL) and the resulting biphasic mixture was stirred vigorously at rt for 16 h. The reaction mixture was then diluted with water and washed with EtOAc. The aqueous layer was acidified with 1N HCl and extracted with EtOAc. The combined organic layers were dried (MgSO$_4$), filtered and concentrated to yield Cap L-7 (0.65 g). $^1$H NMR (500 MHz, DMSO-d$_6$) δ ppm 12.58 (br. s., 1H), 3.31 (br. s., 4H), 1.58-1.50 (m, 2H), 1.48-1.40 (m, 4H), 1.34-1.28 (m, 2H), 1.15-1.10 (m, 2H).

Cap L-8

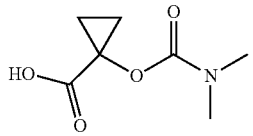

Cap L-8 was prepared by employing the procedures described for the synthesis of Cap L-7 starting from dimethylcarbamic chloride. $^1$H NMR (500 MHz, DMSO-d$_6$) ppm 12.48 (br. s., 1H), 2.82 (d, J=9.0 Hz, 6H), 1.34-1.29 (m, 2H), 1.15-1.10 (m, 2H).

Cap L-9

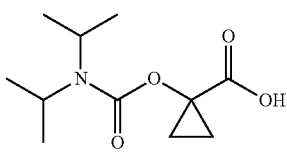 [SMILES: CC(C)N(C(=O)OC1(C(=O)O)CC1)C(C)C]

Cap L-9

Step a

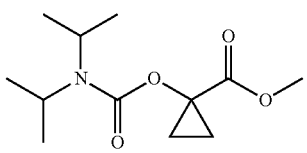 [SMILES: COC(=O)C1(OC(=O)N(C(C)C)C(C)C)CC1]

To a solution of methyl 1-hydroxycyclopropanecarboxylate (0.741 mL, 8.61 mmol) was added diisopropylcarbamic chloride (1.550 g, 9.47 mmol) and DIEA (2.256 mL, 12.92 mmol) in DCM (15 mL). The resulting solution was stirred at rt for 2 h, then diluted with DCM and the organic layer was washed with 1 N HCl, water and brine, dried (MgSO$_4$), filtered and concentrated. The residue was purified via Biotage (15% to 30% EtOAc/Hex; 25 g column) to yield Cap L-9 Step a (0.66 g).

A solution of LiOH (0.130 g, 5.43 mmol) in water (3 mL) was added to a solution of Cap L-9 Step a (0.66 g, 2.71 mmol) in THF (15 mL) and the resulting yellowish mixture was stirred at rt for 3 h, then diluted with EtOAc and water. The aqueous layer was acidified with 1 N HCl to pH ~2 and then extracted with EtOAc (3×). The combined organic layers were dried (MgSO$_4$), filtered and concentrated to yield 1 Cap L-9 (0.12 g). $^1$H NMR (400 MHz, DMSO-d$_6$) δ ppm 12.49 (br. s., 1H), 3.90 (br. s., 1H), 3.77 (br. s., 1H), 1.36-1.27 (m, 2H), 1.18-1.08 (m, 14H).

Cap L-10

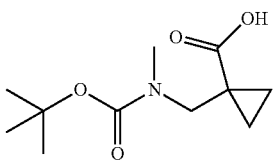 [SMILES: CN(CC1(C(=O)O)CC1)C(=O)OC(C)(C)C]

To a stirred and cold (ice-bath) solution of 1-(((tert-butoxycarbonyl)amino)methyl)cyclopropanecarboxylic acid (0.5 g, 2.323 mmol) in THF (10 mL) was added NaH (60% oil suspension) (0.465 g, 11.61 mmol) under N$_2$ and then MeI (1.16 mL, 18.58 mmol) and the mixture was stirred under N$_2$ at rt for 3 days. The mixture was diluted with water (20 mL) and washed with EtOAc (20 mL). The aqueous phase was acidified with citric acid and extracted with EtOAc. The organic extracts were washed with 1M Na$_2$S$_2$O$_3$, brine, dried (Na$_2$SO$_4$), filtered and concentrated to Cap L-10 (0.37 g). $^1$H NMR (400 MHz, DMF) ppm 11.84 (s, 1H), 3.02 (s, 2H), 2.34 (d, J=16.6 Hz, 3H), 0.92 (s, 9H), 0.63 (br. s., 2H), 0.39 (br. s., 2H).

Cap L-11

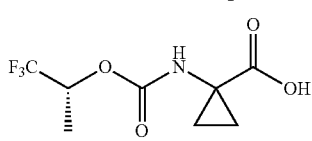

Cap L-11 was prepared by employing the procedures described for the synthesis of Cap L-6 starting from (R)-1,1,1-trifluoropropan-2-ol. $^1$H NMR (400 MHz, DMSO-$d_6$) δ ppm 12.49 (s, 1H), 8.25-7.89 (m, 1H), 5.26 (spt, J=6.7 Hz, 1H), 1.35-1.27 (m, 5H), 1.08-0.95 (m, 2H).

Cap L-12

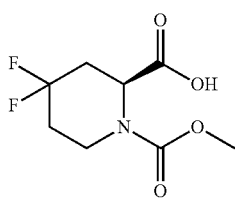

Cap L-12

Step a

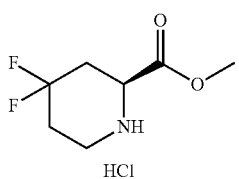

To a mixture of Cap L-2 Step a (0.3 g, 1.074 mmol) in DCM (10 mL) was added HCl (4 N in dioxane, 2 mL, 8.00 mmol). The resulting suspension was stirred at rt for 2 h. Volatiles were removed to yield Cap L-12 Step a (0.23 g). $^1$H NMR (400 MHz, DMSO-$d_6$) δ ppm 10.11 (br. s., 2H), 4.44 (dd, J=11.2, 3.9 Hz, 1H), 3.85-3.75 (m, 3H), 3.50-3.38 (m, 1H), 3.17-3.00 (m, 1H), 2.68-2.51 (m, 2H), 2.48-2.25 (m, 2H).

Cap L-12

Step b

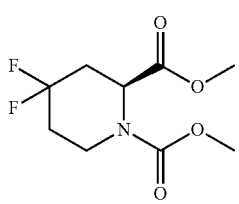 [SMILES: COC(=O)[C@@H]1CC(F)(F)CCN1C(=O)OC]

To a solution of Cap L-12 Step a (75 mg, 0.348 mmol) and DIEA (0.152 mL, 0.870 mmol) in DCM (2 mL) was added methyl chloroformate (0.030 mL, 0.383 mmol) and the resulting solution was stirred at rt for 16 h. The reaction mixture was diluted with EtOAc (10 mL) and washed with H$_2$O and brine, dried (MgSO$_4$), filtered and concentrated to yield Cap L-12 Step b (80 mg).

To a solution of Cap L-12 Step b (80 mg, 0.337 mmol) in THF (3 mL) was added a solution of LiOH (16.15 mg, 0.675 mmol) in water (0.5 mL) and the resulting mixture was stirred at rt for 3 h. The reaction mixture was diluted with H$_2$O (10 mL) and washed with Et$_2$O (15 mL). The aqueous layer was then acidified with 1 N HCl to pH ~2 and extracted with EtOAc. The combined organic layers were dried (MgSO$_4$), filtered and concentrated to give Cap L-12 (48 mg). $^1$H NMR (400 MHz, DMSO-$d_6$) δ ppm 13.09 (1H, br. s.), 4.75-4.93 (1H, m), 3.95-4.14 (1H, m), 3.55-3.70 (3H, m), 3.20-3.10 (1H, t, J=12.17 Hz), 2.52-2.36 (2H, d, J=12.55 Hz), 2.29 (1H, br. s.), 2.03 (1H, d, J=14.05 Hz).

Cap L-13

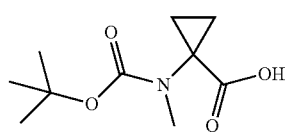

To a stirred and cold solution of 1-(tert-butoxycarbonylamino)cyclopropanecarboxylic acid (1.01 g, 5.02 mmol) in THF (20 mL) was added 60% sodium hydride (1.004 g, 25.10 mmol) and iodomethane (5.70 g, 40.2 mmol) and the mixture was stirred under N$_2$ at rt for 3 days. The mixture was diluted with water and EtOAc. The aqueous phase was acidified with citric acid and extracted with EtOAc. The organic extracts were washed with 1 M Na$_2$S$_2$O$_3$, brine, dried (Na$_2$SO$_4$), filtered and concentrated to yield Cap L-13 as white crystalline solid. $^1$H NMR (500 MHz, CDCl$_3$) δ ppm 2.79-2.94 (3H, m), 1.70 (2H, br. s.), 1.36-1.50 (9H, m), 1.11-1.34 (2H, m).

Cap L-14

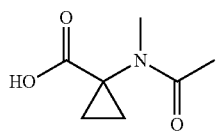

Cap L-14

Step a

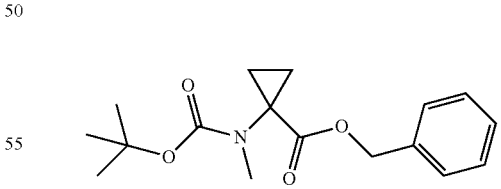

A reaction mixture of Cap L-13 (1.05 g, 4.88 mmol), K$_2$CO$_3$ (1.348 g, 9.76 mmol) and (bromomethyl)benzene (0.876 g, 5.12 mmol) in DMF (5 mL) was stirred at rt for 18 h. The mixture was partitioned between EtOAc and water, and the organic extract was washed with brine, dried (Na$_2$SO$_4$) and concentrated to yield Cap L-14 Step a (1.44 g). $^1$H NMR (500 MHz, CDCl$_3$) δ ppm 7.26-7.40 (5H, m), 5.05-5.23 (2H, m), 2.82-2.90 (3H, m), 1.49-1.82 (2H, m), 1.32-1.46 (9H, m), 1.06-1.28 (2H, m).

Cap L-14

Step b

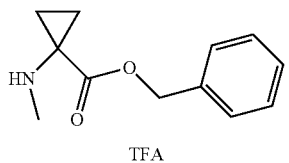

TFA

To a solution of Cap L-14 Step a (1.40 g, 4.58 mmol) in DCM (10 mL) was added TFA (1 mL) and the mixture was stirred at rt for 2 h, then concentrated to dryness to yield Cap L-14 Step b (1.96 g).

Cap L-14

Step c

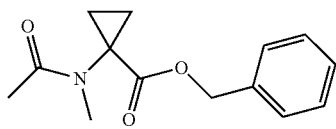 [SMILES: CC(=O)N(C)C1(C(=O)OCc2ccccc2)CC1]

To a cold and stirred solution of Cap L-14 Step b (0.93 g) and TEA (1.502 mL) in DCM (5 mL) was added acetyl chloride (0.508 g, 6.47 mmol) and the mixture was stirred at rt for 2.5 h. The mixture was diluted with DCM and washed with water, 1 N HCl, sat. NaHCO$_3$, brine, dried (Na$_2$SO$_4$) and concentrated to yield Cap L-14 Step c (0.89 g).

To a solution of benzyl Cap L-14 Step c (440 mg, 1.050 mmol) in EtOH (10 mL) and EtOAc (10.00 mL) was added 10% Pd—C (80 mg, 0.075 mmol) and the mixture was hydrogenated at 1 atm of H$_2$ for 72 h. The mixture was filtered and washed with EtOH. The combined filtrate was concentrated to dryness to yield Cap L-14 (277 mg) as off-white crystalline powder. $^1$H NMR (500 MHz, CDCl$_3$) δ ppm 10.29 (1H, br. s.), 2.95 (3H, s), 2.04-2.19 (3H, m), 1.85-1.93 (1H, m), 1.56-1.68 (1H, m), 1.33-1.43 (1H, m), 1.26-1.33 (1H, m).

Cap L-15

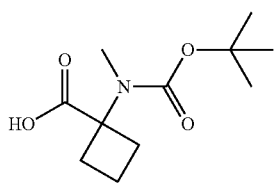

Cap L-15 was prepared from appropriate starting material by employing the procedures described for the synthesis of Cap L-13. $^1$H NMR (500 MHz, DMSO-d$_6$) δ ppm 12.50 (br. s., 1H), 2.83-2.65 (m, 3H), 2.42-2.20 (m, 4H), 2.02-1.89 (m, 1H), 1.71 (d, J=8.8 Hz, 1H), 1.42-1.23 (m, 9H).

Cap L-16

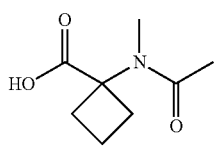

Cap L-16 was prepared appropriate starting material by employing the procedures described for the synthesis of Cap L-14. $^1$H NMR (500 MHz, CDCl$_3$) δ ppm 7.02 (1H, br. s.), 2.92 (3H, s), 2.55-2.67 (2H, m), 2.21-2.32 (2H, m), 2.07-2.10 (3H, m), 2.00-2.07 (1H, m), 1.67-1.82 (1H, m).

Cap L-17

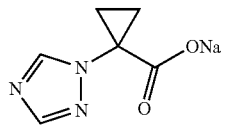

Cap L-17

Step a

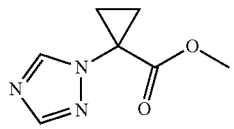

To a solution of methyl 2,4-dibromobutanoate (2.60 g, 10.00 mmol) in DMF (5 mL) was added sodium 1,2,4-triazol-1-ide (1.012 g, 10.00 mmol) under N$_2$ at 0° C. The reaction mixture was stirred at 0-5° C. for 30 min then stirred at rt for 18 h. The reaction mixture was concentrated and the residue was diluted with EtOAc, washed with water, brine, dried (Na$_2$SO$_4$) and concentrated. The crude oil was purified by silica gel chromatography to yield methyl Cap L-17 Step a (279 mg) as colorless oil. $^1$H NMR (500 MHz, CDCl$_3$) δ ppm 1.46-1.61 (2H, m, 3a,4a-CH$_2$), 1.71-1.82 (2H, m, 3b,4b-CH$_2$), 3.57 (3H, s, 7-OCH$_3$), 7.80 (1H, s, 6-CH), 8.13 (1H, s, 5-CH).

To a solution of Cap L-17 Step a (174 mg) in MeOH (2 mL) was added 1 N NaOH (1.041 mL) and the reaction mixture was stirred at rt for 2 h. The mixture was concentrated and the residue was treated with EtOH and concentrated to dryness to yield Cap L-17. $^1$H NMR (500 MHz, MEOD-d$_4$) δ ppm 8.54 (s, 1H), 7.92 (s, 1H), 1.77-1.67 (m, 2H), 1.47-1.36 (m, 2H).

Cap N-3

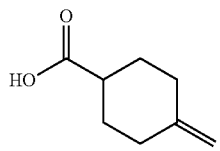

To a solution of ethyl 4-methylenecyclohexanecarboxylate (0.05 g) in THF (2 mL) and MeOH (0.5 mL) was added 1 N NaOH (1 mL). The resulting solution was stirred at rt for 16 hrs. The reaction mixture was diluted with 1 N HCl and EtOAc. The organic phase was washed with sat. NaCl and dried over anhydrous Na$_2$SO$_4$, filtered and dried to yield Cap N-3 as a yellow oil (0.042 g). $^1$H NMR (400 MHz, CDCl$_3$) δ ppm 4.62-4.73 (2H, m), 2.50 (1H, tt, J=11.01, 3.54 Hz), 2.30-2.41 (2H, m), 1.98-2.14 (4H, m), 1.54-1.69 (2H, m).

Cap N-4

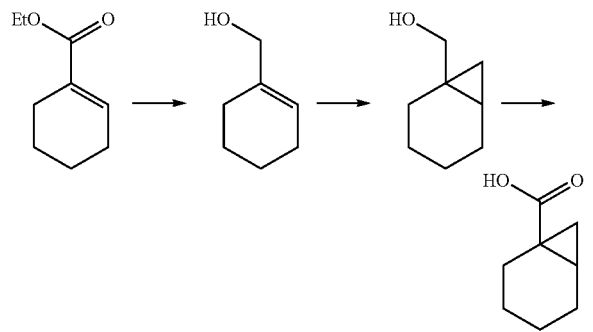

To ether (10 mL) was added LiAlH$_4$ (0.369 g, 9.73 mmol) under N$_2$, then ethyl cyclohex-1-enecarboxylate (1 g, 6.48 mmol) in ether (4 mL) was added dropwise under N$_2$ at 0° C. After the addition, the reaction mixture was stirred at 0° C. for 1 hr, then stirred at rt for 18 hr. The reaction mixture was carefully quenched by the addition of 6 mL of EtOAc and then 3 mL of water at 0° C. The solid was filtered and washed with DCM. The filtrate was concentrated to yield an oil. The crude product was charged to a 40 g silica gel cartridge which was eluted with a 20 min gradient of 0-80% EtOAc in hexane to yield cyclohex-1-en-1-ylmethanol (0.66 g) as a clear oil. $^1$H NMR (400 MHz, DMSO-d$_6$) ppm 5.57 (1H, tt, J=3.51, 1.63 Hz), 4.60 (1H, t, J=5.65 Hz), 3.70-3.81 (2H, m), 1.97 (2H, dtt, J=7.84, 3.86, 3.86, 1.88, 1.88 Hz), 1.87-1.94 (2H, m), 1.46-1.64 (4H, m).

To a solution of cyclohex-1-en-1-ylmethanol (0.6 g, 5.35 mmol) in DCE (5 mL) at 0° C., was added 1 N diethylzinc in hexane (8.56 mL), the reaction mixture was stirred for 10 min, then chloroiodomethane (1.242 ml, 17.12 mmol) was added. The reaction mixture was stirred at 0° C. for 1 h, and then stirred at rt for 16 hr. The reaction was diluted with EtOAc and 1 N HCl, the organic phase was washed with sat. NaCl, dried over anhydrous Na$_2$SO$_4$, filtered and concentrated to yield an oil. The crude product was charged to a 25 g silica gel cartridge which was eluted with a 20 min gradient of 0-40% EtOAc in hexane to afford bicyclo[4.1.0]heptan-1-ylmethanol (0.12 g). $^1$H NMR (400 MHz, CDCl$_3$) ppm 3.27-3.38 (2H, m), 1.81-1.92 (2H, m), 1.54-1.78 (2H, m), 1.11-1.37 (4H, m), 0.81 (1H, dddd, J=9.16, 7.22, 5.46, 1.51 Hz), 0.46 (1H, dd, J=9.29, 4.52 Hz), 0.24 (1H, t, J=5.02 Hz).

To a solution of bicyclo[4.1.0]heptan-1-ylmethanol (0.12 g) in acetonitrile (3 mL) and CCl$_4$ (3 mL) was added sodium periodate (0.610 g, 2.85 mmol) in water (4 mL), and then ruthenium(III) chloride (4.14 mg, 0.020 mmol) was added as solid. The reaction mixture was stirred vigorously at rt for 16 hr. The reaction was diluted with water and extracted with DCM (3×). The organic phase was filtered through diatomaceous earth (Celite®), and then washed with sat. NaCl, dried over anhydrous Na$_2$SO$_4$, filtered and concentrated to yield an oil. The residue was charged to a 12 g silica gel cartridge which was eluted with a 20 min gradient of 0-15% MeOH in methylene chloride to yield Cap N-4 (0.06 g). $^1$H NMR (400 MHz, CDCl$_3$) ppm 2.46-2.58 (1H, m), 1.86-2.00 (1H, m), 1.69-1.77 (1H, m), 1.59-1.69 (1H, m), 1.45 (1H, dd, J=9.79, 4.02 Hz), 1.24-1.37 (3H, m), 1.13-1.24 (1H, m), 0.86-0.94 (1H, m), 0.73 (1H, dd, J=7.03, 4.02 Hz).

Cap N-5

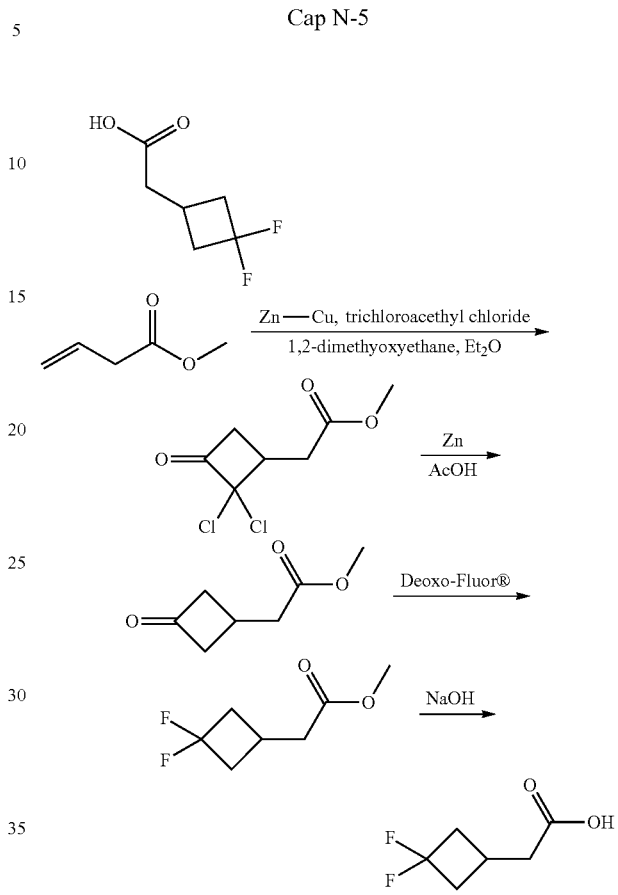

To a reaction mixture of methyl but-3-enoate (1.0 g, 10 mmol) and zinc-copper couple (2.0 g, 15.5 mmol) in DME (5 mL) and ether (30 mL) was added trichloroacetyl chloride (2.98 mL, 26.7 mmol) under N$_2$ at rt. The reaction mixture was stirred at rt for 2.5 days. The reaction mixture was filtrated through diatomaceous earth (Celite®) and washed with DCM. The filtrate was concentrated and purified by 80 g silica gel cartridge which was eluted with a 20 min gradient of 0-60% EtOAc in hexane to yield methyl 2-(2,2-dichloro-3-oxocyclobutyl)acetate (1.0 g). $^1$H NMR (400 MHz, CDCl$_3$) ppm 3.66-3.70 (3H, m), 3.42-3.55 (1H, m), 3.23-3.39 (1H, m), 3.05 (1H, dd, J=17.82, 8.78 Hz), 2.90 (1H, dd, J=16.94, 6.65 Hz), 2.67 (1H, dd, J=16.94, 8.16 Hz).

To a reaction mixture of methyl 2-(2,2-dichloro-3-oxocyclobutyl)acetate (0.6 g) in AcOH (5 mL) was added zinc powder (0.929 g). The reaction mixture was stirred at 100° C. for 15 hr.

The reaction mixture was cooled to rt, then diluted with EtOAc, carefully neutralized by the ice cold sat. NaHCO$_3$ at 0° C. The aqueous phase was extracted with EtOAc, and the combined organic phase was washed with sat. NaCl, dried over anhydrous Na$_2$SO$_4$, filtered and concentrated. The crude material was purified by 40 g silica gel cartridge which was eluted with a 20 min gradient of 0-90% EtOAc in hexane to yield methyl 2-(3-oxocyclobutyl)acetate (0.27 g). $^1$H NMR (400 MHz, CDCl$_3$) ppm 3.63 (3H, s), 3.12-3.27 (2H, m), 2.68-2.81 (3H, m), 2.56-2.64 (2H, m).

To a solution of methyl 2-(3-oxocyclobutyl)acetate (0.17 g) in CH₂Cl₂ (3.6 mL) was added Deoxo-Fluor® (0.485 mL, 2.63 mmol) and EtOH (0.021 mL). The resulting solution was stirred at rt for 16 hr.

The reaction mixture was diluted with sat. NaHCO₃ and DCM. The organic phase was washed with water, sat. NaCl and dried over anhydrous Na₂SO₄, filtered and dried to yield methyl 2-(3,3-difluorocyclobutyl)acetate (0.19 g). ¹H NMR (400 MHz, CDCl₃) ppm 3.69 (3H, s), 2.70-2.85 (2H, m), 2.47-2.58 (3H, m), 2.17-2.35 (2H, m).

To a solution of methyl 2-(3,3-difluorocyclobutyl)acetate (0.19 g) in THF (2 mL) and MeOH (0.5 mL) was added 10 N NaOH (1 mL). The resulting solution was stirred at rt for 13 hr. The reaction mixture was diluted with 1 N HCl and EtOAc. The organic phase was washed with sat. NaCl and dried over anhydrous Na₂SO₄, filtered and dried to yield Cap N-5 (0.17 g). ¹H NMR (400 MHz, CDCl₃) ppm 10.28 (1H, br. s.), 2.69-2.86 (2H, m), 2.56-2.60 (2H, m), 2.44-2.56 (1H, m), 2.19-2.35 (2H, m).

Cap N-6

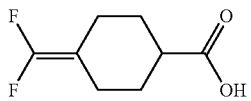

To a solution of ethyl 4-oxocyclohexanecarboxylate (0.47 mL, 2.94 mmol) and dibromodifluoromethane (0.54 mL, 5.88 mmol) in N,N-dimethylacetamide (3.5 mL) was added triphenylphosphine (1.54 g, 5.88 mmol) in N,N-dimethylacetamide (3.5 mL) dropwise under N₂ at 0° C. over 15 min. The reaction mixture was stirred at ambient temperature for 1 h, then zinc (0.384 g, 5.88 mmol) was added over 1 min. The mixture was stirred at rt for 20 min and then heated at 70° C. for 16 hr. The reaction was diluted with DCM, filtered through diatomaceous earth (Celite®) and the filtrate was washed with sat. NaHCO₃, water and sat. NaCl, dried over anhydrous Na₂SO₄, filtered and concentrated to an oil. The crude product was charged to a 40 g silica gel cartridge which was eluted with a 20 min gradient of 0-20% EtOAc in hexane to yield ethyl 4-(difluoromethylene)cyclohexanecarboxylate (0.015 g). ¹H NMR (400 MHz, CDCl₃) ppm 4.10-4.20 (2H, m), 2.35-2.52 (3H, m), 1.95-2.05 (2H, m), 1.79-1.93 (2H, m), 1.48-1.63 (3H, m), 1.25-1.31 (3H, m).

To a solution of ethyl 4-(difluoromethylene)cyclohexanecarboxylate (0.015 g) in THF (2 mL) and MeOH (0.5 mL) was added 1 N NaOH (0.735 mL). The resulting solution was stirred at rt for 16 hr. The reaction mixture was diluted with 1 N HCl and EtOAc. The organic phase was washed with sat. NaCl and dried over anhydrous Na₂SO₄, filtered and dried to yield Cap N-6 (0.013 g) as a white solid.

Cap N-7

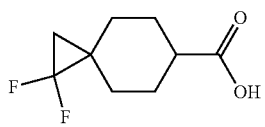 [SMILES: O=C(O)C1CCC2(CC1)CC2(F)F]

To a solution of ethyl 4-methylenecyclohexanecarboxylate (0.15 g, 0.892 mmol) in diglyme (3 mL) was added a solution of sodium 2-chloro-2,2-difluoroacetate (0.544 g, 3.57 mmol) in 5 ml of diglyme via syringe pump at 0.5 ml/h at 150° C. The reaction was cooled to rt, then diluted with DCM and washed with water, brine, dried over Na₂SO₄, filtered and concentrated. The residue was charged to a 40 g silica gel cartridge which was eluted with a 20 min gradient of 0-20% EtOAc in hexane to yield ethyl 1,1-difluorospiro[2.5]octane-6-carboxylate. ¹H NMR (400 MHz, CDCl₃) ppm 4.09-4.19 (2H, m), 2.29-2.45 (1H, m), 1.89-2.03 (2H, m), 1.55-1.72 (5H, m), 1.45-1.54 (1H, m), 1.31-1.39 (1H, m), 1.21-1.30 (3H, m), 0.84-0.94 (1H, m).

To a solution of ethyl 1,1-difluorospiro[2.5]octane-6-carboxylate (0.015 g, 0.069 mmol) in THF (2 mL) and MeOH (0.5 mL) was added 1 N NaOH (0.687 mL). The resulting solution was stirred at rt for 16 hrs. The reaction mixture was diluted with 1 N HCl and EtOAc. The organic phase was washed with sat. NaCl and dried over anhydrous Na₂SO₄, filtered and dried to yield Cap N-7 as a white solid (0.015 g).

Cap N-8

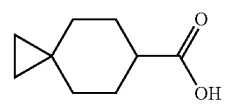

At 0° C., to a solution of ethyl 4-methylenecyclohexanecarboxylate (0.08 g) in DCE (1 mL) was added chloroiodomethane (0.110 mL, 1.522 mmol), followed by the addition of 1 N diethylzinc in hexane (0.761 mL, 0.761 mmol). The reaction was stirred at 0° C. for 1 hr, then stirred at rt for 18 hrs. The reaction mixture was diluted with EtOAc and 1 N HCl, the organic phase was washed with sat. NaCl, dried over anhydrous Na₂SO₄, filtered and concentrated. The crude product was charged to a 25 g silica gel cartridge which was eluted with a 20 min gradient of 0-6% EtOAc in hexane to yield ethyl spiro[2.5]octane-6-carboxylate. ¹H NMR (400 MHz, CDCl₃) δ ppm 4.08-4.18 (2H, m), 2.32 (1H, tq, J=11.01, 3.53 Hz), 1.85-1.93 (2H, m), 1.53-1.74 (4H, m), 1.28-1.35 (2H, m), 1.22-1.28 (3H, m), 0.28 (2H, ddd, J=8.53, 5.52, 1.51 Hz), 0.17-0.25 (2H, m).

To a solution of ethyl spiro[2.5]octane-6-carboxylate (0.03 g, 0.165 mmol) in THF (3 mL) and MeOH (1 mL) was added 1 N sodium hydroxide (0.165 mL). The reaction was stirred at rt for 18 hrs. The reaction mixture was diluted with 1 N HCl and EtOAc. The organic phase was washed with sat. NaCl and dried over anhydrous Na₂SO₄, filtered and dried to yield Cap N-8 (0.02 g).

Cap P-16

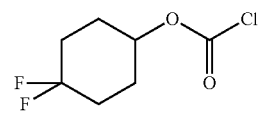

Neat 4,4-difluorocyclohexanol (136 mg, 0.999 mmol) was added to a cold (−20° C.) solution of phosgene (2.0 mL, 3.80 mmol) in toluene and the mixture was allowed to warm to rt and stirred overnight. Excess phosgene was removed carefully to afford Cap P-16 as a solution of toluene and used without further purification.

Cap P-17

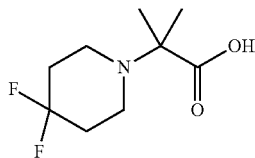

A stirred mixture of 4,4-difluoropiperidine/HCl (158 mg), benzyl 2-bromo-2-methylpropanoate (257 mg) and TEA (0.279 mL) in acetonitrile (1.5 mL) in a capped vial was heated at 85° C. overnight. The reaction mixture was evaporated to dryness and the residue was dissolved in ether, washed with satd. NaHCO$_3$, water, brine and dried (MgSO$_4$). The crude product was purified by silica gel FCC (0-1% MeOH in DCM) to afford benzyl 2-(4,4-difluoropiperidin-1-yl)-2-methylpropanoate as a viscous oil (33.7 mg). $^1$H NMR (400 MHz, CDCl$_3$) δ ppm 7.31-7.46 (5H, m), 5.18 (2H, s), 2.66 (4H, t, J=5.40 Hz), 1.86-2.08 (4H, m), 1.36 (6H, s). Benzyl 2-(4,4-difluoropiperidin-1-yl)-2-methylpropanoate was debenzylated by hydrogenation (10% Pd/C, EtOAc) to afford Cap P-16 as a beige solid. $^1$H NMR (400 MHz, CDCl$_3$) δ ppm 3.00 (4H, br. s.), 2.18-2.43 (4H, m), 1.45 (6H, s).

Cap P-18

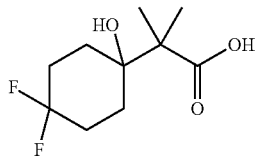

Neat BF$_3$.OEt$_2$ (1.014 mL, 8.00 mmol) was added dropwise to a cold (−78° C.) stirred solution of 4,4-difluorocyclohexanone (0.671 g, 5 mmol) and ((1-methoxy-2-methylprop-1-en-1-yl)oxy)trimethylsilane (1.937 g, 10.00 mmol) in DCM (10 mL) and the mixture was gradually allowed to warm to rt and stirred at rt for 5 h. The reaction mixture was quenched with sat. NaHCO$_3$ (10 mL), and diluted with DCM (20 mL). The organic layer was separated and washed with 0.25M aq. HF, water, brine and dried (MgSO$_4$). Evaporation of solvents afforded a clear oil (1.34 g) which was purified by silica gel FCC (0-2% EtOAc in DCM) to afford methyl 2-(4,4-difluoro-1-hydroxycyclohexyl)-2-methylpropanoate as a colorless oil (1.14 g).

A stirred solution of methyl 2-(4,4-difluoro-1-hydroxycyclohexyl)-2-methylpropanoate (1.137 g, 4.81 mmol) in THF (4 mL), MeOH (3 mL) and water (3 mL) was heated at 60° C. overnight. MeOH and THF were evaporated and the aqueous residue was acidified and extracted with EtOAc, washed with water, brine and dried (MgSO$_4$). Evaporation of solvent afforded Cap P-18 as a white solid (0.997 g). $^1$H NMR (500 MHz, CDCl$_3$) δ ppm 2.12-2.30 (2H, m), 1.92-2.03 (2H, m), 1.78-1.87 (2H, m), 1.66-1.75 (2H, m), 1.32 (6H, s).

Cap P-19

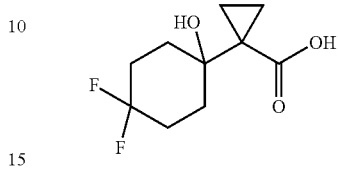

A solution of LDA prepared from diisopropylamine (304 mg, 3.00 mmol) and butyllithium (1.20 mL, 3.00 mmol) in THF was added to a cold (−78° C.) solution of tert-butyl cyclopropanecarboxylate (427 mg, 3.00 mmol) in THF (2 mL), and the mixture was stirred at −78° C. for 1 h. A solution of 4,4-difluorocyclohexanone (268 mg, 2 mmol) in THF (0.5 mL) was added dropwise and the mixture was stirred at −78° C. for 2 h and allowed to warm to rt overnight. The crude product was purified by silica gel FCC (DCM) to afford tert-butyl 1-(4,4-difluoro-1-hydroxycyclohexyl)cyclopropanecarboxylate as a clear oil (0.273 g). $^1$H NMR (500 MHz, CDCl$_3$) δ ppm 2.12-2.30 (2H, m), 1.79-1.96 (4H, m), 1.48-1.53 (2H, m), 1.41-1.47 (9H, m), 1.21-1.34 (1H, m), 1.11-1.17 (2H, m), 0.90-0.97 (2H, m).

Neat TFA (0.446 mL, 5.79 mmol) was added to a solution of tert-butyl 1-(4,4-difluoro-1-hydroxycyclohexyl)cyclopropanecarboxylate (80 mg, 0.290 mmol) in DCM (1 mL) and the mixture was stirred at rt for 1-2 h. The reaction was evaporated to dryness to afford Cap P-19 (64 mg). $^1$H NMR (500 MHz, CDCl$_3$) δ ppm 2.09-2.29 (2H, m), 1.84-2.00 (4H, m), 1.57 (2H, td, J=13.85, 3.43 Hz), 1.34-1.40 (2H, m), 1.10-1.15 (2H, m).

Cap P-20

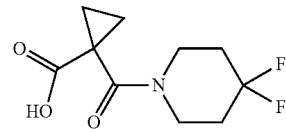 [SMILES: O=C(O)C1(C(=O)N2CCC(F)(F)CC2)CC1]

To solution of 1-(methoxycarbonyl)cyclopropanecarboxylic acid (144 mg, 1 mmol) was added 2M oxalyl dichloride (1.0 mL, 2.0 mmol) in DCM followed by a few drops of DMF. The reaction mixture was stirred until gas evolution ceased (~1 h). Excess oxalyl chloride and DCM were evaporated to afford methyl 1-(chlorocarbonyl)cyclopropanecarboxylate. To a solution of methyl 1-(chlorocarbonyl)cyclopropanecarboxylate in DCM (2 mL) was added 4,4-difluoropiperidine/HCl (173 mg) and DIPEA (0.384 mL) at 0° C., and then the reaction mixture was allowed to warm to rt. The reaction mixture was purified by silica gel FCC to yield Cap P-20. $^1$H NMR (500 MHz, CDCl$_3$) δ ppm 3.77-3.82 (2H, m), 3.75 (3H, s), 3.64 (2H, t, J=5.42 Hz), 1.96-2.09 (4H, m), 1.51-1.57 (2H, m), 1.33-1.39 (2H, m). Hydrolysis of methyl 1-(4,4-difluoropiperidine-1-carbonyl)cyclopropanecarboxylate (by 2 mL of 1N NaOH, 1 mL of THF and 1 mL of MeOH) to afford Cap P-20 as a white solid (194 mg). $^1$H NMR (500 MHz, CDCl$_3$) δ ppm 3.78-3.73 (4H, m), 1.97-2.10 (4H, m), 1.59-1.65 (2H, m), 1.42-1.48 (2H, m).

Cap P-21

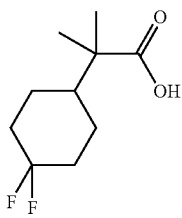

To a solution of 2-methyl-2-(4-oxocyclohexyl)propanoic acid (0.184 g, 1 mmol) and DIPEA (0.192 mL, 1.100 mmol) in acetonitrile (1 mL) and CHCl$_3$ (1 mL) was added benzyl bromide (0.131 mL, 1.100 mmol) and the mixture was stirred at rt overnight. The reaction mixture was evaporated to dryness and purified by silica gel FCC (0-5% EtOAC in DCM) to afford benzyl 2-methyl-2-(4-oxocyclohexyl)propanoate as a clear oil (184 mg), which was dissolved in CH$_2$Cl$_2$ (2 mL) was treated with Deoxo-Fluor® (0.442 mL, 2.40 mmol), followed by the addition of EtOH (5.8 mL). The resulting yellowish solution was stirred at rt overnight. The reaction mixture was diluted with sat. NaHCO$_3$ and EtOAc. The organic phase was separated and washed with water, sat. NaCl, dried over anhydrous MgSO$_4$, filtered and dried to yield a yellow oil. The crude product was purified by silica gel FCC (1:1 hexane-DCM) to afford benzyl 2-(4,4-difluorocyclohexyl)-2-methylpropanoate as a clear oil (143 mg) which was hydrogenated (0.053 g of 10% Pd—C, EtOAc) under balloon pressure for 4 h. The suspension was filtered and evaporated to dryness to afford Cap P-21. $^1$H NMR (500 MHz, CDCl$_3$) δ ppm 2.08-2.23 (2H, m), 1.64-1.85 (5H, m), 1.36-1.54 (2H, m), 1.12-1.29 (6H, m).

Cap P-22

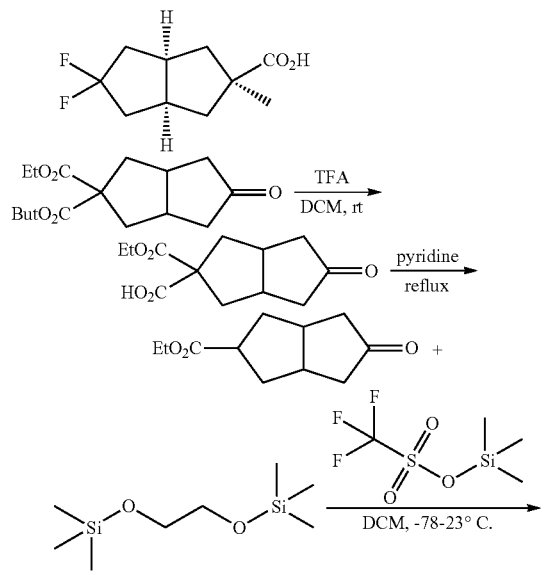

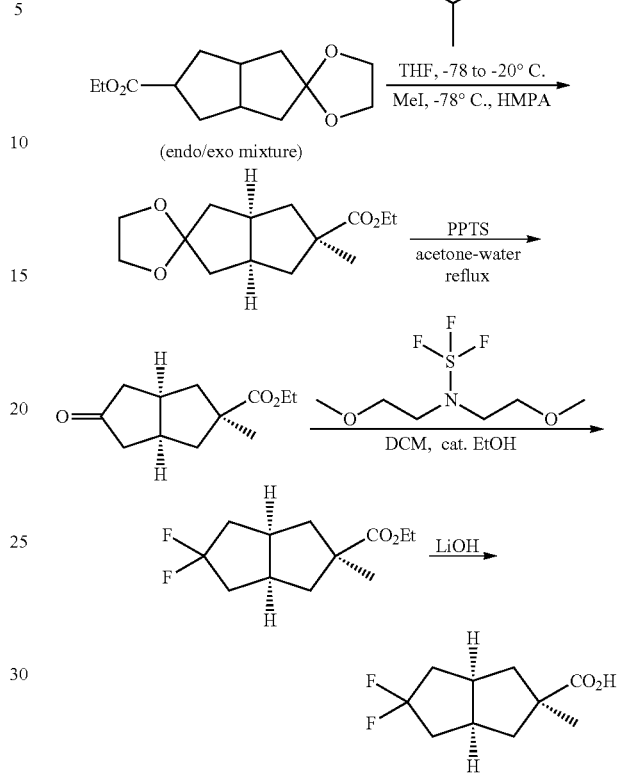

To a solution of 2-tert-butyl 2-ethyl 5-oxohexahydropentalene-2,2(1H)-dicarboxylate (0.8 g, 2.70 mmol) in DCM (4 mL) was added TFA (2.080 mL) and the reaction mixture was stirred at rt for 4 h. The reaction mixture was evaporated to dryness and the residue was dissolved in pyridine (5 mL) and heated to reflux for 4 h until decarboxylation was complete. Pyridine was evaporated and the residue was purified by silica gel chromatography (10% EtOAC in DCM) to afford ethyl 5-oxooctahydropentalene-2-carboxylate (a mixture of endo/exo isomers) as a clear oil. $^1$H NMR (500 MHz, CDCl$_3$) δ ppm 4.10-4.18 (2H, m), 2.85-3.02 (2H, m), 2.69-2.80 (1H, m), 2.44-2.56 (2H, m), 2.20-2.36 (2H, m), 2.10-2.20 (1H, m), 2.04 (1H, dd, J=19.45, 4.65 Hz), 1.66-1.80 (2H, m), 1.22-1.31 (3H, m).

To a solution of ethyl 5-oxooctahydropentalene-2-carboxylate (210 mg) in DCM (5 mL) cooled to −78° C. were added slowly trimethylsilyl trifluoromethanesulfonate (11.89 mg, 0.054 mmol) and 2,2,7,7-tetramethyl-3,6-dioxa-2,7-disilaoctane (287 mg, 1.391 mmol) under nitrogen. After stirring at −78° C. for 30 min, the reaction mixture was warmed to rt and stirred at rt for 16 h. The reaction was quenched with anhydrous pyridine at −78° C. followed by sat. NaHCO$_3$, and then extracted with EtOAc. The combined organic layers were dried over anhydrous MgSO$_4$ and concentrated in vacuo. The residue was purified by flash chromatography to afford ethyl hexahydro-1'H-spiro[[1,3]dioxolane-2,2'-pentalene]-5'-carboxylate (a mixture of endo/exo isomers) as a clear oil.

At −78° C., to a solution of LDA prepared from diisopropylamine (0.176 mL, 1.248 mmol) and butyllithium (0.499 mL, 1.248 mmol), HMPA (0.217 mL, 1.248 mmol) was added a solution of ethyl hexahydro-1'H-spiro[[1,3]dioxolane-2,2'-pentalene]-5'-carboxylate (200 mg, 0.832 mmol) in THF (1 ml). The reaction mixture was stirred at −78° C. for 2 h, then a solution of iodomethane (0.104 mL, 1.665 mmol) in THF (1 mL) was added. The reaction mixture was stirred at −78° C. for 2 h and then allowed to warm to 0° C. over 3 h. The reaction mixture was quenched with sat. NH₄Cl and extracted with ether. The combined organic layers were dried and concentrated in vacuo. The residue was purified by silica gel flash chromatography (EtOAc/hexane). The major isomer product isolated was (3a'R,5's,6a'S)-ethyl 5'-methylhexahydro-1'H-spiro[[1,3]dioxolane-2,2'-pentalene]-5'-carboxylate (89 mg). ¹H NMR (500 MHz, CDCl₃) δ ppm 4.10-4.18 (2H, m), 3.86-3.95 (4H, m), 2.62-2.74 (2H, m), 1.97-2.05 (2H, m), 1.83-1.96 (4H, m), 1.60-1.69 (2H, m), 1.25-1.29 (3H, m), 1.21 (3H, s).

A stirred solution of (3a'R,5's,6a'S)-ethyl 5'-methylhexahydro-1'H-spiro[[1,3]dioxolane-2,2'-pentalene]-5'-carboxylate (89 mg, 0.350 mmol) and PPTS (22 mg, 0.088 mmol) in acetone (3 mL) and water (1 mL) was heated to reflux for 4 h. Acetone was evaporated and the residue was diluted with sat. NaHCO₃ and extracted with EtOAc. The organic phase was washed with sat. NaCl and dried over MgSO₄, filtered and concentrated. The residue was purified by silica gel flash chromatography (EtOAc/hexane) to afford (2s,3aR,6aS)-ethyl 2-methyl-5-oxooctahydropentalene-2-carboxylate as a clear oil. ¹H NMR (500 MHz, CDCl₃) δ ppm 4.13 (2H, q, J=7.12 Hz), 2.82-2.93 (2H, m), 2.44-2.54 (2H, m), 2.11-2.19 (2H, m), 1.90-2.02 (4H, m), 1.28-1.31 (3H, m), 1.23-1.28 (3H, m).

To a cold (0° C.) solution of (2s,3aR,6aS)-ethyl 2-methyl-5-oxooctahydropentalene-2-carboxylate (63 mg, 0.300 mmol) in DCM (2 mL) was added Deoxo-Fluor® (133 mL) followed by addition of EtOH (3 mL). The resulting yellowish solution was stirred at rt for 18 h. The reaction was quenched with sat. NaHCO₃ and extracted with DCM. The combined organic layers were washed with water, brine and dried (MgSO₄), filtered and evaporated to give a yellow-orange oil which was purified by silica gel flash chromatography (EtOAc/hexane) to afford (2s,3aR,6aS)-ethyl 5,5-difluoro-2-methyloctahydropentalene-2-carboxylate (58 mg). ¹H NMR (500 MHz, CDCl₃) δ ppm 4.11-4.20 (2H, m), 2.71-2.84 (2H, m), 2.28 (2H, qd, J=13.58, 9.31 Hz), 1.86-1.99 (6H, m), 1.26-1.31 (3H, m), 1.17-1.25 (3H, m).

To a solution of (2s,3aR,6aS)-ethyl 5,5-difluoro-2-methyloctahydropentalene-2-carboxylate in THF (1 mL) and MeOH (1 mL) was added a solution LiOH (25.1 mg) in water (0.5 mL). The mixture was stirred at rt for 2 h. Standard acidic workup and isolation by extraction afforded Cap P-22 as a off-white solid (42 mg). ¹H NMR (500 MHz, CDCl₃) δ ppm 2.72-2.85 (2H, m), 2.21-2.36 (2H, m), 1.88-2.01 (6H, m), 1.25-1.27 (3H, m).

Cap P-23

A stirred suspension of benzyl 2-bromo-2-methylpropanoate (0.748 g, 2.91 mmol), tetrahydro-2H-pyran-2-one (0.260 g, 2.60 mmol) and indium (0.341 g, 2.97 mmol) in THF (3 mL) was sonicated for 6 h. The reaction was quenched with sat. NaHCO₃ and extracted with ether, then concentrated. The residue was purified by silica gel flash chromatography to afford benzyl 2-(2-hydroxytetrahydro-2H-pyran-2-yl)-2-methylpropanoate. ¹H NMR (500 MHz, CDCl₃) δ ppm 7.30-7.43 (5H, m), 5.18 (2H, s), 3.51-3.61 (2H, m), 2.41 (2H, t, J=7.10 Hz), 1.56-1.66 (2H, m), 1.35-1.47 (8H, m). Benzyl 2-(2-hydroxytetrahydro-2H-pyran-2-yl)-2-methylpropanoate was dissolved in triethylsilane (0.415 mL, 2.60 mmol) and treated with TFA (0.200 mL, 2.60 mmol) and the reaction mixture was stirred at rt for 16 h, then evaporated to dryness to yield benzyl 2-methyl-2-(tetrahydro-2H-pyran-2-yl)propanoate. ¹H NMR (500 MHz, CDCl₃) δ ppm 7.30-7.41 (5H, m), 5.22 (1H, d, J=12.66 Hz), 5.10 (1H, d, J=12.51 Hz), 3.91-4.01 (1H, m), 3.53 (1H, dd, J=11.22, 1.75 Hz), 3.39 (1H, td, J=11.56, 2.37 Hz), 1.82-1.92 (1H, m), 1.44-1.59 (4H, m), 1.30-1.41 (1H, m), 1.19-1.25 (3H, m), 1.11-1.19 (3H, m). A stirred suspension of 10% Pd—C (16.63 mg) and benzyl 2-methyl-2-(tetrahydro-2H-pyran-2-yl)propanoate (82 mg, 0.313 mmol) in EtOAc (5 mL) was stirred under H₂ for 6 h, and then filtered and concentrated to yield Cap P-23 (54 mg). ¹H NMR (500 MHz, CDCl₃) δ ppm 4.09-4.19 (1H, m), 3.48-3.57 (1H, m), 3.33-3.42 (1H, m), 1.88-1.97 (1H, m), 1.71 (1H, d, J=13.12 Hz), 1.47-1.65 (3H, m), 1.29-1.40 (1H, m), 1.23-1.27 (3H, m), 1.14-1.20 (3H, m).

Cap P-24

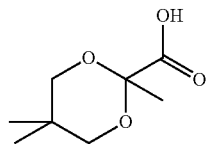

To a solution of ethyl 2-oxopropanoate (0.581 g, 5 mmol) and 2,2-dimethylpropane-1,3-diol (0.521 g, 5.00 mmol) in acetonitrile (5 mL) cooled to 0° C. was added BF₃.OEt₂ (0.063 mL, 0.500 mmol), and the mixture was allowed to warm to rt and stirred at rt for 18 h. The reaction mixture was quenched with sat. NaHCO₃ (5 mL) and diluted with ether/hexane (1:1, 20 mL). The organic layer was washed with water, brine and dried (MgSO₄). The solvent was evaporated to yield ethyl 2,5,5-trimethyl-1,3-dioxane-2-carboxylate as a clear oil (681 mg). ¹H NMR (500 MHz, CDCl₃) δ ppm 4.31 (2H, q, J=7.07 Hz), 3.48-3.58 (4H, m), 1.55 (3H, s), 1.35 (3H, t, J=7.17 Hz), 1.22 (3H, s), 0.69-0.75 (3H, m). Ethyl 2,5,5-trimethyl-1,3-dioxane-2-carboxylate (90 mg) was saponified (1 N NaOH, MeOH-THF) to afford Cap P-24 (69 mg). ¹H NMR (500 MHz, CDCl₃) δ ppm 3.53-3.64 (4H, m), 1.63 (3H, s), 1.23 (3H, s), 0.78 (3H, s).

Cap P-25

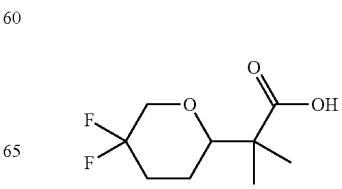

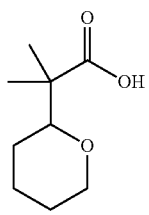

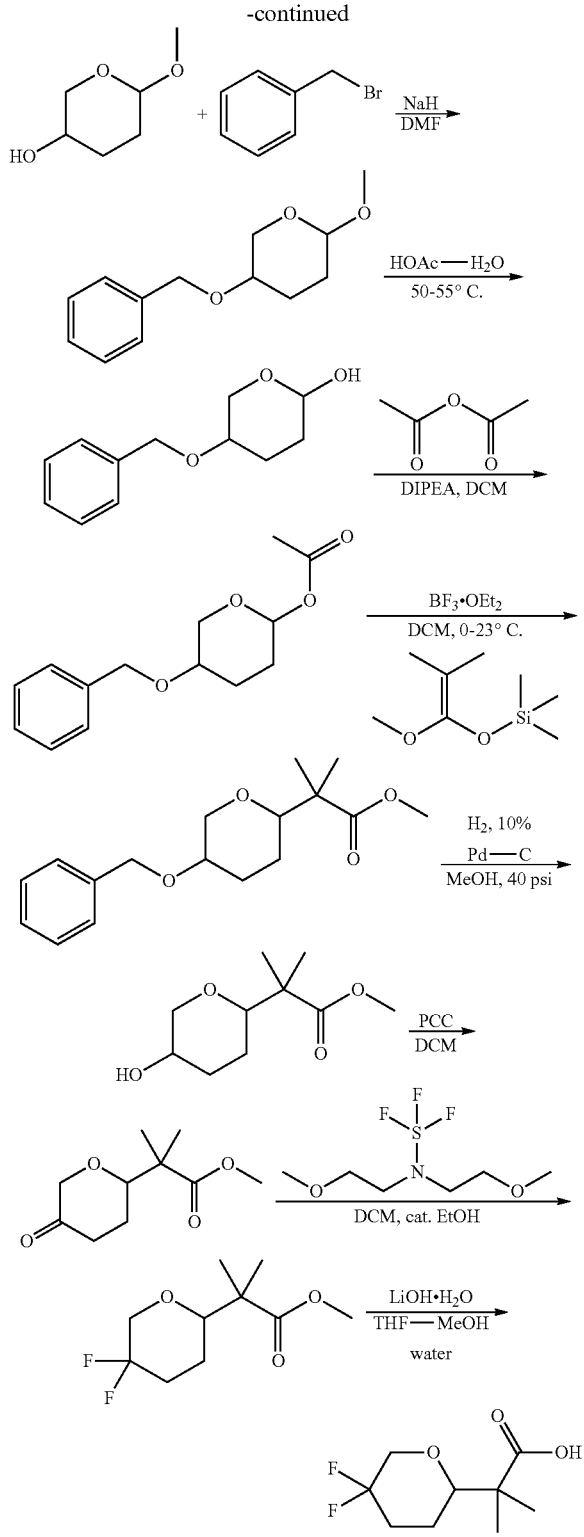

hexanes) to afford 5-(benzyloxy)-2-methoxytetrahydro-2H-pyran. $^1$H NMR (400 MHz, CDCl$_3$) δ ppm 7.29-7.41 (5H, m), 4.53-4.64 (3H, m), 3.90 (1H, dd, J=12.05, 2.51 Hz), 3.56-3.65 (1H, m), 3.46-3.53 (1H, m), 3.43 (3H, s), 1.97-2.14 (2H, m), 1.69-1.81 (1H, m), 1.48-1.60 (1H, m).

A solution of 5-(benzyloxy)-2-methoxytetrahydro-2H-pyran (317 mg, 1.426 mmol) in AcOH (10 mL) and water (5 mL) was heated at 55° C. for 12 h and then evaporated to dryness to afford 5-benzyloxyoxytetrahydropyran-2-ol (300 mg). 5-Benzyloxyoxytetrahydropyran-2-ol was dissolved in DCM (3 mL) and treated with DIPEA (0.374 mL, 2.139 mmol) and acetic anhydride (218 mg, 2.139 mmol). The mixture was stirred at rt for 4 h, quenched with sat. NaHCO$_3$ and extracted with DCM. The organic phase was washed with water, brine, dried (MgSO$_4$) and concentrated to yield 5-(benzyloxy)tetrahydro-2H-pyran-2-yl acetate as a clear oil (281 mg).

To a solution of 5-(benzyloxy)tetrahydro-2H-pyran-2-yl acetate (281 mg, 1.123 mmol) and ((1-methoxy-2-methyl-prop-1-en-1-yl)oxy)trimethylsilane (783 mg, 4.49 mmol) in DCM (5 mL) at −78° C. was added BF$_3$.OEt$_2$ (0.228 mL, 1.796 mmol). The reaction mixture was gradually allowed to warm to rt and stirred at rt for 18 h. The reaction mixture was quenched with sat. NaHCO$_3$ (5 mL) and diluted with DCM (20 mL). The organic layer was separated, washed with water, brine, dried (MgSO$_4$) and concentrated. The crude product was purified by silica gel FCC (10-20% EtOAc in hexanes) to afford methyl 2-(5-(benzyloxy)tetrahydro-2H-pyran-2-yl)-2-methylpropanoate as a colorless oil (253 mg). To a solution of methyl 2-(5-(benzyloxy)tetrahydro-2H-pyran-2-yl)-2-methylpropanoate (250 mg) in MeOH (20 mL) was added 10% Pd—C (59.7 mg) and the reaction mixture was hydrogenated at 40 psi overnight. The suspension was filtered and the filtrate was evaporated to dryness to afford methyl 2-(5-hydroxytetrahydro-2H-pyran-2-yl)-2-methylpropanoate as a clear oil (188 mg).

To a stirred solution of methyl 2-(5-hydroxytetrahydro-2H-pyran-2-yl)-2-methylpropanoate (187 mg, 0.925 mmol) in DCM (5 mL) containing 4 Å molecular seives (~250 mg) was added PCC (259 mg, 1.202 mmol). The reaction mixture was stirred at rt for 3 h, then loaded onto a silica gel column and eluted with 10-20% EtOAc in DCM to afford methyl 2-methyl-2-(5-oxotetrahydro-2H-pyran-2-yl)propanoate as a clear oil (105 mg). $^1$H NMR (400 MHz, CDCl$_3$) δ ppm 4.18 (1H, dd, J=16.56, 1.76 Hz), 3.87-4.01 (2H, m), 3.73 (3H, s), 2.59-2.69 (1H, m), 2.48 (1H, dt, J=17.13, 8.63 Hz), 1.93-2.04 (2H, m), 1.27 (3H, s), 1.15-1.24 (3H, m).

To a cold solution of methyl 2-methyl-2-(5-oxotetrahydro-2H-pyran-2-yl)propanoate (98.5 mg, 0.492 mmol) in DCM (2 mL) was added Deoxo-Fluor® (261 mg, 1.181 mmol) and EtOH (4.31 μl, 0.074 mmol). The reaction mixture was allowed to warm to rt and stirred overnight. The reaction was quenched with sat. NaHCO$_3$ and extracted with DCM (2×). The combined organic layers were washed with water, brine and dried (MgSO$_4$), filtered and concentrated. The residue was purified by silica gel chromatography to afford methyl 2-(5,5-difluorotetrahydro-2H-pyran-2-yl)-2-methylpropanoate as a colorless oil (58 mg). $^1$H NMR (500 MHz, CDCl$_3$) δ ppm 3.92-4.01 (1H, m), 3.69-3.72 (3H, m), 3.61 (1H, dd, J=10.30, 2.21 Hz), 3.44-3.56 (1H, m), 2.21-2.32 (1H, m), 1.83-2.02 (1H, m), 1.65-1.78 (2H, m), 1.22-1.26 (3H, m), 1.14-1.19 (3H, m). Methyl 2-(5,5-difluorotetrahydro-2H-pyran-2-yl)-2-methylpropanoate was saponified (LiOH.H$_2$O, MeOH/THF/H$_2$O) to afford Cap P-25 (48 mg). $^1$H NMR (500

At 0° C. to a solution of 6-methoxytetrahydro-2H-pyran-3-ol (222 mg, 1.680 mmol) in DMF (2 mL) was added 60% NaH (81 mg, 2.02 mmol) and the mixture was allowed to warm to rt and stirred at rt for 30 min. A solution of (bromomethyl)benzene (345 mg, 2.016 mmol) in DMF (1 ml) was added and the mixture was stirred at rt for 18 h. The reaction mixture was diluted with ether and quenched with water. The crude product was purified by silica gel FCC (20% EtOAc in MHz, CDCl₃) δ ppm 3.94-4.07 (1H, m), 3.44-3.67 (2H, m), 2.21-2.35 (1H, m), 1.83-2.01 (1H, m), 1.71-1.83 (2H, m), 1.17-1.27 (6H, m).

Cap Y-8a and Y-8b

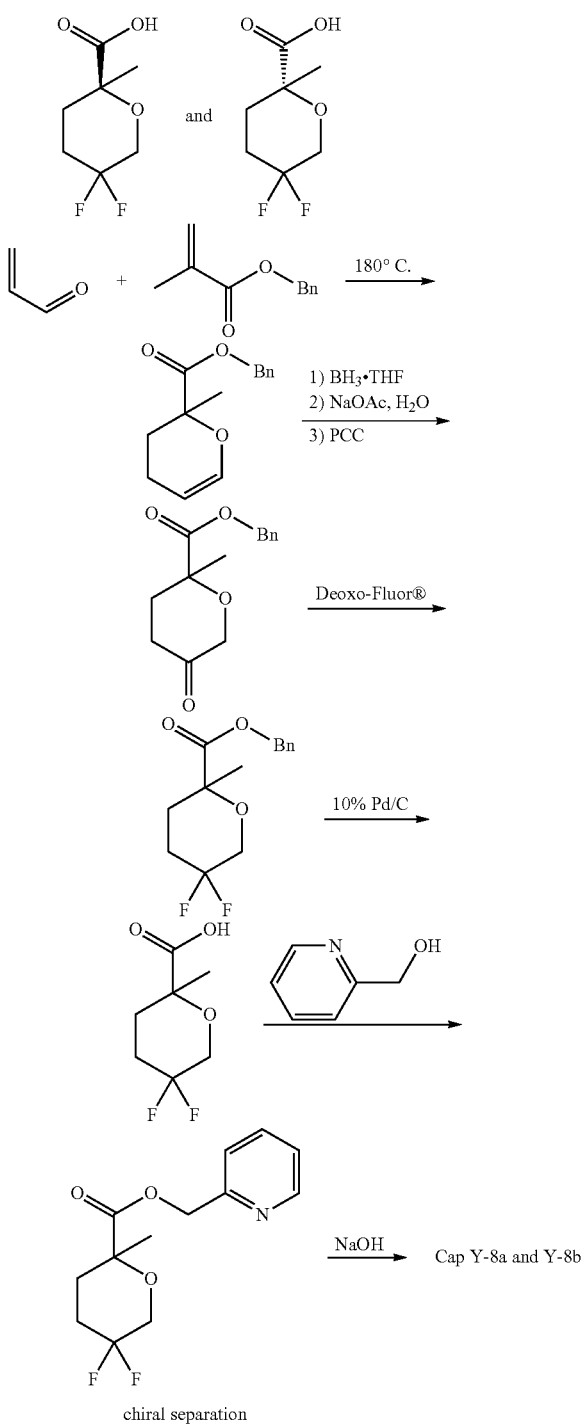

chiral separation

A reaction mixture of hydroquinone (150 mg), acrylaldehyde (3.225 mL), and benzyl 2-methyl-3,4-dihydro-2H-pyran-2-carboxylate (2.5 g) in a sealed tube was heated at 180° C. for 18 h. The reaction mixture was cooled down and directly purified on silica gel column to afford benzyl 2-methyl-3,4-dihydro-2H-pyran-2-carboxylate (1 g) (Thomson 80 g column EtOAc/hexane: 0 to 10%). ¹H NMR (400 MHz, CDCl₃) ppm 7.30-7.44 (5H, m), 6.41 (1H, dt, J=6.27, 1.88 Hz), 5.12-5.27 (2H, m), 4.67-4.81 (1H, m), 2.27 (1H, dt, J=13.11, 4.49 Hz), 1.87-2.03 (2H, m), 1.72-1.83 (1H, m), 1.51 (3H, s).

To a solution of benzyl 2-methyl-3,4-dihydro-2H-pyran-2-carboxylate (1.0 g, 3.44 mmol) in THF (10 mL) was added BH₃·THF (2.07 mL, 2.07 mmol) dropwise in an ice/acetone bath in 10 min. The reaction mixture was stirred in the bath for 4 h. The reaction mixture was quenched by the addition of a solution of sodium acetate (0.283 g, 3.44 mmol) in water (3 mL). After being stirred for 10 min, H₂O₂ (0.3 mL, 4.89 mmol) was added. The reaction mixture was stirred at rt for 2 h. The reaction mixture was diluted with EtOAc and washed with sat. NH₄Cl, brine, and dried (MgSO₄). The solvent was removed in vacuum to afford benzyl 5-hydroxy-2-methyltetrahydro-2H-pyran-2-carboxylate.

To a mixture of benzyl 5-hydroxy-2-methyltetrahydro-2H-pyran-2-carboxylate (1.1 g, 3.52 mmol) and molecular sieves (4 Å, 2 g, powdered) in DCM (20 mL) was added PCC (1.137 g, 5.27 mmol) in two portions at 0° C. The reaction mixture was stirred at rt for 17 h. The reaction mixture was directly loaded and purified on a 40 g silica gel cartridge (EtOAc/Hexane: 0 to 40%) to yield benzyl 2-methyl-5-oxotetrahydro-2H-pyran-2-carboxylate (0.47 g). ¹H NMR (400 MHz, CDCl₃) ppm 7.45-7.31 (m, 5H), 5.25 (s, 2H), 4.27 (d, J=17.6 Hz, 1H), 4.07 (d, J=17.3 Hz, 1H), 2.59-2.34 (m, 3H), 2.14-2.04 (m, 1H), 1.56 (s, 3H).

To a solution of benzyl 2-methyl-5-oxotetrahydro-2H-pyran-2-carboxylate (0.47 g, 1.893 mmol) in CH₂Cl₂ (5 mL) was added Deoxo-Fluor® (0.838 mL, 4.55 mmol), followed by the addition of EtOH (5 µL). The resulting yellowish solution was stirred at rt for 18 hrs, and then partitioned between sat. NaHCO₃ and EtOAc. The organic phase was washed with sat. NaHCO₃, water, sat. NaCl and dried over anhydrous MgSO₄, filtered and dried to yield a yellow oil. The crude product contained vinyl byproduct as judged by ¹HNMR. The mixture was dissolved in acetone (2 mL), THF (8 mL), and then water (2 mL), NMO (0.444 g, 3.79 mmol), osmium tetroxide (0.238 ml, 0.019 mmol) were added. The ice bath was removed and the reaction mixture was stirred at rt for 40 h, then diluted with EtOAc and washed with water, NH₄Cl, brine, and dried (MgSO₄). The crude material was purified on a 12 g silica gel column (EtOAc/hexane: 0 to 20%) to afford benzyl 5,5-difluoro-2-methyltetrahydro-2H-pyran-2-carboxylate. ¹H NMR (400 MHz, CDCl₃) ppm 7.35-7.43 (5H, m), 5.25 (2H, s), 3.68-3.90 (2H, m), 2.36-2.45 (1H, m), 2.07-2.18 (1H, m), 1.72-1.89 (2H, m), 1.43-1.51 (3H, m).

To a suspension of benzyl 5,5-difluoro-2-methyltetrahydro-2H-pyran-2-carboxylate (0.22 g, 0.814 mmol) in MeOH (5 mL) was added 10% Pd/C (0.12 g). The reaction mixture was stirred under H₂ for 1 h. The reaction was filtered and concentrated to dryness to yield 5,5-difluoro-2-methyltetrahydro-2H-pyran-2-carboxylic acid (100 mg). ¹H NMR (400 MHz, CDCl₃) δ ppm 3.79-3.91 (2H, m), 2.29-2.42 (1H, m), 2.12-2.26 (1H, m), 1.85-2.08 (2H, m), 1.54 (3H, s).

A mixture of pyridin-2-ylmethanol (91 mg, 0.833 mmol), 5,5-difluoro-2-methyltetrahydro-2H-pyran-2-carboxylic acid (100 mg, 0.555 mmol), HBTU (274 mg, 0.722 mmol) and DIEA (0.2 ml, 1.145 mmol) in DCM (2 mL) was stirred at rt for 4 h. The reaction mixture was diluted with EtOAc and washed with NaHCO₃, brine, dried (MgSO₄), concentrated and the residue was purified by silica gel chromatography (EtOAc/hexane) to afford pyridin-2-ylmethyl 5,5-difluoro-2-methyltetrahydro-2H-pyran-2-carboxylate as racemate. Two enantiomers (elute-1 @ 4.04 min and elute-2 @ 4.61 min) were separated by chiral SFC (Chiralpak AD-H preparative column, 20×250 mm, 5 μm, mobile Phase: 10% 2:1 heptane:EtOH in $CO_2$, 150 bar; temp: 35° C.; flow rate: 45 mL/min, UV: 258 nm).

A mixture of elute-1 (collected at 4.04 min) (25 mg, 0.092 mmol), sodium hydroxide (1N, 1 mL, 1 mmol), THF (3 mL) and MeOH (2 mL) was stirred at rt for 20 h. The reaction mixture was diluted with EtOAc and washed with HCl (1N, 2×5 mL), brine (2×), dried ($MgSO_4$), filtered and removed the solvent to afford (R)-5,5-difluoro-2-methyltetrahydro-2H-pyran-2-carboxylic acid (14 mg).

A mixture of elute-2 (collected at 4.61 min) (21 mg, 0.077 mmol), sodium hydroxide (1N, 1 mL, 1 mmol), THF (3 mL) and MeOH (2 mL) was stirred at rt for 20 h. The reaction mixture was diluted with EtOAc and washed with HCl (1N, 2×5 mL), brine (2×), dried ($MgSO_4$), filtered and removed the solvent to afford (S)-5,5-difluoro-2-methyltetrahydro-2H-pyran-2-carboxylic acid (13 mg).

Cap Y-8b

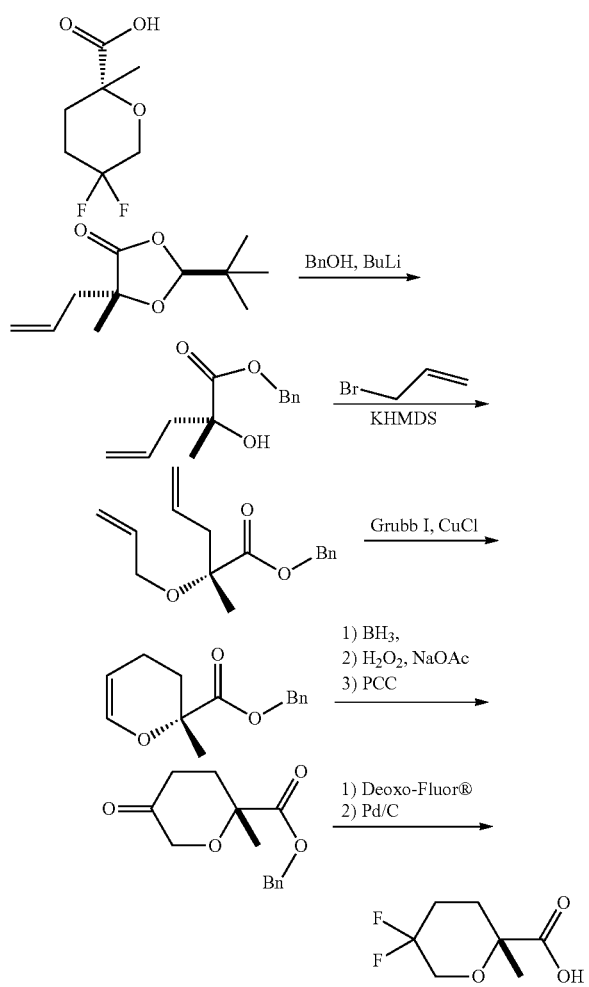

To a solution of phenylmethanol (15 mL, 144 mmol) in THF (100 mL) was added n-butyllithium (51.0 mL, 128 mmol) dropwise at 0° C. The generated solution was stirred for 20 min before the dropwise addition of (2S,5R)-5-allyl-2-(tert-butyl)-5-methyl-1,3-dioxolan-4-one (25.3 g, 128 mmol, prepared by the method described in HELVETICA CHIMICA ACTA—Vol. 70 (1987), p 1194) in THF (80 mL) at 0° C. The reaction mixture was stirred at rt for 18 h and quenched by aq. cold $NH_4Cl$. The mixture was extracted with EtOAc (2×). The combined organic solution was washed with brine, dried ($MgSO_4$) and purified by silica gel flash chromatography to afford the product (21.1 g, 75%). $^1H$ NMR (400 MHz, CHLOROFORM-d) ppm 7.43-7.33 (m, 5H), 5.74 (ddt, J=17.2, 10.2, 7.3 Hz, 1H), 5.20 (s, 2H), 5.13-4.99 (m, 2H), 2.57-2.48 (m, 1H), 2.45-2.36 (m, 1H), 1.45 (s, 3H).

To a solution of (R)-benzyl 2-hydroxy-2-methylpent-4-enoate (11 g, 49.9 mmol) in THF (100 mL) was added a solution of potassium hexamethyldisilazide/toluene (120 mL, 60 mmol) at −78° C. dropwise during 0.5 h. The reaction mixture was stirred at −78° C. for 15 min and added with allyl bromide (5.5 mL, 63.6 mmol). The reaction mixture was stirred in the bath for 18 h and let it warm up to rt in the process. The reaction mixture was quenched by cold 1N HCl, and extracted with EtOAc (2×). The combined organic solution was washed with water, brine, dried ($MgSO_4$), removed the solvent and purified by silica gel flash chromatography to afford the product (9.4 g, 72.3%). $^1H$ NMR (400 MHz, CHLOROFORM-d) ppm 7.40-7.34 (m, 5H), 6.06-5.87 (m, 1H), 5.87-5.69 (m, 1H), 5.36-5.27 (m, 1H), 5.26-5.03 (m, 5H), 4.00-3.89 (m, 2H), 2.63-2.48 (m, 2H), 1.44 (s, 3H).

A solution of (R)-benzyl 2-(allyloxy)-2-methylpent-4-enoate (4.3 g, 16.52 mmol) in toluene (150 mL) was purged with $N_2$ for 5 min before the addition of GrubbsI (0.26 g, 0.311 mmol). The reaction mixture was stirred at rt for 1.5 h. The reaction mixture was purged with $N_2$ and added CuCl (20 mg, 0.202 mmol), stirred at rt for 10 min. GrubbsI (0.26 g, 0.311 mmol) and trimethylsilane (2.2 mL, 13.77 mmol) were added. The reaction mixture was heated in 110° C. bath in a sealed tube for overnight and concentrated to dryness, purified on a 80 g silica gel cartridge (EtOAc/hex: 0 to 30%) to afford the product as an oil (3.5 g, 91%). $^1H$ NMR (400 MHz, CHLOROFORM-d) ppm 7.42-7.32 (m, 5H), 6.41 (dt, J=6.3, 1.9 Hz, 1H), 5.21 (s, 2H), 4.75-4.69 (m, 1H), 2.30-2.23 (m, 1H), 1.98-1.88 (m, 2H), 1.82-1.72 (m, 1H), 1.52 (s, 3H).

To a solution of (R)-benzyl 2-methyl-3,4-dihydro-2H-pyran-2-carboxylate (3.5 g, 15.07 mmol) in THF (30 ml) was added $BH_3 \cdot THF$ (10.55 ml, 10.55 mmol) dropwise in ice water bath in 10 min. The reaction mixture was stirred at rt for 3 h. The reaction mixture was recooled in ice-water bath and quenched by addition a solution of sodium acetate (1.3 g, 15.85 mmol) in water (15 ml). The reaction mixture was stirred for 10 min at the temperature, hydrogen peroxide (3 mL, 48.9 mmol) was added in and stirred at rt for 1 h. The reaction mixture was diluted with EtOAc and washed with $NH_4Cl$, brine, dried ($MgSO_4$), removed the solvent to afford the crude product (3.4 g, 90%). The crude product was used in next reaction without purification.

To a mixture of (2R)-benzyl 5-hydroxy-2-methyltetrahydro-2H-pyran-2-carboxylate (3.4 g, 13.58 mmol) and MS (4 Å, 15 g, powdered) in DCM (30 mL) was added PCC (4 g, 18.56 mmol) in two portions in ice bath. The reaction mixture was stirred at rt for 20 h and was diluted with 20 mL of hexane, directly purified on a pad of silica gel (20% EtOAc/hex to 100%) to afford the product (2.3 g, 68%).

To a solution of Deoxo-Fluor® (4.27 mL, 23.16 mmol) in DCM (15 mL) was added boron trifluoride etherate (2.93 mL, 23.16 mmol) at 0° C. dropwise. The mixture was stirred at rt for 1 h. A solution of (R)-benzyl 2-methyl-5-oxotetrahydro-2H-pyran-2-carboxylate (2.3 g, 9.26 mmol) in DCM (5 mL) was added dropwise in a 0° C. bath. The reaction mixture was stirred at rt for overnight. Another portion of Deoxo-Fluor® (3.6 mL, 19.53 mmol) was added dropwise at 0° C. The reaction mixture was stirred at rt for 2 h. The reaction mixture was cautionly poured into a stirring ice cold aq. NaHCO₃ solution and extracted with EtOAc (2×). The organic extraction was washed with NaHCO₃, brine, dried (MgSO₄). The crude product was dissolved in acetone (4 mL), THF (16 ml), and added water (4 mL), NMO (1.5 g, 12.80 mmol) and osmium tetroxide (0.4 mL, 0.032 mmol) in ice bath. The reaction mixture was stirred at rt for 3 days. The reaction mixture was diluted with EtOAc and washed with water, NH₄Cl, brine, dried (MgSO₄) and purified by silica gel flash chromatography to afford the product (1.5 g, 59.9%).

A mixture of (R)-benzyl 5,5-difluoro-2-methyltetrahydro-2H-pyran-2-carboxylate (0.51 g, 1.887 mmol) and Pd/C (0.05 g, 0.047 mmol) in MeOH (20 mL) was degassed and refilled H₂. The reaction mixture was stirred at rt under H₂ balloon pressure for 1 day. The reaction mixture was filtered and the filtration was concentrated to dryness to afford Cap Y-8b (0.33 g, 96%).

Cap Y-9

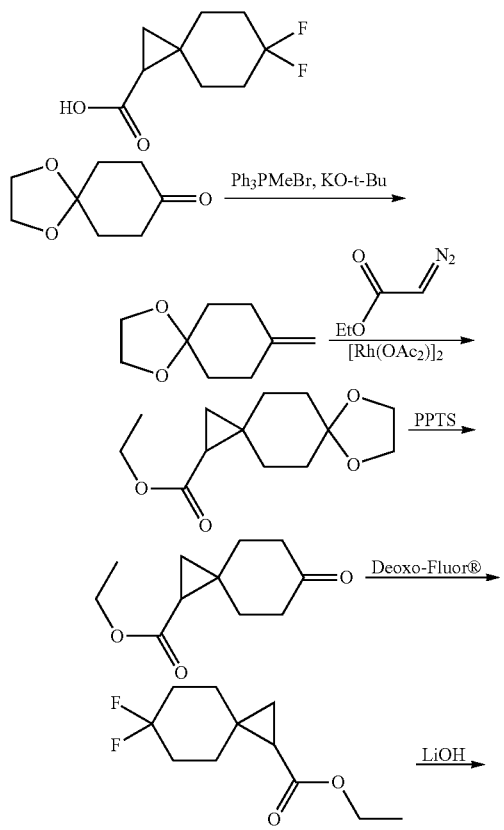

A mixture of KO-tBu (7.4 g, 65.9 mmol) and bromo(methyl)triphenylphosphorane (21.6 g, 60.5 mmol) in ether (100 mL) was refluxed for 0.5 h. Then a solution of 1,4-dioxaspiro[4.5]decan-8-one (6.24 g, 40.0 mmol) in ether (100 mL) was added dropwise during 1.5 h. The reaction mixture was stirred for 2 h, cooled to rt, filtered and the filtrate was concentrated. The residue was purified by silica gel chromatography (EtOAc/hexane) to afford 8-methylene-1,4-dioxaspiro[4.5]decane (1.5 g) as a clear oil. ¹H NMR (400 MHz, CDCl₃) δ ppm 4.62-4.74 (2H, m), 3.98 (4H, s), 2.30 (4H, dd, J=7.03, 6.02 Hz), 1.66-1.77 (4H, m).

A solution of diacetoxyrhodium (0.14 g, 0.317 mmol) and 8-methylene-1,4-dioxaspiro[4.5]decane (1.5 g, 9.73 mmol) in DCM (20 mL) was heated to reflux, and a solution of ethyl 2-diazoacetate (2.018 mL, 19.45 mmol) in DCM (6 mL) was added to it via syringe pump at 3.0 mL/h. The reaction mixture was stirred for 2 h after the completion of the addition, cooled to rt and concentrated. The residue was purified by silica gel chromatography (EtOAc/hexane) to afford ethyl (1S)-6-oxospiro[2.5]octane-1-carboxylate (1.9 g). ¹H NMR (400 MHz, CDCl₃) δ ppm 4.08-4.18 (2H, m), 3.94-3.99 (4H, m), 1.83 (4H, m), 1.59-1.67 (2H, m), 1.49-1.58 (2H, m), 1.35-1.46 (1H, m), 1.23-1.30 (3H, m), 1.15 (1H, t, J=4.89 Hz), 0.90 (1H, dd, J=7.91, 4.39 Hz).

To a solution of ethyl (1S)-6-oxospiro[2.5]octane-1-carboxylate (1.9 g, 7.91 mmol) in acetone (20 mL) and water (5 mL) was added PPTS (0.1 g, 0.398 mmol). The reaction mixture was heated at 60° C. for 5 h, and then stirred at rt for 45 h. The reaction mixture was diluted with EtOAc, washed with water, brine, dried (MgSO₄) and concentrated to afford ethyl 6-oxospiro[2.5]octane-1-carboxylate as an oil (1.32 g). ¹H NMR (400 MHz, CDCl₃) δ ppm 4.13-4.21 (2H, m), 2.35-2.51 (3H, m), 2.19-2.30 (1H, m), 2.00-2.09 (3H, m), 1.86 (1H, ddd, J=13.68, 8.16, 5.27 Hz), 1.64-1.77 (2H, m), 1.23-1.35 (3H, m), 1.08 (1H, dd, J=8.16, 4.64 Hz).

To a solution of ethyl 6-oxospiro[2.5]octane-1-carboxylate (1.32 g, 6.73 mmol) in CH₂Cl₂ (5 mL) was added Deoxo-Fluor® (2.7 mL, 14.64 mmol) and EtOH (5 μL). The resulting yellowish solution was stirred at rt for 18 h. The reaction mixture was partitioned between sat. NaHCO₃ and EtOAc. The organic phase was washed with sat. NaHCO₃, water, sat. NaCl and dried over anhydrous MgSO₄, filtered and dried to yield ethyl 6,6-difluorospiro[2.5]octane-1-carboxylate (0.72 g).

To a solution of ethyl 6,6-difluorospiro[2.5]octane-1-carboxylate (0.72 g, 3.30 mmol) in THF (5 mL) and MeOH (2.5 mL) was added water (2.500 mL) and lithium hydroxide, H₂O (1.108 g, 26.4 mmol). The reaction mixture was stirred at rt for 32 h. The reaction mixture was diluted with EtOAc and washed with 1 N HCl (30 mL), brine, dried (MgSO₄) and concentrated to dryness to afford Cap Y-9 (0.627 g). ¹H NMR (400 MHz, CDCl₃) δ ppm 2.37-2.19 (m, 1H), 2.08-1.77 (m, 4H), 1.61 (s, 2H), 1.57-1.36 (m, 1H), 1.35-1.19 (m, 2H), 1.11-1.00 (m, 1H).

Cap Y-10

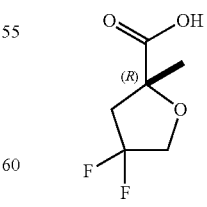

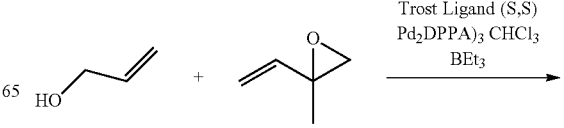

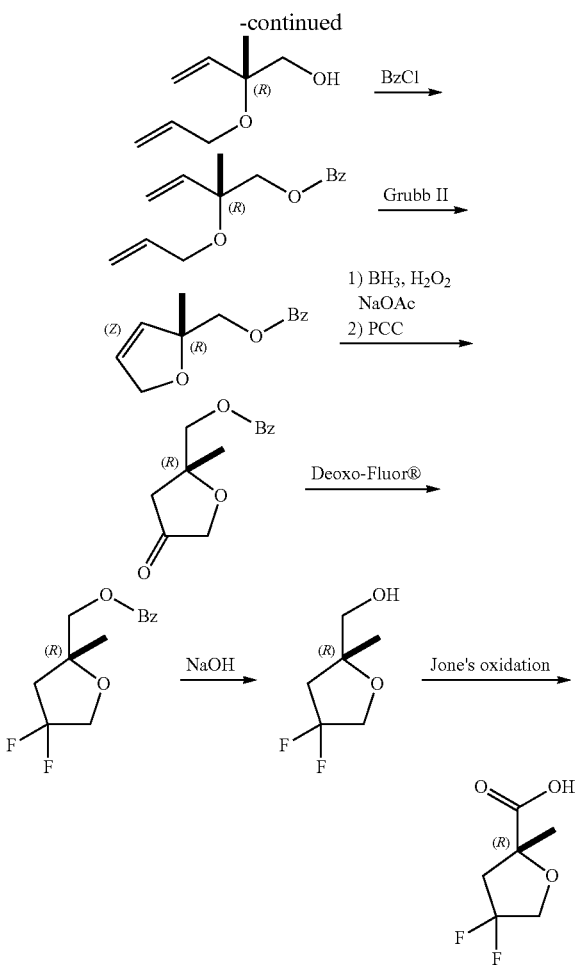

To a dry flask was added Pd$_2$(dba)$_3$ CHCl$_3$ adduct (0.1 g, 0.097 mmol), N,N'-((1S,2S)-cyclohexane-1,2-diyl)bis(2-(diphenylphosphino)benzamide) (0.2 g, 0.290 mmol). The flask was degassed and purged with N$_2$. DCM (200 mL) was added then degassed and purged with N$_2$. Allyl alcohol (3 mL, 44.1 mmol) was added and degassed, refilled N$_2$. The mixture was stirred at rt for 20 min and the color changed to orange. Triethylborane/hexane (0.4 mL, 0.400 mmol) was added and stirred for 2 min before the addition of 2-methyl-2-vinyloxirane (4 mL, 40.8 mmol). The reaction mixture was stirred at rt for 17 h and concentrated to dryness to afford the product (5.8 g, 100%). The crude product was used in the next step without purification. $^1$H NMR (400 MHz, CHLOROFORM-d) ppm 5.98-5.77 (m, 2H), 5.35-5.22 (m, 3H), 5.15 (dq, J=10.4, 1.5 Hz, 1H), 3.90 (dt, J=5.3, 1.5 Hz, 2H), 3.57-3.42 (m, 2H), 1.32 (s, 3H).

To a solution of (R)-2-(allyloxy)-2-methylbut-3-en-1-ol (5.8 g, 40.8 mmol) in DCM (100 mL) was added DIPEA (8.6 ml, 49.2 mmol) and benzoyl chloride (5.2 mL, 44.8 mmol) dropwise in an ice bath. The reaction mixture was stirred at rt for 5 h. Ether (100 mL) and TEA (5 mL, 35.9 mmol) were added and stirred for another 20 h. The reaction mixture was diluted with EtOAc and hexane, washed with HCl (1 N, 2×), NaOH (1 N, 2×), brine, dried (MgSO$_4$), removed the solvents and purified by silica gel flash chromatography to afford the product (5.4 g, 54%). $^1$H NMR (400 MHz, CHLOROFORM-d) ppm 8.11-8.02 (m, 2H), 7.62-7.55 (m, 1H), 7.49-7.41 (m, 2H), 5.99-5.86 (m, 2H), 5.39-5.28 (m, 3H), 5.14 (dq, J=10.5, 1.6 Hz, 1H), 4.38-4.30 (m, 2H), 4.01-3.96 (m, 2H), 1.43 (s, 3H).

A solution of (R)-2-(allyloxy)-2-methylbut-3-en-1-yl benzoate (5.4 g, 21.92 mmol) in DCM (200 mL) was degassed and purged with N$_2$ for 5 min. Grubbs II (0.16 g, 0.188 mmol) was added and the reaction mixture was stirred at rt for 16 h. The reaction mixture was concentrated and purified by silica gel flash chromatography (EtOAc/hexane: 0 to 20%) to afford the product (3.7 g, 77%). $^1$H NMR (400 MHz, CHLOROFORM-d) ppm 8.08-8.01 (m, 2H), 7.63-7.53 (m, 1H), 7.49-7.36 (m, 2H), 5.96 (dt, J=6.2, 1.5 Hz, 1H), 5.77 (dt, J=6.3, 2.5 Hz, 1H), 4.75-4.68 (m, 2H), 4.40 (d, J=11.3 Hz, 1H), 4.26 (d, J=11.3 Hz, 1H), 1.42 (s, 3H).

To a solution of (R)-(2-methyl-2,5-dihydrofuran-2-yl)methyl benzoate (3.6 g, 16.49 mmol) in THF (40 mL) was added borane-methyl sulfide complex (6 mL, 12.00 mmol) dropwise in ice bath. The reaction mixture was stirred at rt for 2 h. The reaction mixture was cooled in ice bath and a solution of sodium acetate (1.353 g, 16.49 mmol) in water (15 mL) was added to the reaction mixture with caution. The reaction mixture was stirred at rt for 25 min before the addition of hydrogen peroxide (1.516 mL, 24.74 mmol). The reaction mixture was stirred at rt for overnight. Another portion of hydrogen peroxide (1.516 mL, 24.74 mmol) was added and stirred at rt for 2 h. The reaction mixture was diluted with EtOAc and washed with water, brine, dried (MgSO$_4$), removed solvents to afford the product (3.9 g, 100%). The crude product was used in the next reaction without purification.

To a mixture of (5R)-5-((benzyloxy)methyl)-5-methyltetrahydrofuran-3-ol (3.9 g, 17.55 mmol) and MS (4 Å, 6 g, powdered) was added PCC (5.29 g, 24.56 mmol) in two portions in ice bath temperature. The reaction mixture was stirred at rt for 20 h and diluted with 20 mL of hexane, directly purified on silica gel column (10% EtOAc/hex to 80%) to afford the product (1.6 g, 39%). $^1$H NMR (400 MHz, CHLOROFORM-d) ppm 8.02-7.94 (m, 2H), 7.62-7.54 (m, 1H), 7.50-7.38 (m, 2H), 4.42-4.32 (m, 2H), 4.21 (d, J=17.1 Hz, 1H), 4.13 (d, J=17.1 Hz, 1H), 2.69 (d, J=18.1 Hz, 1H), 2.45 (d, J=17.8 Hz, 1H), 1.52 (s, 3H).

To a solution of Deoxo-Fluor® (3.8 mL, 20.61 mmol) in DCM (10 mL) was added boron trifluoride etherate (2.60 mL, 20.49 mmol) at 0° C. The mixture was stirred at rt for 1 h. The reaction mixture was cooled to 0° C. and added triethylamine trihydrofluoride (0.2 mL, 1.228 mmol), (R)-(2-methyl-4-oxotetrahydrofuran-2-yl)methyl benzoate (1.6 g, 6.83 mmol) in DCM (5 mL). The reaction mixture was stirred at rt for 20 h and cautiously poured into a stirring ice cold aq. NaHCO$_3$ solution, extracted with EtOAc. The organic extraction was washed with NaHCO$_3$, brine, dried (MgSO$_4$), concentrated and purified on a 25 g silica gel cartridge (EtOAc/hex: 0 to 30%) to afford the product (1.1 g, 63%). $^1$H NMR (500 MHz, CHLOROFORM-d) ppm 8.12-8.03 (m, 2H), 7.61 (tt, J=7.4, 1.3 Hz, 1H), 7.51-7.41 (m, 2H), 4.40-4.27 (m, 2H), 4.20-4.04 (m, 2H), 2.63 (dt, J=16.1, 14.1 Hz, 1H), 2.33 (dddd, J=17.4, 14.3, 9.6, 0.9 Hz, 1H), 1.48 (s, 3H).

A mixture of (R)-(4,4-difluoro-2-methyltetrahydrofuran-2-yl)methyl benzoate (1.1 g, 4.29 mmol) in THF (10 mL), MeOH (10.00 mL) and sodium hydroxide (1 N, 25.00 mmol) was stirred at rt for overnight. The reaction mixture was concentrated partially and the residue was partitioned between 1 N NaOH and ether. The aq. layer was extracted with ether (2×). The combined organic solution was washed with 1 N NaOH, water, brine, dried (MgSO$_4$), removed the solvent to afford the product (0.65 g, 100%). $^1$H NMR (400 MHz, CHLOROFORM-d) ppm 4.13-4.00 (m, 2H), 3.66-3.42 (m, 2H), 2.73-2.49 (m, 1H), 2.25-2.08 (m, 1H), 1.32 (s, 3H).

To a solution of (R)-(4,4-difluoro-2-methyltetrahydrofuran-2-yl)methanol (0.65 g, 4.27 mmol) in acetone (10 mL)

was added Jones' Reagent (2.5 M, 3.4 mL, 8 mmol) at 0° C. The reaction mixture was stirred in the bath for 18 h and let it warm up to rt in the process. The reaction mixture was diluted with EtOAc and washed with water, brine, dried (MgSO$_4$), removed the solvents and purified on 25 g silica gel cartridge (MeOH/DCM: 0 to 20%) to afford Cap Y-10 (0.16 g, 23%). $^1$H NMR (500 MHz, CHLOROFORM-d) ppm 4.21-4.08 (m, 2H), 3.01-2.90 (m, 1H), 2.46-2.36 (m, 1H), 1.64 (s, 3H).

Cap Y-11

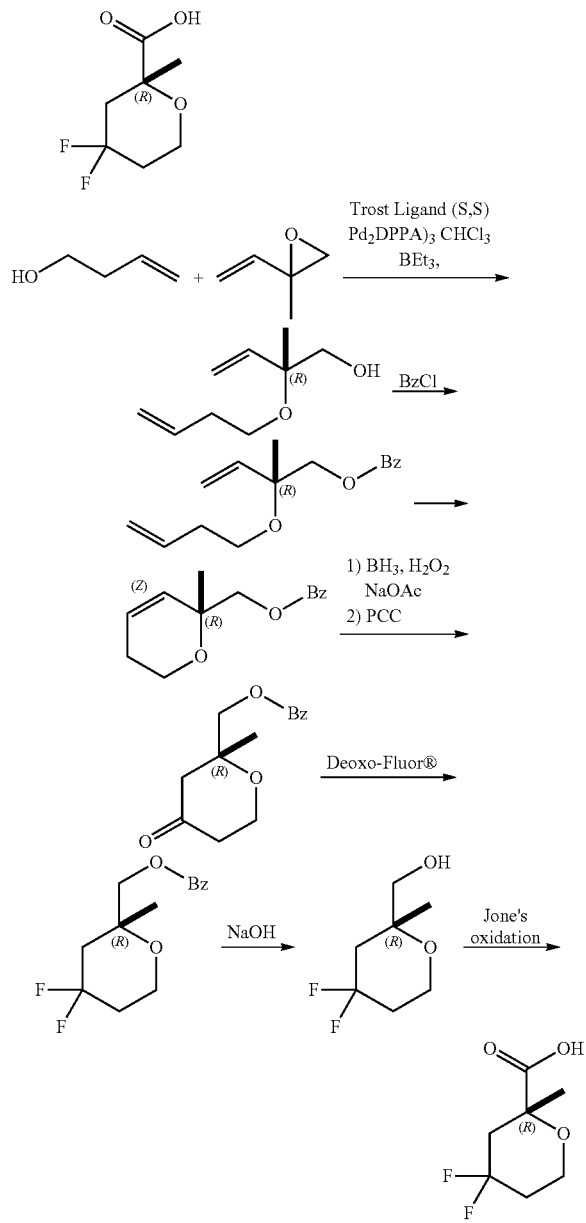

To a dry flask was added Pd$_2$(dba)$_3$ CHCl$_3$ adduct (0.15 g, 0.145 mmol), N,N'-((1S,2S)-cyclohexane-1,2-diyl)bis(2-(diphenylphosphino)benzamide) (0.3 g, 0.434 mmol). The flask was degassed under vacuum and purged with N$_2$. Repeated the procedure for 2 times. DCM (200 mL) was added then degassed under vacuum and purged with N$_2$. But-3-en-1-ol (4.4 mL, 51.9 mmol) was added and degassed, refilled N$_2$. The mixture was stirred at rt for 20 min. The color changed to orange. triethylborane/hexane (0.8 mL, 0.800 mmol) was added. After stirring for 2 min. 2-methyl-2-vinyloxirane (4 mL, 40.8 mmol) was added at rt. The reaction mixture was stirred at rt for 19 h. The reaction mixture was concentrated to dryness to afford the product. The crude product was used in next reaction without purification (6.37 g, 100%).

To a solution of (R)-2-(but-3-en-1-yloxy)-2-methylbut-3-en-1-ol (6.4 g, 41.0 mmol) in DCM (80 ml) was added DIPEA (9.30 mL, 53.3 mmol) and benzoyl chloride (6 mL, 51.7 mmol) dropwise in an ice bath. The reaction mixture was stirred at rt for 1 day. Ether (150 mL) and TEA (8 mL, 57.4 mmol), benzoyl chloride (6 mL, 51.7 mmol) were added to the reaction mixture. The reaction mixture was stirred at rt for 3 h. The reaction mixture was diluted with EtOAc and hexane washed with NaOH (1 N, 2×), brine, dried (MgSO$_4$), removed the solvent and plugged through silica gel pad and purified on a 160 silica gel cartridge (EtOAc/hex: 0 to 15%) to afford the product (10.5 g, 79%). $^1$H NMR (400 MHz, CHLOROFORM-d) ppm 8.14-8.00 (m, 2H), 7.61-7.52 (m, 1H), 7.51-7.38 (m, 2H), 6.00-5.79 (m, 2H), 5.38-5.27 (m, 2H), 5.11-4.96 (m, 2H), 4.31 (d, J=4.0 Hz, 2H), 3.46 (td, J=6.9, 4.5 Hz, 2H), 2.32 (dt, J=6.8, 1.4 Hz, 2H), 1.45-1.37 (m, 3H).

A solution of (R)-2-(but-3-en-1-yloxy)-2-methylbut-3-en-1-yl benzoate (10.5 g, 32.3 mmol) in DCM (600 mL) was degassed and purged with N$_2$ for 5 min. GrubbsII (0.18 g, 0.212 mmol) was added and the reaction mixture was stirred at rt for 3 days. The reaction mixture was concentrated and purified on a 160 g silica gel cartridge (EtOAc/hex: 0 to 18%) to afford the product as a liquid (5.9 g, 79%). 1H NMR (400 MHz, CHLOROFORM-d) ppm 8.11-8.05 (m, 2H), 7.61-7.54 (m, 1H), 7.50-7.41 (m, 2H), 6.05-5.96 (m, 1H), 5.69 (dt, J=10.3, 2.0 Hz, 1H), 4.42 (d, J=11.3 Hz, 1H), 4.18 (d, J=11.3 Hz, 1H), 3.92 (dd, J=11.3, 5.5 Hz, 1H), 3.84 (dd, J=11.2, 5.6 Hz, 1H), 2.16-2.08 (m, 2H), 1.36 (s, 3H).

To a solution of (R)-(2-methyl-5,6-dihydro-2H-pyran-2-yl)methyl benzoate (5.9 g, 25.4 mmol) in THF (60 mL) was added BH$_3$.THF (15.3 mL, 15.30 mmol) dropwise in ice water bath in 10 min. The reaction mixture was stirred at rt for 1 h. Another portion of BH$_3$.THF (15.3 ml, 15.30 mmol) was added in at 0° C. and the reaction mixture was stirred at rt for 0.5 h. The reaction mixture was recooled in ice-water bath and quenched by carefully addition a solution of sodium acetate (2 g, 24 mmol) in water (15 ml). After being stirred for 10 min, hydrogen peroxide (4.67 mL, 76 mmol) was added and stirred at rt for 1 h. The reaction mixture was diluted with EtOAc and washed with NH$_4$Cl, sated Na$_2$S$_2$O$_3$ (2×), brine, dried (MgSO$_4$), removed the solvent and purified on a 160 g silica gel column to afford the product. (1.6 g, 25%).

To a mixture of ((2R)-4-hydroxy-2-methyltetrahydro-2H-pyran-2-yl)methyl benzoate (1.6 g, 6.39 mmol) and MS (4 Å, 3 g, powdered) was added PCC (2 g, 9.28 mmol) in two portions in ice bath. The reaction mixture was stirred at rt for 3 h. The reaction mixture was filtered through a silica gel pad. concentrated and purified by flash chromatography (EtOAc/hex) to afford the product (0.7 g, 44%). 1H NMR (400 MHz, CHLOROFORM-d) ppm 8.08-8.01 (m, 2H), 7.63-7.57 (m, 1H), 7.51-7.43 (m, 2H), 4.34 (s, 2H), 4.25-4.14 (m, 1H), 4.13-4.00 (m, 1H), 2.67 (d, J=14.3 Hz, 1H), 2.62-2.53 (m, 1H), 2.51-2.40 (m, 2H), 1.38 (s, 3H).

To a solution of Deoxo-Fluor® (1.5 mL, 8.14 mmol) in DCM (5 mL) was added boron trifluoride etherate (1 mL, 7.89 mmol) dropwise at 0° C. The mixture was stirred at rt for 1 h. A solution of (R)-(2-methyl-4-oxotetrahydro-2H-pyran-2-yl)methyl benzoate (0.7 g, 2.82 mmol) in DCM (5 mL) and triethylamine trihydrofluoride (0.1 mL, 0.614 mmol) were added dropwise in a 0° C. The reaction mixture was stirred at rt for 18 h and was recooled the reaction mixture in ice bath, added another portion of Deoxo-Fluor® (1 mL, 5.42 mmol) dropwise. The reaction mixture was stirred at rt for another 2 h. The reaction mixture was cautiously poured into a stirred ice cold aq. NaHCO₃ solution and extracted with EtOAc (2×). The combined organic extraction was washed with NaHCO₃, brine, dried (MgSO₄), removed the solvent and purified on a 25 g silica gel cartridge (EtOAc/hex: 0 to 20%) to afford the product contaminated with vinyl by-product. The product was dissolved in acetone (4 mL), THF (16 mL), and added water (4 mL), NMO (0.330 g, 2.82 mmol) and osmium tetroxide (0.4 mL, 0.032 mmol) in ice bath. The reaction mixture was stirred at rt for 3 days and was diluted with EtOAc, washed with water, NH₄Cl, brine, dried (MgSO₄) and purified by silica gel flash chromatography to afford (R)-(4,4-difluoro-2-methyltetrahydro-2H-pyran-2-yl)methyl benzoate (0.48 g, 63%). ¹H NMR (400 MHz, CHLOROFORM-d) ppm 8.13-8.04 (m, 2H), 7.60 (tt, J=7.4, 1.3 Hz, 1H), 7.52-7.39 (m, 2H), 4.42-4.34 (m, 1H), 4.24 (d, J=11.5 Hz, 1H), 4.00-3.84 (m, 2H), 2.21-1.93 (m, 4H), 1.46-1.36 (m, 3H).

A mixture of (R)-(4,4-difluoro-2-methyltetrahydro-2H-pyran-2-yl)methyl benzoate (0.45 g, 1.665 mmol) in THF (5 mL), MeOH (4 mL) and sodium hydroxide (4 mL, 4.00 mmol) was stirred at rt for 5 h. The reaction mixture was diluted with ether and washed with 1 N NaOH, brine. dried (MgSO₄), removed the solvent to afford the product as a liquid (0.22 g, 80%). ¹H NMR (400 MHz, CHLOROFORM-d) ppm 3.92-3.84 (m, 2H), 3.50-3.37 (m, 2H), 2.27-2.09 (m, 1H), 2.08-1.78 (m, 3H), 1.27-1.21 (m, 3H).

To a solution of (R)-(4,4-difluoro-2-methyltetrahydro-2H-pyran-2-yl)methanol (0.22 g, 1.324 mmol) in acetone (10 mL) was added Jones' Reagent (1.1 mL, 2.75 mmol) at 0° C. The reaction mixture was stirred in the bath for 18 h and let it warm up to rt in the process. The mixture was diluted with EtOAc and washed with water, brine, and purified on 4 g silica gel column (MeOH/DCM: 0 to 12%) to afford Cap Y-11 (0.16 g, 67%). ¹H NMR (400 MHz, CHLOROFORM-d) ppm 4.15-3.91 (m, 2H), 2.78-2.64 (m, 1H), 2.11-1.88 (m, 3H), 1.56 (s, 3H).

Cap Y-12

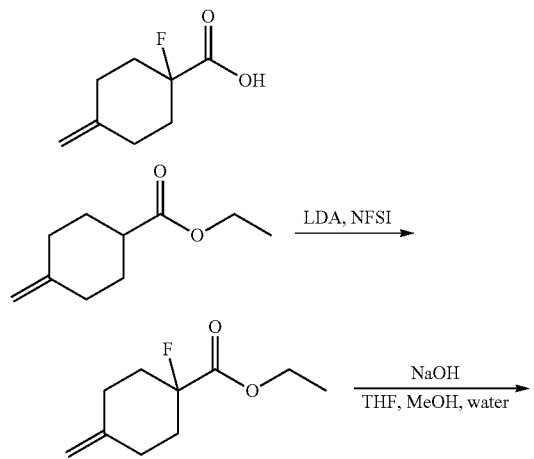

To a solution of DIPEA (1.220 mL, 8.56 mmol) in 10 ml of THF was added n-butyllithium (2.9 mL, 7.25 mmol) at −78° C. dropwise in 10 min and then stirred in ice bath for 20 min. The reaction mixture was recooled in −78° C. bath and a solution of ethyl 4-methylenecyclohexanecarboxylate (1.2 g, 7.13 mmol) in THF (5 mL) was added dropwise at −78° C. The generated solution was stirred at −78° C. for 0.5 h. A solution of N-fluorobenzensulfonimide (2.249 g, 7.13 mmol) in THF (15 mL) was added dropwise in 5 min. The reaction mixture was stirred in the bath for 18 h and let it warm up to rt in the process. The reaction mixture was diluted with EtOAc and washed with aq. satd. NH₄Cl (2×), water, brine, dried (MgSO₄), removed the solvents and purified on a 25 g silica gel cartridge to afford the product (0.8 g, 60%). ¹H NMR (400 MHz, CHLOROFORM-d) ppm 4.75 (t, J=1.5 Hz, 2H), 4.26 (q, J=7.3 Hz, 2H), 2.49-2.37 (m, 2H), 2.32-2.23 (m, 2H), 2.16-2.06 (m, 2H), 2.05-1.82 (m, 2H), 1.37-1.30 (m, 3H).

A mixture of ethyl 1-fluoro-4-methylenecyclohexanecarboxylate (0.2 g, 1.074 mmol) in THF (5 mL), MeOH (4 mL) and sodium hydroxide (3 mL, 3.00 mmol) was stirred at rt for 5 h and acidified with 2 N HCl to pH<2, extracted with EtOAc (2×), The combined organic solvent was washed with brine, dried (MgSO₄), removed the solvent to afford Cap Y-12 (0.17 g, 100%). ¹H NMR (500 MHz, CHLOROFORM-d) ppm 4.77 (t, J=1.5 Hz, 2H), 2.49-2.35 (m, 2H), 2.35-2.27 (m, 2H), 2.22-2.13 (m, 2H), 2.09-1.88 (m, 2H).

Cap Y-13

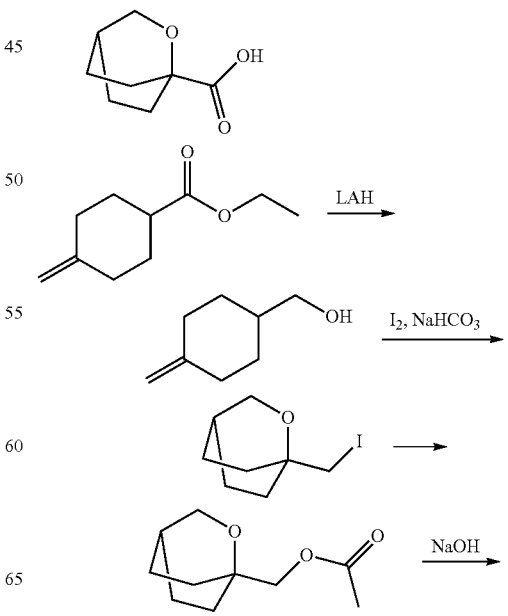

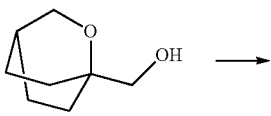

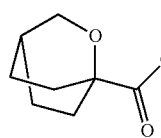

To a solution of ethyl 4-methylenecyclohexanecarboxylate (2 g, 11.89 mmol) in ether (40 mL) was added LAH (0.5 g, 13.17 mmol) portionwise under $N_2$. The reaction mixture was refluxed for 1 h and was quenched by addition of 1 mL of EtOAc carefully and refluxed for 10 min. The reaction mixture was cooled down and added 3 mL of 1 N NaOH and stirred for 5 min, filtered off the solid and washed with ether. The filtration was washed with water, brine, dried ($MgSO_4$), and removed the solvent to afford (4-methylenecyclohexyl)methanol.

To a solution of (4-methylenecyclohexyl)methanol (1.1 g, 8.72 mmol) in acetonitrile (40 mL) was added a mixture of iodine (3.32 g, 13.07 mmol) in acetonitrile (120 mL) at 0° C. The reaction mixture was stirred at 0° C. for 3 h. The reaction mixture was diluted with EtOAc and washed with aq. solution of $Na_2S_2O_3$, 1N NaOH, brine, dried ($MgSO_4$) and purified on a 40 g silica gel cartridge (EtOAc/hexane: 0 to 20%) to afford the product (0.53 g, 24%). $^1$H NMR (400 MHz, CHLOROFORM-d) ppm 3.94 (s, 2H), 3.14 (s, 2H), 2.01-1.93 (m, 2H), 1.90-1.80 (m, 2H), 1.75-1.66 (m, 5H).

To a solution of 1-(iodomethyl)-2-oxabicyclo[2.2.2]octane (0.53 g, 2.102 mmol) in DMF (15 mL) was added potassium acetate (1.5 g, 15.28 mmol). The reaction mixture was stirred in a 110° C. bath for 63 h and at 125° C. for 46 h. The reaction mixture was diluted with ether and washed with water (3×), brine, dried ($MgSO_4$), removed the solvent to afford the crude product (0.3 g, 80%). The crude product was directly used in next reaction. $^1$H NMR (400 MHz, CHLOROFORM-d) ppm 3.96-3.92 (m, 2H), 3.90 (s, 2H), 2.11 (s, 3H), 2.00-1.77 (m, 4H), 1.75-1.49 (m, 5H).

To a solution of 2-oxabicyclo[2.2.2]octan-1-ylmethyl acetate (0.3 g, 1.628 mmol) in THF (4 mL) was added 1 N NaOH (4 mL, 4.00 mmol). The reaction mixture was stirred at rt for 4 h. The reaction mixture was concentrated and partitioned between ether and water. The organic solution was washed with water, brine, dried ($MgSO_4$), and removed the solvent to afford the product (0.23 g, 79%). The crude product was used in next reaction.

To a solution of 2-oxabicyclo[2.2.2]octan-1-ylmethanol (0.23 g, 1.617 mmol) in Acetone (4 mL) was added Jones' Reagent (1.5 mL, 3.75 mmol) at 0° C. The reaction mixture was stirred in the bath and let it warm up to rt in the process. The reaction mixture was stirred for 18 h and diluted with EtOAc and washed with water, brine and purified on 25 g silica gel column (MeOH/DCM: 0 to 20%) to afford Cap Y-13 (0.24 g, the product was contained impurities). $^1$H NMR (400 MHz, CHLOROFORM-d) ppm 4.07-4.00 (m, 2H), 2.52 (dt, J=14.7, 5.6 Hz, 2H), 2.47-2.33 (m, 2H), 2.34-2.19 (m, 2H), 2.20-1.65 (m, 3H).

Cap Y-14

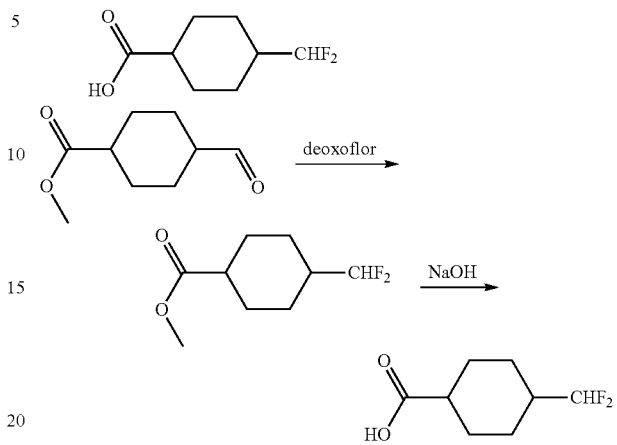

To a solution of methyl 4-formylcyclohexanecarboxylate (0.37 g, 2.174 mmol) in DCM (5 mL) was added Deoxo-Fluor® (1.0 ml, 5.42 mmol), followed by addition of a catalytic amount of ethanol (5 µl, 0.086 mmol). The resulting yellowish solution was stirred at rt for 18 hrs. The reaction mixture was partitioned between sat. $NaHCO_3$ and EtOAc. The organic phase was washed with sat. $NaHCO_3$, water, brine, dried over anhydrous $MgSO_4$, filtered and concentrated to dryness to yield a yellow oil, purified on a 25 g silica gel column (EtOAc/hexane: 0 to 50%) to afford the product as syns and trans mixtures.

To a solution of methyl 4-(difluoromethyl)cyclohexanecarboxylate (0.18 g, 0.937 mmol) in THF (3 mL) was added MeOH (2 mL) and 1 N sodium hydroxide (2 mL, 2.000 mmol). The reaction mixture was stirred at rt for 3 h. removed the solvent and partitioned the residue between 1 N NaOH and EtOAc. The aq. layer was acidified to pH<2 and extracted with EtOAc. The extraction was dried ($MgSO_4$) and concentrated to dryness to afford Cap Y-14 (0.12 g, 72%). $^1$H NMR (500 MHz, CHLOROFORM-d) ppm 5.96-5.40 (m, 1H).

Cap N-9

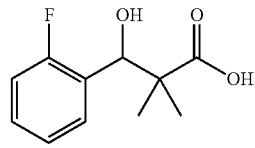

To a solution of diisopropylamine (3.31 mL, 23.22 mmol) in THF (5 mL) was added n-BuLi/hexane (9.29 mL, 23.22 mmol) dropwise at −78° C. The reaction mixture was stirred at −78° C. for 5 min and then stirred in ice bath for 20 min. The reaction mixture was added dropwise with a solution of isobutyric acid (1.055 mL, 11.61 mmol) in THF (5 mL) at 0° C. The reaction mixture was stirred at 0° C. for 30 min and 60° C. for 2 h. The flask was recooled to 0° C., and a solution of 2-fluorobenzaldehyde (1.441 g, 11.61 mmol) in THF (5 mL) was added dropwise. Then the solution was allowed to warm to rt and stirred for 16 h. The reaction was quenched with 1 N HCl until pH~3 and extracted with EtOAc. The combined organic layers were washed with 1 N NaOH. The combined basic washes were acidified with HCl and extracted with EtOAc. Then organic phase was washed with sat. NaCl, dried over anhydrous MgSO4, and concentrated to yield 3-(2-fluorophenyl)-3-hydroxy-2,2-dimethylpropanoic acid (1.5 g, 60.9% yield) as Cap N-9. $^1$H NMR (400 MHz, DMSO-$d_6$) ppm 7.50 (td, J=7.5, 1.8 Hz, 1H), 7.32 (tdd, J=7.7, 5.4, 1.8 Hz, 1H), 7.22 (td, J=7.5, 1.0 Hz, 1H), 7.14 (ddd, J=10.5, 8.3, 1.3 Hz, 1H), 5.28-5.11 (m, 1H), 3.33 (br. s., 1H), 1.06-0.97 (m, 3H), 0.93 (d, J=2.8 Hz, 3H).

Cap N-10

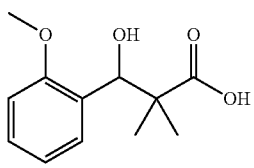 [SMILES: COc1ccccc1C(O)C(C)(C)C(=O)O]

Cap N-10 was prepared in a similar fashion starting from 2-methoxybenzaldehyde isobutyric acid according to the procedure described for the preparation Cap N-9. $^1$H NMR (400 MHz, DMSO-$d_6$) ppm 7.40 (dd, J=7.5, 1.8 Hz, 1H), 7.28-7.18 (m, 1H), 7.00-6.89 (m, 2H), 5.47-5.35 (m, 1H), 3.80 (d, J=5.5 Hz, 3H), 1.00-0.94 (m, 3H), 0.92-0.79 (m, 3H).

Cap N-11

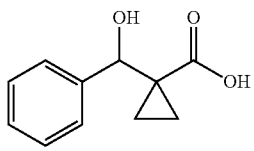 [SMILES: O=C(O)C1(C(O)c2ccccc2)CC1]

To a solution of diisopropylamine (1.203 mL, 8.44 mmol) in THF (10 mL) was added n-BuLi/hexane (3.38 mL, 8.44 mmol) dropwise at −78° C. The reaction mixture was stirred in the bath for 5 min and then stirred in ice bath for 30 min. The reaction mixture was added dropwise a solution of tert-butyl cyclopropanecarboxylate (1 g, 7.03 mmol) in THF (5 mL) at −78° C. The reaction mixture was stirred at −78° C. for 2 h. The solution of benzaldehyde (0.746 g, 7.03 mmol) in THF (2 mL) was added dropwise at −78° C. Then the solution was allowed to warm to room temperature and stirred for 1 h. The reaction was quenched with NH$_4$Cl, then diluted with EtOAc. Then organic phase was washed with sat. NaHCO$_3$, water, sat. NaCl, dried over anhydrous Na$_2$SO$_4$, and concentrated to yield an oil. The crude was purified by silica chromatography with 0-50% EtOAc/Hex to yield tert-butyl 1-(hydroxy(phenyl)methyl)cyclopropanecarboxylate (1.01 g, 57.8% yield) as a clear oil. $^1$H NMR (400 MHz, CHLOROFORM-d) ppm 7.48-7.40 (m, 2H), 7.38-7.23 (m, 3H), 4.70 (d, J=7.5 Hz, 1H), 3.55 (d, J=7.8 Hz, 1H), 1.43-1.33 (m, 10H), 1.17 (ddd, J=9.6, 6.6, 3.9 Hz, 1H), 0.99-0.79 (m, 2H).

To a solution of tert-butyl 1-(hydroxy(phenyl)methyl)cyclopropanecarboxylate (0.56 g, 2.255 mmol) in THF (4 mL) and MeOH (1 mL) was added 10 N sodium hydroxide (3 mL, 30.0 mmol). The reaction mixture was stirred at rt for 12 h. The reaction was diluted with 1 N HCl, extracted with 2×EtOAc, and the combined organic phase was washed with sat. NaCl, dried (anhydrous Na$_2$SO$_4$), filtered and concentrated to yield 1-(hydroxy(phenyl)methyl)cyclopropanecarboxylic acid (0.35 g, 81% yield) as Cap N-11. $^1$H NMR (400 MHz, CHLOROFORM-d) ppm 7.48-7.26 (m, 5H), 4.94 (s, 1H), 1.46 (ddd, J=9.8, 7.0, 4.3 Hz, 1H), 1.38-1.30 (m, 1H), 1.08 (ddd, J=9.5, 7.1, 4.3 Hz, 1H), 0.93-0.84 (m, 1H).

Cap N-12

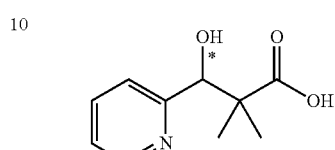

Cap N-12A and N-12B

Two Enantiomers

To a solution of diisopropylamine (1.675 mL, 11.75 mmol) in THF (10 mL) was added n-BuLi/hexane (4.70 mL, 11.75 mmol) dropwise at −78° C. The reaction mixture was stirred in the bath for 5 min and then stirred in ice bath for 30 min. The reaction mixture was added dropwise a solution of methyl isobutyrate (1 g, 9.79 mmol) in THF (5 mL) at −78° C. The reaction mixture was stirred at −78° C. for 2 hr. The solution of picolinaldehyde (1.258 g, 11.75 mmol) in THF (2 mL) was added dropwise at −78° C. Then the solution was allowed to warm to room temperature and stirred for 1 hr. The reaction was quenched with NH$_4$Cl, then diluted with EtOAc. Then organic phase was washed with sat. NaHCO$_3$, water, sat. NaCl, dried over anhydrous Na$_2$SO$_4$, and concentrated to yield an oil. The crude was purified by silica chromatography with 0-100% EtOAc/Hex to yield methyl 3-hydroxy-2,2-dimethyl-3-(pyridin-2-yl)propanoate (1.0 g) as a clear oil. $^1$H NMR (400 MHz, CHLOROFORM-d) ppm 8.61-8.44 (m, 1H), 7.66 (td, J=7.7, 1.8 Hz, 1H), 7.26-7.12 (m, 2H), 4.96 (d, J=7.5 Hz, 1H), 4.67 (d, J=7.5 Hz, 1H), 3.74 (s, 3H), 1.18 (s, 3H), 1.10 (s, 3H).

Methyl 3-hydroxy-2,2-dimethyl-3-(pyridin-2-yl)propanoate (0.42 g) was separated by chiral HPLC (chiralpak AD, 21×250 mm, 10 u, UV=254 nm, flow rate=15 mL/min, isocratic 30% B for 17 min, solvent A: 0.1% diethylamine/heptane, solvent B: 100% ethanol.) to yield two enantiomers. Enantiomer 1: RT=6.071 min, Enantiomer 2: RT=9.356 min. Each enantiomer was subjected to NaOH hydrolysis to yield Cap N-12A and N-12B respectively.

Cap N-13

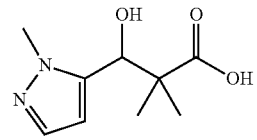

Cap N-13 was prepared in a similar fashion starting from 2-methoxybenzaldehyde isobutyric acid and 1-methyl-1H- pyrazole-5-carbaldehyde according to the procedure described for the preparation Cap N-11.

Cap P-26

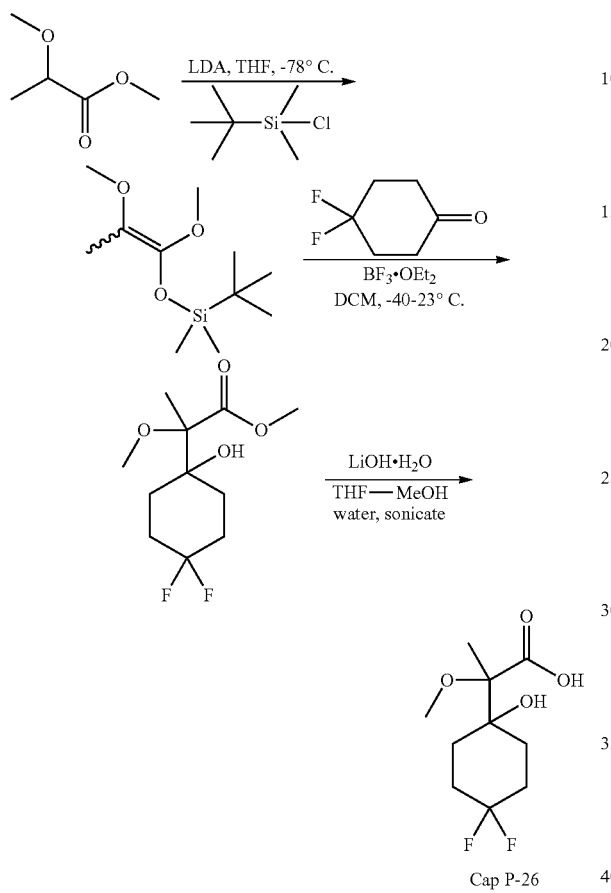

Cap P-26

A solution of methyl 2-methoxypropionate (177 mg, 1.5 mmol) in THF (1 mL) was added to a solution of LDA prepared from diisopropylamine (0.212 mL, 1.50 mmol) and butyllithium (0.60 mL, 1.50 mmol) in THF (2 mL) at −78° C. under nitrogen. The mixture was gradually allowed to warm to −20° C. over 1 h, re-cooled to −78° C. and then a solution of tert-butylchlorodimethylsilane (233 mg, 1.50 mmol) in THF (1 mL) was added. The mixture was allowed to warm to rt over 2 h and stirred overnight. The reaction was quenched with satd. NaHCO$_3$ (5 mL), diluted with DCM (10 mL). The organic layer was separated, washed with water, brine and dried (MgSO$_4$). Evaporation of solvents afforded tert-butyl ((1,2-dimethoxyprop-1-en-1-yl)oxy)dimethylsilane as a clear oil and used in the next step without further purification.

Neat BF$_3$.OEt$_2$ (0.152 mL, 1.200 mmol) was added dropwise to a cold (−40° C.) stirred solution of 4,4-difluorocyclohexanone (0.134 g, 1 mmol) and tert-butyl((1,2-dimethoxyprop-1-en-1-yl)oxy)dimethylsilane (0.311 g, 1.338 mmol) in an. DCM (2 mL) and the mixture was gradually allowed to warm to rt overnight. The reaction was quenched with satd. NaHCO$_3$, diluted with DCM (10 mL). The organic layer was separated, washed with water, brine and dried (MgSO$_4$). Evaporation of solvents afforded a light brown oil (238 mg) which was purified by silica gel FCC (5% EtOAC in DCM) to afford methyl 2-(4,4-difluoro-1-hydroxycyclohexyl)-2-methoxypropanoate as a clear oil (177 mg). $^1$H NMR (500 MHz, CHLOROFORM-d) δ ppm 3.79 (s, 3H), 3.34 (s, 3H), 2.89 (br. s., 1H), 2.26-2.03 (m, 2H), 2.00-1.91 (m, 2H), 1.87-1.60 (m, 4H), 1.45 (s, 3H).

A small sample (~37 mg) of the methyl ester was saponified (LiOH.H$_2$O, MeOH-THF-water) to afford Cap P-26 as a off-white semi-solid (35 mg). $^1$H NMR (500 MHz, CHLOROFORM-d) δ ppm 3.40 (s, 3H), 2.25-2.06 (m, 2H), 2.05-1.95 (m, 2H), 1.94-1.67 (m, 4H), 1.47 (s, 3H).

Cap P-27

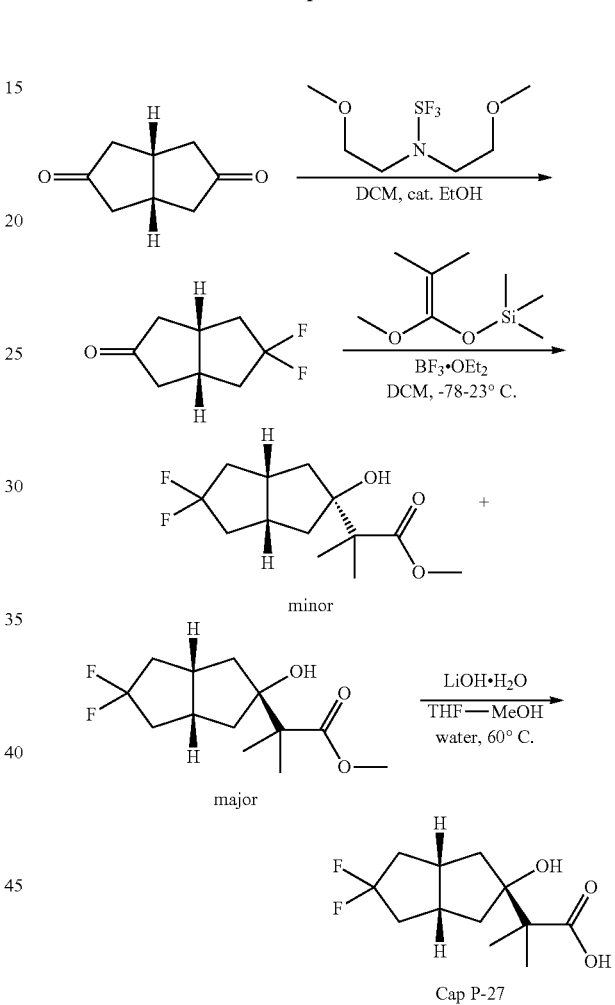

Cap P-27

A solution of Deoxo-Fluor® (0.737 mL, 4.00 mmol) in DCM (4 ml) was added to a cold (0° C.) solution of (3as,6as)-tetrahydropentalene-2,5(1H,3H)-dione (276 mg, 2 mmol) in DCM (20 mL) followed by addition of a catalytic amount of EtOH (0.035 mL, 0.600 mmol). The resulting yellowish solution was stirred at rt overnight. The reaction was quenched with sat. aq. NaHCO$_3$ and the mixture was extracted with DCM (2×). The combined organic layers were washed with water, brine and dried (MgSO$_4$), filtered and dried to give a yellow-orange oil. The desired difluorinated mono-ketone, (3aR,6aS)-5,5-difluorohexahydropentalen-2(1H)-one was isolated by silica gel FCC (DCM) as a colorless oil.

Neat BF$_3$.OEt$_2$ (0.104 ml, 0.819 mmol) was added dropwise to a cold (−78° C.) stirred solution of (3aR,6aS)-5,5-difluorohexahydropentalen-2(1H)-one (82 mg, 0.512 mmol) and ((1-methoxy-2-methylprop-1-en-1-yl)oxy)trimethylsilane (198 mg, 1.024 mmol) in an. DCM (1 mL) and the mixture was gradually allowed to warm to rt and stirred overnight. The reaction was quenched with satd. NaHCO₃ (5 mL), diluted with DCM (10 mL), then the organic layer separated and washed with 0.25 M aq. HF, water, brine and dried (MgSO₄). Evaporation of solvents afforded a clear oil which was purified by silica gel FCC (0-2% EtOAc in DCM). The major isomer methyl 2-((2s,3aR,6aS)-5,5-difluoro-2-hydroxyoctahydropentalen-2-yl)-2-methylpropanoate was isolated as a colorless oil.

A stirred solution of methyl 2-((3aR,6aS)-5,5-difluoro-2-hydroxyoctahydropentalen-2-yl)-2-methylpropanoate (58 mg, 0.221 mmol) and lithium hydroxide monohydrate (27.8 mg, 0.663 mmol) in THF (0.5 mL), MeOH (0.5 mL) and water (0.5 mL) was heated at 60° C. overnight. Acidic workup and EtOAc extraction afforded Cap P-27 as a off-white solid.

Cap P-28 & P-29

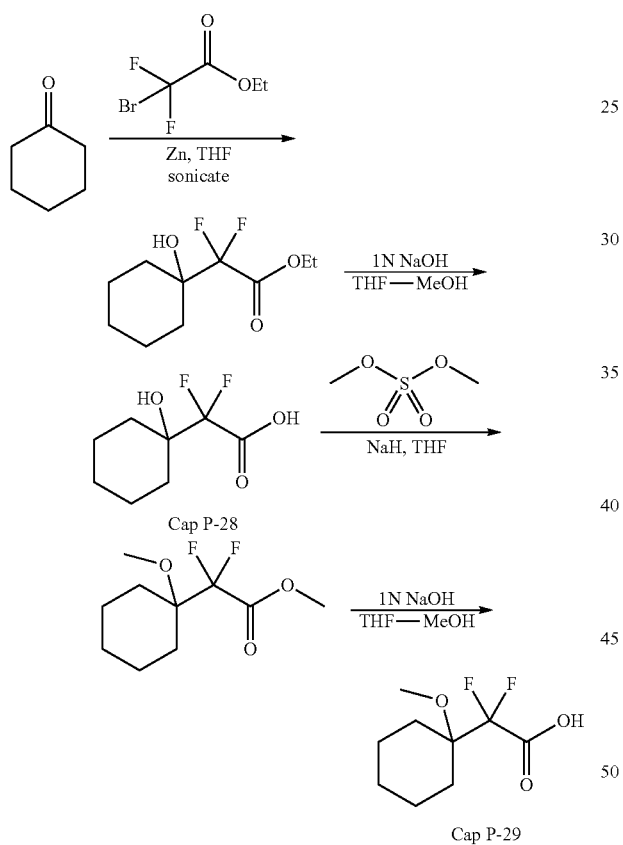

Cap P-28

Cap P-29

A stirred suspension of zinc (0.981 g, 15.01 mmol) in a solution of cyclohexanone (0.491 g, 5.0 mmol) and ethyl 2-bromo-2,2-difluoroacetate (2.031 g, 10.01 mmol) in an. THF (5 mL) was sonicated for 4-5 h and then heated to reflux for 1-2 h. The reaction mixture was cooled and diluted with ether and washed with 1 N HCl, satd. NaHCO₃, water, brine and dried (MgSO₄). Evaporation of solvents afforded an oil which was purified by silica gel FCC (5-10% EtOAc in DCM) to afford ethyl 2,2-difluoro-2-(1-hydroxycyclohexyl)acetate as a clear oil (770 mg, ~70%). ¹H NMR (500 MHz, CHLOROFORM-d) δ ppm 4.37 (q, J=7.2 Hz, 2H), 2.10-2.01 (m, J=3.4 Hz, 1H), 1.82-1.69 (m, 3H), 1.68-1.54 (m, 6H), 1.38 (t, J=7.2 Hz, 3H), 1.20 (br. s, 1H).

The ethyl ester was saponified (1 N NaOH, THF-MeOH, rt) to afford Cap P-28 as a white solid. ¹H NMR (500 MHz, CHLOROFORM-d) δ 4.34 (br. s., 2H), 1.89-1.53 (m, 8H), 1.32-1.17 (m, 1H).

60% NaH (88 mg, 2.204 mmol) was added to a cold (0° C.) solution of Cap P-28 (194.5 mg, 1.002 mmol) in THF (2 mL) and the mixture was stirred for ~30 min and then dimethyl sulfate (0.227 mL, 2.404 mmol) was added. The mixture was allowed to warm to rt and stirred overnight. The crude product was purified by silica gel FCC (DCM) to afford methyl 2,2-difluoro-2-(1-methoxycyclohexyl)acetate as a clear oil. ¹H NMR (500 MHz, CHLOROFORM-d) δ ppm 3.90 (s, 3H), 3.39 (t, J=1.7 Hz, 3H), 2.04-1.97 (m, 2H), 1.73-1.66 (m, J=13.0, 1.5, 1.5 Hz, 1H), 1.66-1.59 (m, J=8.5, 2.7 Hz, 2H), 1.54-1.44 (m, 4H), 1.27-1.17 (m, J=12.8 Hz, 1H).

The methyl ester intermediate was saponified (1 N NaOH, THF-MeOH, rt) to afford Cap P-29 as a white solid.

Cap P-30

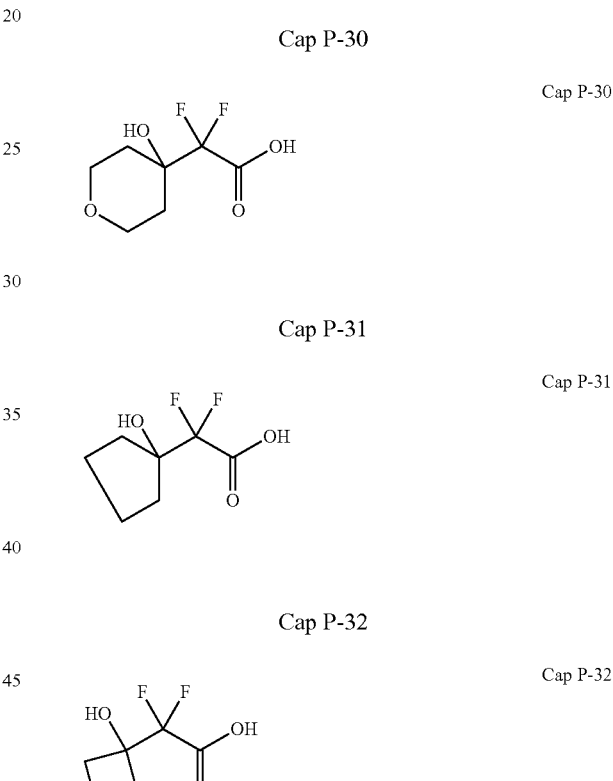

Cap P-30

Cap P-31

Cap P-31

Cap P-32

Cap P-32

Caps P-30, P-31 and P-32 were prepared by using the method described in Cap P-28.

Cap P-33

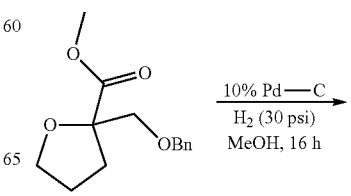

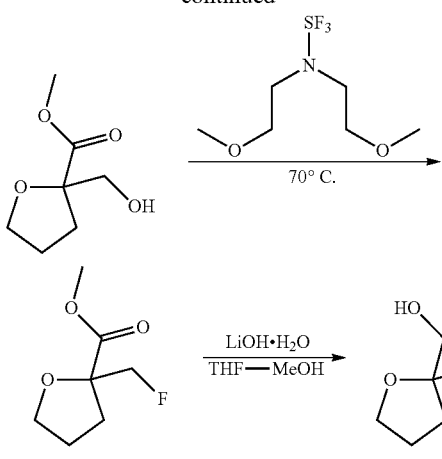

Cap P-33

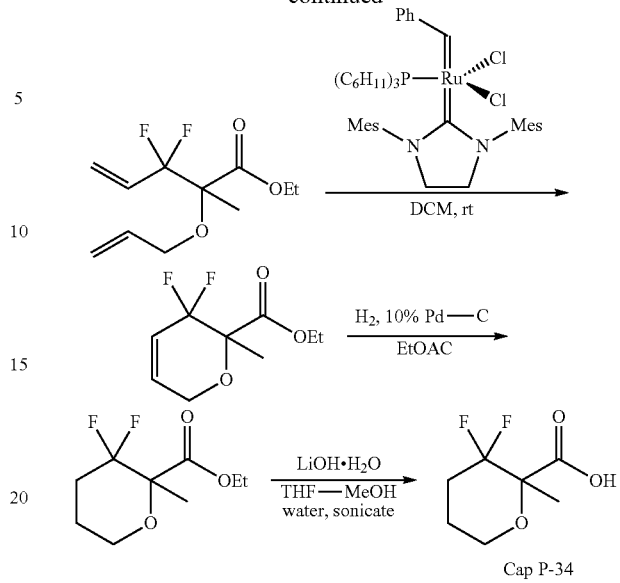

Cap P-34

10% Pd—C (80 mg, 0.753 mmol) was added under nitrogen to a solution of methyl 2-((benzyloxy)methyl)tetrahydrofuran-2-carboxylate (377 mg, 1.506 mmol) in MeOH (20 mL) in a Parr shaker bottle and hydrogenated at 30 psi overnight. The suspension was filtered and the filtrate was evaporated to dryness to afford methyl 2-(hydroxymethyl)tetrahydrofuran-2-carboxylate as a clear oil (0.43 g, 97.5%). $^1$H NMR (500 MHz, CHLOROFORM-d) δ ppm 4.10-3.98 (m, 2H), 3.85 (d, J=11.4 Hz, 1H), 3.78 (s, 3H), 3.69 (d, J=11.4 Hz, 1H), 2.19-2.12 (m, 1H), 2.09-2.02 (m, 1H), 2.01-1.93 (m, 2H).

A neat stirred mixture of Deoxo-Fluor® (800 mg, 1.808 mmol) and ethyl 4,4-difluoro-1-(hydroxymethyl)cyclohexanecarboxylate (224 mg) was heated at 70° C. overnight. The reaction was cooled to rt and quenched with ice and extracted with DCM, washed with satd. NaHCO$_3$, water, brine and dried (MgSO$_4$). Evaporation of DCM gave a light brown oil which was purified by silica gel FCC (1:2 hexanes-DCM) to afford methyl 2-(fluoromethyl)tetrahydrofuran-2-carboxylate as a colorless oil (184 mg, 82%).

A solution of LiOH.H$_2$O (42 mg, 1 mmol) in water (0.5 mL) was added to a solution of ethyl 4,4-difluoro-1-(fluoromethyl)cyclohexanecarboxylate (180 mg, 0.80 mmol) in THF (1 mL) and MeOH (1 mL) and the mixture was stirred at rt overnight. After acidic workup product was extracted with EtOAc, washed with brine and dried (MgSO$_4$). Evaporation of solvents afforded Cap P-33 as a white solid.

Cap P-34

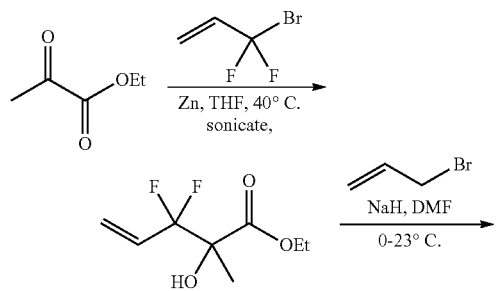

A stirred suspension of zinc (294 mg, 4.50 mmol) in a solution of ethyl 2-oxopropanoate (348 mg, 3 mmol) and 3-bromo-3,3-difluoroprop-1-ene (565 mg, 3.60 mmol) in an. THF (3 mL) was sonicated for ~30 min and then heated at 40° C. overnight. The reaction mixture was cooled in an ice-bath and diluted with ether (20 mL) and stirred with 1 N HCl (10 mL). The layers were separated, and the organic phase was washed with water, satd. NaHCO$_3$, water, brine and dried (Na$_2$SO$_4$). The crude product was purified by silica gel FCC (DCM) to afford ethyl 3,3-difluoro-2-hydroxy-2-methylpent-4-enoate as a clear oil.

60% NaH (48.5 mg, 1.212 mmol) was added to a cold (–20° C.) solution of ethyl 3,3-difluoro-2-hydroxy-2-methylpent-4-enoate (214 mg, 1.102 mmol) in DMF (2 mL) and the mixture was allowed to warm to rt (~30 min) and then 3-bromoprop-1-ene (0.113 mL, 1.323 mmol) was added. The mixture was stirred at rt overnight, diluted with ether (20 mL) and washed with water, brine and dried (MgSO$_4$). The crude product was purified by silica gel FCC (2:1 DCM-hexanes) to afford ethyl 2-(allyloxy)-3,3-difluoro-2-methylpent-4-enoate as a clear oil.

A stirred de-gas solution of ethyl 2-(allyloxy)-3,3-difluoro-2-methylpent-4-enoate (165 mg, 0.704 mmol) and Grubbs II (29.9 mg, 0.035 mmol) in DCM (20 mL) was stirred at rt overnight. The reaction mixture was evaporated to dryness and purified by silica gel FCC (2% EtOAc in hexanes) to afford ethyl 3,3-difluoro-2-methyl-3,6-dihydro-2H-pyran-2-carboxylate as a clear oil (~138 mg, 95%). $^1$H NMR (500 MHz, CHLOROFORM-d) δ ppm 6.26-6.20 (m, J=10.5, 2.4, 2.4 Hz, 1H), 5.96-5.87 (m, 1H), 4.57-4.48 (m, 1H), 4.36-4.26 (m, 3H), 1.60 (s, 3H), 1.33 (t, J=7.2 Hz, 3H).

A stirred suspension of 10% Pd—C (37.5 mg, 0.035 mmol) in a solution of ethyl 3,3-difluoro-2-methyl-3,6-dihydro-2H-pyran-2-carboxylate in EtOAc (10 mL) was hydrogenated under balloon pressure for 1 h. The suspension filtered and evaporated to dryness to yield ethyl 3,3-difluoro-2-methyltetrahydro-2H-pyran-2-carboxylate as a clear oil (136 mg, 96%). $^1$H NMR (400 MHz, CHLOROFORM-d) δ ppm 4.35-4.24 (m, 2H), 3.89-3.80 (m, 1H), 3.78-3.69 (m, 1H), 2.34-2.09 (m, 2H), 2.03-1.90 (m, 1H), 1.85-1.75 (m, 1H), 1.57-1.51 (m, J=1.5, 0.5 Hz, 3H), 1.34 (t, J=7.2 Hz, 3H).

The ethyl ester intermediate was dissolved in THF (2 mL) and MeOH (1.5 mL) and treated with a solution of lithium hydroxide monohydrate (59.1 mg, 1.409 mmol) in water (1.5 mL) and the mixture was sonicated for 2 h. The reaction mixture was evaporated, acidified and extracted with EtOAc to afford Cap P-34 as a clear viscous oil. $^1$H NMR (500 MHz, CHLOROFORM-d) δ ppm 3.96-3.89 (m, 1H), 3.88-3.80 (m, 1H), 2.29-2.18 (m, 1H), 2.17-2.07 (m, 1H), 2.00-1.87 (m, 2H), 1.64 (t, J=1.2 Hz, 3H).

Cap P-35

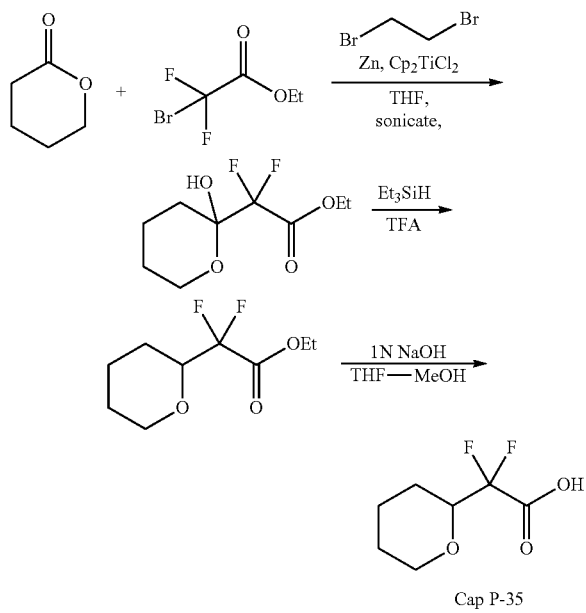

Cap P-35

Neat 1,2-dibromoethane (0.094 g, 0.500 mmol) was added to a suspension of zinc (1.308 g, 20.00 mmol) in THF (7 mL). The reaction mixture was sonicated for 3 h and cooled to rt and was added with titanocene dichloride (0.062 g, 0.250 mmol) and stirred for 10-15 min. A solution of tetrahydro-2H-pyran-2-one (0.501 g, 5 mmol) in THF (3 ml) was added, then followed by addition of a solution of ethyl 2-bromo-2,2-difluoroacetate (1.218 g, 6.0 mmol) in THF (3 mL) and the mixture was stirred at rt overnight. The reaction was cooled (0° C.) and diluted with ether and washed with 1 N HCl, water, brine and dried (MgSO$_4$). Evaporation of solvents afforded an oil which was purified by silica gel FCC (5-10% EtOAc in DCM) to afford ethyl 2,2-difluoro-2-(2-hydroxytetrahydro-2H-pyran-2-yl)acetate as a clear oil (365 mg, 32.5%). A neat mixture of ethyl 2,2-difluoro-2-(2-hydroxytetrahydro-2H-pyran-2-yl)acetate (~200 mg), triethylsilane (0.799 mL, 5.00 mmol) and TFA (0.385 mL, 5.00 mmol) was heated at 60° C. for 3 h and evaporated to dryness to afford an oil which was purified by silica gel FCC (DCM0 to yield ethyl 2,2-difluoro-2-(tetrahydro-2H-pyran-2-yl)acetate as a clear oil (145 mg, 78%) which was saponified (1 N NaOH, THF-MeOH, rt) to provide Cap P-35 as a white solid (75 mg, 83%). $^1$H NMR (500 MHz, CHLOROFORM-d) δ ppm 7.35-7.13 (m, 1H), 4.14-4.05 (m, J=11.2, 4.3 Hz, 1H), 3.95-3.82 (m, 1H), 3.57-3.47 (m, J=11.7, 11.7, 2.3 Hz, 1H), 2.05-1.94 (m, 1H), 1.86-1.76 (m, 1H), 1.73-1.50 (m, 4H).

Cap P-36

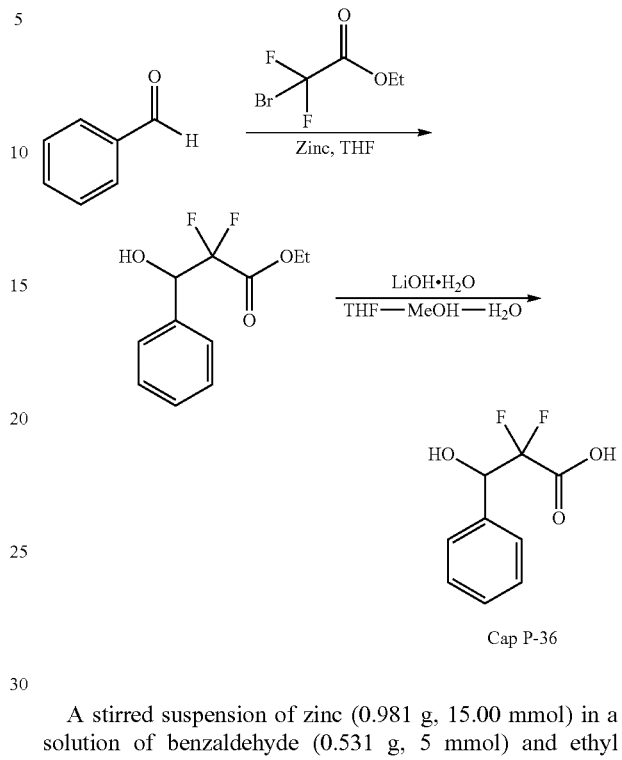

Cap P-36

A stirred suspension of zinc (0.981 g, 15.00 mmol) in a solution of benzaldehyde (0.531 g, 5 mmol) and ethyl 2-bromo-2,2-difluoroacetate (1.522 g, 7.50 mmol) in an. THF (10 mL) was sonicated for 4-5 h and then stirred at rt overnight. The reaction was cooled and diluted with ether and washed with 1 N HCl, water, brine and dried (MgSO$_4$). Evaporation of solvents afforded a clear oil which was purified by silica gel FCC (0-10% EtOAc in DCM) to afford ethyl 2,2-difluoro-3-hydroxy-3-phenylpropanoate as a clear oil (619 mg, ~54%). $^1$H NMR (500 MHz, CHLOROFORM-d) δ ppm 7.49-7.44 (m, 2H), 7.43-7.39 (m, 3H), 5.23-5.12 (m, J=15.3, 8.0, 5.5 Hz, 1H), 4.32 (q, J=7.1 Hz, 2H), 2.87-2.76 (m, 1H), 1.31 (t, J=7.2 Hz, 3H).

The ethyl ester intermediate was saponified (LiOH.H$_2$O, THF-MeOH-water) to afford Cap P-36 as a white solid. $^1$H NMR (500 MHz, CHLOROFORM-d) δ ppm 7.52-7.47 (m, 2H), 7.46-7.41 (m, 3H), 5.22 (dd, J=16.0, 7.2 Hz, 1H).

Cap P-37

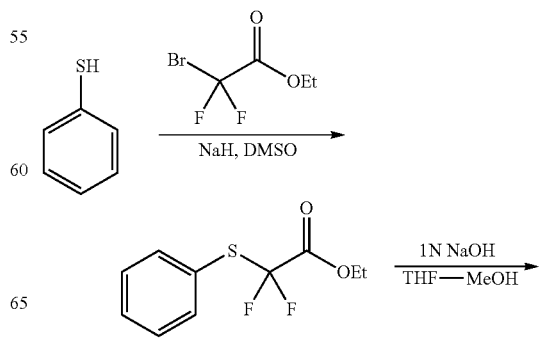

-continued

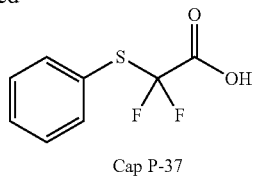

Cap P-37

60% NaH (0.233 g, 5.81 mmol) was added to a cold (0° C.) solution of thiophenol (0.566 mL, 5.54 mmol) in DMSO (6 mL) and the reaction mixture was allowed to warm to rt over 30 min. Then neat ethyl 2-bromo-2,2-difluoroacetate (1.236 g, 6.09 mmol) was added and the mixture was stirred at rt overnight. The reaction was quenched with satd. $NH_4Cl$ and extracted with ether, washed with water, brine and dried ($MgSO_4$). The crude isolate was purified by silica gel FCC (1:1 DCM-hexanes) to afford ethyl 2,2-difluoro-2-(phenylthio)acetate as a clear oil (1.076 g, 84%): $^1$H NMR (500 MHz, CHLOROFORM-d) δ 7.67-7.62 (m, 2H), 7.52-7.46 (m, 1H), 7.45-7.39 (m, 2H), 4.27 (q, J=7.2 Hz, 2H), 1.28 (t, J=7.2 Hz, 3H).

The ethyl ester intermediate was saponified (1N NaOH, MeOH-THF) to afford to Cap P-37 as a tan solid. $^1$H NMR (500 MHz, CHLOROFORM-d) δ ppm 8.43 (br. s., 1H), 7.72-7.61 (m, 2H), 7.55-7.47 (m, 1H), 7.46-7.40 (m, 2H).

Cap P-38

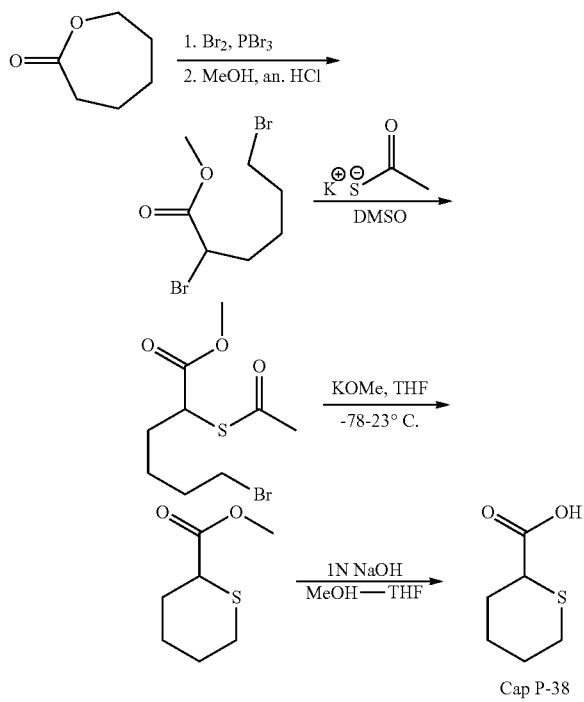

Cap P-38

Neat dibromine (16.78 g, 105 mmol) was added dropwise to a stirred mixture of epsilon-caprolactone (11.41 g, 100 mmol) and tribromophosphine (0.05 ml, 100 μmol) at 100° C. while keeping the pot temperature below 120° C. by the rate $Br_2$ addition. The heating was continued until HBr evolution ceased. The crude mixture was cooled in an ice-bath, diluted with MeOH (100 mL), saturated with HCl and stirred at rt overnight. Excess MeOH was evaporated and the residue was extracted with 1:1 ether-hexanes and dried over $MgSO_4$, concentrated and distilled under reduced pressure to afford methyl 2,6-dibromohexanoate as a clear oil (bp 75-80° C. @ ~1 torr).

Neat potassium ethanethioate (571 mg, 5 mmol) was added to a solution of methyl 2,6-dibromohexanoate (1440 mg, 5 mmol) in DMSO (5 mL) and the mixture was stirred at rt overnight. The reaction was quenched with water and extracted with ether, washed with water, brine and dried ($MgSO_4$). The crude isolate was purified by silica gel FCC (DCM) to afford methyl 2-(acetylthio)-6-bromohexanoate as a clear oil.

Neat potassium methoxide (133 mg, 1.893 mmol) was added to a solution of methyl 2-(acetylthio)-6-bromohexanoate (536 mg, 1.893 mmol) in an. THF (18 mL) and the mixture was stirred at rt for 2 days under nitrogen. The crude isolate was purified by silica gel FCC (DCM) to afford methyl tetrahydro-2H-thiopyran-2-carboxylate as a clear oil which was saponified (1N NaOH, MeOH-THF) to afford Cap P-38.

Cap P-39

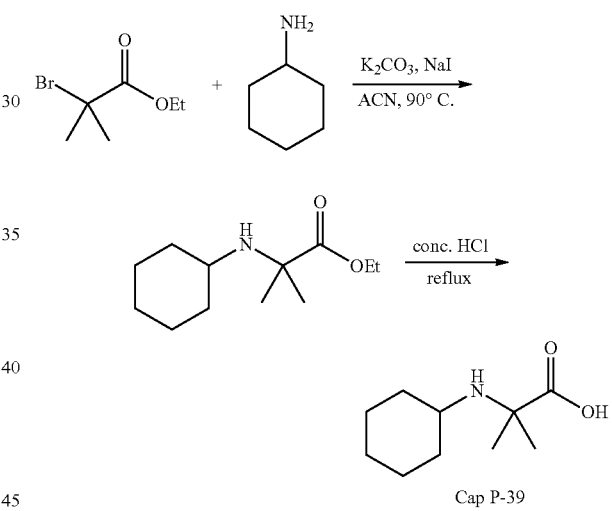

Cap P-39

A stirred suspension of ethyl 2-bromo-2-methylpropanoate (0.975 g, 5 mmol), cyclohexanamine (0.496 g, 5.00 mmol), potassium carbonate (1.382 g, 10.00 mmol) and sodium iodide (0.600 g, 4.00 mmol) in acetonitrile (10 ml) was heated at 90° C. overnight under nitrogen. The reaction mixture was cooled, filtered and evaporated to dryness and then purified by silica gel FCC (5% EtOAc in DCM) to afford ethyl 2-(cyclohexylamino)-2-methylpropanoate as a clear oil (215 mg, ~20%). $^1$H NMR (500 MHz, CHLOROFORM-d) δ ppm 4.16 (q, J=7.2 Hz, 2H), 2.38-2.29 (m, 1H), 1.86-1.78 (m, 2H), 1.74-1.67 (m, J=13.5, 3.4, 3.4 Hz, 2H), 1.66-1.55 (m, 2H), 1.31 (s, 6H), 1.30-1.27 (m, 3H), 1.27-1.19 (m, 2H), 1.15-1.04 (m, 2H).

The ethyl ester intermediate was hydrolyzed by refluxing in conc. HCl for 3 h and then evaporated to dryness to yield Cap P-39. $^1$H NMR (500 MHz, CHLOROFORM-d) δ ppm 3.02 (br. s., 1H), 2.27-2.17 (m, 2H), 1.89-1.83 (m, 2H), 1.83-1.78 (m, 1H), 1.76 (s, 6H), 1.73-1.63 (m, 2H), 1.34-1.16 (m, 4H).

Cap P-40

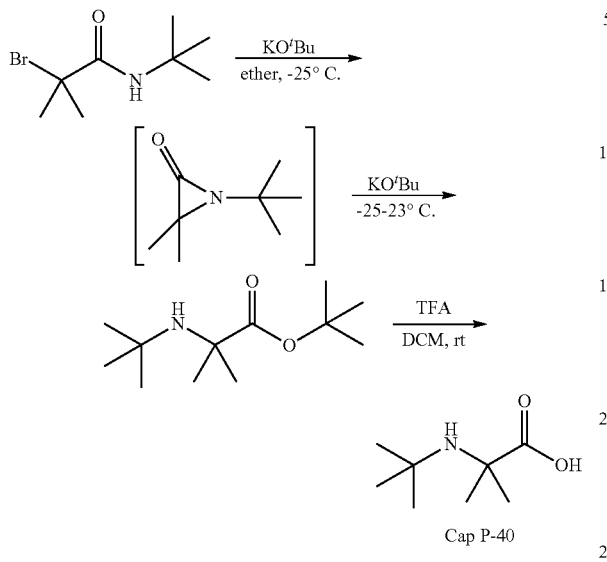

Cap P-40

A 1M solution of potassium tert-butoxide (3.00 mL, 3.00 mmol) in THF was added to a cold (0° C.) stirred solution of 2-bromo-N-(tert-butyl)-2-methylpropanamide (0.666 g, 3 mmol) in an. ether (30 mL) and the mixture was stirred at 0° C. for 2-3 h. Then 2nd equivalent of potassium tert-butoxide (3.00 mL, 3.00 mmol) was added and the mixture allowed to warm to rt and stirred overnight. The reaction was quenched with satd. NH$_4$Cl, the organic layer was separated and washed with water, brine and dried (Na$_2$SO$_4$). The crude isolate was purified by silica gel FCC (3% MeOH in DCM) to afford tert-butyl 2-(tert-butylamino)-2-methylpropanoate (365 mg) as a light brown oil. $^1$H NMR (500 MHz, CHLOROFORM-d) δ ppm 1.93 (br. s, 7H), 1.46 (s, 9H), 1.14 (s, 9H).

The tert-butyl ester intermediate dissolved in DCM and treated with TFA for 1 h and then evaporated to dryness to afford Cap P-40. $^1$H NMR (500 MHz, CHLOROFORM-d) δ ppm 1.98-1.92 (brd s, 6H), 1.50 (s, 9H).

Cap P-41

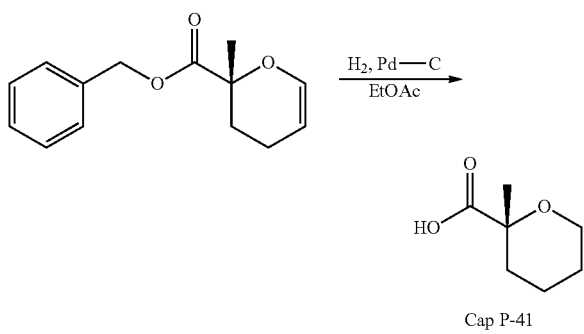

Cap P-41

A stirred suspension of 10% Pd—C (45.8 mg, 0.043 mmol) in a solution of (R)-benzyl 2-methyl-3,4-dihydro-2H-pyran-2-carboxylate (200 mg, 0.861 mmol) in EtOAc (10 mL) was hydrogenated in a Parr shaker bottle under 50 psi overnight. The suspension was filtered and evaporated to dryness to afford Cap P-41 as a clear oil.

Cap P-42

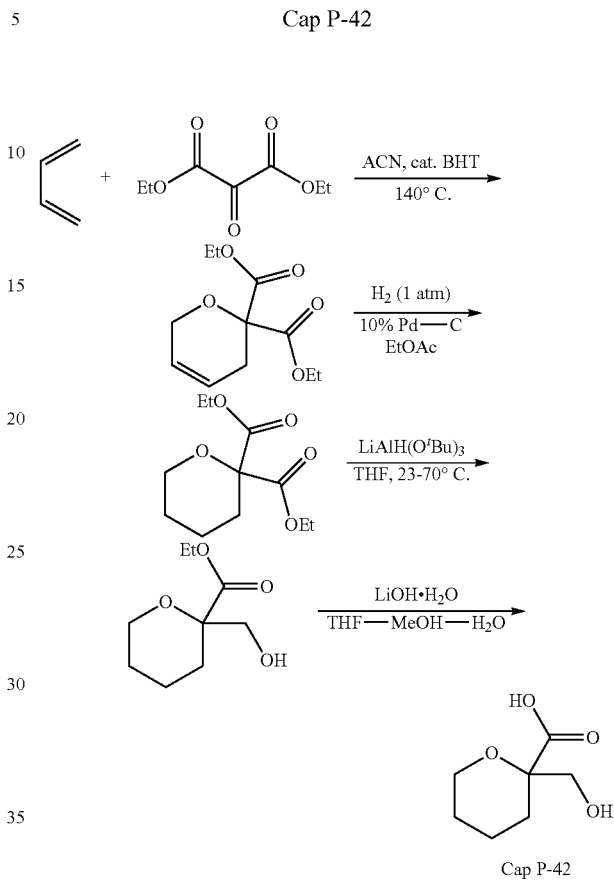

Cap P-42

Buta-1,3-diene (9.68 g, 179 mmol) gas was condensed by bubbling through a cold (−60° C.) stirred solution of diethyl 2-oxomalonate (5 g, 28.7 mmol) and few crystals of BHT in acetonitrile (50 mL) in a stainless steel Hoke cylinder. The cylinder was capped and sealed and heated at 140° C. for 24 h. The reaction mixture was cooled to rt and concentrated to half volume, then 25 ml of ethanol was added. The precipitated solid was filtered off and the filtrate was evaporated to dryness to afford a light yellow viscous oil (5.89 g) which was purified by silica gel FCC (DCM) to afford diethyl 2H-pyran-2,2(3H,6H)-dicarboxylate as a clear oil. $^1$H NMR (400 MHz, CHLOROFORM-d) δ ppm 5.85 (ddt, J=10.3, 4.0, 2.0 Hz, 1H), 5.77-5.67 (m, 1H), 4.45-4.37 (m, 2H), 4.35-4.23 (m, 4H), 2.76-2.67 (m, 2H), 1.33-1.28 (m, 6H).

A stirred suspension of 10% Pd—C (0.511 g, 0.480 mmol) in a solution of diethyl 2H-pyran-2,2(3H,6H)-dicarboxylate (2.74 g, 12.00 mmol) in EtOAc (50 mL) was hydrogenated under balloon pressure for 3 h. The suspension was filtered and the filtrate was evaporated to dryness to afford diethyl tetrahydro-2H-pyran-2,2-dicarboxylate as a clear oil. $^1$H NMR (400 MHz, CHLOROFORM-d) δ ppm 4.33-4.24 (m, 4H), 3.88-3.81 (m, 2H), 2.15-2.08 (m, 2H), 1.79-1.69 (m, 2H), 1.67-1.57 (m, 2H), 1.33-1.28 (m, 6H).

A 1M solution of lithium tri-tert-butoxyaluminum hydride (8.79 mL, 8.79 mmol) was added dropwise to a cold (0° C.) stirred solution of diethyl tetrahydro-2H-pyran-2,2-dicarboxylate (0.810 g, 3.52 mmol) in an. THF (9 mL). After the addition is complete the mixture was allowed to warm to rt and heated to reflux for 4-5 h. The reaction mixture was cooled, diluted with ether and quenched with 20% NaHSO₄ solution with vigorous stirring. The organic layer was separated, washed with brine and dried over MgSO₄. The crude isolate was purified by silica gel FCC (5% MeOH in DCM) to afford ethyl 2-(hydroxymethyl)tetrahydro-2H-pyran-2-carboxylate as a clear oil. ¹H NMR (400 MHz, CHLOROFORM-d) δ ppm 4.29 (q, J=7.0 Hz, 2H), 3.95-3.87 (m, 2H), 3.71 (dd, J=11.2, 8.2 Hz, 1H), 3.62 (dd, J=11.2, 5.1 Hz, 1H), 2.24-2.16 (m, J=8.0, 5.3 Hz, 1H), 2.14-2.06 (m, 1H), 1.84-1.72 (m, 1H), 1.64-1.50 (m, 4H), 1.37-1.29 (m, 3H).

A stirred solution of ethyl 2-(hydroxymethyl)tetrahydro-2H-pyran-2-carboxylate (52 mg, 0.276 mmol) and lithium hydroxide monohydrate (39 mg, 0.929 mmol) in THF (1 mL), MeOH (0.5 mL) and water (0.5 mL) was sonicated for 1-2 h. Solvents were evaporated and the aqueous residue was acidified with 6 N HCl (0.5 mL) and extracted with EtOAc, washed with brine and dried (MgSO₄). Evaporation of solvents afforded Cap P-42 as a viscous oil. ¹H NMR (400 MHz, CHLOROFORM-d) δ ppm 3.98-3.83 (m, 2H), 3.83-3.69 (m, 2H), 2.38 (s, 1H), 2.16-2.05 (m, 1H), 1.79 (br. s., 1H), 1.66-1.47 (m, 4H).

Cap P-43

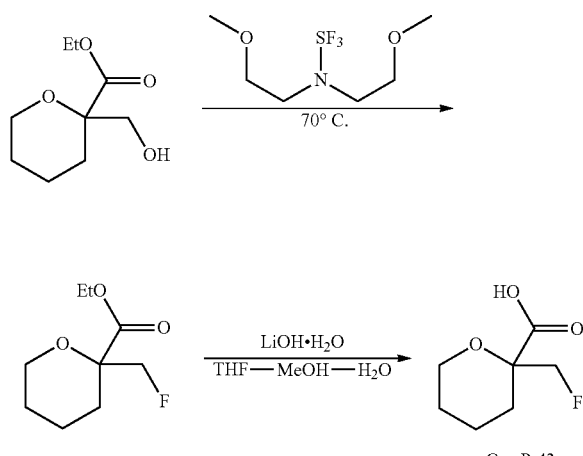

Neat Deoxo-Fluor® (342 mg, 1.546 mmol) was added to a cold (0° C.) stirred ethyl 2-(hydroxymethyl)tetrahydro-2H-pyran-2-carboxylate (194 mg, 1.031 mmol) and the mixture was heated at 70° C. overnight. The reaction was quenched with ice and neutralized with sat. aq. NaHCO₃ and extracted with DCM (2×). The combined organic layers were washed with water, brine and dried (MgSO₄), filtered and dried to give a yellow-orange oil which was purified by silica gel FCC (0-5% EtOAc in DCM) to afford ethyl 2-(fluoromethyl)tetrahydro-2H-pyran-2-carboxylate as a colorless oil (125 mg, 63%) which was saponified (LiOH.H₂O, MeOH-THF—H₂O, sonicate) to afford Cap P-43 as a viscous oil (82 mg, 77%). ¹H NMR (400 MHz, CHLOROFORM-d) δ ppm 4.66-4.54 (m, 1H), 4.54-4.41 (m, 1H), 4.02-3.84 (m, 2H), 1.98-1.84 (m, 1H), 1.84-1.72 (m, 2H), 1.69-1.52 (m, 4H).

Cap P-44

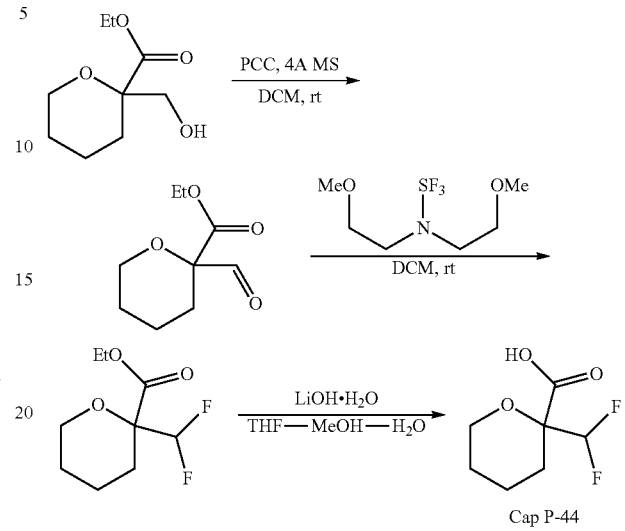

Neat PCC was added to a stirred suspension of powdered 4 Å molecular sieve (~0.5 g) in a solution of ethyl 2-(hydroxymethyl)tetrahydro-2H-pyran-2-carboxylate (165 mg, 0.877 mmol) in DCM (6 mL) and the mixture was stirred at rt 5 h. The suspension was filtered through a plug of silica gel and eluted with (0-2% EtOAc in DCM) afford ethyl 2-formyltetrahydro-2H-pyran-2-carboxylate. ¹H NMR (400 MHz, CHLOROFORM-d) δ ppm 9.53 (s, 1H), 4.35-4.20 (m, 2H), 3.97-3.77 (m, 2H), 2.23-2.12 (m, 1H), 1.90-1.77 (m, 1H), 1.77-1.69 (m, 1H), 1.64-1.56 (m, 3H), 1.32 (t, J=7.2 Hz, 3H).

Neat Deoxo-Fluor® (196 mg, 0.886 mmol) was added to a solution of ethyl 2-formyltetrahydro-2H-pyran-2-carboxylate (55 mg, 0.295 mmol) in DCM (1 mL) and the mixture was stirred at rt overnight. The reaction was quenched with ice cold satd. NaHCO₃ and extracted with DCM, washed with water, brine and dried (MgSO₄). The crude isolate was purified by silica gel FCC (DCM) to afford ethyl 2-(difluoromethyl)tetrahydro-2H-pyran-2-carboxylate as a clear oil. ¹H NMR (500 MHz, CHLOROFORM-d) δ ppm 5.70 (t, J=1.0 Hz, 1H), 4.33 (q, J=7.2 Hz, 2H), 4.03-3.93 (m, 1H), 3.73 (td, J=12.1, 2.7 Hz, 1H), 2.26-2.17 (m, 1H), 1.91-1.80 (m, 1H), 1.73-1.62 (m, 2H), 1.59-1.47 (m, 2H), 1.38-1.30 (m, 3H).

The ethyl ester intermediate was saponified (LiOH.H₂O, MeOH-THF—H₂O, sonicate) to afford Cap P-44 as a viscous oil.

Cap P-45

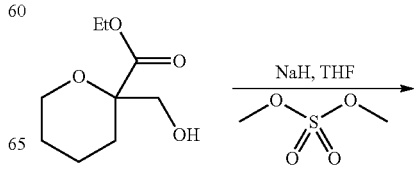

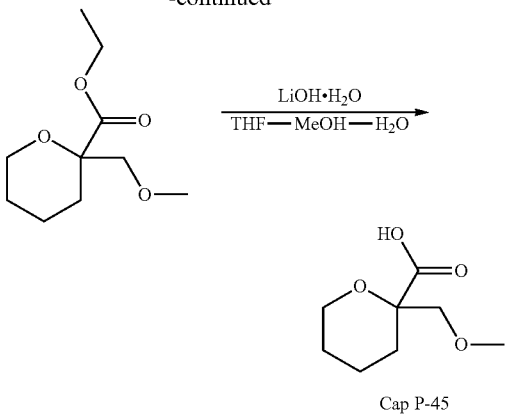

Cap P-45

60% NaH (40.3 mg, 1.007 mmol) was added to a cold (−20° C.) solution of ethyl 2-(hydroxymethyl)tetrahydro-2H-pyran-2-carboxylate (158 mg, 0.839 mmol) in THF (3 mL) and the mixture was allowed to warm to rt over ~30 min. Neat dimethyl sulfate (127 mg, 1.007 mmol) was added at 0° C. and allowed to warm to rt and stirred overnight. Excess dimethyl sulfate was quenched with TEA, and then acidified with 1N HCl, product was extracted with ether, washed with water, brine and dried (MgSO$_4$). Crude isolate was purified by silica gel FCC (0-2% MeOH in DCM) to afford ethyl 2-(methoxymethyl)tetrahydro-2H-pyran-2-carboxylate. $^1$H NMR (400 MHz, CHLOROFORM-d) δ ppm 4.34-4.22 (m, J=7.2, 7.2, 7.2, 4.1 Hz, 2H), 3.96-3.87 (m, 1H), 3.86-3.77 (m, 1H), 3.55-3.43 (m, 2H), 3.36 (s, 3H), 2.17-2.07 (m, 1H), 1.80-1.70 (m, 1H), 1.69-1.56 (m, 2H), 1.55-1.42 (m, 3H), 1.32 (t, J=7.2 Hz, 3H).

The ethyl ester intermediate was saponified (LiOH·H$_2$O, THF-MeOH—H$_2$O) to afford Cap P-45 as a viscous oil (59 mg, 40%). $^1$H NMR (400 MHz, CHLOROFORM-d) δ ppm 3.99-3.88 (m, 1H), 3.87-3.76 (m, 1H), 3.69-3.58 (m, 1H), 3.58-3.48 (m, 1H), 3.41 (s, 3H), 2.16-2.02 (m, 1H), 1.80-1.69 (m, 1H), 1.67-1.47 (m, 4H).

Cap L-18

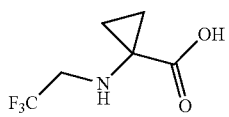

Cap L-18

Step a

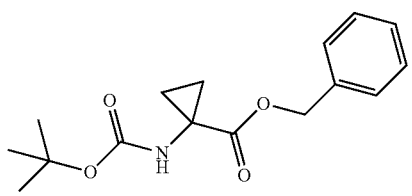 [SMILES: CC(C)(C)OC(=O)NC1(C(=O)OCc2ccccc2)CC1]

To a solution of 1-((tert-butoxycarbonyl)amino)cyclopropanecarboxylic acid (2, 9.94 mmol) and Et$_3$N (3.32 mL, 23.85 mmol) in DMF (40 mL) was added benzyl bromide (2.84 mL, 23.85 mmol) dropwise and the resulting mixture was stirred at rt for 16 h. After diluting with EtOAc (40 mL) and water (75 mL), the aqueous layer was separated and back-extracted with EtOAc (50 mL). The combined organic layers were washed with sat. NH$_4$Cl, water and brine, dried (MgSO$_4$), filtered and concentrated to give an off-white solid. The residue was purified by flash chromatography (10% EtOAc/hexanes) to give a white solid corresponding to Cap L-18 Step a (1.81 g). $^1$H NMR (400 MHz, CDCl$_3$) δ 7.45-7.28 (m, 5H), 5.14 (s, 2H), 1.56 (br. s., 2H), 1.42 (br. s., 9H), 1.19 (br. s., 2H); $^{13}$C NMR (101 MHz, CDCl$_3$) δ 172.9, 155.9, 135.7, 128.5 (3C), 128.1, 127.9, 80.0, 67.0, 34.4, 28.2 (3C), 17.9 (2C).

Cap L-18

Step b

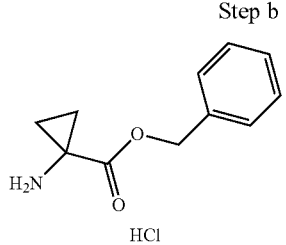

HCl (7.77 mL, 31.1 mmol, 2N in dioxanes) was added to a solution of to Cap L-18 Step a (1.81 g, 6.21 mmol) in DCM (25 mL) and the resulting solution was stirred at rt for 2 h. Volatiles were removed under reduced pressure and the remaining residue was triturated with Et2O. An off-white solid corresponding to Cap L-18 Step b, HCl (1.39 g) was isolated and used without further purification. $^1$H NMR (400 MHz, DMSO-d$_6$) δ 9.11 (br. s., 3H), 7.47-7.30 (m, 5H), 5.20 (s, 2H), 1.54-1.47 (m, 2H), 1.46-1.39 (m, 2H); $^{13}$C NMR (101 MHz, DMSO-d$_6$) δ 169.5, 135.3, 128.5 (2C), 128.3, 127.9 (2C), 67.1, 33.6, 13.4 (2C).

Cap L-18

Step c

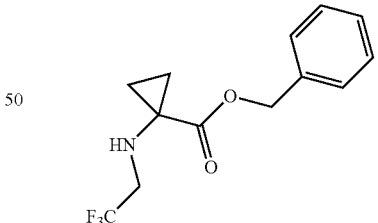

1-ethoxy-2,2,2-trifluoroethanol (0.172 mL, 1.318 mmol) was added to a suspension of Cap L-18 Step b, HCl (300 mg, 1.318 mmol) and MgSO$_4$ (1063 mg, 8.83 mmol) in DCM (10 mL), followed by addition of TFA (0.531 mL, 6.89 mmol). The white suspension was then stirred at room temperature for 16 h. NaCNBH$_3$ (166 mg, 2.64 mmol) was then added and stirring continued for another 3 h. The reaction was filtered and the filtrate was diluted with EtOAc (50 mL), washed with water (50 mL), and brine (50 mL), dried over MgSO$_4$, filtered, and concentrated in vacuo. A clear oil was recovered. The residue was purified by flash chromatography (10%

EtOAc/Hexanes) and a clear oil corresponding to Cap L-18 Step c (100 mg)) was isolated. $^1$H NMR (400 MHz, CDCl$_3$) δ 7.45-7.30 (m, 5H), 5.15 (s, 2H), 3.44-3.30 (m, 2H), 2.45 (br. s., 1H), 1.40-1.34 (m, 2H), 1.16-1.10 (m, 2H); $^{19}$F NMR (376 MHz, CDCl$_3$) δ −73.13 (s, 3F); $^{13}$C NMR (101 MHz, CDCl$_3$) δ 174.8, 128.6 (2C), 128.3, 128.0 (2C), 125.0 (q, J=278.2 Hz, 1C), 66.8, 49.5 (q, J=32.4 Hz, 1C), 41.3, 18.1 (2C).

To a solution of benzyl Cap L-18 Step c (100 mg, 0.366 mmol) in MeOH (3 mL) was added 10% Pd—C (20 mg, 0.019 mmol) and the mixture was hydrogenated at 1 atm of H$_2$ for 16 h. The mixture was filtered and washed with MeOH. The combined filtrate was concentrated to dryness to yield Cap L-18 (63 mg) as a white solid. $^1$H NMR (400 MHz, DMSO-d$_6$) δ 3.38 (q, J=10.5 Hz, 2H), 1.16-1.10 (m, 2H), 0.91 (q, J=3.8 Hz, 2H); $^{19}$F NMR (376 MHz, DMSO-d$_6$) δ −71.30 (br. s., 3F); $^{13}$C NMR (101 MHz, DMSO-d$_6$) δ 176.2, 125.7 (q, J=276.7 Hz, 1C), 48.5 (q, J=30.8 Hz, 1C), 40.4, 17.0 (2C).

Cap L-19

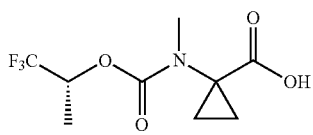

Cap L-19

Step a

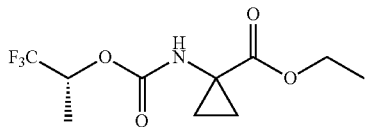 [SMILES: CCOC(=O)C1(NC(=O)O[C@H](C)C(F)(F)F)CC1]

Cap L-19 Step a was prepared by employing the procedures described for the synthesis of Cap L-6 Step a starting from (R)-1,1,1-trifluoropropan-2-ol and ethyl 1-aminocyclopropanecarboxylate hydrochloride. $^1$H NMR (500 MHz, CDCl$_3$) δ 5.46 (br. s., 1H), 5.29-5.18 (m, 1H), 4.16 (q, J=6.9 Hz, 2H), 1.57 (br. s., 2H), 1.41 (d, J=6.6 Hz, 3H), 1.30-1.12 (m, 5H); $^{19}$F NMR (376 MHz, CDCl$_3$) δ −79.02 (br. s., 3F); $^{13}$C NMR (126 MHz, CDCl$_3$) δ 172.3, 154.7, 123.6 (q, J=280.4 Hz, 1C), 67.6 (q, J=34.3 Hz, 1C), 61.6, 34.6, 17.6 (br. s., 2C), 14.0, 13.7.

Cap L-19

Step b

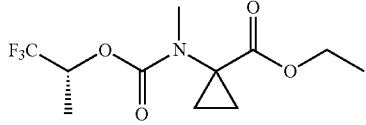

KOtBu (0.173 g, 1.538 mmol) was added to a solution of Cap L-19 Step a (0.36 g, 1.337 mmol) in DMF (10 mL) and the resulting solution was stirred at rt for 45 min. The reaction was quenched with sat NaCO$_3$ (10 mL) and the mixture was then extracted with Et$_2$O (3×). The combined organic layers were washed with brine, dried (MgSO$_4$), filtered and concentrated. The residue was purified by flash chromatography (10% EtOAc/Hexanes) and a clear oil corresponding to Cap L-19 Step b (0.21 g) was isolated. $^1$H NMR (400 MHz, CDCl$_3$) δ 5.31-5.18 (m, 1H), 4.20-4.11 (m, 2H), 2.96 (s, 3H), 1.59 (br. s., 1H), 1.45-1.32 (m, 4H), 1.24 (t, J=7.0 Hz, 3H), 1.31-1.13 (m, 5H); $^{19}$F NMR (376 MHz, CDCl$_3$) δ −79.13 (br. s., 3F) minor rotamer: −78.96; $^{13}$C NMR (101 MHz, CDCl$_3$) δ 172.2 (s, 2C), 155.6, 124.2 (q, J=267.4 Hz, 1C), 68.67-67.71 (m, 1C), 61.4, 41.3, 35.3, 21.2, 17.3 (br. s., 1C), 14.0, 13.8 (br. s., 1C) minor rotamer: 172.0, 155.3, 67.9, 42.2.

To a solution of Cap L-19 Step b (0.21 g, 0.741 mmol) in THF (7 mL) was added a solution of LiOH (36 mg, 1.483 mmol) in water (3 mL) and the resulting mixture was stirred at rt for 72 h. The reaction mixture was diluted with H$_2$O (7 mL) and washed with Et$_2$O (10 mL). The aqueous layer was then acidified with 1 N HCl to pH ~2 and extracted with EtOAc. The combined organic layers were dried (MgSO$_4$), filtered and concentrated to give Cap L-19 (0.18 g). $^1$H NMR (500 MHz, CDCl$_3$) δ 5.27-5.20 (m, 1H), 2.97 (s, 3H), 1.45-1.35 (m, 7H).

Cap L-20

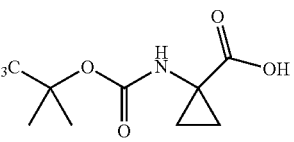

Cap L-20 was prepared by employing the procedures described for the synthesis of Cap L-6 starting from 1,1,1-trifluoro-2-methylpropan-2-ol. $^1$H NMR (400 MHz, DMSO-d$_6$) δ 7.92 (br. s., 1H), 1.60 (s, 6H), 1.26 (br. s., 2H), 0.97 (br. s., 2H).

Cap L-21

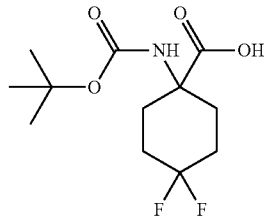 [SMILES: CC(C)(C)OC(=O)NC1(C(=O)O)CCC(F)(F)CC1]

Cap L-21

Step a

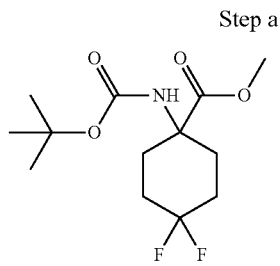

Deoxo-Fluor® (0.449 mL, 2.433 mmol) was added to a solution of methyl 1-((tert-butoxycarbonyl)amino)-4-oxocyclohexanecarboxylate (300 mg, 1.106 mmol) in DCM (15 mL), followed by addition of a catalytic amount of EtOH (0.032 mL, 0.553 mmol) and the resulting solution was stirred at room temperature for 16 h. The reaction was quenched with sat. NaHCO₃ and extracted with DCM (2×). The combined organic layers were washed with water, brine and dried (MgSO₄), filtered and evaporated to provide a yellow-orange oil, which was purified by flash chromatography (20% EtOAc/hexanes) to afford Cap L-21 Step a as a colorless oil (619 mg). ¹H NMR (400 MHz, CDCl₃) δ 3.72 (s, 3H), 2.18-2.07 (m, 4H), 2.07-1.88 (m, 4H), 1.41 (s, 9H); ¹⁹F NMR (376 MHz, CDCl₃) δ -94.27 (d, J=227.3 Hz, 1F), -101.43 (d, J=227.1 Hz, 1F); ¹³C NMR (101 MHz, CDCl₃) δ 174.0, 155.2 (s, 2C), 122.2 (t, J=242.0 Hz, 2C), 80.4 (br. s., 1C), 57.6, 52.4, 29.75-29.47 (m, 2C), 29.4, 29.1, 28.2 (s, 3C).

A solution of LiOH (22.86 mg, 0.955 mmol) in Water (3 mL) was added to a solution of Cap L-21 Step a (140 mg, 0.477 mmol) in THF (5 mL) and the resulting mixture was stirred at room temperature for 3 h. The mixture was diluted with H₂O (10 mL) and washed with E₂O (10 mL). The aqueous layer was then acidified with 1N HCl to pH ~2 and extracted with EtOAc (3×10 mL). The combined organic layers were dried (MgSO4), filtered and concentrated, to give a white solid corresponding to Cap L-21 (50 mg) which was used without further purification. ¹H NMR (400 MHz, DMSO-d₆) δ 12.48 (br. s., 1H), 7.45-7.21 (m, 1H), 2.10 (br. s., 2H), 1.98-1.78 (m, 6H), 1.38 (s, 9H).

Cap L-22

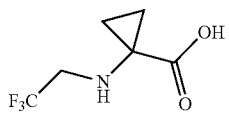 [SMILES: O=C(O)C1(NCC(F)(F)F)CC1]

Cap L-22 was prepared by employing the procedures described for the synthesis of Cap L-18 starting from (2-((tert-butoxycarbonyl)amino)-2-methylpropanoic acid. ¹H NMR (500 MHz, DMSO-d₆) δ 7.41 (br. s., 1H), 3.18 (q, J=10.1 Hz, 2H), 1.19 (s, 6H); ¹⁹F NMR (376 MHz, DMSO-d₆) δ -71.13 (s, 3F).

Cap L-23

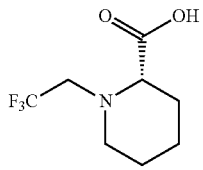 [SMILES: O=C(O)[C@@H]1CCCCN1CC(F)(F)F]

Cap L-23

Step a

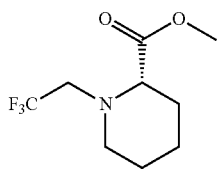

A solution of (S)-methyl piperidine-2-carboxylate, HCl (0.5 g, 2.78 mmol), 2,2,2-trifluoroethyl trifluoromethanesulfonate (0.802 mL, 5.57 mmol) and DIEA (1.458 mL, 8.35 mmol) in DMF (20 mL) was heated to 50° C. for 24 h. Volatiles were removed under reduced pressure and the residue was purified by flash chromatography (15% EtOAc/Hex). A clear oil corresponding to Cap L-23 step a (0.385 g) was isolated. ¹H NMR (400 MHz, CDCl₃) δ 3.71 (s, 3H), 3.55 (t, J=4.8 Hz, 1H), 3.22-3.03 (m, 3H), 2.71 (dt, J=11.2, 4.4 Hz, 1H), 1.98 (dq, J=13.3, 4.4 Hz, 1H), 1.87-1.77 (m, 1H), 1.64-1.48 (m, 3H), 1.33-1.23 (m, 1H); ¹⁹F NMR (376 MHz, CDCl₃) δ -71.28 (s, 3F); ¹³C NMR (101 MHz, CDCl₃) δ 173.5, 125.7 (q, J=279.7 Hz, 1C), 62.8, 57.0 (q, J=30.8 Hz, 1C), 51.5, 50.3, 28.8, 25.5, 20.9.

LiOH (0.082 g, 3.42 mmol) in Water (3 mL) was added to a solution of Cap L-23 step a (0.385 g, 1.710 mmol) in THF (10 mL) at 0° C. and the resulting mixture was stirred at rt for 3 h. The mixture was then diluted with H2O (10 mL) and washed with Et₂O (10 mL). The aqueous layer was then acidified with a 10% aq. citric acid solution and extracted with EtOAc (3×10 ml). The combined organic layers were dried (MgSO₄), filtered and concentrated under reduced pressure to give a white solid corresponding to Cap L-23 (0.35 g) which was used without further purification. ¹H NMR (400 MHz, DMSO-d₆) δ 12.51 (br. s., 1H), 3.50 (t, J=4.3 Hz, 1H), 3.44-3.16 (m, 3H), 3.00 (t, J=10.7 Hz, 1H), 2.63 (d, J=11.3 Hz, 1H), 2.00-1.83 (m, 1H), 1.73-1.59 (m, 1H), 1.57-1.40 (m, 3H), 1.24-1.07 (m, 1H); ¹⁹F NMR (376 MHz, DMSO-d₆) δ -70.03 (s, 3F); ¹³C NMR (101 MHz, DMSO-d₆) δ 174.0, 129.59-117.32 (m, J=234.3, 234.3, 234.3 Hz, 1C), 61.8, 56.0 (q, J=29.3 Hz, 1C), 49.4, 28.3, 25.2, 20.6.

Cap L-24

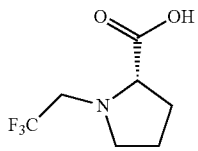 [SMILES: O=C(O)[C@@H]1CCCN1CC(F)(F)F]

Cap L-24 was prepared by employing the procedures described for the synthesis of Cap L-22 starting from (S)-benzyl pyrrolidine-2-carboxylate hydrochloride. ¹H NMR (400 MHz, CDCl₃) δ 9.37 (br. s., 1H), 3.54 (dd, J=9.4, 3.6 Hz, 1H), 3.43-3.18 (m, 3H), 2.83-2.68 (m, 1H), 2.31-2.17 (m, 1H), 2.14-2.01 (m, 1H), 1.99-1.77 (m, 2H); ¹⁹F NMR (376 MHz, CDCl₃) δ -70.35 (s, 3F); ¹³C NMR (101 MHz, CDCl₃) δ 175.7, 124.8 (q, J=276.7 Hz, 1C), 66.7, 55.8 (q, J=31.6 Hz, 1C), 55.2, 30.2, 24.5.

Cap L-25

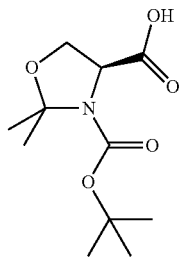 [SMILES: CC(C)(C)OC(=O)N1[C@H](C(=O)O)COC1(C)C]

A solution of LiOH (0.046 g, 1.928 mmol) in water (2 mL) was added to a solution of (S)-3-tert-butyl 4-methyl 2,2-dimethyloxazolidine-3,4-dicarboxylate (0.5 g, 1.928 mmol) in THF (6 mL). The resulting mixture was stirred at rt for 48 h, acidified to pH 4 with a 1 N aqueous solution of hydrochloric acid and extracted three times with ethyl acetate. The combined organic phases were dried (MgSO₄), filtered and concentrated under vacuum to afford Cap L-25 (0.2 g) as a yellow oil. Used without further purification. ¹H NMR (400 MHz, DMSO-d₆, mixture of rotomers) δ 12.72 (br. s., 1H), 4.33-4.23 (m, 1H), 4.18-4.09 (m, 1H), 3.93 (dt, J=9.0, 3.3 Hz, 1H), 1.56-1.51 (m, 3H), 1.42 (s, 7H), 1.39-1.33 (m, 6H); ¹³C NMR (101 MHz, DMSO-d₆, mixture of rotomers) δ 172.32-171.83 (m), 150.7, 93.76-93.42 (m), 79.66-79.01 (m), 65.94-65.54 (m), 58.79-58.57 (m), 28.05-27.74 (m, 3C), 24.93-24.75 (m), 24.16-23.99 (m).

Cap L-26

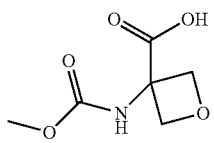

Cap L-26 was prepared by employing the procedures described for the synthesis of Cap L-3 starting from 3-aminooxetane-3-carboxylic acid. ¹H NMR (400 MHz, CDCl₃) δ 5.04 (d, J=6.5 Hz, 2H), 4.81 (d, J=8.0 Hz, 2H), 3.73 (s, 3H); ¹³C NMR (101 MHz, CDCl₃) δ 174.1, 152.8, 76.6, 58.2, 54.5.

Cap L-27

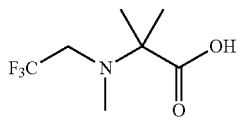

Cap L-27 was prepared by employing the procedures described for the synthesis of Cap L-18 starting from 2-((tert-butoxycarbonyl)(methyl)amino)-2-methylpropanoic acid. ¹H NMR (400 MHz, DMSO-d₆) δ 3.30-3.22 (m, 2H), 2.42 (s, 3H), 1.26 (s, 6H); ¹⁹F NMR (376 MHz, DMSO-d₆) δ −70.48 (s, 3F); ¹³C NMR (101 MHz, DMSO-d₆) δ 176.9, 126.0 (q, J=268.2 Hz, 1C), 62.1, 53.0 (d, J=30.1 Hz, 1C), 39.00-38.91 (m, 1C), 24.8 (s, 2C).

Cap L-28

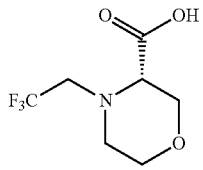

Cap L-28

Step a

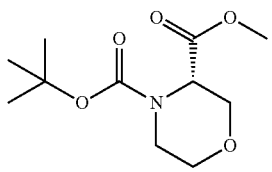 [SMILES: COC(=O)[C@@H]1COCCN1C(=O)OC(C)(C)C]

TMS-Diazomethane (2M in Et2O) (2.011 mL, 4.02 mmol) was added dropwise to a solution of (S)-4-(tert-butoxycarbonyl)morpholine-3-carboxylic acid (0.93 g, 4.02 mmol) in benzene (20 mL) and MeOH (15 mL) until the solution remained yellow and no more gas evolution was observed. The solvent was removed under reduced pressure and a clear oil corresponding to Cap L-28 step a (0.96 g) was isolated. Used without further purification. ¹H NMR (400 MHz, CDCl₃, mixture of rotomers) δ 4.60-4.21 (m, 2H), 3.89 (d, J=10.5 Hz, 1H), 3.77 (s, 3H), 3.74-3.66 (m, 1H), 3.63 (dd, J=11.8, 3.8 Hz, 1H), 3.53-3.41 (m, 1H), 3.36-3.13 (m, 1H), 1.46 (d, J=15.1 Hz, 9H); ¹³C NMR (101 MHz, CDCl₃, mixture of rotomers) δ 170.98-170.37 (m, 1C), 155.7 (br. s., 1C), 80.6, 68.09-66.99 (m, 1C), 66.81-66.19 (m, 1C), 55.71-53.50 (m, 1C), 52.3, 42.46-39.94 (m, 1C), 28.2 (br. s., 3C).

Cap L-28

Step b

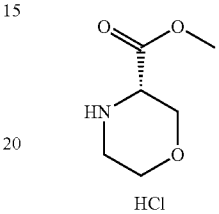

HCl (5.10 mL, 20.39 mmol) was added dropwise to a solution of Cap L-28 step a (1 g, 4.08 mmol) in DCM (30 mL) and the mixture was stirred at rt for 3 h. Solvent was removed under reduced pressure and a white solid corresponding to Cap L-28 step b, HCl (0.73 g) was isolated. Used without further purification. ¹H NMR (400 MHz, DMSO-d₆) δ 4.37 (dd, J=7.5, 3.5 Hz, 1H), 4.08 (dd, J=12.4, 3.9 Hz, 1H), 3.94-3.84 (m, 2H), 3.82-3.75 (m, 4H), 3.28-3.20 (m, 1H), 3.15-3.03 (m, 1H); ¹³C NMR (101 MHz, DMSO-d₆) δ 166.6, 64.5, 62.9, 53.7, 53.0, 41.6.

Cap L-28 was then prepared by employing the procedures described for the synthesis of Cap L-23. ¹H NMR (400 MHz, DMSO-d₆) δ 12.75 (br. s., 1H), 4.03 (d, J=11.3 Hz, 1H), 3.71 (d, J=10.8 Hz, 1H), 3.66-3.57 (m, 1H), 3.54-3.27 (m, 4H), 3.23-3.09 (m, 1H), 2.56 (d, J=9.8 Hz, 1H); ¹⁹F NMR (376 MHz, DMSO-d₆) δ −70.22 (br. s., 3F); ¹³C NMR (101 MHz, DMSO-d₆) δ 172.3, 132.72-118.59 (q, J=277.4, Hz, 1C), 68.5, 66.5, 61.2, 56.22-55.26 (t, J=30.1 Hz, 1C), 48.3.

Cap L-29

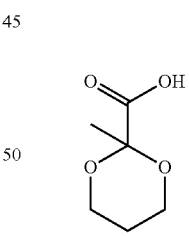

A mixture of 2-oxopropanoic acid (1.200 mL, 17.03 mmol), propane-1,3-diol (1.834 mL, 25.6 mmol) and Amberlite 15 (2 g, 17.03 mmol) in benzene (50 mL) was heated at reflux in a Dean-Stark apparatus for 16 h. After cooling, the reaction mixture was filtrated and concentrated under reduced pressure. The residue was redissolved in 2 M aqueous NaOH (10 mL) and heated to reflux for 2 h. The reaction mixture was then acidified to pH=1 with an ice-cold 6M aq. solution of H₃PO₄ and rapidly extracted with EtOAc (3×). The combined organic layers were dried (MgSO₄), filtered and concentrated under vacuum to yield a yellowish oil corresponding to Cap L-29, which solidified upon standing. ¹H NMR (400 MHz, CDCl₃) δ 4.08-3.98 (m, 2H), 3.97-3.88 (m, 2H), 2.18-2.07 (m, 1H), 1.57 (s, 2H), 1.41 (dd, J=13.6, 1.5 Hz, 1H); $^{13}$C NMR (101 MHz, CDCl$_3$) δ 175.2, 98.1, 63.2 (s, 2C), 26.0, 24.4.

Cap L-30

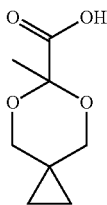

Cap L-30 was prepared by employing the procedures described for the synthesis of Cap L-29 starting from cyclopropane-1,1-diyldimethanol. $^1$H NMR (400 MHz, DMSO-d$_6$) δ 13.10 (br. s., 1H), 4.06 (d, J=11.8 Hz, 2H), 3.07 (d, J=12.0 Hz, 2H), 1.38 (s, 3H), 0.62-0.51 (m, 2H), 0.33-0.27 (m, 2H); $^{13}$C NMR (101 MHz, DMSO-d$_6$) δ 171.4, 97.7, 69.0 (s, 2C), 25.6, 16.5, 12.8, 4.4.

Cap L-31

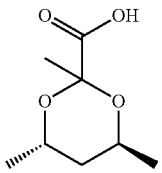

Cap L-31

Step a

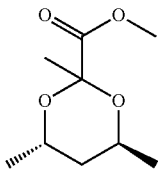

To a solution of methyl 2-oxopropanoate (0.867 mL, 9.60 mmol) and (2S,4S)-pentane-2,4-diol (0.5 g, 4.80 mmol) in MeCN (15 mL) was added dropwise BF$_3$.OEt$_2$ (1.217 mL, 9.60 mmol) and the mixture was stirred at rt for 24 h. The reaction was carefully quenched with sat aq. NaHCO$_3$ and stirred at rt for 30 min. The volumen of the reaction mixture was reduced under vacuum to one third of its original volumen and then extracted with CH$_2$Cl$_2$ (3×10 mL) and the combined organic layers were dried (MgSO$_4$), filtered and concentrated under vacuum. A yellow oil was recovered and purified by flash chromatography (10% EtOAc/Hex). A clear oil corresponding to Cap L-31 step a (0.32 g) was recovered. $^1$H NMR (400 MHz, CDCl$_3$) δ 4.20-4.03 (m, 2H), 3.76 (s, 3H), 1.73-1.64 (m, 1H), 1.59-1.50 (m, 1H), 1.48 (s, 3H), 1.23 (dd, J=6.3, 2.0 Hz, 6H); $^{13}$C NMR (101 MHz, CDCl$_3$) δ 172.0, 97.1, 65.6, 64.7, 52.3, 38.4, 25.0, 21.6, 20.2.

A solution of Cap L-31 step a (0.27 g, 1.434 mmol) and NaOH (0.258 g, 6.46 mmol) in THF (10 mL) and H$_2$O (5 mL) was stirred at rt for 3 h. The reaction mixture was concentrated under vacuo and the remaining aqueous layer was acidified with cold 6 N H$_3$PO$_4$ to pH=2 and quickly extracted with EtOAc (3×). The combined organic layers were dried (MgSO$_4$), filtered and concentrated to give a yellow oil corresponding to Cap L-31 (0.22 g). Used without further purification. $^1$H NMR (400 MHz, DMSO-d$_6$) δ 4.17-4.00 (m, 2H), 1.63-1.53 (m, 1H), 1.53-1.45 (m, 1H), 1.32 (s, 3H), 1.16 (d, J=6.8 Hz, 3H), 1.11 (d, J=6.3 Hz, 3H); $^{13}$C NMR (101 MHz, DMSO-d$_6$) δ 172.7, 96.1, 65.1, 63.8, 37.7, 25.0, 21.6, 20.2.

Cap L-32

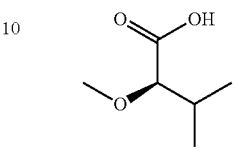

Cap L-32

Step a

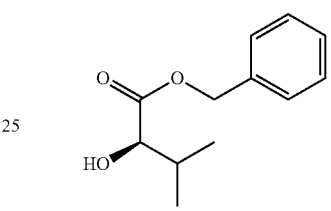

DBU (1.021 mL, 6.77 mmol) was added to a solution of (R)-2-hydroxy-3-methylbutanoic acid (0.8 g, 6.77 mmol) and benzyl bromide (1.390 g, 8.13 mmol) in DMF (10 mL) and the resulting yellowish solution was stirred at rt for 16 h. The mixture was then taken up in EtOAc (50 mL) and water (30 ml) and the organic layer was separated. The aqueous layer was extracted with EtOAc and the combined organic layers were washed with brine, dried (MgSO$_4$), filtered and concentrated to give a clear oil. The residue was purified by flash chromatography (10% EtOAc/Hexanes). A clear oil corresponding to Cap L-32 step a (1.3 g) was recovered. $^1$H NMR (400 MHz, CDCl$_3$) δ 7.44-7.31 (m, 5H), 5.30-5.17 (m, 2H), 4.10 (dd, J=6.1, 3.4 Hz, 1H), 2.73 (dd, J=6.1, 1.9 Hz, 1H), 2.11 (dtd, J=13.8, 6.9, 3.5 Hz, 1H), 1.02 (d, J=7.0 Hz, 3H), 0.84 (d, J=7.0 Hz, 3H); $^{13}$C NMR (101 MHz, CDCl$_3$) δ 174.8, 135.2, 128.6 (s, 2C), 128.5, 128.4 (s, 2C), 75.0, 67.3, 32.2, 18.8, 15.9.

Cap L-32

Step b

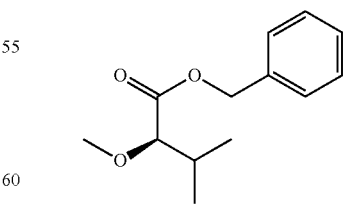

Silver (I) oxide (1.113 g, 4.80 mmol) was added to a solution of Cap L-32 step a (0.5 g, 2.401 mmol) and MeI (0.751 mL, 12.00 mmol) in E$_2$O (10 mL) and the suspension was stirred at 40° C. for 72 h. The suspension was filtered through a glass fiber filter to remove the silver salts and concentrated under reduced pressure. A clear oil was recovered and this residue was purified by flash chromatography (2% EtOAc/Hexanes). A clear oil corresponding to Cap L-32 step b (0.14 g) was recovered. ¹H NMR (400 MHz, CDCl₃) δ 7.42-7.30 (m, 5H), 5.26-5.16 (m, 2H), 3.56 (d, J=5.5 Hz, 1H), 3.38 (s, 3H), 2.07 (quind, J=6.8, 5.5 Hz, 1H), 0.95 (d, J=4.5 Hz, 3H), 0.93 (d, J=4.3 Hz, 3H); ¹³C NMR (101 MHz, CDCl₃) δ 172.1, 135.7, 128.5 (s, 2C), 128.3 (s, 2C), 128.3, 85.9, 66.3, 58.5, 31.5, 18.6, 17.5.

Pd/C (0.029 g, 0.027 mmol) was added to a solution of Cap L-32 step b (0.12 g, 0.540 mmol) in EtOAc (5 mL) and the mixture was placed under 1 atm of H₂ (1.088 mg, 0.540 mmol) (balloon) and stirred at rt for 3 h. The catalyst was filtered though a pad of Celite and concentrated under vacuum. A clear oil corresponding to Cap L-32 (0.07 g) was recovered. ¹H NMR (400 MHz, CDCl₃) δ 8.78 (br. s., 1H), 3.56 (d, J=4.8 Hz, 1H), 3.41 (s, 3H), 2.09 (dq, J=11.8, 6.8 Hz, 1H), 1.00 (d, J=7.0 Hz, 3H), 0.95 (d, J=6.8 Hz, 3H); ¹³C NMR (101 MHz, CDCl₃) δ 177.3, 85.4, 58.8, 31.3, 18.6, 17.2.

Cap L-33

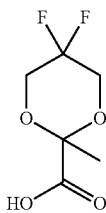

Cap L-33

Step a

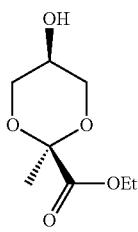

To a mixture of ethanol (15 mL) and NaOEt (21% in Ethano-1, 1.619 mL, 4.34 mmol) was added solid (1s,4s)-1-methyl-2,5,7-trioxabicyclo[2.2.2]octan-6-one (2.5 g, 17.35 mmol, obtained from methyl pyruvate and glycerol according to the method of Gellas and Thiallier, *Carbohydrate Research*, 1973, 20, 21) forming a clear solution. The mixture was stirred at RT for 16 hours. To this ethanolic solution was added at rt 2.5 mL wet volume of the acidic form of dowex resin (50 W 8X-200) and stirring continued for 30 minutes before it was removed by filtration. The filtrate was dried under high vacuum to give a yellow syrup corresponding to Cap L-33 step a (2.5 g) which was used without further purification. ¹H NMR (400 MHz, CDCl₃) δ 4.79-4.76 (m, 1H), 4.29 (q, J=7.3 Hz, 2H), 4.12-4.10 (m, 1H), 4.07-4.01 (m, 2H), 3.93-3.84 (m, 1H), 3.52-3.43 (m, 2H), 1.50 (s, 3H), 1.33 (t, J=7.2 Hz, 3H); ¹³C NMR (101 MHz, CDCl₃) δ 170.0, 97.8, 67.5 (s, 2C), 61.9, 61.1, 24.3, 14.1.

Cap L-33

Step b

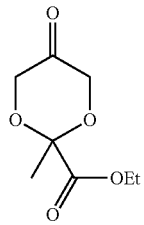

Oxalyl dichloride (1.376 mL, 15.77 mmol) was added to a 250 ml RBF containing DCM (25 mL) at −78° C. The mixture was re-cooled to −78° C., and DMSO (1.213 mL, 17.09 mmol) was added dropwise at a rate slow enough to allow for proper venting of evolving gases. The mixture was stirred at −78° C. for 30 min, followed by addition of Cap L-33 step a (2.5 g, 13.14 mmol) in DCM (10 mL). Stirring continued at −78° C. for 45 min before the reaction mixture was treated with Et₃N (4.40 mL, 31.5 mmol). The resulting white suspension was stirred at −78° C. for 30 min and then at 0° C. from another 30 min. The reaction was quenched with 50 ml of sat. aqueous NaHCO₃ and the aqueous layer was extracted with DCM (4×20 mL). The combined organic layers were dried (MgSO₄) and concentrated under reduced pressure to give a clear yellow oil. The residue was purified by flash chromatography (15% EtOAc/Hexanes) to give Cap L-33 step b (0.54 g) as a clear oil. ¹H NMR (400 MHz, CDCl₃) δ 4.42-4.34 (m, 2H), 4.28 (q, J=7.2 Hz, 2H), 4.29-4.23 (m, J=1.0 Hz, 2H), 1.62 (s, 3H), 1.33 (t, J=7.2 Hz, 3H).

Cap L-33

Step c

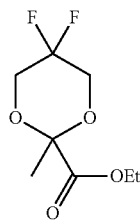

Cap L-33 Step b (0.36 g, 1.913 mmol) in DCM (10 mL) was treated with Deoxo-Fluor® (0.882 mL, 4.78 mmol) and the yellow solution was stirred at rt for 2 h. The reaction mixture was cooled to 0° C., diluted with CH₂Cl₂ (5 mL) and carefully quenched with sat. aqueous NaHCO₃. The mixture was stirred for 15 min until gas evolution ceased and the aqueous layer was extracted with CH₂Cl₂ (2×). The combined organic layers were dried (MgSO₄), filtered and concentrated. A yellow oil corresponding to crude Cap L-33 step c (0.1 g) was recovered and was used without further purification. ¹H NMR (400 MHz, CDCl₃) δ 4.31 (q, J=7.0 Hz, 2H), 4.06-3.88 (m, 4H), 1.58 (s, 3H), 1.35 (t, J=7.0 Hz, 3H); ¹⁹F NMR (376 MHz, CDCl₃) δ −112.09 (d, J=251.4 Hz, 1F), −116.34 (d, J=251.4 Hz, 1F); ¹³C NMR (101 MHz, CDCl₃) δ 168.6, 113.3 (t, J=243.5 Hz, 1C), 98.3, 65.7 (d, J=27.7 Hz, 1C), 65.2 (d, J=28.5 Hz, 1C), 62.2, 24.2, 14.1.

A solution of LiOH.H₂O (23.96 mg, 0.571 mmol) in H₂O (1.5 mL) was added to a solution of Cap L-33 step c (60 mg, 0.285 mmol) in THF (5 mL) and the resulting mixture was stirred at rt for 3 h. The reaction mixture was then acidified with 6 M H₃PO₄ until pH ~2 and the aqueous layer was extracted with EtOAc (3×). The combined organic layers were dried (MgSO₄), filtered and concentrated to give Cap L-33 (50 mg) as a brown oil. Used without further purification. ¹H NMR (400 MHz, CDCl₃) δ 8.31 (br. s., 1H), 4.14-3.95 (m, 4H), 1.66 (s, 3H); ¹⁹F NMR (376 MHz, CDCl₃) δ −111.89 (d, J=250.4 Hz, 1F), −116.17 (d, J=250.4 Hz, 1F); ¹³C NMR (101 MHz, CDCl₃) δ 173.4, 114.6 (d, J=242.8 Hz, 1C), 112.1 (d, J=243.5 Hz, 1C), 98.1, 65.8 (d, J=28.5 Hz, 1C), 65.4 (d, J=28.5 Hz, 1C), 24.0.

Cap L-34

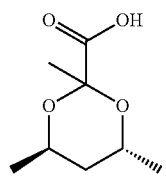

Cap L-34 was prepared by employing the procedures described for the synthesis of Cap L-31 starting from (2R, 4R)-pentane-2,4-diol. ¹H NMR (400 MHz, CDCl₃) δ 10.08 (br. s., 1H), 4.15 (dq, J=13.2, 6.4 Hz, 1H), 4.11-4.02 (m, 1H), 1.75-1.59 (m, 2H), 1.55 (s, 3H), 1.29 (d, J=6.5 Hz, 3H), 1.25 (d, J=6.3 Hz, 3H); ¹³C NMR (101 MHz, CDCl₃) δ 175.5 (br. s., 1C), 97.5, 65.5 (s, 2C), 38.8, 24.2, 21.6, 20.7

Cap W-16

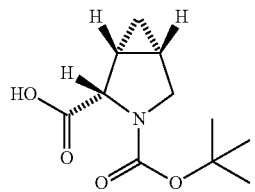

To an ice cooled solution of N,N-di-iso-propylethylamine (6.11 mL, 35.1 mmol) in DCM (50 mL) was added (1R,2S, 5S)-3-azabicyclo[3.1.0]hexane-2-carboxylic acid (3.715 g, 29.2 mmol) as a solid. To this mixture was added a solution of di-t-butyldicarbonate (8.29 g, 38.0 mmol) in DCM (25.00 mL), dropwise through an addition funnel. The final mixture was stirred at rt overnight. The organic phase was washed with 5% citric acid aqueous solution, saturated NaCl aqueous solution, dried over MgSO₄ and evaporated to yield 7.6 g of a viscous oil, which failed to solidified upon standing in a freezer. Residue was redissolved into EtOAc (100 mL), washed it with 0.2 M NaOH (100 mL) and the separated aqueous layer was acidified with 1 M HCl at 0° C. to pH 2, saturated with solid NaCl and extracted with EtOAc. The organic layer was washed with brine, dried over MgSO₄, filtered and evaporated in vacuo to afford Cap W-16 (3.90 g) as a foam. ¹H NMR (400 MHz, CDCl₃) δ 4.53-4.27 (m, 1H), 3.72-3.52 (m, 2H), 2.00-1.83 (m, 1H), 1.67 (dd, J=6.7, 3.4 Hz, 1H), 1.56-1.34 (m, 9H), 0.90-0.64 (m, 2H).

Cap W-17

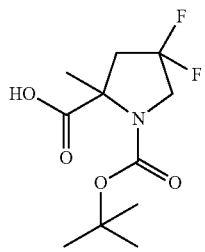 [SMILES: CC(C)(C)OC(=O)N1CC(F)(F)CC1(C)C(=O)O]

Cap W-17

Step A

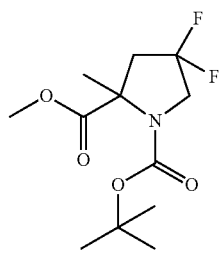 [SMILES: COC(=O)C1(C)CC(F)(F)CN1C(=O)OC(C)(C)C]

To a solution of (S)-1-tert-butyl 2-methyl 4,4-difluoropyrrolidine-1,2-dicarboxylate (1.552 g, 5.68 mmol) in THF (50 mL) at −78° C. was added 2 M lithium diisopropylamide in THF (3.12 mL, 6.24 mmol) dropwise via a syringe. After stirring the light yellow solution at −78° C. for 30 min (during which time it turned into a light brown solution), iodomethane (0.389 mL, 6.24 mmol) was added dropwise via a syringe. After stirring at −78° C. for 2 h, the reaction mixture was stirred at 0° C. for 2 h and quenched with saturated aqueous solution of ammonium chloride and extracted with ethyl acetate. The combined organic extracts were washed with brine, dried (magnesium sulfate), filtered, and concentrated in vacuo. The residual oil was purified by FCC (90 g silica gel cartridge), eluting with gradient 0-30% ethyl acetate/hexane to afford Cap W-17 Step A (526 mg) as a colorless oil. ¹H NMR (400 MHz, CDCl₃) δ 3.98-3.81 (m, 2H), 3.80-3.74 (m, 3H), 2.81-2.57 (m, 1H), 2.48-2.26 (m, 1H), 1.75-1.60 (m, 3H), 1.53-1.40 (m, 9H).

A vial containing 1-tert-butyl 2-methyl 4,4-difluoro-2-methylpyrrolidine-1,2-dicarboxylate (118 mg, 0.423 mmol), THF (4 mL), and 1 M Sodium hydroxide (4.23 mL, 4.23 mmol) was sealed and heated in a microwave system at 80° C. for 2 h. Removed the volatile in vacuo. The remaining aqueous layer was extracted with ether, the separated aq. layer was acidified with 5% citric acid to pH 3, and saturated with NaCl, extracted with EtOAc (10 ml, 3×). The combined organic layers were washed with brine, dried over MgSO4, filtered, evaporated in vacuo to afford Cap W-17 (100 mg, 0.377 mmol, 89% yield) as a colorless viscous oil, which solidified upon standing on the bench. ¹H NMR (400 MHz, CD₃OD) δ

3.93-3.77 (m, 2H), 2.86-2.61 (m, 1H), 2.60-2.42 (m, 1H), 1.71-1.59 (m, 3H), 1.54-1.42 (m, 9H).

Cap W-18

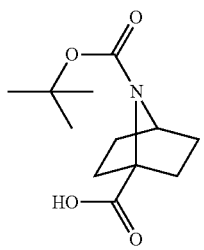 [SMILES: CC(C)(C)OC(=O)N1C2CCC1(C(=O)O)CC2]

Cap W-18

Step A

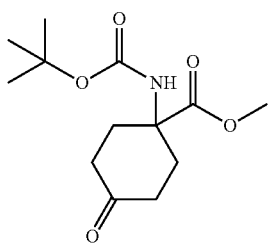 [SMILES: COC(=O)C1(NC(=O)OC(C)(C)C)CCC(=O)CC1]

To an ice cooled solution of 1-((tert-butoxycarbonyl) amino)-4-oxocyclohexanecarboxylic acid (988 mg, 3.72 mmol) in methanol (15 mL) was added 2 M Trimethylsilyl-diazomethane in hexanes (7.45 mL, 14.90 mmol) dropwise until the solution became light yellow. Stirred it at rt overnight. Removed the volatiles in vacuo. The residue (1.2 g) was purified by FCC (90 g silica gel cartridge), eluted with gradient 20%~50% EtOAc-Hexanes to afford Cap W-18 Step A (1.01 g) as white solid. $^1$H NMR (400 MHz, CDCl$_3$) δ 4.93 (s, 1H), 3.84-3.73 (m, 3H), 2.59-2.19 (m, 8H), 1.56-1.39 (m, 9H).

Cap W-18

Step B

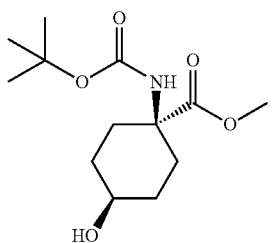 [SMILES: COC(=O)[C@]1(NC(=O)OC(C)(C)C)CC[C@@H](O)CC1]

To a 100 ml 3-necked RBF was charged in Cap W-18 Step A (1.00 g, 3.69 mmol) and THF (20 mL), cooled with a dry ice-acetone bath. To this solution was added 1 M L-Selectride in THF (4.43 mL, 4.43 mmol) dropwise through addition funnel (it took 5 min to finish). Stirred at −78° C. for 3 h. and the reaction was then quenched by addition of sat aq. NH$_4$Cl (20 mL) at −78° C., then diluted with EtOAc (20 mL) and water (20 mL) and stirred it at rt for 1 h. The separated organic layer was washed with brine, dried over MgSO$_4$, filtered, removed the solvent in vacuo. The residual oil was purified by flash chromatography (30% to 70% acetone-hexanes). Combined fractions were concentrated in vacuo to give the desired product Cap W-18 Step B (910 mg) as a white foam. $^1$H NMR (400 MHz, CDCl$_3$) δ 4.74 (br. s., 1H), 3.96 (d, J=2.8 Hz, 1H), 3.81-3.67 (m, 4H), 2.38-2.09 (m, 2H), 1.96-1.63 (m, 6H), 1.62-1.39 (m, 9H).

Cap W-18

Step C

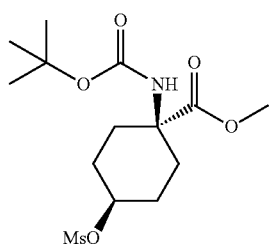 [SMILES: COC(=O)[C@]1(NC(=O)OC(C)(C)C)CC[C@@H](OS(C)(=O)=O)CC1]

To an ice cooled solution of Cap W-18 Step B (890 mg, 3.26 mmol) and N,N-Di-iso-propylethylamine (0.851 mL, 4.88 mmol) in DCM (20 mL) was added Methanesulfonyl chloride (0.302 mL, 3.91 mmol) dropwise via a syringe. The formed light yellow solution was stirred at rt for 2 h. Quenched with sat. NaHCO$_3$, The separated organic layer was washed with 5% citric acid and brine, dried over MgSO$_4$, filtered, evaporated in vacuo. The residual solid was purified by FCC (90 g silica gel cartridge), eluted with gradient 30%~60% EtOAc-Hexanes to afford the desired product Cap W-18 Step C (893 mg) as a white foam. $^1$H NMR (400 MHz, CDCl$_3$) δ 4.96 (br. s., 1H), 4.81-4.57 (m, 1H), 3.82-3.70 (m, 3H), 3.12-2.99 (m, 3H), 2.32-1.76 (m, 8H), 1.61 (s, 1H), 1.46 (s, 8H).

Cap W-18

Step D

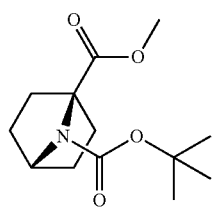 [SMILES: COC(=O)[C@]12CC[C@H](CC1)N2C(=O)OC(C)(C)C]

To a solution of Cap W-18 Step C (883 mg, 2.51 mmol) in THF (15 mL) was added 1 M potassium tert-butoxide in THF (3.27 mL, 3.27 mmol) dropwise via a syringe. The formed light yellow solution was stirred at rt overnight (it became cloudy after 1 h). The reaction was quenched with water (100 ml) and extracted with EtOAc (20 mL). The separated aq. layer was saturated with NaCl and extracted with EtOAc (20 mL). The combined organic layers were washed with brine, dried over MgSO₄, filtered and evaporated in vacuo. The residual oil was purified by flash chromatography (10% to 40% EtOAc-Hexane)s to afford Cap W-18 Step C (324 mg) as a colorless oil. $^1$H NMR (500 MHz, CDCl₃) δ 4.33 (t, J=4.8 Hz, 1H), 3.89 (s, 3H), 2.28-2.11 (m, 2H), 2.05-1.88 (m, 2H), 1.77 (ddd, J=11.5, 9.2, 4.5 Hz, 2H), 1.58-1.39 (m, 9H).

A vial containing Cap W-18 Step C (128 mg, 0.5 mmol), THF (5 mL), and 1 M Sodium hydroxide (5.00 mL, 5 mmol) was sealed and heated in a microwave system at 100° C. for 2 h. The volatiles were removed in vacuo and the remaining aqueous layer was diluted with water (5 mL) and extracted with ether (10 mL). The separated aq. layer was acidified with 2 M HCl to pH 3, saturated with NaCl and extracted with EtOAc (5 mL, ×3). The combined organic layers were washed with brine, dried over MgSO₄, filtered, evaporated in vacuo to provide Cap W-18 (85 mg) as a white solid. $^1$H NMR (500 MHz, CD₃OD) δ 4.28 (t, J=4.8 Hz, 1H), 2.21-2.09 (m, 2H), 1.97-1.85 (m, 2H), 1.79 (ddd, J=11.4, 9.2, 4.5 Hz, 2H), 1.57 (ddd, J=11.5, 9.1, 4.3 Hz, 2H), 1.50-1.42 (m, 9H).

Cap W-19

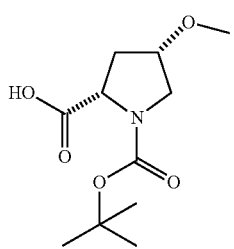 [SMILES: CO[C@H]1C[C@@H](C(=O)O)N(C(=O)OC(C)(C)C)C1]

Cap W-19

Step A

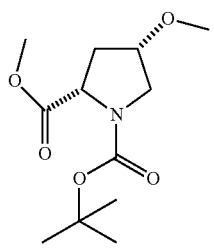 [SMILES: COC(=O)[C@@H]1C[C@H](OC)CN1C(=O)OC(C)(C)C]

To an ice cooled mixture of Sodium hydride (228 mg, 5.71 mmol) (prewashed with hexanes) and DMF (10 mL) was added (2S,4S)-1-(tert-butoxycarbonyl)-4-hydroxypyrrolidine-2-carboxylic acid (600 mg, 2.59 mmol) as a solid in one portion. The formed slurry was stirred at this temperature for 30 min before addition of iodomethane (0.485 mL, 7.78 mmol) dropwise. The final reaction mixture was stirred at rt overweekend. Poured into water (100 mL), extracted with EtOAc (20 mL, ×2). The combined organic layer was washed with water and brine, dried over MgSO4, filtered, evaporated in vacuo. The residue was purified by FCC (0% to 50% EtOAc-Hexanes) to afford Cap W-19 Step A (550 mg) as a colorless oil. $^1$H NMR (500 MHz, CD₃OD) δ 4.38 (td, J=8.6, 3.2 Hz, 1H), 3.99 (dt, J=5.1, 2.4 Hz, 1H), 3.81-3.68 (m, 3H), 3.64-3.53 (m, 1H), 3.50-3.40 (m, 1H), 2.45-2.21 (m, 2H), 1.55-1.40 (m, 9H)

To a solution of Cap W-19 Step A (140 mg, 0.540 mmol) in MeOH (2 mL) and THF (2.0 mL) was added a premade solution of lithium hydroxide monohydrate (45.3 mg, 1.080 mmol) in Water (2.0 mL). The formed cloudy solution was stirred at rt overnight. Removed volatiles in vacuo. The remaining aqueous layer was diluted with water (10 mL), and extracted with ether (10 mL). The separated aqueous phase was cooled with ice and acidified with 2 M HCl to pH 2, and saturated with NaCl, extracted with EtOAc (10 mL, ×3). The combined organic layers were washed with brine, dried over MgSO₄, filtered, evaporated in vacuo to yield Cap W-19 (123 mg) as a colorless oil, which solidified upon standing. $^1$H NMR (500 MHz, CD₃OD) δ 4.42-4.22 (m, 1H), 4.05-3.93 (m, 1H), 3.69-3.56 (m, 1H), 3.45 (dd, J=11.5, 2.5 Hz, 1H), 3.31-3.24 (m, 3H), 2.47-2.17 (m, 2H), 1.56-1.37 (m, 9H).

Cap W-20

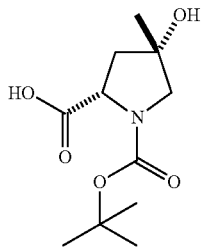

To a solution of (S)-1-(tert-butoxycarbonyl)-4-oxopyrrolidine-2-carboxylic acid (229 mg, 0.999 mmol) in THF (5 mL) at −42° C. was added dropwise a 3 M solution of methyl magnesium bromide in ether (0.832 mL, 2.497 mmol). The mixture was stirred at this temperature for 1 h and cooled with an ice bath and stirred overnight. The mixture was then poured it into iced 1 M HCl and extracted with EtOAc. The separated organic layer was washed with brine, dried over MgSO₄, filtered and evaporated in vacuo to provide a white solid, which was triturated with 4:1 Hexane-EtOAc (5 mK) to afford the desired product Cap W-20 (156 mg) as a white powder. $^1$H NMR (500 MHz, CD₃OD) δ 4.43-4.25 (m, 1H), 3.52-3.35 (m, 2H), 2.38-2.07 (m, 2H), 1.59-1.42 (m, 11H), 1.40-1.30 (m, 3H).

Intermediate W-1

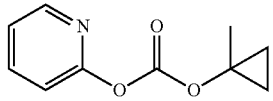

Pre-washed (hexanes) sodium hydride (183 mg, 4.58 mmol) was suspended in THF (20 mL) at 4° C. followed by slow addition of 1-methylcyclopropanol (300 mg, 4.16 mmol). The formed light yellow cloudy solution was stirred at this temperature for 30 min and then di(pyridin-2-yl)carbonate (899 mg, 4.16 mmol) was added. The final mixture was stirred at rt overnight, poured into iced water, and extracted with EtOAc. The organic layer was washed with water and brine, dried over MgSO₄, filtered, evaporated in vacuo. The residue was purified by FCC (0% to 50% EtOAc-Hexanes) to afford Intermediate W-1 (264 mg, 1.298 mmol, 31.2% yield) as a colorless oil. $^1$H NMR (400 MHz, CDCl$_3$) δ 8.50-8.38 (m, 1H), 7.92-7.76 (m, 1H), 7.36-7.22 (m, 1H), 7.19-7.08 (m, 1H), 1.82-1.63 (m, 3H), 1.19-1.04 (m, 2H), 0.83-0.68 (m, 2H).

Cap W-21

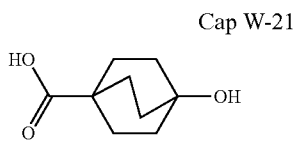

A mixture of methyl 4-bromobicyclo[2.2.2]octane-1-carboxylate (183 mg, 0.741 mmol) and 0.25 M sodium hydroxide (15 mL, 3.75 mmol) in a seal tube was heated in an oil bath at 100° C. for 24 h. The mixture was extracted with ether and the separated aqueous phase was chilled with an ice bath, acidified with 2 M HCl to pH 3 and extracted with EtOAc (20 mL, ×3). The combined organic layers were washed with brine, dried over MgSO$_4$, filtered and evaporated to afford Cap W-21 (110 mg) as a white solid. $^1$H NMR (500 MHz, DMSO-d$_6$) δ 11.97 (br. s., 1H), 4.29 (s, 1H), 1.98-1.65 (m, 6H), 1.61-1.36 (m, 6H).

Cap W-22

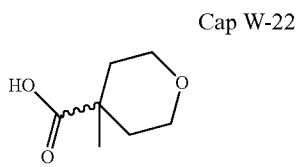

Cap W-22

Step A

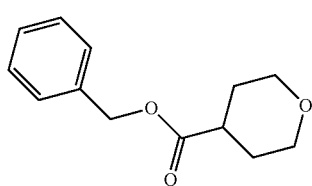 [SMILES: O=C(OCc1ccccc1)C1CCOCC1]

A mixture of tetrahydro-2H-pyran-4-carboxylic acid (1.36 g, 10.45 mmol) and thionyl chloride (7.63 mL, 105 mmol) was heated to gentle reflux for 2.5 h. The mixture was then cooled to room temperature and evaporated in vacuo. To a solution of this tetrahydro-2H-pyran-4-carbonyl chloride in DCM (15 mL) was added Et$_3$N (4.36 mL, 31.4 mmol) and benzyl alcohol (1.622 mL, 15.68 mmol) dropwise while cooled with an ice bath. The formed slurry was stirred with cooling for 30 min, and then at rt 30 min. The mixture was then washed in turn with water, 5% citric acid and saturated aqueous sodium chloride solution. The organic solution was dried over MgSO$_4$, and then, concentrated under reduced pressure. The resulting residue was purified by column chromatography (5% to 30% EtOAc-hexane) to give Cap W-22 Step A (1.83 g) as colorless oil. $^1$H NMR (500 MHz, CDCl$_3$) δ 7.52-7.31 (m, 5H), 5.16 (s, 2H), 3.99 (dt, J=11.5, 3.6 Hz, 2H), 3.45 (td, J=11.2, 2.9 Hz, 2H), 2.69-2.49 (m, 1H), 2.03-1.73 (m, 4H).

Cap W-22

Step B

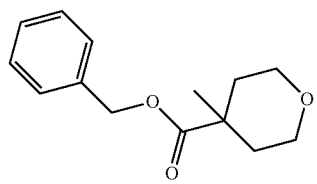 [SMILES: CC1(C(=O)OCc2ccccc2)CCOCC1]

To a solution of bis(isopropyl)amine (0.308 mL, 2.197 mmol) in THF (10 mL) at −78° C. was added 1.6 M butyl lithium in hexanes (1.373 mL, 2.197 mmol) dropwise via a syringe. After stirring the formed solution at −78° C. for 30 min, Cap W-22 Step A (440 mg, 1.998 mmol) was added and the resultant yellow solution was stirred for another 30 min. Thereafter, iodomethane (0.149 mL, 2.397 mmol) was added dropwise via a syringe. After stirring at −78° C. for 30 min, the reaction mixture was stirred at 0° C. for 2 h, quenched with a saturated aqueous solution of ammonium chloride and extracted with ethyl acetate. The organic extract was washed with brine, dried (MgSO$_4$), filtered, and concentrated in vacuo. The residual oil was purified by FCC (5%~30% EtOAc-Hexanes) to afford Cap W-22 Step B as a colorless oil. LC/MS (Cond. W-2): [M+H]+ 235.2, Rt=1.95 min.

A mixture of Cap W-22 Step B (100 mg, 0.427 mmol) and Pd/C (45.4 mg, 0.043 mmol) in MeOH (2 mL) was placed in a Parr shaker under H$_2$ (40 psi) for 4 h. The mixture was filtered though Celite. and evaporated in vacuo. The residue was triturated with hexanes, washed hexanes and the filtrate was dried under vacuo to afford Cap W-22 (25 mg) as a white powder. The hexanes washing solution was slowly evaporated by blowing N$_2$ to afford additional 28 mg of the product as a white solid. $^1$H NMR (500 MHz, CD$_3$OD) δ 3.80 (dt, J=11.9, 4.2 Hz, 2H), 3.53 (ddd, J=11.8, 10.4, 2.5 Hz, 2H), 2.13-1.95 (m, 2H), 1.50 (ddd, J=14.0, 10.2, 4.3 Hz, 2H), 1.25 (s, 3H).

Cap W-23

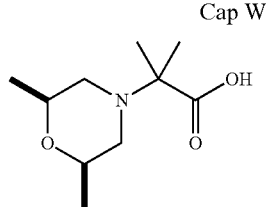

Cap W-23

Step A

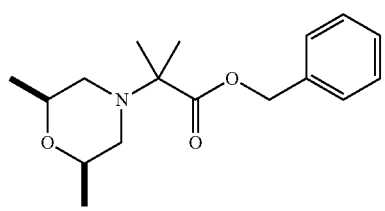 [SMILES: C[C@@H]1CN(C(C)(C)C(=O)OCc2ccccc2)C[C@H](C)O1]

A mixture of cis-2,6-dimethylmorpholine (460 mg, 4.00 mmol), benzyl 2-bromo-2-methylpropanoate (514 mg, 1.999 mmol) and N,N-Di-iso-propylethylamine (1.393 mL, 8.00 mmol) in acetonitrile (10 mL) in a capped vial was heated in a microwave system at 105° C. for 8 h. The solvent was removed in vacuo and the residue was take up into EtOAc. The mixture was washed with water and brine, dried over MgSO₄, filtered and evaporated in vacuo. The residue was purified by Prep-HPLC (MeOH—H₂O-TFA). The collected fractions were concentrated to give the TFA salt of the product as a gummy solid. This residue was dissolved into MeOH, poured into sat. NaHCO₃ and extracted with EtOAc. The separated organic layer was washed with brine, dried over MgSO₄, filtered and evaporated to afford Cap W-23 Step A (286 mg) as an off-white oil. ¹H NMR (400 MHz, CDCl₃) δ 7.54-7.32 (m, 5H), 5.27 (s, 2H), 4.08 (ddd, J=10.7, 6.3, 1.9 Hz, 2H), 3.40 (d, J=11.3 Hz, 2H), 2.74 (t, J=11.2 Hz, 2H), 1.72 (s, 6H), 1.19 (d, J=6.3 Hz, 6H).

A vessel containing 10% Pd/C (53.3 mg, 0.050 mmol), Cap W-23 Step A (286 mg, 0.932 mmol) and MeOH (4 mL) was placed on a Parr shaker under 50 psi H₂ overnight. The suspension was filtered though Celite and evaporated in vacuo to afford the Cap W-23 (90 mg) as a white solid. ¹H NMR (400 MHz, CD₃OD) δ 4.10-3.86 (m, 2H), 3.35-3.30 (m, 2H), 2.71 (t, J=11.4 Hz, 2H), 1.49 (s, 6H), 1.25 (d, J=6.5 Hz, 6H).

Cap W-24

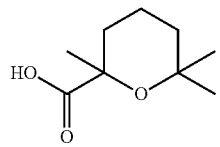

Cap W-24

Step A

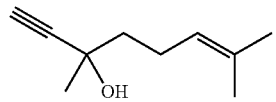

To a solution of 6-methylhept-5-en-2-one (5.05 g, 40 mmol) in THF (100 mL) at −78° C. was added 0.5 M ethynylmagnesium bromide in THF (96 mL, 48.0 mmol) dropwise through an addition funnel. The formed white slurry was allowed to warm up to rt and stirred for 2 h. Quenched with sat. NH₄Cl, extracted with Ether. The separated organic layers were washed with brine, dried over Na₂SO₄, filtered, evaporated in vacuo. The residual oil was purified by FCC (0% to 35% EtOAc-Hexanes) to afford the desired product Cap W-24 Step A (5.87 g) as a colorless oil. ¹H NMR (500 MHz, CDCl₃) δ 5.28-5.12 (m, 1H), 2.48 (s, 1H), 2.39-2.26 (m, 1H), 2.24-2.15 (m, 1H), 2.09 (br. s., 1H), 1.79-1.65 (m, 8H), 1.56-1.50 (m, 3H).

Cap W-24

Step B

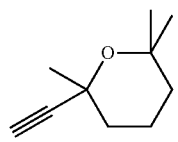

A mixture of Cap W-24 Step A (3.87 g, 25.4 mmol) and Amberlyst(R) 15 (1.00 g, 25.4 mmol) in DCM (50 mL) was heated to gentle reflux for 6 h. The mixture was cooled to rt, filtered and the resin was washed with DCM. The filtrate was washed with sat NaHCO₃ and brine, dried over MgSO₄, filtered and evaporated in vacuo without heating. The residual oil was purified by distillation under house vacuum, collecting the fractions that distilled between 90 to 95° C. to yield Cap W-24 Step B (3.50 g) as a colorless oil. ¹H NMR (500 MHz, CDCl₃) δ 2.37 (s, 1H), 2.03 (qt, J=13.5, 3.4 Hz, 1H), 1.91-1.82 (m, 1H), 1.70-1.54 (m, 2H), 1.53-1.47 (m, 6H), 1.45-1.31 (m, 2H), 1.23-1.18 (m, 3H).

Cap W-24

Step C

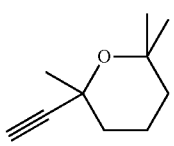

To a solution of Cap W-24 Step B (228 mg, 1.5 mmol) in acetone (8 mL) at 4° C. was added dropwise a premade solution of potassium permanganate (711 mg, 4.50 mmol) in water (8 mL) through an addition funnel. The resulting mixture was stirred at rt overnight and quenched with isopropyl alcohol (2 ml), stirred for 1 h, filtered through Celite bed and evaporated in vacuo. The remaining aqueous layer was diluted with 1 M HCl and extracted with EtOAc. The separated organic layer was washed with brine, dried over MgSO₄, filtered and evaporated in vacuo to afford the desired product Cap W-24 (265 mg) as a colorless oil. ¹H NMR (500 MHz, CDCl₃) δ 2.06-1.98 (m, 1H), 1.73 (quin, J=6.1 Hz, 2H), 1.63-1.44 (m, 6H), 1.29 (d, J=16.6 Hz, 6H).

Cap W-25 and Cap W-26

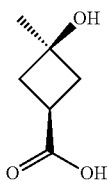

W-25

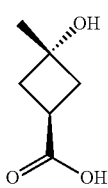

W-26

Cap W-25/Cap W-26

Step A

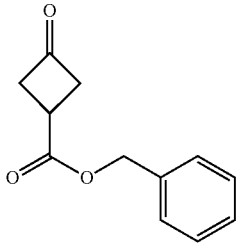 [SMILES: O=C1CC(C(=O)OCc2ccccc2)C1]

A mixture of 3-oxocyclobutanecarboxylic acid (2.15 g, 18.84 mmol), benzyl alcohol (2.145 mL, 20.73 mmol) and N1-((ethylimino)methylene)-N3,N3-dimethylpropane-1,3-diamine, HCl (5.42 g, 28.3 mmol) in DCM (100 mL) was stirred at room temperature for 18 hours. The reaction mixture was washed with water (3×) and the combined aqueous layers were extracted with DCM. The combined organic layers were washed with brine, dried over anhydrous MgSO$_4$, and concentrated in vacuo. Crude product was purified by FCC (0% to 35% EtOAc-Hexanes) to yield the desired product Cap W-25/Cap W-26 Step A (3.15 g) as a colorless oil. $^1$HNMR (400 MHz, CDCl$_3$) δ 7.39 (m, 5H), 5.21 (s, 2H), 3.49-3.41 (m, 2H), 3.36-3.28 (m, 3H).

Cap W-25/Cap W-26

Step B

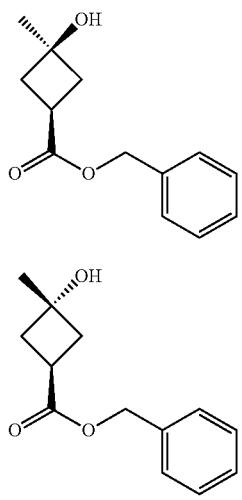

Cap W-25 Step B

Cap W-26 Step B

To a solution of Cap W-25/Cap W-26 Step A (613 mg, 3 mmol) in THF (10 mL) at 0° C. was added a 3.18 M solution of methyl magnesium bromide in ether (1.321 mL, 4.2 mmol) dropwise. The formed tan solution was stirred at this temperature for 4 h and poured into iced 1 M HCl. The mixture was then saturated with NaCl, extracted with EtOAc and the separated organic layer was washed with brine, dried over MgSO$_4$, filtered and evaporated in vacuo. The residual oil was purified by prep-HPLC (CH$_3$CN—H$_2$O—NH$_4$OAc) to afford a major product that corresponded to Cap W-25 Step B (160 mg) as a colorless oil. $^1$H NMR (500 MHz, CDCl$_3$) δ 7.50-7.32 (m, 5H), 5.15 (s, 2H), 2.90-2.67 (m, 1H), 2.48-2.27 (m, 4H), 2.24-2.09 (m, 2H), 1.40 (s, 3H). A more polar and minor product was also isolated and it corresponded to Cap W-26 Step B (60 mg). $^1$H NMR (500 MHz, CDCl$_3$) δ 7.50-7.30 (m, 5H), 5.16 (s, 2H), 3.23 (tt, J=9.7, 6.8 Hz, 1H), 2.50-2.30 (m, 4H), 1.48-1.36 (m, 3H).

A vessel containing Cap W-25 Step B (80 mg, 0.363 mmol), Pd/(38.7 mg, 0.036 mmol) and MeOH (5 mL) was placed on a Parr shaker under H$_2$ at 30 psi for 5 h. The suspension was filtered through a Celite bed and evaporated in vacuo to afford Cap W-25 (25 mg) as a white solid. $^1$H NMR (500 MHz, CD$_3$OD) δ 3.69 (s, 1H), 2.84-2.60 (m, 1H), 2.41-2.21 (m, 4H), 1.48-1.29 (m, 3H).

Cap W-26 was made by the same procedure as described above for Cap W-25. $^1$H NMR (400 MHz, CD$_3$OD) δ 3.20-2.99 (m, 1H), 2.41-2.21 (m, 4H), 1.43-1.27 (m, 3H)

Cap W-27

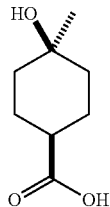

Cap W-27 was made by the same procedure as described in Cap W-25. $^1$H NMR (500 MHz, CD$_3$OD) δ 2.44-2.28 (m, 1H), 1.98-1.88 (m, 2H), 1.75-1.58 (m, 4H), 1.57-1.45 (m, 2H), 1.22 (s, 3H).

Cap W-28

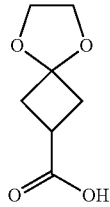 [SMILES: O=C(O)C1CC2(C1)OCCO2]

Cap W-28

Step A

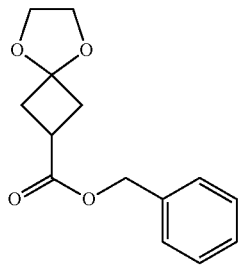 [SMILES: O=C(OCc1ccccc1)C1CC2(C1)OCCO2]

A 250 ml RBF equipped with a Dean-Stork trap was charged with Cap W-25/Cap W-26 Step A (2 g, 9.79 mmol), polyethylene glycol (1.638 mL, 29.4 mmol), p-toluenesulfonic acid monohydrate (0.186 g, 0.979 mmol) and toluene (50 mL). The mixture was heated to gentle reflux for 2 h and the water formed was separated. The solvent was removed in vacuo and the remaining residue was taken up into EtOAc (50 mL), washed with sat. NaHCO$_3$ and brine, dried over Na$_2$SO$_4$, filtered and evaporated in vacuo. The residual oil was purified by FCC (0% to 50% EtOAc-Hexanes) to afford Cap W-28 Step A (1.90 g) as a colorless oil. $^1$H NMR (500 MHz, CDCl$_3$) δ 7.49-7.31 (m, 5H), 5.16 (s, 2H), 4.01-3.85 (m, 4H), 3.08-2.91 (m, 1H), 2.79-2.65 (m, 2H), 2.63-2.51 (m, 2H).

Cap W-28 was hydrogenated by the same procedure as described in Cap W-25. $^1$H NMR (500 MHz, CD$_3$OD) δ 3.98-3.82 (m, 4H), 2.87 (t, J=8.7 Hz, 1H), 2.65-2.46 (m, 4H).

Cap W-29 and Cap W30

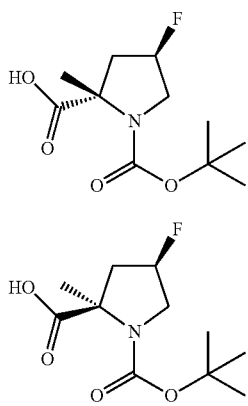

Cap W-29/Cap W-30

Step A

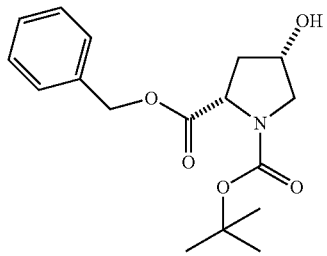 [SMILES: CC(C)(C)OC(=O)N1C[C@@H](O)C[C@H]1C(=O)OCc1ccccc1]

A mixture of (2S,4S)-1-(tert-butoxycarbonyl)-4-hydroxy-pyrrolidine-2-carboxylic acid (5.22 g, 22.57 mmol), cesium carbonate (16.18 g, 49.7 mmol) and benzyl bromide (3.22 mL, 27.1 mmol) in DMF (70 mL) was heated in an oil bath at 65° C. for 3 h. The mixture was then poured into iced water (500 ml) and extracted with EtOAc (100 mL, ×2). The organic layer was washed with water, 0.2 M NaOH, and brine, dried over MgSO$_4$, filtered and evaporated in vacuo. The residual oil was purified by FCC (20% to 60% Acetone-Hexane) to yield Cap W-29/Cap W-30 Step A (2.98 g) as a colorless viscous oil. $^1$H NMR (400 MHz, CDCl$_3$) δ 7.54-7.31 (m, 5H), 5.42-5.27 (m, 1H), 5.27-5.11 (m, 2H), 4.40-4.26 (m, 1H), 3.80-3.51 (m, 2H), 2.36 (dtd, J=14.4, 9.8, 4.6 Hz, 1H), 2.22-2.03 (m, 1H), 1.57-1.41 (m, 5H), 1.37 (s, 5H).

Cap W-29/Cap W-30

Step B

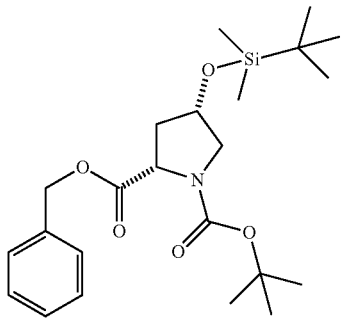

To an ice cooled solution of Cap W-29/Cap W-30 Step A (2.98 g, 9.27 mmol), imidazole (3.16 g, 46.4 mmol) and 4-dimethylaminopyridine (0.113 g, 0.927 mmol) in DMF (20 mL) was dropwise added a solution of tert-butyldimethylsilyl chloride (2.59 mL, 20.40 mmol) in DMF (10.00 mL). The formed solution was stirred at rt overnight, poured into iced water (300 mL) and extracted with EtOAc (50 mL, ×2). The separated organic layer was washed with water and brine, dried over MgSO$_4$, filtered and evaporated in vacuo. The residual oil was purified by FCC (0% to 30% EtOAc-Hexane) to afford Cap W-29/Cap W-30 Step B (3.64 g) as a colorless viscous oil, which solidified upon standing. $^1$H NMR (400 MHz, CDCl$_3$) δ 7.49-7.31 (m, 5H), 5.36-5.00 (m, 2H), 4.56-4.23 (m, 2H), 3.79-3.52 (m, 1H), 3.48-3.24 (m, 1H), 2.49-2.25 (m, 1H), 2.14 (dt, J=12.9, 4.7 Hz, 1H), 1.48 (s, 3H), 1.41-1.30 (m, 6H), 0.98-0.79 (m, 9H), 0 (s, 6H).

Cap W-29/Cap W-30

Step C

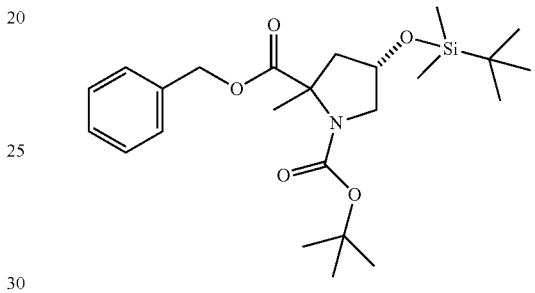

To a solution of bis(isopropyl)amine (1.281 mL, 9.14 mmol) in THF (40 mL) at −78° C. was added 1.6 M butyllithium in hexanes (5.45 mL, 8.73 mmol) dropwise through an addition funnel. After stirring the formed solution at −78° C. for 30 min, a solution of Cap W-29/Cap W-30 Step B (3.62 g, 8.31 mmol) in THF (10.00 mL) was added and stirred for another 30 min. Then, iodomethane (0.673 mL, 10.80 mmol) was added dropwise via a syringe. After stirring at −78° C. for 2 h, the reaction mixture was stirred at 0° C. for 2 h, quenched with a saturated aqueous solution of ammonium chloride and extracted with ethyl acetate. The organic extract was washed with brine, dried (MgSO$_4$), filtered, and concentrated in vacuo. The residual oil was purified by FCC (0% to 30% EtOAc-Hexane) to afford Cap W-29/Cap W-30 Step C (1.05 g) as a colorless viscous oil. $^1$H NMR (500 MHz, CDCl$_3$) δ 7.49-7.32 (m, 5H), 5.38-4.93 (m, 2H), 4.54-4.25 (m, 1H), 3.92-3.57 (m, 1H), 3.52-3.20 (m, 1H), 2.41-1.84 (m, 2H), 1.81-1.54 (m, 5H), 1.52-1.30 (m, 10H), 1.03-0.68 (m, 9H), 0.20-0.01 (m, 6H).

Cap W-29

Step D

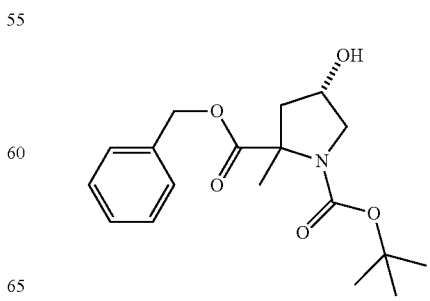

To an iced cooled solution of Cap W-29/Cap W-30 Step C (950 mg, 2.113 mmol) in THF (10 mL) was added dropwise 1 M tetrabutylammonium fluoride in THF (4.23 mL, 4.23 mmol). After stirring the formed solution at this temperature for 2 h., it was quenched with water (50 ml) and extracted with ethyl acetate (20 mL, ×2). The organic extract was washed with brine, dried (MgSO$_4$), filtered, and concentrated in vacuo. The residual oil was purified by FCC (0% to 50% Acetone-Hexane) to afford Cap W-29/Cap W-30 Step D (590 mg) as a colorless viscous oil. $^1$H NMR (400 MHz, CDCl$_3$) δ 7.50-7.31 (m, 5H), 5.38-4.96 (m, 2H), 4.48 (d, J=2.3 Hz, 1H), 3.88-3.65 (m, 1H), 3.62-3.42 (m, 1H), 2.98-2.97 (m, 1H), 2.47-2.29 (m, 1H), 2.16-1.96 (m, 1H), 1.87-1.61 (m, 5H), 1.55-1.30 (m, 9H).

Cap W-29/Cap W-30

Step E

Cap W-29 Step E

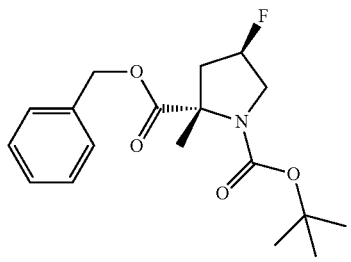 [SMILES: CC(C)(C)OC(=O)N1C[C@@H](O)CC1(C)C(=O)OCc1ccccc1]

Cap W-30 Step E

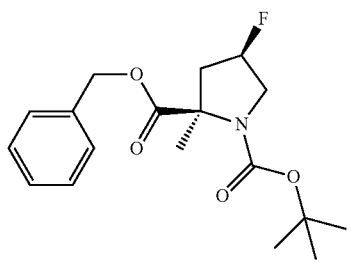

To a solution of Cap W-29/Cap W-30 Step D (540 mg, 1.610 mmol) in DCM (5 mL) at 0° C. was added dropwise diethylaminosulfur trifluoride (0.642 mL, 4.83 mmol). The formed solution was stirred at rt for 3 days. After cooling it with an ice bath and diluting with DCM, the reaction was quenched with sat. aq. Na$_2$HPO$_4$. The organic layer was separated and washed with brine, dried over MgSO$_4$, filtered and evaporated in vacuo. The residue was purified by FCC (0% to 30% EtOAc-Hexanes). The first elution compound from the column was collected as diastereomerically pure Cap W-29 Step E (124 mg, the absolute stereochemistry of alpha carbon was assigned as 2-(S)) as an oil. $^1$H NMR (400 MHz, CD$_3$OD) δ 7.44-7.27 (m, 5H), 5.31-5.02 (m, 3H), 3.88-3.56 (m, 2H), 2.53-2.19 (m, 2H), 1.64 (s, 3H), 1.43-1.32 (m, 9H)

The second eluting compound from the column was collected as diastereomerically pure Cap W-30 Step E (280 mg, the absolute stereochemistry of alpha carbon was assigned as 2-(R)) as a pale yellow oil, which solidified upon standing. $^1$H NMR (400 MHz, CD$_3$OD) δ 7.42-7.27 (m, 5H), 5.25-5.03 (m, 3H), 3.92-3.62 (m, 2H), 2.67-2.50 (m, 1H), 2.39-2.15 (m, 1H), 1.65 (d, J=18.1 Hz, 3H), 1.43-1.31 (m, 9H)

A vessel containing Cap W-29 Step E (100 mg, 0.296 mmol), 10% Pd/C (63 mg, 0.059 mmol) and MeOH (5 mL) was placed on a Parr shaker under H$_2$ at 30 psi for 24 h. The suspension was filtered through a Celite bed and evaporated in vacuo. The residue was triturated with hexanes, filtered and dried in vacuo to afford Cap W-29 (61 mg) as a white solid. $^1$H NMR (400 MHz, CD$_3$OD) δ 5.40-5.12 (m, 1H), 3.90-3.55 (m, 2H), 2.64-2.13 (m, 2H), 1.72-1.57 (m, 3H), 1.54-1.39 (m, 9H). (The absolute stereochemistry was confirmed by NOE studies).

Cap W-30

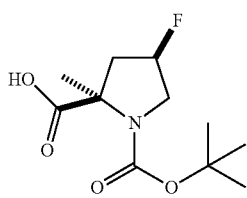 [SMILES: CC(C)(C)OC(=O)N1C[C@H](F)C[C@]1(C)C(=O)O]

Cap W-30 was obtained by hydrogenation according to the procedure used for the synthesis of Cap W-29. $^1$H NMR (500 MHz, CD$_3$OD) δ 5.29-5.04 (m, 1H), 3.93-3.59 (m, 2H), 2.72-2.53 (m, 1H), 2.41-2.12 (m, 1H), 1.73-1.57 (m, 3H), 1.54-1.41 (m, 9H). (The absolute stereochemistry was confirmed by NOE studies).

Cap B-1

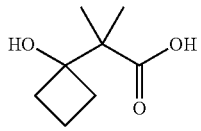

Cap B-1

Step a

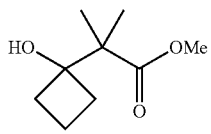

To a solution of cyclobutanone (500 mg, 7.13 mmol) and ((1-methoxy-2-methylprop-1-en-1-yl)oxy)trimethylsilane (2487 mg, 14.27 mmol) in DCM (10 mL) was added neat BF$_3$.OEt$_2$ (1.446 mL, 11.41 mmol) drop wise at −78° C. and the reaction mixture was stirred for 5 h while warming to RT. The reaction mixture was quenched with saturated NaHCO$_3$ (50 mL), diluted with DCM (50 mL). The organic layer was separated and washed with 10% NaHCO$_3$ solution (50 mL), brine (50 mL), dried over Na$_2$SO$_4$, filtered and concentrated under reduced pressure. The crude was purified by column chromatography ((Silica gel 60-120, 5-10% EtOAc/petroleum ether) to obtain hydroxyester B-1a (220 mg) as color less liquid. $^1$H NMR (CDCl$_3$, δ=7.26 ppm, 400 MHz): δ 3.67 (s, 3H), 3.22 (s, 1H), 2.34-2.20 (m, 2H), 2.02-1.89 (m, 3H), 1.63-1.48 (m, 1H), 1.24 (s, 6H).

Cap B-1

To a solution of hydroxyester B-1a (50 mg, 0.290 mmol) in THF (3 mL), MeOH (1.5 mL) and water (1.5 mL) was added LiOH (69.5 mg, 2.90 mmol) at 0° C. and stirred for 12 h at room temperature. Then the reaction mixture was cooled to 0° C. and adjusted the pH of the reaction mixture to (~3) with 1.5N HCl solution. Then the reaction mixture was extracted with DCM (2×50 mL) and the organic later was washed with brine (25 mL), dried over $Na_2SO_4$, filtered, and concentrated under reduced pressure to obtain Cap B-1 (22 mg). $^1$H NMR (DMSO-$d_6$, δ=2.50 ppm, 400 MHz): δ 2.40-2.29 (m, 2H), 1.87-1.75 (m, 3H), 1.47-1.38 (m, 1H), 1.05 (s, 6H).

Cap B-2

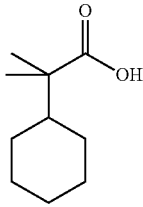

Cap B-2

Step a

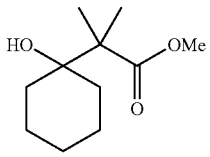

To a solution of cyclohexanone (10.0 g, 102 mmol) and ((1-methoxy-2-methylprop-1-en-1-yl)oxy)trimethylsilane (35.5 g, 204 mmol) in DCM (100 mL) was added neat $BF_3 \cdot OEt_2$ (20.66 mL, 163 mmol) drop wise at −78° C. and the reaction mixture was stirred for 5 h while warming to RT. The reaction mixture was quenched with saturated $NaHCO_3$ (50 mL), diluted with DCM (250 mL). The organic layer was separated and washed with 10% $NaHCO_3$ solution (3×50 mL), brine (50 mL), dried over $Na_2SO_4$, filtered and concentrated under reduced pressure. The crude was purified by column chromatography (Silica gel 60-120, 5-10% EtOAc/petroleum ether) to obtain hydroxyester B-2a (10.2 g) as color less liquid. $^1$H NMR (CDCl$_3$, δ=7.26 ppm, 400 MHz): δ 3.69 (s, 3H), 3.14 (s, 1H), 1.75-1.59 (m, 3H), 1.56-1.32 (m, 7H), 1.21 (s, 6H).

Cap B-2

Step b

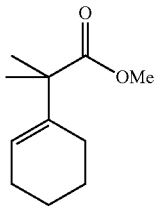

To a solution of hydroxyester B-2a (2 g, 9.99 mmol) in DCM (10 mL) was added DAST (1.319 mL, 9.99 mmol) at 0° C. and stirred for 11 h at RT. The reaction mixture is poured in to 10% $NaHCO_3$ (50 mL) and extracted with DCM (50 mL). The organic layer was washed with brine (50 mL), dried over $Na_2SO_4$, filtered and concentrated under reduced pressure. The residue was purified by column chromatography to give ester B-2b (750 mg) as a color less liquid. $^1$H NMR (CDCl$_3$, δ=7.26 ppm, 400 MHz): δ 5.59-5.54 (m, 1H), 3.65 (s, 3H), 2.09-2.03 (m, 2H), 1.94-1.87 (m, 2H), 1.63-1.52 (m, 4H), 1.28 (s, 6H).

Cap B-2

Step c

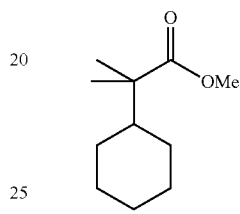

To a solution of ester B-2b (650 mg, 3.57 mmol) and in MeOH (10 mL) was added Pt/C (5%, 69.6 mg, 0.178 mmol). Then AcOH (0.204 mL, 3.57 mmol) was added and the reaction mixture was purged with nitrogen for 2 minutes. Then the reaction mixture was hydrogenated for 2 h at ambient temperature. The reaction mixture was filtered through celite and washed with MeOH (10 mL). Then the filtrate was concentrated under reduced pressure to obtain ester Cap B-2b (220 mg) as a color less liquid which was used as such in the next step without any further purification. $^1$H NMR (CDCl$_3$, δ=7.26 ppm, 400 MHz): δ 3.65 (s, 3H), 2.00-1.50 (m, 6H), 1.28-1.14 (m, 3H), 1.12 (s, 6H), 1.10-0.90 (m, 2H).

Cap B-2

To a solution of ester B-2b (50 mg, 0.271 mmol) in THF (3 mL), MeOH (1.5 mL) and water (1.5 mL) was added LiOH (65.0 mg, 2.71 mmol) at 0° C. and heated at 70° C. for 12 h. Then the reaction mixture was cooled to 0° C. and adjusted the pH of the reaction mixture to (~3) with 1.5N HCl solution. Then the reaction mixture was extracted with EtOAc (2×50 mL) and the organic later was washed with brine (25 mL), dried over $Na_2SO_4$, filtered, and concentrated under reduced pressure to obtain Cap B-2 (20 mg) as white solid. $^1$H NMR (CDCl$_3$, δ=7.26 ppm, 400 MHz): δ 1.82-1.57 (m, 6H), 1.30-1.15 (m, 3H), 1.13 (s, 6H), 1.11-0.95 (m, 2H).

Cap B-3 & B-4

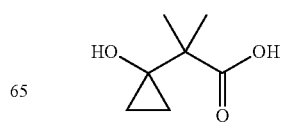

Cap B-3

Cap B-4

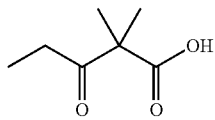

Cap B-3 & B-4

Step a

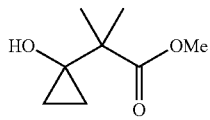

To a solution of (1-ethoxycyclopropoxy)trimethylsilane (500 mg, 2.87 mmol) and ((1-methoxy-2-methylprop-1-en-1-yl)oxy)trimethylsilane (1.163 mL, 5.74 mmol) in DCM (10 mL) was added neat BF$_3$.OEt$_2$ (0.582 mL, 4.59 mmol) drop wise at −78° C. and the reaction mixture was stirred for 5 h while warming to RT. The reaction mixture was quenched with saturated NaHCO$_3$ (50 mL), diluted with DCM (50 mL). The organic layer was separated and washed with 10% NaHCO$_3$ solution (50 mL), brine (50 mL), dried over Na$_2$SO$_4$, filtered and concentrated under reduced pressure. The crude was purified by column chromatography (Silica gel 60-120, 5-10% EtOAc/petroleum ether) to obtain hydroxyester B-3a (120 mg) as color less liquid. $^1$H NMR (CDCl$_3$, δ=7.26 ppm, 400 MHz): δ 3.73 (s, 3H), 3.20 (s, 1H), 1.16 (s, 6H), 0.74-0.68 (m, 4H).

Cap B-3 & B-4

To a solution of hydroxyester B-3a (50 mg, 0.316 mmol) in THF (3 mL), MeOH (1.5 mL) and water (1.5 mL) was added LiOH (76 mg, 3.16 mmol) at 0° C. and stirred for 12 h at room temperature. Then the reaction mixture was cooled to 0° C. and adjusted the pH of the reaction mixture to (~3) with 1.5N HCl solution. Then the reaction mixture was extracted with DCM (2×50 mL) and the organic later was washed with brine (25 mL), dried over Na$_2$SO$_4$, filtered, and concentrated under reduced pressure to obtain mixture of Cap B-3 and B-4 (40 mg) as a yellow liquid. Cap B-4: $^1$H NMR (CDCl$_3$, δ=7.26 ppm, 400 MHz): δ $^1$H NMR (CDCl$_3$, δ=7.26 ppm, 400 MHz): δ 2.58 (q, J=7.2, 2H), 1.20 (s, 6H), 1.08 (t, J=7.2, 3 H).

Cap B-5

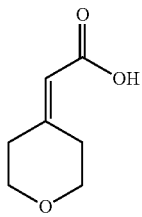

Cap B-5

Step a

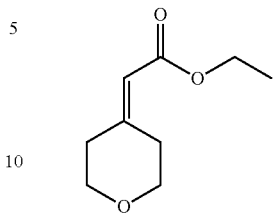

A solution of dihydro-2H-pyran-4(3H)-one (1.887 mL, 19.98 mmol) and ethyl 2-(triphenylphosphoranylidene)acetate (13.92 g, 40.0 mmol) in toluene (50 mL) was heated at 90° C. for 12 h. The reaction mixture was cooled to RT and concentrated under vacuum. The resulting crude was purified by Combi-flash (Silica gel, 40 g, Redisep, 5-10% EtOAc/petroleum ether) to obtain ester B-5a (3.7 g) as a color less liquid. $^1$H NMR (CDCl$_3$, δ=7.26 ppm, 300 MHz): δ 5.68-5.67 (m, 1H), 4.15 (q, J=7.2, 3H), 3.75 (dt, J=13.6, 5.6, 4H), 3.00 (dt, J=6.0, 1.2, 2H), 2.32 (dt, J=6.0, 1.2, 2H), 1.27 (t, J=7.2, 3 H).

Cap B-5

To a solution of ester B-5a (500 mg, 2.94 mmol) in THF (3 mL), MeOH (1.5 mL) and water (1.5 mL) was added LiOH (704 mg, 29.4 mmol) at 0° C. and stirred for 12 h at room temperature. Then the reaction mixture was cooled to 0° C. and adjusted the pH of the reaction mixture to (~3) with 1.5N HCl solution. Then the reaction mixture was extracted with DCM (2×50 mL) and the organic layer was washed with brine (25 mL), dried over Na$_2$SO$_4$, filtered, and concentrated under reduced pressure to obtain Cap B-5 (300 mg) as a color less liquid. $^1$H NMR (CDCl$_3$, δ=7.26 ppm, 400 MHz): δ 5.73 (s, 1H), 3.86-3.72 (m, 4H), 3.05-2.99 (m, 2H), 2.41-2.36 (m, 2H).

Cap B-6

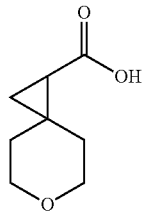

Cap B-6

Step a

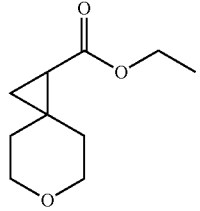

A solution of trimethylsulfoxonium iodide (800 mg, 3.63 mmol) and NaH (60% in mineral oil, 153 mg, 6.37 mmol) in DMSO (10 mL) was stirred at 0° C. to RT for 20 minutes. Then the reaction mixture was cooled to 0° C. and ester B-5a (500 mg, 2.94 mmol) in DMSO (5 mL) was added and stirred at RT for 18 h. The reaction mixture was quenched with water (20 mL) and extracted with EtOAc (2×50 mL). The organic layer was washed with water (2×50 mL), brine (50 mL), dried over Na$_2$SO$_4$, filtered and concentrated under reduced pressure. The crude was purified by column chromatography (Silica gel 60-120, 10-15% EtOAc/petroleum ether) to obtain ester B-6a (280 mg) as color less liquid. $^1$H NMR (CDCl$_3$, δ=7.26 ppm, 400 MHz): δ 4.13 (q, J=7.2, 2H), 3.74-3.56 (m, 4H), 1.77-1.73 (m, 2H), 1.56-1.42 (m, 3H), 1.27 (t, J=7.2, 3H), 1.17-1.15 (m, 1H), 0.93-0.88 (m, 1H).

Cap B-6

To a solution of ester B-6a (50 mg, 0.271 mmol) in (2:1:1) of THF (3 mL), MeOH (1.5 mL) and water (1.5 mL) was added LiOH (65.0 mg, 2.71 mmol) at 0° C. and stirred for 12 h at room temperature. Then the reaction mixture was cooled to 0° C. and adjusted the pH of the reaction mixture to (~3) with 1.5N HCl solution. Then the reaction mixture was extracted with DCM (2×50 mL) and the organic later was washed with brine (25 mL), dried over Na$_2$SO$_4$, filtered, and concentrated under reduced pressure to obtain Cap B-6 (35 mg) as a color less liquid. $^1$H NMR (CDCl$_3$, δ=7.26 ppm, 300 MHz): δ 3.83-3.68 (m, 4H), 1.85-1.81 (m, 2H), 1.62-1.42 (m, 3H) 1.21 (t, J=6.4, 1H), 1.07-1.01 (m, 1H).

Cap B-7

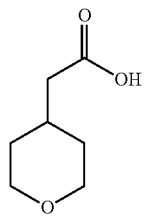

To a solution of Cap B-5 (100 mg, 0.703 mmol) in MeOH (5 mL) was added Pd/C (374 mg, 0.352 mmol) and the reaction mixture was purged with nitrogen for 2 minutes. Then the reaction mixture was hydrogenated for 12 h at ambient temperature. The reaction mixture was filtered through celite and washed with MeOH (2×10 mL). The filtrate was concentrated under reduced pressure to obtain Cap B-7 (82 mg) as a color less liquid. $^1$H NMR (CDCl$_3$, δ=7.26 ppm, 400 MHz): δ 3.98-3.94 (m, 2H), 3.45-3.41 (m, 2H), 2.30 (d, J=6.8, 2H), 2.05-1.95 (m, 1H), 1.71-1.66 (m, 2H), 1.43-1.28 (m, 2H).

Cap B-8

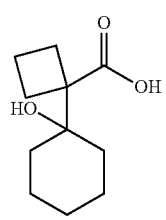

Cap B-8

Step a

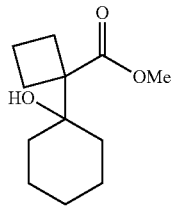

To a stirred solution of methyl cyclobutanecarboxylate (250 mg, 2.190 mmol) in THF (3 mL) was added LDA (1.095 mL, 2.190 mmol) (2 M in THF) drop wise at −78° C. and the reaction mixture was stirred at −78° C. for 1 h. A solution of cyclohexanone (150 mg, 1.533 mmol) in THF (2 mL) was added drop wise to the reaction mixture and stirring was continued at −78° C. for 2 h and at room temperature for overnight. Ice cold saturated NH$_4$Cl solution (10 mL) was added to the reaction mixture and extracted with EtOAc (2×10 mL). The organic layer was washed with water (20 mL), brine (20 mL), dried over Na$_2$SO$_4$ and concentrated under reduced pressure. The crude was purified by column chromatography (Silica gel 230-400, 3% EtOAc/petroleum ether) to yield hydroxyester B-8a (145 mg) as a colorless oil. $^1$H NMR (CDCl$_3$, δ=7.26 ppm, 400 MHz): δ 3.75 (s, 3H), 2.76 (s, 1H), 2.41-2.23 (m, 4H), 1.87-1.73 (m, 2H), 1.71-1.55 (m, 8H), 1.45-1.33 (m, 2H).

Cap B-8

LiOH (56.4 mg, 2.355 mmol) was added to a stirred solution of hydroxyester B-8a (50 mg, 0.236 mmol) in THF (0.5 mL) and water (0.5 mL) at 0° C. and the reaction mixture was stirred at room temperature for overnight. The reaction mixture was concentrated under reduced pressure. Water (10 mL) was added to the residue and extracted with 10% EtOAc/Petroleum ether (10 mL). The aqueous layer was acidified with 1.5 N HCl and extracted with DCM (2×10 mL). The organic layer was dried over Na$_2$SO$_4$ and concentrated under reduced pressure to yield Cap B-8 (16 mg) as an off white solid. $^1$H NMR (MeOD, δ=3.34 ppm, 400 MHz): δ 2.41-2.25 (m, 4H), 1.89-1.51 (m, 9H), 1.49-1.37 (m, 2H), 1.18-1.11 (m, 1H).

Cap B-9

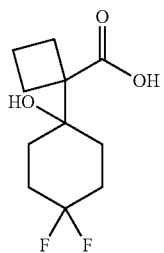

Cap B-9

Step a

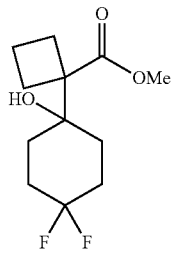

To a stirred solution of methyl cyclobutanecarboxylate (200 mg, 1.752 mmol) in THF (2 mL) was added LDA (0.876 mL, 1.752 mmol) (2 M in THF) drop wise at −78° C. and the reaction mixture was stirred at −78° C. for 1 h. A solution of 4,4-difluorocyclohexanone (165 mg, 1.227 mmol) in THF (2 mL) was added drop wise to the reaction mixture; stirring was continued at −78° C. for 2 h and at room temperature for overnight. Ice cold saturated NH$_4$Cl solution (10 mL) was added to the reaction mixture and extracted with EtOAc (2×10 mL). The organic layer was washed with water (20 mL) and brine (20 mL), dried over Na$_2$SO$_4$ and concentrated under reduced pressure. The crude was purified by column chromatography (Silica gel 230-400, 3% EtOAc/petroleum ether) to yield hydroxyester B-9a (220 mg) as an off white solid. $^1$H NMR (CDCl$_3$, δ=7.26 ppm, 400 MHz): δ 3.79 (s, 3H), 3.26 (s, 1H), 2.46-2.35 (m, 2H), 2.28-2.10 (m, 4H), 2.01-1.63 (m, 8H).

Cap B-9

LiOH (48.2 mg, 2.014 mmol) was added to a stirred solution of hydroxyester B-9a (50 mg, 0.201 mmol) in THF (0.5 mL) and water (0.5 mL) at 0° C. and the reaction mixture was stirred at room temperature for overnight. LiOH (48.2 mg, 2.014 mmol) was again added to the reaction mixture and stirring was continued for further 24 h. The volatile components were removed under reduced pressure. Water (10 mL) was added to the residue and extracted with 10% EtOAc/Petroleum ether (10 mL). The aqueous layer was acidified with 1.5 N HCl and extracted with DCM (2×10 mL). The organic layer was dried over Na$_2$SO$_4$ and concentrated under reduced pressure to yield Cap B-9 (32 mg) as an off white solid. $^1$H NMR (CDCl$_3$, δ=7.26 ppm, 400 MHz): δ 2.53-2.42 (m, 2H), 2.32-2.09 (m, 4H), 2.05-1.92 (m, 3H), 1.89-1.72 (m, 5H).

Cap B-10

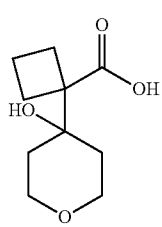

Cap B-10

Step a

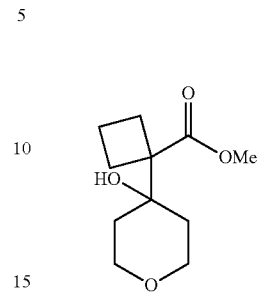

To a stirred solution of methyl cyclobutanecarboxylate (200 mg, 1.752 mmol) in THF (2 mL) was added LDA (0.876 mL, 1.752 mmol) (2 M in THF) drop wise at −78° C. and the reaction mixture was stirred at −78° C. for 1 h. A solution of dihydro-2H-pyran-4(3H)-one (123 mg, 1.227 mmol) in THF (1 mL) was added drop wise to the reaction mixture; stirring was continued at −78° C. for 2 h and at room temperature for overnight. Ice cold saturated NH$_4$Cl solution (10 mL) was added to the reaction mixture and extracted with EtOAc (2×10 mL). The organic layer was washed with water (20 mL) and brine (20 mL), dried over Na$_2$SO$_4$ and concentrated under reduced pressure. The crude was purified by column chromatography (Silica gel 230-400, 18% EtOAc/petroleum ether) to yield hydroxyester B-10a (150 mg) as a colorless oil. $^1$H NMR (CDCl$_3$, δ=7.26 ppm, 400 MHz): δ 3.85-3.79 (m, 4H), 3.77 (s, 3H), 3.20 (s, 1H), 2.44-2.34 (m, 2H), 2.31-2.20 (m, 2H), 1.96-1.77 (m, 4H), 1.45-1.38 (m, 2H).

Cap B-10

LiOH (168 mg, 7.00 mmol) was added to a stirred solution of hydroxyester B-10a (150 mg, 0.700 mmol) in THF (1 mL) and water (1 mL) at 0° C. and the reaction mixture was stirred at room temperature for 48 h. The reaction mixture was concentrated under reduced pressure. Water (10 mL) was added to the residue and extracted with 10% EtOAc/Petroleum ether (10 mL). The aqueous layer was acidified with 1.5N HCl and extracted with DCM (2×10 mL). The organic layer was dried over Na$_2$SO$_4$ and concentrated under reduced pressure to yield Cap B-10 (28 mg) as a white solid. $^1$H NMR (MeOD, δ=3.34 ppm, 400 MHz): δ 3.79-3.75 (m, 4H), 2.39-2.32 (m, 4H), 1.93-1.74 (m, 4H), 1.53-1.47 (m, 2H).

Cap B-11

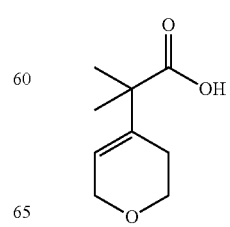

Cap B-11

Step a

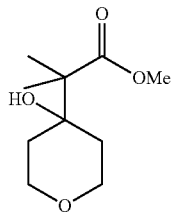

To a stirred solution of dihydro-2H-pyran-4(3H)-one (2 g, 19.98 mmol) and ((1-methoxy-2-methylprop-1-en-1-yl)oxy)trimethylsilane (6.96 g, 40.0 mmol) in DCM (20 mL) was added $BF_3.OEt_2$ (4.05 mL, 32.0 mmol) drop wise at −78° C. and the reaction mixture was gradually allowed to warm to room temperature. Ice cold saturated $NH_4Cl$ solution (100 mL) was added to the reaction mixture and extracted with EtOAc (2×100 mL). The organic layer was washed with water (100 mL), brine (100 mL), dried over $Na_2SO_4$, filtered and concentrated under reduced pressure. The crude was purified by column chromatography (Silica gel 60-120, 15% EtOAc/petroleum ether) to yield hydroxyester B-11a (4 g) as a colorless oil. $^1$H NMR ($CDCl_3$, δ=7.26 ppm, 400 MHz): δ 3.87-3.75 (m, 4H), 3.72 (s, 3H), 3.51-3.50 (m, 1H), 1.88-1.75 (m, 2H), 1.37-1.31 (m, 2H), 1.24 (s, 6H).

Cap B-11

Step b

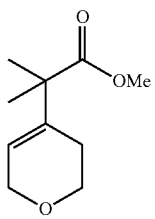

To a stirred solution of hydroxyester B-11a (1 g, 4.94 mmol) in DCM (10 mL) was added DAST (1.307 mL, 9.89 mmol) at −78° C. and the reaction mixture was gradually brought to room temperature and stirred for 12 h. The reaction mixture was cooled to 0° C. and quenched with cold 10% $NaHCO_3$ solution (50 mL). The reaction mixture was extracted with DCM (2×50 mL) and washed with water (100 mL). The organic layer was dried over $Na_2SO_4$ and concentrated under reduced pressure. The crude was purified by column chromatography (Silica gel 60-120, 5% EtOAc/petroleum ether) to yield ester Cap B-11b (600 mg) as a yellow oil. $^1$H NMR ($CDCl_3$, δ=7.26 ppm, 400 MHz): δ 5.59-5.57 (m, 1H), 4.19 (dd, J=2.8, 2.4, 2H), 3.76 (t, J=5.4, 2H), 3.65-3.67 (s, 3H), 2.08-2.02 (m, 2H), 1.31 (s, 6H).

Cap B-11

To a stirred solution of ester Cap B-11b (100 mg, 0.543 mmol) in water (1 mL) and THF (1 mL) was added LiOH (195 mg, 8.14 mmol) and the reaction mixture was stirred at room temperature for 24 h. The volatile components were removed under reduced pressure. Water (10 mL) was added to the residue and extracted with 10% EtOAc/Petroleum ether (10 mL). The aqueous layer was acidified with 1.5N HCl and extracted with DCM (2×10 mL). The organic layer was dried over $Na_2SO_4$ and concentrated under reduced pressure to yield Cap B-11 (80 mg) as brown oil. $^1$H NMR (MeOD, δ=3.34 ppm, 400 MHz): δ 5.67-5.65 (m, 1H), 4.19 (dd, J=2.8, 2.4, 2H), 3.78 (t, J=5.4, 2H), 2.17-2.01 (m, 2H), 1.32 (s, 6H).

Cap B-12

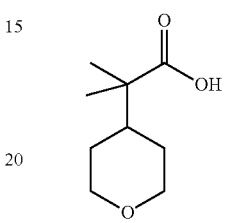

To a stirred solution of Cap B-11 (25 mg, 0.147 mmol) in MeOH (1.5 mL) was added AcOH (0.05 mL) followed by Pd/C (15.63 mg, 0.015 mmol) and the reaction mixture was stirred in a tinyclave under hydrogen atmosphere (5 kg/cm$^2$) for overnight. The reaction mixture was filtered through celite and the filter cake was washed with MeOH (2×5 mL). The combined filtrate was concentrated under reduced pressure to yield Cap B-12 (17 mg) as an off-white solid. $^1$H NMR (MeOD, δ=3.34 ppm, 400 MHz): δ 3.99 (dd, J=11.2, 4.4, 2H), 3.41 (dt, J=11.6, 2.4, 2H), 1.90-1.81 (m, 1H), 1.56-1.41 (m, 4H), 1.14 (s, 6H).

Cap B-13

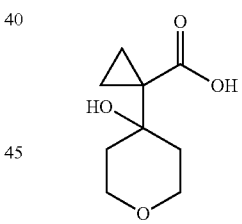

Cap B-13

Step a

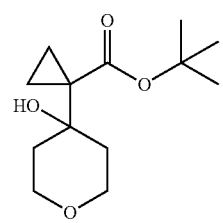 [SMILES: CC(C)(C)OC(=O)C1(C2(O)CCOCC2)CC1]

To a stirred solution of tert-butyl cyclopropanecarboxylate (350 mg, 2.461 mmol) in THF (2 mL) was added LDA (1.600 mL, 3.20 mmol) (2 M in THF) drop wise at −78° C. and the reaction mixture was stirred at −78° C. for 1 h. Then dihydro-2H-pyran-4(3H)-one (172 mg, 1.723 mmol) in THF (1 mL) was added drop wise; stirring was continued at −78° C. for 1 h and at RT for overnight. Ice cold saturated NH$_4$Cl solution (10 mL) was added to the reaction mixture and extracted with EtOAc (2×20 mL). The organic layer was washed with water (20 mL), brine (20 mL), dried over Na$_2$SO$_4$, filtered, and concentrated under reduced pressure. The crude was purified by Combiflash Isco (Silica gel, 4 g, Redisep, 18% EtOAc/petroleum ether) to yield hydroxyester B-13a (350 mg) as a colorless oil. $^1$H NMR (CDCl$_3$, δ=7.26 ppm, 400 MHz): δ 4.51-4.48 (m, 1H), 3.84 (dt, J=11.6, 2.4, 2H), 3.78-3.72 (m, 2H), 1.62-1.48 (m, 4H), 1.42 (s, 9H), 1.12-1.08 (m, 2H), 0.95-0.91 (m, 2H).

Cap B-13

To a stirred solution of hydroxyester B-13a (100 mg, 0.413 mmol) in DCM (0.5 mL) was added TFA (0.6 mL, 7.79 mmol) in DCM (1.2 mL) at 0° C. and the reaction mixture was stirred at room temperature for 2 h. The reaction mixture was concentrated to dryness under reduced pressure. The residue was co-evaporated with DCM (3×5 mL) to yield Cap B-13 (85 mg) as an off-white solid. $^1$H NMR (MeOD, δ=3.34 ppm, 400 MHz): δ 3.81-3.75 (m, 4H), 2.20-2.11 (m, 2H), 1.49-1.45 (m, 2H), 1.14-1.11 (m, 2H), 1.08-1.05 (m, 2H).

Cap B-14

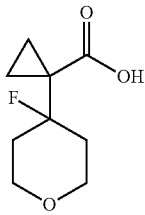 [SMILES: O=C(O)C1(C2(F)CCOCC2)CC1]

Cap B-14

Step a

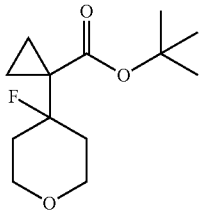 [SMILES: CC(C)(C)OC(=O)C1(C2(F)CCOCC2)CC1]

To a stirred solution of hydroxyester B-13a (100 mg, 0.413 mmol) in DCM (2 mL) was added DAST (0.109 mL, 0.825 mmol) at −78° C. and the reaction mixture was gradually brought to room temperature and stirred for 12 h. The reaction mixture was cooled to 0° C. and quenched with ice cold 10% NaHCO$_3$ solution (10 mL). The reaction mixture was extracted with DCM (2×20 mL) and washed with water (30 mL). The organic layer was dried over Na$_2$SO$_4$ and concentrated under reduced pressure. The crude was purified by column chromatography (Silica gel 60-120, 5% EtOAc/petroleum ether) to obtain ester B-14a (35 mg) as a yellow oil. $^1$H NMR (CDCl$_3$, δ=7.26 ppm, 400 MHz): δ 3.86 (dd, J=11.6, 6.0, 2H), 3.66 (dt, J=11.2, 2.0, 2H), 2.62-2.43 (m, 2H), 1.65-1.56 (m, 2H), 1.46 (s, 9H), 1.10-1.01 (m, 4H).

Cap B-14

To a stirred solution of ester B-14a (200 mg, 0.819 mmol) in DCM (0.5 mL) was added a solution of TFA (0.378 mL, 4.91 mmol) in DCM (0.3 mL) at 0° C. and the reaction mixture was stirred at room temperature for 2 h. The reaction mixture was concentrated to dryness under reduced pressure. The residue was co-evaporated with DCM (3×5 mL) to yield Cap B-14 (150 mg) as an off-white solid. $^1$H NMR (CDCl$_3$, δ=7.26 ppm, 400 MHz): δ 3.92 (dd, J=11.6, 5.6, 2H), 3.69 (dt, J=11.2, 2.0, 2H), 2.67-2.46 (m, 2H), 1.65-1.53 (m, 2H), 1.34-1.20 (m, 4H).

Cap B-15

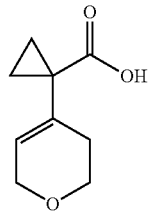 [SMILES: O=C(O)C1(C2=CCOCC2)CC1]

To a stirred solution of Cap B-14 (330 mg, 1.753 mmol) in DCM (1 mL) at 0° C. was added BF$_3$.OEt$_2$ (1.111 mL, 8.77 mmol) drop wise and the reaction mixture was stirred at 0° C. for 1 h and at room temperature for 12 h. The reaction mixture was concentrated under reduced pressure at room temperature. Water (15 mL) was added to the residue followed by 10% NaHCO$_3$ solution (25 mL) and extracted with 10% EtOAc/petroleum ether (50 mL). The aqueous layer was acidified with 1.5N HCl and extracted with EtOAc (2×50 mL). The organic layer was washed with brine (50 mL), dried over Na$_2$SO$_4$ and concentrated under reduced pressure to yield Cap B-15 (200 mg) as a brown solid. $^1$H NMR (MeOD, δ=3.34 ppm, 400 MHz): δ 5.67-5.64 (m, 1H), 4.14-4.11 (m, 2H), 3.82-3.77 (m, 2H), 2.31-2.26 (m, 2H), 1.32-1.28 (m, 2H), 1.02-0.95 (m, 2H).

Cap B-16

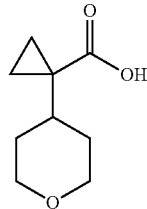 [SMILES: O=C(O)C1(C2CCOCC2)CC1]

To a stirred solution of Cap B-15 (85 mg, 0.505 mmol) in MeOH (2 mL) was added AcOH (0.01 mL) followed by Pd/C (26.9 mg, 0.025 mmol) and the reaction mixture was stirred in a tinyclave hydrogen atmosphere (5 kg/cm$^2$) at room temperature for 12 h. The reaction mixture was filtered and the filtrate was concentrated under reduced pressure. 10% NaHCO₃ solution (20 mL) was added to the residue and extracted with 10% EtOAc in petroleum ether (20 mL). The aqueous layer was acidified with 1.5N HCl and extracted with EtOAc (2×20 mL). The organic layer was washed with brine (20 mL), dried over Na₂SO₄ and concentrated under reduced pressure to yield Cap B-16 (65 mg) as a brown gummy solid. ¹H NMR (DMSO-d₆, δ=2.50 ppm, 300 MHz): δ 3.89-3.80 (m, 2H), 3.30-3.12 (m, 2H), 1.59-1.38 (m, 5H), 0.95-0.70 (m, 4H).

Cap B-17

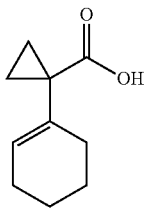 [SMILES: O=C(O)C1(C2=CCCCC2)CC1]

Cap B-17

Step a

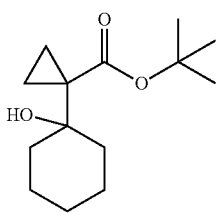 [SMILES: CC(C)(C)OC(=O)C1(C2(O)CCCCC2)CC1]

To a stirred solution of tert-butyl cyclopropanecarboxylate (0.5 g, 3.52 mmol) in THF (4 mL) was added LDA (0.452 g, 4.22 mmol) at −78° C. and stirred for 2 h. Then cyclohexanone (0.207 g, 2.110 mmol) was added drop wise at −78° C. and stirred for 2 h at same temperature and the reaction mixture was slowly brought to ambient temperature and stirred for 12 h. The reaction was quenched with water (50 mL) and extracted with EtOAc (250 mL), washed with brine, dried over Na₂SO₄, filtered and evaporated under reduced pressure. The crude was purified by flash chromatography (Silica gel 230-400, 5-10% EtOAc/petroleum ether) to give hydroxyester B-17a (0.3 g) as a pale yellow sold. ¹H NMR (DMSO-d₆, δ=2.50 ppm, 400 MHz): δ 3.82 (s, 1H), 2.03 (dt, J=13.2, 4.4, 2H), 1.65-1.49 (m, 3H), 1.46-1.32 (m, 4H), 1.37 (s, 9H), 1.13-1.10 (m, 1H), 0.97-0.94 (m, 2H), 0.80-0.77 (m, 2H).

Cap B-17

To a stirred solution of hydroxyester B-17a (0.1 g, 0.416 mmol) in DCM (1 mL) was added TFA (0.5 mL, 6.49 mmol) drop wise at ambient temperature and the reaction mixture was stirred for 2 h. The volatile components were evaporated under reduced pressure to get Cap B-17 (0.08 g) as an off-white solid. ¹H NMR (DMSO-d₆, δ=2.50 ppm, 400 MHz): δ 12.08 (s, 1H), 5.55-5.53 (m, 1H), 2.07-2.05 (m, 2H), 1.97-1.95 (m, 2H), 1.58-1.48 (m, 4H), 1.13-1.08 (m, 2H), 0.84-0.80 (m, 2H).

Cap B-18

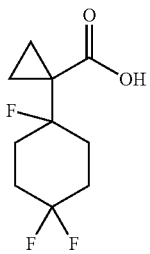 [SMILES: O=C(O)C1(C2(F)CCC(F)(F)CC2)CC1]

Cap B-18

Step a

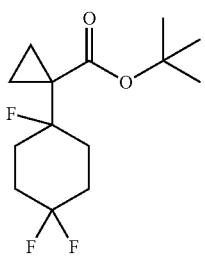 [SMILES: CC(C)(C)OC(=O)C1(C2(F)CCC(F)(F)CC2)CC1]

To a stirred solution of tert-butyl 1-(4,4-difluoro-1-hydroxycyclohexyl)cyclopropanecarboxylate (0.2 g, 0.724 mmol) in DCM (4 mL) was added DAST (0.096 mL, 0.724 mmol) drop wise at −20° C. and the reaction mixture was slowly brought to ambient temperature and stirred for 1 h. Then the reaction mixture was saturated NaHCO₃ (25 mL) and extracted with DCM (200 mL). The organic layer was dried over Na₂SO₄, filtered and evaporated under reduced pressure. The crude was purified by flash chromatography (Silica gel 230-400, 4% EtOAc/petroleum ether) to give ester B-18a (0.07 g). ¹H NMR (CDCl₃, δ=7.26 ppm, 400 MHz): δ 2.70-2.49 (m, 2H), 2.10-1.92 (m, 4H), 1.87-1.78 (m, 2H), 1.43 (s, 9H), 1.12-1.09 (m, 2H), 1.06-1.03 (m, 2H).

Cap B-18

To a stirred solution of ester B-18a (0.06 g, 0.216 mmol) in DCM (1 mL) was added TFA (0.083 mL, 1.078 mmol) at 0° C. and stirred for 1 h at same temperature. The reaction mixture was evaporated under reduced pressure and the resulting crude was co-evaporated with DCM (3×5 mL), dried under high vacuum to give Cap B-18 (0.045 g) as an off-white solid. ¹H NMR (CDCl₃, δ=7.26 ppm, 400 MHz): δ 2.75-2.50 (m, 2H), 2.09-1.97 (m, 4H), 1.85-1.78 (m, 2H), 1.24-1.21 (m, 2H), 1.12-1.05 (m, 2H).

Cap B-19

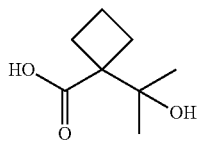

Cap B-19

Step a

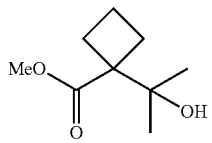

To a stirred solution of methyl cyclobutanecarboxylate (0.44 g, 3.85 mmol) in THF (2 mL) was added LDA (0.496 g, 4.63 mmol) drop wise at −78° C. and the resulting mixture was stirred at same temperature for 2 h. Then anhydrous acetone (0.198 mL, 2.70 mmol) was added drop wise at −78° C.; reaction mixture was slowly brought to ambient temperature and stirred for 12 h. The reaction mixture was quenched with crushed ice and extracted with EtOAc (100 mL), dried over $Na_2SO_4$, filtered and evaporated under reduced pressure. The crude was purified by (Silica gel 230-400, 8% EtOAc/petroleum ether) to give hydroxyester B-19a (0.25 g) as pale yellow liquid. $^1H$ NMR (DMSO-$d_6$, δ=2.50 ppm, 400 MHz): δ 4.63 (s, 1H), 3.62 (s, 3H), 2.40-2.34 (m, 2H), 2.18-2.12 (m, 2H), 1.67-1.63 (m, 2H), 1.01 (s, 6H).

Cap B-19

To a stirred solution of hydroxyester B-19a (0.12 g, 0.697 mmol) in THF (2 mL), MeOH (2 mL) and water (2 mL) was added LiOH (0.083 g, 3.48 mmol) and the resulting reaction mixture was stirred at RT for 12 h. Then, the volatile components were evaporated under reduced pressure. The resulting residue was dissolved in water (50 mL) and pH was adjusted to 4-5 with 0.5N HCl solution. The aqueous solution was extracted with DCM (250 mL), dried over $Na_2SO_4$, filtered and evaporated under reduced pressure to give Cap B-19 (0.065 g) as a colourless liquid. $^1H$ NMR (CDCl$_3$, δ=7.26 ppm, 300 MHz): δ 2.55-2.44 (m, 2H), 2.28-2.17 (m, 2H), 2.05-1.84 (m, 2H), 1.37 (s, 6H).

Cap B-20

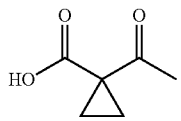

Cap B-20

Step a

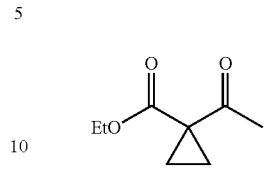

To a stirred solution of ethyl 3-oxobutanoate (1 g, 7.68 mmol) in DMSO (10 mL) was added $K_2CO_3$ (3.19 g, 23.05 mmol) at RT followed by drop-wise addition of 1, 2 dibromo ethane (3.61 g, 19.2 mmol). The reaction mixture was stirred at ambient temperature for 48 h and quenched with water (50 mL). The reaction mixture was extracted with EtOAc (200 mL), washed with brine (50 mL), dried over $Na_2SO_4$, filtered and evaporated under reduced pressure. The crude was purified flash chromatography (Silica gel 230-400, 2% EtOAc/petroleum ether) to give ketoester B-20a (0.6 g). $^1H$ NMR (CDCl$_3$, δ=7.26 ppm, 400 MHz): 4.20 (q, d=7.2, 2H), 2.46 (s, 3H), 1.46 (s, 4H), 1.28 (t, J=7.2, 3 H).

Cap B-20

To a stirred solution of ketoester B-20a (0.3 g, 1.921 mmol) in MeOH (4 mL) was added LiOH (0.460 g, 19.21 mmol) and the resulting mixture was stirred at room temperature for 12 h. The volatile components were evaporated under reduced pressure and diluted with water (50 mL). The pH of the reaction mixture was adjusted to 3-4 with 1N HCl and extracted with DCM (250 mL). The organic layer was dried over $Na_2SO_4$, filtered and evaporated under reduced pressure to give Cap B-20 (0.07 g). $^1H$ NMR (CDCl$_3$, δ=7.26 ppm, 300 MHz): δ 2.12 (s, 3H), 2.01-1.98 (m, 2H), 1.76-1.73 (m, 2H).

Cap B-21

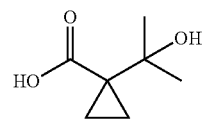

Cap B-21

Step a

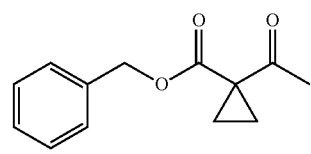 [SMILES: CC(=O)C1(C(=O)OCc2ccccc2)CC1]

To a stirred solution of 3-(((3-oxobutanoyl)oxy)methyl) benzene-1-ylium (1 g, 5.23 mmol) in DMSO (10 mL) was added $K_2CO_3$ (2.168 g, 15.69 mmol) at RT followed by drop-wise addition of 1,2-dibromoethane (2.456 g, 13.08 mmol). The reaction mixture was stirred at ambient temperature for 24 h and then heated to 80° C. for 24 h. The reaction was quenched with water (100 mL) and extracted with EtOAc (200 mL). The organic layer was washed with brine (50 mL), dried over Na₂SO₄, filtered and evaporated under reduced pressure. The crude was purified by reverse phase HPLC (ACN/water/NH₄OAc) to give ketoester B-21a (0.3 g). ¹H NMR (MeOD, δ=3.34 ppm, 400 MHz): δ 7.39-7.33 (m, 5H), 5.20 (s, 2H), 2.40 (s, 3H), 1.50-1.42 (m, 4H).

Cap B-21

Step b

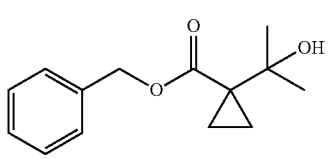 [SMILES: CC(C)(O)C1(C(=O)OCc2ccccc2)CC1]

To a stirred solution of ketoester B-21a (0.5 g, 2.291 mmol) in THF (10 mL) was added MeMgBr (0.273 g, 2.291 mmol) at 0° C. and the resulting mixture was slowly brought to ambient temperature and stirred for 12 h. The reaction was quenched with water and extracted with EtOAc (200 mL). The organic layer was washed with brine (50 mL), dried over Na₂SO₄, filtered and evaporated under reduced pressure. The crude was purified by flash chromatography (Silica gel 230-400, 12% EtOAc/petroleum ether) to give hydroxyester B-21b (0.3 g). ¹H NMR (MeOD, δ=3.34 ppm, 400 MHz): δ 7.38-7.33 (m, 5H), 5.08 (s, 2H), 1.39 (s, 6H), 1.10-1.09 (m, 4H).

Cap B-21

To a stirred solution of hydroxyester B-21b (0.1 g, 0.427 mmol) in EtOAc (5 mL) was added Pd/C (0.018 g, 0.017 mmol) and the resulting mixture was subjected to hydrogenation under balloon pressure for 12 h. The reaction mixture was filtered through celite and the filter cake was washed with EtOAc (3×5 mL). The filtrate was evaporated under reduced pressure to give Cap B-21 (0.06 g) as a white solid. ¹H NMR (MeOD, δ=3.34 ppm, 400 MHz): δ 1.37 (s, 6H), 1.09-1.05 (m, 4H).

Cap B-22

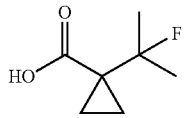

Cap B-22

Step a

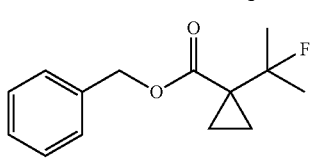

To a stirred solution of hydroxyester B-21b (0.2 g, 0.854 mmol) in DCM (5 mL) was added DAST (0.135 mL, 1.024 mmol) drop wise at −20° C. and the reaction mixture was slowly brought to ambient temperature and stirred for 2 h. The reaction was cooled to 0° C. and quenched with saturated NaHCO₃ (50 mL) and extracted with DCM (200 mL). The organic layer was dried over Na₂SO₄, filtered and evaporated under reduced pressure to give ester Cap B-22a (0.15 g) as a brown liquid. ¹H NMR (CDCl₃, δ=7.26 ppm, 400 MHz): δ 7.36-7.28 (m, 5H), 5.07 (s, 2H), 1.58 (d, J=23.6, 6H), 1.22-1.19 (m, 2H), 1.15-1.13 (m, 2H).

Cap B-22

To a stirred solution of ester B-22a (0.1 g, 0.423 mmol) in EtOAc (5 mL) was added Pd/C (0.018 g, 0.017 mmol) and the resulting mixture was subjected to hydrogenation under balloon pressure for 12 h. The reaction mixture was filtered through celite pad and the filter cake was washed with EtOAc (3×5 mL). The filtrate was evaporated under reduced pressure to give Cap B-22 (0.04 g) as white solid. ¹H NMR (MeOD, δ=3.34 ppm, 400 MHz): δ 1.58 (d, J=23.6, 6H), 1.17-1.15 (m, 2H), 1.10-1.08 (m, 2H).

Cap B-23

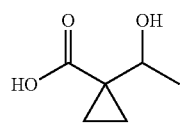

Cap B-23

Step a

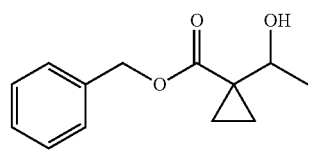

To a stirred solution of ketoester Cap B-21a (0.4 g, 1.833 mmol) in MeOH (10 mL) was added NaBH₄ (0.069 g, 1.833 mmol) portion wise at 0° C. and the resulting mixture was stirred at same temperature for 1 h. The solvent was evaporated under reduced pressure and the resulting crude was dissolved in water (20 mL). The pH of the reaction mixture was adjusted to 5-6 with 1.5N HCl. The aqueous layer was extracted with DCM (200 mL) and organic layer was dried over Na₂SO₄, filtered and evaporated under reduced pressure to give hydroxyester B-23a (0.3 g). ¹H NMR (CDCl₃, δ=7.26 ppm, 400 MHz): δ 7.38-7.25 (m, 5H), 5.12 (ABq, J=12.4, 2H), 3.63 (q, J=6.4, 1H), 1.32-1.22 (m, 2H), 1.26 (d, J=6.4, 3H), 0.97-0.92 (m, 1H), 0.86-0.82 (m, 1H).

Cap B-23

To a stirred solution of hydroxyester B-23a (0.2 g, 0.908 mmol) in EtOAc (5 mL) was added Pd/C (0.966 g, 0.908 mmol) and the resulting mixture was subjected to hydrogenation under balloon pressure for 12 h. The reaction mixture was filtered through celite pad and the filter cake was washed with EtOAc (3×5 mL). The filtrate was evaporated under reduced pressure to give Cap B-23 (0.09 g) as a pale yellow liquid. ¹H NMR (CDCl₃, δ=7.26 ppm, 400 MHz): δ 3.61-3.57 (m, 1H), 1.37-1.21 (m, 2H), 1.28 (d, J=6.4, 3H), 1.00-0.95 (m, 1H), 0.87-0.81 (m, 1H).

Cap B-24

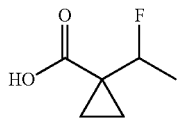

Cap B-24

Step a

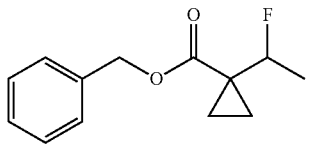 [SMILES: CC(F)C1(C(=O)OCc2ccccc2)CC1]

To a stirred solution of hydroxyester B-23a (0.2 g, 0.908 mmol) in DCM (5 mL) was added DAST (0.144 mL, 1.090 mmol) drop wise at −20° C. and the reaction mixture was slowly brought to ambient temperature and stirred for 2 h. The reaction was cooled to 0° C. and quenched with saturated NaHCO₃ (50 mL). The reaction mixture was extracted with DCM (200 mL), dried over Na₂SO₄ and evaporated under reduced pressure to give ester Cap B-24a (0.15 g) as a pale yellow liquid. ¹H NMR (CDCl₃, δ=7.26 ppm, 400 MHz): δ 7.38-7.28 (m, 5H), 5.12 (dq, J=47.2, 6.4, 1H), 5.11 (s, 2H), 1.37 (dd, J=27.6, 6.4, 3H), 1.31-1.20 (m, 2H), 1.14-1.08 (m, 1H), 0.98-0.92 (m, 1H).

Cap B-24

To a stirred solution of ester B-24a (0.15 g, 0.675 mmol) in EtOAc (5 mL) was added Pd/C (0.718 g, 0.675 mmol) and the resulting mixture was subjected to hydrogenation under balloon pressure for 12 h. The reaction mixture was filtered through celite pad and the filter cake was washed with EtOAc (3×5 mL). The filtrate was evaporated under reduced pressure to give Cap B-24 (0.06 g). ¹H NMR (CDCl₃, δ=7.26 ppm, 300 MHz): δ 7.53 (br s, 1H), 5.55 (dq, J=47.2, 6.4, 1H), 1.38 (dd, J=24.4, 6.4, 3H), 1.36-1.24 (m, 2H), 1.17-1.12 (m, 1H), 1.02-0.98 (m, 1H).

Cap B-25

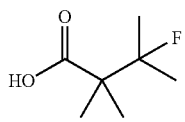

Cap B-25

Step a

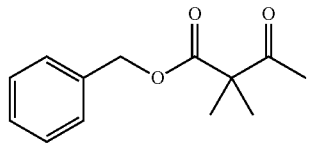 [SMILES: CC(=O)C(C)(C)C(=O)OCc1ccccc1]

To a stirred solution of benzyl 3-oxobutanoate (3 g, 15.61 mmol) in DMSO (30 mL) was added K₂CO₃ (6.47 g, 46.8 mmol) at RT followed by drop-wise addition of MeI (2.93 mL, 46.8 mmol). Then the reaction mixture was stirred at ambient temperature for 24 h. The reaction was quenched with water (100 mL) and extracted with EtOAc (200 mL). The organic layer was washed with brine (50 mL), dried over Na₂SO₄ and evaporated under reduced pressure. The crude was purified by reverse phase HPLC (ACN/water/NH₄OAc) to give ketoester B-25a (3 g). ¹H NMR (CDCl₃, δ=7.26 ppm, 400 MHz): 7.36-7.31 (m, 5H), 5.17 (s, 2H), 2.08 (s, 3H), 1.38 (s, 6H).

Cap B-25

Step b

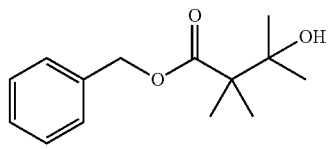 [SMILES: CC(C)(O)C(C)(C)C(=O)OCc1ccccc1]

To a stirred solution of ketoester B-25a (0.5 g, 2.270 mmol) in THF (10 mL) was added MeMgBr (0.271 g, 2.270 mmol) at 0° C. and the resulting mixture was slowly brought to ambient temperature and stirred for 12 h. The reaction was quenched with water and extracted with EtOAc (200 mL). The organic layer was washed with brine (50 mL), dried over Na₂SO₄ and evaporated under reduced pressure. The crude material was purified by flash chromatography (Silica gel 230-400, 15% EtOAc/petroleum ether) to give hydroxyester B-25b (0.3 g). ¹H NMR (CDCl₃, δ=7.26 ppm, 400 MHz): δ 7.38-7.33 (m, 5H), 5.16 (s, 2H), 3.59 (s, 1H), 1.26 (s, 6H), 1.17 (s, 6H).

Cap B-25

Step c

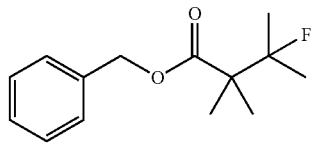 [SMILES: CC(C)(F)C(C)(C)C(=O)OCc1ccccc1]

To a stirred solution of hydroxyester B-25b (0.2 g, 0.846 mmol) in DCM (5 mL) was added DAST (0.134 mL, 1.016 mmol) drop wise at −20° C. and the reaction mixture was slowly brought to ambient temperature and stirred for 2 h. The reaction was cooled to 0° C. and quenched with saturated NaHCO₃ (50 mL) and extracted with DCM (200 mL). The organic layer was washed with brine (50 mL), dried over Na₂SO₄ and evaporated under reduced pressure to give ester B-25c (0.12 g) as a brown liquid. ¹H NMR (CDCl₃, δ=7.26 ppm, 400 MHz): 7.37-7.30 (m, 5H), 5.12 (s, 2H), 1.33 (s, 6H), 1.31-1.10 (m, 6H).

Cap B-25

To a stirred solution of ester B-25c (0.1 g, 0.420 mmol) in EtOAc (5 mL) was added Pd/C (0.018 g, 0.017 mmol) and the resulting mixture was subjected to hydrogenation under balloon pressure for 12 h. The reaction mixture was filtered through celite pad and the filter cake was washed with EtOAc (3×5 mL). The filtrate was evaporated under reduced pressure to give to give Cap B-25 (0.04 g). ¹H NMR (CDCl₃, δ=7.26 ppm, 400 MHz): δ 1.43 (d, J=22.4, 6H), 1.27 (s, 6H).

Cap B-26

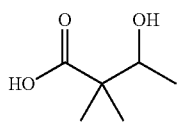

Cap B-26

Step a

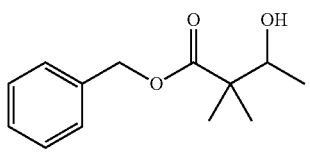 [SMILES: CC(O)C(C)(C)C(=O)OCc1ccccc1]

To a stirred solution of ketoester B-25a (0.8 g, 3.63 mmol) in MeOH (10 mL) was added NaBH₄ (0.137 g, 3.63 mmol) portion wise at 0° C. and the resulting mixture was stirred at same temperature for 1 h. The solvent was evaporated under reduced pressure and the resulting crude was dissolved in water (20 mL). The pH of the reaction mixture was adjusted to 5-6 with 1.5N HCl. The aqueous layer was extracted with DCM (200 mL) and organic layer was dried over Na₂SO₄, filtered and evaporated under reduced pressure to give hydroxyester B-26a (0.7 g) as a pale yellow liquid. ¹H NMR (CDCl₃, δ=7.26 ppm, 400 MHz): 7.39-7.31 (m, 5H), 5.15 (s, 2H), 3.90-3.87 (m, 1H), 2.54 (br s, 1H), 1.20 (s, 6H), 1.13 (d, J=6.4, 3 H).

Cap B-26

To a stirred solution of hydroxyester B-26a (0.5 g, 2.249 mmol) in EtOAc (5 mL) was added Pd/C (2.394 g, 2.249 mmol) and the resulting mixture was subjected to hydrogenation under balloon pressure for 12 h. The reaction mixture was filtered through celite pad and the filter cake was washed with EtOAc (3×5 mL). The filtrate was evaporated under reduced pressure to give Cap B-26 (0.2 g) as a colourless liquid. ¹H NMR (CDCl₃, δ=7.26 ppm, 300 MHz): 3.92-3.87 (m, 1H), 1.24 (s, 6H), 1.21 (d, J=6.4, 3 H).

Cap B-27

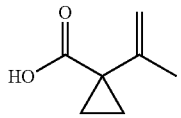

Cap B-27

Step a

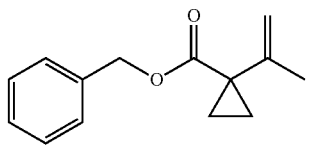 [SMILES: C=C(C)C(C)(C)C(=O)OCc1ccccc1]

To a stirred solution of ketoester B-21a (0.5 g, 2.291 mmol) in Et₂O (5 mL) was added methylenetriphenylphosphorane (0.760 g, 2.75 mmol) portion-wise at room temperature and stirred for 4 h. The reaction was quenched with water (50 mL) and extracted with EtOAc (200 mL). The organic layer was dried over Na₂SO₄, filtered and evaporated under reduced pressure. The crude material was purified by flash chromatography (Silica gel 230-400, 5% EtOAc/petroleum ether) to give ester B-27a (0.5 g) as a pale yellow liquid. ¹H NMR (CDCl₃, δ=7.26 ppm, 400 MHz): δ 7.38-7.29 (m, 5H), 5.12 (s, 2H), 4.94-4.89 (m, 2H), 1.88 (dd, J=1.2, 0.8, 3H), 1.37-1.35 (m, 2H), 0.97-0.94 (m, 2H).

Cap B-27

To a stirred solution of ester B-27a (0.2 g, 0.925 mmol) in MeOH (5 mL) and water (3 mL) was added LiOH (0.111 g, 4.62 mmol) and the resulting mixture was stirred for 14 h at ambient temperature. The volatile components were evaporated under reduced pressure and the resulting residue was diluted with water (25 mL). The pH of the reaction mixture was adjusted to 3-4 with 1N HCl and extracted with DCM (200 mL). The organic layer was dried over Na₂SO₄, filtered and evaporated under reduced pressure to give Cap B-27 (0.045 g) as a brown solid. ¹H NMR (CDCl₃, δ=7.26 ppm, 400 MHz): δ 4.98-4.91 (m, 2H), 1.90 (dd, J=1.2, 0.8, 3H), 1.42-1.39 (m, 2H), 1.03-1.00 (m, 2H).

Cap B-28

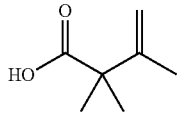

Cap B-28

Step a

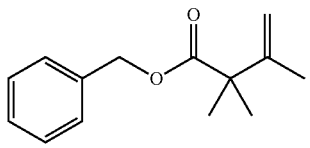

To a stirred solution of ketoester B-25a (0.5 g, 2.270 mmol) in Et$_2$O (5 mL) was added methylenetriphenylphosphorane (0.753 g, 2.72 mmol) portion-wise at room temperature and stirred for 4 h. The reaction was quenched with water (50 mL) and extracted with EtOAc (200 mL). The organic layer was dried over Na$_2$SO$_4$, filtered and evaporated under reduced pressure. The crude material was purified by flash chromatography (Silica gel 230-400, 5% EtOAc/petroleum ether) to give ester Cap B-28a (0.5 g) as a pale yellow liquid. $^1$H NMR (CDCl$_3$, δ=7.26 ppm, 400 MHz): δ 7.35-7.29 (m, 5H), 5.12 (s, 2H), 4.88-4.86 (m, 2H), 1.70 (dd, J=1.2, 0.8, 3H), 1.35 (s, 6H).

Cap B-28

To a stirred solution of ester B-28a (0.2 g, 0.916 mmol) in MeOH (5 mL) and water (3 mL) was added LiOH (0.110 g, 4.58 mmol) and the resulting mixture was stirred for 14 h at ambient temperature. The volatile components were evaporated under reduced pressure and the resulting residue was diluted with water (25 mL). The pH of the reaction mixture was adjusted to 3-4 with 1N HCl and extracted with DCM (200 mL). The organic layer was dried over Na$_2$SO$_4$, filtered and evaporated under reduced pressure to give Cap B-28 (0.035 g) as a pale yellow liquid. $^1$H NMR (CDCl$_3$, δ=7.26 ppm, 400 MHz): δ 4.95-4.92 (m, 2H), 1.80 (dd, J=1.2, 0.8, 3H), 1.35 (s, 6H).

Cap B-29

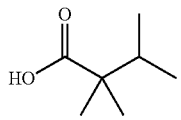

To a stirred solution of ester B-28a (0.12 g, 0.550 mmol) in MeOH (5 mL) was added Pd/C (0.059 g, 0.550 mmol) and the resulting mixture was subjected to hydrogenation (40 psi) in a tiny clave for 12 h. The reaction mixture was filtered through celite pad and the filter cake was washed with EtOAc (3×5 mL). The filtrate was evaporated under reduced pressure to give Cap B-29 (0.03 g) as a white solid. $^1$H NMR (MeOD, δ=3.34 ppm, 400 MHz): δ ppm 2.02-1.95 (m, 1H), 1.10 (s, 6H), 0.90 (d, J=8.0, 6H).

Cap B-30

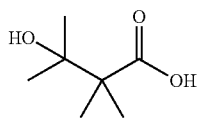

Cap B-30

Step a

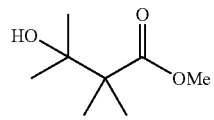

To a stirred solution of propan-2-one (0.5 g, 8.61 mmol) and ((1-methoxy-2-methylprop-1-en-1-yl)oxy)trimethylsilane (3.00 g, 17.22 mmol) in DCM (15 mL) was added BF$_3$.OEt$_2$ (1.745 mL, 13.77 mmol) drop wise at −78° C. The reaction mixture was stirred for 6 h while warming to ambient temperature. The reaction mixture was quenched with 10% NaHCO$_3$ (50 mL) and the reaction mixture was dissolved in EtOAc (50 mL). The organic layer was separated and washed with brine (25 mL), dried over Na$_2$SO$_4$ and concentrated under reduced pressure. The crude material was purified by flash chromatography (Silical gel 230-400, 16% EtOAc/petroleum ether) to obtain hydroxyester B-30a (910 mg) as colorless oil. $^1$H NMR (DMSO-d$_6$, δ=2.50 ppm, 400 MHz): δ 4.33 (s, 1H), 3.58 (s, 3H), 1.12 (s, 6H), 1.11 (s, 6H).

Cap B-30

To a solution of hydroxyester B-30a (800 mg, 4.99 mmol) in THF (10 mL) and water (10 mL) was added LiOH (598 mg, 24.97 mmol) at RT and stirred for overnight. The crude was extracted with diethyl ether (25 mL) and the organic layer was separated. The aqueous layer was acidified with 1.5N HCl to pH to 3-4. Then the aqueous phase was extracted with 5% MeOH/DCM (3×25 mL), dried over Na$_2$SO$_4$, filtered and concentrated under reduced pressure to give Cap B-30 (496 mg) as an off-white solid. $^1$H NMR (DMSO-d$_6$, δ=2.50 ppm, 400 MHz): δ 1.15 (s, 6H), 1.10 (s, 6H).

Cap B-31

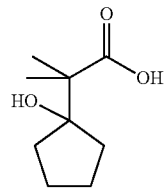

Cap B-31

Step a-1 & a-2

31 a-1

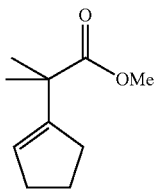

31 a-2

To a stirred solution of cyclopentanone (5 g, 59.4 mmol) and ((1-methoxy-2-methylprop-1-en-1-yl)oxy)trimethylsilane (20.72 g, 119 mmol) in DCM (150 mL) was added BF$_3$.OEt$_2$ (12.05 mL, 95 mmol) drop wise at −78° C. The reaction mixture was stirred for 6 h while warming to ambient temperature. The reaction mixture was quenched with 10% NaHCO$_3$ (300 mL) and the organic layer was separated, dried over Na$_2$SO$_4$ and concentrated under reduced pressure. The crude material was purified by flash chromatography (Silica gel 230-400, 20% EtOAc/petroleum ether) to obtain hydroxyester B-31a-1 (6.3 g, colourless oil) and ester B-31a-2 (2.92 g, colourless oil). B-31a-1: $^1$H NMR (DMSO-d$_6$, δ=2.50 ppm, 300 MHz): δ 4.18 (s, 1H), 3.56 (s, 3H), 1.72-1.65 (m, 4H), 1.51-1.44 (m, 4H), 1.14 (s, 6H). B-31a-2: $^1$H NMR (DMSO-d$_6$, δ=2.50 ppm, 300 MHz): δ 5.48 (t, J=2.1, 1H), 3.59 (s, 3H), 2.30-2.18 (m, 4H), 1.85-1.71 (m, 2H), 1.24 (s, 6H).

Cap B-31

To a solution of hydroxyester B-31a-1 (320 mg, 1.718 mmol) in THF (3 mL) and water (3 mL) was added LiOH (411 mg, 17.18 mmol) at room temperature and stirred for overnight. The crude was extracted with diethyl ether (25 mL) and the organic layer was separated. The aqueous layer was acidified with 1.5N HCl to pH to 3-4. Then the aqueous phase was extracted with 5% MeOH/DCM (2×25 mL), washed with water (25 mL), dried over Na$_2$SO$_4$, filtered and concentrated under reduced pressure to give Cap B-31 (261 mg) as a pale yellow solid. The crude was used as such in the next step without further purification. $^1$H NMR (DMSO-d$_6$, δ=2.50 ppm, 400 MHz): δ 1.77-1.67 (m, 4H), 1.56-1.42 (m, 4H), 1.12 (s, 6H).

Cap B-32

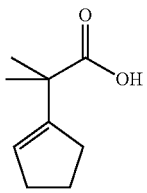

To a stirred solution of ester B-31a-2 (110 mg, 0.654 mmol) in THF (3 mL) and water (3 mL) was added LiOH (157 mg, 6.54 mmol) at RT. The reaction mixture was stirred for 3 days. The crude was extracted with diethyl ether (25 mL) and the organic layer was separated. The aqueous layer was acidified with 1.5N HCl to pH to 3-4. Then the aqueous phase was extracted with 5% MeOH/DCM (3×25 mL), washed with water (25 mL), dried over Na$_2$SO$_4$, filtered and concentrated under reduced pressure to give Cap B-32 (67 mg) as a gummy material. This material was used as such in the next step without any further purification. $^1$H NMR (MeOD, δ=3.34 ppm, 400 MHz): δ 5.56 (dd, J=4.0, 2.0, 1H), 2.36-2.31 (m, 4H), 1.92-1.85 (m, 2H), 1.33 (s, 6H).

Cap B-33

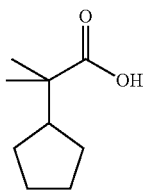

A solution of Cap B-32 (70 mg, 0.454 mmol) in MeOH (3 mL) was purged with nitrogen for 5 minutes. Then Pd/C (50 mg, 0.047 mmol) was added and applied vacuum to remove the nitrogen. Then the reaction mixture was stirred at ambient temperature under hydrogen atmosphere (balloon pressure) for overnight. The catalyst was filtered through a syringe filter and washed with MeOH (4×10 mL). The filtrate was concentrated under reduced pressure to obtain Cap B-33 (58 mg) as a gummy material. The crude was used as such in the next step without further purification. $^1$H NMR (MeOD, δ=3.34 ppm, 400 MHz): δ 2.20-2.15 (m, 1H), 1.69-1.53 (m, 6H), 1.38-1.29 (m, 2H), 1.14 (s, 6H).

Cap B-34

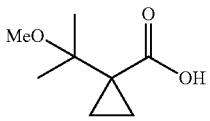

Cap B-34

Step a

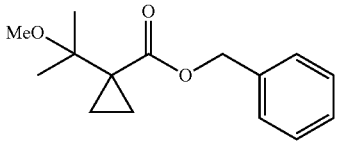 [SMILES: COC(C)(C)C1(C(=O)OCc2ccccc2)CC1]

To a stirring solution of benzyl 1-(2-hydroxypropan-2-yl) cyclopropanecarboxylate (750 mg, 3.20 mmol) in THF (15 mL) was taken in a sealed tube at 0° C., was added NaH (192 mg, 4.80 mmol) and stirred at room temperature for 30 minutes. Then MeI (4.00 mL, 64.0 mmol) was added drop wise into the reaction mixture at the same temperature and was heated to 50° C. and maintained for 12 h. After completion of reaction mixture, it was poured into ice cold water (100 mL) and extracted with EtOAc (3×50 mL). The combined organic layer was washed with brine (50 mL), dried over anhydrous Na$_2$SO$_4$ and solvent was removed under reduced pressure. The crude material was purified by Combiflash (Redisep, 24 g silica, 3% EtOAc in petroleum ether) to yield ester B-34a (275 mg, 1.107 mmol, 34.6% yield) as a colorless oil. $^1$H NMR (CDCl₃, δ=7.26 ppm, 400 MHz): δ 7.35-7.29 (m, 5H), 5.07 (s, 2H), 3.14 (s, 3H), 1.35 (s, 6H), 1.10-1.06 (m, 4H).

Cap B-34

Benzyl 1-(2-methoxypropan-2-yl)cyclopropanecarboxylate (215 mg, 0.866 mmol) was dissolved in MeOH (8 mL) taken into a tinyclave, to this 10% Pd/C (46.1 mg, 0.043 mmol) was added. The mixture was stirred at room temperature under H₂ atmosphere (2.5 kg/cm²) for 2.5 h. The catalyst was filtered off through celite bed; bed was washed with MeOH (15 mL). The combined filtrate was concentrated under reduced pressure to yield Cap B-34 (113 mg, 0.714 mmol, 83% yield) as a white solid. ¹H NMR (CD₃OD, δ=3.34 ppm, 400 MHz): δ 3.22 (s, 3H); 1.36 (s, 6H); 1.08 (s, 4H).

Cap B-35

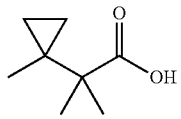

Cap B-35

Step a

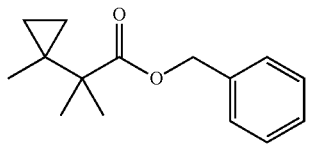 [SMILES: CC1(C(C)(C)C(=O)OCc2ccccc2)CC1]

To a stirred suspension of diethylzinc (5.50 mL, 5.50 mmol) in toluene (2 mL) was added chloroiodomethane (0.798 mL, 10.99 mmol) slowly drop wise at −20° C. and stirred for 1 h. A solution of benzyl 2,2,3-trimethylbut-3-enoate (0.4 g, 1.832 mmol) in toluene (2 mL) was added drop wise to the reaction mixture at −20° C. and stirring was continued at the same temperature for 6 h and then allowed to 25° C. After completion of reaction, it was cooled to 0° C. and quenched with saturated aq. NH4Cl solution (25 mL). Product was extracted into EtOAc (3×50 mL), washed with brine, dried over anhydrous sodium sulfate, filtered and organic portion was evaporated under reduced pressure. Crude residue thus obtained was purified on column chromatography (silica, 230-400, 2% EtoAc/Pet ether) to obtain B-35a (0.2 g, 0.861 mmol, 47.0% yield) as a pale yellow liquid. ¹H NMR (CDCl₃, δ=7.26 ppm, 300 MHz): δ 7.40-7.31 (m, 5H), 5.15 (s, 2H), 1.11 (s, 6H), 0.99 (s, 3H), 0.68-0.64 (m, 2H), 0.23-0.21 (m, 2H).

Cap B-35

To a stirred solution of benzyl 2-methyl-2-(1-methylcyclopropyl)propionate (150 mg, 0.646 mmol) in MeOH (3 mL) was added 15% aq. NaOH (51.6 mg, 1.291 mmol) at 0° C. and it was stirred for 48 h. Solvent was evaporated under reduced pressure. Residue was taken into the water (20 mL) and washed with diethyl ether (50 mL). pH of aqueous layer was adjusted to 3-4 with 1.5 N HCl and extracted with DCM (3×50 mL). After evaporation of solvent under reduced pressure to yield Cap B-35 (0.02 g, 0.141 mmol, 21.78% yield) was obtained as off white solid. ¹H NMR (CDCl₃, δ=7.26 ppm, 400 MHz): δ 1.08 (s, 6H), 1.06 (s, 3H), 0.69-0.67 (m, 2H), 0.23-0.20 (m, 2H).

Cap B-36

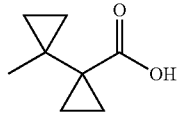

Cap B-36

Step a

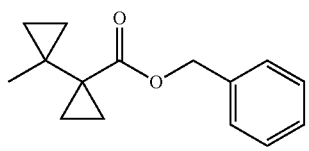 [SMILES: CC1(C2(C(=O)OCc3ccccc3)CC2)CC1]

To a stirred suspension of diethylzinc (5.55 mL, 5.55 mmol) in toluene (2 mL) was added chloroiodomethane (0.805 mL, 11.10 mmol) slowly drop wise at −20° C. and it was stirred for 1 h. To this mixture a solution of benzyl 1-(prop-1-en-2-yl)cyclopropane carboxylate (0.4 g, 1.849 mole) in toluene (2 mL) was added drop wise at −20° C. and stirred it for 6 h at the same and allowed to come to 25° C. After completion of reaction, it was again cooled to 0° C. and quenched with saturated aq. NH₄Cl (20 mL) solution and was extracted with EtOAc (2×50 mL), dried over anhydrous sodium sulfate and evaporated under reduced pressure. Residue was purified on column chromatography (silica, 230-400, 2% EtOAc/Pet-ether) to obtain dicyclo-propylbenzyl ester B-36a (0.15 g, 0.651 mmol, 35.2% yield) as a pale yellow liquid. ¹H NMR (CDCl₃, δ=7.26 ppm, 400 MHz): δ 7.37-7.30 (m, 5H), 5.14 (s, 2H), 1.20 (s, 3H), 1.11 (app. q, J=3.6 Hz, 2H), 0.70 (app. q, J=3.6 Hz, 2H), 0.39-0.31 (m, 4H).

Cap B-36

To a stirred solution of dicyclopropylbenzyl ester B-36a (200 mg, 0.868 mmol) in MeOH (5 mL) was added LiOH (83 mg, 3.47 mmol) and was stirred for 12 h at 10-15° C. The solvent was evaporated under reduced pressure and residue was taken into water (20 mL), and washed with diethyl ether (50 mL). pH of aqueous layer was adjusted to 3-4 using 1.5 N HCl and extracted with dichloromethane (3×50 mL). The organic layer was evaporated under reduced pressure to give dicyclopropylcarboxylic acid B-36 (0.03 mg, 0.214 mmol, 0.025% yield) as a white solid. ¹H NMR (CDCl₃, δ ppm=7.26, 400 MHz): δ 1.22 (s, 3H), 1.19 (app. q, J≈3.6 Hz, 2H), 0.70 (app. q, J≈3.6 Hz, 2H), 0.33 (s, 4H).

Cap B-37

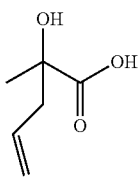

Cap B-37

Step a

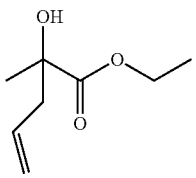

Ethyl 2-oxopropanoate (1 g, 8.61 mmol) was taken in to DCM (5M) and cooled to −78 C. To this titanium tetrachloride (8.61 mL, 8.61 mmol) in dichloromethane (5 mL) was added and stirred the reaction mixture for 30 min at this temperature. To this reaction mixture allyltrimethylsilane (1.279 g, 11.20 mmol) was added drop wise at −78° C. and stirring was continued for 2 h. Then it was brought to 0° C. and quenched with saturated aq. sodium bicarbonate solution and stirred for 15 min, and filtered through celite bed and filtrate was evaporated under reduced pressure to afford colorless oil. The residue was purified by flash chromatography (silica, 230-400, 10% EtoAc/Pet ether) to obtain ethyl 2-hydroxy-2-methylpent-4-enoate B-37a (0.8 g, 5.06 mmol, 58.7% yield) as yellow liquid. $^1$H NMR (CDCl$_3$, δ=7.26 ppm, 400 MHz): δ 5.84-5.72 (m, 1H), 5.15-5.09 (m, 2H), 4.29-4.19 (m, 2H), 2.56-2.37 (m, 2H), 1.43 (s, 3H), 1.31 (t, J=9.6 Hz, 3H).

Cap B-37

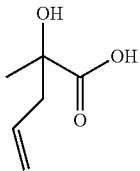

To a stirred solution of ethyl 2-hydroxy-2-methylpent-4-enoate (0.5 g, 3.16 mmol) in MeOH (3 mL) was added LiOH (0.378 g, 15.80 mmol) and it was stirred for 12 h. The solvent was evaporated under reduced pressure and the residue was dissolved in water (20 ml). The aqueous portion was treated with Diethyl ether (50 mL). Then the pH of aqueous layer was adjusted to 6 with HCl (1.5 N) and extracted into dichloromethane (250 mL). The obtained organic layer was dried over sodium sulfate and evaporated the solvent under reduced pressure to give Cap B-37 (0.2 g, 1.537 mmol, 48.6% yield) as a brown semi solid. $^1$H NMR (CDCl$_3$, δ=7.26 ppm, 400 MHz): δ 5.91-5.81 (m, 1H), 5.14-5.08 (m, 2H), 2.51 (dd, J=14, 7.2 Hz, 1H), 2.40 (dd, J=14, 7.2 Hz, 1H), 1.39 (s, 3H).

Cap B-38

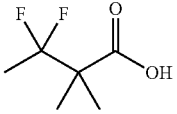

Cap B-38

Step a

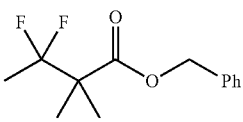 [SMILES: CC(F)(F)C(C)(C)C(=O)OCc1ccccc1]

To a 10 mL round bottom flask containing ketoester B-25a (200 mg, 0.908 mmol) under inert atmosphere at 0° C., were added Deoxo-Fluor (837 µl, 4.54 mmol) and catalytic amount of ethanol (1.060 µl, 0.018 mmol). The reaction mixture was heated at 50° C. for overnight. It was cooled to 0° C. and was added saturated NaHCO3 solution (10 mL). The mixture was extracted with (3×15 mL) of dichloromethane. Combined organic layer was washed with brine, dried over anhydrous sodium sulfate and solvent was removed under reduced pressure to a yield dark brown liquid which was purified by column chromatography (60-120 silica gel, 8-10% Ethyl acetate in Pet-ether) to yield difluoro ester B-38a (135 mg) as a pale yellow liquid. $^1$H NMR (CDCl$_3$, δ=7.26 ppm, 400 MHz): δ 7.40-7.29 (m, 5H), 5.2 (s, 2H), 1.64 (t, J$_{H-F}$=19.2 Hz, 3H), 1.35 (s, 6H); $^{19}$F NMR (CDCl$_3$, 376 MHz): δ=−97.5 (s, 2F)

Cap B-38

To a stirred solution of benzyl 3,3-difluoro-2,2-dimethylbutanoate (130 mg, 0.537 mmol) in Ethyl acetate (5 mL) was added Pd—C (10%) (57.1 mg, 0.537 mmol) and the resulting mixture was subjected to hydrogenation (under bladder pressure) for 4 h at room temperature. The reaction mixture was filtered through celite pad and the filter cake was washed with EtOAC (3×5 mL). The filtrate was evaporated under reduced pressure to give Cap B-38 (80 mg) as a colorless thick liquid. $^1$H NMR (CDCl$_3$, δ=7.26 ppm, 400 MHz): δ 1.72 (t, J$_{H-F}$=19.2 Hz, 3H), 1.36 (s, 6H); $^{19}$F NMR (CDCl$_3$, 376 MHz): δ=−97.6 (s, 2F).

Cap B-39

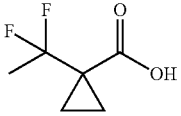

Cap B-39

Step a

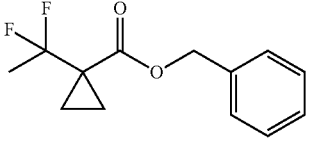 [SMILES: CC(F)(F)C1(C(=O)OCc2ccccc2)CC1]

To a solution of cyclopropyl ketoester B-21a (250 mg, 1.145 mmol) in Deoxo-Fluor (2 mL, 11.45 mmol) was added ethanol (3.34 µl, 0.057 mmol) at 0° C. The mixture was warmed to room temperature and was heated at 50° C. for 36 h. It was cooled at 0° C. and diluted with 25 mL of DCM and quenched with aq. saturated NaHCO₃ (10 mL). The aqueous layer was extracted with DCM (2×50 mL). The combined the organic layer was washed with brine, dried over Na₂SO₄, concentrated under reduced pressure. The crude was purified by Combiflash (Silica gel, 12 g, Redisep, EtOAc/petroleum ether, 10:90) to yield B-39a (220 mg, 0.916 mmol, 80% yield) as a colorless liquid. $^1$H NMR (CDCl₃, δ=7.26 ppm, 400 MHz): δ 7.38-7.30 (m, 5H), 5.14 (s, 2H), 1.89 (t, $J_{H-F}$=18.4 Hz, 3H), 1.34-1.29 (m, 2H), 1.27-1.23 (m, 2H); $^{19}$F NMR (CDCl₃, 376 MHz): δ=−93.8 (s, 2F).

Cap B-39

To a solution of B-39a (200 mg, 0.832 mmol) in ethyl acetate (10 mL) was added, 10% Pd/C (20.00 mg, 0.019 mmol) and the mixture was stirred for 3 h at ambient temperature under hydrogen atmosphere (bladder pressure). The reaction mixture was filtered the through the celite bed and washed the bed with EtOAc (2×20 mL), combined organic layer was concentrated under reduced pressure to obtain corresponding acid Cap B-39 (150 mg, 0.999 mmol, 95% yield) as a white solid. $^1$H NMR (CDCl₃, δ=7.26 ppm, 400 MHz): δ 1.95 (t, J=37.0 Hz, 3H), 1.40-1.36 (m, 2H), 1.33-1.30 (m, 2H); $^{19}$F NMR (CDCl₃, 376 MHz): δ 94.14 (s, 2F).

Cap B-40

DCM (25 mL), washed with 1.5 N aq. HCl solution (5×100 mL) and dried over anhydrous sodium sulfate. It was filtered and solvent was removed under reduced pressure to yield crude material which was purified by Combiflash (Silica gel, 24 g, Redisep, EtOAc/petroleum ether, 10:90) to obtain cyclopropyl vinyl ester B-40a (110 mg, 0.544 mmol, 23.96% yield) as a colorless liquid. $^1$H NMR (CDCl₃, δ=7.26 ppm, 300 MHz): δ 7.39-7.31 (m, 5H), 6.56 (dd, J=17.4, 10.8 Hz, 1H), 5.16 (s, 2H), 4.99 (dd, J=10.8, 0.9 Hz, 1H), 4.93 (dd, J=17.4, 0.9 Hz, 1H), 1.51 (app. q, J≈3.7 Hz, 2H), 1.10 (app. q, J≈3.7 Hz, 2H).

Cap B-40

Benzyl 1-vinylcyclopropanecarboxylate 40a (50 mg, 0.247 mmol) was taken into Methanol (2.5 mL)-Water (0.5 mL) mixture, then NaOH (1N) (1 mL, 0.247 mmol) was added at 0° C. The mixture was stirred for 10 min. and warmed to 25° C. and continued stirring for further 12 h. After completion of reaction, solvent was removed completely, and 5 mL of water was added. This mixture extracted with diethyl ether (2×10 mL). The aqueous layer was acidified with 1.5 N HCl (pH ~2) and extracted with DCM (3×10 mL). The combined organic layer was washed with brine solution (10 mL), dried over anhyd. Na₂SO₄, filtered and organic solvent was removed under reduced pressure to obtain Cap B-40 (42 mg, 0.375 mmol, 152% yield) as a colorless liquid $^1$H NMR (CDCl₃, δ=7.26 ppm, 300 MHz): δ 6.51 (dd, J=17.4, 10.8 Hz, 1H), 5.01 (dd, J=10.8, 0.9 Hz, 1H), 4.94 (dd, J=17.4, 0.9 Hz, 1H), 1.56 (app. q, J≈4.1 Hz, 2H), 1.16 (app. q, J≈4.0 Hz, 2H).

Cap B-41

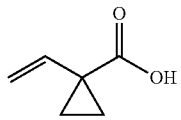

Cap B-40

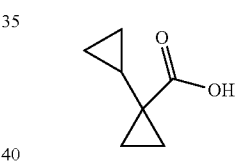

Cap B-41

Step a

Step a

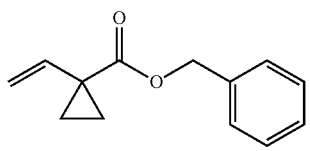

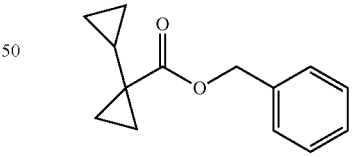

To a solution of hydroxyl ketoester 23a (500 mg, 2.270 mmol) in Benzene (10 mL) was added pyridine (0.459 mL, 5.67 mmol) followed by PBr₃ (0.535 mL, 5.67 mmol) at −5° C. to 0° C. temperature and stirred for 1 h. The reaction mixture was warmed to 25° C. and continued the stirring for 12 h. After completion of the reaction, it was quenched with 10 mL of saturated aq. Na₂CO₃ solution and aqueous portion was extracted with DCM (3×50 mL). The organic layer was washed with 10% aq. NaHCO₃ (50 mL) solution, dried over anhydrous sodium sulfate and solvent was removed under reduced pressure to yield a crude material. This crude was dissolved in DBU (1.711 mL, 11.35 mmol) and heated to 100° C. for 4 h. The reaction mixture was cooled, diluted with In a 25 mL single neck round bottomed flask were taken diethylzinc 15% in toluene (4.49 mL, 4.94 mmol) and chloroiodomethane (0.538 mL, 7.42 mmol) in toluene (5 mL) and stirred for 30 min. at −20° C. To this mixture benzyl 1-vinyl-cyclopropanecarboxylate 40a (250 mg, 1.236 mmol) in toluene (2 mL) was added and stirred for 6 h at −20° C. The reaction was quenched with 10% NaHCO₃ (10 mL) and diluted with DCM (25 mL). The organic layer was washed with 10% aq. NaHCO₃ (50 mL), brine solution (50 mL), dried over anhydrous Na2SO4, filtered and concentrated under reduced pressure. The crude was purified by Combiflash (Silica gel, 12 g, Redisep, EtOAc/petroleum ether, 10:90) to obtain dicyclopropyl benzyl ester B-41a (220 mg, 1.017 mmol, 82% yield) as a colorless liquid, ¹H NMR (CDCl₃, δ=7.26 ppm, 400 MHz): δ 7.36-7.30 (m, 5H), 5.14 (s, 2H), 1.56-1.49 (m, 1H), 1.10 (app. q J=3.6 Hz, 2H), 0.57 (app. q, J≈3.6 Hz, 2H), 0.48-0.44 (m, 2H), 0.03-0.01 (m, 2H).

Cap B-41

To a solution of ester B-41a (100 mg, 0.462 mmol) in a mixture of methanol (2.5 mL) and water (0.5 mL) at 0° C. was added aq. NaOH (1N) (1 mL, 0.247 mmol) and stirred for 10 min at 0° C., warmed to 25° C. and stirred for 12 h. The volatile components were removed completely under reduced pressure. Water was added (5 mL) and extracted with diethyl ether (2×10 mL). The aqueous layer was acidified with 1.5 N HCl (pH ~2) and extracted with 10% MeOH/DCM (3×10 mL) mixture. The combined organic layer was washed with brine solution (10 mL) and dried over anhyd. Na₂SO₄. Solvent was removed under reduced pressure to obtain Cap B-41 (60 mg, 0.476 mmol, 93% yield) as a off-white solid. ¹H NMR (CDCl₃, δ=7.26 ppm, 400 MHz): δ 1.49-1.46 (m, 1H), 1.15 (app. q J=3.6 Hz, 2H), 0.62 (app. q J=3.6 Hz, 2H), 0.49-0.44 (m, 2H), 0.04-0.008 (m, 2H).

Cap B-42

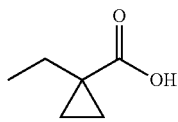

Cap B-42

Step a

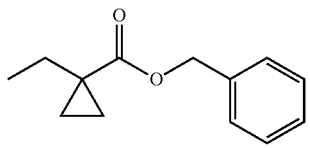

To a solution of benzyl 1-vinylcyclopropanecarboxylate B-40a (100 mg, 0.494 mmol) in ethyl acetate (10 mL) was added platinum (IV) oxide (28.1 mg, 0.124 mmol). The reaction mixture was stirred for 1 h at 25° C. under hydrogen atmosphere (bladder pressure). After completion of reaction, it was filtered through the celite bed and washed the bed with EtOAc (2×20 mL). The solvent was removed under reduced pressure to obtain benzyl 1-ethyl-cyclopropanecarboxylate B-42a (70 mg, 0.343 mmol, 69.3% yield) as a colorless liquid. ¹H NMR (CDCl₃, δ=7.26 ppm, 400 MHz): δ 7.36-7.30 (m, 5H), 5.10 (s, 2H), 1.59 (q, J=7.2 Hz, 2H), 1.21 (app. q, J≈3.6 Hz, 2H), 0.99 (t, J=7.2 Hz, 3H), 0.69 (app. q, J≈3.6 Hz, 2H).

Cap B-42

To a solution of ester 42a (200 mg, 0.979 mmol) in methanol (2.5 mL) and water (0.5 mL) mixture, was added aq. NaOH (1 N) (1 mL, 0.247 mmol) at 0° C. and stirred. for 10 min. at 0° C. It was warmed to room temperature and stirred for 12 h. The volatile components were removed under reduced pressure. Water was added to the residue and extracted with diethyl ether (2×10 mL). The aqueous layer was acidified with 1.5 N HCl (upto pH ~2) and extracted with DCM (3×10 mL). The combined organic portion was washed with brine solution (10 mL), dried over anhydrous Na₂SO₄ and organic solvent was removed under reduced pressure to yield Cap B-42 (53 mg, 0.464 mmol, 47.4% yield) as a colorless liquid. ¹H NMR (CDCl₃, δ=7.26 ppm, 300 MHz): δ=1.56 (q, J=7.2 Hz, 2H), 1.26 (app. q, J≈3.6 Hz, 2H), 1.01 (t, J=7.2 Hz, 3H), 0.75 (app. q, J≈3.6 Hz, 2H).

Cap B-43

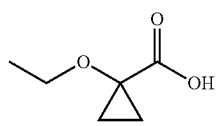

Cap B-43

Step a

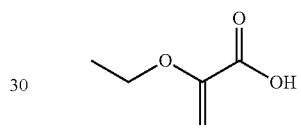

A solution of potassium tert-butoxide (15.93 g, 142 mmol) and 2-oxopropanoic acid (5 g, 56.8 mmol) in tetrahydrofuran (30 mL) was stirred at −70° C. for 10 mints HMPA (19.76 mL, 114 mmol) in tetrahydrofuran (10 mL) was added into the reaction mixture and stirred for 20 min. at −70° C. To this mixture, n-butyllithium (89 mL, 142 mmol) was added and stirred for 1 h at −70° C. followed by addition of diethyl sulfate (26.3 g, 170 mmol). It was stirred for 10 min at −70° C. and slowly warmed to 25° C. and stirring was continued for 12 h. The reaction mixture was quenched with water (20 mL). The organic layer was washed with water (2×20 mL) and the combined aqueous layer was extracted with CHCl₃ (2×100 mL). The aqueous layer was acidified with 1.5 N HCl (pH ~2) and extracted with diethyl ether (2×100 mL). The organic layer was dried over anhydrous Na₂SO₄, filtered and solvent was removed under reduced pressure to yield 2-ethoxyacrylic acid B-43a (3.8 g, 32.7 mmol, and 57.6% yield) as a colorless liquid. This crude it was taken to the next step without purification. ¹H NMR (CDCl₃, δ=7.26 ppm, 300 MHz): δ 5.49 (d, J=2.7 Hz, 1H), 4.71 (d, J=2.7 Hz, 1H), 3.87 (q, J=7.0 Hz, 2H), 1.41 (t, J=7.0 Hz, 3H).

Cap B-43

Step b

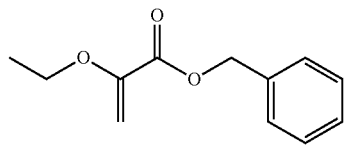

To a solution of 2-ethoxyacrylic acid B-43a (1 g, 8.61 mmol) in DMF (10 mL) under a nitrogen atmosphere was added (bromomethyl)benzene (1.620 g, 9.47 mmol) followed by potassium carbonate (1.309 g, 9.47 mmol) and stirred for 12 h at 25° C. The reaction mixture was quenched with water (25 mL) and extracted with DCM (3×100 mL). The combined organic layer was washed with water (3×50 mL) followed by brine solution (50 mL) and dried over anhyd. $Na_2SO_4$. It was filtered and concentrated under reduced pressure. The crude was purified by Combiflash (Silica gel, 12 g, Redisep, EtOAc/petroleum ether, 10:90) to obtain benzyl 2-ethoxyacrylate B-43b (550 mg, 2.67 mmol, 31.0% yield) as a colorless liquid. $^1$H NMR ($CDCl_3$, δ=7.26 ppm, 400 MHz): δ 7.39-7.31 (m, 5H), 5.36 (d, J=2.8 Hz, 1H), 5.25 (s, 2H), 4.61 (d, J=2.4 Hz, 1H), 3.82 (q, J=7.0 Hz, 2H), 1.39 (t, J=7.0 Hz, 3H).

Cap B-43

Step c

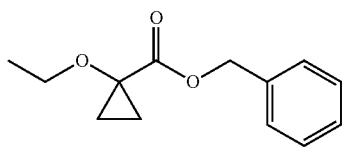 [SMILES: CCOC1(C(=O)OCc2ccccc2)CC1]

To a solution of diethylzinc 15% in toluene (9.70 mL, 10.67 mmol) was added chloroiodomethane (1.161 mL, 16.00 mmol) in toluene (5 mL) and stirred for 30 min at −20° C. To this mixture, was added benzyl 2-ethoxyacrylate B-43b (550 mg, 2.67 mmol) in toluene (2 mL) and stirred for another 6 h at −20° C. The reaction mixture was warmed to ambient temperature and stirring was continued for 12 h. The mixture was quenched with 10% aq. $NaHCO_3$ (10 mL) and diluted with DCM (30 mL). The organic portion was washed with 10% aq. $NaHCO_3$ (50 mL) followed by brine solution (50 mL) and dried over anhyd. $Na_2SO_4$. It was filtered and concentrated under reduced pressure. The residue was purified by reverse phase HPLC (ACN/water/$NH_4OAc$) to obtain benzyl ester B-43c (55 mg, 0.250 mmol, 9.36% yield) as a colorless liquid (free base). $^1$H NMR ($CDCl_3$, δ=7.26 ppm, 300 MHz): δ 7.37-7.31 (m, 5H), 5.17 (s, 2H), 3.64 (q, J=7.0 Hz, 2H), 1.33-1.30 (m, 2H), 1.25-1.15 (m, 5H).

Cap B-43

To a solution of methanol (2.5 mL) and water (0.5 mL), was added benzyl 1-ethoxycyclopropanecarboxylate B-43c (55 mg, 0.250 mmol) and stirred for 10 min at 0° C. Then aq. NaOH (1 N) (1 mL, 0.247 mmol) was added and stirred for 10 min. The reaction mixture was warmed to room temperature and stirring was continued for 12 h. The volatile components were removed under reduced pressure and water was added to the residue and extracted with diethyl ether (2×10 mL). The aqueous layer was acidified with 1.5 N HCl (up to pH ~2) and extracted with DCM (3×10 mL). The combined organic layer was washed with brine solution (10 mL) and dried over anhydrous $Na_2SO_4$, filtered and solvent was removed under reduced pressure to yield Cap B-43 (25 mg, 0.192 mmol, 77% yield) as a colorless liquid. $^1$H NMR ($CDCl_3$, δ=7.26 ppm, 400 MHz): δ3.65 (q, J=7.0 Hz, 2H), 1.38-1.35 (m, 2H), 1.27-1.18 (m, 5H).

Cap B-44

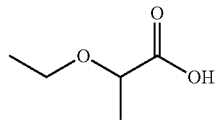

To a solution of benzyl 2-ethoxyacrylate B-43a (100 mg, 0.485 mmol) in ethyl acetate (10 mL) was added 10% Pd/C (5.00 mg, 4.70 μmol), and the reaction mixture was purged with nitrogen for 2 minutes. Then it was hydrogenated for 1 h at ambient temperature. The reaction mixture was filtered through celite and washed with EtOAc (2×20 mL). The filtrate was concentrated under reduced pressure to obtain Cap B-44 (55 mg, 0.466 mmol, 96% yield) as a colorless liquid which was used as such in the next step without any further purification. $^1$H NMR ($CDCl_3$, δ=7.26 ppm, 300 MHz): δ 4.03 (q, J=6.9 Hz, 1H), 3.68-3.55 (m, 2H), 1.48-1.46 (d, J=6.9 Hz, 3H), 1.28 (t, J=6.9 Hz, 3H).

Cap B-45

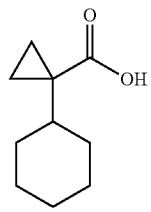 [SMILES: O=C(O)C1(C2CCCCC2)CC1]

A solution of 1-phenylcyclopropanecarboxylic acid (100 mg, 0.617 mmol) and $PtO_2$ (7.00 mg, 0.031 mmol) in EtOH (5 mL) and AcOH (0.035 mL, 0.617 mmol) was and stirred for 2 h under hydrogen atmosphere. The reaction mixture was filtered through celite bed and washed the bed with EtOH (2×10 mL). The filtrate was concentrated under reduced pressure to obtain Cap B-45 (90 mg) as a white solid. $^1$H NMR (MeOD, δ=3.34 ppm, 400 MHz): δ 1.77-1.66 (m, 5H), 1.14-1.18 (m, 6H), 1.10-1.08 (m, 2H), 0.76-0.74 (m, 2H).

Cap B-46

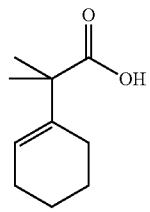

To a solution of ester B-2b (100 mg, 0.549 mmol) in MeOH (1 mL), THF (2 mL) and Water (1 mL) was added LiOH (12.3 mg, 0.514 mmol) at 0° C. and stirred the reaction mixture for 12 h at room temperature. Then the reaction mixture was cooled to 0° C. and adjusted the pH of the reaction mixture to (~3) with 1.5N HCl solution. Then the reaction mixture was extracted with EtOAc (2×100 mL) and the organic later was washed with brine (25 mL), dried over $Na_2SO_4$, filtered, and concentrated under reduced pressure to obtain Cap B-46 (10 mg) as a colorless liquid. $^1$H NMR (CDCl$_3$, δ=7.26 ppm, 400 MHz): 5.63-5.60 (m, 1H), 2.10-2.03 (m, 2H), 2.00-1.94 (m, 2H), 1.64-1.52 (m, 4H), 1.31 (s, 6H).

Biological Activity

The NS5A synergistic inhibitory effect of test compounds can be determined using various amounts of an NS5A-targeting compound with titration of a second compound of interest. Both the NS5A-targeting compound and the second compound of interest, when tested individually versus HCV variants, are understood to be essentially inactive or weakly active and only regain synergistic inhibitory potency of 3-fold or greater inhibition when tested in combination versus HCV variants. In one embodiment, compound BMS-790052, as an NS5A-targeting compound, can be held constant at a fixed concentration of 200 nM with subsequent titration of the test compound on a variant of HCV. In one embodiment, the HCV genotype strain can be genotype 1a containing a change at amino acid 30 of the NS5A protein consisting of glutamine to glutamate. The test compound can be chosen from compounds listed above or from others present in the literature. One skilled in the art can readily test compounds in the HCV replicon cell based assay as has been demonstrated previously in the art and one can readily determine the effective concentration for 50% inhibition (EC$_{50}$) of a particular compound.

For illustration, Compound P-55 can be titrated in the HCV replicon cell-based assay consisting of the genotype-1a variant with glutamine 30 changed to glutamate in the NS5A protein. Titration of BMS-790052 singly would yield an EC$_{50}$ value ~200 nM while titration of P-55 singly would yield an EC$_{50}$ value >200 nM. The titration of P-55 in the presence of a fixed amount of BMS-790052 at 200 nM afforded an EC$_{50}$ values of ~2 nM for P-55 demonstrating a synergistic inhibitory effect with the combination of >100-fold. Similarly, the titration of BMS-790052 in the presence of a fixed amount of P-55 at 200 nM afforded an EC$_{50}$ values of ~2 nM for BMS-790052, demonstrating a reciprocal synergistic inhibitory effect ~100-fold for the combination (PCT/US2011/043785, filed Jul. 13, 2011), Table 3). Additional compounds can be tested in a similar manner and a ranking of synergist activities determined; these rankings for the genotype 1a Q→E variant are shown for selected compounds in the table below.

It is understood that the genotype is not limited to the genotype 1a variant but can encompass all genotypic variants of HCV including but not limited to HCV variants of 1b, 2a, 3a, 4a, 5a, 6a as demonstrated in PCT/US2011/043785, filed Jul. 13, 2011. It is also understood that the synergy effect is not limited to BMS-790052 or P-55 combinations but can be derived from other combinations of NS5A targeting compounds that by themselves have reduced or no potency towards HCV variants.

| Example | Fold-Synergistic 1a (Q30E) |
|---|---|
| N-1 | >10 |
| N-2 | >100 |
| N-3 | >10 |
| N-4 | <10 |
| N-5 | >10 |
| N-6 | >10 |
| N-7 | <10 |
| N-8 | >10 |
| N-9 | >10 |
| P-1 | <10 |
| P-2 | >10 |
| N-10 | <10 |
| N-11 | <10 |
| N-12 | <10 |
| N-13 | <10 |
| N-14 | <10 |
| N-15 | <10 |
| N-16 | <10 |
| N-17 | <10 |
| N-18 | <10 |
| N-19 | <10 |
| N-20 | <10 |
| N-21 | <10 |
| N-22 | >10 |
| N-23 | <10 |
| N-24 | <10 |
| N-25 | <10 |
| N-26 | <10 |
| N-27 | |
| N-28 | >100 |
| N-29 | >10 |
| N-30 | <10 |
| N-31 | >10 |
| N-32 | >10 |
| N-33 | >10 |
| N-34 | >100 |
| N-35 | >100 |
| N-36 | >100 |
| N-37 | >10 |
| N-38 | <10 |
| N-39 | >10 |
| N-40 | >100 |
| N-41 | >10 |
| N-42 | >100 |
| N-43 | >10 |
| N-44 | >100 |
| P-3 | >10 |
| P-4 | >10 |
| P-5 | >100 |
| P-6 | >10 |
| P-7 | <10 |
| P-8 | <10 |
| P-9 | >100 |
| P-10 | >100 |
| N-45a | >100 |
| N-45b | >100 |
| N-45c | >100 |
| N-46 | >100 |
| N-47 | >100 |
| N-48 | >100 |
| N-49 | >100 |
| N-50 | >100 |
| N-51 | >100 |
| N-52 | >100 |
| N-53 | >100 |
| N-54 | >100 |
| N-55 | >100 |
| N-56 | >100 |
| N-57 | >100 |
| N-58 | >100 |
| N-59 | >100 |
| N-60 | >100 |
| N-61 | >100 |
| N-62 | >100 |
| N-63 | >100 |
| N-64 | >100 |
| N-65 | >100 |
| N-66 | >100 |
| N-111A | >100 |
| N-111B | >100 |
| N-112 | >100 |
| N-113 | >100 |
| N-114 | >100 |
| N-115 | >100 |
| N-116 | <10 |
| N-117 | >100 |

| | Fold-Synergistic 1a (Q30E) |
|---|---|
| P-11 | >100 |
| P-12 | >100 |
| P-13 | >100 |
| P-14 | >100 |
| P-15 | >100 |
| P-16 | >100 |
| P-17 | >100 |
| P-18 | >100 |
| P-19 | >100 |
| P-20 | >100 |
| P-21 | >100 |
| P-22 | >100 |
| P-23 | >100 |
| P-24 | >100 |
| P-25 | >100 |
| P-26 | >100 |
| P-27 | >100 |
| P-28 | >100 |
| P-29 | >100 |
| P-30 | >100 |
| P-31 | >100 |
| P-32 | >100 |
| P-33 | >100 |
| P-34 | >100 |
| P-35 | >100 |
| P-36 | >10 |
| P-37 | >100 |
| P-38 | >100 |
| P-39 | >100 |
| P-40 | >100 |
| P-41 | >100 |
| P-42 | >100 |
| P-43 | >100 |
| P-44 | >100 |
| P-45 | >100 |
| P-46 | >100 |
| P-47 | >100 |
| Y-1 | >100 |
| Y-2 | >100 |
| Y-3 | >100 |
| Y-4 | >100 |
| Y-5 | >100 |
| Y-6 | >100 |
| Y-7 | >100 |
| Y-8 | >100 |
| Y-9 | >100 |
| Y-10 | >100 |
| N-67 | >10 |
| N-68 | >100 |
| N-69 | >100 |
| N-70 | >100 |
| N-71 | >100 |
| N-72 | >100 |
| N-73 | >100 |
| N-74 | >100 |
| N-75 | >100 |
| N-76 | >100 |
| N-77 | >100 |
| N-78 | >100 |
| N-79 | >100 |
| N-80 | >100 |
| N-81 | >100 |
| N-82 | >100 |
| N-83 | >100 |
| N-84 | >100 |
| N-85 | >100 |
| N-86 | >100 |
| N-87 | >100 |
| N-88 | >100 |
| N-89 | >100 |
| N-90 | >100 |
| N-91 | >100 |
| N-92 | >100 |
| N-93 | >100 |
| N-94 | >100 |
| N-95 | >100 |
| N-96 | >100 |
| N-97 | >100 |
| N-98 | >100 |
| N-99 | >100 |
| N-100 | >100 |
| N-101 | >100 |
| N-102 | >100 |
| N-103 | >100 |
| N-104 | >100 |
| N-105 | >100 |
| Y-11 | >100 |
| Y-12 | >100 |
| N-106A | >100 |
| N-106B | >100 |
| N-106C | >100 |
| N-107A | >100 |
| N-107B | >10 |
| N-108A | >100 |
| N-108B | >10 |
| N-109B | >100 |
| N-110 | >100 |
| Y-13 | >100 |
| Y-14 | >100 |
| Y-15 | >10 |
| Y-16 | >10 |
| Y-17 | >10 |
| Y-18 | <10 |
| P-48 | >100 |
| P-49 | >100 |
| P-50 | <10 |
| P-51 | <10 |
| P-52 | >10 |
| P-53 | <10 |
| P-54 | >100 |
| P-54.1 | >100 |
| V-1 | >100 |
| Y-19 | >100 |
| Y-20 | >100 |
| S-1 | >100 |
| S-2 | >100 |
| S-3 | >100 |
| S-4 | >100 |
| S-5 | >100 |
| S-6 | >100 |
| S-7 | >100 |
| S-8 | >100 |
| S-9 | >10 |
| S-10 | >100 |
| S-11 | >100 |
| S-12 | >100 |
| S-13 | >10 |
| S-14 | >100 |
| S-15 | >10 |
| S-16 | >100 |
| S-17 | >100 |
| S-18 | >100 |
| S-19 | >100 |
| S-20 | >100 |
| S-21 | >100 |
| S-22 | >100 |
| S-23 | >100 |
| S-24 | >100 |
| S-25 | >100 |
| S-26 | >100 |
| S-27 | >10 |
| S-28 | >100 |
| S-29 | >100 |
| S-30 | >100 |
| S-31 | >100 |
| S-32 | >100 |
| S-33 | >100 |
| S-34 | >100 |
| S-35 | >100 |
| S-36 | >10 |
| S-37 | >100 |
| S-38 | >100 |
| S-39 | >100 |
| S-40 | >100 |

| | Fold-Synergistic 1a (Q30E) |
|---|---|
| S-41 | >10 |
| S-42 | >100 |
| S-43 | >100 |
| S-44 | >100 |
| S-45 | >100 |
| S-46 | >10 |
| S-47 | >100 |
| S-48 | >100 |
| S-49 | >10 |
| S-50 | >10 |
| S-51 | >10 |
| S-52 | >100 |
| S-53 | >100 |
| S-54 | >100 |
| S-55 | >100 |
| S-56 | >100 |
| S-57 | >100 |
| S-58 | <10 |
| S-59 | <10 |
| S-60 | <10 |
| S-61 | >10 |
| S-62 | <10 |
| S-63 | >100 |
| S-64 | >100 |
| S-65 | >100 |
| S-66 | >100 |
| S-67 | >100 |
| S-68 | >100 |
| S-69 | >100 |
| S-70 | >100 |
| S-71 | >100 |
| S-72 | >100 |
| S-73 | >100 |
| S-74 | >100 |
| S-75 | >100 |
| S-76 | >100 |
| S-77 | >100 |
| S-78 | >100 |
| S-79 | >100 |
| S-80 | >100 |
| S-81 | >100 |
| S-82 | >100 |
| S-83 | >100 |
| S-84 | >100 |
| S-85 | >100 |
| S-86 | >100 |
| S-87 | >100 |
| S-88 | >100 |
| S-89 | >100 |
| S-90 | >100 |
| S-91 | >100 |
| S-92 | >100 |
| S-93 | >100 |
| S-94 | >100 |
| S-95 | >10 |
| S-96 | >100 |
| S-97 | >100 |
| S-98 | >100 |
| S-99 | >10 |
| S-100 | >100 |
| S-101 | >100 |
| S-102 | >100 |
| S-103 | >100 |
| S-104 | >100 |
| S-105 | <10 |
| P-55 | >100 |
| P-56 | >100 |
| P-57 | >100 |
| P-58 | >10 |
| P-59 | >100 |
| P-60 | >100 |
| P-61 | >100 |
| P-62 | >100 |
| P-63 | >100 |
| P-64 | >100 |
| P-65 | >100 |
| P-66 | >100 |
| P-67 | >100 |
| P-68 | >100 |
| P-69 | >100 |
| P-70 | >100 |
| P-71 | >100 |
| P-72 | >100 |
| P-73 | >100 |
| P-74 | >100 |
| P-75 | >100 |
| P-76 | >10 |
| P-77 | >100 |
| P-78 | >100 |
| P-79 | >100 |
| P-80 | >100 |
| P-81 | >100 |
| P-82 | >100 |
| P-83 | >100 |
| P-84 | >100 |
| P-85 | >100 |
| P-86 | >100 |
| P-87 | >100 |
| P-88 | >100 |
| P-89 | >100 |
| P-90 | >100 |
| P-91 | >100 |
| P-92 | >10 |
| P-93 | >100 |
| P-94 | >10 |
| P-95 | >10 |
| P-96 | >100 |
| P-97 | >100 |
| P-98 | >100 |
| P-99 | >100 |
| P-100 | >100 |
| P-101 | >100 |
| P-102 | >10 |
| P-103 | >100 |
| P-104 | >100 |
| P-105 | >100 |
| P-106 | >100 |
| P-107 | >100 |
| P-108 | >100 |
| P-109 | >100 |
| P-110 | >100 |
| P-111 | <10 |
| P-112 | >100 |
| P-113 | >100 |
| P-114 | >100 |
| P-115 | >100 |
| P-116 | >100 |
| P-117 | >100 |
| P-118 | >100 |
| P-119 | >100 |
| P-120 | >100 |
| P-121 | >100 |
| P-122 | >100 |
| P-123 | >100 |
| P-124 | >100 |
| P-125 | >100 |
| P-126 | >100 |
| P-127 | >100 |
| P-128 | >100 |
| P-129 | >100 |
| Y-21 | >100 |
| Y-22 | >100 |
| Y-23 | >100 |
| Y-24 | >100 |
| Y-25 | >100 |
| Y-26 | >100 |
| Y-27 | >100 |
| Y-28 | >100 |
| Y-29 | >100 |
| Y-30 | >100 |
| Y-31 | >100 |
| Y-32 | >100 |
| Y-33 | >100 |
| S-106 | <10 |

| | Fold-Synergistic 1a (Q30E) |
|---|---|
| S-107 | <10 |
| S-108 | <10 |
| S-109 | <10 |
| S-110 | <10 |
| S-111 | <10 |
| S-112 | <10 |
| S-113 | <10 |
| S-114 | <10 |
| S-115 | <10 |
| S-116 | <10 |
| S-117 | >10 |
| S-118 | <10 |
| S-119 | >10 |
| S-120 | <10 |
| S-121 | <10 |
| S-122 | >10 |
| S-123 | >100 |
| S-124 | >10 |
| S-125 | <10 |
| S-126 | >100 |
| S-127 | <10 |
| S-128 | >10 |
| S-129 | >100 |
| S-130 | >10 |
| S-131 | >10 |
| S-132 | <10 |
| S-133 | <10 |
| S-134 | <10 |
| S-135 | <10 |
| S-136 | <10 |
| S-137 | >10 |
| S-138 | >100 |
| S-139 | >10 |
| S-140 | >10 |
| S-141 | >10 |
| S-142 | >10 |
| S-143 | >10 |
| S-144 | >10 |
| S-145 | >10 |
| S-146 | <10 |
| S-147 | <10 |
| S-148 | >10 |
| S-149 | <10 |
| S-150 | <10 |
| S-151 | >10 |
| S-152 | <10 |
| S-153 | >10 |
| S-154 | >10 |
| S-155 | <10 |
| S-156 | <10 |
| S-157 | >10 |
| S-158 | <10 |
| S-159 | <10 |
| S-160 | <10 |
| S-161 | >10 |
| S-162 | <10 |
| S-163 | <10 |
| S-164 | <10 |
| S-165 | >10 |
| S-166 | >10 |
| S-167 | <10 |
| S-168 | >10 |
| S-169 | <10 |
| S-170 | <10 |
| S-171 | <10 |
| S-172 | >10 |
| S-173 | <10 |
| S-174 | <10 |
| S-175 | <10 |
| S-176 | >10 |
| S-177 | <10 |
| S-178 | <10 |
| S-179 | <10 |
| S-180 | <10 |
| S-181 | >10 |
| S-182 | <10 |
| S-183 | <10 |

| | Fold-Synergistic 1a (Q30E) |
|---|---|
| S-184 | <10 |
| S-185 | <10 |
| S-186 | <10 |
| S-187 | <10 |
| S-188 | <10 |
| S-189 | >10 |
| S-190 | <10 |
| S-191 | <10 |
| S-192 | <10 |
| S-193 | <10 |
| S-194 | <10 |
| S-195 | <10 |
| S-196 | <10 |
| S-197 | <10 |
| S-198 | >100 |
| S-199 | >100 |
| S-200 | >100 |
| S-201 | >100 |
| S-202 | >100 |
| S-203 | <10 |
| S-204 | >100 |
| S-205 | >100 |
| S-206 | >100 |
| P-136 | >10 |
| S-207 | >10 |
| S-208 | >100 |
| S-209 | >100 |
| S-210 | >100 |
| S-211 | >100 |
| S-212 | >10 |
| S-213 | >100 |
| S-214 | |
| S-215 | >100 |
| S-216 | >10 |
| S-217 | >10 |
| S-218 | >10 |
| S-219 | >10 |
| S-220 | >10 |
| S-221 | >10 |
| S-222 | >10 |
| S-223 | >100 |
| S-224 | >10 |
| S-225 | >10 |
| S-226 | >100 |
| S-227 | >100 |
| S-228 | >100 |
| S-229 | >100 |
| S-230 | >100 |
| S-231 | >10 |
| S-232 | >100 |
| S-233 | >100 |
| S-234 | >100 |
| S-235 | >10 |
| P-130 | >100 |
| S-236 | <10 |
| S-237 | >10 |
| S-238 | >10 |
| S-239 | >10 |
| S-240 | <10 |
| S-241 | >10 |
| S-242 | >100 |
| S-243 | >10 |
| S-244 | <10 |
| P-131 | >100 |
| S-245 | >100 |
| S-246 | >100 |
| S-247 | >100 |
| S-248 | >100 |
| S-249 | >100 |
| S-250 | >100 |
| S-251 | >100 |
| S-252 | >100 |
| S-253 | >100 |
| Y-34 | >100 |
| Y-35 | >100 |
| Y-36 | >100 |
| Y-37 | >100 |

| Example # | Fold-Synergistic 1a (Q30E) |
|---|---|
| P-132 | >100 |
| P-133 | >100 |
| P-134 | >100 |
| P-135 | >100 |
| Y-38 | >100 |
| Y-39 | >100 |
| Y-40 | >100 |
| Y-41 | >100 |
| Y-42 | >100 |
| Y-43 | >100 |
| Y-44 | >100 |
| Y-45 | >100 |
| Y-46 | >100 |
| Y-47 | >100 |
| Y-48 | >100 |
| Y-49 | >100 |
| Y-50 | >100 |
| Y-51 | >100 |
| Y-52 | |
| Y-53 | >100 |
| Y-54 | >100 |
| Y-55 | >10 |
| Y-56 | >100 |
| Y-57 | >100 |
| Y-58 | >100 |
| Y-59 | >100 |
| Y-60 | >100 |
| Y-61 | <10 |
| Example # | |
| L-1 | >100 |
| L-2 | >100 |
| L-3 | >100 |
| L-4 | |
| L-5 | >100 |
| L-6 | >100 |
| L-7 | >100 |
| L-8 | >100 |
| L-9 | >10 |
| L-10 | >10 |
| L-11 | >100 |
| L-12 | >100 |
| L-13 | >100 |
| L-14 | >100 |
| L-15 | >100 |
| L-16 | >100 |
| L-17 | >100 |
| L-18 | >100 |
| L-19 | >100 |
| L-21 | >100 |
| L-22 | >100 |
| L-23 | >100 |
| L-24 | >100 |
| L-25 | >10 |
| L-26 | >100 |
| L-27 | >100 |
| L-28 | >100 |
| L-29 | >100 |
| L-31 | >100 |
| L-32 | >100 |
| L-33 | >100 |
| L-38 | >100 |
| L-40 | >100 |
| L-43 | >100 |
| W-1 | >100 |
| W-2 | >100 |
| W-3 | >100 |
| W-4 | >100 |
| W-5 | >100 |
| W-6 | >100 |
| W-7 | >100 |
| W-8 | >100 |
| W-9 | >100 |
| W-12 | >100 |
| W-13 | >100 |
| W-14 | >100 |
| W-15 | >100 |
| W-16A | >10 |
| W-16B | <10 |
| W-17 | |
| W-23A | >100 |
| W-23B | >100 |
| W-23C | >100 |
| W-51 | >100 |
| W-67 | >100 |
| W-68 | >100 |
| W-69 | >100 |
| L-30 | >100 |
| L-39 | >100 |
| L-42 | >100 |
| W-70 | >100 |
| W-71 | >100 |
| W-72 | >100 |
| W-10 | >100 |
| W-11 | >100 |
| W-18 | |
| W-19 | >100 |
| W-20 | >100 |
| W-21 | >100 |
| W-22 | >100 |
| W-24 | >100 |
| W-25 | >100 |
| W-26 | >100 |
| W-27 | >100 |
| W-28 | >100 |
| W-30 | >100 |
| W-31 | >10 |
| W-32 | >100 |
| W-33 | >100 |
| W-34 | >100 |
| W-35 | >100 |
| W-36 | >100 |
| W-37 | >100 |
| W-38 | >100 |
| W-60 | >100 |
| W-63 | >100 |
| W-66 | >100 |
| W-39 | >100 |
| W-40A | >100 |
| W-40B | >100 |
| W-40C | >100 |
| W-41 | >100 |
| W-41A | >100 |
| W-41B | >100 |
| W-42 | >10 |
| W-43A | >100 |
| W-43B | >100 |
| W-44 | >10 |
| W-45 | >100 |
| W-46A | >100 |
| W-47 | >100 |
| W-48 | >100 |
| W-49 | >100 |
| W-50 | >100 |
| W-57 | >100 |
| W-58 | >100 |
| W-59 | >100 |
| W-61 | >100 |
| W-62 | >100 |
| W-66 | >100 |
| W-73 | >100 |
| L-20 | >100 |
| L-41 | >100 |
| Q-1 | >100 |
| Q-2 | >100 |
| Q-3 | >100 |
| Q-4 | >100 |
| Q-5 | >100 |
| Q-6 | >100 |
| Q-7 | >100 |
| N-118 | >100 |
| N-119 | >100 |
| N-120 | >100 |
| N-121 | >100 |

| | Fold-Synergistic 1a (Q30E) |
|---|---|
| N-122 | >100 |
| N-123 | >100 |
| P-137 | >10 |
| P-138 | >100 |
| P-139 | >100 |
| P-141 | >100 |
| P-146 | >100 |
| P-148 | >100 |
| P-149 | >100 |
| P-150 | >100 |
| P-152 | >100 |
| P-153 | >100 |
| P-154 | >100 |
| P-155 | >100 |
| Y-62 | >100 |
| Y-65 | >100 |
| Y-67A | >100 |
| Y-67B | >100 |
| Y-70 | >100 |
| P-140 | >100 |
| P-142 | >100 |
| P-143 | >100 |
| P-144 | >100 |
| P-145 | >100 |
| P-147 | >100 |
| P-151 | >100 |
| P-152 | >100 |
| Y-63 | >100 |
| Y-64 | >100 |
| Y-66 | >100 |
| Y-68 | >100 |
| Y-69 | >100 |
| L-34 | >100 |
| L-35 | >100 |
| L-36 | >100 |
| L-37 | >100 |
| W-51 | >100 |
| W-52 | >100 |
| W-53 | >100 |
| W-54 | >100 |
| W-55 | >100 |
| W-56 | >100 |
| W-64 | >100 |
| W-65 | >100 |
| B1 | >100 |
| B2 | >100 |
| B3 | >100 |
| B4 | >100 |
| B5 | >100 |
| B6 | >100 |
| B7 | >100 |
| B8 | >100 |
| B9 | >100 |
| B10 | >100 |
| B11 | >100 |
| B12 | >100 |
| B13 | >100 |
| B14 | >100 |
| B15 | >100 |
| B16 | >100 |
| B17 | >100 |
| B18 | >100 |
| B19 | >100 |
| B20 | >100 |
| B21 | >100 |
| B22 | >100 |
| B23 | >100 |
| B24 | >100 |
| B25 | >100 |
| B26 | >100 |
| B27 | >100 |
| B28 | >100 |
| B29 | >100 |
| B30 | >100 |
| B31 | >100 |
| B32 | >100 |
| B33 | >100 |
| B34 | >100 |
| B35 | >100 |
| B36 | >100 |
| B37 | >100 |
| B38 | >100 |
| B39 | >100 |
| B40 | >100 |
| B41 | >100 |
| B42 | >100 |
| B43 | >100 |
| B44 | >100 |
| B45 | >100 |
| B46 | >100 |
| B47 | >100 |
| B48 | >100 |
| B49 | >100 |
| B50 | >100 |
| B51 | >100 |
| B52 | >100 |
| B53 | >100 |
| B54 | >100 |
| B55 | >100 |
| B56 | >100 |
| B57 | >100 |
| B58 | >100 |
| B59 | >100 |
| B60 | >100 |
| B61 | >100 |
| B62 | >10 |
| B63 | >10 |
| B64 | |
| B65 | >100 |
| B66 | >10 |
| Example | |
| Y-81 | >100 |
| Y-82 | >100 |
| Y-83 | >100 |
| Y-84 | >100 |
| N-124A | >100 |
| N-124B | >100 |
| N-124C | >100 |
| N-125A | >100 |
| N-125B | >100 |
| N-125C | >100 |
| N-126A | >100 |
| N-126B | >100 |
| N-126C | >100 |
| N-127A | >100 |
| N-127B | >100 |
| N-127C | >100 |
| N-128A | >100 |
| N-128B | >100 |
| N-129 | >100 |
| N-130 | >100 |
| N-131 | >100 |
| N-132 | >100 |
| N-133 | >100 |
| N-134 | >100 |
| Y-71 | >100 |
| Y-72 | >100 |
| Y-73 | >100 |
| Y-74 | >100 |
| Y-75 | >100 |
| Y-76 | |
| Y-77 | >100 |
| Y-78 | >100 |
| Y-79 | >100 |
| Y-80 | >100 |
| S-254 | >100 |
| S-255 | >100 |
| S-256 | >100 |
| S-257 | >10 |
| S-258 | >100 |
| S-260 | >100 |
| S-261 | >100 |
| S-263 | >10 |

| | Fold-Synergistic 1a (Q30E) |
|---|---|
| S-264 | >100 |
| S-265 | >100 |
| S-266 | >100 |
| S-267 | >100 |
| S-268 | >10 |
| S-269 | >100 |
| S-270 | >100 |
| S-271 | >100 |
| S-272 | >100 |
| S-273 | >100 |
| S-274 | >100 |
| S-275 | >100 |
| S-276 | >100 |
| S-277 | >100 |
| S-278 | >100 |
| S-279 | >10 |
| S-280 | >100 |
| S-281 | >100 |
| S-282 | >100 |
| S-283 | >100 |
| S-284 | >100 |
| S-285 | >100 |
| S-286 | >100 |
| S-287 | >100 |
| S-288 | >100 |
| S-289 | >100 |
| S-290 | >100 |
| S-291 | >100 |
| S-292 | >100 |
| S-293 | >100 |
| S-294 | >100 |
| S-295 | >100 |
| S-296 | >100 |
| S-297 | >10 |
| S-298 | >100 |
| S-299 | >100 |
| S-301 | >100 |
| S-302 | >100 |
| S-303 | |
| S-304 | >100 |
| S-305 | >100 |
| P-156 | >100 |
| P-157 | >100 |
| P-158 | >100 |
| P-159 | >100 |
| P-160 | >100 |
| P-161 | >100 |
| P-162 | >100 |
| P-163 | >100 |
| P-164 | >100 |
| P-165 | >100 |
| P-166 | >100 |
| P-167 | >100 |
| P-168 | >100 |
| P-169 | >100 |
| P-170 | >100 |
| P-171 | >100 |
| P-172 | >100 |
| P-173 | >100 |
| P-174 | >100 |
| P-175 | >100 |
| P-176 | >100 |
| P-177 | >100 |
| P-178 | >100 |
| P-179 | >100 |
| P-180 | >100 |
| P-181 | >100 |
| P-182 | >100 |
| P-183 | >100 |
| P-184 | >100 |
| P-185 | >100 |
| P-186 | <10 |
| P-187 | >100 |
| W-74 | >100 |
| W-75 | >100 |
| W-76 | >100 |
| W-77 | >100 |
| W-78 | >100 |
| W-79 | >100 |
| W-80 | >100 |
| W-81 | >100 |
| W-82 | >100 |
| W-83 | >100 |
| W-84 | >100 |
| W-85 | >100 |
| W-86 | >100 |
| W-87 | >100 |
| W-88 | >100 |
| W-89 | >100 |
| W-90 | >100 |
| W-91 | >100 |
| W-92 | >10 |
| W-93 | >100 |
| W-94 | >100 |
| W-95 | >100 |
| W-96 | >100 |
| W-97 | >100 |
| W-98 | >100 |
| W-99 | >100 |
| W-100 | >100 |
| W-101 | >10 |
| W-102 | >10 |
| W-103 | >100 |
| W-104 | >100 |
| W-105 | >100 |
| W-106 | >100 |
| W-107 | >100 |
| W-108 | >100 |
| W-109 | >100 |
| W-110 | >100 |
| W-111 | >100 |
| W-112 | >100 |
| W-113 | >100 |
| W-114 | >100 |
| W-115 | >100 |
| W-116 | >100 |
| W-117 | >100 |
| W-118 | >100 |
| W-119 | >100 |
| W-120 | >100 |
| W-121 | >100 |
| W-122 | >100 |
| W-123 | >100 |
| W-124 | >100 |
| W-125 | >100 |
| W-126 | >100 |
| W-127 | >100 |
| W-128 | >100 |
| W-129 | >10 |
| W-130 | >100 |
| W-131 | >100 |
| W-132 | >100 |
| W-133 | <10 |
| W-134 | >100 |
| W-135 | >10 |
| W-136 | >10 |
| W-137 | >10 |
| W-138 | >100 |
| W-139 | >100 |
| W-140 | <10 |
| W-141 | >100 |
| W-142 | >100 |
| W-143 | >100 |
| W-144 | >10 |
| W-145 | >10 |
| W-146 | >100 |
| W-147 | >100 |
| W-148 | >100 |
| W-149 | >100 |
| W-150 | >100 |
| W-151 | >10 |
| W-152 | >100 |
| W-153 | >100 |
| W-154 | >100 |

| | Fold-Synergistic 1a (Q30E) |
|---|---|
| W-155 | >100 |
| W-156 | >100 |
| W-157 | >10 |
| W-158 | >100 |
| W-159 | >100 |
| W-160 | >10 |
| W-161 | >100 |
| W-162 | >100 |
| W-163 | >100 |
| W-164 | >100 |
| W-165 | >100 |
| W-166 | >100 |
| W-167 | >100 |
| W-168 | >10 |
| W-169 | >100 |
| W-170 | >100 |
| W-171 | >100 |
| W-172 | >10 |
| W-173 | >100 |
| W-174 | >100 |
| W-175 | >100 |
| W-176 | >100 |
| W-177 | >100 |
| W-178 | >100 |
| W-179 | >10 |
| W-180 | <10 |
| W-181 | >100 |
| W-182 | >100 |
| W-183 | >10 |
| W-184 | >100 |
| W-185 | >100 |
| W-186 | >100 |
| W-187 | >100 |
| W-188 | >10 |
| W-189 | >100 |
| L-96 | >100 |
| L-44 | >100 |
| L-90 | >100 |
| L-91 | >100 |
| L-45 | >100 |
| L-46a | >100 |
| L-46b | >100 |
| L-47 | >100 |
| L-48 | >100 |
| L-49 | >100 |
| L-50 | >100 |
| L-46c | >100 |
| L-51 | >100 |
| L-52 | >100 |
| L-53 | >100 |
| L-54 | >100 |
| L-55 | >100 |
| L-56 | >100 |
| L-57 | >100 |
| L-58a | >100 |
| L-58b | >100 |
| L-58c | >100 |
| L-59 | >10 |
| L-60 | >100 |
| L-61 | >100 |
| L-62 | >100 |
| L-63 | >100 |
| L-64 | >100 |
| L-65 | >100 |
| L-66a | >100 |
| L-66b | >100 |
| L-66c | |
| L-67 | >100 |
| L-68 | >100 |
| L-92 | >100 |
| L-69 | >100 |
| L-70 | >100 |
| L-71 | >100 |
| L-72 | >10 |
| L-73 | >100 |
| L-93a | >100 |
| L-93b | >100 |

| | Fold-Synergistic 1a (Q30E) |
|---|---|
| L-93c | >100 |
| L-74 | >100 |
| L-75 | >100 |
| L-76 | >100 |
| L-77 | >100 |
| L-78 | >100 |
| L-79 | <10 |
| L-80 | >100 |
| L-81 | >100 |
| L-82 | >100 |
| L-83 | >100 |
| L-84 | >100 |
| L-85 | >100 |
| L-94 | >100 |
| L-95 | >100 |
| L-86 | >100 |
| L-87 | >100 |
| L-88 | |
| L-89 | >10 |
| B-69 | >100 |
| B-67 | >100 |
| B48A | >100 |
| B58A | >100 |
| B13A | >100 |
| B5A | >100 |
| B-116 | >100 |
| B41A | >100 |
| B-103 | >100 |
| B-86 | >100 |
| B-87 | >100 |
| B-105 | >100 |
| B48B | >100 |
| B58B | >100 |
| B41B | >100 |
| B-117 | >100 |
| B-82 | >100 |
| B-83 | >100 |
| B5B | >100 |
| B13B | >100 |
| B-104 | >100 |
| B-107 | >100 |
| B-94 | |
| B-108 | >100 |
| B-95 | >100 |
| B-79 | >100 |
| B-80 | >100 |
| B-106 | >100 |
| B-81 | >100 |
| B-92 | >100 |
| B-96 | >100 |
| B-85 | >10 |
| B-84 | >100 |
| B-70 | >100 |
| B-71 | >100 |
| B-72 | >100 |
| B-93 | >100 |
| B-109 | >10 |
| B-97 | >100 |
| B-99 | >100 |
| B-98 | >100 |
| B-110 | >100 |
| B-111 | >100 |
| B-100 | >100 |
| B-112 | >100 |
| B-73 | >100 |
| B-74 | >100 |
| B-113 | >100 |
| B-101 | >100 |
| B-88 | >100 |
| B-77 | |
| B-75 | >100 |
| B-89 | |
| B-68 | >100 |
| B-114 | >100 |
| B-115 | >100 |
| B-76 | >100 |
| B-78 | >100 |

| | Fold-Synergistic 1a (Q30E) |
|---|---|
| B-149 | >100 |
| B-148 | >100 |
| B-102 | >100 |
| B-140 | >100 |
| B-139 | >100 |
| B-135 | >100 |
| B-141 | >100 |
| B-137 | >100 |
| B-136 | >100 |
| B-142 | >100 |
| B-138 | >100 |
| B-144 | >100 |
| B-143 | >100 |
| B-145 | >100 |
| B-146 | >100 |
| B-147 | >100 |
| B-90 | >100 |
| B-91 | >100 |
| B-126 | >100 |
| B-119 | >100 |
| B-123 | >100 |
| B-122 | >100 |
| B-127 | >100 |
| B-132 | >100 |
| B-125 | >100 |
| B-124 | >100 |
| B-120 | >100 |
| B-133 | >100 |
| B-121 | >100 |
| B-134 | >10 |
| B-118 | >100 |
| B-129 | >100 |
| B-131 | >100 |
| B-130 | >100 |
| B-128 | >10 |

A method has been described to identify compounds that demonstrate synergistic inhibition of HCV replicon activity when combined with NS5A-targeting compounds such as BMS-790052 (PCT/US2011/043785, filed Jul. 13, 2011). In brief, NS5A synergists were identified using titrations of test compounds in the presence of fixed concentrations of BMS-790052. The synergist compounds were subsequently used to identify additional NS5A-targeting inhibitors that have synergistic activity in combination with them (shown in Table below).

Each compound, when tested individually versus some HCV variants, is understood to be essentially inactive or much less active and only has synergistic inhibitory potency of 3-fold or greater when tested in combinations. Combinations can be examined for synergistic activity using a variety of putative NS5A-targeting compounds and a variety of test compounds. In one embodiment compound N47, a known NS5A synergist that is virtually inactive against genotype 1a wild type, Y93H and L31V variants ($EC_{50}$ values >1,000 nM), can be held constant at a fixed concentration of 200 nM with subsequent titration of the test compound on a variant of HCV. The test compound can be chosen from compounds exemplified below, which were prepared by methods known in the art, or from others disclosed in the literature. One skilled in the art can readily test compounds in the HCV replicon cell based assay as has been demonstrated previously in the art, and one can readily determine the effective concentration for 50% inhibition ($EC_{50}$) of a particular compound.

For illustration, compound BMS-790052 can be titrated both singly and in combination with a fixed amount of compound N47 in the HCV replicon cell based assay consisting of the genotype 1a L31V variant with leucine 31 changed to valine in the NS5A protein. Titration of BMS-790052 singly would yield an $EC_{50}$ value of ~56 nM; similarly, titration of compound N47 singly would yield a value >1,000 nM. Titration of BMS-790052 in combination with a fixed amount of 200 nM compound N47 would result an $EC_{50}$ value <0.5 nM for BMS-790052, demonstrating a synergistic inhibitory effect >100-fold with the combination. Similarly, BMS-790052 can be tested singly and in combination with a fixed amount of compound N47 in the HCV replicon cell based assay consisting of the genotype 1a Y93H variant with tyrosine 93 changed to histidine in the NS5A protein. Titration of BMS-790052 singly would yield an $EC_{50}$ of ~69 nM; similarly, titration of compound N47 singly would yield an $EC_{50}$>1,000 nM. Titration of BMS-790052 in combination with a fixed amount of 200 nM compound N47 would result in $EC_{50}$ values <0.5 nM for BMS-790052, demonstrating a synergistic inhibitory effect >100-fold for the combination. Additional compounds can be titrated in combination with compound N47 held at 200 nM, and ranked with respect to synergistic activity; the fold change for both the genotype 1a L31V and Y93H variants is shown for selected compounds in the table below.

It is understood that the genotype is not limited to the genotype 1a variant but can encompass all genotypic variants of HCV including but not limited to HCV variants of 1b, 2a, 3a, 4a, 5a, 6a as demonstrated in PCT/US2011/043785, filed Jul. 13, 2011. It is also understood that the synergy effect is not limited to compound N47 or BMS-790052 combinations but can be derived from other combinations of compounds that by themselves have reduced or no potency towards specific HCV variants.

| | Fold-Synergistic G-1a (L31V) | Fold-Synergistic G-1a (Y93H) |
|---|---|---|
| | <10 | <10 |

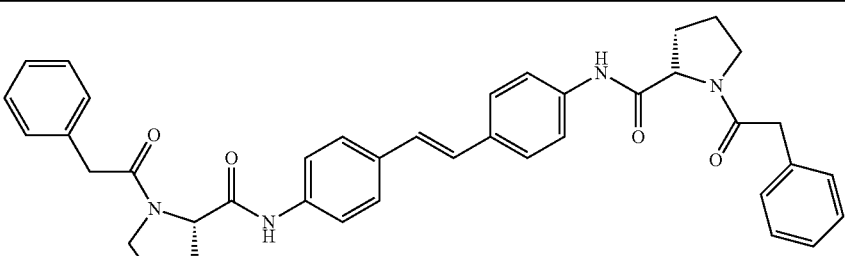

| | Fold-Synergistic G-1a (L31V) | Fold-Synergistic G-1a (Y93H) |
|---|---|---|
| 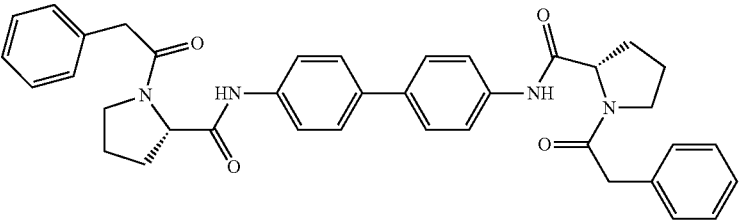 [SMILES: O=C(Nc1ccc(-c2ccc(NC(=O)[C@@H]3CCCN3C(=O)Cc3ccccc3)cc2)cc1)[C@@H]1CCCN1C(=O)Cc1ccccc1] | <10 | <10 |
| 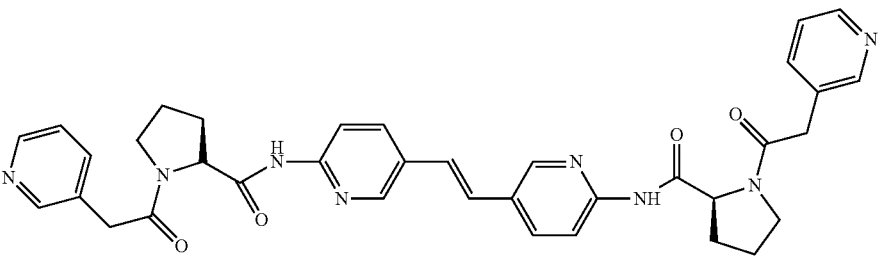 | <10 | <10 |
| 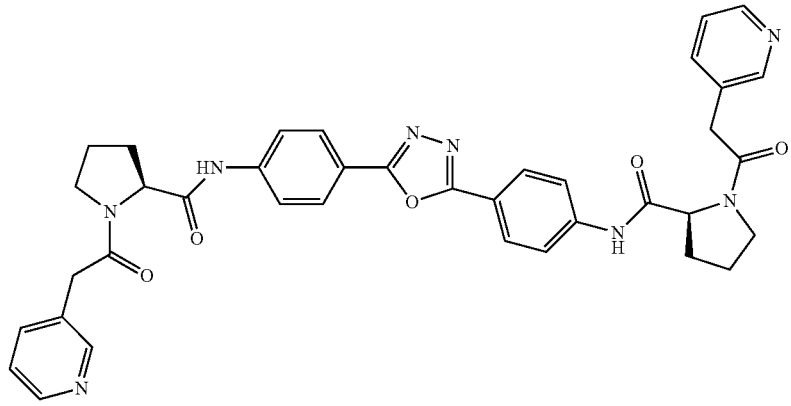 [SMILES: O=C(Nc1ccc(-c2nnc(-c3ccc(NC(=O)[C@@H]4CCCN4C(=O)Cc4cccnc4)cc3)o2)cc1)[C@@H]1CCCN1C(=O)Cc1cccnc1] | <10 | <10 |
| 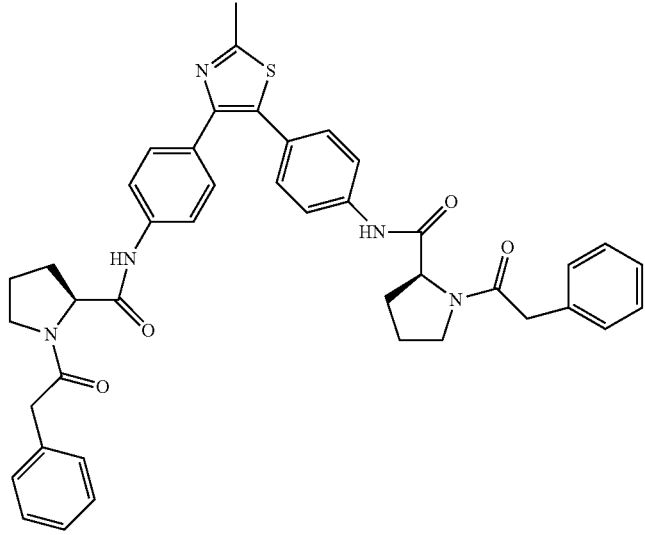 [SMILES: Cc1nc(-c2ccc(NC(=O)[C@@H]3CCCN3C(=O)Cc3ccccc3)cc2)c(-c2ccc(NC(=O)[C@@H]3CCCN3C(=O)Cc3ccccc3)cc2)s1] | <10 | <10 |

|  | Fold-Synergistic G-1a (L31V) | Fold-Synergistic G-1a (Y93H) |
|---|---|---|
| 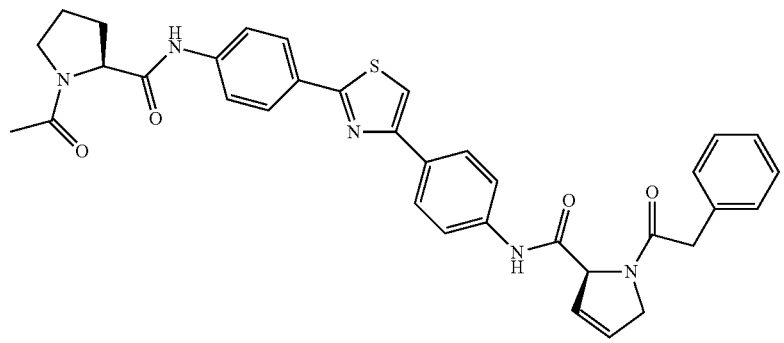 [SMILES: CC(=O)N1CCC[C@H]1C(=O)Nc1ccc(-c2nc(-c3ccc(NC(=O)[C@@H]4C=CCN4C(=O)Cc4ccccc4)cc3)cs2)cc1] | <10 | <10 |
| 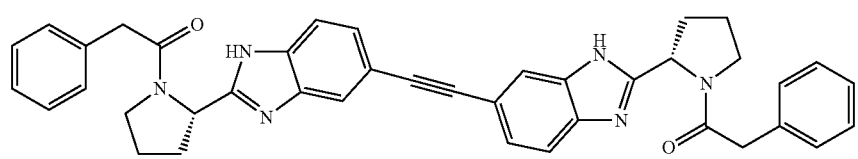 [SMILES: O=C(Cc1ccccc1)N1CCC[C@H]1c1nc2cc(C#Cc3ccc4nc([C@@H]5CCCN5C(=O)Cc5ccccc5)[nH]c4c3)ccc2[nH]1] | <10 | <10 |
| 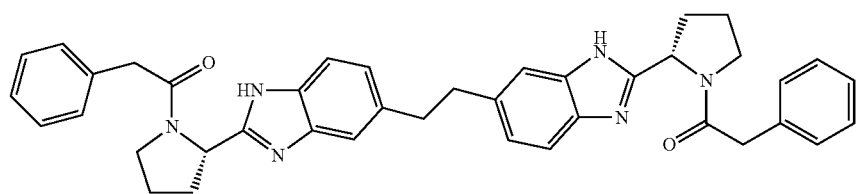 [SMILES: O=C(Cc1ccccc1)N1CCC[C@H]1c1nc2cc(CCc3ccc4nc([C@@H]5CCCN5C(=O)Cc5ccccc5)[nH]c4c3)ccc2[nH]1] | <10 | <10 |
| 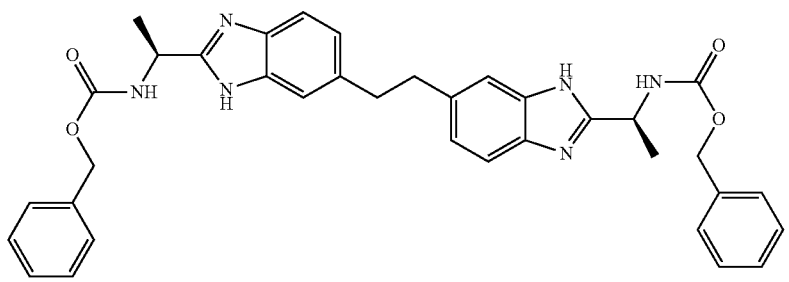 [SMILES: C[C@H](NC(=O)OCc1ccccc1)c1nc2ccc(CCc3ccc4nc([C@H](C)NC(=O)OCc5ccccc5)[nH]c4c3)cc2[nH]1] | <10 | <10 |
| 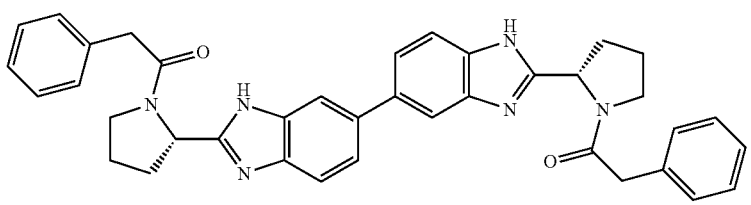 [SMILES: O=C(Cc1ccccc1)N1CCC[C@H]1c1nc2cc(-c3ccc4nc([C@@H]5CCCN5C(=O)Cc5ccccc5)[nH]c4c3)ccc2[nH]1] | <10 | <10 |

|  | Fold-Synergistic G-1a (L31V) | Fold-Synergistic G-1a (Y93H) |
| --- | --- | --- |
| 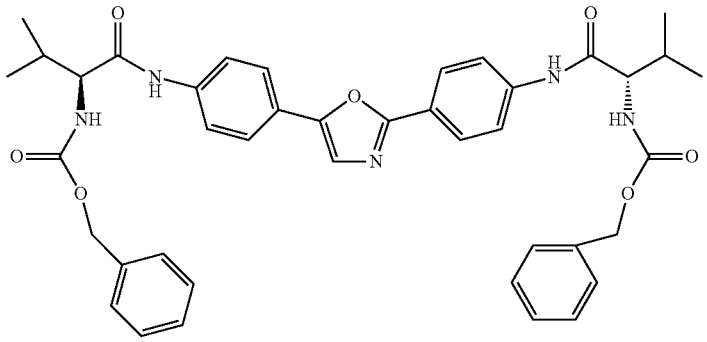 [SMILES: CC(C)[C@H](NC(=O)OCc1ccccc1)C(=O)Nc1ccc(-c2cnc(-c3ccc(NC(=O)[C@@H](NC(=O)OCc4ccccc4)C(C)C)cc3)o2)cc1] | <10 | <10 |
| 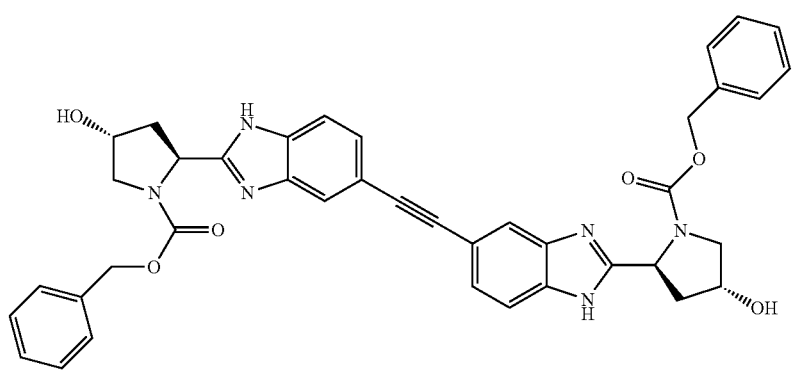 [SMILES: O=C(OCc1ccccc1)N1C[C@H](O)C[C@H]1c1nc2cc(C#Cc3ccc4[nH]c([C@@H]5C[C@@H](O)CN5C(=O)OCc5ccccc5)nc4c3)ccc2[nH]1] | <10 | <10 |
| 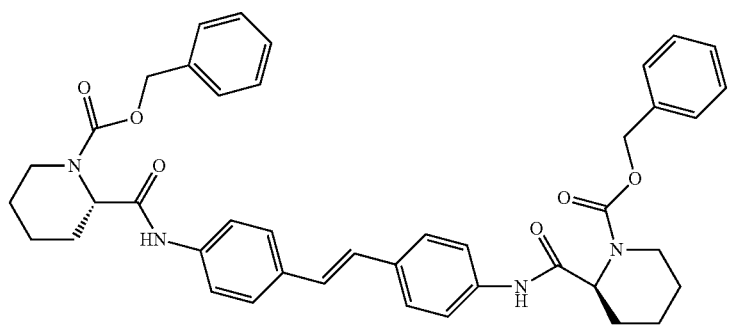 [SMILES: O=C(Nc1ccc(/C=C/c2ccc(NC(=O)[C@@H]3CCCCN3C(=O)OCc3ccccc3)cc2)cc1)[C@@H]1CCCCN1C(=O)OCc1ccccc1] | <10 | <10 |
| 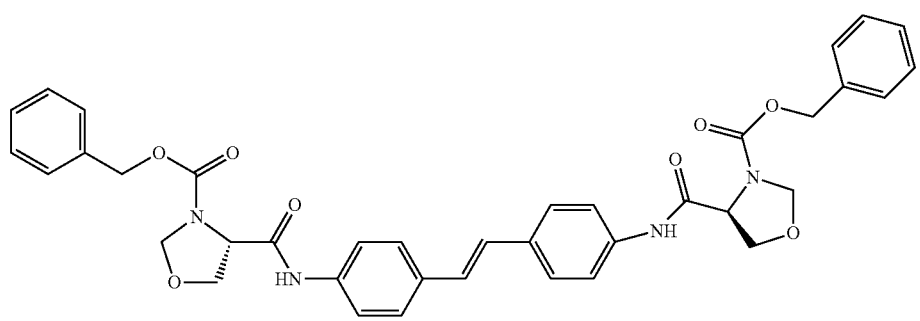 [SMILES: O=C(Nc1ccc(/C=C/c2ccc(NC(=O)[C@@H]3COCN3C(=O)OCc3ccccc3)cc2)cc1)[C@@H]1COCN1C(=O)OCc1ccccc1] | <10 | <10 |

-continued
| | Fold-Synergistic G-1a (L31V) | Fold-Synergistic G-1a (Y93H) |
|---|---|---|
| 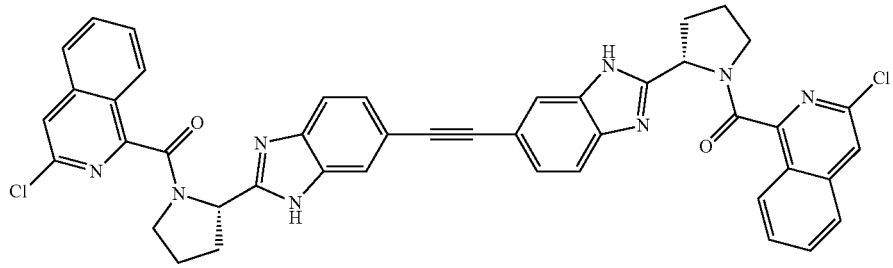 [SMILES: O=C(c1nc(Cl)cc2ccccc12)N1CCC[C@H]1c1nc2ccc(C#Cc3ccc4nc([C@@H]5CCCN5C(=O)c5nc(Cl)cc6ccccc56)[nH]c4c3)cc2[nH]1] | <10 | <10 |
| 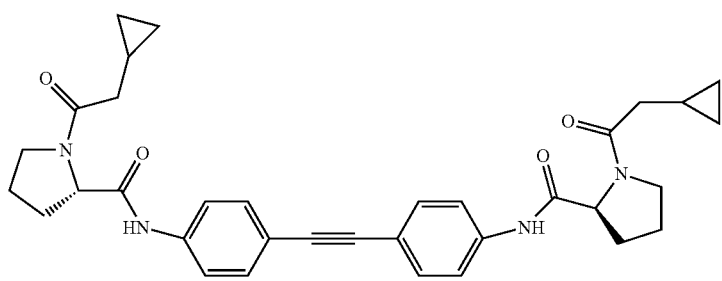 [SMILES: O=C(Nc1ccc(C#Cc2ccc(NC(=O)[C@@H]3CCCN3C(=O)CC3CC3)cc2)cc1)[C@@H]1CCCN1C(=O)CC1CC1] | <10 | <10 |
| 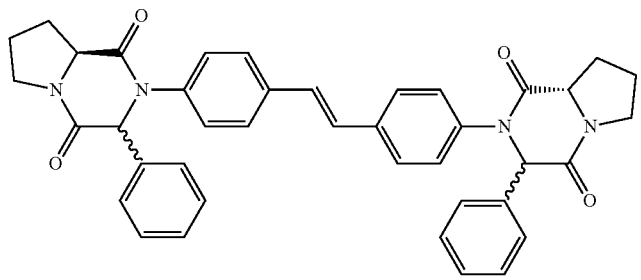 | <10 | <10 |
| 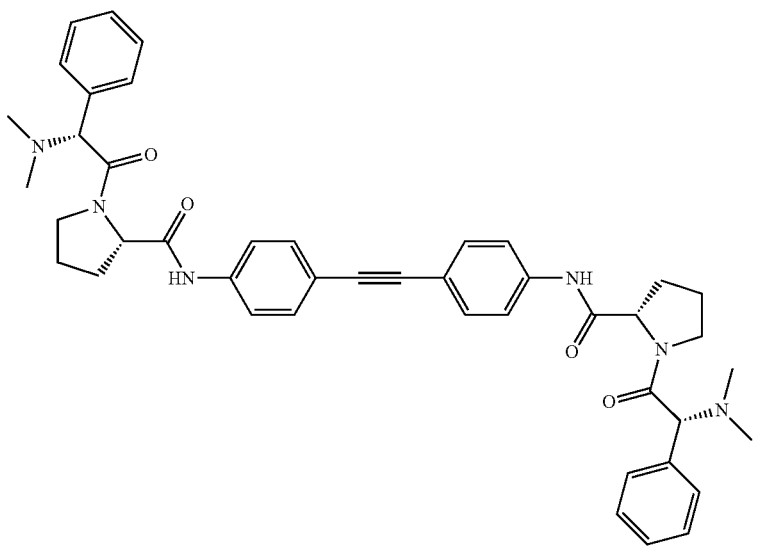 | <10 | <10 |

-continued
| | Fold-Synergistic G-1a (L31V) | Fold-Synergistic G-1a (Y93H) |
|---|---|---|
| 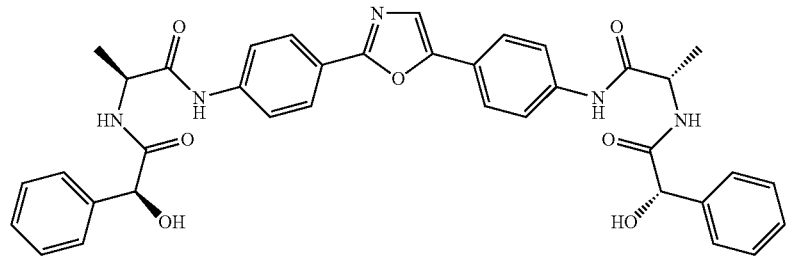 [SMILES: C[C@H](NC(=O)[C@@H](O)c1ccccc1)C(=O)Nc1ccc(-c2cnc(-c3ccc(NC(=O)[C@H](C)NC(=O)[C@@H](O)c4ccccc4)cc3)o2)cc1] | <10 | <10 |
| 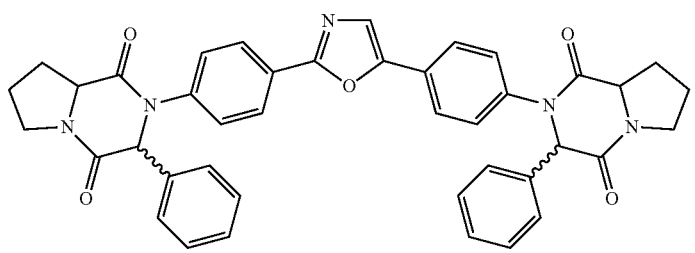 [SMILES: O=C1C(c2ccccc2)N(c2ccc(-c3cnc(-c4ccc(N5C(=O)C6CCCN6C(=O)C5c5ccccc5)cc4)o3)cc2)C(=O)C2CCCN12] | <10 | <10 |
| 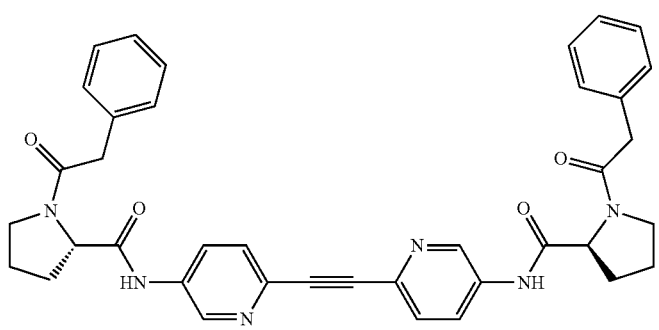 [SMILES: O=C(Nc1ccc(C#Cc2ccc(NC(=O)[C@@H]3CCCN3C(=O)Cc3ccccc3)cn2)nc1)[C@@H]1CCCN1C(=O)Cc1ccccc1] | <10 | <10 |
| 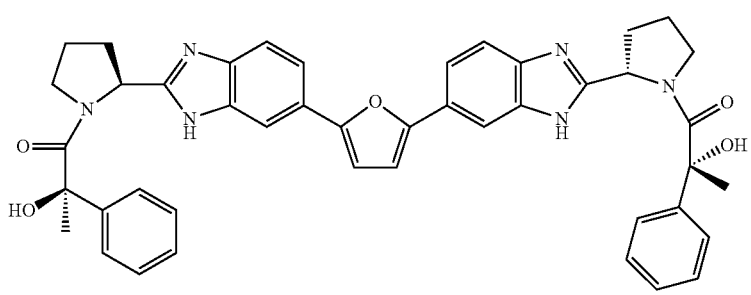 [SMILES: C[C@](O)(C(=O)N1CCC[C@H]1c1nc2ccc(-c3ccc(-c4ccc5nc([C@@H]6CCCN6C(=O)[C@](C)(O)c6ccccc6)[nH]c5c4)o3)cc2[nH]1)c1ccccc1] | <10 | <10 |

| | Fold-Synergistic G-1a (L31V) | Fold-Synergistic G-1a (Y93H) |
|---|---|---|
| 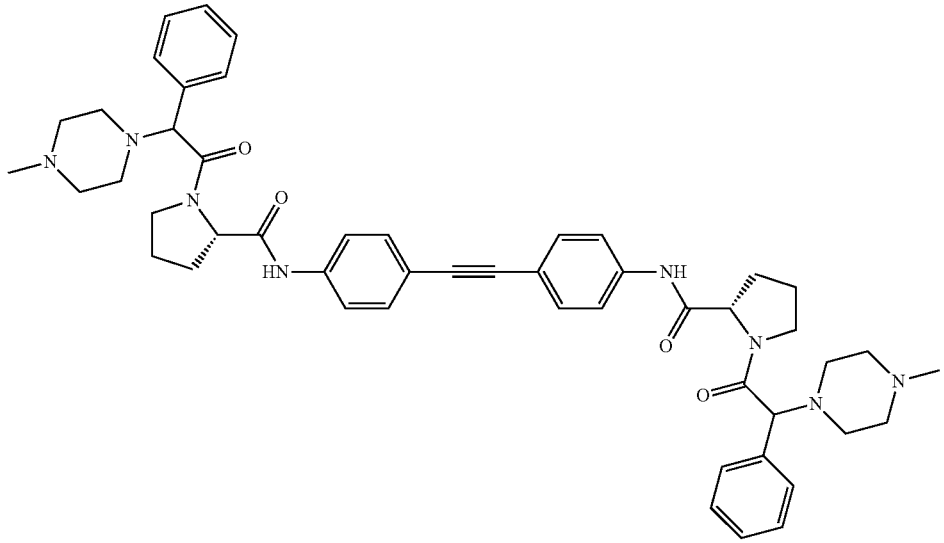 | <10 | <10 |
| 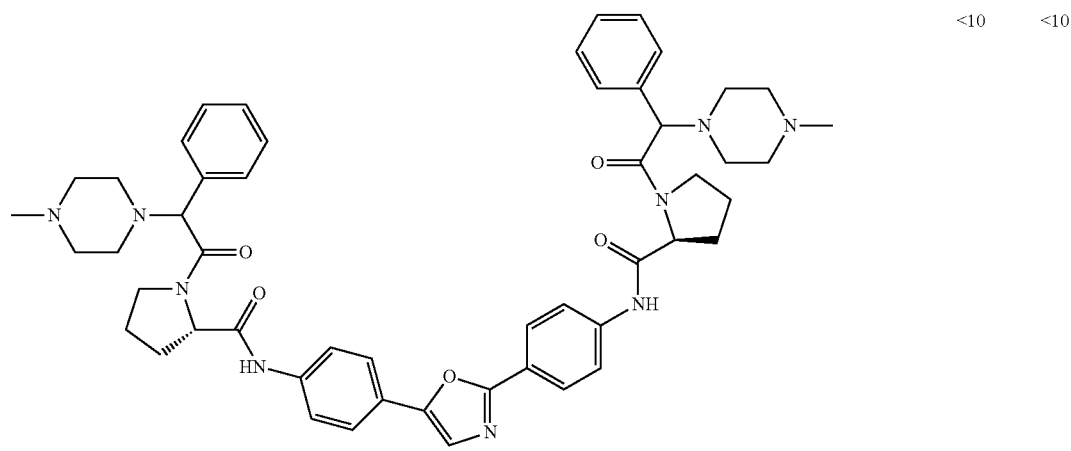 | <10 | <10 |
| 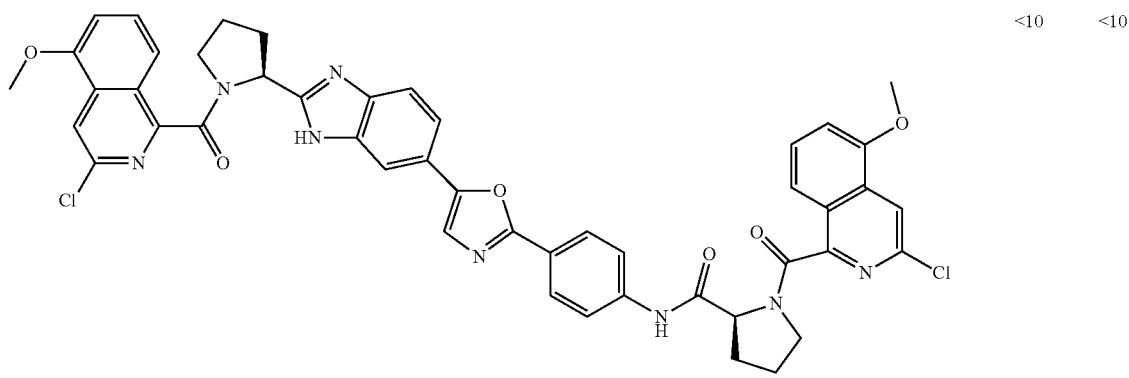 | <10 | <10 |

| | Fold-Synergistic G-1a (L31V) | Fold-Synergistic G-1a (Y93H) |
|---|---|---|
| 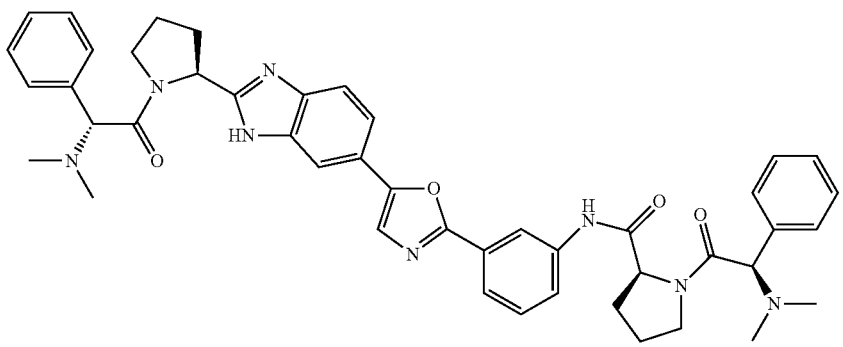 [SMILES: CN(C)[C@@H](C(=O)N1CCC[C@H]1C(=O)Nc1cccc(-c2ncc(-c3ccc4nc([C@@H]5CCCN5C(=O)[C@@H](c5ccccc5)N(C)C)[nH]c4c3)o2)c1)c1ccccc1] | <10 | <10 |
| 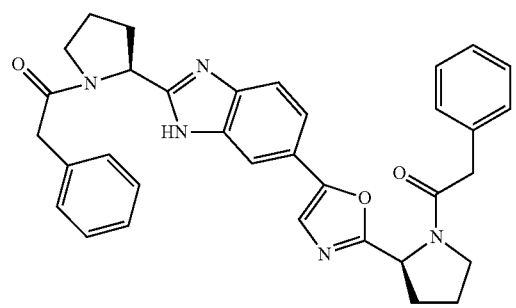 [SMILES: O=C(Cc1ccccc1)N1CCC[C@H]1c1nc2ccc(-c3cnc([C@@H]4CCCN4C(=O)Cc4ccccc4)o3)cc2[nH]1] | <10 | <10 |
| 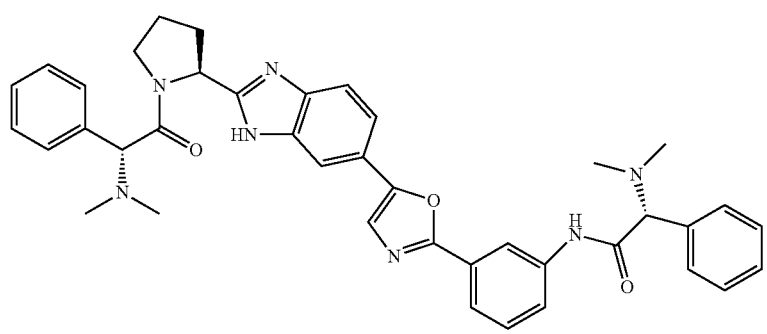 [SMILES: CN(C)[C@@H](C(=O)Nc1cccc(-c2ncc(-c3ccc4nc([C@@H]5CCCN5C(=O)[C@@H](c5ccccc5)N(C)C)[nH]c4c3)o2)c1)c1ccccc1] | <10 | <10 |
| 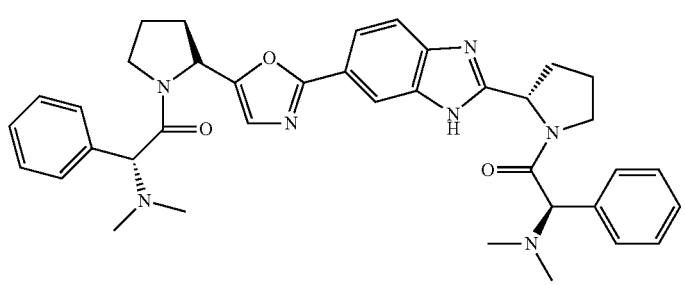 | <10 | <10 |

-continued

| | Fold-Synergistic G-1a (L31V) | Fold-Synergistic G-1a (Y93H) |
|---|---|---|
| | <10 | <10 |
| | <10 | <10 |
| | <10 | <10 |
| | <10 | <10 |
| | <10 | <10 |

| | Fold-Synergistic G-1a (L31V) | Fold-Synergistic G-1a (Y93H) |
|---|---|---|
| 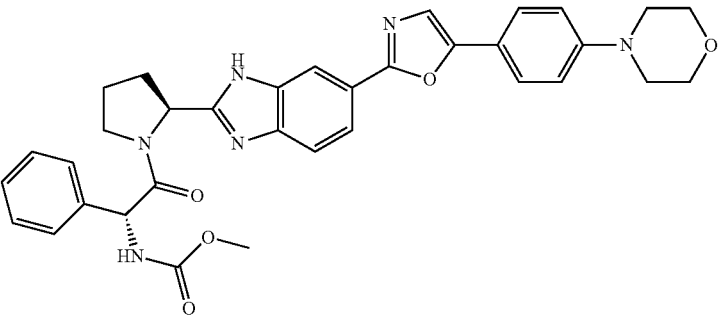 [SMILES: COC(=O)N[C@@H](C(=O)N1CCC[C@H]1c1nc2ccc(-c3ncc(-c4ccc(N5CCOCC5)cc4)o3)cc2[nH]1)c1ccccc1] | <10 | <10 |
| 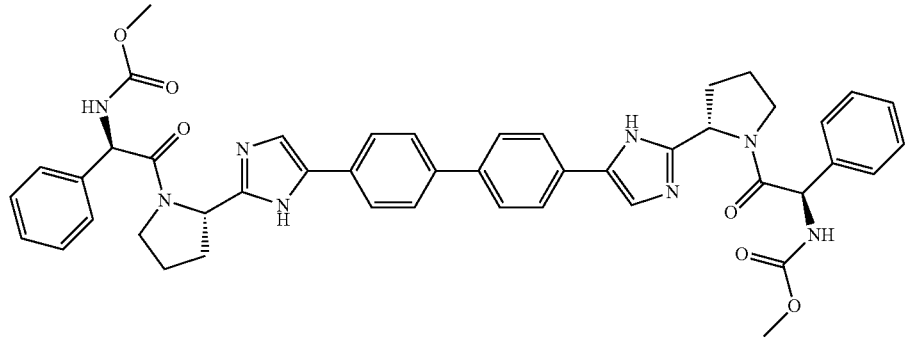 [SMILES: COC(=O)N[C@@H](C(=O)N1CCC[C@H]1c1ncc(-c2ccc(-c3ccc(-c4cnc([C@@H]5CCCN5C(=O)[C@H](NC(=O)OC)c5ccccc5)[nH]4)cc3)cc2)[nH]1)c1ccccc1] | <10 | <10 |
| 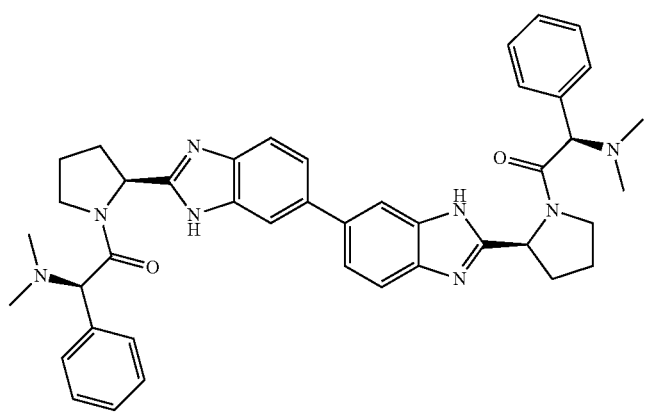 | <10 | <10 |
| 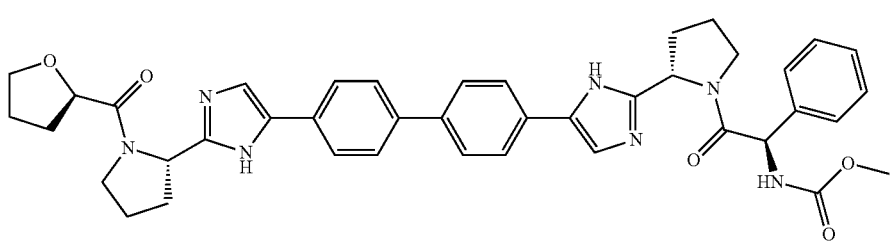 [SMILES: COC(=O)N[C@@H](C(=O)N1CCC[C@H]1c1ncc(-c2ccc(-c3ccc(-c4cnc([C@@H]5CCCN5C(=O)[C@H]5CCCO5)[nH]4)cc3)cc2)[nH]1)c1ccccc1] | <10 | <10 |

|  | Fold-Synergistic G-1a (L31V) | Fold-Synergistic G-1a (Y93H) |
|---|---|---|
| 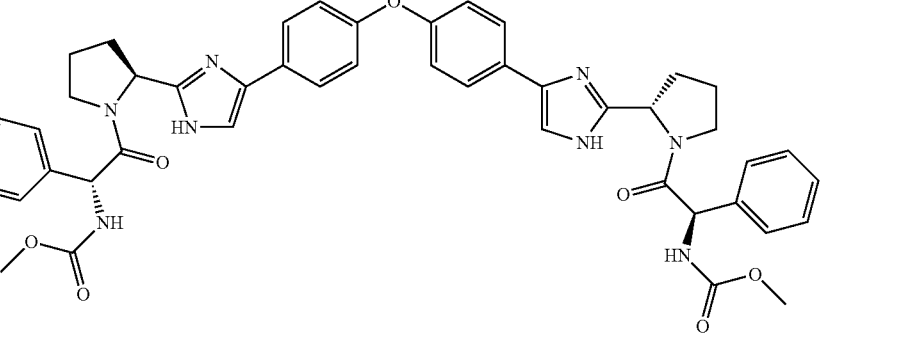 | <10 | <10 |
| 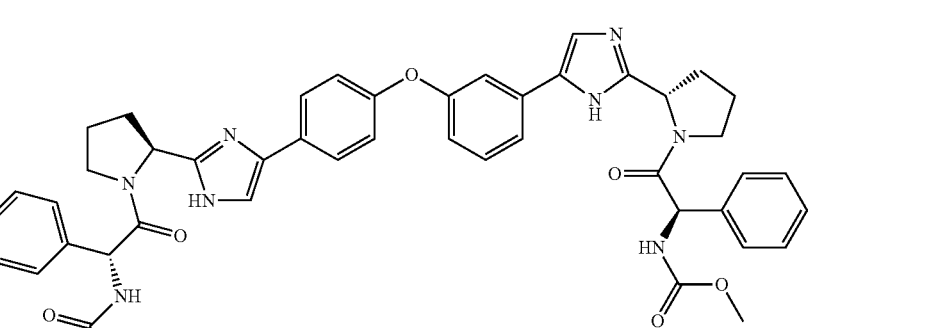 | <10 | <10 |
| 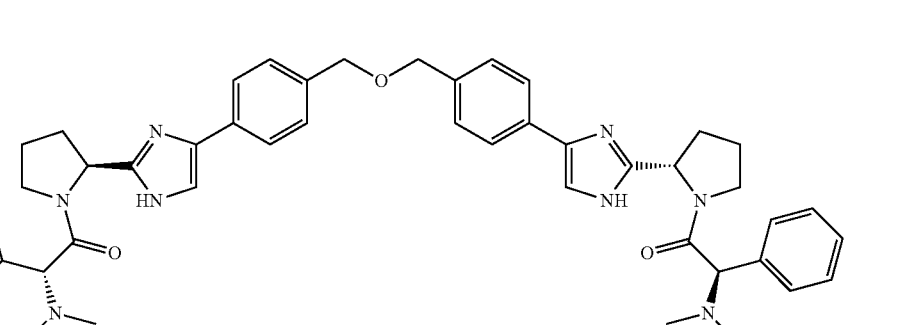 | <10 | <10 |
| 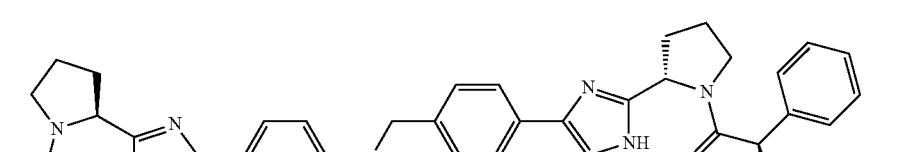 | <10 | <10 |

| | Fold-Synergistic G-1a (L31V) | Fold-Synergistic G-1a (Y93H) |
|---|---|---|
| 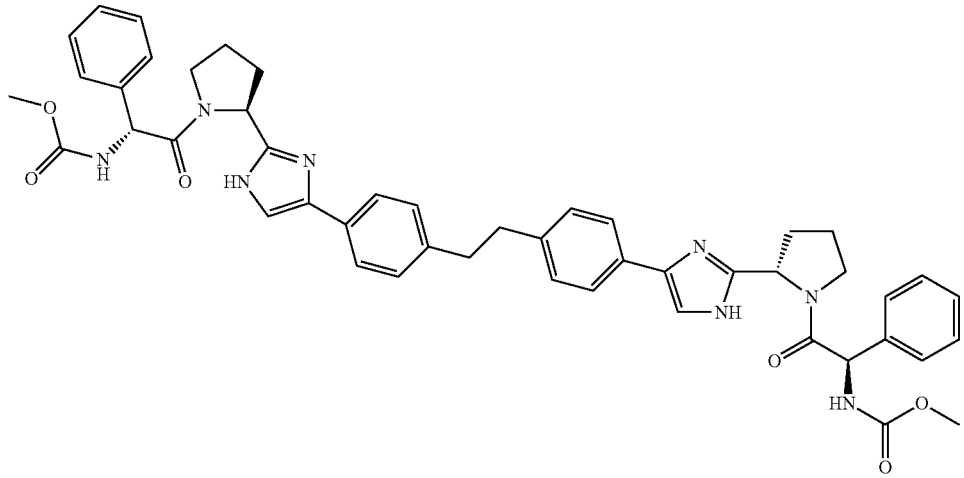 [SMILES: COC(=O)N[C@@H](C(=O)N1CCC[C@H]1c1nc(-c2ccc(CCc3ccc(-c4c[nH]c([C@@H]5CCCN5C(=O)[C@H](NC(=O)OC)c5ccccc5)n4)cc3)cc2)c[nH]1)c1ccccc1] | <10 | <10 |
| 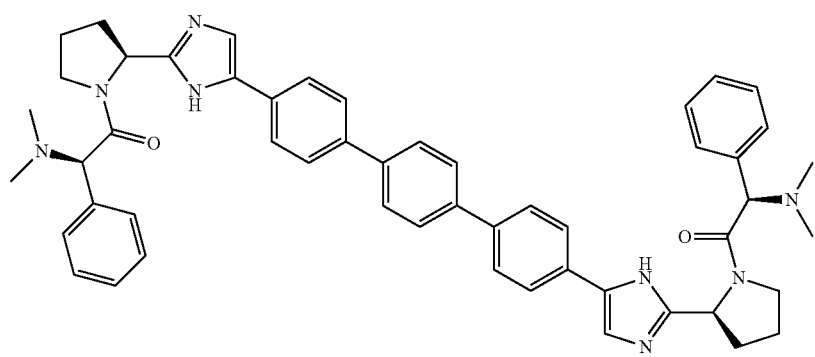 | <10 | <10 |
| 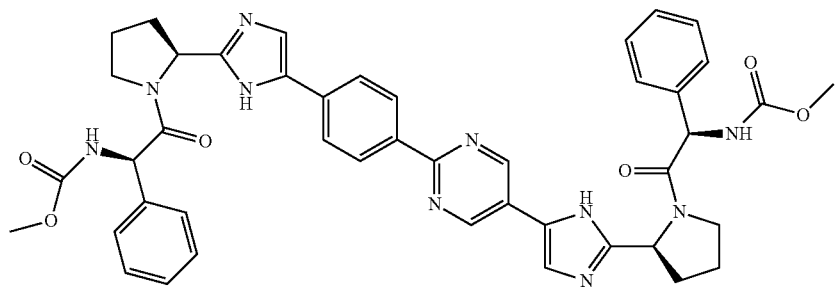 | <10 | <10 |

|  | Fold-Synergistic G-1a (L31V) | Fold-Synergistic G-1a (Y93H) |
|---|---|---|
| 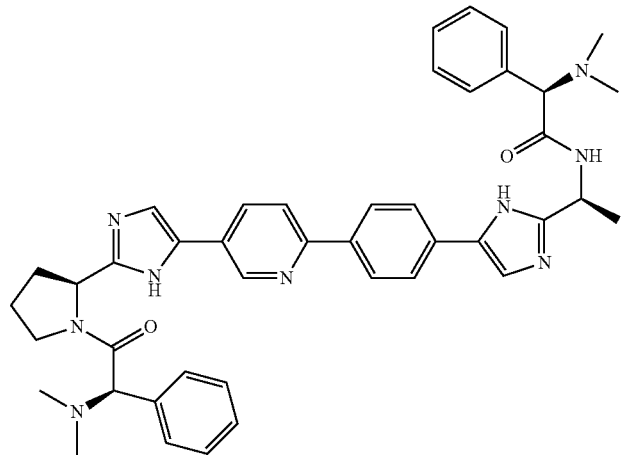 [SMILES: C[C@H](NC(=O)[C@@H](c1ccccc1)N(C)C)c1ncc(-c2ccc(-c3ccc(-c4cnc([C@@H]5CCCN5C(=O)[C@@H](c5ccccc5)N(C)C)[nH]4)cn3)cc2)[nH]1] | <10 | <10 |
| 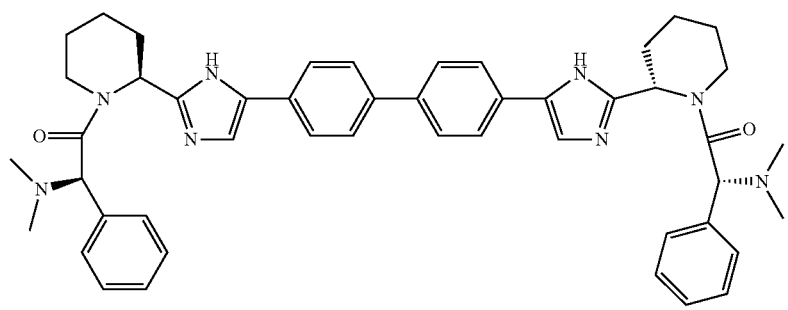 | <10 | <10 |
| 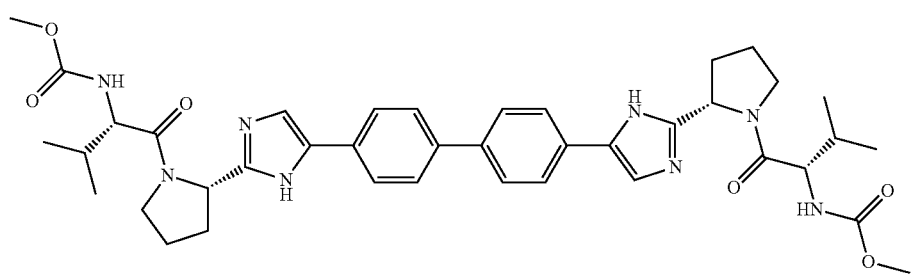<br>(BMS-790052) | >100 | >100 |

-continued
| | Fold-Synergistic G-1a (L31V) | Fold-Synergistic G-1a (Y93H) |
|---|---|---|
| 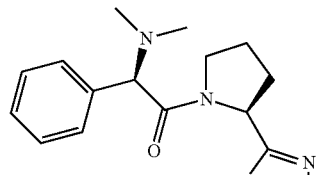 | <10 | <10 |
| 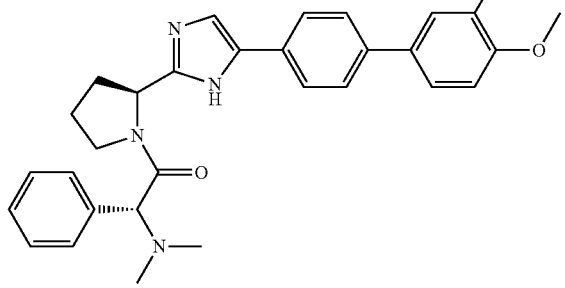 | >100 | >100 |
| 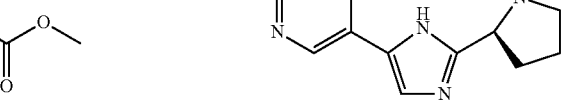 | <10 | <10 |
| 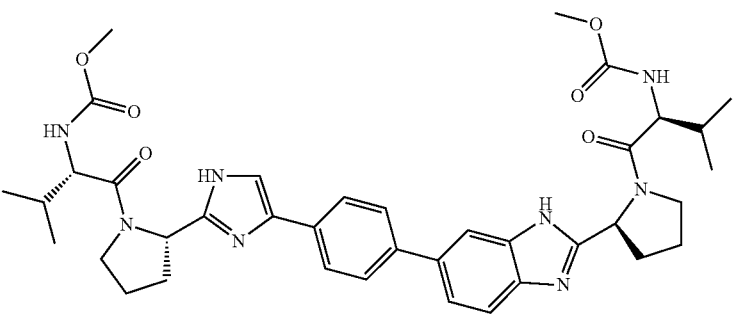 [SMILES: COC(=O)N[C@H](C(=O)N1CCC[C@H]1c1nc(-c2ccc(-c3ccc4nc([C@@H]5CCCN5C(=O)[C@@H](NC(=O)OC)C(C)C)[nH]c4c3)cc2)c[nH]1)C(C)C] | >10 | >100 |

-continued

| | Fold-Synergistic G-1a (L31V) | Fold-Synergistic G-1a (Y93H) |
|---|---|---|
| | <10 | <10 |
| | <10 | >100 |
| | >100 | >100 |
| | <10 | <10 |

| | Fold-Synergistic G-1a (L31V) | Fold-Synergistic G-1a (Y93H) |
|---|---|---|
| 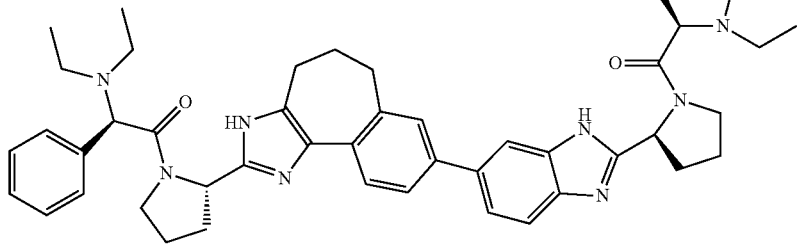 | <10 | <10 |
| 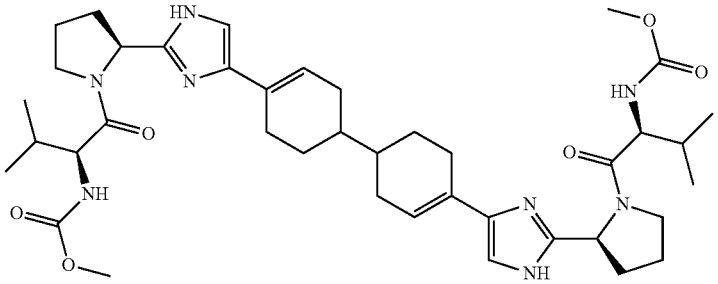 [SMILES: COC(=O)N[C@H](C(=O)N1CCC[C@H]1c1nc(C2=CCC(C3CC=C(c4c[nH]c([C@@H]5CCCN5C(=O)[C@@H](NC(=O)OC)C(C)C)n4)CC3)CC2)c[nH]1)C(C)C] | >100 | >100 |
| 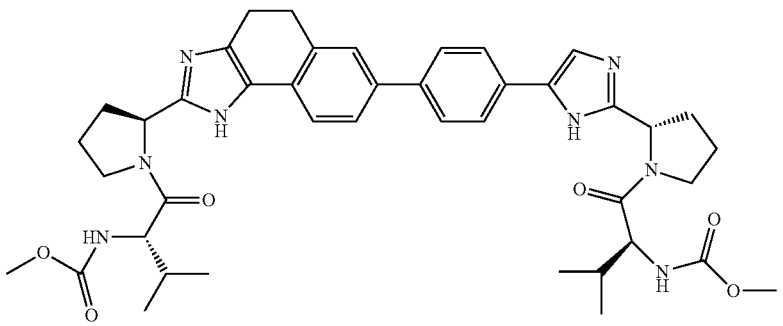 | >100 | >100 |
| 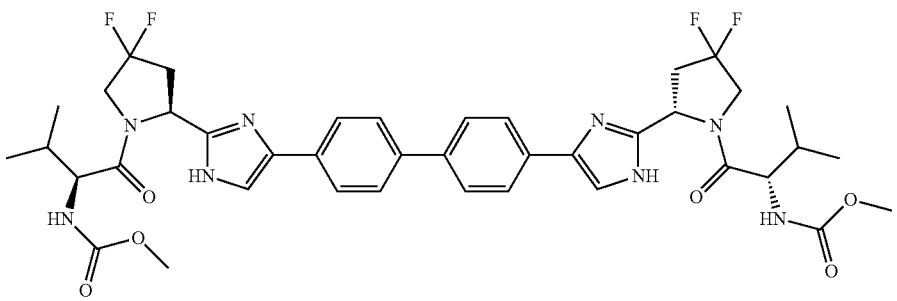 [SMILES: COC(=O)N[C@H](C(=O)N1CC(F)(F)C[C@H]1c1nc(-c2ccc(-c3ccc(-c4c[nH]c([C@@H]5CC(F)(F)CN5C(=O)[C@@H](NC(=O)OC)C(C)C)n4)cc3)cc2)c[nH]1)C(C)C] | >100 | >100 |

-continued
| | Fold-Synergistic G-1a (L31V) | Fold-Synergistic G-1a (Y93H) |
|---|---|---|
| 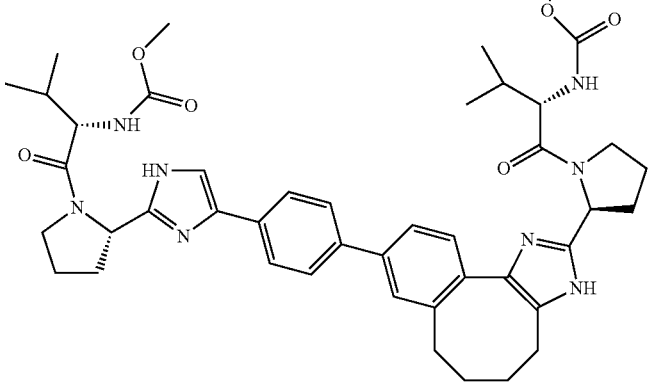 | >100 | >100 |
| 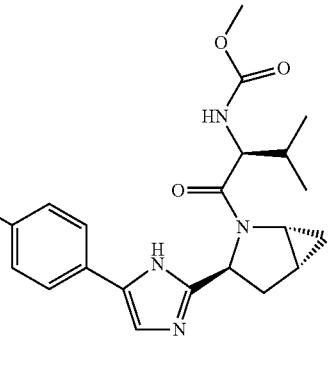 | >100 | >100 |
| 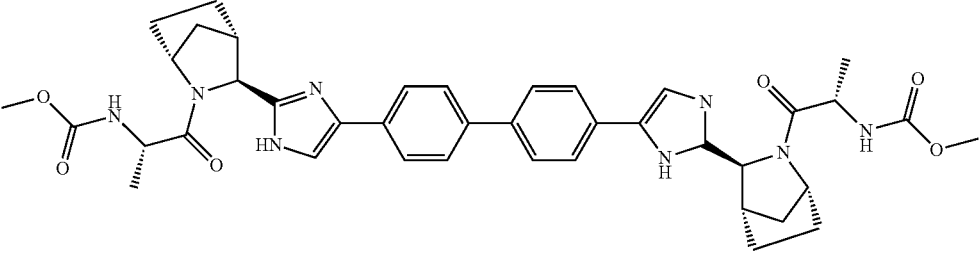 | >10 | <10 |
| 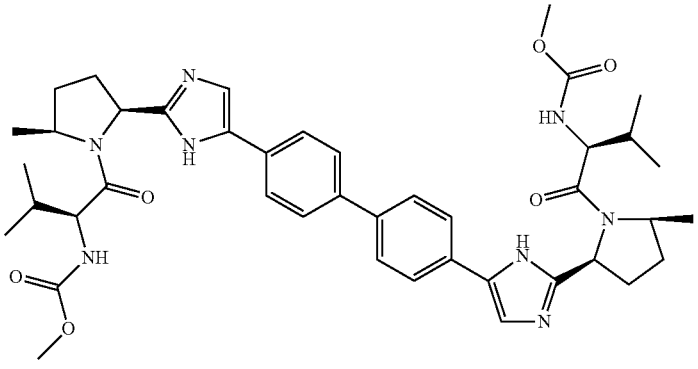 [SMILES: COC(=O)N[C@H](C(=O)N1[C@@H](C)CC[C@H]1c1ncc(-c2ccc(-c3ccc(-c4cnc([C@@H]5CC[C@H](C)N5C(=O)[C@@H](NC(=O)OC)C(C)C)[nH]4)cc3)cc2)[nH]1)C(C)C] | >100 | >100 |

-continued
| | Fold-Synergistic G-1a (L31V) | Fold-Synergistic G-1a (Y93H) |
|---|---|---|
| 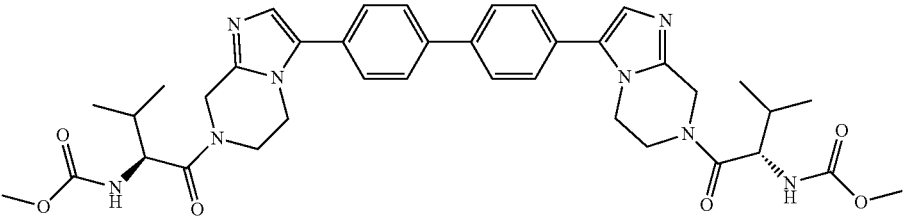 | <10 | <10 |
| 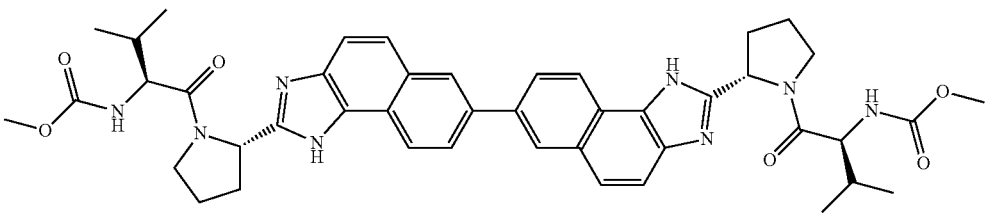 | >100 | >100 |
| 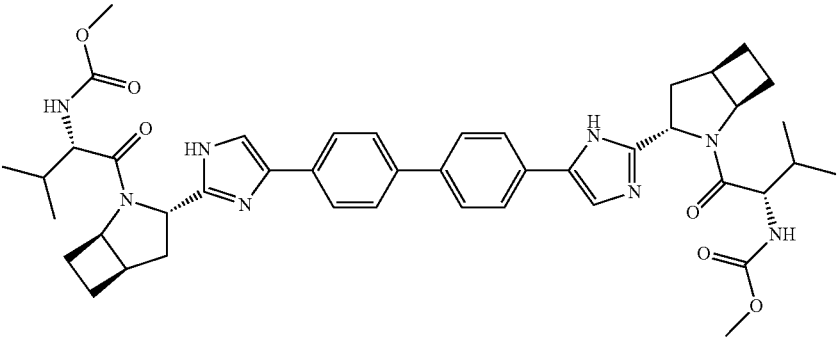 [SMILES: COC(=O)N[C@H](C(=O)N1[C@@H]2CC[C@@H]2C[C@H]1c1nc(-c2ccc(-c3ccc(-c4cnc([C@@H]5C[C@H]6CC[C@H]6N5C(=O)[C@@H](NC(=O)OC)C(C)C)[nH]4)cc3)cc2)c[nH]1)C(C)C] | >100 | >100 |
| 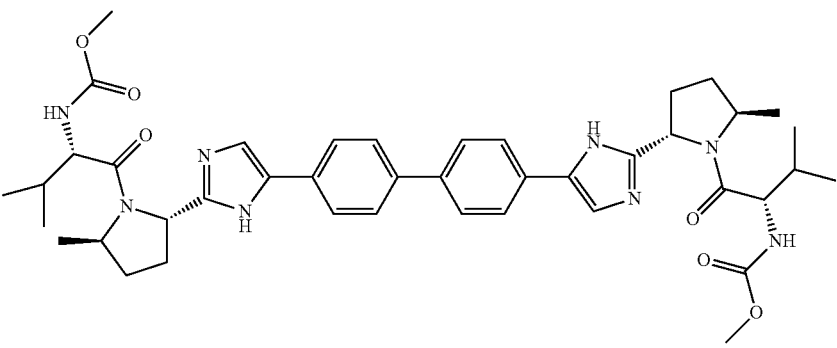 [SMILES: COC(=O)N[C@H](C(=O)N1[C@H](C)CC[C@H]1c1ncc(-c2ccc(-c3ccc(-c4cnc([C@@H]5CC[C@@H](C)N5C(=O)[C@@H](NC(=O)OC)C(C)C)[nH]4)cc3)cc2)[nH]1)C(C)C] | >100 | >100 |
| 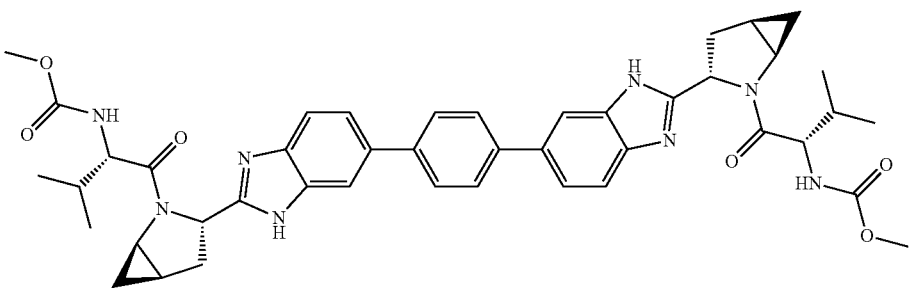 | >10 | >100 |

-continued
| | Fold-Synergistic G-1a (L31V) | Fold-Synergistic G-1a (Y93H) |
|---|---|---|
| 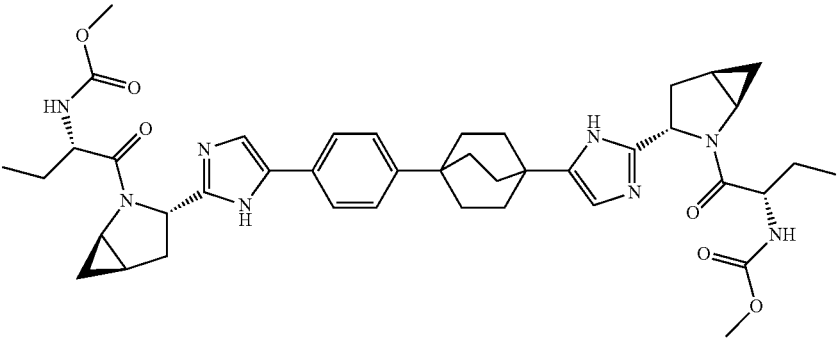 [SMILES: CC[C@H](NC(=O)OC)C(=O)N1[C@@H]2C[C@@H]2C[C@H]1c1ncc(-c2ccc(C34CCC(c5cnc([C@@H]6C[C@H]7C[C@H]7N6C(=O)[C@H](CC)NC(=O)OC)[nH]5)(CC3)CC4)cc2)[nH]1] | >100 | >100 |
| 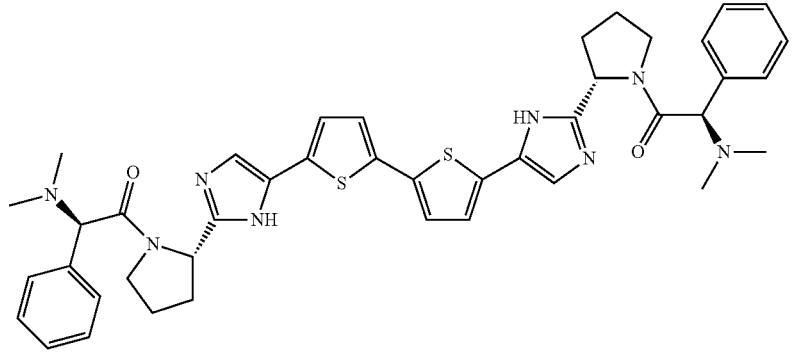 | <10 | <10 |
| 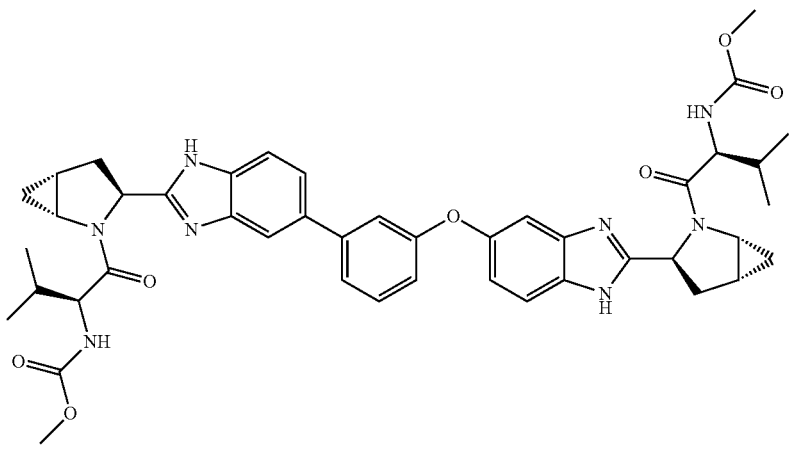 [SMILES: COC(=O)N[C@H](C(=O)N1[C@@H]2C[C@@H]2C[C@H]1c1nc2cc(Oc3cccc(-c4ccc5[nH]c([C@@H]6C[C@H]7C[C@H]7N6C(=O)[C@@H](NC(=O)OC)C(C)C)nc5c4)c3)ccc2[nH]1)C(C)C] | >10 | >10 |
| 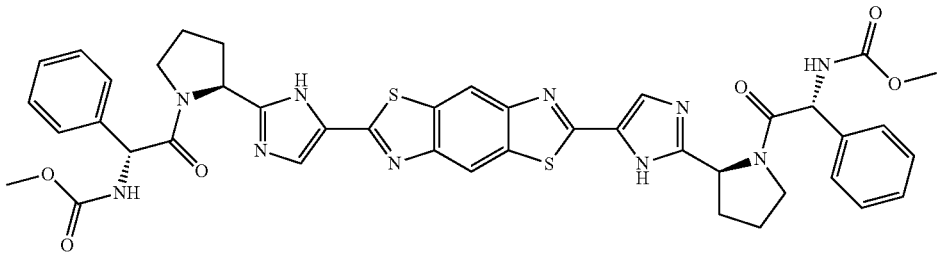 | <10 | >100 |

-continued
| | Fold-Synergistic G-1a (L31V) | Fold-Synergistic G-1a (Y93H) |
|---|---|---|
| 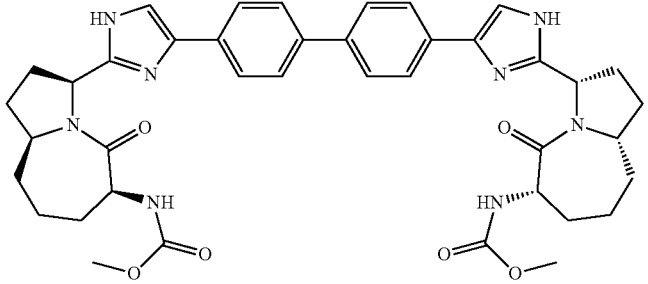 [SMILES: COC(=O)N[C@H]1CCC[C@H]2CC[C@@H](c3nc(-c4ccc(-c5ccc(-c6c[nH]c([C@@H]7CC[C@@H]8CCC[C@H](NC(=O)OC)C(=O)N87)n6)cc5)cc4)c[nH]3)N2C1=O] | <10 | <10 |
| 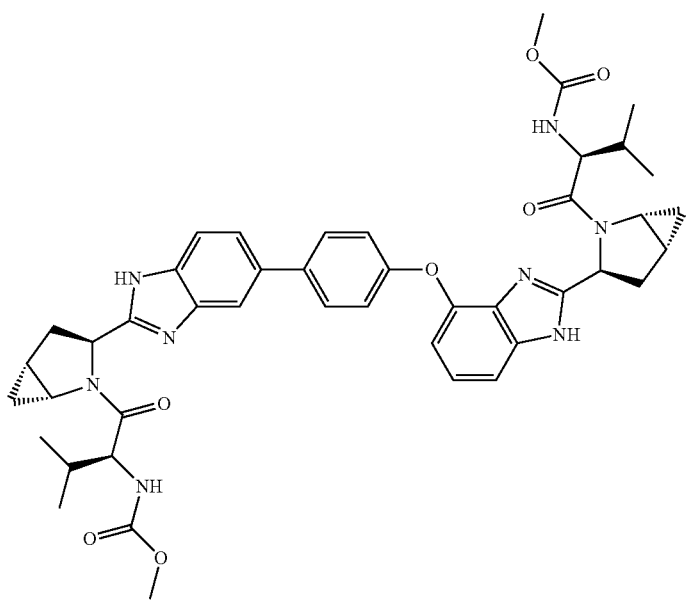 [SMILES: COC(=O)N[C@H](C(=O)N1[C@@H]2C[C@@H]2C[C@H]1c1nc2cc(-c3ccc(Oc4cccc5[nH]c([C@@H]6C[C@H]7C[C@H]7N6C(=O)[C@@H](NC(=O)OC)C(C)C)nc45)cc3)ccc2[nH]1)C(C)C] | >10 | >100 |
| 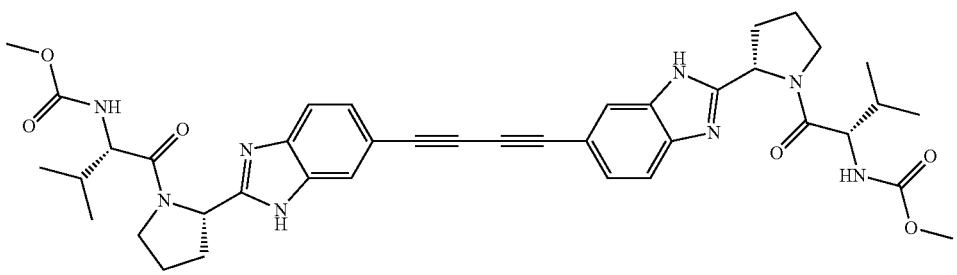 | >100 | >10 |
| 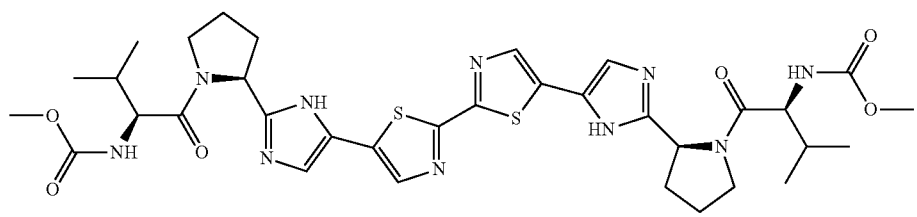 | >10 | >100 |

-continued
| | Fold-Synergistic G-1a (L31V) | Fold-Synergistic G-1a (Y93H) |
|---|---|---|
| 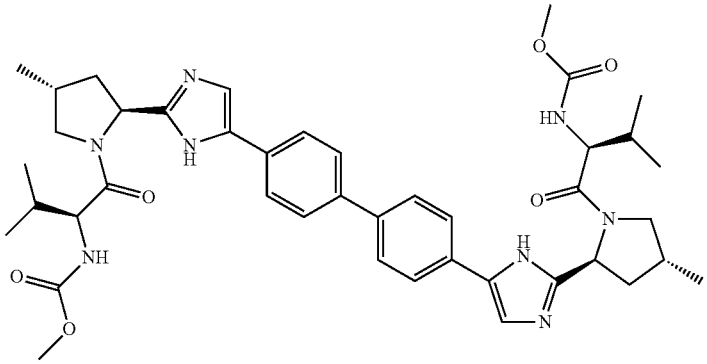 [SMILES: COC(=O)N[C@H](C(=O)N1C[C@H](C)C[C@H]1c1ncc(-c2ccc(-c3ccc(-c4cnc([C@@H]5C[C@@H](C)CN5C(=O)[C@@H](NC(=O)OC)C(C)C)[nH]4)cc3)cc2)[nH]1)C(C)C] | >100 | >100 |
| 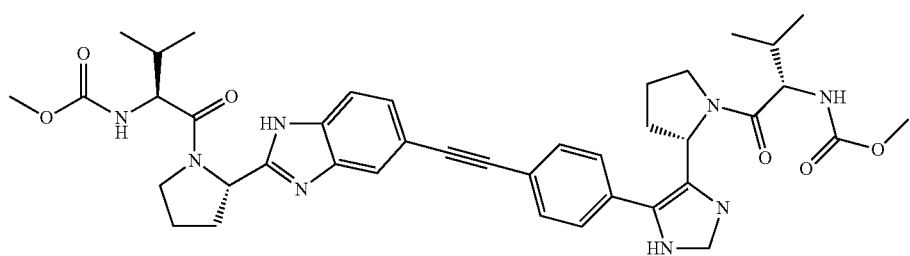 | <10 | >10 |
| 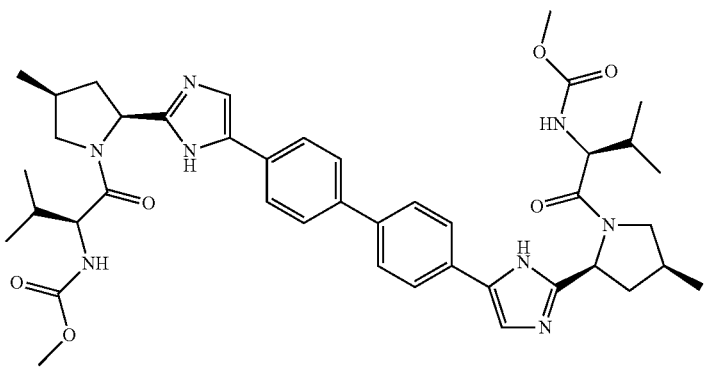 [SMILES: COC(=O)N[C@H](C(=O)N1C[C@@H](C)C[C@H]1c1ncc(-c2ccc(-c3ccc(-c4cnc([C@@H]5C[C@H](C)CN5C(=O)[C@@H](NC(=O)OC)C(C)C)[nH]4)cc3)cc2)[nH]1)C(C)C] | >10 | >100 |
| 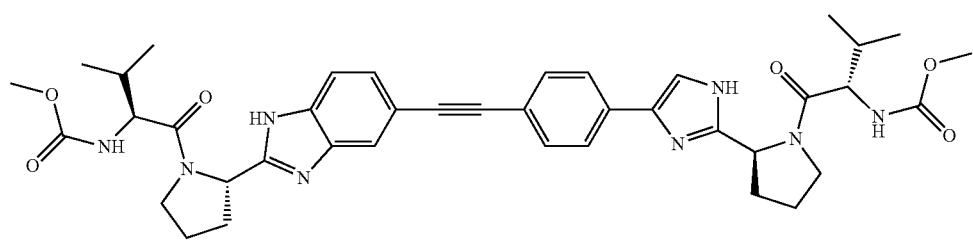 | >100 | >100 |

|  | Fold-Synergistic G-1a (L31V) | Fold-Synergistic G-1a (Y93H) |
|---|---|---|
| 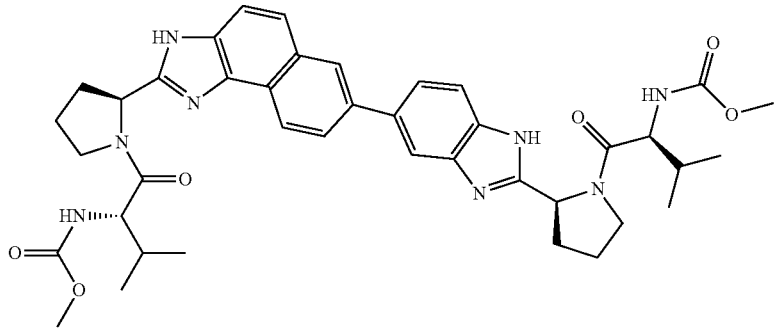 [SMILES: COC(=O)N[C@H](C(=O)N1CCC[C@H]1c1nc2cc(-c3ccc4c(ccc5[nH]c([C@@H]6CCCN6C(=O)[C@@H](NC(=O)OC)C(C)C)nc54)c3)ccc2[nH]1)C(C)C] | >10 | >100 |
| 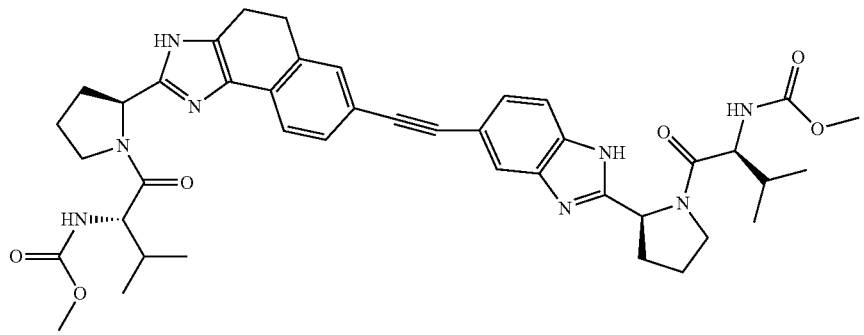 [SMILES: COC(=O)N[C@H](C(=O)N1CCC[C@H]1c1nc2c([nH]1)CCc1cc(C#Cc3ccc4[nH]c([C@@H]5CCCN5C(=O)[C@@H](NC(=O)OC)C(C)C)nc4c3)ccc1-2)C(C)C] | >100 | >100 |
| 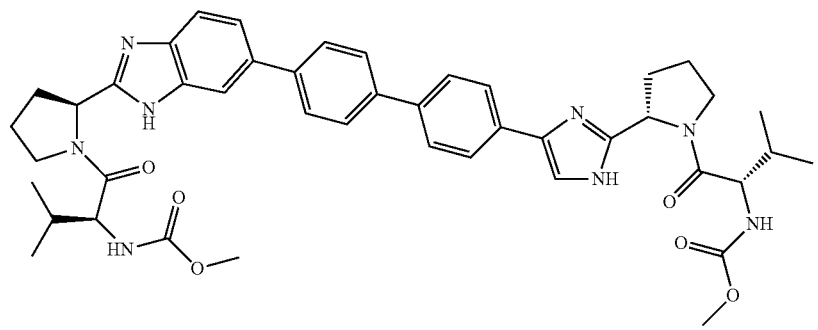 [SMILES: COC(=O)N[C@H](C(=O)N1CCC[C@H]1c1nc(-c2ccc(-c3ccc(-c4ccc5nc([C@@H]6CCCN6C(=O)[C@@H](NC(=O)OC)C(C)C)[nH]c5c4)cc3)cc2)c[nH]1)C(C)C] | >10 | >10 |
| 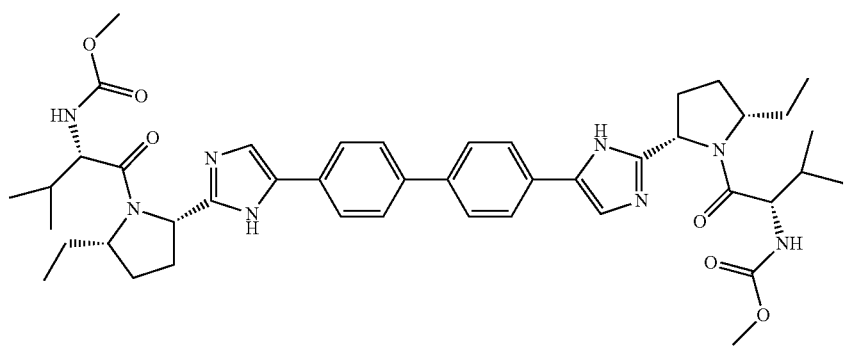 [SMILES: CC[C@H]1CC[C@@H](c2ncc(-c3ccc(-c4ccc(-c5cnc([C@@H]6CC[C@H](CC)N6C(=O)[C@@H](NC(=O)OC)C(C)C)[nH]5)cc4)cc3)[nH]2)N1C(=O)[C@@H](NC(=O)OC)C(C)C] | >100 | >100 |

-continued
| | Fold-Synergistic G-1a (L31V) | Fold-Synergistic G-1a (Y93H) |
|---|---|---|
| 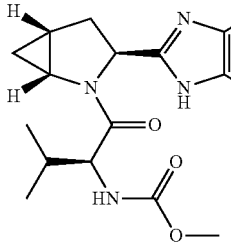 | >10 | >100 |
| 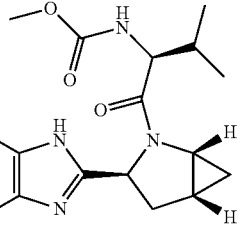 | >10 | >10 |
| 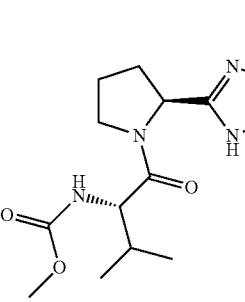 | >10 | >10 |
| 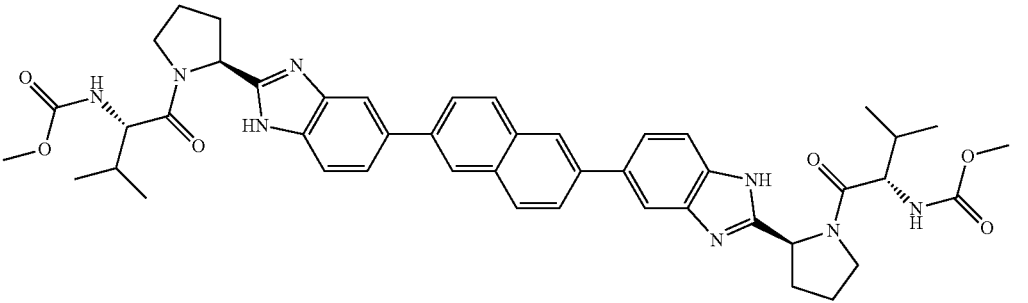 | >10 | >10 |

-continued

| | Fold-Synergistic G-1a (L31V) | Fold-Synergistic G-1a (Y93H) |
|---|---|---|
| | >100 | >100 |
| | <10 | <10 |
| | >100 | >100 |
| | <10 | <10 |

-continued
| | Fold-Synergistic G-1a (L31V) | Fold-Synergistic G-1a (Y93H) |
|---|---|---|
| 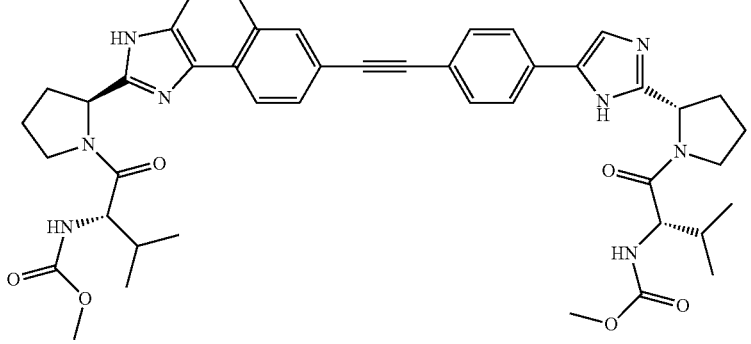 | <10 | >100 |
| 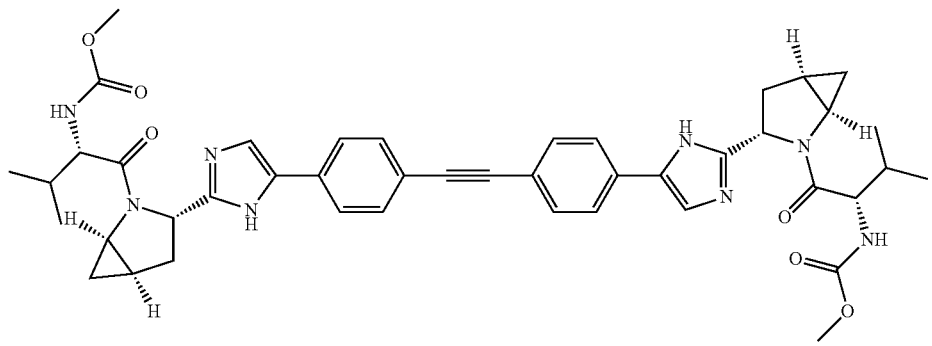 [SMILES: COC(=O)N[C@H](C(=O)N1[C@@H]2C[C@@H]2C[C@H]1c1ncc(-c2ccc(C#Cc3ccc(-c4cnc([C@@H]5C[C@H]6C[C@H]6N5C(=O)[C@@H](NC(=O)OC)C(C)C)[nH]4)cc3)cc2)[nH]1)C(C)C] | <10 | >10 |
| 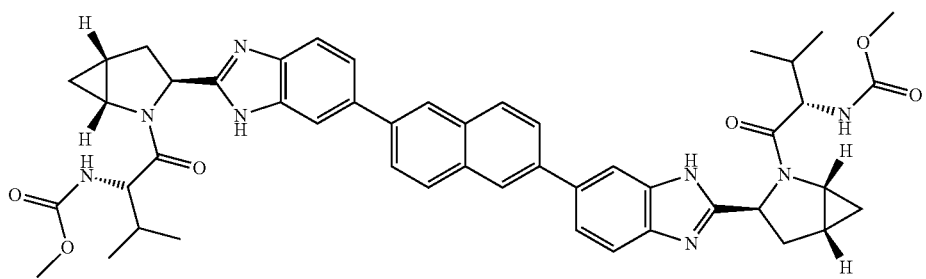 | >10 | >10 |
| 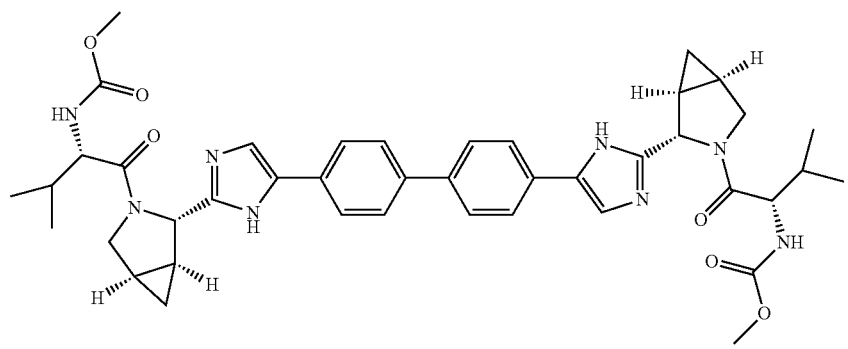 [SMILES: COC(=O)N[C@H](C(=O)N1C[C@@H]2C[C@@H]2[C@H]1c1ncc(-c2ccc(-c3ccc(-c4cnc([C@@H]5[C@H]6C[C@H]6CN5C(=O)[C@@H](NC(=O)OC)C(C)C)[nH]4)cc3)cc2)[nH]1)C(C)C] | >100 | >100 |

-continued

| | Fold-Synergistic G-1a (L31V) | Fold-Synergistic G-1a (Y93H) |
|---|---|---|
| | >100 | >100 |
| | >10 | >10 |
| | <10 | >10 |
| | >10 | <10 |
| | >100 | >100 |

US 9,326,973 B2

725                                                                         726

-continued

| | Fold-Synergistic G-1a (L31V) | Fold-Synergistic G-1a (Y93H) |
|---|---|---|
| [structure] | >10 | >100 |
| [structure] | <10 | >100 |
| [structure] Chiral | >10 | <10 |
| [structure] | <10 | <10 |

| | Fold-Synergistic G-1a (L31V) | Fold-Synergistic G-1a (Y93H) |
|---|---|---|
| | <10 | >10 |
| | >10 | >10 |
| | <10 | >10 |
| | <10 | >10 |

| | Fold-Synergistic G-1a (L31V) | Fold-Synergistic G-1a (Y93H) |
|---|---|---|
| | >10 | >10 |
| | <10 | <10 |
| | >100 | >100 |
| | >100 | >100 |

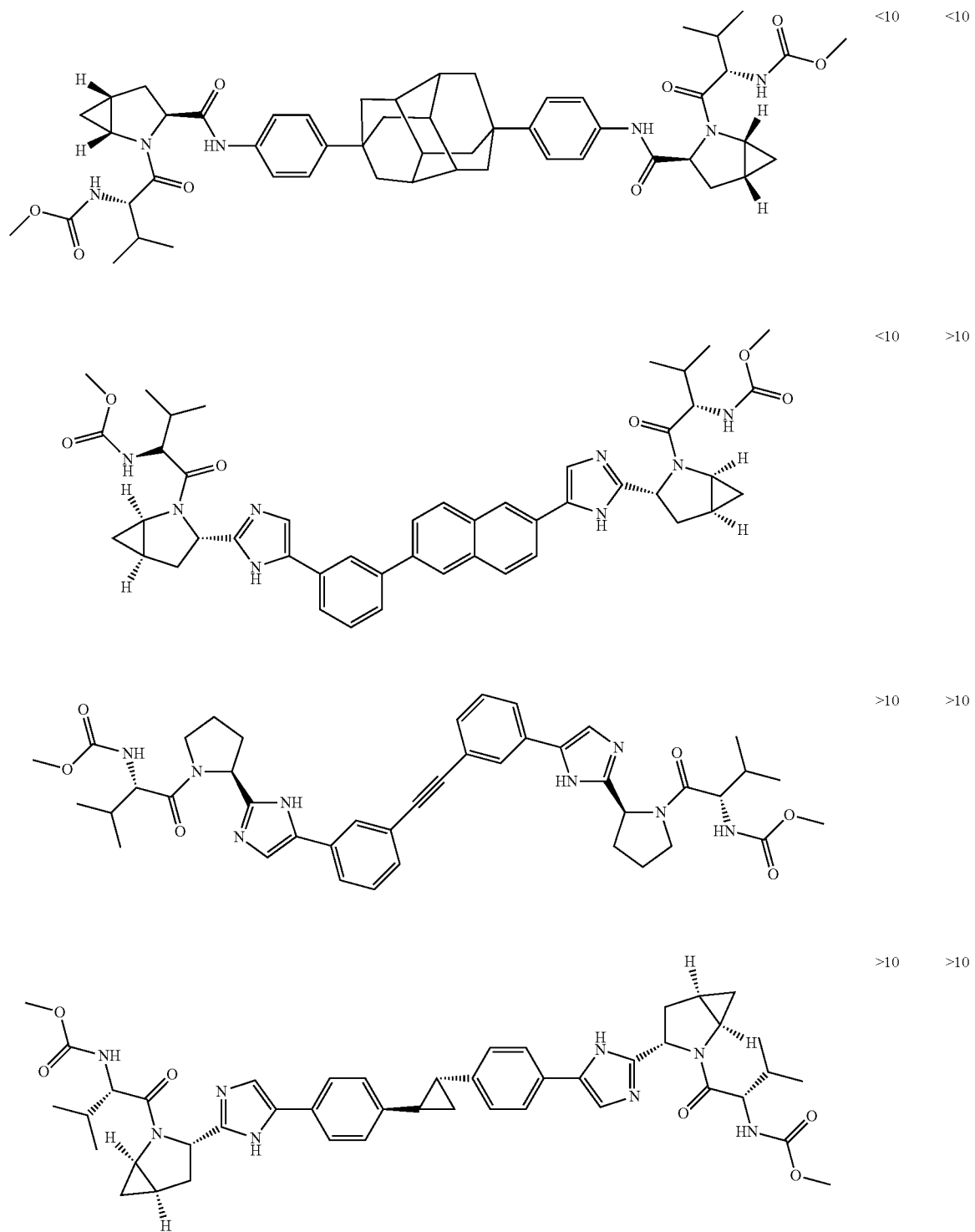

-continued

| | Fold-Synergistic G-1a (L31V) | Fold-Synergistic G-1a (Y93H) |
|---|---|---|
| | >10 | <10 |
| (A single homodimeric stereoisomer) | >100 | >100 |
| | >100 | >100 |
| | >100 | >100 |

-continued
|   | Fold-Synergistic G-1a (L31V) | Fold-Synergistic G-1a (Y93H) |
|---|---|---|
| 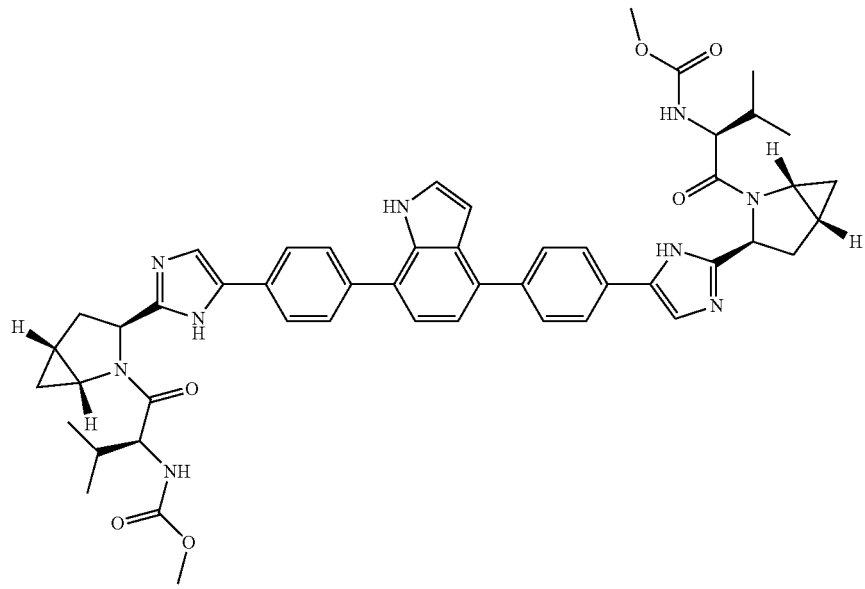 [SMILES: COC(=O)N[C@H](C(=O)N1[C@@H]2C[C@@H]2C[C@H]1c1ncc(-c2ccc(-c3ccc(-c4ccc(-c5cnc([C@@H]6C[C@H]7C[C@H]7N6C(=O)[C@@H](NC(=O)OC)C(C)C)[nH]5)cc4)c4[nH]ccc34)cc2)[nH]1)C(C)C] | >10 | >10 |
| 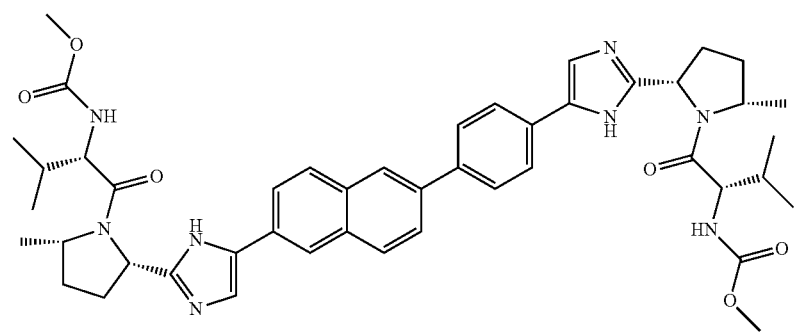 [SMILES: COC(=O)N[C@H](C(=O)N1[C@@H](C)CC[C@H]1c1ncc(-c2ccc(-c3ccc4cc(-c5cnc([C@@H]6CC[C@H](C)N6C(=O)[C@@H](NC(=O)OC)C(C)C)[nH]5)ccc4c3)cc2)[nH]1)C(C)C] | <10 | >100 |
| 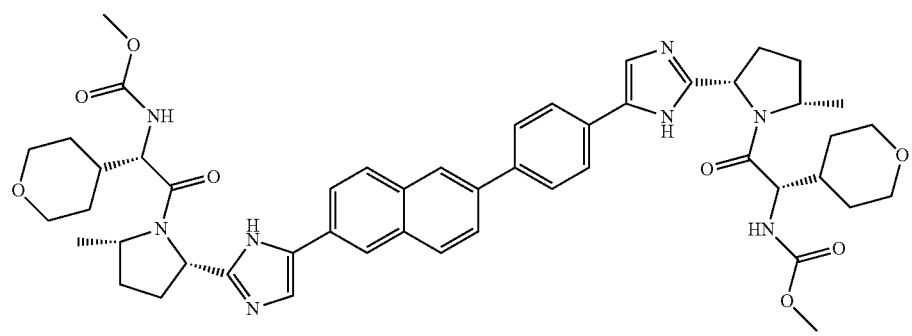 [SMILES: COC(=O)N[C@H](C(=O)N1[C@@H](C)CC[C@H]1c1ncc(-c2ccc(-c3ccc4cc(-c5cnc([C@@H]6CC[C@H](C)N6C(=O)[C@@H](NC(=O)OC)C6CCOCC6)[nH]5)ccc4c3)cc2)[nH]1)C1CCOCC1] | <10 | >10 |

|   | Fold-Synergistic G-1a (L31V) | Fold-Synergistic G-1a (Y93H) |
|---|---|---|
| 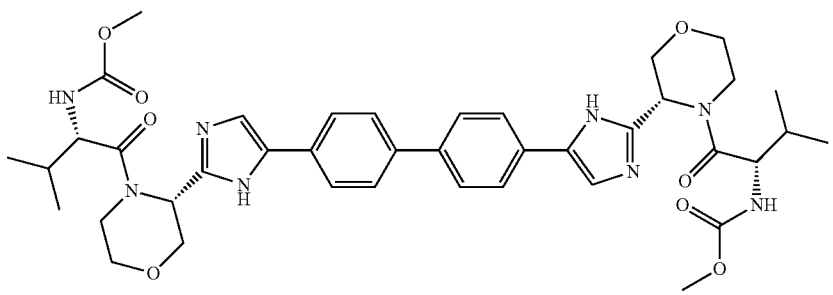 [SMILES: COC(=O)N[C@H](C(=O)N1CCOC[C@H]1c1ncc(-c2ccc(-c3ccc(-c4cnc([C@@H]5COCCN5C(=O)[C@@H](NC(=O)OC)C(C)C)[nH]4)cc3)cc2)[nH]1)C(C)C] | >100 | >100 |
| 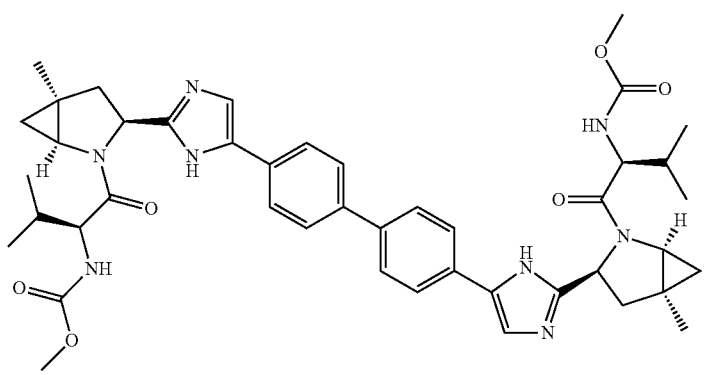 [SMILES: COC(=O)N[C@H](C(=O)N1[C@H]2C[C@@]2(C)C[C@H]1c1ncc(-c2ccc(-c3ccc(-c4cnc([C@@H]5C[C@]6(C)C[C@@H]6N5C(=O)[C@@H](NC(=O)OC)C(C)C)[nH]4)cc3)cc2)[nH]1)C(C)C] | >100 | >100 |
| 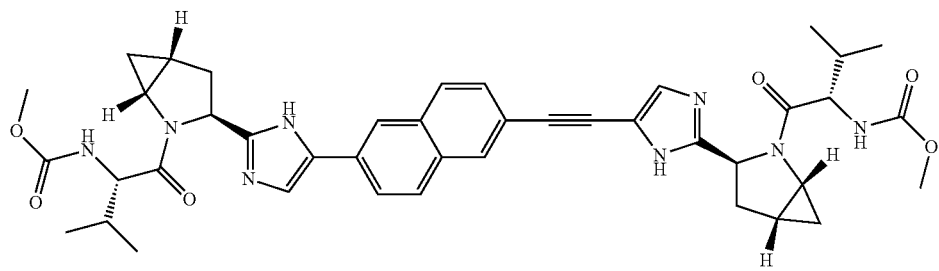 [SMILES: COC(=O)N[C@H](C(=O)N1[C@@H]2C[C@@H]2C[C@H]1c1ncc(C#Cc2ccc3cc(-c4cnc([C@@H]5C[C@H]6C[C@H]6N5C(=O)[C@@H](NC(=O)OC)C(C)C)[nH]4)ccc3c2)[nH]1)C(C)C] | >100 | >100 |
| 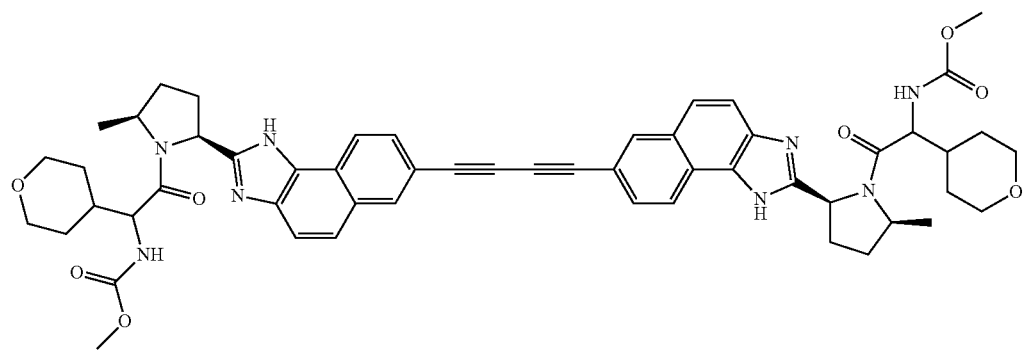 [SMILES: COC(=O)NC(C(=O)N1[C@@H](C)CC[C@H]1c1nc2ccc3cc(C#CC#Cc4ccc5c(ccc6nc([C@@H]7CC[C@H](C)N7C(=O)C(NC(=O)OC)C7CCOCC7)[nH]c65)c4)ccc3c2[nH]1)C1CCOCC1] | <10 | <10 |

| | Fold-Synergistic G-1a (L31V) | Fold-Synergistic G-1a (Y93H) |
|---|---|---|
| 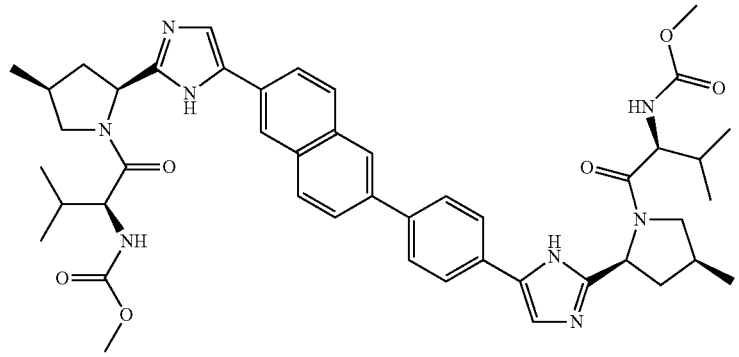 | <10 | >10 |
| 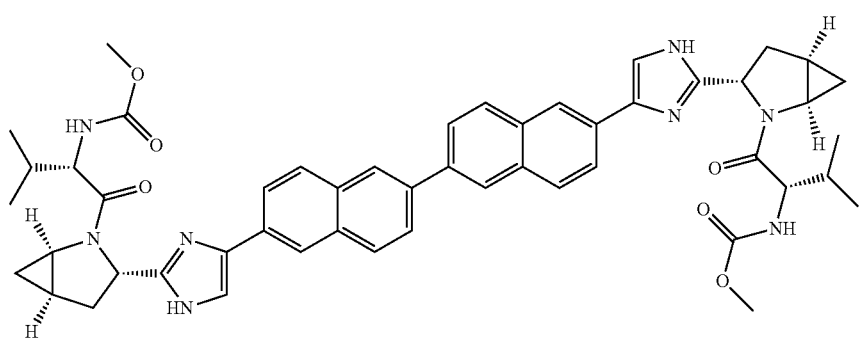 [SMILES: COC(=O)N[C@H](C(=O)N1[C@@H]2C[C@@H]2C[C@H]1c1nc(-c2ccc3cc(-c4ccc5cc(-c6c[nH]c([C@@H]7C[C@H]8C[C@H]8N7C(=O)[C@@H](NC(=O)OC)C(C)C)n6)ccc5c4)ccc3c2)c[nH]1)C(C)C] | <10 | <10 |
| 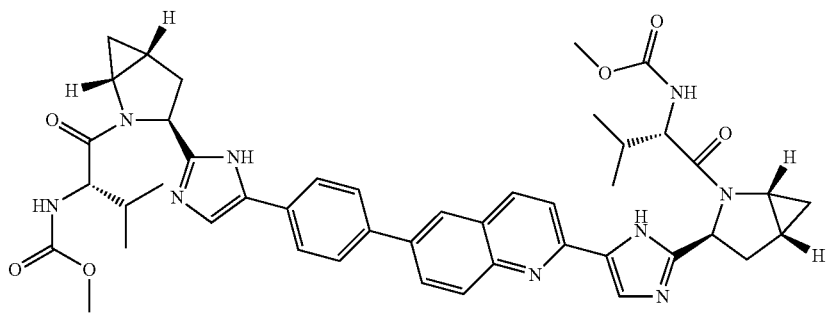 [SMILES: COC(=O)N[C@H](C(=O)N1[C@@H]2C[C@@H]2C[C@H]1c1ncc(-c2ccc(-c3ccc4nc(-c5cnc([C@@H]6C[C@H]7C[C@H]7N6C(=O)[C@@H](NC(=O)OC)C(C)C)[nH]5)ccc4c3)cc2)[nH]1)C(C)C] | <10 | >10 |
| 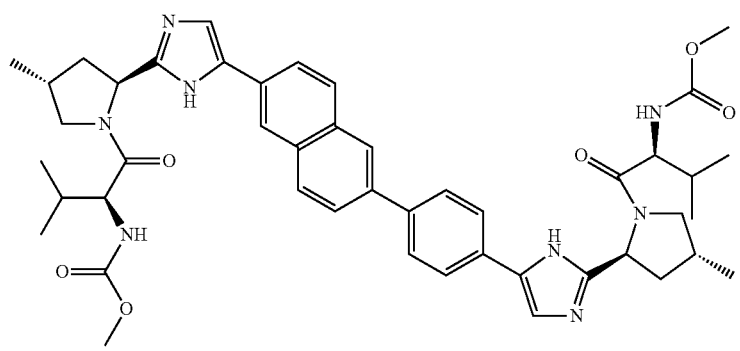 | <10 | >10 |

|   | Fold-Synergistic G-1a (L31V) | Fold-Synergistic G-1a (Y93H) |
|---|---|---|
|   | >100 | >100 |
|   | >10 | >10 |
|   | >100 | >100 |
|   | >100 | >100 |

| | Fold-Synergistic G-1a (L31V) | Fold-Synergistic G-1a (Y93H) |
|---|---|---|
| 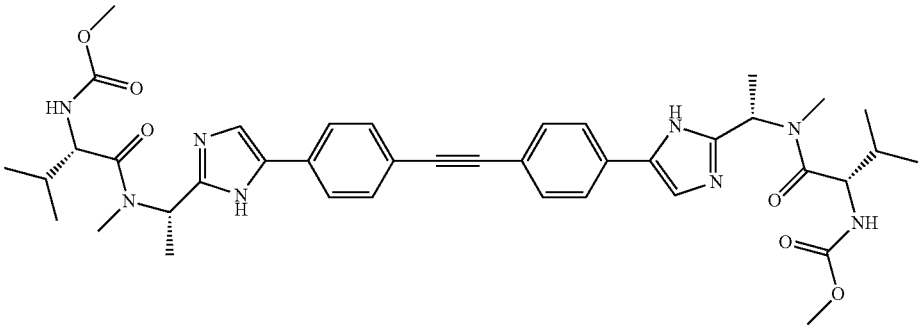 [SMILES: COC(=O)N[C@H](C(=O)N(C)[C@@H](C)c1ncc(-c2ccc(C#Cc3ccc(-c4cnc([C@H](C)N(C)C(=O)[C@@H](NC(=O)OC)C(C)C)[nH]4)cc3)cc2)[nH]1)C(C)C] | >10 | <10 |
| 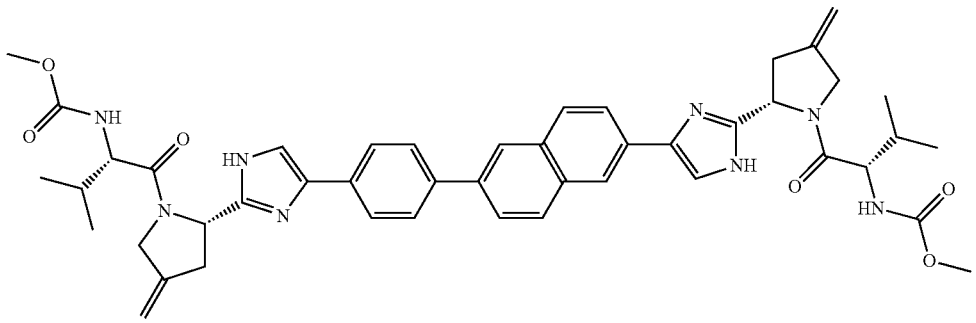 | <10 | >100 |
| 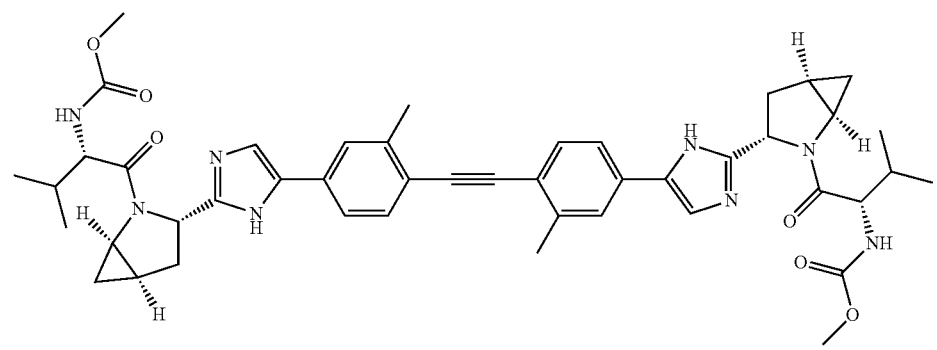 [SMILES: COC(=O)N[C@H](C(=O)N1[C@@H]2C[C@@H]2C[C@H]1c1ncc(-c2ccc(C#Cc3ccc(-c4cnc([C@@H]5C[C@H]6C[C@H]6N5C(=O)[C@@H](NC(=O)OC)C(C)C)[nH]4)cc3C)c(C)c2)[nH]1)C(C)C] | <10 | <10 |
| 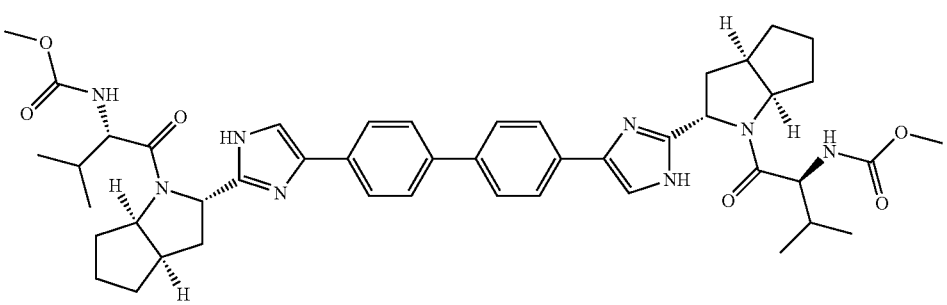 | >100 | >100 |

|  | Fold-Synergistic G-1a (L31V) | Fold-Synergistic G-1a (Y93H) |
|---|---|---|
| 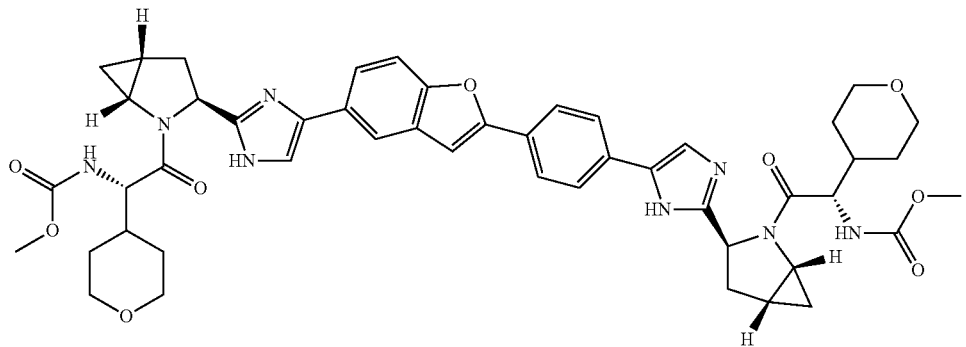 | <10 | <10 |
| 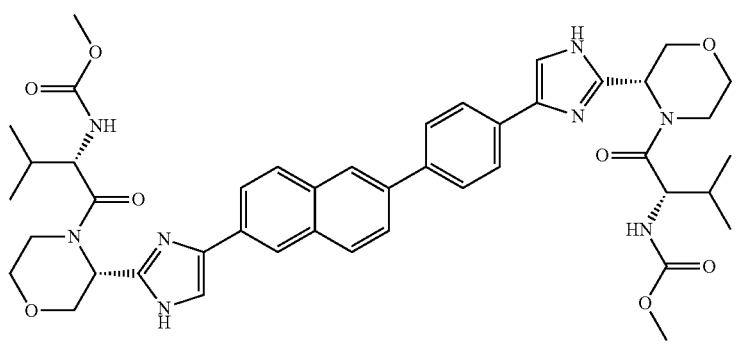 [SMILES: COC(=O)N[C@H](C(=O)N1CCOC[C@H]1c1nc(-c2ccc(-c3ccc4cc(-c5c[nH]c([C@@H]6COCCN6C(=O)[C@@H](NC(=O)OC)C(C)C)n5)ccc4c3)cc2)c[nH]1)C(C)C] | >10 | >10 |
| 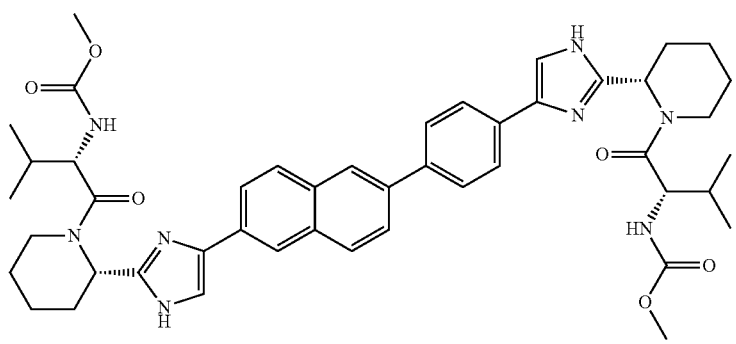 [SMILES: COC(=O)N[C@H](C(=O)N1CCCC[C@H]1c1nc(-c2ccc(-c3ccc4cc(-c5c[nH]c([C@@H]6CCCCN6C(=O)[C@@H](NC(=O)OC)C(C)C)n5)ccc4c3)cc2)c[nH]1)C(C)C] | >10 | <10 |
| 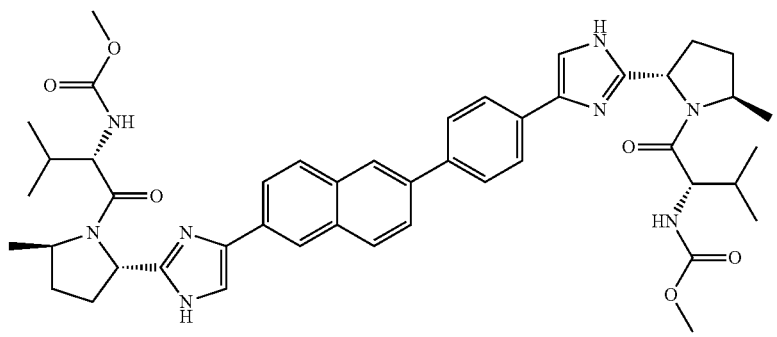 | >10 | <10 |

| | Fold-Synergistic G-1a (L31V) | Fold-Synergistic G-1a (Y93H) |
|---|---|---|
| 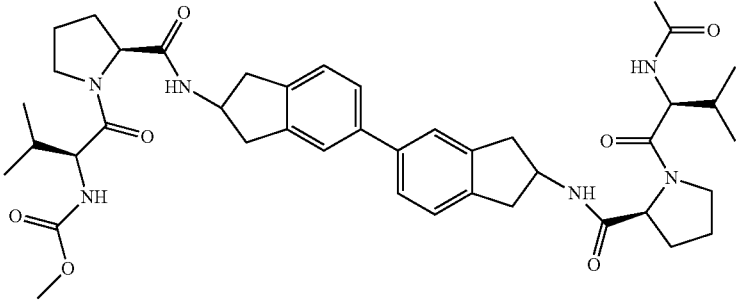 | >10 | >10 |
| 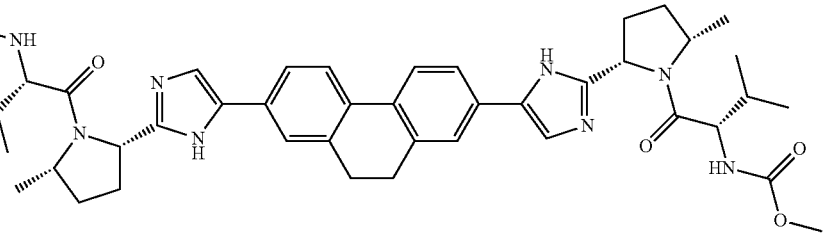 | >100 | >100 |
| 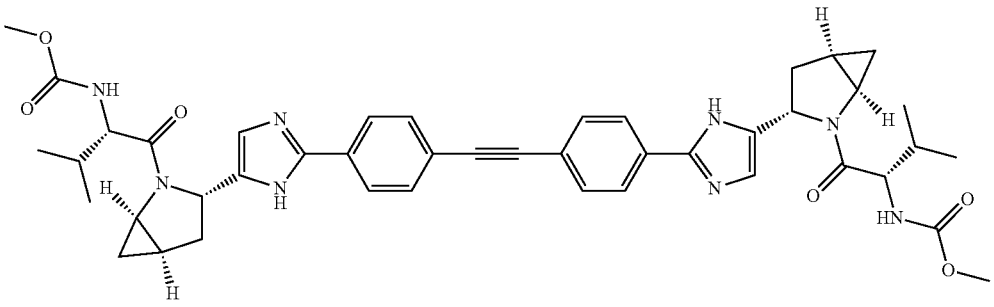 | <10 | >10 |
| 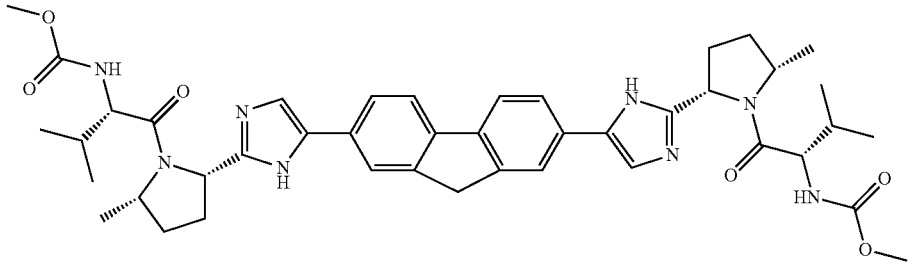 | >100 | >100 |

-continued
| | Fold-Synergistic G-1a (L31V) | Fold-Synergistic G-1a (Y93H) |
|---|---|---|
| 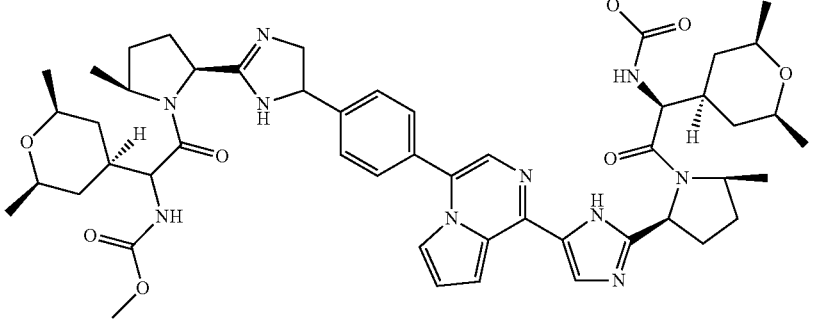 | >10 | >100 |
| 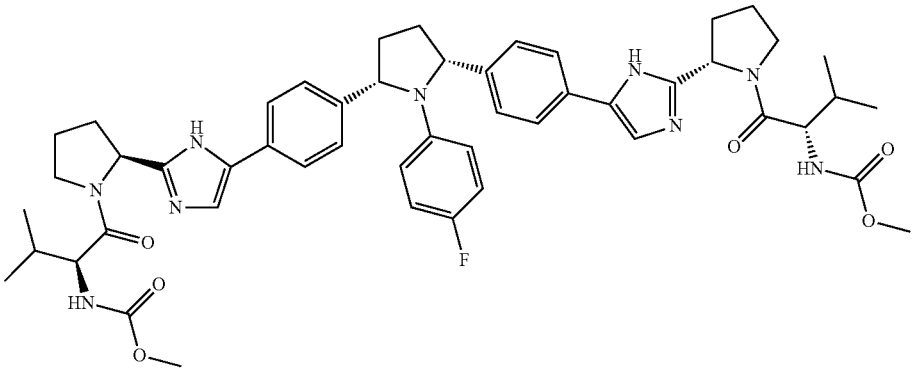 [SMILES: COC(=O)N[C@H](C(=O)N1CCC[C@H]1c1ncc(-c2ccc([C@H]3CC[C@@H](c4ccc(-c5cnc([C@@H]6CCCN6C(=O)[C@@H](NC(=O)OC)C(C)C)[nH]5)cc4)N3c3ccc(F)cc3)cc2)[nH]1)C(C)C] | ND | >10 |
| 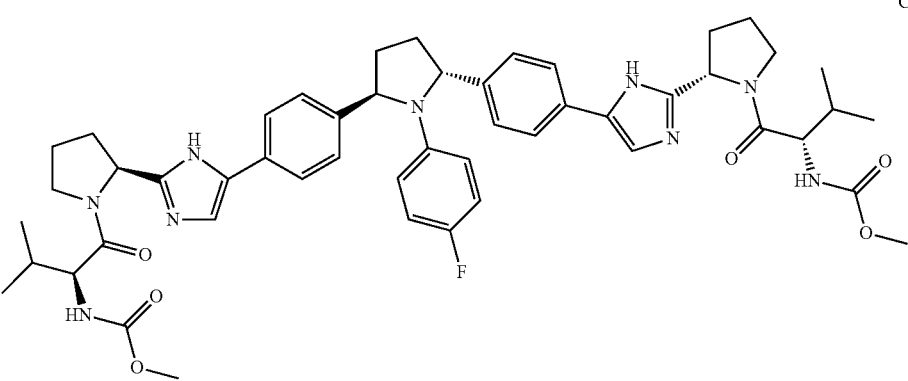 Chiral | ND | >10 |
| 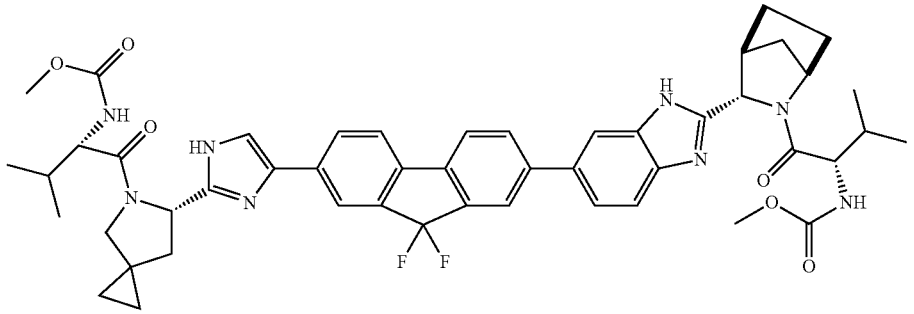 [SMILES: COC(=O)N[C@H](C(=O)N1CC2(CC2)C[C@H]1c1nc(-c2ccc3c(c2)C(F)(F)c2cc(-c4ccc5nc([C@@H]6[C@H]7CC[C@H](C7)N6C(=O)[C@@H](NC(=O)OC)C(C)C)[nH]c5c4)ccc2-3)c[nH]1)C(C)C] | >10 | >100 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A combination comprising an NS5A-targeting compound of formula (I):

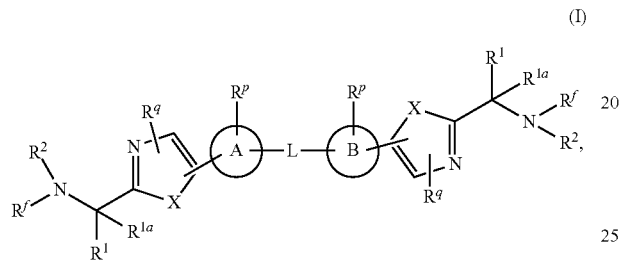

or a pharmaceutically acceptable salt thereof, wherein
- L is absent or selected from $C_2$alkyl, $C_2$alkenyl, $C_2$alkynyl, $C_4$alkynyl, and $C_3$cycloalkyl
- A is absent or selected from isoquinolinyl, naphthyl, phenyl, pyrazinyl, pyridinyl, pyrimidinyl, and quinolinyl;
- B is selected from anthracenyl, benzofuranyl, bicycloalkyl, indanyl, indolyl, naphthyl, phenyl, pyridinyl, pyrimidinyl, pyrazinyl, tetrahydronaphthyl, thienyl, and

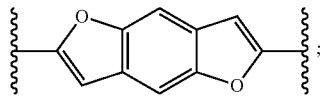 [SMILES: *c1cc2cc3oc(*)cc3cc2o1]

- each X is independently selected from O and $NR^{q'}$, wherein $R^{q'}$ is selected from hydrogen, alkyl, hydroxy, and —$NH_2$;
- each $R^1$ is independently selected from alkoxyalkyl, alkyl, aryl, arylalkyl, cycloalkyl, haloalkyl, heterocyclyl, and hydroxyalkyl;
- each $R^{1a}$ is independently selected from hydrogen and alkyl; or
- $R^1$ and $R^{1a}$, together with the carbon atom to which they are attached, form a saturated or unsaturated 3- to 6-membered spirocyclic ring, wherein the spirocyclic ring, when between 4- and 6-members, can be optionally fused to a phenyl ring, and wherein each ring system is optionally substituted with one or two groups independently selected from alkyl and halo;
- each $R^f$ is independently selected from hydrogen, methyl, hydroxy, and —$NH_2(R^z)$, wherein $R^z$ is alkyl;
- each $R^p$ is independently selected from hydrogen, alkyl, cyano, halo, haloalkoxy, and haloalkyl;
- each $R^q$ is independently selected from hydrogen, alkyl, halo, and —P(O)—(OR)$_2$, wherein each R is the same or a different alkyl group; and
- each $R^2$ is independently selected from hydrogen, alkenylcarbonyl, alkoxyalkylcarbonyl, alkoxyalkylcarbonylcarbonyl, alkoxycarbonyl, alkoxycarbonylalkylcarbonyl, alkoxycarbonylcarbonyl, alkyl, alkylcarbonyl, alkylcarbonylalkylcarbonyl, alkylcarbonylcarbonyl, alkylsulfinyl, alkylsulfonyl, alkynyl, alkynyloxycarbonyl, alkynylcarbonyl, arylcarbonyl, arylcarbonylcarbonyl, arylalkenylcarbonyl, arylalkoxycarbonyl, arylalkylcarbonyl, aryloxyalkylcarbonyl, arylsulfanylalkylcarbonyl, arylsulfinyl, arylsulfonyl, bicycloalkylcarbonyl, carboxyalkylcarbonyl, carboxycarbonyl, cyanoalkylcarbonyl, (cycloalkenyl)alkylcarbonyl, (cycloalkyl)alkyl, (cycloalkyl)alkylcarbonyl, cycloalkylcarbonyl, cycloalkylcarbonylcarbonyl, cycloalkyloxycarbonyl, haloalkenylcarbonyl, haloalkoxyalkylcarbonyl, haloalkylcarbonyl, haloalkylcarbonylcarbonyl, heterocyclyl, (heterocyclyl)alkylcarbonyl, heterocyclylcarbonyl, heterocyclylcarbonylalkylcarbonyl, heterocyclylcarbonylcarbonyl, hydroxyalkenylcarbonyl, hydroxyalkylcarbonyl, (NR$^c$R$^d$)alkylcarbonyl, (NR$^c$R$^d$)carbonyl, (NR$^c$R$^d$)carbonylalkylcarbonyl, (NR$^c$R$^d$)carbonylcarbonyl, and

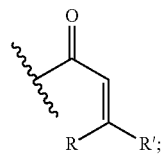

wherein R and R' are each alkyl, or, together with the carbon atom to which they are attached, form a five- or six-membered ring optionally containing one oxygen or nitrogen atom; or $R^2$ and $R^f$, together with the nitrogen atom to which they are attached, forms a five- or six-membered ring optionally substituted with one or two groups independently selected from alkoxycarbonylamino and oxo; or $R^2$ and $R^f$, together with the nitrogen atom to which they are attached, form

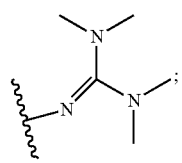 [SMILES: *N=C(N(C)C)N(C)C]

and an NS5A synergist of formula (VII):

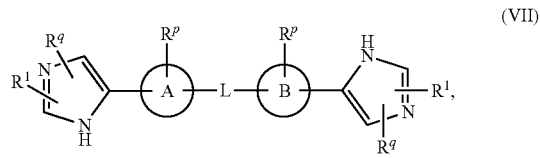

or a pharmaceutically acceptable salt thereof, wherein:
- L is absent or selected from —O—, —$CH_2$—O—$CH_2$—, —$OCH_2$—, $C_2$alkyl, $C_2$alkynyl, cyclopropyl, ethynylbenzyl, phenyl, pyrazinyl, and pyridinyl;
- A is selected from aryl, cycloalkenyl, and heteroaryl;
- B is selected from aryl, bicycloalkyl, cycloalkenyl, and heteroaryl;

each R¹ is independently selected from

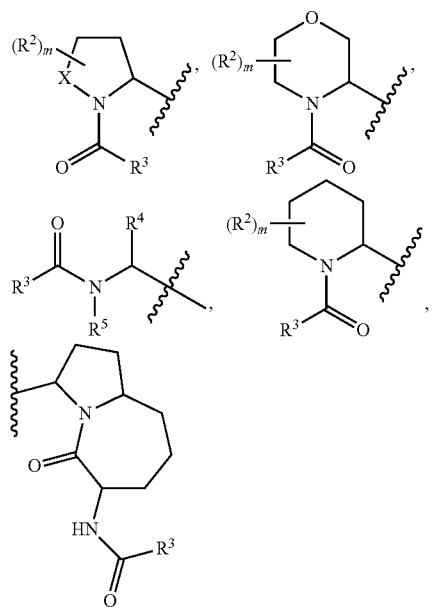

each m is independently 0, 1, or 2;
each X is independently selected from CH₂, NH, and NR$^a$; wherein R$^a$ is alkyl;
each R² is independently selected from alkyl, halo, and hydroxy; wherein the alkyl can optionally form a fused three- to six-membered ring with an adjacent carbon, a bridged four- or five-membered ring with another carbon atom on the ring, or a spirocyclic three- to six-membered ring with the carbon atom to which it is attached; wherein each ring is optionally substituted with one or two groups independently selected from alkyl, halo, and haloalkyl; or
R², together with the carbon atom to which it is attached, forms a C₂ olefin;
each R³ is independently selected from alkoxy, alkyl, arylalkoxy, arylalkyl, cycloalkyl, (cycloalkyl)alkyl, cycloalkyloxy, heterocyclyl, heterocyclylalkyl, (NR$^c$R$^d$)alkenyl, and (NR$^c$R$^d$)alkyl;
each R⁴ is independently selected from hydrogen, alkyl, cycloalkyl, and haloalkyl;
each R⁵ is independently selected from hydrogen and alkyl;
each R$^p$ is independently selected from hydrogen, alkyl, cyano, halo, haloalkoxy, and haloalkyl; and
each R$^q$ is independently selected from hydrogen, alkyl, halo, and —P(O)—(OR)₂, wherein each R is the same or a different alkyl group;
which, when administered, provides synergistic anti-HCV activity against variants that contain mutation(s) conferring resistance to the NS5A-targeting compound alone.

2. The combination of claim 1 which comprises two or more pharmaceutically acceptable carriers.

3. The combination of claim 1 wherein the NS5A-targeting compound and the NS5A synergist are combined in the same pharmaceutically acceptable carrier.

4. A composition comprising a combination of claim 1, or a pharmaceutically acceptable salt thereof, and a pharmaceutically acceptable carrier.

5. The composition of claim 4 further comprising one or two additional compounds having anti-HCV activity.

6. The composition of claim 5 wherein at least one of the additional compounds is an interferon or a ribavirin.

7. The composition of claim 6 wherein the interferon is selected from interferon alpha 2B, pegylated interferon alpha, pegylated interferon lambda, consensus interferon, interferon alpha 2A, and lymphoblastoid interferon tau.

8. The composition of claim 5 wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

9. A method of treating an HCV infection in a patient, comprising administering to the patient a therapeutically effective amount of a combination of claim 1, or a pharmaceutically acceptable salt thereof.

10. The method of claim 9 further comprising administering one or two additional compounds having anti-HCV activity prior to, after or simultaneously with the combination, or a pharmaceutically acceptable salt thereof.

11. The method of claim 10 wherein at least one of the additional compounds is an interferon or a ribavirin.

12. The method of claim 11 wherein interferon is selected from interferon alpha 2B, pegylated interferon alpha, pegylated interferon lambda, consensus interferon, interferon alpha 2A, and lymphoblastoid interferon tau.

13. The method of claim 10 wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

* * * * *